United States Patent
Wilson, Jr. et al.

(10) Patent No.: US 12,281,148 B2
(45) Date of Patent: *Apr. 22, 2025

(54) ANTI-PD-1 ANTIBODY-ATTENUATED IL-2 IMMUNOCONJUGATES AND USES THEREOF

(71) Applicant: Cephalon LLC, West Chester, PA (US)

(72) Inventors: David S. Wilson, Jr., Redwood City, CA (US); Kim Tran Yap, Atherton, CA (US); Paul Ayton, San Francisco, CA (US); Debasish Sen, Redwood City, CA (US); Julia Rozenfeld, Gordon (AU); Sachin Badrinath Surade, Macquarie Park (AU); Anthony Gerard Doyle, Macquarie Park (AU)

(73) Assignee: Cephalon LLC

( * ) Notice: Subject to any disclaimer, the term of this patent is extended or adjusted under 35 U.S.C. 154(b) by 0 days.

This patent is subject to a terminal disclaimer.

(21) Appl. No.: 18/823,422

(22) Filed: Sep. 3, 2024

(65) Prior Publication Data
US 2024/0425562 A1 Dec. 26, 2024

Related U.S. Application Data

(63) Continuation of application No. 18/335,650, filed on Jun. 15, 2023.
(Continued)

(51) Int. Cl.
*C07K 14/55* (2006.01)
*C07K 16/28* (2006.01)

(52) U.S. Cl.
CPC .......... *C07K 14/55* (2013.01); *C07K 16/2818* (2013.01); *C07K 2317/21* (2013.01);
(Continued)

(58) Field of Classification Search
CPC ................ C07K 14/55; C07K 16/2818; C07K 2317/21; C07K 2317/75; C07K 2317/92; C07K 2319/33; C07K 2319/75
See application file for complete search history.

(56) References Cited

U.S. PATENT DOCUMENTS 8,124,066 B2 2/2012 Epstein et al.
9,617,338 B1 4/2017 Campbell et al.
(Continued)

FOREIGN PATENT DOCUMENTS

EP 0109748 A1 5/1984
NZ 205922 A 11/1987
(Continued)

OTHER PUBLICATIONS

Almagro, "Identification of differences in the specificity-determining residues of antibodies that recognize antigens of different size: implications for the rational design of antibody repertoires", Mol. Recognit., 2004, 17, 132-143.
(Continued)

*Primary Examiner* — Adam Weidner
*Assistant Examiner* — Laura Ann Essex
(74) *Attorney, Agent, or Firm* — BakerHostetler

(57) ABSTRACT

Disclosed herein are modified human interleukin-2 (hIL-2) proteins, human antibody molecules, or antigen-binding fragments thereof, that immunospecifically bind to human programmed cell death protein-1 (hPD-1), and immunoconjugates comprising the same.

10 Claims, 26 Drawing Sheets

Specification includes a Sequence Listing.

IH3-hIgG1-L6-hCD25(1-164)-L20-hIL-2

Related U.S. Application Data

(60) Provisional application No. 63/502,746, filed on May 17, 2023, provisional application No. 63/481,630, filed on Jan. 26, 2023, provisional application No. 63/352,842, filed on Jun. 16, 2022.

(52) U.S. Cl.
CPC ...... *C07K 2317/75* (2013.01); *C07K 2317/92* (2013.01); *C07K 2319/33* (2013.01); *C07K 2319/75* (2013.01)

(56) References Cited

U.S. PATENT DOCUMENTS

| | | |
|---|---|---|
| 11,865,082 B2 | 1/2024 | Codarri Deak et al. |
| 2006/0292140 A1 | 12/2006 | Ponath et al. |
| 2007/0148774 A1 | 6/2007 | Mccafferty et al. |
| 2009/0217401 A1 | 8/2009 | Korman et al. |
| 2018/0326010 A1 | 11/2018 | Codarri et al. |
| 2021/0340208 A1 | 11/2021 | Ye et al. |
| 2022/0185899 A1* | 6/2022 | Rosenthal ............... A61P 21/02 |

FOREIGN PATENT DOCUMENTS

| | | |
|---|---|---|
| WO | 85/00817 A1 | 2/1985 |
| WO | 88/01649 A1 | 3/1988 |
| WO | 92/01047 A1 | 1/1992 |
| WO | 94/13804 A1 | 6/1994 |
| WO | 98/06248 A2 | 2/1998 |
| WO | 98/44001 A1 | 10/1998 |
| WO | 99/60128 A1 | 11/1999 |
| WO | 03/15697 A2 | 2/2003 |
| WO | 03/48334 A2 | 6/2003 |
| WO | 2008/156712 A1 | 12/2008 |
| WO | 2009/085462 A1 | 7/2009 |
| WO | 2012/107417 A1 | 8/2012 |
| WO | 2012/146628 A1 | 11/2012 |
| WO | 2013/059885 A2 | 5/2013 |
| WO | 2016/164937 A2 | 10/2016 |
| WO | 2017/220990 A1 | 12/2017 |
| WO | 2018/119114 A1 | 6/2018 |
| WO | 2018/184964 A1 | 10/2018 |
| WO | 2018/189220 A1 | 10/2018 |
| WO | 2018/217989 A1 | 11/2018 |
| WO | 2019/125732 A1 | 6/2019 |
| WO | 2020/247843 A2 | 12/2020 |
| WO | 2020/252421 A2 | 12/2020 |
| WO | 2021/102063 A1 | 5/2021 |
| WO | 2021/116444 A1 | 6/2021 |
| WO | 2021/185361 A1 | 9/2021 |
| WO | 2021/201615 A1 | 10/2021 |
| WO | 2021/253360 A1 | 12/2021 |
| WO | 2022/006380 A2 | 1/2022 |
| WO | 2022/048640 A1 | 3/2022 |
| WO | 2022/159508 A1 | 7/2022 |
| WO | 2022/212614 A1 | 10/2022 |

OTHER PUBLICATIONS

Ching et al., "Chickens with humanized immunoglobulin genes generate antibodies with high affinity and broad epitope coverage to conserved targets", mAbs, 2018, 71-80.

Chothia et al., "Canonical Structures for the Hypervariable Regions of Immunoglobulins", J. Mol. Biol., 1987, 901-917.

Collins et al., "Identification of specific residues of human interleukin 2 that affect binding to the 70-kDa subunit (p70) of the interleukin 2 receptor", Proc Natl Acad Sci USA, Oct. 1988, vol. 85, No. 20, 7709-7713.

Kabat et al., Sequences of Proteins of Immunological Interest, 5th Ed. Public Health Service, National Institutes of Health, Bethesda, Md., 1991.

Klein et al., "A novel PD1-IL2v immunocytokine for preferential cis-activation of IL-2R signaling on PD-1 expressing T cell subsets strongly potentiates anti-tumor T cell activity of PD-1 checkpoint inhibition and IL-2R-beta-gamma agonism", Cancer Research, 2019, vol. 79, (13_Supplement): 1552.

Knappik et al., "Fully synthetic human combinatorial anitbody libraries (HuCAL) based on moduler consensus frameworks and CDRs randomized with trinucleotides", J. Mol. Biol., 2000, 296, 57-86.

Lefranc et al., "IMGT unique numbering for immunoglobulin and T cell receptor variable domains and Ig superfamily V-like domains", Dev. Comparat. Immunol., 2003, 27, 55-77.

Matsumoto et al., "B7-DC Regulates Asthmatic Response by an IFN-Dependent Mechanism", J. Immunol. Feb. 2004. 15, 2004, 172(4), 2530-2541.

Mettler Izquierdo "High-efficiency antibody discovery achieved with multiplexed microscopy", Microscopy (Oxford, England), 2016, 65(4), 341-352.

Raeber et al., "A systematic review of interleukin-2-based immunotherapies in clinical trials for cancer and autoimmune diseases", eBioMedicine, 2023, vol. 90, 104539, Mar. 31, 2023, pp. 1-25.

Ren et al., "Selective delivery of low-affinity IL-2 to PD-1+ T cells rejuvenates antitumor immunity with reduced toxicity", J. Clin. Invest., Feb. 1, 2022, vol. 132, No. 3, :e153604, 1-13.

Shen et al., "Engineered IL-21 Cytokine Muteins Fused to Anti-PD-1 Antibodies Can Improve CD8+ T Cell Function and Anti-tumor Immunity", Front. Immunol., May 2020, vol. 11, Article 83, pp. 1-14.

Shi et al., "De Novo Selection of High-Affinity Antibodies from Synthetic Fab Libraries Displayed on Phage as pIX Fusion Proteins", J. Mol. Biol., 2010, 397, 385-396.

Ward et al., "Binding Activities of a repertoire of single immunoglobulin variable domains secreted from *Escherichia coli*", Nature, 1989, 341, 544-546.

Wu et al., "An Analysis of the sequences of the variable regions of bence jones proteins and myeloma light chains and their implications for anti-body complementarity", J. Exp. Med., 1970, 132, 211-250.

\* cited by examiner

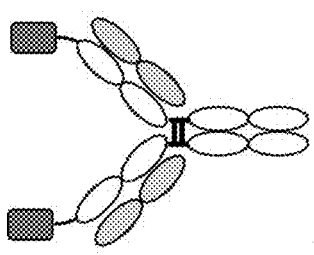
FIG. 1A — hIL-2 Nterm light chain df
FIG. 1B — hIL-2 Nterm light chain L6 fusion
FIG. 1C — hIL-2 Nterm heavy chain df
FIG. 1D — hIL-2 Nterm heavy chain L6 fusion
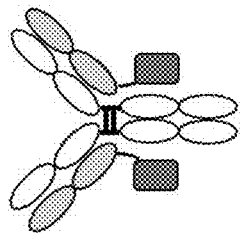
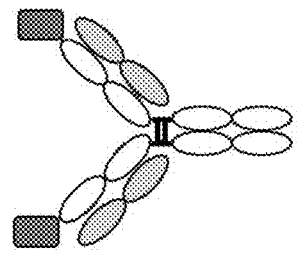
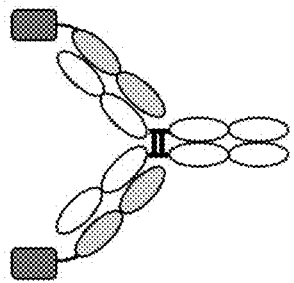
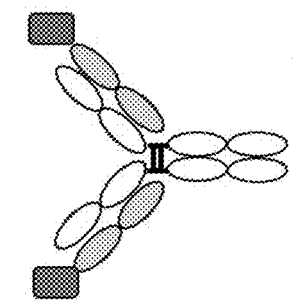
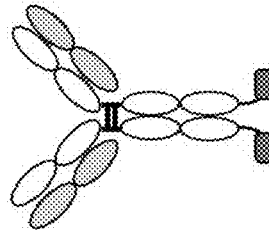
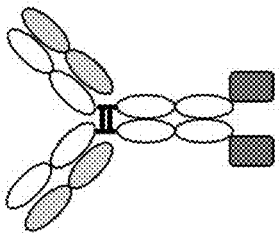
FIG. 1E — hIL-2 Cterm heavy chain df
FIG. 1F — hIL-2 Cterm heavy chain L6 fusion
FIG. 1G — hIL-2 Cterm light chain df
FIG. 1H — hIL-2 Cterm light chain L6 fusion
hIL-2
L6

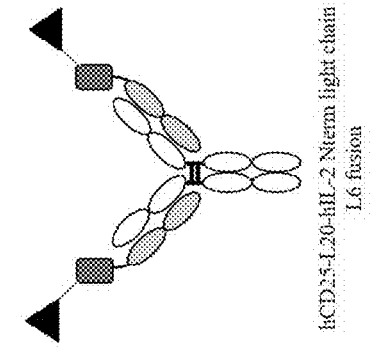
FIG. 2A / FIG. 2B / FIG. 2C / FIG. 2D
hCD25-L20-hIL-2 Nterm heavy chain df / hCD25-L20-hIL-2 Nterm heavy chain L6 fusion / hCD25-L20-hIL-2 Nterm light chain df / hCD25-L20-hIL-2 Nterm light chain L6 fusion
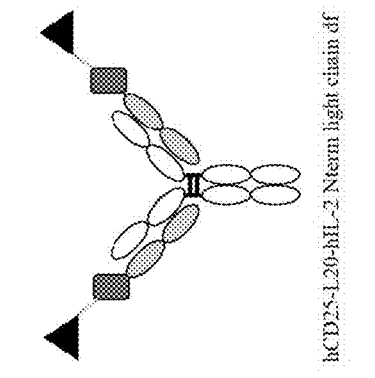
FIG. 2E / FIG. 2F / FIG. 2G / FIG. 2H
hCD25-L20-hIL-2 Cterm heavy chain df / hCD25-L20-hIL-2 Cterm heavy chain L6 fusion / hCD25-L20-hIL-2 Cterm light chain df / hCD25-L20-hIL-2 Cterm light chain L6 fusion
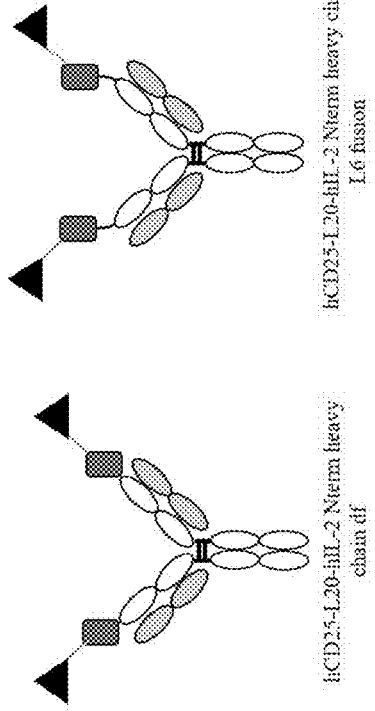
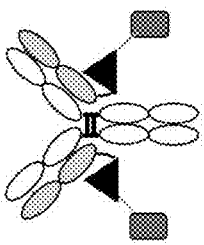
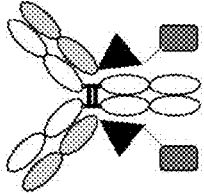
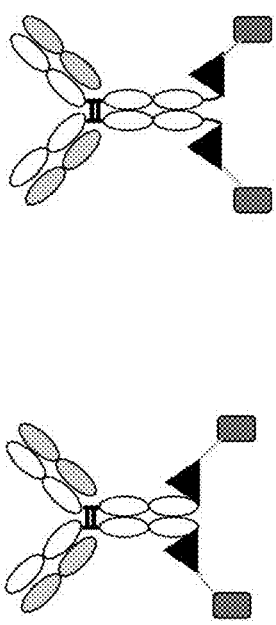
hCD25 (1-164)   hIL-2
L20
L6

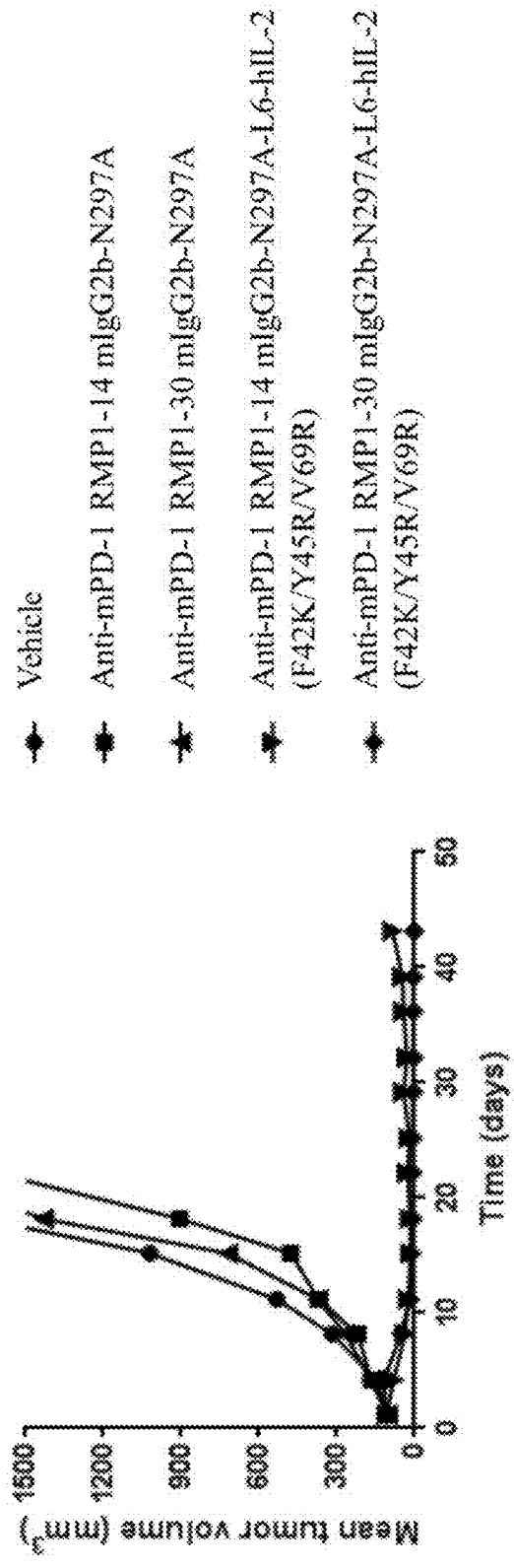

FIG. 9C
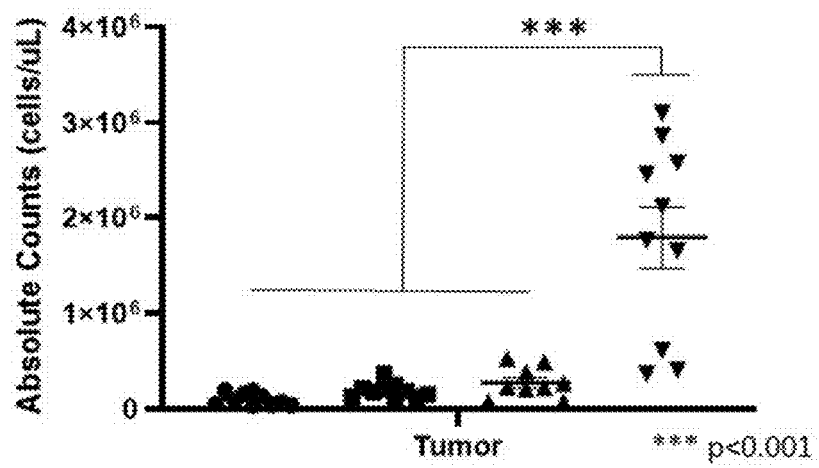
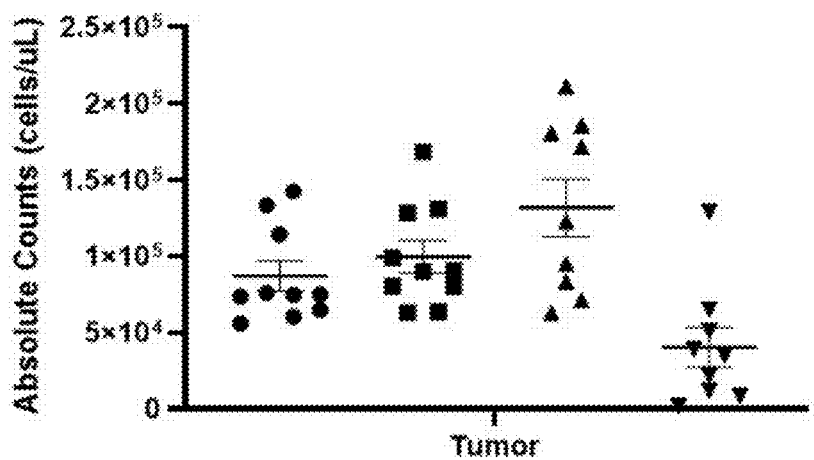
→ Vehicle (PBS)
→ Anti-KLH-C3-mIgG2b-N297A-L6-hIL-2 (F42K/Y45R/V69R)
→ Anti-mPD1 RMP1-30-mIgG2b-N297A
→ Anti-mPD1 RMP1-30-mIgG2b-N297A-L6-hIL-2 (F42K/Y45R/V69R)

ANTI-PD-1 ANTIBODY-ATTENUATED IL-2 IMMUNOCONJUGATES AND USES THEREOF

CROSS REFERENCE TO RELATED APPLICATIONS

This application is a continuation of U.S. application Ser. No. 18/335,650, which was filed on Jun. 15, 2023, which claims priority to U.S. Provisional Application No. 63/352,842, which was filed on Jun. 16, 2022, U.S. Provisional Application No. 63/481,630, which was filed on Jan. 26, 2023, and U.S. Provisional Application No. 63/502,746, which was filed on May 17, 2023, the disclosure of each of which are hereby incorporated by reference in their entirety.

SEQUENCE LISTING

The instant application contains a Sequence Listing which is being submitted herewith electronically in XML format and is hereby incorporated by reference in its entirety. Said XML copy, created on Aug. 26, 2024, is named 102085.002045_Sequence Listing.xml and is 696,000 bytes in size.

TECHNICAL FIELD

Disclosed herein are modified human interleukin-2 (hIL-2) proteins, human antibody molecules, or antigen-binding fragments thereof, that immunospecifically bind to human programmed cell death protein-1 (hPD-1), and immunoconjugates comprising the same.

BACKGROUND

Human IL-2 (hIL-2) is a Type 1 four α-helical bundle, glycosylated cytokine produced by CD4+ T cells and CD8+ T cells. Autocrine and paracrine IL-2 signaling occurs through engagement of either a high-affinity trimeric receptor complex comprising IL-2Rα (CD25), IL-2Rβ (CD122), and IL-2Rγ (CD132), or an intermediate-affinity dimeric receptor complex which comprises IL-2Rβ (CD122) and IL-2Rγ (CD132). IL-2 has dual opposing and pleiotropic roles, in that it can both stimulate T cell proliferation to generate T cell effector, T cell memory, and activated NK cells, but can also stimulate suppressive regulatory T cells for maintenance of immune homeostasis. Low-dose IL-2 primarily stimulates regulatory T cells as well as some T effector and NK cells, whereas high-dose IL-2 broadly stimulates cytotoxic T cells, T effector, and NK cells and regulatory T cells. The use of IL-2 in the treatment of autoimmune diseases and as a cancer immunotherapy has, however, been limited by off-target effects and toxicity associated with the administration of IL-2.

SUMMARY

Disclosed herein are modified human interleukin-2 (hIL-2) proteins comprising a substitution at amino acid position 20 and a substitution at amino acid position 38 relative to the non-modified hIL-2 amino acid sequence of SEQ ID NO: 345, wherein the modified hIL-2 protein exhibits reduced potency on both a high affinity hIL-2 receptor and on an intermediate affinity hIL-2 receptor relative to the non-modified hIL-2.

Also disclosed herein are modified human interleukin-2 (hIL-2) proteins comprising a D20A, D20S, D20Q, D20M, D20I, D20V, D20N, D20G, D20T, or D20E substitution at amino acid position 20 and a R38E substitution at amino acid position 38 relative to the non-modified hIL-2 amino acid sequence of SEQ ID NO: 345.

Also disclosed herein are human antibody molecules, or antigen-binding fragments thereof, that immunospecifically bind to human programmed cell death protein-1 (hPD-1), wherein the human antibody molecule or antigen-binding fragment thereof comprises:

a) a heavy chain complementarity determining region 1 (CDR1) comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423;

b) a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391;

c) a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401; or d) a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

Also disclosed herein are immunoconjugates comprising:
(a) a modified hIL-2 protein comprising a substitution at amino acid position 20 and a substitution at amino acid position 38 relative to the non-modified hIL-2 amino acid sequence of SEQ ID NO: 345; and
(b) a human antibody molecule, or antigen-binding fragment thereof, that immunospecifically binds to hPD-1, wherein the human antibody molecule or antigen-binding fragment thereof comprises:
(i) a heavy chain CDR1 comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423;
  (ii) a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391;
  (iii) a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401; or
  (iv) a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

Pharmaceutical compositions comprising any of the herein disclosed modified hIL-2 proteins, human antibody molecules, or antigen-binding fragments thereof, or immunoconjugates are also disclosed.

Also disclosed herein are polynucleotides comprising a nucleic acid sequence encoding any of the herein disclosed modified hIL-2 proteins, human antibody molecules, or antigen-binding fragments thereof, or immunoconjugates, as well as vectors comprising the polynucleotides and transformed cells comprising the vectors.

Disclosed herein are methods of treating a disease or disorder in a subject, the methods comprising administering a therapeutically effective amount of any of the herein disclosed immunoconjugates or pharmaceutical compositions to the subject to thereby treat the disease or disorder.

Also disclosed are uses of any of the herein disclosed immunoconjugates or pharmaceutical compositions in the preparation of a medicament for the treatment of a disease, and uses of any of the herein disclosed immunoconjugates or pharmaceutical compositions for the treatment of a disease or disorder.

BRIEF DESCRIPTION OF THE DRAWINGS

The summary, as well as the following detailed description, is further understood when read in conjunction with the appended drawings. For the purpose of illustrating the disclosed modified hIL-2 proteins, anti-hPD-1 antibodies or antigen-binding fragments thereof, and immunoconjugates, there are shown in the drawings exemplary embodiments of the modified hIL-2 proteins, anti-hPD-1 antibodies or antigen-binding fragments thereof, and immunoconjugates; however, the modified hIL-2 proteins, anti-hPD-1 antibodies or antigen-binding fragments thereof, and immunoconjugates are not limited to the specific embodiments disclosed. In the drawings:

FIG. 1A, FIG. 1B, FIG. 1C, FIG. 1D, FIG. 1E, FIG. 1F, FIG. 1G, and FIG. 1H illustrate exemplary antibody-hIL-2 immunoconjugates as described in Example 1 herein. Non-attenuated human IL-2 cytokine (grey rectangle) was fused either directly (df) or via an L6 linker (L6) to either the N-terminus or C-terminus of both heavy chains or both kappa light chains of the antibody.

FIG. 2A, FIG. 2B, FIG. 2C, FIG. 2D, FIG. 2E, FIG. 2F, FIG. 2G, and FIG. 2H illustrate exemplary antibody-hIL-2 immunoconjugates with hCD25 (1-164) extracellular domain designed to interfere with the immunoconjugate's hIL-2 binding to the human IL-2Rα. For N-terminal variants, the human CD25/IL-2Rα extracellular domain (black triangle) was fused to a non-attenuated hIL-2 cytokine (grey rectangle) via an L20 linker (light grey line). Non-attenuated hIL-2 cytokine was then either directly fused (df) or fused to the antibody with an L6 linker. For C-terminal variants, the hCD25/IL-2Rα extracellular domain moiety was either directly fused (df) or fused to the antibody using an L6 linker, followed by an L20 linker and non-attenuated hIL-2 cytokine.

FIG. 8 shows the results of experiments analyzing the effect of the administration of vehicle, surrogate anti-PD-1 antibodies (anti-mPD-1 RMP1-14 mIgG2b-N297A and anti-mPD-1 RMP1-30 mIgG2b-N297A), and surrogate anti-PD-1-attenuated hIL-2 immunoconjugates (anti-mPD-1 RMP1-14 mIgG2b-N297A-L6-hIL-2 (F42K/Y45R/V69R) or antimPD-1 RMP1-30 mIgG2b-N297A-L6-hIL-2 (F42K/Y45R/V69R)) on the growth of established subcutaneous MC38 syngeneic tumors in C57BL/6 mice, as described in Example 18. Test agents were dosed intraperitoneally at 5 mg/kg twice weekly for 4 weeks, starting on day 1. The points on the graph represent mean tumor volumes of an average of 10 mice per group.

FIG. 9A, FIG. 9B, and FIG. 9C illustrate the results of studies conducted to determine the efficacy of surrogate anti-hPD-1-attenuated hIL-2 immunoconjugate anti-mPD-1 RMP1-30 mIgG2b-N297A-hIL-2 (F42K/Y45R/V69R) in an MC38 murine colon adenocarcinoma model. FIG. 9A depicts the mean subcutaneous tumor volumes (mm$^3$) measured every 3-4 days for 8 days after the first dose of test agents (3 doses on days 1, 4, and 8 at 5 mg/kg). Tumor growth curves represent an average of 15 animals per group. FIG. 9B summarizes results from immunophenotyping tumors by flow cytometry on day 9, showing the proportion of different CD8$^+$ T cell subsets as fractions of the total CD8$^+$ T cell average absolute counts. FIG. 9C illustrates immunophenotyping results on day 9 which demonstrated that there was a significant expansion of CD8$^+$ T effector memory and a trend towards decreased regulatory T cells in tumors (cells/µL) following exposure to the surrogate immunoconjugate.

FIG. 18A and FIG. 18B show results from the titration of anti-hPD-1 #1 or anti-hPD-1 #2 in the presence of fixed concentration anti-hPD-1-attenuated hIL-2 immunoconjugates. FIG. 18C and FIG. 18D show the results from the converse experiment in which anti-hPD-1-attenuated hIL-2 immunoconjugates were titrated with a fixed concentration of 100 nM of anti-hPD-1 #1 (FIG. 18C) or 100 nM of anti-hPD-1 #2 (FIG. 18D).

DETAILED DESCRIPTION OF ILLUSTRATIVE EMBODIMENTS

Figure 3:
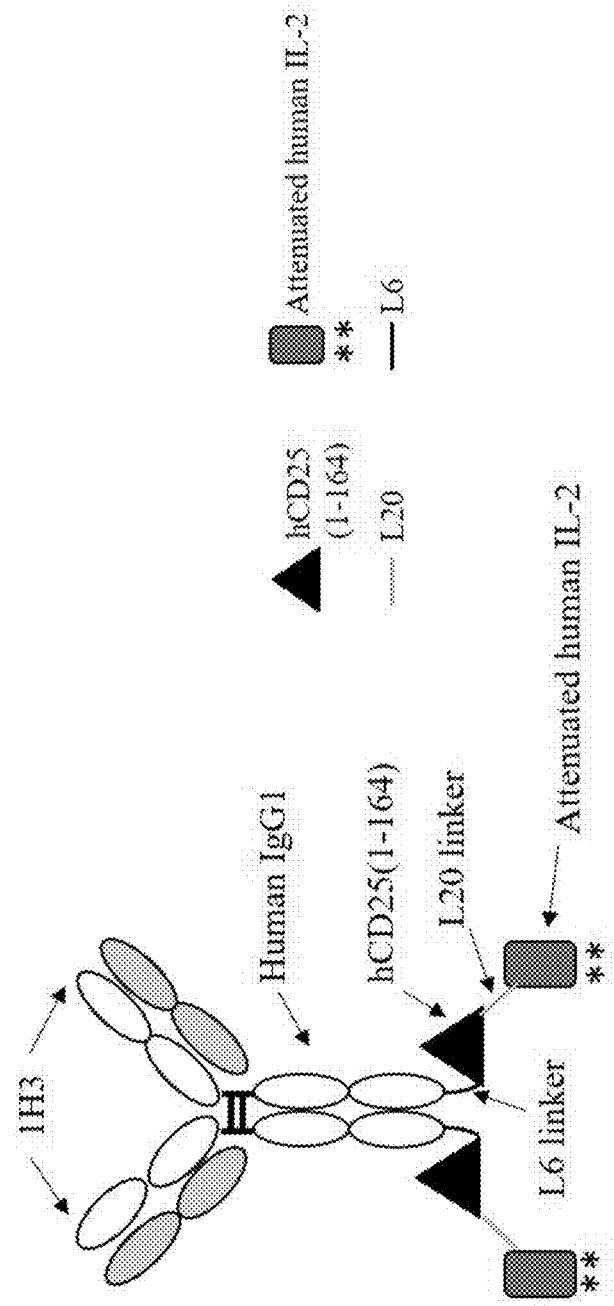
FIG. 3 illustrates an exemplary 1H3-hIgG1-L6-hIL-2 immunoconjugate that contains a CD25/IL-2Rα extracellular domain moiety. The hCD25/IL-2Rα extracellular domain moiety was fused to the 1H3-hIgG1-L6-hIL-2 at the C-terminus of each heavy chain via an L6 linker followed by an L20 linker and hIL-2 cytokine moiety containing substitutions predicted to modulate binding to CD122/IL-2Rβ as described in Example 2 (attenuated hIL-2).

The disclosed modified hIL-2 proteins, human antibody molecules or antigen-binding fragments thereof, and immunoconjugates may be understood more readily by reference to the following detailed description taken in connection with the accompanying figures, which form a part of this disclosure. It is to be understood that the disclosed modified hIL-2 proteins, human antibody molecules or antigen-binding fragments thereof, and immunoconjugates are not limited to the specific modified hIL-2 proteins, human antibody molecules or antigen-binding fragments thereof, and immunoconjugates described and/or shown herein, and that the terminology used herein is for the purpose of describing particular embodiments by way of example only and is not intended to be limiting of the claimed modified hIL-2 proteins, human antibody molecules or antigen-binding fragments thereof, and immunoconjugates.

Unless specifically stated otherwise, any description as to a possible mechanism or mode of action or reason for improvement is meant to be illustrative only, and the disclosed modified hIL-2 proteins, human antibody molecules or antigen-binding fragments thereof, and immunoconjugates are not to be constrained by the correctness or incorrectness of any such suggested mechanism or mode of action or reason for improvement.

Throughout this text, the descriptions refer to modified hIL-2 proteins, human antibody molecules or antigen-binding fragments thereof, and immunoconjugates, as well as methods of using the modified hIL-2 proteins, human antibody molecules or antigen-binding fragments thereof, and immunoconjugates. Where the disclosure describes or claims a feature or embodiment associated with a modified hIL-2 protein, human antibody molecule or antigen-binding fragment thereof, and immunoconjugate, such a feature or embodiment is equally applicable to the methods of using the modified hIL-2 proteins, human antibody molecules or antigen-binding fragments thereof, and immunoconjugates. Likewise, where the disclosure describes or claims a feature or embodiment associated with a method of using a modified hIL-2 protein, human antibody molecule or antigen-binding fragment thereof, and immunoconjugate, such a feature or embodiment is equally applicable to the modified hIL-2 proteins, human antibody molecules or antigen-binding fragments thereof, and immunoconjugates.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the herein disclosure. Where a range of numerical values is stated herein as being less than a stated value, the range is nevertheless bounded on its lower end by a non-zero value. It is not intended that the scope of the modified hIL-2 proteins, human antibody molecules or antigen-binding fragments thereof, and immunoconjugates be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise. The term "about" when used in reference to numerical ranges, cutoffs, or specific values is used to indicate that the recited values may vary by up to as much as 10% from the listed value. Thus, the term "about" is used to encompass variations of +10% or less, variations of +5% or less, variations of +1% or less, variations of +0.5% or less, or variations of +0.1% or less from the specified value.

It is to be appreciated that certain features of the disclosed modified hIL-2 proteins, human antibody molecules or antigen-binding fragments thereof, and immunoconjugates which are, for clarity, described herein in the context of separate embodiments, may also be provided in combination in a single embodiment. Conversely, various features of the disclosed modified hIL-2 proteins, human antibody molecules or antigen-binding fragments thereof, and immunoconjugates that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

The term "antibody molecule" is meant in a broad sense and includes full length immunoglobulin molecules and antigen-binding fragments thereof.

Immunoglobulins can be assigned to five major classes, namely IgA, IgD, IgE, IgG, and IgM, depending on the heavy chain constant domain amino acid sequence. IgA and IgG are further sub-classified as the isotypes IgA1, IgA2, IgG1, IgG2, IgG3, and IgG4. Antibody light chains of any vertebrate species can be assigned to one of two clearly distinct types, namely kappa (κ) and lambda (2), based on the amino acid sequences of their constant domains.

"Antigen-binding fragment" refers to a portion of an immunoglobulin molecule that retains the antigen binding properties of the parental full length antibody (i.e., "antigen-binding fragment thereof"). Exemplary antigen binding fragments can have: heavy chain complementarity determining regions (CDR) 1, 2, and/or 3; light chain CDR1, 2, and/or 3; a heavy chain variable region (VH); a light chain variable region (VL); and combinations thereof. Antigen binding fragments include: a Fab fragment, a monovalent fragment consisting of the VL, VH, constant light (CL), and constant heavy 1 (CH1) domains; a F (ab) 2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; and a domain antibody (dAb) fragment (Ward et al., Nature 341:544-546, 1989), which consists of a VH domain or a VL domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody, described for example in Int'l Pat. Pub. Nos. WO1998/44001, WO1988/01649, WO1994/13804, and WO1992/01047. These antibody fragments are obtained using techniques well known to those of skill in the art, and the fragments are screened for utility in the same manner as are full length antibodies.

The phrase "immunospecifically binds" refers to the ability of the disclosed antibody molecules to preferentially bind to its target (hPD-1 in the case of anti-hPD-1 antibody molecules) without preferentially binding other molecules in a sample containing a mixed population of molecules. Antibody molecules that immunospecifically bind hPD-1 are substantially free of other antibodies having different antigenic specificities (e.g., an anti-hPD-1 antibody is substantially free of antibodies that specifically bind antigens other than hPD-1). Antibody molecules that immunospecifically bind hPD-1, however, can have cross-reactivity to other antigens, such as orthologs of hPD-1, including *Macaca fascicularis* (cynomolgus monkey) PD-1. The antibody molecules disclosed herein are able to immunospecifically bind both naturally-produced hPD-1 and to PD-1 which is recombinantly produced in mammalian or prokaryotic cells.

An antibody variable region consists of four "framework" regions interrupted by three "antigen binding sites." The antigen binding sites are defined using various terms: (i) Complementarity Determining Regions (CDRs), three in the VH (HCDR1, HCDR2, HCDR3), and three in the VL (LCDR1, LCDR2, LCDR3) are based on sequence variability (Wu and Kabat J Exp Med 132:211-50, 1970; Kabat et al., Sequences of Proteins of Immunological Interest, 5th Ed. Public Health Service, National Institutes of Health, Bethesda, Md., 1991); and (ii) "Hypervariable regions" ("HVR" or "HV"), three in the VH (H1, H2, H3) and three in the VL (L1, L2, L3) refer to the regions of the antibody variable domains which are hypervariable in structure as defined by Chothia and Lesk (Chothia and Lesk Mol Biol 196:901-17, 1987). The AbM definition of CDRs is also widely used; it is a compromise between Kabat and Chothia numbering schemes and is so-called because it was used by Oxford Molecular's AbM antibody modelling software (Rees, A. R., Searle, S. M. J., Henry, A. H. and Pedersen, J. T. (1996) In Sternberg M. J. E. (ed.), Protein Structure Prediction. Oxford University Press, Oxford, 141-172). Other terms include "IMGT-CDRs" (Lefranc et al., Dev Comparat Immunol 27:55-77, 2003) and "Specificity Determining Residue Usage" (SDRU) (Almagro Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Human antibody," "fully human antibody," and like terms refers to an antibody having heavy and light chain variable regions in which both the framework and the antigen binding sites are derived from sequences of human origin. If the antibody contains a constant region, the constant region also is derived from sequences of human origin. A human antibody comprises heavy and/or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice or chicken carrying human immunoglobulin loci as described herein. "Human antibody" may contain amino acid differences when compared to the human germline or rearranged immunoglobulin sequences due to, for example, naturally occurring somatic mutations or intentional introduction of substitutions in the variable domain (framework and antigen binding sites), or constant domain. Typically, a "human antibody" is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical in amino acid sequence to an amino acid sequence encoded by a human germline or rearranged immunoglobulin gene. In some cases, a "human antibody" may contain consensus framework sequences derived from human framework sequence analyses, for example as described in Knappik et al., J Mol Biol 296:57-86, 2000, or synthetic HCDR3 incorporated into human immunoglobulin gene libraries displayed on phage, as described in, for example, Shi et al., J Mol Biol 397:385-96, 2010 and Int'l Pat. Pub. No. WO2009/085462. Antibodies in which antigen binding sites are derived from a non-human species are not included in the definition of "human antibody."

Human antibodies, while derived from human immunoglobulin sequences, may be generated using systems such as phage display incorporating synthetic CDRs and/or synthetic frameworks, or can be subjected to in vitro mutagenesis to improve antibody properties in the variable regions or the constant regions or both, resulting in antibodies that do not naturally exist within the human antibody germline repertoire in vivo.

"Recombinant antibody" includes all antibodies that are prepared, expressed, created, or isolated by recombinant means, such as: antibodies isolated from an animal (e.g., a mouse) that is transgenic or transchromosomal for human immunoglobulin genes or a hybridoma prepared therefrom (described further below); antibodies isolated from a host cell transformed to express the antibody; antibodies isolated from a recombinant, combinatorial antibody library; and antibodies prepared, expressed, created, or isolated by any other means that involve splicing of human immunoglobulin gene sequences to other DNA sequences, or antibodies that are generated in vitro using Fab arm exchange.

"Monoclonal antibody" refers to a population of antibody molecules of a single molecular composition. A monoclonal antibody composition displays a single binding specificity and affinity for a particular epitope, or in a case of a bispecific monoclonal antibody, a dual binding specificity to two distinct epitopes. Monoclonal antibody therefore refers to an antibody population with single amino acid composition in each heavy and each light chain, except for possible well known alterations such as removal of C-terminal lysine from the antibody heavy chain. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" refers to a portion of an antigen to which an antibody specifically binds. Epitopes usually consist of chemically active (such as polar, non-polar, or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions, or deletions. The term "mutation" as used herein is intended to mean one or more intentional substitutions which are made to a polypeptide or polynucleotide.

"Treat," "treatment," and like terms refer to both therapeutic treatment and prophylactic or preventative measures, and includes reducing the severity and/or frequency of symptoms, eliminating symptoms and/or the underlying cause of the symptoms, reducing the frequency or likelihood of symptoms and/or their underlying cause, and improving or remediating damage caused, directly or indirectly, by the disease or disorder. Treatment also includes prolonging survival as compared to the expected survival of a subject not receiving treatment. Subjects to be treated include those that have the disease or disorder as well as those prone to have the disease or disorder or those in which the disease or disorder is to be prevented.

As used herein, "administering to the subject" and similar terms indicate a procedure by which the disclosed modified hIL-2 proteins, immunoconjugates, or pharmaceutical compositions are injected into a subject such that target cells, tissues, or segments of the body of the subject are contacted with the disclosed modified hIL-2 proteins or immunoconjugates comprising the same.

The phrase "therapeutically effective amount" refers to an amount of the modified hIL-2 proteins, immunoconjugates, or pharmaceutical compositions, as described herein, effective to achieve a particular biological or therapeutic result such as, but not limited to, biological or therapeutic results disclosed, described, or exemplified herein. The therapeutically effective amount may vary according to factors such as the disease state, age, sex, and weight of the individual, and the ability of the modified hIL-2 proteins, immunoconjugates, or pharmaceutical compositions to cause a desired response in a subject. Exemplary indicators of a therapeutically effect amount include, for example, improved well-being of the patient, reduction of a disease symptom, arrested or slowed progression of disease symptoms, and/or absence of disease symptoms.

The term "subject" as used herein is intended to mean any animal, in particular, mammals. Thus, the methods are applicable to human and nonhuman animals, although most preferably used with humans. "Subject" and "patient" are used interchangeably herein.

Immunoconjugate and fusion protein are used interchangeably herein.

Modified Human Interleukin-2 (hIL-2) Proteins

Disclosed herein are modified hIL-2 proteins comprising a substitution at amino acid position 20 and a substitution at amino acid position 38 relative to the non-modified hIL-2 amino acid sequence of SEQ ID NO: 345, wherein the modified hIL-2 protein exhibits reduced potency on both a high affinity hIL-2 receptor and on an intermediate affinity hIL-2 receptor relative to a non-modified hIL-2. The disclosed modified hIL-2 proteins are also referred to as "attenuated" hIL-2 herein.

Suitable substitutions at amino acid position 20 include, for example, any one of a D20A, D20S, D20Q, D20M, D20I, D20V, D20N, D20G, D20T, or D20E substitution.

Suitable substitutions at amino acid position 38 include, for example, any one of an R38E, R38N, R38G, R38H, R38I, R38L, R38M, R38F, R38P, R38S, R38T, R38W, R38Y, R38V, R38A, R38Q, R38D, or an R38K substitution.

In some embodiments, any one of the D20A, D20S, D20Q, D20M, D20I, D20V, D20N, D20G, D20T, or D20E substitutions can be combined with an R38E substitution.

The modified hIL-2 proteins can comprise the amino acid sequence of any one of SEQ ID NOs: 134-150, 307, 344, 607-611, 614, 617, or 620. The modified hIL-2 proteins can comprise the amino acid sequence of any one of SEQ ID NOs: 134-150, 307, 344, 608, 611, 614, or 620. In some embodiments, the modified hIL-2 proteins comprise the amino acid sequence of SEQ ID NO: 134. In some embodiments, the modified hIL-2 proteins comprise the amino acid sequence of SEQ ID NO: 135. In some embodiments, the modified hIL-2 proteins comprise the amino acid sequence of SEQ ID NO: 136. In some embodiments, the modified hIL-2 proteins comprise the amino acid sequence of SEQ ID NO: 137. In some embodiments, the modified hIL-2 proteins comprise the amino acid sequence of SEQ ID NO: 138. In some embodiments, the modified hIL-2 proteins comprise the amino acid sequence of SEQ ID NO: 139. In some embodiments, the modified hIL-2 proteins comprise the amino acid sequence of SEQ ID NO: 140. In some embodiments, the modified hIL-2 proteins comprise the amino acid sequence of SEQ ID NO: 141. In some embodiments, the modified hIL-2 proteins comprise the amino acid sequence of SEQ ID NO: 142. In some embodiments, the modified hIL-2 proteins comprise the amino acid sequence of SEQ ID NO: 143. In some embodiments, the modified hIL-2 proteins comprise the amino acid sequence of SEQ ID NO: 144. In some embodiments, the modified hIL-2 proteins comprise the amino acid sequence of SEQ ID NO: 145. In some embodiments, the modified hIL-2 proteins comprise the amino acid sequence of SEQ ID NO: 146. In some embodiments, the modified hIL-2 proteins comprise the amino acid sequence of SEQ ID NO: 147. In some embodiments, the modified hIL-2 proteins comprise the amino acid sequence of SEQ ID NO: 148. In some embodiments, the modified hIL-2 proteins comprise the amino acid sequence of SEQ ID NO: 149. In some embodiments, the modified hIL-2 proteins comprise the amino acid sequence of SEQ ID NO: 150. In some embodiments, the modified hIL-2 proteins comprise the amino acid sequence of SEQ ID NO: 307. In some embodiments, the modified hIL-2 proteins comprise the amino acid sequence of SEQ ID NO: 344. In some embodiments, the modified hIL-2 proteins comprise the amino acid sequence of SEQ ID NO: 607. In some embodiments, the modified hIL-2 proteins comprise the amino acid sequence of SEQ ID NO: 608. In some embodiments, the modified hIL-2 proteins comprise the amino acid sequence of SEQ ID NO: 609. In some embodiments, the modified hIL-2 proteins comprise the amino acid sequence of SEQ ID NO: 610. In some embodiments, the modified hIL-2 proteins comprise the amino acid sequence of SEQ ID NO: 611. In some embodiments, the modified hIL-2 proteins comprise the amino acid sequence of SEQ ID NO: 614. In some embodiments, the modified hIL-2 proteins comprise the amino acid sequence of SEQ ID NO: 617. In some embodiments, the modified hIL-2 proteins comprise the amino acid sequence of SEQ ID NO: 620. The modified hIL-2 protein of any one of amino acid sequences SEQ ID NOs: 134-150, 307, 344, 607-611, 614, 617, or 620 can further comprise a T3A substitution and/or a C125A substitution. In some embodiments, the modified hIL-2 protein of any one of amino acid sequences SEQ ID NOs: 134-150, 307, 344, 607-611, 614, 617, or 620 further comprises a T3A substitution. In some embodiments, the modified hIL-2 protein of any one of amino acid sequences SEQ ID NOs: 134-150, 307, 344, 607-611, 614, 617, or 620 further comprises a C125A substitution. In some embodiments, the modified hIL-2 protein of any one of amino acid sequences SEQ ID NOs: 134-150, 307, 344, 607-611, 614, 617, or 620 further comprises a T3A substitution and a C125A substitution.

The modified hIL-2 proteins may comprise a D20A substitution and a R38E substitution.

As described herein the term "reduced potency" and related terms such as "reduction in potency" or "attenuation" of IL-2 activity refer to a reduction in potency of the modified hIL-2 as determined by an increased $EC_{50}$ value relative to the $EC_{50}$ value for an non-modified-hIL-2 in an IL-2-dependent assay. As described herein the reduction in potency of the modified hIL-2 will be on both the high affinity and on the intermediate affinity IL-2 receptors. The IL-2-dependent assay for determining potency may be an engineered human erythroleukemic TF1 (TF1+IL-2RB) or a human natural killer NK-92 cell proliferation assay as described herein. In one embodiment, the IL-2-dependent assay for determining potency is an engineered human erythroleukemic TF1 (TF1+IL-2RB) cell proliferation assay. In another embodiment, the IL-2-dependent assay for determining potency is a human natural killer NK-92 cell proliferation assay. Other IL-2-dependent assays for determining potency may also be a TF1+IL-2Rβ or a human natural killer NK-92 pSTAT5 assay as described herein. The non-modified-hIL-2 may be a prokaryote-expressed hIL-2 such as Proleukin® (which has the native human IL-2 amino acid sequence apart from a C125S substitution to remove an unbound cysteine, and which does not bear the normal human carbohydrate expression on residue T3), or the non-modified-hIL-2 may be an hIL-2 with the amino acid sequence of SEQ ID NO: 345 or with the amino acid sequence of SEQ ID NO: 345 with a C125S substitution, which is expressed in a mammalian cell line, such as a CHO or HEK cell line.

The modified hIL-2 proteins can further comprise a substitution at amino acid position 3 relative to the non-modified hIL-2 amino acid sequence of SEQ ID NO: 345. A suitable substitution includes, for example, a T3A. In some embodiments, the modified hIL-2 proteins comprise a T3A substitution, a D20A substitution, and a R38E substitution. In some aspects, the modified hIL-2 proteins comprise the amino acid sequence of SEQ ID NO: 216.

Alternatively, the modified hIL-2 proteins can further comprise a deletion of amino acid position 3 relative to the non-modified hIL-2 amino acid sequence of SEQ ID NO: 345. In some embodiments, the modified hIL-2 proteins comprise a deletion of amino acids 1-3, a D20A substitution, and a R38E substitution. In some aspects, the modified hIL-2 proteins comprise the amino acid sequence of SEQ ID NO: 218.

The modified hIL-2 proteins can further comprise a deletion or substitution at amino acid position 125 relative to the non-modified hIL-2 amino acid sequence of SEQ ID NO: 345. The substitution at amino acid position 125 can be C125A. In some embodiments, the modified hIL-2 proteins comprise a D20A substitution, a R38E substitution, and a C125A substitution. In some embodiments, the modified hIL-2 proteins comprise the amino acid sequence of SEQ ID NO: 215. In some embodiments, the modified hIL-2 proteins comprise a T3A substitution, a D20A substitution, a R38E substitution, and a C125A substitution. In some embodiments, the modified hIL-2 proteins comprise the amino acid sequence of SEQ ID NO: 217. In some embodiments, the modified hIL-2 proteins comprise a deletion of amino acids 1-3, a D20A substitution, a R38E substitution, and a C125A substitution. In some embodiments, the modified hIL-2 proteins comprise the amino acid sequence of SEQ ID NO: 219.

The modified hIL-2 proteins can exhibit a reduction in potency of at least about 200-fold, at least about 500-fold, at least about 1,000-fold, at least about 2,000-fold, at least about 5,000-fold, at least about 6,500-fold, or at least about 10,000-fold on the high affinity IL-2 receptor (hIL-2Rαβγ) relative to a non-modified hIL-2, for example as quantified by a comparison in $EC_{50}$ values in an hIL-2-dependent cell proliferation assay described herein. In some embodiments, the modified hIL-2 proteins can exhibit a reduction in potency of greater than about 10,000-fold on the high affinity IL-2 receptor (hIL-2Rαβγ) relative to a non-modified hIL-2. A greater reduction in hIL-2 potency on the high affinity hIL-2 receptor may be possible and acceptable for the modified hIL-2 proteins described herein, but such a reduction may not be quantifiable with the methods described herein due to limits of the cell proliferation assay conditions.

In addition, the modified hIL-2 proteins can exhibit a reduction in potency of at least about 200-fold, at least about 500-fold, at least about 1,000-fold, at least about 2,000-fold, at least about 5,000-fold, at least about 6,500-fold, or at least about 10,000-fold on the intermediate affinity IL-2 receptor (hIL-2Rβγ) relative to an non-modified hIL-2, for example as quantified by a comparison in $EC_{50}$ values in an hIL-2-dependent cell proliferation assay described herein. In some embodiments, the modified hIL-2 proteins can exhibit a reduction in potency of greater than about 10,000-fold on the intermediate affinity IL-2 receptor (hIL-2Rβγ) relative to a non-modified hIL-2.

The modified hIL-2 proteins can exhibit a reduction in potency of up to about 10,000-fold on the high affinity IL-2 receptor (hIL-2Rαβγ) and a reduction in potency of up to about 10,000-fold on the intermediate affinity IL-2 receptor (hIL-2Rβγ) relative to a non-modified hIL-2, for example as quantified by a comparison in $EC_{50}$ values in an hIL-2-dependent cell proliferation assay described herein. The modified hIL-2 proteins can exhibit a reduction in potency of greater than about 10,000-fold on the high affinity IL-2 receptor (hIL-2Rαβγ) and a reduction in potency of greater than about 10,000-fold on the intermediate affinity IL-2 receptor (hIL-2Rβγ) relative to a non-modified hIL-2

As demonstrated herein, the modified hIL-2 proteins can be fused to an anti-PD-1 antibody or an antigen-binding fragment thereof. The hIL-2 proteins can fused to the anti-PD-1 antibody or an antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment. In some embodiments, the modified hIL-2 protein is directly fused by a peptide bond to the anti-PD-1 antibody or an antigen-binding fragment thereof. The modified hIL-2 proteins can be, for example, directly fused by a peptide bond to the C-terminal amino acid residue of the anti-PD-1 antibody heavy chain. In some embodiments, the modified hIL-2 protein is fused to the anti-PD-1 antibody or an antigen-binding fragment thereof through a linker.

Fusion of the modified hIL-2 proteins to the antibody or antigen-binding fragments thereof can rescue the modified hIL-2 proteins' ability to bind to and activate the human intermediate affinity IL-2 receptor on PD-1-expressing cells such as T cells and in particular tumor-infiltrating lymphocytes. In some embodiments, the hIL-2 protein that is fused to the antibody or an antigen-binding fragment thereof exhibits potency on the intermediate affinity IL-2 receptor on PD-1-expressing cells that is comparable to the potency of wild type hIL-2 on the intermediate affinity IL-2 receptor.

Fusion of the modified hIL-2 protein to an antibody or antigen-binding fragment thereof can be used to selectively deliver IL-2 signaling to cells expressing the PD-1 target of the antibody or antigen-binding fragment thereof. Without being bound by theory, it is believed that targeting the modified hIL-2 protein to specific cell populations can dramatically amplify the therapeutic effects of the IL-2 (e.g., anti-tumor immunity) without off-target systemic toxicities.

Also disclosed herein are modified human interleukin-2 (hIL-2) proteins comprising a D20A, D20S, D20Q, D20M, D20I, D20V, D20N, D20G, D20T, or D20E substitution at amino acid position 20 and a R38E substitution at amino acid position 38 relative to the non-modified hIL-2 amino acid sequence of SEQ ID NO: 345.

The modified hIL-2 proteins can comprise the amino acid sequence of any one of SEQ ID NOs: 307, 607-611, 614, 617, or 620. In some embodiments, the modified hIL-2 proteins comprise the amino acid sequence of SEQ ID NO: 307. In some embodiments, the modified hIL-2 proteins comprise the amino acid sequence of SEQ ID NO: 607. In some embodiments, the modified hIL-2 proteins comprise the amino acid sequence of SEQ ID NO: 608. In some embodiments, the modified hIL-2 proteins comprise the amino acid sequence of SEQ ID NO: 609. In some embodiments, the modified hIL-2 proteins comprise the amino acid sequence of SEQ ID NO: 610. In some embodiments, the modified hIL-2 proteins comprise the amino acid sequence of SEQ ID NO: 611. In some embodiments, the modified hIL-2 proteins comprise the amino acid sequence of SEQ ID NO: 614. In some embodiments, the modified hIL-2 proteins comprise the amino acid sequence of SEQ ID NO: 617. In some embodiments, the modified hIL-2 proteins comprise the amino acid sequence of SEQ ID NO: 620. The modified hIL-2 protein of any one of amino acid sequences SEQ ID NOs: 307, 607-611, 614, 617, or 620 can further comprise a T3A substitution and/or a C125A substitution. In some embodiments, the modified hIL-2 protein of any one of amino acid sequences SEQ ID NOs: 307, 607-611, 614, 617, or 620 further comprises a T3A substitution. In some embodiments, the modified hIL-2 protein of any one of amino acid sequences SEQ ID NOs: 307, 607-611, 614, 617, or 620 further comprises a C125A substitution. In some embodiments, the modified hIL-2 protein of any one of amino acid sequences SEQ ID NOs: 307, 607-611, 614, 617, or 620 further comprises a T3A substitution and a C125A substitution.

The modified hIL-2 proteins may comprise a D20A substitution and a R38E substitution. In some embodiments, the modified hIL-2 proteins comprise the amino acid sequence of SEQ ID NO: 149.

The modified hIL-2 proteins can further comprise a substitution at amino acid position 3 relative to the non-modified hIL-2 amino acid sequence of SEQ ID NO: 345. A suitable substitution includes, for example, a T3A. In some embodiments, the modified hIL-2 proteins comprise a T3A substitution, a D20A substitution, and a R38E substitution. In some aspects, the modified hIL-2 proteins comprise the amino acid sequence of SEQ ID NO: 216.

Alternatively, the modified hIL-2 proteins can further comprise a deletion of amino acid position 3 relative to the non-modified hIL-2 amino acid sequence of SEQ ID NO: 345. In some embodiments, the modified hIL-2 proteins comprise a deletion of amino acids 1-3, a D20A substitution, and a R38E substitution. In some aspects, the modified hIL-2 proteins comprise the amino acid sequence of SEQ ID NO: 218.

The modified hIL-2 proteins can further comprise a deletion or substitution at amino acid position 125 relative to the non-modified hIL-2 amino acid sequence of SEQ ID NO: 345. The substitution at amino acid position 125 can be C125A. In some embodiments, the modified hIL-2 proteins comprise a D20A substitution, a R38E substitution, and a C125A substitution. In some embodiments, the modified hIL-2 proteins comprise the amino acid sequence of SEQ ID NO: 215. In some embodiments, the modified hIL-2 proteins comprise a T3A substitution, a D20A substitution, a R38E substitution, and a C125A substitution. In some embodiments, the modified hIL-2 proteins comprise the amino acid sequence of SEQ ID NO: 217. In some embodiments, the modified hIL-2 proteins comprise a deletion of amino acids 1-3, a D20A substitution, a R38E substitution, and a C125A substitution. In some embodiments, the modified hIL-2 proteins comprise the amino acid sequence of SEQ ID NO: 219.

The modified hIL-2 proteins can exhibit a reduction in potency of at least about 200-fold, at least about 500-fold, at least about 1,000-fold, at least about 2,000-fold, at least about 5,000-fold, at least about 6,500-fold, or at least about 10,000-fold on the high affinity IL-2 receptor (hIL-2Rαβγ) relative to a non-modified hIL-2, for example as quantified by a comparison in $EC_{50}$ values in an hIL-2-dependent cell proliferation assay described herein. In some embodiments, the modified hIL-2 proteins can exhibit a reduction in potency of greater than about 10,000-fold on the high affinity IL-2 receptor (hIL-2Rαβγ) relative to a non-modified hIL-2. A greater reduction in hIL-2 potency on the high affinity hIL-2 receptor may be possible and acceptable for the modified hIL-2 proteins described herein, but such a reduction may not be quantifiable with the methods described herein due to limits of the cell proliferation assay conditions.

In addition, the modified hIL-2 proteins can exhibit a reduction in potency of at least about 200-fold, at least about 500-fold, at least about 1,000-fold, at least about 2,000-fold, at least about 5,000-fold, at least about 6,500-fold, or at least about 10,000-fold on the intermediate affinity IL-2 receptor (hIL-2Rβγ) relative to an non-modified hIL-2, for example as quantified by a comparison in $EC_{50}$ values in an hIL-2-dependent cell proliferation assay described herein. In some embodiments, the modified hIL-2 proteins can exhibit a reduction in potency of greater than about 10,000-fold on the intermediate affinity IL-2 receptor (hIL-2Rβγ) relative to a non-modified hIL-2.

The modified hIL-2 proteins can exhibit a reduction in potency of up to about 10,000-fold on the high affinity IL-2 receptor (hIL-2Rβγ) and a reduction in potency of up to about 10,000-fold on the intermediate affinity IL-2 receptor (hIL-2Rβγ) relative to a non-modified hIL-2, for example as quantified by a comparison in $EC_{50}$ values in an hIL-2-dependent cell proliferation assay described herein. The modified hIL-2 proteins can exhibit a reduction in potency of greater than about 10,000-fold on the high affinity IL-2 receptor (hIL-2Rαβγ) and a reduction in potency of greater than about 10,000-fold on the intermediate affinity IL-2 receptor (hIL-2Rβγ) relative to a non-modified hIL-2.

As demonstrated herein, the modified hIL-2 proteins can be fused to an anti-PD-1 antibody or an antigen-binding fragment thereof. The hIL-2 proteins can fused to the anti-PD-1 antibody or an antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment. In some embodiments, the modified hIL-2 protein is directly fused by a peptide bond to the anti-PD-1 antibody or an antigen-binding fragment thereof. The modified hIL-2 proteins can be, for example, directly fused by a peptide bond to the C-terminal amino acid residue of the anti-PD-1 antibody heavy chain. In some embodiments, the modified hIL-2 protein is fused to the anti-PD-1 antibody or an antigen-binding fragment thereof through a linker.

Fusion of the modified hIL-2 proteins to the antibody or antigen-binding fragments thereof can rescue the modified hIL-2 proteins' ability to bind to and activate the human intermediate affinity IL-2 receptor on PD-1-expressing cells such as T cells and in particular tumor-infiltrating lymphocytes. In some embodiments, the hIL-2 protein that is fused to the antibody or an antigen-binding fragment thereof exhibits potency on the intermediate affinity IL-2 receptor on PD-1-expressing cells that is comparable to the potency of wild type hIL-2 on the intermediate affinity IL-2 receptor.

Fusion of the modified hIL-2 protein to an antibody or antigen-binding fragment thereof can be used to selectively deliver IL-2 signaling to cells expressing the PD-1 target of the antibody or antigen-binding fragment thereof. Without being bound by theory, it is believed that targeting the modified hIL-2 protein to specific cell populations can dramatically amplify the therapeutic effects of the IL-2 (e.g., anti-tumor immunity) without off-target systemic toxicities.
Human Anti-Human Programmed Cell Death Protein-1 (hPD-1) Antibodies Disclosed herein are human antibody molecules, or antigen-binding fragments thereof, that immunospecifically bind to hPD-1, wherein the human antibody molecule or antigen-binding fragment thereof comprises:
  a) a heavy chain complementarity determining region 1 (CDR1) comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423;
  b) a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391;
  c) a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401; or
  d) a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

In some embodiments, the human antibody molecules, or antigen-binding fragments thereof, comprise a heavy chain CDR1 comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423 (referred to herein as "H7-632").

In some embodiments, the human antibody molecules, or antigen-binding fragments thereof, comprise a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391 (referred to herein as "2H7").

In some embodiments, the human antibody molecules, or antigen-binding fragments thereof, comprise a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401 (referred to herein as "C51E6-5").

In some embodiments, the human antibody molecules, or antigen-binding fragments thereof, comprise a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411 (referred to herein as "A2").

The disclosed human antibody molecules or antigen-binding fragments thereof, can exhibit one or more of the following activities:
  Bind to PD-1 without inhibiting PD-L1 binding to PD-1;
  Bind to PD-1 in the presence of standard-of-care anti-PD-1 antibodies used in the clinic (e.g., KEYTRUDAX and OPDIVOX);
  Be highly selective for PD-1 and do not immunospecifically bind other related B7 family members; and
  Bind to PD-1 on activated human T cells ($EC_{50}$~0.1-0.2 nM in a flow cytometry binding assay).

The human antibody molecules, or antigen-binding fragments thereof, can comprise a heavy chain variable region comprising the amino acid sequence of SEQ ID NO: 416 and a light chain variable region comprising the amino acid sequence of SEQ ID NO: 417 (referred to herein as "H7-632").

The human antibody molecules, or antigen-binding fragments thereof, can comprise a heavy chain variable region comprising the amino acid sequence of SEQ ID NO: 384 and a light chain variable region comprising the amino acid sequence of SEQ ID NO: 385 (referred to herein as "2H7").

The human antibody molecules, or antigen-binding fragments thereof, can comprise a heavy chain variable region comprising the amino acid sequence of SEQ ID NO: 394 and a light chain variable region comprising the amino acid sequence of SEQ ID NO: 395 (referred to herein as "C51E6-5").

The human antibody molecules, or antigen-binding fragments thereof, can comprise a heavy chain variable region comprising the amino acid sequence of SEQ ID NO: 404 and a light chain variable region comprising the amino acid sequence of SEQ ID NO: 405 (referred to herein as "A2").

The human antibody molecules, or antigen-binding fragments thereof, can comprise a human IgG1 heavy chain constant region.

The human antibody molecules, or antigen binding fragments thereof, can have substitutions or deletions within the constant region to minimize Fc-mediated immune effector function, such as FcγRIIIA-mediated antibody-dependent cell-mediated cytotoxicity (ADCC), FcγRI- and FcγRIIa-dependent antibody-dependent cellular phagocytosis (ADCP), and C1q binding-mediated complement-dependent cytotoxicity (CDC). In some embodiments, the human antibody molecules comprise a L235A substitution, wherein the amino acid numbering is according to EU numbering. In some embodiments, the human antibody molecules comprise a G237A substitution, wherein the amino acid numbering is according to EU numbering. In some embodiments, the human antibody molecules comprise an L235A and a G237A substitution, wherein the amino acid numbering is according to EU numbering.

The human antibody molecules, or antigen-binding fragments thereof, can comprise a heavy chain comprising the amino acid sequence of SEQ ID NO: 414 and a light chain comprising the amino acid sequence of SEQ ID NO: 415 (referred to herein as "H7-632-hIgG1-LAGA").

The human antibody molecules, or antigen-binding fragments thereof, can comprise a heavy chain comprising the amino acid sequence of SEQ ID NO: 424 and a light chain comprising the amino acid sequence of SEQ ID NO: 425 (referred to herein as "2H7-hIgG4").

The human antibody molecules, or antigen-binding fragments thereof, can comprise a heavy chain comprising the amino acid sequence of SEQ ID NO: 426 and a light chain comprising the amino acid sequence of SEQ ID NO: 427 (referred to herein as "C51E6-5-hIgG4").

The human antibody molecules, or antigen-binding fragments thereof, can comprise a heavy chain comprising the amino acid sequence of SEQ ID NO: 428 and a light chain comprising the amino acid sequence of SEQ ID NO: 429 (referred to herein as "A2-hIgG4").

The human antibody molecules, or antigen-binding fragments thereof, can be fused to a modified hIL-2 protein comprising a substitution at amino acid position 20 and a substitution at amino acid position 38 relative to the non-modified hIL-2 amino acid sequence of SEQ ID NO: 345. The human antibody molecule, or antigen-binding fragments thereof, can be fused to any of the herein disclosed modified hIL-2 proteins.

When not fused to the antibody molecule or antigen-binding fragment thereof, the modified hIL-2 protein can exhibit reduced potency on both a high affinity hIL-2 receptor and on an intermediate affinity hIL-2 receptor relative to a non-modified hIL-2.

Suitable substitutions at amino acid position 20 of the modified hIL-2 include, for example, any one of a D20A, D20S, D20Q, D20M, D20I, D20V, D20N, D20G, D20T, or D20E substitution.

Suitable substitutions at amino acid position 38 of the modified hIL-2 protein include, for example, any one of an R38E, R38N, R38G, R38H, R38I, R38L, R38M, R38F, R38P, R38S, R38T, R38W, R38Y, R38V, R38A, R38Q, R38D, or a R38K substitution.

In some embodiments, any one of the D20A, D20S, D20Q, D20M, D20I, D20V, D20N, D20G, D20T, or D20E substitutions can be combined with an R38E substitution.

The modified hIL-2 proteins can comprise the amino acid sequence of any one of SEQ ID NOs: 134-150, 307, 344, 607-611, 614, 617, or 620. The modified hIL-2 proteins can comprise the amino acid sequence of any one of SEQ ID NOs: 134-150, 307, 344, 608, 611, 614, or 620. In some embodiments, the modified hIL-2 protein comprises the amino acid sequence of SEQ ID NO: 134. In some embodiments, the modified hIL-2 protein comprises the amino acid sequence of SEQ ID NO: 135. In some embodiments, the modified hIL-2 protein comprises the amino acid sequence of SEQ ID NO: 136. In some embodiments, the modified hIL-2 protein comprises the amino acid sequence of SEQ ID NO: 137. In some embodiments, the modified hIL-2 protein comprises the amino acid sequence of SEQ ID NO: 138. In some embodiments, the modified hIL-2 protein comprises the amino acid sequence of SEQ ID NO: 139. In some embodiments, the modified hIL-2 protein comprises the amino acid sequence of SEQ ID NO: 140. In some embodiments, the modified hIL-2 protein comprises the amino acid sequence of SEQ ID NO: 141. In some embodiments, the modified hIL-2 protein comprises the amino acid sequence of SEQ ID NO: 142. In some embodiments, the modified hIL-2 protein comprises the amino acid sequence of SEQ ID NO: 143. In some embodiments, the modified hIL-2 protein comprises the amino acid sequence of SEQ ID NO: 144. In some embodiments, the modified hIL-2 protein comprises the amino acid sequence of SEQ ID NO: 145. In some embodiments, the modified hIL-2 protein comprises the amino acid sequence of SEQ ID NO: 146. In some embodiments, the modified hIL-2 protein comprises the amino acid sequence of SEQ ID NO: 147. In some embodiments, the modified hIL-2 protein comprises the amino acid sequence of SEQ ID NO: 148. In some embodiments, the modified hIL-2 protein comprises the amino acid sequence of SEQ ID NO: 149. In some embodiments, the modified hIL-2 protein comprises the amino acid sequence of SEQ ID NO: 150. In some embodiments, the modified hIL-2 protein comprises the amino acid sequence of SEQ ID NO: 307. In some embodiments, the modified hIL-2 protein comprises the amino acid sequence of SEQ ID NO: 344. In some embodiments, the modified hIL-2 protein comprises the amino acid sequence of SEQ ID NO: 607. In some embodiments, the modified hIL-2 protein comprises the amino acid sequence of SEQ ID NO: 608. In some embodiments, the modified hIL-2 protein comprises the amino acid sequence of SEQ ID NO: 609. In some embodiments, the modified hIL-2 protein comprises the amino acid sequence of SEQ ID NO: 610. In some embodiments, the modified hIL-2 protein comprises the amino acid sequence of SEQ ID NO: 611. In some embodiments, the modified hIL-2 protein comprises the amino acid sequence of SEQ ID NO: 614. In some embodiments, the modified hIL-2 protein comprises the amino acid sequence of SEQ ID NO: 617. In some embodiments, the modified hIL-2 protein comprises the amino acid sequence of SEQ ID NO: 620. The modified hIL-2 protein of any one of amino acid sequences SEQ ID NOs: 134-150, 307, 344, 607-611, 614, 617, or 620 can further comprise a T3A substitution and/or a C125A substitution. In some embodiments, the modified hIL-2 protein of any one of amino acid sequences SEQ ID NOs: 134-150, 307, 344, 607-611, 614, 617, or 620 further comprises a T3A substitution. In some embodiments, the modified hIL-2 protein of any one of amino acid sequences SEQ ID NOs: 134-150, 307, 344, 607-611, 614, 617, or 620 further comprises a C125A substitution. In some embodiments, the modified hIL-2 protein of any one of amino acid sequences SEQ ID NOs:

134-150, 307, 344, 607-611, 614, 617, or 620 further comprises a T3A substitution and a C125A substitution.

The modified hIL-2 protein can comprise a D20A substitution and a R38E substitution.

The modified hIL-2 protein can further comprise a substitution at amino acid position 3 relative to the non-modified hIL-2 amino acid sequence of SEQ ID NO: 345. A suitable substitution includes, for example, a T3A. In some embodiments, the modified hIL-2 protein comprises a T3A substitution, a D20A substitution, and a R38E substitution. In some aspects, the modified hIL-2 protein comprises the amino acid sequence of SEQ ID NO: 216.

Alternatively, the modified hIL-2 protein can further comprise a deletion of amino acid position 3 relative to the non-modified hIL-2 amino acid sequence of SEQ ID NO: 345. In some embodiments, the modified hIL-2 protein comprises a deletion of amino acids 1-3, a D20A substitution, and a R38E substitution. In some aspects, the modified hIL-2 protein comprises the amino acid sequence of SEQ ID NO: 218.

The modified hIL-2 protein can further comprise a deletion or substitution at amino acid position 125 relative to the non-modified hIL-2 amino acid sequence of SEQ ID NO: 345. The substitution at amino acid position 125 can be C125A. In some embodiments, the modified hIL-2 protein comprises a D20A substitution, a R38E substitution, and a C125A substitution. In some embodiments, the modified hIL-2 protein comprises the amino acid sequence of SEQ ID NO: 215. In some embodiments, the modified hIL-2 protein comprises a T3A substitution, a D20A substitution, a R38E substitution, and a C125A substitution. In some embodiments, the modified hIL-2 protein comprises the amino acid sequence of SEQ ID NO: 217. In some embodiments, the modified hIL-2 protein comprises a deletion of amino acids 1-3, a D20A substitution, a R38E substitution, and a C125A substitution. In some embodiments, the modified hIL-2 protein comprises the amino acid sequence of SEQ ID NO: 219.

When not fused to the human antibody molecules or antigen-binding fragments thereof, the modified hIL-2 proteins can exhibit a reduction in potency of at least about 200-fold, at least about 500-fold, at least about 1,000-fold, at least about 2,000-fold, at least about 5,000-fold, at least about 6,500-fold, or at least about 10,000-fold on the high affinity IL-2 receptor (hIL-2Rαβγ) relative to a non-modified hIL-2, for example as quantified by a comparison in $EC_{50}$ values in an hIL-2-dependent cell proliferation assay described herein. In some embodiments, when not fused to the human antibody molecules or antigen-binding fragments thereof, the modified hIL-2 proteins can exhibit a reduction in potency of greater than about 10,000-fold on the high affinity IL-2 receptor (hIL-2Rαβγ) relative to a non-modified hIL-2. A greater reduction in hIL-2 potency on the high affinity hIL-2 receptor may be possible and acceptable for the modified hIL-2 proteins described herein, but such a reduction may not be quantifiable with the methods described herein due to limits of the cell proliferation assay conditions.

In addition, when not fused to the human antibody molecules or antigen-binding fragments thereof, the modified hIL-2 proteins can exhibit a reduction in potency of at least about 200-fold, at least about 500-fold, at least about 1,000-fold, at least about 2,000-fold, at least about 5,000-fold, at least about 6,500-fold, or at least about 10,000-fold on the intermediate affinity IL-2 receptor (hIL-2Rβγ) relative to an non-modified hIL-2, for example as quantified by a comparison in $EC_{50}$ values in an hIL-2-dependent cell proliferation assay described herein. In some embodiments, when not fused to the human antibody molecules or antigen-binding fragments thereof, the modified hIL-2 proteins can exhibit a reduction in potency of greater than about 10,000-fold on the intermediate affinity IL-2 receptor (hIL-2Rβγ) relative to an non-modified hIL-2.

When not fused to the human antibody molecules or antigen-binding fragments thereof, the modified hIL-2 proteins can exhibit a reduction in potency of up to about 10,000-fold on the high affinity IL-2 receptor (hIL-2Rαβγ) and a reduction in potency of up to about 10,000-fold on the intermediate affinity IL-2 receptor (hIL-2Rβγ) relative to a non-modified hIL-2, for example as quantified by a comparison in $EC_{50}$ values in an hIL-2-dependent cell proliferation assay described herein. When not fused to the human antibody molecules or antigen-binding fragments thereof, the modified hIL-2 proteins can exhibit a reduction in potency of greater than about 10,000-fold on the high affinity IL-2 receptor (hIL-2Rαβγ) and a reduction in potency of greater than about 10,000-fold on the intermediate affinity IL-2 receptor (hIL-2Rβγ) relative to a non-modified hIL-2.

Fusion of the modified hIL-2 proteins to the antibody or antigen-binding fragments thereof can rescue the modified hIL-2 proteins' ability to bind to and activate the human intermediate affinity IL-2 receptor on PD-1-expressing cells such as T cells and in particular tumor-infiltrating lymphocytes. In some embodiments, the hIL-2 protein that is fused to the antibody or an antigen-binding fragment thereof exhibits potency on the intermediate affinity IL-2 receptor on PD-1-expressing cells that is comparable to the potency of wild type hIL-2 on the intermediate affinity IL-2 receptor The modified hIL-2 proteins can be fused to the human antibody molecules or antigen-binding fragments thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment. In some embodiments, the hIL-2 protein is directly fused by a peptide bond to the antibody or an antigen-binding fragment thereof. The hIL-2 can be, for example, directly fused by a peptide bond to the C-terminal amino acid residue of the antibody heavy chain. In some embodiments, the hIL-2 protein is fused to the antibody or an antigen-binding fragment thereof through a linker.

Fusion of the human antibody molecules or antigen-binding fragments thereof to the modified hIL-2 proteins can be used to selectively deliver IL-2 signaling to cells expressing PD-1. Without being bound by theory, it is believed that targeting the modified hIL-2 protein to specific cell populations expressing PD-1 can dramatically amplify the therapeutic effects of the IL-2 (e.g., anti-tumor immunity) while reducing or minimizing off-target systemic toxicities.

Immunoconjugates

Disclosed herein are immunoconjugates comprising any of the herein disclosed modified hIL-2 proteins and any of the herein disclosed human antibody molecules, or antigen-binding fragments thereof. The immunoconjugates can comprise:

(a) a modified hIL-2 protein comprising a substitution at amino acid position 20 and a substitution at amino acid position 38 relative to the non-modified hIL-2 amino acid sequence of SEQ ID NO: 345; and (b) a human antibody molecule, or antigen-binding fragment thereof, that immunospecifically binds to hPD-1, wherein the human antibody molecule or antigen-binding fragment thereof comprises:
  (i) a heavy chain CDR1 comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423;
  (ii) a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391;
  (iii) a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401; or
  (iv) a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

Suitable substitutions at amino acid position 20 of the modified hIL-2 portion of the immunoconjugates include, for example, any of a D20A, D20S, D20Q, D20M, D20I, D20V, D20N, D20G, D20T, or D20E substitution.

Suitable substitutions at amino acid position 38 of the modified hIL-2 portion of the immunoconjugates include, for example, any of an R38E, R38N, R38G, R38H, R38I, R38L, R38M, R38F, R38P, R38S, R38T, R38W, R38Y, R38V, R38A, R38Q, R38D, or a R38K substitution.

In some embodiments, any one of the D20A, D20S, D20Q, D20M, D20I, D20V, D20N, D20G, D20T, or D20E substitutions can be combined with an R38E substitution.

The modified hIL-2 protein portion of the immunoconjugates can comprise the amino acid sequence of any one of SEQ ID NOs: 134-150, 307, 344, 607-611, 614, 617, or 620. The modified hIL-2 protein portion of the immunoconjugates can comprise the amino acid sequence of any one of SEQ ID NOs: 134-150, 307, 344, 608, 611, 614, or 620. In some embodiments, the modified hIL-2 proteins comprise the amino acid sequence of SEQ ID NO: 134. In some embodiments, the modified hIL-2 proteins comprise the amino acid sequence of SEQ ID NO: 135. In some embodiments, the modified hIL-2 proteins comprise the amino acid sequence of SEQ ID NO: 136. In some embodiments, the modified hIL-2 proteins comprise the amino acid sequence of SEQ ID NO: 137. In some embodiments, the modified hIL-2 proteins comprise the amino acid sequence of SEQ ID NO: 138. In some embodiments, the modified hIL-2 proteins comprise the amino acid sequence of SEQ ID NO: 139. In some embodiments, the modified hIL-2 proteins comprise the amino acid sequence of SEQ ID NO: 140. In some embodiments, the modified hIL-2 proteins comprise the amino acid sequence of SEQ ID NO: 141. In some embodiments, the modified hIL-2 proteins comprise the amino acid sequence of SEQ ID NO: 142. In some embodiments, the modified hIL-2 proteins comprise the amino acid sequence of SEQ ID NO: 143. In some embodiments, the modified hIL-2 proteins comprise the amino acid sequence of SEQ ID NO: 144. In some embodiments, the modified hIL-2 proteins comprise the amino acid sequence of SEQ ID NO: 145. In some embodiments, the modified hIL-2 proteins comprise the amino acid sequence of SEQ ID NO: 146. In some embodiments, the modified hIL-2 proteins comprise the amino acid sequence of SEQ ID NO: 147. In some embodiments, the modified hIL-2 proteins comprise the amino acid sequence of SEQ ID NO: 148. In some embodiments, the modified hIL-2 proteins comprise the amino acid sequence of SEQ ID NO: 149. In some embodiments, the modified hIL-2 proteins comprise the amino acid sequence of SEQ ID NO: 150. In some embodiments, the modified hIL-2 proteins comprise the amino acid sequence of SEQ ID NO: 307. In some embodiments, the modified hIL-2 proteins comprise the amino acid sequence of SEQ ID NO: 344. In some embodiments, the modified hIL-2 proteins comprise the amino acid sequence of SEQ ID NO: 607. In some embodiments, the modified hIL-2 proteins comprise the amino acid sequence of SEQ ID NO: 608. In some embodiments, the modified hIL-2 proteins comprise the amino acid sequence of SEQ ID NO: 609. In some embodiments, the modified hIL-2 proteins comprise the amino acid sequence of SEQ ID NO: 610. In some embodiments, the modified hIL-2 proteins comprise the amino acid sequence of SEQ ID NO: 611. In some embodiments, the modified hIL-2 proteins comprise the amino acid sequence of SEQ ID NO: 614. In some embodiments, the modified hIL-2 proteins comprise the amino acid sequence of SEQ ID NO: 617. In some embodiments, the modified hIL-2 proteins comprise the amino acid sequence of SEQ ID NO: 620. The modified hIL-2 protein of any one of amino acid sequences SEQ ID NOs: 134-150, 307, 344, 607-611, 614, 617, or 620 can further comprise a T3A substitution and/or a C125A substitution. In some embodiments, the modified hIL-2 protein of any one of amino acid sequences SEQ ID NOs: 134-150, 307, 344, 607-611, 614, 617, or 620 further comprises a T3A substitution. In some embodiments, the modified hIL-2 protein of any one of amino acid sequences SEQ ID NOs: 134-150, 307, 344, 607-611, 614, 617, or 620 further comprises a C125A substitution. In some embodiments, the modified hIL-2 protein of any one of amino acid sequences SEQ ID NOs: 134-150, 307, 344, 607-611, 614, 617, or 620 further comprises a T3A substitution and a C125A substitution.

The modified hIL-2 protein portion of the immunoconjugates can comprise a D20A substitution and a R38E substitution.

The modified hIL-2 protein portion of the immunoconjugates can further comprise a substitution at amino acid position 3 relative to the non-modified hIL-2 amino acid sequence of SEQ ID NO: 345. A suitable substitution includes, for example, a T3A. In some embodiments, the modified hIL-2 protein portion of the immunoconjugates comprise a T3A substitution, a D20A substitution, and a R38E substitution. In some aspects, the modified hIL-2 protein portion of the immunoconjugates comprise the amino acid sequence of SEQ ID NO: 216.

Alternatively, the modified hIL-2 protein portion of the immunoconjugates can further comprise a deletion of amino acid position 3 relative to the non-modified hIL-2 amino acid sequence of SEQ ID NO: 345. In some embodiments, the modified hIL-2 protein portion of the immunoconjugates comprise a deletion of amino acids 1-3, a D20A substitution, and a R38E substitution. In some aspects, the modified hIL-2 protein portion of the immunoconjugates comprise the amino acid sequence of SEQ ID NO: 218.

The modified hIL-2 protein portion of the immunoconjugates can further comprise a deletion or substitution at amino acid position 125 relative to the non-modified hIL-2 amino acid sequence of SEQ ID NO: 345. The substitution at amino acid position 125 can be C125A. In some embodiments, the modified hIL-2 protein portion of the immunoconjugates comprise a D20A substitution, a R38E substitution, and a C125A substitution. In some embodiments, the modified hIL-2 protein portion of the immunoconjugates comprise the amino acid sequence of SEQ ID NO: 215. In some embodiments, the modified hIL-2 protein portion of the immunoconjugates comprise a T3A substitution, a D20A substitution, a R38E substitution, and a C125A substitution. In some embodiments, the modified hIL-2 protein portion of the immunoconjugates comprise the amino acid sequence of SEQ ID NO: 217. In some embodiments, the modified hIL-2 protein portion of the immunoconjugates comprise a deletion of amino acids 1-3, a D20A substitution, a R38E substitution, and a C125A substitution. In some embodiments, the modified hIL-2 protein portion of the immunoconjugates comprise the amino acid sequence of SEQ ID NO: 219.

The modified hIL-2 protein portion of the immunoconjugates can exhibit a reduction in potency of at least about 200-fold, at least about 500-fold, at least about 1,000-fold, at least about 2,000-fold, at least about 5,000-fold, at least about 6,500-fold, or at least about 10,000-fold on the high affinity IL-2 receptor (hIL-2Rαβγ) relative to a non-modified hIL-2, for example as quantified by a comparison in $EC_{50}$ values in an hIL-2-dependent cell proliferation assay described herein. In some embodiments, the modified hIL-2 protein portion of the immunoconjugates can exhibit a reduction in potency of greater than about 10,000-fold on the high affinity IL-2 receptor (hIL-2Rαβγ) relative to a non-modified hIL-2. A greater reduction in hIL-2 potency on the high affinity hIL-2 receptor may be possible and acceptable for the modified hIL-2 proteins described herein, but such a reduction may not be quantifiable with the methods described herein due to limits of the cell proliferation assay conditions.

In addition, the modified hIL-2 protein portion of the immunoconjugates can exhibit a reduction in potency of at least about 200-fold, at least about 500-fold, at least about 1,000-fold, at least about 2,000-fold, at least about 5,000-fold, at least about 6,500-fold, or at least about 10,000-fold on the intermediate affinity IL-2 receptor (hIL-2Rβγ) relative to an non-modified hIL-2, for example as quantified by a comparison in $EC_{50}$ values in an hIL-2-dependent cell proliferation assay described herein. In some embodiments, the modified hIL-2 protein portion of the immunoconjugates can exhibit a reduction in potency of greater than about 10,000-fold on the intermediate affinity IL-2 receptor (hIL-2Rβγ) relative to an non-modified hIL-2.

The modified hIL-2 protein portion of the immunoconjugates can exhibit a reduction in potency of up to about 10,000-fold on the high affinity IL-2 receptor (hIL-2Rαβγ) and a reduction in potency of up to about 10,000-fold on the intermediate affinity IL-2 receptor (hIL-2Rβγ) relative to a non-modified hIL-2, for example as quantified by a comparison in $EC_{50}$ values in an hIL-2-dependent cell proliferation assay described herein. The modified hIL-2 protein portion of the immunoconjugates can exhibit a reduction in potency of greater than about 10,000-fold on the high affinity IL-2 receptor (hIL-2Rαβγ) and a reduction in potency of greater than about 10,000-fold on the intermediate affinity IL-2 receptor (hIL-2Rβγ) relative to a non-modified hIL-2.

The hIL-2 protein portion of the immunoconjugates can be fused to the antibody or an antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment. In some embodiments, the hIL-2 protein portion of the immunoconjugates is directly fused by a peptide bond to the human antibody molecule or an antigen-binding fragment thereof. The hIL-2 protein portion of the immunoconjugates can be, for example, directly fused by a peptide bond to the C-terminal amino acid residue of the antibody heavy chain. In some embodiments, the hIL-2 protein portion of the immunoconjugates is fused to the human antibody molecule or an antigen-binding fragment thereof through a linker.

Fusion of the modified hIL-2 proteins to the human antibody molecules or antigen-binding fragments thereof can rescue the modified hIL-2 proteins' ability to activate the intermediate affinity IL-2 receptor. In some embodiments, the immunoconjugate is able to activate the intermediate affinity IL-2 receptor to a degree that is comparable to wild type hIL-2 activation of the intermediate affinity IL-2 receptor.

In some embodiments, the human antibody molecule, or antigen-binding fragment thereof, portion of the immunoconjugates comprise a heavy chain CDR1 comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423.

In some embodiments, the human antibody molecule, or antigen-binding fragment thereof, portion of the immunoconjugates comprise a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391.

In some embodiments, the human antibody molecule, or antigen-binding fragment thereof, portion of the immunoconjugates comprise a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401.

In some embodiments, the human antibody molecule, or antigen-binding fragment thereof, portion of the immunoconjugates comprise a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

The human antibody molecule, or antigen-binding fragment thereof, portion of the immunoconjugates can comprise a heavy chain variable region comprising the amino acid sequence of SEQ ID NO: 416 and a light chain variable region comprising the amino acid sequence of SEQ ID NO: 417.

The human antibody molecule, or antigen-binding fragment thereof, portion of the immunoconjugates can comprise a heavy chain variable region comprising the amino acid sequence of SEQ ID NO: 384 and a light chain variable region comprising the amino acid sequence of SEQ ID NO: 385.

The human antibody molecule, or antigen-binding fragment thereof, portion of the immunoconjugates can comprise a heavy chain variable region comprising the amino acid sequence of SEQ ID NO: 394 and a light chain variable region comprising the amino acid sequence of SEQ ID NO: 395.

The human antibody molecule, or antigen-binding fragment thereof, portion of the immunoconjugates can comprise a heavy chain variable region comprising the amino acid sequence of SEQ ID NO: 404 and a light chain variable region comprising the amino acid sequence of SEQ ID NO: 405.

The human antibody molecule, or antigen-binding fragment thereof, portion of the immunoconjugates can comprise an IgG1 heavy chain constant region.

The human antibody molecule, or antigen-binding fragment thereof, portion of the immunoconjugates can have substitutions or deletions within the constant region to minimize Fc-mediated immune effector function, such as FcγRIIIA-mediated antibody-dependent cell-mediated cytotoxicity (ADCC), FcγRI- and FcγRIIa-dependent antibody-dependent cellular phagocytosis (ADCP), and C1q binding-mediated complement-dependent cytotoxicity (CDC). In some embodiments, the human antibody molecule portion of the immunoconjugates comprise a L235A substitution, wherein the amino acid numbering is according to EU numbering. In some embodiments, the human antibody molecule portion of the immunoconjugates comprise a G237A substitution, wherein the amino acid numbering is according to EU numbering. In some embodiments, the human antibody molecule portion of the immunoconjugates comprise an L235A and a G237A substitution, wherein the amino acid numbering is according to EU numbering.

The human antibody molecule, or antigen-binding fragment thereof, portion of the immunoconjugates can comprise a heavy chain comprising the amino acid sequence of SEQ ID NO: 414 and a light chain comprising the amino acid sequence of SEQ ID NO: 415.

The human antibody molecule, or antigen-binding fragment thereof, portion of the immunoconjugates can comprise a heavy chain comprising the amino acid sequence of SEQ ID NO: 424 and a light chain comprising the amino acid sequence of SEQ ID NO: 425.

The human antibody molecule, or antigen-binding fragment thereof, portion of the immunoconjugates can comprise a heavy chain comprising the amino acid sequence of SEQ ID NO: 426 and a light chain comprising the amino acid sequence of SEQ ID NO: 427.

The human antibody molecule, or antigen-binding fragment thereof, portion of the immunoconjugates can comprise a heavy chain comprising the amino acid sequence of SEQ ID NO: 428 and a light chain comprising the amino acid sequence of SEQ ID NO: 429.

The immunoconjugates can have one or more of the following properties:
Binds to PD-1 but does not inhibit PD-L1 binding to PD-1;
Binds to PD-1 in the presence of standard-of-care anti-PD-1 antibodies used in the clinic (e.g., KEYTRUDA" and OPDIVOR);
Is highly selective for PD-1 and does not immunospecifically bind other related B7 family members;
Binds PD-1 on activated human T cells ($EC_{50}$~0.1-0.2 nM in a flow binding assay);
Has a reduction in potency of at least about 200-fold, at least about 500-fold, at least about 1,000-fold, at least about 2,000-fold, at least about 5,000-fold, at least about 6,500-fold, or at least about 10,000-fold on the high affinity IL-2 receptor (hIL-2Rαβγ) relative to a non-modified hIL-2, for example as quantified by a comparison in $EC_{50}$ values in an hIL-2-dependent cell proliferation assay described herein. In some embodiments, the modified hIL-2 protein portion of the immunoconjugates can exhibit a reduction in potency of greater than about 10,000-fold on the high affinity IL-2 receptor (hIL-2Rαβγ) relative to a non-modified hIL-2. A greater reduction in hIL-2 potency on the high affinity hIL-2 receptor may be possible and acceptable for the modified hIL-2 proteins described herein, but such a reduction may not be quantifiable with the methods described herein due to limits of the cell proliferation assay conditions;
Has a reduction in potency of at least about 200-fold, at least about 500-fold, at least about 1,000-fold, at least about 2,000-fold, at least about 5,000-fold, at least about 6,500-fold, or at least about 10,000-fold on the intermediate affinity IL-2 receptor (hIL-2Rβγ) relative to an non-modified hIL-2, for example as quantified by a comparison in $EC_{50}$ values in an hIL-2-dependent cell proliferation assay described herein. In some embodiments, the modified hIL-2 protein portion of the immunoconjugates can exhibit a reduction in potency of greater than about 10,000-fold on the intermediate affinity IL-2 receptor (hIL-2Rβγ) relative to a non-modified hIL-2;
Rescues and expands PD-1-expressing human memory T cell subsets in a GvHD animal model; and
Has minimal or no impact on body weight, blood chemistry, or hematology parameters after single dose at 1 and 10 mg/kg in cynomolgus monkeys.

In some embodiments, the immunoconjugate comprises a modified hIL-2 protein comprising a T3A substitution, a R38E substitution, a D20A substitution, and a C125A substitution fused to the C-terminus of the antibody heavy chain of a human anti-hPD-1 antibody comprising a human IgG1 framework with a L235A substitution and a G237A substitution. In some embodiments, the immunoconjugate comprises a light chain comprising the amino acid sequence of SEQ ID NO: 415 and a heavy chain-hIL-2 protein fusion comprising the amino acid sequence of SEQ ID NO: 532.

The disclosed immunoconjugates can selectively deliver IL-2 signaling to PD-1-expressing T cells. The human antibody molecule, or antigen-binding fragment thereof, portion of the immunoconjugate is utilized solely to deliver the modified hIL-2 to PD-1-expressing cells and does not block PD-1 receptor function, as do classical anti-PD-1 inhibitor antibodies such as OPDIVOR and KEYTRUDAR. The primary mechanism-of-action of the herein disclosed immunoconjugates is via the T cell selective activity of IL-2. The human PD-1 receptor is primarily expressed on a minor subset of T cells with potent tumor reactivity. Without being bound by theory, it is believed that targeting the modified hIL-2 protein portion of the immunoconjugate to this population of T cells can dramatically amplify anti-tumor immunity while reducing or minimizing off-target systemic IL-2-mediated toxicities mediated by cell populations that lack PD-1 expression.

Pharmaceutical Compositions, Polynucleotides, Vectors, and Cells

Disclosed herein are pharmaceutical compositions comprising any of the herein disclosed modified hIL-2 proteins, any of the herein disclosed human antibody molecules or antigen-binding fragments thereof, or any of the herein disclosed immunoconjugates. In some embodiments, the pharmaceutical compositions comprise any of the herein disclosed modified hIL-2 proteins. In some embodiments, the pharmaceutical compositions comprise any of the herein disclosed human antibody molecules or antigen-binding fragments thereof. In some embodiments, the pharmaceutical compositions comprise any of the herein disclosed immunoconjugates.

Disclosed herein are polynucleotides comprising a nucleic acid sequence encoding any of the herein disclosed modified hIL-2 proteins, any of the herein disclosed human antibody molecules or antigen-binding fragments thereof, or any of the herein disclosed immunoconjugates. In some embodiments, the polynucleotides comprise a nucleic acid sequence encoding any of the herein disclosed modified hIL-2 proteins. In some embodiments, the polynucleotides comprise a nucleic acid sequence encoding any of the herein disclosed human antibody molecules or antigen-binding fragments thereof. In some embodiments, the polynucleotides comprise a nucleic acid sequence encoding any of the herein disclosed immunoconjugates.

Disclosed herein are vectors comprising a polynucleotide comprising a nucleic acid sequence that encodes any of the herein disclosed modified hIL-2 proteins, any of the herein disclosed human antibody molecules or antigen-binding fragments thereof, or any of the herein disclosed immunoconjugates. In some embodiments, the vectors comprise a polynucleotide comprising a nucleic acid sequence that encodes any of the herein disclosed modified hIL-2 proteins. In some embodiments, the vectors comprise a polynucleotide comprising a nucleic acid sequence that encodes any of the herein disclosed human antibody molecules or antigen-binding fragments thereof. In some embodiments, the vectors comprise a polynucleotide comprising a nucleic acid sequence that encodes any of the herein disclosed immunoconjugates.

Also disclosed herein are transformed cells comprising any of the herein disclosed vectors.

Methods of Treatment and Uses

Disclosed herein are methods of treating a disease or disorder in a subject, the methods comprising administering a therapeutically effective amount of any of the herein disclosed immunoconjugates or pharmaceutical compositions to the subject to thereby treat the disease.

Also disclosed are uses of any of the herein disclosed immunoconjugates or pharmaceutical compositions in the preparation of a medicament for the treatment of a disease. Also disclosed are uses of any of the herein described immunoconjugates or pharmaceutical compositions for the treatment of a disease or disorder.

The disclosed immunoconjugates and pharmaceutical compositions can be used to treat diseases or disorders in which stimulation of the subject's immune system would be beneficial. In some embodiments, the subject has an insufficient or deficient immune response and the disclosed immunoconjugates and pharmaceutical compositions stimulate the subject's immune response. The antibody portion of the immunoconjugate can serve to direct the modified hIL-2 protein to the subject's immune cells by, for example, binding to an antigen expressed on the surface of the immune cell. In the case of the disclosed modified hIL-2 protein-human anti-hPD-1 antibody immunoconjugates, for example, the anti-PD-1 antibody (or antigen-binding fragment thereof) portion of the immunoconjugate can bind PD-1 expressed on T cells, thereby delivering the modified hIL-2 protein to the T cells. Targeting the modified IL-2 protein to specific cells can dramatically amplify the therapeutic efficacy of the IL-2 protein without off-target systemic toxicities mediated by cell populations that lack the antigen expression. The disclosed methods and uses can be used to treat, for example, cancer, autoimmune diseases and inflammatory diseases, and chronic infections and infectious diseases. Exemplary cancers include bladder cancer, brain cancer, head and neck cancer, pancreatic cancer, lung cancer, non-small cell lung carcinoma, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, melanoma, squamous cell carcinoma, bone cancer, and kidney cancer. Exemplary autoimmune diseases and inflammatory disease include systemic lupus erythematosus (SLE), Type 1 diabetes, rheumatoid arthritis, ankylosing spondylitis, psoriasis, Behcet's disease, granulomatosis with polyangiitis, Takayasu's disease, Crohn's disease, ulcerative colitis, autoimmune hepatitis, sclerosing cholangitis, Sjoren's syndrome, alopecia areata, and inflammatory myopathies. Exemplary infectious diseases include HIV and hepatitis B.

In some embodiments, the disease is cancer. The methods and uses can comprise administering a therapeutically effective amount of any of the herein disclosed modified hIL-2 protein-antibody conjugates to the subject to thereby treat the cancer. In some aspects, the cancer is melanoma. In some aspects, the cancer is non-small cell lung carcinoma.

EXAMPLES

The following examples are provided to further describe some of the embodiments disclosed herein. The examples are intended to illustrate, not to limit, the disclosed embodiments.

General Methods

Protocol A. Flow Cytometry Screen for Binding of Anti-hPD-1 Antibodies or Anti-hPD-1 Antibody-Attenuated hIL-2 Fusions to Human PD-1

To test for binding to hPD-1, antibodies and antibody-attenuated hIL-2 fusion proteins were characterized in full titration curves. A Jurkat cell line was transfected with a mammalian vector which encoded amino acids 1-185 of human PD-1 (SEQ ID NO: 346) to stably express the extracellular domain and a portion of the transmembrane domain of human PD-1, and this transfected cell line was used to determine binding of anti-hPD-1 antibodies. Jurkat+ hPD-1 cells were washed and added to 96-well plates at 100,000 cells per well in FACS buffer (PBS, 0.2% Heat-inactivated Fetal Bovine Serum). Cells were blocked with 1:50 dilution of human FcR Block (Miltenyi) for 10 minutes at 4° C. and washed with FACS buffer.

Antibodies or antibody-attenuated hIL-2 immunoconjugates (fusion proteins) were serially diluted six-fold in FACS buffer for an 8-point curve and added to human PD-1 expressing Jurkat cells for 1 hour on ice in 100 µL volume. Cells were washed and re-suspended in FACS buffer containing 1:40 dilution of Allophycocyanin conjugated anti-human IgG Fc monoclonal antibody. Cells were washed once more, re-suspended in FACS buffer containing 1:1000 dilution of Sytox Green (Thermo Fisher) and flow cytometric analysis was conducted on the BD FACS Canto II, BD Celesta or BD Fortessa (BD Biosciences) flow cytometers. The geometric mean fluorescent intensity (gMFI) was calculated using FlowJo software version 10. Half maximal effective concentration ($EC_{50}$) values were calculated from the gMFI of the Allophycocyanin signal across the titrated concentrations using GraphPad Prism 7 software.

Protocol B. Flow Cytometry Competition Screen for Binding of Anti-hPD-1 Antibodies or Anti-hPD-1 Antibody-Attenuated hIL-2 Fusions to Human PD-1

Antibodies and antibody-attenuated hIL-2 fusion proteins were tested for the ability to bind human PD-1 in the presence of a saturating concentration of anti-hPD-1 #1-mIgG2b-N297A (sequence comprising the heavy and light chain variable region sequences of nivolumab, clone 5C4, as described in U.S. Patent Pub. No. US 2009/0217401A1, formatted onto a murine IgG2b-N297A background) (SEQ ID NOs: 348 and 349) or anti-hPD-1 #2-mIgG2b-N297A (sequence comprising the heavy and light chain variable region sequences of pembrolizumab (clone 109A-H/K09A-L-11) as described in Int'l Pub. No. WO2008/156712A1, formatted onto a murine IgG2b-N297A background) (SEQ ID NOs: 350 and 351).

Antibodies or antibody-attenuated hIL-2 fusion proteins were serially diluted six-fold for an 8-point titration curve with and without saturating amounts of 10 UM anti-hPD-1 #1-mIgG2b-N297A or anti-hPD-1 #2-mIgG2b-N297A. Briefly, Jurkat cells stably expressing hPD-1 (as described in Protocol A above) were washed and re-suspended in FACS buffer containing 1:50 dilution of human FcR Blocking reagent. Cells were incubated at 4° C. for 10 minutes and washed. Cells were then re-suspended in 100 µL volume with anti-hPD-1 #1-mIgG2b-N297A or anti-hPD-1 #2-mIgG2b-N287A diluted in FACS buffer to 10 UM and incubated at 4° C. for one hour. Cells were washed and incubated with test antibodies or antibody-attenuated hIL-2 fusion proteins serially diluted six-fold for an 8-point curve in 100 µL volume for one hour at 4° C. To detect bound test anti-hPD-1 antibodies or anti-hPD-1-attenuated hIL-2 fusion proteins, cells were washed again and incubated with 1:40 dilution of Allophycocyanin-conjugated anti-human IgG Fc monoclonal antibody for 45 minutes on ice. Cells were washed and re-suspended in FACS buffer containing 1:1000 dilution of Sytox Green (Thermo Fisher). To generate a comparison, Jurkat cells stably expressing human PD-1 were incubated with only the titrated test antibodies or antibody-attenuated hIL-2 fusion proteins (without anti-hPD-1 #1-mIgG2b-N297A or anti-hPD-1 #2-mIgG2b-N297A) and subsequently with 1:40 dilution of Allophycocyanin-conjugated anti-human IgG Fc secondary. As a control, the variable regions of anti-hPD-1 #1 and anti-hPD-1 #2 were cloned into hIgG4 frameworks and were assessed with and without the addition of anti-hPD-1 #1-mIgG2b-N297A or anti-hPD-1 #2-mIgG2b-N297A. Flow cytometry was carried out on the BD Canto II, BD Celesta, or BD Fortessa (BD Biosciences) flow cytometers and gMFI was calculated using FlowJo software version 10. $EC_{50}$ values were calculated from the gMFI of the Allophycocyanin signal across the titrated concentrations using GraphPad Prism 7 software.

Protocol C. Cell-Based Screen for Characterization of Non-Antagonist Anti-hPD-1 Antibodies or Anti-hPD-1 Antibody-Attenuated hIL-2 Fusions Human PD-1 antibodies and anti-hPD-1-attenuated hIL-2 fusion proteins were characterized for the ability to block hPD-1 from binding to ligand hPD-L1 (SEQ ID NO: 584). Anti-hPD-1 antibodies and anti-hPD-1-attenuated hIL-2 fusion proteins were either characterized as an antagonist or non-antagonist using an in vitro cell-based human PD-1/PD-L1 blockade bioassay (Promega, Cat #J1255). This co-culture assay utilized two cell lines: FCγR11b artificial Antigen Presenting Cells/Chinese Ovary Hamster K1 (aAPC/CHO-K1) and Jurkat Effector cells. aAPC/CHO K1 cells stably express both human PD-L1 ligand and a cell surface protein to activate cognate T cell receptors (TCRs) while Jurkat Effector cells express hPD-1 and a luciferase reporter under the control of Nuclear Factor of Activated T cells response element (NFAT-RE). When these cells are co-cultured in the presence of a non-antagonistic antibody, hPD-1/hPD-L1 interaction inhibits TCR signaling and no luminescence is detected. In the presence of an antibody that antagonizes hPD-1 interaction with hPD-L1 (SEQ ID NO: 584), the inhibitory signal is disrupted and luminescence is detected.

Figure 7:
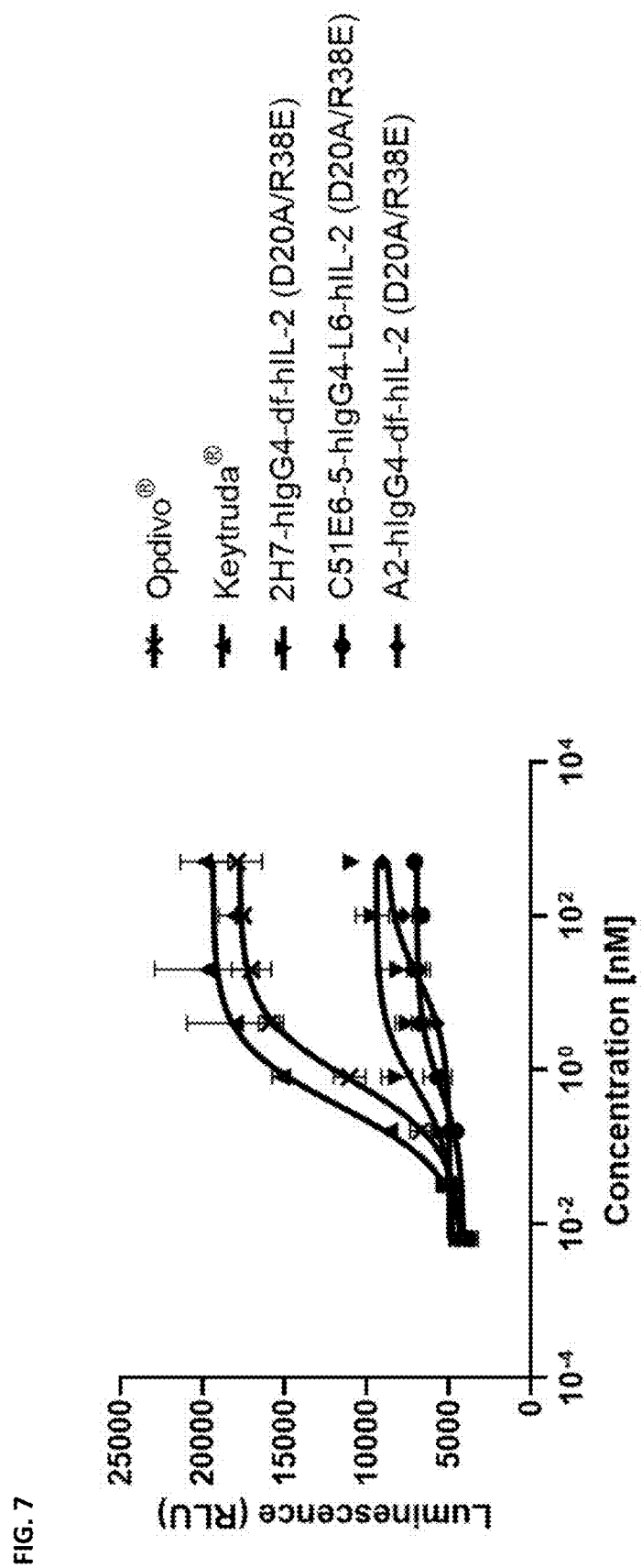
FIG. 7 shows the results of competition assays demonstrating that the anti-hPD-1-attenuated hIL-2 immunoconjugates 2H7-hIgG4-df-hIL-2 (D20A/R38E), C51E6-5-L6-hIgG4-hIL-2 (D20A/R38E), and A2-hIgG4-df-hIL-2 (D20A/R38E) do not inhibit the binding of human PD-L1 to the human PD-1 receptor using the PD-1/PD-L1 Blockade Bioassay.

The thaw-and-use assay was performed according to manufacturer's instructions. In short, aAPC/CHO-K1 cells were first thawed and plated at 30,000 cells per well in flat-bottom 96-well plates for 18 hours at 37° C. in a 5% $CO_2$ incubator. After cells had adhered, the media was removed and 200 nM or 1000 nM test antibodies or antibody-attenuated hIL-2 fusion proteins were diluted in 40 µL assay buffer (RPMI 1640 medium+1% FBS) and added to the aAPC/CHO-K1 cells. A human IgG4 isotype control monoclonal antibody which targeted Keyhole Limpet Hemocyanin (KLH) clone C3 (SEQ ID NOs: 585 and 586) was used as a negative control. Jurkat effector cells expressing hPD-1 were added at 24,000 cells per well in 40 µL volume. The final concentration of fixed antibodies tested was 100 nM or 500 nM. In some examples, a range of concentrations of anti-hPD-11 or anti-hPD-1-attenuated hIL-2 fusion proteins were tested in this co-culture assay, with the top concentration in a five-fold titration series of 500 nM (FIG. 7).

The co-culture assay was incubated at 37° C. in a 5% $CO_2$ incubator for an additional 18-20 hours. To read the luminescence signal, plates were allowed to come to room temperature, and 80 µL of the Bio-Glo™ reagent was added to each well. The plates were incubated for 15 minutes in the dark at room temperature and luminescence was read on a Victor X luminometer (Perkin Elmer). Relative luminescence units (RLU) were averaged for each triplicate and graphed using GraphPad Prism 7 software.

Protocol D. In Vitro Phosphorylated STAT5 Assay to Test Attenuation of hIL-2 Variants The level of attenuation of hIL-2 receptor activation activity of antibody-attenuated hIL-2 fusion proteins was characterized using a phosphorylated STAT5 assay. Variants were tested in both hIL-2 responsive human natural killer NK-92 cells and engineered human erythroleukemic TF1 cells. The NK-92 cell line naturally expresses the high-affinity hIL-2 receptor (IL-2Rαβγ) at physiologic levels, while the TF1 cell line that naturally expresses the IL-2Rγ (SEQ ID NO: 352) was engineered to also stably express human CD122 (IL-2RB) (SEQ ID NO: 353) for expression of the intermediate affinity hIL-2 receptor complex (IL-2Rβγ). This TF1+IL-2Rβ stable cell line does not express the IL-2Rα(SEQ ID NO: 354). Both NK-92 and TF1+IL-2Rβ cell lines were used to assess the level of attenuation of IL-2 potency in these cell-based potency assays as fixed concentration screens and full titration curves.

To perform the fixed concentration screen, 100,000 NK-92 cells or TF1+IL-2Rβ cells were plated into 96 wells in 50 μL of fresh growth medium lacking human IL-2 cytokine and incubated overnight at 37° C. in a $CO_2$ incubator. After 15-16 hours, human IL-2 starved cells were treated with 25.7 nM recombinant hIL-2 (denoted as rhIL-2) (SEQ ID NO: 345) or test antibody-attenuated hIL-2 fusion proteins for the NK-92 cell assay, or with 33.3 nM hIL-2 or test hIL-2 variants for the TF1+IL-2Rβ cell assay. Cells were incubated at 37° C., 5% $CO_2$ for 10 minutes. Cells were fixed with Cytofix Buffer (BD Biosciences) for 10 minutes at 37° C. and then permeabilized after treatment with Perm Buffer III (BD Biosciences) for 30 minutes on ice. hIL-2-dependent Stat5 phosphorylation was detected after staining fixed and permeabilized cells with Alexa Fluor-647 conjugated anti-Stat5 antibody (BD Biosciences) at 0.5 μL per sample for 45 minutes at room temperature in the dark. Cells were washed and reagents were diluted in BD Pharmingen Buffer (BD Biosciences). Stained cells were acquired on a FACS-Celesta cytometer (BD Biosciences) and analyzed using FlowJo software version 10.7.2. The assays were performed in cohorts but normalized using the rhIL-2 for each plate. The degree of attenuation of selected antibody-attenuated hIL-2 fusion proteins were evaluated in an 8-point, 6-fold serially titrated curve ranging from 1200 nM to 7 pM on both NK-92 and TF1+IL-2Rβ cell lines. The procedure for the pStat5 curves was performed in the same manner as the method described above. $EC_{50}$ values were calculated from the geometric mean fluorescent intensity (gMFI) across the titrated concentrations using GraphPad Prism 7 software. The fold change in activity from rhIL-2 was calculated by dividing the $EC_{50}$ values for the variants by the $EC_{50}$ of hIL-2.

Protocol E. In Vitro Cell-Based Proliferation Assay to Test Attenuation of Antibody-Attenuated hIL-2 Fusion Proteins The antibody-attenuated hIL-2 fusion proteins were also tested for attenuated hIL-2 activity in hIL-2 dependent cell proliferation assays. 10,000 NK-92 cells (expressing the high affinity receptor hIL-2Rαβγ) or TF1+IL-2Rβ cells (expressing the intermediate affinity receptor hIL-2Rβγ) suspended in 50 μL of fresh growth medium without hIL-2 cytokine were plated per well in 96-well U-bottom cell culture plate. Eight point, 6-fold serial titrations of antibody-attenuated hIL-2 fusion proteins with a highest concentration of 996 nM were diluted in fresh media and overlaid on cells in wells. Cells were incubated at 37° C. in a 5% $CO_2$ incubator for 3 days for TF1+IL-2Rβ cells or 4 days for NK-92 cells. To measure proliferation, Cell-Titer-Glo (Promega) was added to wells, incubated for 10 minutes at room temperature and luminescence was read for 0.1 second per well using a VictorX Multilabel Plate Reader (Perkin Elmer). $EC_{50}$ values were calculated from the relative luminescence units (RLU) across the titrated concentrations using GraphPad Prism 7 software. The fold change in activity from rhIL-2 was calculated by dividing the $EC_{50}$ values for the variants by the $EC_{50}$ of hIL-2. The assays were performed in cohorts but normalized using the rhIL-2 $EC_{50}$ value for each plate.

Example 1: Optimization of Antibody-Attenuated hIL-2 Fusion Protein Variants and Determination of their hIL-2 Activity on the Intermediate and High-Affinity hIL-2 Receptor Complexes In order to determine the optimal structures for an antibody-attenuated hIL-2 fusion protein, non-attenuated hIL-2 was fused to an anti-DNase I antibody (clone 1H3) designated as 1H3-hIgG1 (SEQ ID NO: 379, SEQ ID NO: 374) in the antibody variable region in a variety of ways as illustrated in FIG. 1. Variations included the hIL-2 fused at the N-terminus of the human anti-DNase I antibody (clone 1H3) immunoglobulin hIgG1 heavy chain or human kappa light chain via a direct fusion (df) denoted as hIL-2 Nterm light chain df (SEQ ID NO: 379, SEQ ID NO: 356), hIL-2 Nterm heavy chain df (SEQ ID NO: 358, SEQ ID NO: 374) or six amino acid linker (L6) (SEQ ID NO: 355) denoted as hIL-2 Nterm light chain L6 fusion (SEQ ID NO: 379, SEQ ID NO: 357) and hIL-2 Nterm heavy chain L6 fusion (SEQ ID NO: 359, SEQ ID NO: 374). Variations in which the hIL-2 moiety was fused to the C-terminus of both the heavy chains and light chains via df or L6 were also created and denoted as hIL-2 Cterm heavy chain df (SEQ ID NO: 360, SEQ ID NO: 374), hIL-2 Cterm heavy chain L6 fusion (SEQ ID NO: 361, SEQ ID: 374), hIL-2 Cterm light chain df (SEQ ID NO:379, SEQ ID NO: 362), hIL-2 Cterm light chain L6 fusion (SEQ ID NO:379, SEQ ID NO: 363). Further variations were generated in which a CD25/IL-2Rα extracellular domain (amino acids 1-164) (SEQ ID NO: 126) was fused to the N-terminus or C-terminus of the heavy chains or the kappa light chains to interfere with the binding of the IL-2 to CD25 of the IL-2 receptor (FIG. 2). In these constructs, human CD25 extracellular domain (amino acids 1-164) (SEQ ID NO: 126) was fused to human IL-2 via a 20 amino acid linker (L20) (SEQ ID NO: 364), which was then directly fused or fused via an L6 linker (SEQ ID NO: 355) to 1H3-hIgG1 heavy chain or light chain at the N terminus: hCD25-L20-hIL-2 Nterm heavy chain df (SEQ ID NO: 365, SEQ ID NO: 374), hCD25-L20-hIL-2 Nterm heavy chain L6 fusion (SEQ ID NO: 366, SEQ ID NO: 374), hCD25-L20-hIL-2 Nterm light chain df (SEQ ID NO: 379, SEQ ID NO: 367), hCD25-L20-hIL-2 Nterm light chain L6 fusion (SEQ ID NO: 379, SEQ ID NO: 368). Lastly, a final set of variants in which the CD25/IL-2Rα extracellular domain moiety (SEQ ID NO: 126) fused to the C-terminus of the heavy chain and kappa light chains were created: hCD25-L20-hIL-2 Cterm heavy chain df (SEQ ID NO: 369, SEQ ID NO: 374), hCD25-L20-hIL-2 Cterm heavy chain L6 fusion (SEQ ID NO: 370, SEQ ID NO: 374), hCD25-L20-hIL-2 Cterm light chain df (SEQ ID NO: 379, SEQ ID NO: 371), hCD25-L20-hIL-2 Cterm light chain L6 fusion (SEQ ID NO: 379, SEQ ID NO:372). These antibody-hIL-2 fusion proteins were produced, expressed, and Protein-A purified using standard techniques. The 16 N- or C-terminus and linker variants described above were evaluated in an in vitro cell-based phosphorylated STAT5 assay using an 8-point, 6-fold serial titration, as described in Protocol D.

Table 1 summarizes the $EC_{50}$ calculated over the 8-point, 6-fold serially titrated curves using the geometric mean fluorescence intensity (gMFI) calculated by the FlowJo version 10 software. The fold change from rhIL-2 was also calculated for each variant as a measurement of the level of attenuation as compared to the activity of the rhIL-2 positive control. Some $EC_{50}$ values were unable to be calculated by the GraphPad Prism 7 software and were marked as Not Calculated (NC); however, based on dose-titration curves there was no attenuation for these variants.

Fusions of the hIL-2 moiety to the N-terminus or C-terminus of the immunoglobulin heavy chain resulted in no reduction in IL-2 activity when compared to rhIL-2 on cell lines expressing the high-affinity hIL-2 receptor (NK-92) or intermediate-affinity hIL-2 receptor (TF1+IL-2RB). The direct fusion (df) of hIL-2 to the antibody component of the fusion protein resulted in no change in IL-2 activity when compared with fusion employing a six amino acid linker (L6) between the IL-2 and antibody components. Similarly, fusions of the IL-2 component to the heavy chain or light chain of the antibody component resulted in no change in IL-2 activity when compared to rhIL-2. All N- or C-terminus and linker fusion protein variants in which the hCD25/hIL-2Rα moiety was fused to hIL-2 were predicted to exhibit reduced binding of the fusion protein to the CD25 of the hIL-2 receptor on cells. Experimentally these constructs exhibited strongly attenuated hIL-2 activity (by at least 45-fold) on the high affinity IL-2 receptor (NK-92) and by 18-fold on the intermediate hIL-2 receptor (TF1+IL-2RB).

TABLE 1 pSTAT5 $EC_{50}$ and fold change on fusion protein domain variants

| HC or LC Component Of Fusion Protein | HC and LC SEQ ID NOs: | pSTAT5 $EC_{50}$ (NK-92) | Fold change from rhIL-2 (NK-92) | Attenuation based on dose-titration curves (NK-92) | pSTAT5 $EC_{50}$ (TF1 + IL-2Rβ) | Fold change from rhIL-2 (TF1 + IL-2Rβ) | Attenuation based on dose-titration curves (TF1 + IL-2Rβ) |
|---|---|---|---|---|---|---|---|
| hIL-2 Nterm heavy chain df | 358, 374 | <0.1 [a] | 1 [a] | Not Attenuated | 1.11 | 2 | Not Attenuated |
| hIL-2 Nterm heavy chain L6 fusion | 359, 374 | NC [a] | NC [a] | Not Attenuated | 0.19 | 0 | Not Attenuated |
| hIL-2 Nterm light chain df | 379, 356 | <0.1 [a] | 1 [a] | Not Attenuated | 0.52 | 1 | Not Attenuated |
| hIL-2 Nterm light chain L6 fusion | 379, 357 | <0.1 [a] | 0 [a] | Not Attenuated | 0.13 | 0 | Not Attenuated |
| hIL-2 Cterm heavy chain df | 360, 374 | <0.1 [a] | 0 [a] | Not Attenuated | <0.1 | 0 | Not Attenuated |
| hIL-2 Cterm heavy chain L6 fusion | 361, 374 | NC [a] | NC [a] | Not Attenuated | <0.1 | 0 | Not Attenuated |
| hIL-2 Cterm light chain df | 379, 362 | NC [a] | NC [a] | Not Attenuated | 1.15 | 1 | Not Attenuated |
| hIL-2 Cterm light chain L6 fusion | 379, 363 | <0.1 [a] | 0 [a] | Not Attenuated | 0.25 | 0 | Not Attenuated |
| hCD25-L20-hIL-2 Nterm heavy chain df | 365, 374 | 7.42 | 1052 | Attenuated | 190.50 [a] | 314 [a] | Attenuated |
| hCD25-L20-hIL-2 Nterm heavy chain L6 fusion | 366, 374 | 2.24 | 318 | Attenuated | 10.70 | 18 | Attenuated |
| hCD25-L20-hIL-2 Nterm light chain df | 379, 367 | 106.80 | 15149 | Attenuated | 328.50 [a] | 542 [a] | Attenuated |
| hCD25-L20-hIL-2 Nterm light chain L6 fusion | 379, 368 | 4.45 | 631 | Attenuated | 27.88 | 46 | Attenuated |
| hCD25-L20-hIL-2 Cterm heavy chain df | 369, 374 | 1.89 | 149 | Attenuated | 93.89 [a] | 104 [a] | Attenuated |
| hCD25-L20-hIL-2 Cterm heavy chain L6 fusion | 370, 374 | 6.09 | 479 | Attenuated | 90.53 [a] | 101 [a] | Attenuated |
| hCD25-L20-hIL-2 Cterm light chain df | 379, 371 | 0.58 | 45 | Attenuated | 156.90 [a] | 174 [a] | Attenuated |
| hCD25-L20-hIL-2 Cterm light chain L6 fusion | 379, 372 | 1.76 | 138 | Attenuated | 221.90 [a] | 247 [a] | Attenuated |

NC = Not Calculated;
[a] = Fold change is an estimate only since a full four parameter logistic curve was not reached Example 2: Antibody-Attenuated hIL-2 Fusion Protein Variant Production and Determination of their Binding Kinetics to Recombinant Human CD25 and/or Human CD122

Since there was no reduction in hIL-2 activity in the various N-terminus or C-terminus immunoglobulin heavy chain fusion proteins, the hIL-2 Cterm heavy chain L6 fusion (SEQ ID NOs: 361, 374), designated as "1H3-hIgG1-L6-hIL-2", was used as the base construct for antibody-attenuated-hIL-2 fusion protein variants with substitutions in the hIL-2 moiety. Single, double and/or multiple amino acid substitutions were introduced into selected residues of human IL-2 in order to investigate the role those residues play in the recognition of either human CD25/IL-2Rα and/or human CD122/IL-2Rβ or CD132/IL-2Rγ (human IL-2R subunits). Over three hundred antibody-attenuated hIL-2 fusion protein variants with substitutions in the hIL-2 moiety were generated and evaluated in 6 rounds. These variants were first screened using a flow-based phosphorylated STAT5 (pSTAT5) assay at a fixed concentration on IL-2 dependent cell lines (NK-92 and TF1+IL-2RB) as well as in dose-titration curves. Phosphorylated STAT5 is a downstream signal of IL-2 activity and was used as a snapshot measurement of IL-2 potency. IL-2 dependent cell proliferation assays were also performed to measure IL-2 activity over a period of 3-4 days. Criteria for attenuated hIL-2 selection included: (1) reduced IL-2 potency on both NK-92 and TF1+IL-2Rβ cell lines with greater than 50% agonist activity on both cell lines; and (2) moderate-to-high production yield.

Human anti-DNase I antibody-hIL-2 fusion proteins were generated by fusing the human IL-2 or the human IL-2 variants (SEQ ID NOs: 1-344, 377, 378, and 575) to the C-terminus of a human anti-DNase I antibody (clone 1H3, having a human IgG1 isotype) heavy chain via the L6 linker, which were combined with the hIgG1 light chain (1H3-hkappa LC; SEQ ID NO: 374) to generate the 1H3-hIgG1-L6-hIL-2 fusion proteins (provided in Table 28). Mouse anti-yellow fever virus antibody-hIL-2 fusion proteins were also generated by fusing human IL-2 variants to the C-terminus of a mouse anti-yellow fever virus antibody (clone 2D12, having a mouse IgG1 isotype) heavy chain with a D265A substitution for decreased immune effector function via the L6 linker, which were combined with the 2D12-mIgG1 light chain (2D12-mKappa LC; SEQ ID NO: 376) to generate the 2D12-mIgG1-D265A-L6-hIL-2 fusion proteins (provided in Table 28). Some of these mouse anti-yellow fever virus antibody-hIL-2 fusion proteins were formatted onto a human IgG1 constant region and were generated in the same manner as described above using, which was combined with 2D12-hKappa light chain (2D12-hKappa LC; SEQ ID NO: 573). Iterations of IL-2 amino acid substitutions were performed in six rounds, designated Groups 1 to 6. 1H3-hIgG1-L6-hIL-2, 2D12-mIgG1-D265A-L6-hIL-2, and 2D12-hIgG1-L6-hIL-2 fusion proteins were produced, expressed, and Protein-A purified using standard techniques.

Group 1 contained an initial series of only 2D12-mIgG1-D265A-L6-hIL-2 or 2D12-hIgG1-L6-hIL-2 fusion proteins which comprised a substitution or combination of substitutions in human IL-2 which were predicted to be involved in binding to only one of the IL-2 receptor subunits CD25/IL-2Rα, CD122/IL-2Rβ, or CD132/IL-2Rγ. The fusion proteins in this group included the following substitutions to IL-2 predicted to modulate binding to CD25/IL-2Rα: F42K (SEQ ID NO: 1), V69A (SEQ ID NO: 2), V69E (SEQ ID NO: 3), V69F (SEQ ID NO: 4), V69G (SEQ ID NO: 5), V69H (SEQ ID NO: 6), V69I (SEQ ID NO: 7), V69K (SEQ ID NO: 8), V69L (SEQ ID NO: 9), V69M (SEQ ID NO: 10), V69Q (SEQ ID NO: 11), V69S (SEQ ID NO: 12), V69T (SEQ ID NO: 13), V69W (SEQ ID NO: 14), V69Y (SEQ ID NO: 15), V69R (SEQ ID NO: 581), (F42K/F44K) (SEQ ID NO: 16), (F44K/Y45R) (SEQ ID NO: 17), (F42K/V69R) (SEQ ID NO: 18), (Y45R/V69R) (SEQ ID NO: 19), (F42K/F44K/Y45R) (SEQ ID NO: 20), (F42A/Y45A/L72G) (SEQ ID NO: 574), (R38A/F42K/Y45R) (SEQ ID NO: 21), (R38E/F42K/Y45R) (SEQ ID NO: 22), (K43E/F42K/Y45R) (SEQ ID NO: 23), (K43T/F42K/Y45R) (SEQ ID NO: 24), (F42K/Y45R/E62A) (SEQ ID NO: 25), (P65R/F42K/Y45R) (SEQ ID NO: 26), (P65S/F42K/Y45R) (SEQ ID NO: 27), (V69A/F42K/Y45R) (SEQ ID NO: 28), (V69D/F42K/Y45R) (SEQ ID NO: 29), or (V69R/F42K/Y45R) (SEQ ID NO: 30). The substitutions in this group included the following predicted to modulate binding to CD122/IL-2RB: D20A (SEQ ID NO: 31), D20N (SEQ ID NO: 32), D20K (SEQ ID NO: 33), N88A (SEQ ID NO: 34), N88G (SEQ ID NO: 35), N88H (SEQ ID NO: 36), N88K (SEQ ID NO: 37), (D20A/D84A) (SEQ ID NO: 38), (D20A/E15A) (SEQ ID NO: 39), (D20A/E95A) (SEQ ID NO: 40), (D20A/N88A) (SEQ ID NO: 41), (D20A/S87A) (SEQ ID NO: 42), (D84A/N88A) (SEQ ID NO: 43), (E15A/N88A) (SEQ ID NO: 44), or (S87A/N88A) (SEQ ID NO: 45). Group 1 also included the following substitutions to IL-2 predicted to modulate IL-2 binding to CD132/IL-2-Rγ: Q126L (SEQ ID NO: 377) or Q126E (SEQ ID NO: 378). The IL-2 substitutions studied in Group 1 were not predicted to modulate binding to more than one of the IL-2 receptor subunits.

Group 2 contained a series of 1H3-hIgG1-L6-hIL-2 fusion proteins which comprised one or more substitutions in human IL-2 which were predicted to be involved in CD25/IL-2Rα binding only. The fusion proteins in this group included the following substitutions to IL-2 predicted to modulate binding to CD25/IL-2Rα: R38A (SEQ ID NO: 46), R38D (SEQ ID NO: 47), R38E (SEQ ID NO: 48), R38Q (SEQ ID NO: 49), F42R (SEQ ID NO: 50), F42A (SEQ ID NO: 51), F42D (SEQ ID NO: 52), F42H (SEQ ID NO: 53), K43A (SEQ ID NO: 54), K43E (SEQ ID NO: 55), K43Q (SEQ ID NO: 56), Y45A (SEQ ID NO: 57), Y45K (SEQ ID NO: 58), Y45S (SEQ ID NO: 59), Y45R (SEQ ID NO: 60), E61A (SEQ ID NO: 61), E61R (SEQ ID NO: 62), E61K (SEQ ID NO: 63), E62A (SEQ ID NO: 64), E62R (SEQ ID NO: 65), E62K (SEQ ID NO: 66), E62Y (SEQ ID NO: 67), E68Y (SEQ ID NO: 68), E68A (SEQ ID NO: 69), E68K (SEQ ID NO: 70), E68R (SEQ ID NO: 71), E68L (SEQ ID NO: 72), L72Y (SEQ ID NO: 73), L72R (SEQ ID NO: 74), L72A (SEQ ID NO: 75), L72D (SEQ ID NO: 76), L72H (SEQ ID NO: 77), L72F (SEQ ID NO: 78), (R38D/E61R) (SEQ ID NO: 79), (R38D/E61R/K43E) (SEQ ID NO: 80), or (T3A/F42A/Y45A/L72G/C125A) (SEQ ID NO: 81). The substitution T3A was introduced into the IL-2 amino acid sequence to remove the predicted O-linked glycosylation site on human IL-2 (see for example Int'l Pub. No. WO2012/107417) and the substitution C125A was introduced into the IL-2 amino acid sequence to remove an unpaired cysteine residue (see for example Int'l Pub. No. WO2018/184964). The IL-2 substitutions studied in Group 2 were predicted to not modulate IL-2 binding to CD132/IL-2-Rγ, nor were these substitutions predicted to modulate binding to more than one of the IL-2 receptor subunits.

Group 3 contained a series of 1H3-hIgG1-L6-hIL-2 fusion proteins which comprised one or more substitutions in human IL-2 which were predicted to be involved in CD122/IL-2Rβ binding only. The fusion proteins in this group included the following substitutions to IL-2 predicted to modulate binding to CD122/IL-2RB: E15A (SEQ ID NO: 82), E15R (SEQ ID NO: 83), E15K (SEQ ID NO: 84), H16A (SEQ ID NO: 85), H16Y (SEQ ID NO: 86), H16E (SEQ ID NO: 87), L19A (SEQ ID NO: 88), D20I (SEQ ID NO: 89), D20S (SEQ ID NO: 90), D20H (SEQ ID NO: 91), D20T (SEQ ID NO: 92), D20W (SEQ ID NO: 93), D20Y (SEQ ID NO: 94), D20R (SEQ ID NO: 95), D20F (SEQ ID NO: 96), R81A (SEQ ID NO: 97), D84A (SEQ ID NO: 98), D84R (SEQ ID NO: 99), D84K (SEQ ID NO: 100), S87A (SEQ ID NO: 101), N88Y (SEQ ID NO: 102), N88D (SEQ ID NO: 103), N88R (SEQ ID NO: 104), N88E (SEQ ID NO: 10$^5$), N88F (SEQ ID NO: 106), N88I (SEQ ID NO: 107), 192A (SEQ ID NO: 108), 192Y (SEQ ID NO: 109), 192S (SEQ ID NO: 110), 192F (SEQ ID NO: 111), 192R (SEQ ID NO: 112), 192D (SEQ ID NO: 113), 192E (SEQ ID NO: 114), E95A (SEQ ID NO: 115), E95R (SEQ ID NO: 116), E95K (SEQ ID NO: 117), (D20Y/H16E) (SEQ ID NO: 118), (D20Y/H16A) (SEQ ID NO: 119), (D20Y/H16Y) (SEQ ID NO: 120), (D20Y/192A) (SEQ ID NO: 121), (D20Y/192S) (SEQ ID NO: 122), (D20Y/192R) (SEQ ID NO: 123), (D20Y/E95R) (SEQ ID NO: 124), or (D20Y/E95A) (SEQ ID NO: 125).

Group 4 contained a series of fusion proteins containing the 1H3-hIgG1-L6-hIL-2 HC fused to a CD25/IL-2Rα extracellular domain moiety (SEQ ID NO: 126), a 20 amino acid linker (L20) (SEQ ID NO: 364), and human IL-2 variants comprising one or more substitutions to residues predicted to be involved in binding to CD122/IL-2Rβ. The fusion proteins in this group included the following substitutions to IL-2 predicted to modulate binding to CD122/IL-2Rβ: E15A (SEQ ID NO: 82), D20I (SEQ ID NO: 89), D20S (SEQ ID NO: 90), D20H (SEQ ID NO: 91), D20W (SEQ ID NO: 93), D20Y (SEQ ID NO: 94), D20R (SEQ ID NO: 95), D20F (SEQ ID NO: 96), D84K (SEQ ID NO: 100), S87A (SEQ ID NO: 101), N88Y (SEQ ID NO: 102), N88D (SEQ ID NO: 103), N88R (SEQ ID NO: 104), N88E (SEQ ID NO: 10$^5$), N88F (SEQ ID NO: 106), N88I (SEQ ID NO: 107), 192A (SEQ ID NO: 108), E95A (SEQ ID NO: 115), or E95K (SEQ ID NO: 117). The antibody-attenuated hIL-2 fusion proteins in this group are denoted as 1H3-hIgG1-L6-hCD25 (1-164)-L20-hIL-2.

Group 5 contained a series of 1H3-hIgG1-L6-hIL-2 which comprised a combination of substitutions in IL-2 which were predicted to be involved in binding of IL-2 to CD25/IL-2Rα and to CD122/IL-2Rβ or CD132/IL-2Rγ. In addition, some variants had a deletion in the first three amino acids at the N-terminus of the hIL-2 moiety (Δ1-3APT). The fusion proteins in Group 5 included the following substitutions to IL-2 predicted to modulate IL-2 binding to CD25/IL-2Rα and to CD122/IL-2Rβ: (F42D/D20A) (SEQ ID NO: 127), (F42R/D20A) (SEQ ID NO: 128), (F42K/D20A) (SEQ ID NO: 129), (F42A/D20A) (SEQ ID NO: 130), (F42H/D20A) (SEQ ID NO: 131), (Y45R/D20A) (SEQ ID NO: 132), (Y45K/D20A) (SEQ ID NO: 133), (R38N/D20A) (SEQ ID NO: 134), (R38G/D20A) (SEQ ID NO: 135), (R38H/D20A) (SEQ ID NO: 136), (R38I/D20A) (SEQ ID NO: 137), (R38L/D20A) (SEQ ID NO: 138), (R38M/D20A) (SEQ ID NO: 139), (R38F/D20A) (SEQ ID NO: 140), (R38P/D20A) (SEQ ID NO: 141), (R38S/D20A) (SEQ ID NO: 142), (R38T/D20A) (SEQ ID NO: 143), (R38W/D20A) (SEQ ID NO: 144), (R38Y/D20A) (SEQ ID NO: 145), (R38V/D20A) (SEQ ID NO: 146), (R38A/D20A) (SEQ ID NO: 147), (R38Q/D20A) (SEQ ID NO: 148), (D20A/R38E) (SEQ ID NO: 149), (R38D/D20A) (SEQ ID NO: 150), (K43E/D20A) (SEQ ID NO: 151), (E61A/D20A) (SEQ ID NO: 152), (E62A/D20A) (SEQ ID NO: 153), (E62Y/D20A) (SEQ ID NO: 154), (L72D/D20A) (SEQ ID NO: 155), (L72H/D20A) (SEQ ID NO: 156), (L72R/D20A) (SEQ ID NO: 157), (F42D/192D) (SEQ ID NO: 158), (F42R/192D) (SEQ ID NO: 159), (F42H/192D) (SEQ ID NO: 160), (F42A/192D) (SEQ ID NO: 161), (H16A/F42A) (SEQ ID NO: 575), (K43E/192D) (SEQ ID NO: 162), (Y45R/192D) (SEQ ID NO: 163), (Y45K/192D) (SEQ ID NO: 164), (E62A/192D) (SEQ ID NO: 165), (E62Y/192D) (SEQ ID NO: 166), (L72D/192D) (SEQ ID NO: 167), (L72H/192D) (SEQ ID NO: 168), (L72R/192D) (SEQ ID NO: 169), (R38D/192D) (SEQ ID NO: 170), (R38E/192D) (SEQ ID NO: 171), (R38Q/192D) (SEQ ID NO: 172), (R38A/192D) (SEQ ID NO: 173), (R38E/N88R) (SEQ ID NO: 174), (R38E/D84R) (SEQ ID NO: 175), (R38E/D84K) (SEQ ID NO: 176), (F42A/Y45R/D20A) (SEQ ID NO: 177), (F42H/Y45R/D20A) (SEQ ID NO: 178), (R38D/E61R/D20A) (SEQ ID NO: 179), (R38E/E61R/D20A) (SEQ ID NO: 180), (R38Q/E61R/D20A) (SEQ ID NO: 181), (R38A/E61R/D20A) (SEQ ID NO: 182), (R38A/D20A/E95A) (SEQ ID NO: 183), (D20A/E95A/R38D) (SEQ ID NO: 184), (D20A/E95A/R38E) (SEQ ID NO: 185), (D20A/E95A/R38Q) (SEQ ID NO: 186), (D20A/E95A/F42R) (SEQ ID NO: 187), (D20A/E95A/F42A) (SEQ ID NO: 188), (D20A/E95A/F42D) (SEQ ID NO: 189), (D20A/E95A/F42H) (SEQ ID NO: 190), (D20A/E95A/F42K) (SEQ ID NO: 191), (D20A/E95A/K43A) (SEQ ID NO: 192), (D20A/E95A/K43E) (SEQ ID NO: 193), (D20A/E95A/K43Q) (SEQ ID NO: 194), (D20A/E95A/Y45A) (SEQ ID NO: 195), (D20A/E95A/Y45K) (SEQ ID NO: 196), (D20A/E95A/Y45S) (SEQ ID NO: 197), (D20A/E95A/Y45R) (SEQ ID NO: 198), (D20A/E95A/E61A) (SEQ ID NO: 199), (D20A/E95A/E62A) (SEQ ID NO: 200), (D20A/E95A/E62R) (SEQ ID NO: 201), (D20A/E95A/E62K) (SEQ ID NO: 202), (D20A/E95A/E62Y) (SEQ ID NO: 203), (D20A/E95A/E68Y) (SEQ ID NO: 204), (D20A/E95A/E68A) (SEQ ID NO: 205), (D20A/E95A/E68L) (SEQ ID NO: 206), (D20A/E95A/L72Y) (SEQ ID NO: 207), (D20A/E95A/L72R) (SEQ ID NO: 208), (D20A/E95A/L72A) (SEQ ID NO: 209), (D20A/E95A/L72D) (SEQ ID NO: 210), (D20A/E95A/L72H) (SEQ ID NO: 211), (D20A/E95A/L72F) (SEQ ID NO: 212), (F42K/Y45R/D20A/S87A) (SEQ ID NO: 213), (F42K/Y45R/D20A/E95A) (SEQ ID NO: 214), (D20A/R38E/C125A) (SEQ ID NO: 215), (T3A/D20A/R38E) (SEQ ID NO: 216), (T3A/D20A/R38E/C125A) (SEQ ID NO: 217), (Δ-3APT/D20A/R38E) (SEQ ID NO: 218), or (Δ-3APT/D20A/R38E/C125A) (SEQ ID NO: 219). The fusion proteins in Group 5 included the following substitutions to IL-2 predicted to modulate IL-2 binding to CD25/IL-2Rα and to CD132/IL-2R: (R38E/Q22A) (SEQ ID NO: 220), (R38E/T123A) (SEQ ID NO: 221), (R38E/1129A) (SEQ ID NO: 222), (R38E/S130A) (SEQ ID NO: 223), (R38E/Q126A) (SEQ ID NO: 224), (R38E/Q126D) (SEQ ID NO: 225), (R38E/Q126V) (SEQ ID NO: 226), (R38E/Q22A/S130A) (SEQ ID NO: 227), (F42K/Y45R/Q126D) (SEQ ID NO: 228), or (D20A/E95A/Q126D) (SEQ ID NO: 229). Mutations to the hIL-2 sequence for Group 5 antibody-attenuated hIL-2 fusion proteins in which the numbering is according to IL-2 sequence are listed in SEQ ID NO: 127-229 and 575.

Group 6 contained a series of 1H3-hIgG1-L6-hIL-2 fusion proteins which comprised a combination of substitutions in human IL-2 which were predicted to be involved in binding of IL-2 to CD25/IL-2Rα and to CD122/IL-2Rβ, but not to CD132/IL-2Rγ. The fusion proteins in Group 6 included the following combination of substitutions in IL-2 predicted to modulate IL-2 binding to CD25/IL-2Rα and CD122/IL-2Rβ: (D20A/E61R) (SEQ ID NO: 230), (D20A/E61N) (SEQ ID NO: 231), (D20A/E61D) (SEQ ID NO: 232), (D20A/E61Q) (SEQ ID NO: 233), (D20A/E61G) (SEQ ID NO: 234), (D20A/E61H) (SEQ ID NO: 235), (D20A/E61I) (SEQ ID NO: 236), (D20A/E61L) (SEQ ID NO: 237), (D20A/E61K) (SEQ ID NO: 238), (D20A/E61M) (SEQ ID NO: 239), (D20A/E61F) (SEQ ID NO: 240), (D20A/E61P) (SEQ ID NO: 241), (D20A/E61S) (SEQ ID NO: 242), (D20A/E61T) (SEQ ID NO: 243), (D20A/E61W) (SEQ ID NO: 244), (D20A/E61Y) (SEQ ID NO: 245), (D20A/E61V) (SEQ ID NO: 246), (D20A/F42N) (SEQ ID NO: 247), (D20A/F42Q) (SEQ ID NO: 248), (D20A/F42E) (SEQ ID NO: 249), (D20A F42G) (SEQ ID NO: 250), (D20A/F42I) (SEQ ID NO: 251), (D20A/F42L) (SEQ ID NO: 252), (D20A/F42M) (SEQ ID NO: 253), (D20A/F42P) (SEQ ID NO: 254), (D20A/F42S) (SEQ ID NO: 255), (D20A/F42T) (SEQ ID NO: 256), (D20A/F42W) (SEQ ID NO: 257), (D20A/F42Y) (SEQ ID NO: 258), (D20A/F42V) (SEQ ID NO: 259), (D20A/Y45A) (SEQ ID NO: 260), (D20A/Y45N) (SEQ ID NO: 261), (D20A/Y45D) (SEQ ID NO: 262), (D20A/Y45Q) (SEQ ID NO: 263), (D20A/Y45E) (SEQ ID NO: 264), (D20A/Y45G) (SEQ ID NO: 265), (D20A/Y45H) (SEQ ID NO: 266), (D20A/Y45I) (SEQ ID NO: 267), (D20A/Y45L) (SEQ ID NO: 268), (D20A/Y45M) (SEQ ID NO: 269), (D20A/Y45F) (SEQ ID NO: 270), (D20A/Y45P) (SEQ ID NO: 271), (D20A/Y45S) (SEQ ID NO: 272), (D20A/Y45T) (SEQ ID NO: 273), (D20A/Y45W) (SEQ ID NO: 274), (D20A/Y45V) (SEQ ID NO: 275), (I92D/F42N) (SEQ ID NO: 276), (I92D/F42Q) (SEQ ID NO: 277), (I92D/F42E) (SEQ ID NO: 278), (I92D/F42G) (SEQ ID NO: 279), (I92D/F42I) (SEQ ID NO: 280), (I92D/F42L) (SEQ ID NO: 281), (I92D/F42K) (SEQ ID NO: 282), (I92D/F42M) (SEQ ID NO: 283), (I92D/F42P) (SEQ ID NO: 284), (I92D/F42S) (SEQ ID NO: 285), (I92D/F42T) (SEQ ID NO: 286), (I92D/F42W) (SEQ ID NO: 287), (I92D/F42Y) (SEQ ID NO: 288), (I92D/F42V) (SEQ ID NO: 289), (I92D/Y45A) (SEQ ID NO: 290), (I92D/Y45N) (SEQ ID NO: 291), (I92D/Y45D) (SEQ ID NO: 292), (I92D/Y45Q) (SEQ ID NO: 293), (I92D/Y45E) (SEQ ID NO: 294), (I92D/Y45G) (SEQ ID NO: 295), (I92D/Y45H) (SEQ ID NO: 296), (I92D/Y45I) (SEQ ID NO: 297), (I92D/Y45L) (SEQ ID NO: 298), (I92D/Y45M) (SEQ ID NO: 299), (I92D/Y45F) (SEQ ID NO: 300), (I92D/Y45P) (SEQ ID NO: 301), (I92D/Y45S) (SEQ ID NO: 302), (I92D/Y45T) (SEQ ID NO: 303), (I92D/Y45W) (SEQ ID NO: 304), (I92D/Y45V) (SEQ ID NO: 305), (R38E/D20H) (SEQ ID NO: 306), (R38E/D20S) (SEQ ID NO: 307), (F42A/N88R) (SEQ ID NO: 308), (F42A/N88D) (SEQ ID NO: 309), (R38E/D84A) (SEQ ID NO: 310), (R38E/D84N) (SEQ ID NO: 311), (R38E/D84Q) (SEQ ID NO: 312), (R38E/D84E) (SEQ ID NO: 313), (R38E/D84G) (SEQ ID NO: 314), (R38E/D84H) (SEQ ID NO: 315), (R38E/D84I) (SEQ ID NO: 316), (R38E/D84L) (SEQ ID NO: 317), (R38E/D84M) (SEQ ID NO: 318), (R38E/D84F) (SEQ ID NO: 319), (R38E/D84P) (SEQ ID NO: 320), (R38E/D84S) (SEQ ID NO: 321), (R38E/D84T) (SEQ ID NO: 322), (R38E/D84W) (SEQ ID NO: 323), (R38E/D84Y) (SEQ ID NO: 324), (R38E/D84V) (SEQ ID NO: 325), (R38E/I92A) (SEQ ID NO: 326), (R38E/I92R) (SEQ ID NO: 327), (R38E/I92N) (SEQ ID NO: 328), (R38E/I92Q) (SEQ ID NO: 329), (R38E/I92E) (SEQ ID NO: 330), (R38E/I92G) (SEQ ID NO: 331), (R38E/I92H) (SEQ ID NO: 332), (R38E/I92L) (SEQ ID NO: 333), (R38E/I92K) (SEQ ID NO: 334), (R38E/I92M) (SEQ ID NO: 335), (R38E/I92F) (SEQ ID NO: 336), (R38E/I92P) (SEQ ID NO: 337), (R38E/I92S) (SEQ ID NO: 338), (R38E/I92T) (SEQ ID NO: 339), (R38E/I92W) (SEQ ID NO: 340), (R38E/I92Y) (SEQ ID NO: 341), (R38E/I92V) (SEQ ID NO: 342), (R38E/H16E) (SEQ ID NO: 343), or (R38K/D20A) (SEQ ID NO: 344). Mutations to the hIL-2 sequence for TABLE 2-continued Binding kinetics of 1H3-hIgG-L6-hIL-2 fusion proteins to recombinant human CD25 or CD122 by Octet BLI

| 1H3-hIgG1-L6-hIL-2 fusion proteins | SEQ ID NO of hIL-2 variant | Predicted receptor sub-unit targeted by IL-2 substitution | $K_D$ (M) | $k_{on}$ (1/Ms) | $k_{off}$ (1/s) |
|---|---|---|---|---|---|
| 1H3-hIgG1-L6-hIL-2 (L19A) | 88 | CD122 | 1.76E−09 | 2.03E+05 | 3.57E−04 |
| 1H3-hIgG1-L6-hIL-2 (D20I) | 89 | CD122 | 1.16E−09 | 1.70E+05 | 1.98E−04 |
| 1H3-hIgG1-L6-hIL-2 (D20S) | 90 | CD122 | 6.24E−10 | 1.74E+05 | 1.09E−04 |
| 1H3-hIgG1-L6-hIL-2 (D20H) | 91 | CD122 | 1.13E−09 | 1.88E+05 | 2.12E−04 |
| 1H3-hIgG1-L6-hIL-2 (D20W) | 93 | CD122 | 1.01E−09 | 1.87E+05 | 1.90E−04 |
| 1H3-hIgG1-L6-hIL-2 (D20Y) | 94 | CD122 | 1.42E−09 | 1.51E+05 | 2.14E−04 |
| 1H3-hIgG1-L6-hIL-2 (D20R) | 95 | CD122 | 1.21E−09 | 1.44E+05 | 1.75E−04 |
| 1H3-hIgG1-L6-hIL-2 (D20F) | 96 | CD122 | 1.57E−09 | 1.75E+05 | 2.75E−04 |
| 1H3-hIgG1-L6-hIL-2 (R38A) | 46 | CD25 | 5.55E−09 | 1.82E+05 | 1.01E−03 |
| 1H3-hIgG1-L6-hIL-2 (R38D) | 47 | CD25 | 1.86E−09 | 8.84E+05 | 1.64E−03 |
| 1H3-hIgG1-L6-hIL-2 (R38E) | 48 | CD25 | 8.74E−09 | 3.31E+05 | 2.89E−03 |
| 1H3-hIgG1-L6-hIL-2 (R38Q) | 49 | CD25 | 6.33E−09 | 4.83E+05 | 3.05E−03 |
| 1H3-hIgG1-L6-hIL-2 (F42R) | 50 | CD25 | 2.63E−09 | 1.59E+06 | 4.20E−03 |
| 1H3-hIgG1-L6-hIL-2 (F42A) | 51 | CD25 | 9.25E−09 | 9.89E+05 | 9.15E−03 |
| 1H3-hIgG1-L6-hIL-2 (F42D) | 52 | CD25 | 4.51E−09 | 1.70E+06 | 7.64E−03 |
| 1H3-hIgG1-L6-hIL-2 (F42H) | 53 | CD25 | 6.84E−09 | 8.23E+05 | 5.63E−03 |
| 1H3-hIgG1-L6-hIL-2 (K43A) | 54 | CD25 | 4.79E−09 | 2.59E+05 | 1.24E−03 |
| 1H3-hIgG1-L6-hIL-2 (K43E) | 55 | CD25 | 5.66E−09 | 4.52E+05 | 2.56E−03 |
| 1H3-hIgG1-L6-hIL-2 (K43Q) | 56 | CD25 | 2.28E−09 | 4.49E+05 | 1.02E−03 |
| 1H3-hIgG1-L6-hIL-2 (Y45A) | 57 | CD25 | 3.66E−09 | 4.29E+05 | 1.57E−03 |
| 1H3-hIgG1-L6-hIL-2 (Y45K) | 58 | CD25 | 9.03E−09 | 5.22E+05 | 4.71E−03 |
| 1H3-hIgG1-L6-hIL-2 (Y45S) | 59 | CD25 | 2.45E−09 | 5.05E+05 | 1.24E−03 |
| 1H3-hIgG1-L6-hIL-2 (Y45R) | 60 | CD25 | 1.96E−09 | 6.46E+05 | 1.27E−03 |
| 1H3-hIgG1-L6-hIL-2 (E61A) | 61 | CD25 | 7.00E−09 | 3.21E+05 | 2.25E−03 |
| 1H3-hIgG1-L6-hIL-2 (E61R) | 62 | CD25 | 8.84E−09 | 1.22E+06 | 1.08E−02 |
| 1H3-hIgG1-L6-hIL-2 (E61K) | 63 | CD25 | 1.56E−08 | 3.16E+05 | 4.94E−03 |
| 1H3-hIgG1-L6-hIL-2 (E62A) | 64 | CD25 | 1.23E−08 | 3.79E+05 | 4.67E−03 |
| 1H3-hIgG1-L6-hIL-2 (E62R) | 65 | CD25 | No binding observed | | |
| 1H3-hIgG1-L6-hIL-2 (E62K) | 66 | CD25 | No binding observed | | |
| 1H3-hIgG1-L6-hIL-2 (E62Y) | 67 | CD25 | 1.55E−08 | 2.91E+05 | 4.50E−03 |
| 1H3-hIgG1-L6-hIL-2 (E68Y) | 68 | CD25 | 8.18E−09 | 1.80E+05 | 1.47E−03 |
| 1H3-hIgG1-L6-hIL-2 (E68A) | 69 | CD25 | 4.49E−09 | 1.45E+05 | 6.52E−04 |
| 1H3-hIgG1-L6-hIL-2 (E68K) | 70 | CD25 | 9.63E−09 | 2.54E+05 | 2.44E−03 |
| 1H3-hIgG1-L6-hIL-2 (E68R) | 71 | CD25 | 1.16E−08 | 2.54E+05 | 2.96E−03 |
| 1H3-hIgG1-L6-hIL-2 (E68L) | 72 | CD25 | 8.62E−09 | 1.02E+05 | 8.82E−04 |
| 1H3-hIgG1-L6-hIL-2 (I92R) | 112 | CD122 | 2.54E−09 | 1.08E+05 | 2.76E−04 |

TABLE 2-continued

Binding kinetics of 1H3-hIgG-L6-hIL-2 fusion proteins to recombinant human CD25 or CD122 by Octet BLI

| 1H3-hIgG1-L6-hIL-2 fusion proteins | SEQ ID NO of hIL-2 variant | Predicted receptor sub-unit targeted by IL-2 substitution | $K_D$ (M) | $k_{on}$ (1/Ms) | $k_{off}$ (1/s) |
|---|---|---|---|---|---|
| 1H3-hIgG1-L6-hIL-2 (I92D) | 113 | CD122 | 7.94E−09 | 4.95E+04 | 3.93E−04 |
| 1H3-hIgG1-L6-hIL-2 (I92E) | 114 | CD122 | 2.41E−09 | 8.54E+04 | 2.06E−04 |
| 1H3-hIgG1-L6-hIL-2 (E95A) | 115 | CD122 | 3.11E−09 | 1.47E+05 | 4.58E−04 |
| 1H3-hIgG1-L6-hIL-2 (E95R) | 116 | CD122 | 2.29E−09 | 1.14E+05 | 2.61E−04 |
| 1H3-hIgG1-L6-hIL-2 (E95K) | 117 | CD122 | 3.25E−09 | 1.25E+05 | 4.07E−04 |
| 1H3-hIgG1-L6-hIL-2 (F42K/Y45R/D20A/S87A) | 213 | CD25 + CD122 | 3.25E−08 | 1.24E+05 | 4.05E−03 |
| 1H3-hIgG1-L6-hIL-2 (F42K/Y45R/D20A/E95A) | 214 | CD25 + CD122 | No binding observed | | |
| 1H3-hIgG1-L6-hIL-2 (F42K/Y45R/Q126D) | 228 | CD25 + CD132 | No binding observed | | |
| 1H3-hIgG1-L6-hIL-2 (D20A/E95A/Q126D) | 229 | CD122 + CD132 | 3.34E−09 | 4.87E+04 | 1.62E−04 |
| 1H3-hIgG1-L6-hIL-2 (R38D/E61R) | 79 | CD25 | No binding observed | | |
| 1H3-hIgG1-L6-hIL-2 (R38D/E61R/K43E) | 80 | CD25 | No binding observed | | |

Table 3 documents the association (kon) constants, dissociation (kofr) constants, and equilibrium constants ($K_D$)) of 74 1H3-hIgG1-L6-hIL-2 fusion proteins bound to recombinant human CD122.

TABLE 3

Binding kinetics of 1H3-hIgG-L6-hIL-2 fusion proteins to recombinant human CD122 by Octet BLI

| 1H3-hIgG-L6-hIL-2 fusion proteins | SEQ ID NO of hIL-2 variant | Predicted receptor sub-unit targeted by IL-2 substitution | $K_D$ (M) | $k_{on}$ (1/Ms) | $k_{off}$ (1/s) |
|---|---|---|---|---|---|
| 1H3-hIgG1-L6-hIL-2 WT | 345[a] | N/A | 5.60E−09 | 7.00E+05 | 3.90E−03 |
| 1H3-hIgG1-L6-hIL-2 (E15A) | 82[b] | CD122 | 8.89E−09 | 1.75E+05 | 1.56E−03 |
| 1H3-hIgG1-L6-hIL-2 (E15R) | 83 | CD122 | 3.69E−09 | 1.46E+05 | 5.38E−04 |
| 1H3-hIgG1-L6-hIL-2 (E15K) | 84 | CD122 | 3.56E−09 | 2.42E+05 | 8.62E−04 |
| 1H3-hIgG1-L6-hIL-2 (H16A) | 85 | CD122 | 1.78E−09 | 1.55E+06 | 2.76E−03 |
| 1H3-hIgG1-L6-hIL-2 (H16Y) | 86 | CD122 | 4.36E−09 | 9.97E+05 | 4.35E−03 |
| 1H3-hIgG1-L6-hIL-2 (H16E) | 87 | CD122 | No binding observed | | |
| 1H3-hIgG1-L6-hIL-2 (L19A) | 88 | CD122 | 1.03E−08 | 4.72E+05 | 4.87E−03 |
| 1H3-hIgG1-L6-hIL-2 (D20I) | 89 | CD122 | No binding observed | | |
| 1H3-hIgG1-L6-hIL-2 (D20S) | 90 | CD122 | No binding observed | | |
| 1H3-hIgG1-L6-hIL-2 (D20H) | 91 | CD122 | No binding observed | | |
| 1H3-hIgG1-L6-hIL-2 (D20W) | 93 | CD122 | No binding observed | | |
| 1H3-hIgG1-L6-hIL-2 (D20Y) | 94 | CD122 | No binding observed | | |
| 1H3-hIgG1-L6-hIL-2 (D20R) | 95 | CD122 | No binding observed | | |
| 1H3-hIgG1-L6-hIL-2 (D20F) | 96 | CD122 | No binding observed | | |
| 1H3-hIgG1-L6-hIL-2 (R38A) | 46 | CD25 | 1.38E−08 | 2.08E+05 | 2.87E−03 |

TABLE 3-continued

Binding kinetics of 1H3-hIgG-L6-hIL-2 fusion proteins to recombinant human CD122 by Octet BLI

| 1H3-hIgG-L6-hIL-2 fusion proteins | SEQ ID NO of hIL-2 variant | Predicted receptor sub-unit targeted by IL-2 substitution | $K_D$ (M) | $k_{on}$ (1/Ms) | $k_{off}$ (1/s) |
|---|---|---|---|---|---|
| 1H3-hIgG1-L6-hIL-2 (R38D) | 47 | CD25 | 2.20E−09 | 4.28E+05 | 9.42E−04 |
| 1H3-hIgG1-L6-hIL-2 (R38E) | 48 | CD25 | 5.81E−09 | 4.64E+05 | 2.69E−03 |
| 1H3-hIgG1-L6-hIL-2 (R38Q) | 49 | CD25 | 1.01E−09 | 2.81E+05 | 2.84E−04 |
| 1H3-hIgG1-L6-hIL-2 (F42R) | 50 | CD25 | 5.47E−09 | 5.42E+05 | 2.96E−03 |
| 1H3-hIgG1-L6-hIL-2 (F42A) | 51 | CD25 | 5.97E−09 | 4.19E+05 | 2.50E−03 |
| 1H3-hIgG1-L6-hIL-2 (F42D) | 52 | CD25 | 1.04E−08 | 2.38E+05 | 2.46E−03 |
| 1H3-hIgG1-L6-hIL-2 (F42H) | 53 | CD25 | 6.33E−09 | 4.45E+05 | 2.81E−03 |
| 1H3-hIgG1-L6-hIL-2 (K43A) | 54 | CD25 | 1.03E−08 | 2.85E+05 | 2.94E−03 |
| 1H3-hIgG1-L6-hIL-2 (K43E) | 55 | CD25 | 5.47E−09 | 3.65E+05 | 2.00E−03 |
| 1H3-hIgG1-L6-hIL-2 (K43Q) | 56 | CD25 | 4.21E−09 | 5.14E+05 | 2.17E−03 |
| 1H3-hIgG1-L6-hIL-2 (Y45A) | 57 | CD25 | 4.93E−09 | 4.51E+05 | 2.22E−03 |
| 1H3-hIgG1-L6-hIL-2 (Y45K) | 58 | CD25 | 6.56E−09 | 3.55E+05 | 2.33E−03 |
| 1H3-hIgG1-L6-hIL-2 (Y45S) | 59 | CD25 | 6.96E−09 | 5.07E+05 | 3.53E−03 |
| 1H3-hIgG1-L6-hIL-2 (Y45R) | 60 | CD25 | 7.58E−09 | 4.36E+05 | 3.31E−03 |
| 1H3-hIgG1-L6-hIL-2 (E61A) | 61 | CD25 | 1.34E−08 | 3.13E+05 | 4.18E−03 |
| 1H3-hIgG1-L6-hIL-2 (E61R) | 62 | CD25 | 1.30E−08 | 4.56E+05 | 5.91E−03 |
| 1H3-hIgG1-L6-hIL-2 (E61K) | 63 | CD25 | 1.56E−08 | 3.16E+05 | 4.94E−03 |
| 1H3-hIgG1-L6-hIL-2 (E62A) | 64 | CD25 | 1.23E−08 | 3.79E+05 | 4.67E−03 |
| 1H3-hIgG1-L6-hIL-2 (E62R) | 65 | CD25 | No binding observed | | |
| 1H3-hIgG1-L6-hIL-2 (E62K) | 66 | CD25 | No binding observed | | |
| 1H3-hIgG1-L6-hIL-2 (E62Y) | 67 | CD25 | 1.55E−08 | 2.91E+05 | 4.50E−03 |
| 1H3-hIgG1-L6-hIL-2 (E68Y) | 68 | CD25 | 8.18E−09 | 1.80E+05 | 1.47E−03 |
| 1H3-hIgG1-L6-hIL-2 (E68A) | 69 | CD25 | 4.49E−09 | 1.45E+05 | 6.52E−04 |
| 1H3-hIgG1-L6-hIL-2 (E68K) | 70 | CD25 | 1.05E−08 | 2.02E+05 | 2.12E−03 |
| 1H3-hIgG1-L6-hIL-2 (E68R) | 71 | CD25 | 8.51E−09 | 2.27E+05 | 1.93E−03 |
| 1H3-hIgG1-L6-hIL-2 (E68L) | 72 | CD25 | 2.72E−09 | 7.79E+04 | 2.12E−04 |
| 1H3-hIgG1-L6-hIL-2 (L72Y) | 73 | CD25 | 6.39E−09 | 1.94E+05 | 1.24E−03 |
| 1H3-hIgG1-L6-hIL-2 (L72R) | 74 | CD25 | 1.96E−08 | 3.07E+04 | 6.01E−04 |
| 1H3-hIgG1-L6-hIL-2 (L72A) | 75 | CD25 | 9.08E−09 | 1.47E+05 | 1.34E−03 |
| 1H3-hIgG1-L6-hIL-2 (L72D) | 76 | CD25 | 9.52E−09 | 1.57E+05 | 1.50E−03 |
| 1H3-hIgG1-L6-hIL-2 (L72H) | 77 | CD25 | 9.03E−09 | 1.65E+05 | 1.49E−03 |
| 1H3-hIgG1-L6-hIL-2 (L72F) | 78 | CD25 | 5.04E−09 | 2.28E+05 | 1.15E−03 |
| 1H3-hIgG1-L6-hIL-2 (R81A) | 97 | CD122 | 7.08E−09 | 2.20E+05 | 1.56E−03 |
| 1H3-hIgG1-L6-hIL-2 (D84A) | 98 | CD122 | No binding observed | | |
| 1H3-hIgG1-L6-hIL-2 (D84R) | 99 | CD122 | 1.88E−08 | 4.73E+05 | 8.88E−03 |
| 1H3-hIgG1-L6-hIL-2 (S87A) | 101 | CD122 | 7.09E−09 | 3.31E+05 | 2.34E−03 |

TABLE 3-continued

Binding kinetics of 1H3-hIgG-L6-hIL-2 fusion proteins to recombinant human CD122 by Octet BLI

| 1H3-hIgG-L6-hIL-2 fusion proteins | SEQ ID NO of hIL-2 variant | Predicted receptor sub-unit targeted by IL-2 substitution | $K_D$ (M) | $k_{on}$ (1/Ms) | $k_{off}$ (1/s) |
|---|---|---|---|---|---|
| 1H3-hIgG1-L6-hIL-2 (N88Y) | 102 | CD122 | No binding observed | | |
| 1H3-hIgG1-L6-hIL-2 (N88D) | 103 | CD122 | No binding observed | | |
| 1H3-hIgG1-L6-hIL-2 (N88R) | 104 | CD122 | No binding observed | | |
| 1H3-hIgG1-L6-hIL-2 (N88E) | 105 | CD122 | No binding observed | | |
| 1H3-hIgG1-L6-hIL-2 (N88F) | 106 | CD122 | No binding observed | | |
| 1H3-hIgG1-L6-hIL-2 (N88I) | 107 | CD122 | No binding observed | | |
| 1H3-hIgG1-L6-hIL-2 (I92A) | 108 | CD122 | 3.38E−09 | 1.95E+06 | 6.58E−03 |
| 1H3-hIgG1-L6-hIL-2 (I92Y) | 109 | CD122 | 1.23E−08 | 4.53E+05 | 5.57E−03 |
| 1H3-hIgG1-L6-hIL-2 (I92S) | 110 | CD122 | No binding observed | | |
| 1H3-hIgG1-L6-hIL-2 (I92F) | 111 | CD122 | 5.45E−09 | 1.03E+05 | 5.59E−04 |
| 1H3-hIgG1-L6-hIL-2 (I92R) | 112 | CD122 | No binding observed | | |
| 1H3-hIgG1-L6-hIL-2 (I92D) | 113 | CD122 | No binding observed | | |
| 1H3-hIgG1-L6-hIL-2 (I92E) | 114 | CD122 | 1.62E−09 | 9.33E+05 | 1.51E−03 |
| 1H3-hIgG1-L6-hIL-2 (E95A) | 115 | CD122 | 8.17E−09 | 2.87E+05 | 2.35E−03 |
| 1H3-hIgG1-L6-hIL-2 (E95R) | 116 | CD122 | No binding observed | | |
| 1H3-hIgG1-L6-hIL-2 (E95K) | 117 | CD122 | 3.81E−09 | 6.58E+05 | 2.51E−03 |
| 1H3-hIgG1-L6-hIL-2 (F42K/Y45R/D20A/S87A) | 213 | CD25 + CD122 | No binding observed | | |
| 1H3-hIgG1-L6-hIL-2 (F42K/Y45R/D20A/E95A) | 214 | CD25 + CD122 | No binding observed | | |
| 1H3-hIgG1-L6-hIL-2 (F42K/Y45R/Q126D) | 228 | CD25 +CD132 | 9.16E−09 | 3.75E+05 | 3.44E−03 |
| 1H3-hIgG1-L6-hIL-2 (D20A/E95A/Q126D) | 229 | CD122 + CD132 | No binding observed | | |
| 1H3-hIgG1-L6-hIL-2 (R38D/E61R) | 79 | CD25 | 1.29E−08 | 3.68E+05 | 4.73E−03 |
| 1H3-hIgG1-L6-hIL-2 (R38D/E61R/K43E) | 80 | CD25 | 7.47E−09 | 4.52E+05 | 3.38E−03 |

[a]SEQ ID NO: 345 corresponds to wild type hIL-2.
[b]SEQ ID NO: 57 is attenuated IL-2 sequence only.

Example 3: Testing for Attenuation for the High-Affinity and Intermediate-Affinity hIL-2 Receptor with a Fixed Concentration Cell-Based Potency pSTAT5 Screen The attenuation of antibody-attenuated hIL-2 fusion proteins described in Example 2 was tested in a fixed concentration pSTAT5 screen using the NK-92 (expressing the high affinity hIL-2 receptor) and TF1+IL-2Rβ (expressing the intermediate affinity hIL-2 receptor) cell lines as described in Protocol D. Tables 4-8 list the fold change of geometric mean fluorescent intensity (gMFI) of antibody-attenuated hIL-2 fusion proteins from free cytokine wild-type rhIL-2, a measurement of reduction of IL-2 activity. For the fixed concentration screen, the fold change was calculated by dividing the gMFI of the rhIL-2 by the gMFI of the variants. For experiments with full titration curves, fold change from rhIL-2 was calculated by dividing the $EC_{50}$ values for the rhIL-2 by the $EC_{50}$ of variants. Fold change was rounded to the nearest whole number. A reduced gMFI in both NK-92 and TF1+IL-2Rβ cell lines when compared to the gMFI resulting from rhIL-2 was indicative of attenuation of IL-2 activity at both the high- and intermediate-affinity receptors. Group 1 variants described in Example 2 were not tested in the fixed concentration cell-based potency pSTAT5 screen.

Each variant tested was also assessed for IL-2 agonistic activity and characterized either as a full or partial IL-2 agonist, or having no IL-2 activity (inactive). 1H3-hIgG1-L6-hIL-2 fusion protein dose-titration curves that reached the maximal gMFI level exhibited by the rhIL-2 positive control were considered to be antibody-attenuated hIL-2 fusion protein with full agonist activity. Partial agonist activity was calculated as a percentage of full activity using rhIL-2 maximal gMFI as 100%. Antibody-attenuated hIL-2 fusion protein with less than 10% of the rhIL-2 maximal gMFI at the highest concentration of 1200 nM were considered to have no agonist activity (inactive). Some $EC_{50}$ values and level of attenuation could not be accurately calculated using the GraphPad Prism 7 software since activity did not reach a maximum and accordingly these values are an estimate.

pSTAT5 fixed concentration results demonstrated that while some single residue substitutions attenuated IL-2 activity on the high-affinity cell line (NK-92), a combination of substitutions which modulated binding to both the alpha chain and the beta chain or both the alpha chain and gamma chain were required to substantially attenuate IL-2 activity on the high affinity IL-2 receptor (more than 20-fold attenuation from recombinant hIL-2).

TABLE 4

Fold change from rhIL-2 in a fixed concentration pSTAT5 screen on 1H3-hIgG1-L6-hIL-2 fusion proteins from Group 2

| Variants | SEQ ID NO of hIL-2 variant | Fold change from hIL-2 (NK-92) | Fold change from hIL-2 (TF1 + IL-2Rβ) |
|---|---|---|---|
| 1H3-hIgG1-L6-hIL-2 (R38D) | 47 | 7 | 1 |
| 1H3-hIgG1-L6-hIL-2 (R38E) | 48 | 12 | 1 |
| 1H3-hIgG1-L6-hIL-2 (R38Q) | 49 | 1 | 1 |
| 1H3-hIgG1-L6-hIL-2 (F42R) | 50 | 7 | 1 |
| 1H3-hIgG1-L6-hIL-2 (F42A) | 51 | 1 | 1 |
| 1H3-hIgG1-L6-hIL-2 (F42H) | 53 | 1 | 1 |
| 1H3-hIgG1-L6-hIL-2 (K43E) | 55 | 1 | 1 |
| 1H3-hIgG1-L6-hIL-2 (K43Q) | 56 | 1 | 1 |
| 1H3-hIgG1-L6-hIL-2 (Y45A) | 57 | 1 | 1 |
| 1H3-hIgG1-L6-hIL-2 (Y45K) | 58 | 1 | 1 |
| 1H3-hIgG1-L6-hIL-2 (Y45S) | 59 | 1 | 1 |
| 1H3-hIgG1-L6-hIL-2 (Y45R) | 60 | 10 | 1 |
| 1H3-hIgG1-L6-hIL-2 (E68Y) | 68 | 1 | 1 |
| 1H3-hIgG1-L6-hIL-2 (E68A) | 69 | 1 | 1 |
| 1H3-hIgG1-L6-hIL-2 (E68L) | 72 | 2 | 1 |
| 1H3-hIgG1-L6-hIL-2 (L72Y) | 73 | 1 | 1 |
| 1H3-hIgG1-L6-hIL-2 (L72A) | 75 | 1 | 1 |
| 1H3-hIgG1-L6-hIL-2 (L72F) | 78 | 1 | 1 |
| 1H3-hIgG1-L6-hIL-2 (R38D/E61R) | 79 | NT-1 | 1 |
| 1H3-hIgG1-L6-hIL-2 (R38D/E61R/K43E) | 80 | NT-1 | 1 |
| 1H3-hIgG1-L6-hIL-2 (T3A/F42A/Y45A/L72G/C125A) | 81 | 10 | 1 |

NT-1 = Already tested in pSTAT5 full titration first, no data for fixed concentration assay.

TABLE 5

Fold change from rhIL-2 in a fixed concentration pSTAT5 screen on 1H3-hIgG1-L6-hIL-2 fusion proteins from Group 3

| Variants | SEQ ID NO of hIL-2 variant | Fold change from hIL-2 (NK-92) | Fold change from hIL-2 (TF1 + IL-2Rβ) |
|---|---|---|---|
| 1H3-hIgG1-L6-hIL-2 (E15A) | 82 | 1 | 1 |
| 1H3-hIgG1-L6-hIL-2 (E15R) | 83 | 1 | 1 |
| 1H3-hIgG1-L6-hIL-2 (E15K) | 84 | 1 | 1 |
| 1H3-hIgG1-L6-hIL-2 (H16A) | 85 | 1 | 1 |
| 1H3-hIgG1-L6-hIL-2 (H16Y) | 86 | 1 | 1 |
| 1H3-hIgG1-L6-hIL-2 (H16E) | 87 | 1 | NT-1 |
| 1H3-hIgG1-L6-hIL-2 (L19A) | 88 | 1 | NT-1 |
| 1H3-hIgG1-L6-hIL-2 (D20I) | 89 | 12 | NT-1 |
| 1H3-hIgG1-L6-hIL-2 (D20S) | 90 | 4 | NT-1 |
| 1H3-hIgG1-L6-hIL-2 (D20H) | 91 | 10 | NT-1 |
| 1H3-hIgG1-L6-hIL-2 (D20W) | 93 | 16 | NT-1 |
| 1H3-hIgG1-L6-hIL-2 (D20Y) | 94 | 17 | NT-1 |
| 1H3-hIgG1-L6-hIL-2 (D20R) | 95 | 19 | NT-1 |
| 1H3-hIgG1-L6-hIL-2 (D20F) | 96 | 17 | NT-1 |
| 1H3-hIgG1-L6-hIL-2 (R81A) | 97 | 1 | 1 |
| 1H3-hIgG1-L6-hIL-2 (D84A) | 98 | 1 | NT-1 |
| 1H3-hIgG1-L6-hIL-2 (D84R) | 99 | 3 | NT-1 |
| 1H3-hIgG1-L6-hIL-2 (D84K) | 100 | 2 | NT-1 |
| 1H3-hIgG1-L6-hIL-2 (S87A) | 101 | 1 | 1 |
| 1H3-hIgG1-L6-hIL-2 (N88Y) | 102 | 22 | NT-1 |
| 1H3-hIgG1-L6-hIL-2 (N88D) | 103 | 2 | NT-1 |
| 1H3-hIgG1-L6-hIL-2 (N88R) | 104 | 3 | NT-1 |
| 1H3-hIgG1-L6-hIL-2 (N88E) | 105 | 10 | NT-1 |
| 1H3-hIgG1-L6-hIL-2 (N88F) | 106 | 19 | NT-1 |
| 1H3-hIgG1-L6-hIL-2 (N88I) | 107 | 9 | NT-1 |
| 1H3-hIgG1-L6-hIL-2 (I92A) | 108 | 1 | 1 |
| 1H3-hIgG1-L6-hIL-2 (I92Y) | 109 | 1 | NT-1 |
| 1H3-hIgG1-L6-hIL-2 (I92S) | 110 | 1 | NT-1 |
| 1H3-hIgG1-L6-hIL-2 (I92F) | 111 | 1 | 1 |
| 1H3-hIgG1-L6-hIL-2 (I92R) | 112 | 1 | NT-1 |
| 1H3-hIgG1-L6-hIL-2 (I92D) | 113 | 3 | NT-1 |
| 1H3-hIgG1-L6-hIL-2 (I92E) | 114 | 1 | 1 |
| 1H3-hIgG1-L6-hIL-2 (E95A) | 115 | 1 | 1 |
| 1H3-hIgG1-L6-hIL-2 (E95R) | 116 | 1 | NT-1 |
| 1H3-hIgG1-L6-hIL-2 (E95K) | 117 | 1 | 1 |
| 1H3-hIgG1-L6-hIL-2 (D20T) | 92 | 3 | 2 |
| 1H3-hIgG1-L6-hIL-2 (D20A) | 31 | 7 | 2 |
| 1H3-hIgG1-L6-hIL-2 (D20Y/H16E) | 118 | 6 | 4 |
| 1H3-hIgG1-L6-hIL-2 (D20Y/H16A) | 119 | 10 | 3 |
| 1H3-hIgG1-L6-hIL-2 (D20Y/H16Y) | 120 | 10 | 4 |
| 1H3-hIgG1-L6-hIL-2 (D20Y/I92A) | 121 | 11 | 4 |
| 1H3-hIgG1-L6-hIL-2 (D20Y/I92S) | 122 | 11 | 4 |
| 1H3-hIgG1-L6-hIL-2 (D20Y/I92R) | 123 | 12 | 5 |
| 1H3-hIgG1-L6-hIL-2 (D20Y/E95R) | 124 | 12 | 5 |
| 1H3-hIgG1-L6-hIL-2 (D20Y/E95A) | 125 | 11 | 5 |

NT-1 = Already tested in pSTAT5 full titration first, no data for fixed concentration assay.

TABLE 6

Fold change from rhIL-2 in a fixed concentration pSTAT5 screen on 1H3-hIgG1-L6-hIL-2 fusion proteins from Group 4

| Variants | SEQ ID NO of hIL-2 variant | Fold change from hIL-2 (NK-92) | Fold change from hIL-2 (TF1 + IL-2Rβ) |
|---|---|---|---|
| 1H3-hIgG1-L6-hCD25(1-164)-L20-hIL-2 (E15A) | 82 | 17 | 1 |
| 1H3-hIgG1-L6-hCD25(1-164)-L20-hIL-2 (D20I) | 89 | 21 | 15 |
| 1H3-hIgG1-L6-hCD25(1-164)-L20-hIL-2 (D20S) | 90 | 2 | 14 |
| 1H3-hIgG1-L6-hCD25(1-164)-L20-hIL-2 (D20H) | 91 | 22 | 15 |
| 1H3-hIgG1-L6-hCD25(1-164)-L20-hIL-2 (D20W) | 93 | 23 | 15 |
| 1H3-hIgG1-L6-hCD25(1-164)-L20-hIL-2 (D20Y) | 94 | 23 | 16 |
| 1H3-hIgG1-L6-hCD25(1-164)-L20-hIL-2 (D20R) | 95 | 23 | 16 |
| 1H3-hIgG1-L6-hCD25(1-164)-L20-hIL-2 (D20F) | 96 | 23 | 18 |
| 1H3-hIgG1-L6-hCD25(1-164)-L20-hIL-2 (D84K) | 100 | 23 | 17 |
| 1H3-hIgG1-L6-hCD25(1-164)-L20-hIL-2 (S87A) | 101 | 17 | 2 |
| 1H3-hIgG1-L6-hCD25(1-164)-L20-hIL-2 (N88Y) | 102 | 23 | 18 |
| 1H3-hIgG1-L6-hCD25(1-164)-L20-hIL-2 (N88D) | 103 | 23 | 17 |

TABLE 6-continued

Fold change from rhIL-2 in a fixed concentration pSTAT5 screen on 1H3-hIgG1-L6-hIL-2 fusion proteins from Group 4

| Variants | SEQ ID NO of hIL-2 variant | Fold change from hIL-2 (NK-92) | Fold change from hIL-2 (TF1 + IL-2Rβ) |
|---|---|---|---|
| 1H3-hIgG1-L6-hCD25(1-164)-L20-hIL-2 (N88R) | 104 | 24 | 17 |
| 1H3-hIgG1-L6-hCD25(1-164)-L20-hIL-2 (N88E) | 105 | 25 | 18 |
| 1H3-hIgG1-L6-hCD25(1-164)-L20-hIL-2 (N88F) | 106 | 25 | 18 |
| 1H3-hIgG1-L6-hCD25(1-164)-L20-hIL-2 (N88I) | 107 | 25 | 20 |
| 1H3-hIgG1-L6-hCD25(1-164)-L20-hIL-2 I192A) | 108 | 15 | 3 |
| 1H3-hIgG1-L6-hCD25(1-164)-L20-hIL-2 (E95A) | 115 | 14 | 1 |
| 1H3-hIgG1-L6-hCD25(1-164)-L20-hIL-2 (E95K) | 117 | 25 | 8 |

TABLE 7

Fold change from rhIL-2 in a fixed concentration pSTAT5 screen on 1H3-hIgG1-L6-hIL-2 fusion proteins from Group 5

| Variants | SEQ ID NO of hIL-2 variant | Fold change from hIL-2 (NK-92) | Fold change from hIL-2 (TF1 + IL-2Rβ) |
|---|---|---|---|
| 1H3-hIgG1-L6-hIL-2 (F42D/D20A) | 127 | 11 | 3 |
| 1H3-hIgG1-L6-hIL-2 (F42R/D20A) | 128 | 10 | 2 |
| 1H3-hIgG1-L6-hIL-2 (F42K/D20A) | 129 | 10 | 4 |
| 1H3-hIgG1-L6-hIL-2 (F42A/D20A) | 130 | 11 | 3 |
| 1H3-hIgG1-L6-hIL-2 (F42H/D20A) | 131 | 12 | 2 |
| 1H3-hIgG1-L6-hIL-2 (Y45R/D20A) | 132 | 11 | 1 |
| 1H3-hIgG1-L6-hIL-2 (Y45K/D20A) | 133 | 11 | 2 |
| 1H3-hIgG1-L6-hIL-2 (R38N/D20A) | 134 | 14 | 3 |
| 1H3-hIgG1-L6-hIL-2 (R38G/D20A) | 135 | 13 | 2 |
| 1H3-hIgG1-L6-hIL-2 (R38H/D20A) | 136 | 12 | 3 |
| 1H3-hIgG1-L6-hIL-2 (R38I/D20A) | 137 | 11 | 3 |
| 1H3-hIgG1-L6-hIL-2 (R38L/D20A) | 138 | 11 | 4 |
| 1H3-hIgG1-L6-hIL-2 (R38M/D20A) | 139 | 11 | 3 |
| 1H3-hIgG1-L6-hIL-2 (R38F/D20A) | 140 | 12 | 3 |
| 1H3-hIgG1-L6-hIL-2 (R38P/D20A) | 141 | 13 | 3 |
| 1H3-hIgG1-L6-hIL-2 (R38S/D20A) | 142 | 15 | 2 |
| 1H3-hIgG1-L6-hIL-2 (R38T/D20A) | 143 | 13 | 3 |
| 1H3-hIgG1-L6-hIL-2 (R38W/D20A) | 144 | 14 | 2 |
| 1H3-hIgG1-L6-hIL-2 (R38Y/D20A) | 145 | 14 | 3 |
| 1H3-hIgG1-L6-hIL-2 (R38V/D20A) | 146 | 12 | 3 |
| 1H3-hIgG1-L6-hIL-2 (R38A/D20A) | 147 | 13 | 3 |
| 1H3-hIgG1-L6-hIL-2 (R38Q/D20A) | 148 | 14 | 3 |
| 1H3-hIgG1-L6-hIL-2 (R38E/D20A) | 149 | 15 | 3 |
| 1H3-hIgG1-L6-hIL-2 (R38D/D20A) | 150 | 15 | 3 |
| 1H3-hIgG1-L6-hIL-2 (K43E/D20A) | 151 | 13 | 2 |
| 1H3-hIgG1-L6-hIL-2 (E61A/D20A) | 152 | 14 | 2 |
| 1H3-hIgG1-L6-hIL-2 (E62A/D20A) | 153 | 14 | 2 |
| 1H3-hIgG1-L6-hIL-2 (E62Y/D20A) | 154 | 14 | 3 |
| 1H3-hIgG1-L6-hIL-2 (L72D/D20A) | 155 | 14 | 2 |
| 1H3-hIgG1-L6-hIL-2 (L72H/D20A) | 156 | 14 | 3 |
| 1H3-hIgG1-L6-hIL-2 (L72R/D20A) | 157 | 10 | 3 |
| 1H3-hIgG1-L6-hIL-2 (F42D/I92D) | 158 | 12 | 5 |
| 1H3-hIgG1-L6-hIL-2 (F42R/I92D) | 159 | 12 | 3 |
| 1H3-hIgG1-L6-hIL-2 (F42H/I92D) | 160 | 12 | 2 |
| 1H3-hIgG1-L6-hIL-2 (F42A/I92D) | 161 | 12 | 3 |
| 1H3-hIgG1-L6-hIL-2 (K43E/I92D) | 162 | 13 | 4 |
| 1H3-hIgG1-L6-hIL-2 (Y45R/I92D) | 163 | 13 | 1 |
| 1H3-hIgG1-L6-hIL-2 (Y45K/I92D) | 164 | 13 | 1 |
| 1H3-hIgG1-L6-hIL-2 (E62A/I92D) | 165 | 13 | 3 |
| 1H3-hIgG1-L6-hIL-2 (E62Y/I92D) | 166 | 14 | 5 |
| 1H3-hIgG1-L6-hIL-2 (L72D/I92D) | 167 | 14 | 5 |
| 1H3-hIgG1-L6-hIL-2 (L72H/I92D) | 168 | 14 | 5 |
| 1H3-hIgG1-L6-hIL-2 (L72R/I92D) | 169 | 14 | 5 |
| 1H3-hIgG1-L6-hIL-2 (R38D/I92D) | 170 | 15 | 2 |
| 1H3-hIgG1-L6-hIL-2 (R38E/I92D) | 171 | 15 | 2 |
| 1H3-hIgG1-L6-hIL-2 (R38Q/I92D) | 172 | 14 | 2 |
| 1H3-hIgG1-L6-hIL-2 (R38A/I92D) | 173 | 13 | 4 |
| 1H3-hIgG1-L6-hIL-2 (R38E/N88R) | 174 | 16 | 1 |
| 1H3-hIgG1-L6-hIL-2 (R38E/D84R) | 175 | 14 | 2 |

TABLE 7-continued

Fold change from rhIL-2 in a fixed concentration pSTAT5 screen on 1H3-hIgG1-L6-hIL-2 fusion proteins from Group 5

| Variants | SEQ ID NO of hIL-2 variant | Fold change from hIL-2 (NK-92) | Fold change from hIL-2 (TF1 + IL-2Rβ) |
| --- | --- | --- | --- |
| 1H3-hIgG1-L6-hIL-2 (R38E/D84K) | 176 | 14 | 2 |
| 1H3-hIgG1-L6-hIL-2 (F42A/Y45R/D20A) | 177 | 11 | 2 |
| 1H3-hIgG1-L6-hIL-2 (F42H/Y45R/D20A) | 178 | 12 | 2 |
| 1H3-hIgG1-L6-hIL-2 (R38D/E61R/D20A) | 179 | 12 | 3 |
| 1H3-hIgG1-L6-hIL-2 (R38E/E61R/D20A) | 180 | 11 | 3 |
| 1H3-hIgG1-L6-hIL-2 (R38Q/E61R/D20A) | 181 | 12 | 3 |
| 1H3-hIgG1-L6-hIL-2 (R38A/E61R/D20A) | 182 | 13 | 3 |
| 1H3-hIgG1-L6-hIL-2 (D20A/E95A/R38A) | 183 | 6 | 5 |
| 1H3-hIgG1-L6-hIL-2 (D20A/E95A/R38D) | 184 | 21 | 6 |
| 1H3-hIgG1-L6-hIL-2 (D20A/E95A/R38E) | 185 | 21 | 5 |
| 1H3-hIgG1-L6-hIL-2 (D20A/E95A/R38Q) | 186 | 19 | 6 |
| 1H3-hIgG1-L6-hIL-2 (D20A/E95A/F42R) | 187 | 21 | 4 |
| 1H3-hIgG1-L6-hIL-2 (D20A/E95A/F42A) | 188 | 21 | 5 |
| 1H3-hIgG1-L6-hIL-2 (D20A/E95A/F42D) | 189 | 22 | 12 |
| 1H3-hIgG1-L6-hIL-2 (D20A/E95A/F42H) | 190 | 22 | 4 |
| 1H3-hIgG1-L6-hIL-2 (D20A/E95A/F42K) | 191 | 21 | 4 |
| 1H3-hIgG1-L6-hIL-2 (D20A/E95A/K43A) | 192 | 5 | 7 |
| 1H3-hIgG1-L6-hIL-2 (D20A/E95A/K43E) | 193 | 13 | 6 |
| 1H3-hIgG1-L6-hIL-2 (D20A/E95A/K43Q) | 194 | 5 | 6 |
| 1H3-hIgG1-L6-hIL-2 (D20A/E95A/Y45A) | 195 | 4 | 5 |
| 1H3-hIgG1-L6-hIL-2 (D20A/E95A/Y45K) | 196 | 22 | 6 |
| 1H3-hIgG1-L6-hIL-2 (D20A/E95A/Y45S) | 197 | 5 | 6 |
| 1H3-hIgG1-L6-hIL-2 (D20A/E95A/Y45R) | 198 | 25 | 6 |
| 1H3-hIgG1-L6-hIL-2 (D20A/E95A/E61A) | 199 | 10 | 6 |
| 1H3-hIgG1-L6-hIL-2 (D20A/E95A/E62A) | 200 | 23 | 6 |
| 1H3-hIgG1-L6-hIL-2 (D20A/E95A/E62R) | 201 | 25 | 17 |
| 1H3-hIgG1-L6-hIL-2 (D20A/E95A/E62K) | 202 | 25 | 15 |
| 1H3-hIgG1-L6-hIL-2 (D20A/E95A/E62Y) | 203 | 25 | 10 |
| 1H3-hIgG1-L6-hIL-2 (D20A/E95A/E68Y) | 204 | 8 | 5 |
| 1H3-hIgG1-L6-hIL-2 (D20A/E95A/E68A) | 205 | 5 | 8 |
| 1H3-hIgG1-L6-hIL-2 (D20A/E95A/E68L) | 206 | 7 | 9 |
| 1H3-hIgG1-L6-hIL-2 (D20A/E95A/L72Y) | 207 | 1 | 5 |
| 1H3-hIgG1-L6-hIL-2 (D20A/E95A/L72R) | 208 | 12 | 9 |
| 1H3-hIgG1-L6-hIL-2 (D20A/E95A/L72A) | 209 | 2 | 6 |
| 1H3-hIgG1-L6-hIL-2 (D20A/E95A/L72D) | 210 | 21 | 6 |
| 1H3-hIgG1-L6-hIL-2 (D20A/E95A/L72H) | 211 | 14 | 6 |
| 1H3-hIgG1-L6-hIL-2 (D20A/E95A/L72F) | 212 | 2 | 6 |
| 1H3-hIgG1-L6-hIL-2 (D20A/E95A/F42K/Y45R) | 214 | 21 | 5 |
| 1H3-hIgG1-L6-hIL-2 (D20A/R38E/C125A) | 215 | 16 | 3 |
| 1H3-hIgG1-L6-hIL-2 (T3A/D20A/R38E) | 216 | 18 | 2 |
| 1H3-hIgG1-L6-hIL-2 (T3A/D20A/R38E/C125A) | 217 | 18 | 3 |
| 1H3-hIgG1-L6-hIL-2 (Δ1-3APT/D20A/R38E) | 218 | 13 | 1 |
| 1H3-hIgG1-L6-hIL-2 (Δ1-3APT/D20A/R38E/C125A) | 219 | 15 | 4 |
| 1H3-hIgG1-L6-hIL-2 (R38E/Q22A) | 220 | 12 | 0 |
| 1H3-hIgG1-L6-hIL-2 (R38E/T123A) | 221 | 12 | 0 |
| 1H3-hIgG1-L6-hIL-2 (R38E/I129A) | 222 | 13 | 1 |
| 1H3-hIgG1-L6-hIL-2 (R38E/S130A) | 223 | 12 | 0 |
| 1H3-hIgG1-L6-hIL-2 (R38E/Q126A) | 224 | 13 | 1 |
| 1H3-hIgG1-L6-hIL-2 (R38E/Q126D) | 225 | 15 | 4 |
| 1H3-hIgG1-L6-hIL-2 (R38E/Q126V) | 226 | 14 | 1 |
| 1H3-hIgG1-L6-hIL-2 (R38E/Q22A/S130A) | 227 | 13 | 1 |

TABLE 8

Fold change from rhIL-2 in a fixed concentration pSTAT5 screen on 1H3-hIgG1-L6-hIL-2 fusion proteins from Group 6

| Variants | SEQ ID NO of hIL-2 variant | Fold change from hIL-2 (NK-92) | Fold change from hIL-2 (TF1 + IL-2Rβ) |
| --- | --- | --- | --- |
| 1H3-hIgG1-L6-hIL-2 (D20A/E61R) | 230 | 25 | 4 |
| 1H3-hIgG1-L6-hIL-2 (D20A/E61N) | 231 | 15 | 1 |
| 1H3-hIgG1-L6-hIL-2 (D20A/E61D) | 232 | 11 | 0 |
| 1H3-hIgG1-L6-hIL-2 (D20A/E61Q) | 233 | 16 | 2 |
| 1H3-hIgG1-L6-hIL-2 (D20A/E61G) | 234 | 15 | 2 |
| 1H3-hIgG1-L6-hIL-2 (D20A/E61H) | 235 | 15 | 2 |
| 1H3-hIgG1-L6-hIL-2 (D20A/E61I) | 236 | 16 | 1 |
| 1H3-hIgG1-L6-hIL-2 (D20A/E61L) | 237 | 16 | 1 |
| 1H3-hIgG1-L6-hIL-2 (D20A/E61K) | 238 | 17 | 2 |
| 1H3-hIgG1-L6-hIL-2 (D20A/E61M) | 239 | 15 | 2 |
| 1H3-hIgG1-L6-hIL-2 (D20A/E61F) | 240 | 14 | 0 |
| 1H3-hIgG1-L6-hIL-2 (D20A/E61P) | 241 | 15 | 1 |
| 1H3-hIgG1-L6-hIL-2 (D20A/E61S) | 242 | 16 | 1 |
| 1H3-hIgG1-L6-hIL-2 (D20A/E61T) | 243 | 16 | 2 |

TABLE 8-continued

Fold change from rhIL-2 in a fixed concentration pSTAT5 screen on 1H3-hIgG1-L6-hIL-2 fusion proteins from Group 6

| Variants | SEQ ID NO of hIL-2 variant | Fold change from hIL-2 (NK-92) | Fold change from hIL-2 (TF1 + IL-2Rβ) |
|---|---|---|---|
| 1H3-hIgG1-L6-hIL-2 (D20A/E61W) | 244 | 15 | 2 |
| 1H3-hIgG1-L6-hIL-2 (D20A/E61Y) | 245 | 15 | 2 |
| 1H3-hIgG1-L6-hIL-2 (D20A/E61V) | 246 | 17 | 3 |
| 1H3-hIgG1-L6-hIL-2 (D20A/F42N) | 247 | 15 | 2 |
| 1H3-hIgG1-L6-hIL-2 (D20A/F42Q) | 248 | 15 | 2 |
| 1H3-hIgG1-L6-hIL-2 (D20A/F42E) | 249 | 16 | 1 |
| 1H3-hIgG1-L6-hIL-2 (D20A/F42G) | 250 | 17 | 2 |
| 1H3-hIgG1-L6-hIL-2 (D20A/F42I) | 251 | 17 | 2 |
| 1H3-hIgG1-L6-hIL-2 (D20A/F42L) | 252 | 14 | 2 |
| 1H3-hIgG1-L6-hIL-2 (D20A/F42M) | 253 | 15 | 2 |
| 1H3-hIgG1-L6-hIL-2 (D20A/F42P) | 254 | 17 | 2 |
| 1H3-hIgG1-L6-hIL-2 (D20A/F42S) | 255 | 15 | 2 |
| 1H3-hIgG1-L6-hIL-2 (D20A/F42T) | 256 | 16 | 2 |
| 1H3-hIgG1-L6-hIL-2 (D20A/F42W) | 257 | 16 | 2 |
| 1H3-hIgG1-L6-hIL-2 (D20A/F42Y) | 258 | 17 | 2 |
| 1H3-hIgG1-L6-hIL-2 (D20A/F42V) | 259 | 18 | 2 |
| 1H3-hIgG1-L6-hIL-2 (D20A/Y45A) | 260 | 15 | 2 |
| 1H3-hIgG1-L6-hIL-2 (D20A/Y45N) | 261 | 14 | 2 |
| 1H3-hIgG1-L6-hIL-2 (D20A/Y45D) | 262 | 18 | 3 |
| 1H3-hIgG1-L6-hIL-2 (D20A/Y45Q) | 263 | 17 | 3 |
| 1H3-hIgG1-L6-hIL-2 (D20A/Y45E) | 264 | 18 | 3 |
| 1H3-hIgG1-L6-hIL-2 (D20A/Y45G) | 265 | 18 | 2 |
| 1H3-hIgG1-L6-hIL-2 (D20A/Y45H) | 266 | 16 | 2 |
| 1H3-hIgG1-L6-hIL-2 (D20A/Y45I) | 267 | 13 | 2 |
| 1H3-hIgG1-L6-hIL-2 (D20A/Y45L) | 268 | 13 | 2 |
| 1H3-hIgG1-L6-hIL-2 (D20A/Y45M) | 269 | 16 | 3 |
| 1H3-hIgG1-L6-hIL-2 (D20A/Y45F) | 270 | 13 | 2 |
| 1H3-hIgG1-L6-hIL-2 (D20A/Y45P) | 271 | 25 | 4 |
| 1H3-hIgG1-L6-hIL-2 (D20A/Y45S) | 272 | 14 | 3 |
| 1H3-hIgG1-L6-hIL-2 (D20A/Y45T) | 273 | 24 | 3 |
| 1H3-hIgG1-L6-hIL-2 (D20A/Y45W) | 274 | 19 | 3 |
| 1H3-hIgG1-L6-hIL-2 (D20A/Y45V) | 275 | 21 | 3 |
| 1H3-hIgG1-L6-hIL-2 (I92D/F42N) | 276 | 29 | 5 |
| 1H3-hIgG1-L6-hIL-2 (I92D/F42Q) | 277 | 29 | 4 |
| 1H3-hIgG1-L6-hIL-2 (I92D/F42E) | 278 | 30 | 5 |
| 1H3-hIgG1-L6-hIL-2 (I92D/F42G) | 279 | 32 | 5 |
| 1H3-hIgG1-L6-hIL-2 (I92D/F42I) | 280 | 31 | 4 |
| 1H3-hIgG1-L6-hIL-2 (I92D/F42L) | 281 | 31 | 5 |
| 1H3-hIgG1-L6-hIL-2 (I92D/F42K) | 282 | 26 | 4 |
| 1H3-hIgG1-L6-hIL-2 (I92D/F42M) | 283 | 28 | 5 |
| 1H3-hIgG1-L6-hIL-2 (I92D/F42P) | 284 | 29 | 4 |
| 1H3-hIgG1-L6-hIL-2 (I92D/F42S) | 285 | 30 | 5 |
| 1H3-hIgG1-L6-hIL-2 (I92D/F42T) | 286 | 28 | 3 |
| 1H3-hIgG1-L6-hIL-2 (I92D/F42W) | 287 | 18 | 4 |
| 1H3-hIgG1-L6-hIL-2 (I92D/F42Y) | 288 | 22 | 3 |
| 1H3-hIgG1-L6-hIL-2 (I92D/F42V) | 289 | 30 | 3 |
| 1H3-hIgG1-L6-hIL-2 (I92D/Y45A) | 290 | 11 | 3 |
| 1H3-hIgG1-L6-hIL-2 (I92D/Y45N) | 291 | 4 | 3 |
| 1H3-hIgG1-L6-hIL-2 (I92D/Y45D) | 292 | 29 | 5 |
| 1H3-hIgG1-L6-hIL-2 (I92D/Y45Q) | 293 | 25 | 3 |
| 1H3-hIgG1-L6-hIL-2 (I92D/Y45E) | 294 | 27 | 4 |
| 1H3-hIgG1-L6-hIL-2 (I92D/Y45G) | 295 | 20 | 3 |
| 1H3-hIgG1-L6-hIL-2 (I92D/Y45H) | 296 | 7 | 3 |
| 1H3-hIgG1-L6-hIL-2 (I92D/Y45I) | 297 | 20 | 4 |
| 1H3-hIgG1-L6-hIL-2 (I92D/Y45L) | 298 | 5 | 3 |
| 1H3-hIgG1-L6-hIL-2 (I92D/Y45M) | 299 | 14 | 3 |
| 1H3-hIgG1-L6-hIL-2 (I92D/Y45F) | 300 | 10 | 3 |
| 1H3-hIgG1-L6-hIL-2 (I92D/Y45P) | 301 | 28 | 4 |
| 1H3-hIgG1-L6-hIL-2 (I92D/Y45S) | 302 | 11 | 3 |
| 1H3-hIgG1-L6-hIL-2 (I92D/Y45T) | 303 | 28 | 4 |
| 1H3-hIgG1-L6-hIL-2 (I92D/Y45W) | 304 | 27 | 4 |
| 1H3-hIgG1-L6-hIL-2 (I92D/Y45V) | 305 | 28 | 5 |
| 1H3-hIgG1-L6-hIL-2 (R38E/D20H) | 306 | 17 | 5 |
| 1H3-hIgG1-L6-hIL-2 (R38E/D20S) | 307 | 17 | 3 |
| 1H3-hIgG1-L6-hIL-2 (F42A/N88R) | 308 | 18 | 3 |
| 1H3-hIgG1-L6-hIL-2 (F42A/N88D) | 309 | 18 | 3 |
| 1H3-hIgG1-L6-hIL-2 (R38E/D84A) | 310 | 18 | 1 |
| 1H3-hIgG1-L6-hIL-2 (R38E/D84N) | 311 | 18 | 1 |
| 1H3-hIgG1-L6-hIL-2 (R38E/D84Q) | 312 | 18 | 1 |
| 1H3-hIgG1-L6-hIL-2 (R38E/D84E) | 313 | 16 | 1 |
| 1H3-hIgG1-L6-hIL-2 (R38E/D84G) | 314 | 18 | 1 |
| 1H3-hIgG1-L6-hIL-2 (R38E/D84H) | 315 | 19 | 2 |
| 1H3-hIgG1-L6-hIL-2 (R38E/D84I) | 316 | 20 | 1 |
| 1H3-hIgG1-L6-hIL-2 (R38E/D84L) | 317 | 19 | 1 |
| 1H3-hIgG1-L6-hIL-2 (R38E/D84M) | 318 | 20 | 2 |
| 1H3-hIgG1-L6-hIL-2 (R38E/D84F) | 319 | 20 | 2 |
| 1H3-hIgG1-L6-hIL-2 (R38E/D84P) | 320 | 20 | 1 |
| 1H3-hIgG1-L6-hIL-2 (R38E/D84S) | 321 | 21 | 1 |
| 1H3-hIgG1-L6-hIL-2 (R38E/D84T) | 322 | 20 | 1 |
| 1H3-hIgG1-L6-hIL-2 (R38E/D84W) | 323 | 21 | 1 |
| 1H3-hIgG1-L6-hIL-2 (R38E/D84Y) | 324 | 21 | 1 |
| 1H3-hIgG1-L6-hIL-2 (R38E/D84V) | 325 | 22 | 1 |
| 1H3-hIgG1-L6-hIL-2 (R38E/I92A) | 326 | 22 | 1 |
| 1H3-hIgG1-L6-hIL-2 (R38E/I92R) | 327 | 22 | 2 |
| 1H3-hIgG1-L6-hIL-2 (R38E/I92N) | 328 | 22 | 1 |
| 1H3-hIgG1-L6-hIL-2 (R38E/I92Q) | 329 | 22 | 1 |
| 1H3-hIgG1-L6-hIL-2 (R38E/I92E) | 330 | 22 | 2 |
| 1H3-hIgG1-L6-hIL-2 (R38E/I92G) | 331 | 22 | 1 |
| 1H3-hIgG1-L6-hIL-2 (R38E/I92H) | 332 | 21 | 1 |
| 1H3-hIgG1-L6-hIL-2 (R38E/I92L) | 333 | 17 | 1 |
| 1H3-hIgG1-L6-hIL-2 (R38E/I92K) | 334 | 24 | 3 |
| 1H3-hIgG1-L6-hIL-2 (R38E/I92M) | 335 | 20 | 1 |
| 1H3-hIgG1-L6-hIL-2 (R38E/I92F) | 336 | 16 | 1 |
| 1H3-hIgG1-L6-hIL-2 (R38E/I92P) | 337 | 24 | 5 |
| 1H3-hIgG1-L6-hIL-2 (R38E/I92S) | 338 | 22 | 2 |
| 1H3-hIgG1-L6-hIL-2 (R38E/I92T) | 339 | 22 | 1 |
| 1H3-hIgG1-L6-hIL-2 (R38E/I92W) | 340 | 23 | 1 |
| 1H3-hIgG1-L6-hIL-2 (R38E/I92Y) | 341 | 21 | 1 |
| 1H3-hIgG1-L6-hIL-2 (R38E/I92V) | 342 | 21 | 1 |
| 1H3-hIgG1-L6-hIL-2 (R38E/H16E) | 343 | 25 | 3 |
| 1H3-hIgG1-L6-hIL-2 (R38K/D20A) | 344 | 17 | 3 |

Example 4: Testing for Attenuation of IL-2 Fusion Proteins for Each of the High-Affinity and Intermediate-Affinity hIL-2 Receptors with a Cell-Based Potency pSTAT5 Dose-Titration Screen The attenuation of selected antibody-attenuated hIL-2 fusion proteins described in Example 2 (1H3-hIgG1-L6-hIL-2 fusion protein from Groups 2-6) were tested in pSTAT5 titration curves using the NK-92 and TF1+IL-2Rβ cell lines as described in Protocol D.

The gMFI of the Alexa Fluor 647 pSTAT5-positive signal was used to generate four parameter logistic curves and GraphPad Prism 7 software was then used to calculate $EC_{50}$ values. These values were compared to recombinant hIL-2 (rhIL-2) control as a measurement of attenuation. Tables 9-13 summarize the fold change in activity from rhIL-2 calculated using the gMFI of the Alexa Fluor 647 signal.

An increase in the fold change from rhIL-2 was indicative of the degree of attenuation of hIL-2 activity. Each antibody-attenuated hIL-2 fusion protein tested in the pSTAT5 titration curve was also assessed for agonistic activity and characterized as either full, partial, or no activity (inactive). Antibody-attenuated hIL-2 fusion protein dose-titration curves that reached the maximal gMFI level as the rhIL-2 were considered to be variants with full agonist activity. Partial agonist activity was calculated as described in Example 3. Inactive antibody-attenuated hIL-2 fusion proteins were classified as having less than 10% activity in comparison to rhIL-2. Some fold changes from rhIL-2 could not be accurately calculated (denoted as Not Calculated or "NC") using the GraphPad Prism 7 software since a full four parameter logistic curve was not generated and accordingly these values are an estimate (annotated as [a] in Tables 9-13).

However, these variants had greater than 10,000-fold attenuation from rhIL-2 on graphs (data not shown). This is denoted on Tables 9-13 as ">10,000 on graph; NC"

Full titration pSTAT5 curves demonstrated similar findings as presented in Example 3 in which substitutions that modulated binding to both the alpha chain and the beta chain substantially attenuated IL-2 activity on the high affinity IL-2 receptor in comparison to single substitutions for binding to the alpha or beta chain only. The full titration pSTAT5 assay was additionally able to differentiate between variants with substitutions that caused inactivity versus highly attenuated variants. Finally, comparison of dose-titration curves illustrated more accurate of levels of attenuation over a fixed concentration assay.

TABLE 9

Fold change from rhIL-2 and agonistic activity on 1H3-hIgG1-L6-hIL-2 fusion proteins from Group 2

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (R38A) | 46 | 2 | Full | 0 | Full |
| 1H3-hIgG1-L6-hIL-2 (R38D) | 47 | 55 | Full | 1 | Full |
| 1H3-hIgG1-L6-hIL-2 (R38E) | 48 | 99-136 | Full | 0 | Full |
| 1H3-hIgG1-L6-hIL-2 (F42R) | 50 | 65 | Full | 0 | Full |
| 1H3-hIgG1-L6-hIL-2 (F42D) | 52 | 193 | Full | 0 | Full |
| 1H3-hIgG1-L6-hIL-2 (K43A) | 54 | 3 [a] | Full | 0 | Full |
| 1H3-hIgG1-L6-hIL-2 (Y45R) | 57 | 81 [a] | Full | 0 | Full |
| 1H3-hIgG1-L6-hIL-2 (E61A) | 61 | 3 [a] | Full | 0 | Full |
| 1H3-hIgG1-L6-hIL-2 (E61R) | 62 | 22 [a] | Full | 0 | Full |
| 1H3-hIgG1-L6-hIL-2 (E61K) | 63 | 14 [a] | Full | 0 | Full |
| 1H3-hIgG1-L6-hIL-2 (E62A) | 64 | 6 [a] | Full | 0 | Full |
| 1H3-hIgG1-L6-hIL-2 (E62R) | 65 | >10,000 | Partial, 80% | 38 | Full |
| 1H3-hIgG1-L6-hIL-2 (E62K) | 66 | 2048 | Full | 10 | Full |
| 1H3-hIgG1-L6-hIL-2 (E62Y) | 67 | 18 | Full | 0 | Full |
| 1H3-hIgG1-L6-hIL-2 (E68K) | 70 | 2 [a] | Full | 0 | Full |
| 1H3-hIgG1-L6-hIL-2 (E68R) | 71 | 3 [a] | Full | 0 | Full |
| 1H3-hIgG1-L6-hIL-2 (L72R) | 74 | 2 [a] | Full | 1 | Full |
| 1H3-hIgG1-L6-hIL-2 (L72D) | 76 | 4 [a] | Full | 0 | Full |
| 1H3-hIgG1-L6-hIL-2 (L72H) | 77 | 1 [a] | Partial, 80% | 0 | Full |
| 1H3-hIgG1-L6-hIL-2 (R38D/E61R) | 79 | 479 | Partial, 80% | NT | NT |
| 1H3-hIgG1-L6-hIL-2 (R38D/E61R/K43E) | 80 | 598 | Full | NT | NT |
| 1H3-hIgG1-L6-hIL-2 (T3A/F42A/Y45A/L72G/C125A) | 81 | 360-1426 | Full | 0 | Full |

NT = not tested
[a] = Fold change is an estimate only since a full four parameter logistic curve was not reached

TABLE 10

Fold change from rhIL-2 and agonistic activity on 1H3-hIgG1-L6-hIL-2 fusion proteins variants from Group 3

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (H16E) | 87 | 63 | Full | 63 | Full |
| 1H3-hIgG1-L6-hIL-2 (L19A) | 88 | 0 | Full | 0 | Full |
| 1H3-hIgG1-L6-hIL-2 (D20I) | 89 | NT | NT | >10,000 on graph, NC [a] | Inactive |
| 1H3-hIgG1-L6-hIL-2 (D20S) | 90 | 28 | Partial, 80% | 277 [a] | Partial, 80% |
| 1H3-hIgG1-L6-hIL-2 (D20H) | 91 | >10,000 [a] | Partial, 90% | 2767 [a] | Partial, 50% |
| 1H3-hIgG1-L6-hIL-2 (D20W) | 93 | NT | NT | >10,000 on graph, NC [a] | Inactive |
| 1H3-hIgG1-L6-hIL-2 (D20Y) | 94 | >10,000 [a] | Partial, 50-70% | 84-143 [a] | Partial, 80% |
| 1H3-hIgG1-L6-hIL-2 (D20R) | 95 | NT | NT | >10,000 on graph, NC [a] | Inactive |
| 1H3-hIgG1-L6-hIL-2 (D20F) | 96 | NT | NT | >10,000 on graph, NC [a] | Inactive |
| 1H3-hIgG1-L6-hIL-2 (D84A) | 98 | NT | NT | 14 | Full |
| 1H3-hIgG1-L6-hIL-2 (D84R) | 99 | 16 | Full | 244 [a] | Partial, 70% |
| 1H3-hIgG1-L6-hIL-2 (D84K) | 100 | 14 | Partial, 90% | 195 [a] | Full |
| 1H3-hIgG1-L6-hIL-2 (N88Y) | 102 | NT | NT | >10,000 on graph, NC [a] | Inactive |

TABLE 10-continued

Fold change from rhIL-2 and agonistic activity on 1H3-hIgG1-L6-hIL-2 fusion proteins variants from Group 3

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (N88D) | 103 | 21 | Partial, 90% | 130 | Full |
| 1H3-hIgG1-L6-hIL-2 (N88R) | 104 | 5-27 | Partial, 80%-Full | 289-556 | Partial, 40% |
| 1H3-hIgG1-L6-hIL-2 (N88E) | 105 | NT | NT | >10,000 on graph, NC $^a$ | Partial, 40% |
| 1H3-hIgG1-L6-hIL-2 (N88F) | 106 | NT | NT | >10,000 on graph, NC $^a$ | Inactive |
| 1H3-hIgG1-L6-hIL-2 (N88I) | 107 | NT | NT | >10,000 on graph, NC $^a$ | Inactive |
| 1H3-hIgG1-L6-hIL-2 (I92Y) | 109 | NT | NT | 1 | Full |
| 1H3-hIgG1-L6-hIL-2 (I92S) | 110 | NT | NT | 8 | Full |
| 1H3-hIgG1-L6-hIL-2 (I92R) | 112 | NT | NT | 31 | Full |
| 1H3-hIgG1-L6-hIL-2 (I92D) | 113 | 8-20 | Full | 68-365 $^a$ | Partial, 70-90% |
| 1H3-hIgG1-L6-hIL-2 (E95R) | 116 | NT | NT | 5 | Full |
| 1H3-hIgG1-L6-hIL-2 (D20T) | 92 | 8 | Full | 167 $^a$ | Partial, 80% |
| 1H3-hIgG1-L6-hIL-2 (D20A) | 31 | 21 | Partial, 80% | 117 $^a$ | Partial, 80% |
| 1H3-hIgG1-L6-hIL-2 (D20Y/H16E) | 94 | 52 $^a$ | Partial, 80% | 2159 $^a$ | Partial, 30% |
| 1H3-hIgG1-L6-hIL-2 (D20Y/H16A) | 119 | >10,000 $^a$ | Partial, 40% | 30 $^a$ | Partial, 20% |
| 1H3-hIgG1-L6-hIL-2 (D20Y/H16Y) | 120 | >10,000 $^a$ | Partial, 40% | 343 $^a$ | Partial, 20% |
| 1H3-hIgG1-L6-hIL-2 (D20Y/I92A) | 121 | >10,000 $^a$ | Partial, 20% | 4 $^a$ | Partial, 10% |
| 1H3-hIgG1-L6-hIL-2 (D20Y/I92S) | 122 | >10,000 $^a$ | Partial, 10% | 12 $^a$ | Partial, 10% |

NT = Not Tested; NC = Not Calculated by GraphPad Prism 7
$^a$ = Fold change is an estimate only since a full four parameter logistic curve was not reached

TABLE 11

Fold change from rhIL-2 and agonistic activity on 1H3-hIgG1-L6-hIL-2 fusion proteins from Group 4

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hCD25(1-164)-L20-hIL-2 (E15A) | 82 | 184 | Full | 20 | Full |
| 1H3-hIgG1-L6-hCD25(1-164)-L20-hIL-2 (D20I) | 89 | >10,000 $^a$ | Partial, 80% | >10,000 on graph, NC $^a$ | Inactive |
| 1H3-hIgG1-L6-hCD25(1-164)-L20-hIL-2 (D20S) | 90 | 2403 | Full | >10,000 on graph, NC $^a$ | Inactive |
| 1H3-hIgG1-L6-hCD25(1-164)-L20-hIL-2 (D20H) | 91 | >10,000 $^a$ | Partial, 80% | >10,000 on graph, NC $^a$ | Inactive |
| 1H3-hIgG1-L6-hCD25(1-164)-L20-hIL-2 (D20W) | 93 | >10,000 $^a$ | Partial, 60% | >10,000 on graph, NC $^a$ | Inactive |
| 1H3-hIgG1-L6-hCD25(1-164)-L20-hIL-2 (D20Y) | 94 | >10,000 $^a$ | Partial, 90% | >10,000 on graph, NC $^a$ | Inactive |
| 1H3-hIgG1-L6-hCD25(1-164)-L20-hIL-2 (D20R) | 95 | >10,000 $^a$ | Partial, 80% | >10,000 on graph, NC $^a$ | Inactive |
| 1H3-hIgG1-L6-hCD25(1-164)-L20-hIL-2 (D20F) | 96 | >10,000 $^a$ | Partial, 70% | >10,000 on graph, NC $^a$ | Inactive |
| 1H3-hIgG1-L6-hCD25(1-164)-L20-hIL-2 (D84K) | 100 | >10,000 | Full | >10,000 on graph, NC $^a$ | Inactive |
| 1H3-hIgG1-L6-hCD25(1-164)-L20-hIL-2 (S87A) | 101 | 305 | Full | 44 | Full |
| 1H3-hIgG1-L6-hCD25(1-164)-L20-hIL-2 (N88Y) | 102 | >10,000 $^a$ | Partial, 50% | >10,000 on graph, NC $^a$ | Inactive |
| 1H3-hIgG1-L6-hCD25(1-164)-L20-hIL-2 (N88D) | 103 | 393 | Full | >10,000 on graph, NC $^a$ | Inactive |
| 1H3-hIgG1-L6-hCD25(1-164)-L20-hIL-2 (N88R) | 104 | 274 | Full | >10,000 on graph, NC $^a$ | Inactive |
| 1H3-hIgG1-L6-hCD25(1-164)-L20-hIL-2 (N88E) | 105 | >10,000 $^a$ | Full | >10,000 on graph, NC $^a$ | Inactive |
| 1H3-hIgG1-L6-hCD25(1-164)-L20-hIL-2 (N88F) | 106 | >10,000 $^a$ | Partial, 80% | >10,000 on graph, NC $^a$ | Inactive |

TABLE 11-continued

Fold change from rhIL-2 and agonistic activity on 1H3-hIgG1-L6-hIL-2 fusion proteins from Group 4

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hCD25(1-164)-L20-hIL-2 (N88I) | 107 | 7780 | Full | >10,000 on graph, NC [a] | Inactive |
| 1H3-hIgG1-L6-hCD25(1-164)-L20-hIL-2 (I92A) | 108 | 26 | Full | 95 | Full |
| 1H3-hIgG1-L6-hCD25(1-164)-L20-hIL-2 (E95A) | 115 | 30 | Full | 16 | Full |
| 1H3-hIgG1-L6-hCD25(1-164)-L20-hIL-2 (E95K) | 117 | 792 | Full | 434 [a] | Partial, 60% |

NC = Not Calculated by GraphPad Prism 7
[a] = Fold change is an estimate only since a full four parameter logistic curve was not reached

TABLE 12

Fold change from rhIL-2 and agonistic activity on 1H3-hIgG1-L6-hIL-2 fusion proteins from Group 5

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (F42K/D20A) | 129 | >10,000 [a] | Partial, 30% | 219 [a] | Partial, 50% |
| 1H3-hIgG1-L6-hIL-2 (F42A/D20A) | 130 | >10,000 [a] | Partial, 70% | 96 [a] | Partial, 70% |
| 1H3-hIgG1-L6-hIL-2 (R38N/D20A) | 134 | 4497 | Partial, 70% | 121 [a] | Partial, 70% |
| 1H3-hIgG1-L6-hIL-2 (R38G/D20A) | 135 | 2811 | Partial, 70% | 139 [a] | Partial, 70% |
| 1H3-hIgG1-L6-hIL-2 (R38H/D20A) | 136 | 1752 | Partial, 80% | 107 [a] | Partial, 70% |
| 1H3-hIgG1-L6-hIL-2 (R38I/D20A) | 137 | 658 | Partial, 70% | 107 [a] | Partial, 60% |
| 1H3-hIgG1-L6-hIL-2 (R38L/D20A) | 138 | 532 | Partial, 80% | 125 [a] | Partial, 70% |
| 1H3-hIgG1-L6-hIL-2 (R38M/D20A) | 139 | 786 | Partial, 90% | 85 [a] | Partial, 90% |
| 1H3-hIgG1-L6-hIL-2 (R38F/D20A) | 140 | 1072 | Partial, 80% | 124 [a] | Partial, 90% |
| 1H3-hIgG1-L6-hIL-2 (R38P/D20A) | 142 | 337 | Partial, 70% | 337 [a] | Partial, 80% |
| 1H3-hIgG1-L6-hIL-2 (R38S/D20A) | 142 | 571 | Partial, 70% | 571 [a] | Partial, 90% |
| 1H3-hIgG1-L6-hIL-2 (R38V/D20A) | 146 | 765 | Partial, 70% | 765 [a] | Partial, 90% |
| 1H3-hIgG1-L6-hIL-2 (R38A/D20A) | 147 | 619 | Partial, 80% | 70 [a] | Partial, 70% |
| 1H3-hIgG1-L6-hIL-2 (R38Q/D20A) | 148 | 4700 | Partial, 80% | 91 [a] | Partial, 70% |
| 1H3-hIgG1-L6-hIL-2 (D20A/R38E) | 149 | >10,000 [a] | Partial, 60%-Full | 409 [a] | Partial, 50% |
| 1H3-hIgG1-L6-hIL-2 (R38D/D20A) | 150 | >10,000 [a] | Partial, 70% | 172 [a] | Partial, 70% |
| 1H3-hIgG1-L6-hIL-2 (K43E/D20A) | 151 | 584 | Partial, 90% | 231 [a] | Partial, 70% |
| 1H3-hIgG1-L6-hIL-2 (F42R/I92D) | 159 | 801 [a] | Partial, 40% | 52 [a] | Partial, 80% |
| 1H3-hIgG1-L6-hIL-2 (F42H/I92D) | 160 | 194 | Full | 801 [a] | Partial, 80% |
| 1H3-hIgG1-L6-hIL-2 (F42A/I92D) | 161 | 338 [a] | Partial, 70% | 194 [a] | Full |
| 1H3-hIgG1-L6-hIL-2 (R38D/I92D) | 170 | >10,000 [a] | Partial, 80% | 338 [a] | Partial, 80% |
| 1H3-hIgG1-L6-hIL-2 (R38E/I92D) | 171 | >10,000 [a] | Partial, 70% | 51 [a] | Partial, 80% |
| 1H3-hIgG1-L6-hIL-2 (R38Q/I92D) | 172 | 561 | Full | 48 [a] | Partial, 90% |
| 1H3-hIgG1-L6-hIL-2 (R38E/D84R) | 175 | >10,000 [a] | Partial, 60% | 50 [a] | Partial, 80% |
| 1H3-hIgG1-L6-hIL-2 (R38E/D84K) | 176 | >10,000 [a] | Partial, 40% | 45 [a] | Partial, 80% |
| 1H3-hIgG1-L6-hIL-2 (R38D/E61R/D20A) | 179 | >10,000 on graph, NC [a] | Partial, 40% | 62 [a] | Partial, 70% |
| 1H3-hIgG1-L6-hIL-2 (R38E/E61R/D20A) | 180 | >10,000 [a] | Partial, 90% | 181 [a] | Partial, 60% |
| 1H3-hIgG1-L6-hIL-2 (R38Q/E61R/D20A) | 181 | >10,000 [a] | Partial, 40% | 115 [a] | Partial, 80% |
| 1H3-hIgG1-L6-hIL-2 (R38A/E61R/D20A) | 182 | >10,000 [a] | Partial, 40% | 130 [a] | Partial, 60% |
| 1H3-hIgG1-L6-hIL-2 (D20A/E95A/R38A) | 183 | 149-199 | Partial, 70-80% | 157 [a] | Partial, 70% |
| 1H3-hIgG1-L6-hIL-2 (D20A/E95A/R38D) | 184 | >10,000 | Partial, 60-70% | 84-508 [a] | Full |
| 1H3-hIgG1-L6-hIL-2 (D20A/E95A/R38E) | 185 | >10,000 [a] | Partial, 70-90% | 188-427 [a] | Partial, 70%-Full |
| 1H3-hIgG1-L6-hIL-2 (D20A/E95A/R38Q) | 186 | 3725 | Partial, 70% | 124-413 [a] | Partial, 80%-Full |
| 1H3-hIgG1-L6-hIL-2 (D20A/E95A/F42R) | 187 | >10,000 [a] | Partial, 70% | 87 [a] | Partial, 60% |
| 1H3-hIgG1-L6-hIL-2 (D20A/E95A/F42A) | 188 | 3000-5718 [a] | Partial, 90% | 45-244 [a] | Partial, 70%-Full |
| 1H3-hIgG1-L6-hIL-2 (D20A/E95A/F42D) | 189 | >10,000 [a] | Partial, 10% | 1451 [a] | Partial, 30% |
| 1H3-hIgG1-L6-hIL-2 (D20A/E95A/F42H) | 190 | 3579 | Partial, 80% | 411 [a] | Full |
| 1H3-hIgG1-L6-hIL-2 (D20A/E95A/F42K) | 191 | >10,000 [a] | Partial, 50% | 82 [a] | Partial, 60% |
| 1H3-hIgG1-L6-hIL-2 (D20A/E95A/K43E) | 193 | 386-553 | Partial, 80-90% | 46-142 [a] | Partial, 50-0% |
| 1H3-hIgG1-L6-hIL-2 (D20A/E95A/Y45A) | 195 | 62 | Partial, 90% | 300 [a] | Partial, 70% |
| 1H3-hIgG1-L6-hIL-2 (D20A/E95A/Y45K) | 196 | 7951 [a] | Partial, 70% | 205 [a] | Partial, 60% |
| 1H3-hIgG1-L6-hIL-2 (D20A/E95A/Y45R) | 198 | >10,000 [a] | Partial, 80% | 293 [a] | Partial, 60% |
| 1H3-hIgG1-L6-hIL-2 (D20A/E95A/E61A) | 199 | 367 | Partial, 80% | 195 [a] | Partial, 60% |
| 1H3-hIgG1-L6-hIL-2 (D20A/E95A/E62A) | 200 | 3265 [a] | Partial, 70% | 230 [a] | Partial, 50% |
| 1H3-hIgG1-L6-hIL-2 (D20A/E95A/E62R) | 201 | >10,000 [a] | Inactive, 5% | >10,000 on graph, NC [a] | Partial, 10% |
| 1H3-hIgG1-L6-hIL-2 (D20A/E95A/E62K) | 202 | >10,000 [a] | Inactive, 10% | >10,000 on graph, NC [a] | Partial, 10% |

TABLE 12-continued

Fold change from rhIL-2 and agonistic activity on 1H3-hIgG1-L6-hIL-2 fusion proteins from Group 5

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (D20A/E95A/E62Y) | 203 | >10,000 [a] | Partial, 70% | 265 [a] | Partial, 40% |
| 1H3-hIgG1-L6-hIL-2 (D20A/E95A/E68Y) | 204 | 131 | Partial, 80% | 61 [a] | Partial, 50% |
| 1H3-hIgG1-L6-hIL-2 (D20A/E95A/E68A) | 205 | 45 | Partial, 60% | 620 [a] | Partial, 60% |
| 1H3-hIgG1-L6-hIL-2 (D20A/E95A/E68L) | 206 | 187 | Partial, 80% | 172 [a] | Partial, 40% |
| 1H3-hIgG1-L6-hIL-2 (D20A/E95A/L72R) | 208 | 1178 | Full | 499 [a] | Partial, 70% |
| 1H3-hIgG1-L6-hIL-2 (D20A/E95A/L72D) | 210 | >10,000 [a] | Partial, 70% | 456-504 [a] | Partial, 60-70% |
| 1H3-hIgG1-L6-hIL-2 (D20A/E95A/L72H) | 211 | 798 | Partial, 70% | 117 [a] | Partial, 70% |
| 1H3-hIgG1-L6-hIL-2 (D20A/E95A/F42K/Y45R) | 214 | >10,000 [a] | Partial, 60-70% | 155 185 [a] | Partial, 70% |
| 1H3-hIgG1-L6-hIL-2 (F42K/Y45R/D20A/S87A) | 213 | 840 [a] | Partial, 70% | 155 [a] | Partial, 70% |
| 1H3-hIgG1-L6-hIL-2 (D20A/R38E/C125A) | 215 | >10,000 on graph, NC [a] | Partial, 50% | 183-584 [a] | Partial, 50-70% |
| hIgG1-L6-hIL-2(T3A/D20A/R38E) | 216 | >10,000 [a] | Partial, 60-90% | 77-484 [a] | Partial, 60% |
| 1H3-hIgG1-L6-hIL-2 (T3A/D20A/R38E/C125A) | 217 | >10,000 [a] | Partial, 90% | 218-512 [a] | Partial, 50-60% |
| 1H3-hIgG1-L6-hIL-2(A1-3APT/D20A/R38E) | 218 | 24-69 | Full | 6 | Full |
| 1H3-hIgG1-L6-hIL-2 (A1-3APT/D20A/R38E/C125A) | 219 | 49-619 | Partial, 30-70% | 165-619 [a] | Partial, 40-50% |
| 1H3-hIgG1-L6-hIL-2 (R38E/Q126D) | 225 | >10,000 on graph, NC [a] | Partial, 60% | >10,000 on graph, NC [a] | Partial, 40% |
| 1H3-hIgG1-L6-hIL-2 (F42K/Y45R/Q126D) | 228 | >10,000 [a] | Partial, 60% | 226 [a] | Partial, 50% |
| 1H3-hIgG1-L6-hIL-2 (D20A/E95A/Q126D) | 229 | >10,000 on graph, NC [a] | Inactive | >10,000 on graph, NC [a] | Inactive |

NC = Not Calculated by GraphPad Prism 7
[a] = Fold change is an estimate only since a full four parameter logistic curve was not reached

TABLE 13

Fold change from rhIL-2 and agonistic activity on 1H3-hIgG1-L6-hIL-2 fusion proteins from Group 6

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (D20A/F42N) | 247 | >10,000 [a] | Partial, 60% | >10,000 on graph, NC [a] | Partial, 80% |
| 1H3-hIgG1-L6-hIL-2 (D20A/F42Q) | 248 | >10,000 [a] | Partial, 50% | 16 [a] | Partial, 70% |
| 1H3-hIgG1-L6-hIL-2 (D20A/F42P) | 254 | >10,000 [a] | Partial, 60% | 13 [a] | Partial, 80% |
| 1H3-hIgG1-L6-hIL-2 (D20A/F42S) | 255 | >10,000 [a] | Partial, 60% | 17 [a] | Partial, 40% |
| 1H3-hIgG1-L6-hIL-2 (D20A/Y45E) | 264 | 4717 | Partial, 80% | 32 [a] | Partial, 50% |
| 1H3-hIgG1-L6-hIL-2 (I92D/F42Q) | 277 | >10,000 [a] | Partial, 50% | 24 [a] | Partial, 70% |
| 1H3-hIgG1-L6-hIL-2 (I92D/F42I) | 280 | >10,000 [a] | Partial, 30% | 117 [a] | Partial, 20% |
| 1H3-hIgG1-L6-hIL-2 (I92D/F42K) | 282 | >10,000 [a] | Partial, 50% | 58 [a] | Partial, 90% |
| 1H3-hIgG1-L6-hIL-2 (I92D/F42T) | 286 | >10,000 [a] | Partial, 60% | >10,000 on graph, NC [a] | Partial, 80% |
| 1H3-hIgG1-L6-hIL-2 (R38E/D20S) | 307 | >10,000 [a] | Partial, 50% | 25 [a] | Partial, 40% |
| 1H3-hIgG1-L6-hIL-2 (F42A/N88R) | 308 | >10,000 [a] | Partial, 70% | 34 [a] | Partial, 30% |

NC = Not Calculated by GraphPad Prism
[a] = Fold change is an estimate only since a full four parameter logistic curve was not reached Example 5: Testing for Attenuation for the High-Affinity and Intermediate-Affinity hIL-2 Receptor with Cell-Based Proliferation Assays The attenuation of IL-2 activity of antibody-attenuated hIL-2 fusion proteins from Groups 1-6 in Example 2 (2D12-mIgG1-D265A-L6-hIL-2, 2D12-hIgG1-L6-hIL-2, and 1H3-hIgG1-L6-hIL-2 fusion proteins) were tested in proliferation assays in both the NK-92 and TF1+IL-2Rβ cell lines as described in Protocol E. The results of the assays are provided in Tables 14-19.

Selected 1H3-hIgG1-L6-hIL-2 fusion proteins with substantial attenuation in the pSTAT5 titration curves from Example 4 were tested in this cell-based proliferation assay.

pSTAT5 is a downstream read-out of IL-2 activity and assays require only 10 minutes of stimulation which may be a small snapshot of IL-2 dependent activity. For proliferation assays, cells were incubated with 2D12-mIgG1-D265A-L6-hIL-2, 2D12-hIgG1-L6-hIL-2, 1H3-hIgG1-L6-hIL-2 fusion proteins, or recombinant hIL-2 control for 3-4 days, providing a more physiological relevant read-out of IL-2 dependent activity in vivo. Other 2D12-mIgG1-D265A-L6-hIL-2 and 2D12-hIgG1-L6-hIL-2 fusion proteins that were generated but not tested in a pSTAT5 assay were assayed for IL-2 dependent activity using this proliferation assay.

Similar to cell-based pSTAT5 dose-titration experiments, the calculated $EC_{50}$ as determined from relative luminescence units (RLU) instead of gMFI and analysis of the results were performed identically to Example 4 once $EC_{50}$ was calculated. Similar to results identified in Example 4, proliferation curves demonstrated that some substitutions that modulated binding to both the alpha chain and beta chain substantially attenuated IL-2 activity on the high affinity receptor in comparison to single substitutions for binding to the alpha or beta chain only. These selected 1H3-hIgG1-L6-hIL-2 fusion proteins were also tested for proliferation on the TF1+IL-2Rβ cell line and demonstrated that some of these same substitutions substantially attenuated IL-2 activity on the intermediate affinity receptor.

TABLE 14

Fold change from rhIL-2 and agonistic activity on 2D12-mIgG1-D265A-L6-hIL-2 or 2D12-hIgG1-L6-hIL-2 fusion proteins from Group 1 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 2D12-mIgG1-D265A-L6-hIL-2 (F42K) | 1 | 2 | Full | 0 | Full |
| 2D12-mIgG1-D265A-L6-hIL-2 (Y45R) | 60 | 3 | Full | 2 | Full |
| 2D12-hIgG1-L6-hIL-2 (V69A) | 2 | 0 | Full | 0 | Full |
| 2D12-hIgG1-L6-hIL-2 (V69E) | 3 | 13 | Partial, 60% | 83 | Full |
| 2D12-hIgG1-L6-hIL-2 (V69H) | 6 | 41 | Partial, 60% | 544 | Full |
| 2D12-hIgG1-L6-hIL-2 (V69K) | 8 | >10,000 on graph, NC [a] | Inactive | 3033 | Partial, 40% |
| 2D12-hIgG1-L6-hIL-2 (V69L) | 9 | 1 | Full | 1 | Full |
| 2D12-hIgG1-L6-hIL-2 (V69F) | 4 | 0 | Full | 1 | Full |
| 2D12-hIgG1-L6-hIL-2 (V69G) | 5 | 108 | Full | 396 | Full |
| 2D12-hIgG1-L6-hIL-2 (V69I) | 7 | 1 | Full | 1 | Full |
| 2D12-hIgG1-L6-hIL-2 (V69M) | 10 | 2 | Full | 3 | Full |
| 2D12-hIgG1-L6-hIL-2 (V69Q) | 11 | 7 | Full | 16 | Full |
| 2D12-mIgG1-D265A-L6-hIL-2 (V69R) | 581 | 2392 | Partial, 70% | 2973 | Partial, 50% |
| 2D12-hIgG1-L6-hIL-2 (V69S) | 12 | 6 | Full | 13 | Full |
| 2D12-hIgG1-L6-hIL-2 (V69T) | 13 | 3 | Full | 3 | Full |
| 2D12-hIgG1-L6-hIL-2 (V69W) | 14 | 0 | Full | 1 | Full |
| 2D12-hIgG1-L6-hIL-2 (V69Y) | 15 | 1 | Full | 1 | Full |
| 2D12-mIgG1-D265A-L6-hIL-2 (D20A) | 31 | 1 | Full | >10,000 [a] | Full |
| 2D12-mIgG1-D265A-L6-hIL-2 (D20N) | 32 | 0 | Full | >10,000 [a] | Full |
| 2D12-mIgG1-D265A-L6-hIL-2 (D20K) | 33 | 4 | Full | >10,000 on graph, NC [a] | Inactive |
| 2D12-mIgG1-D265A-L6-hIL-2 (N88A) | 34 | 0 | Full | 2289 | Full |
| 2D12-mIgG1-D265A-L6-hIL-2 (N88G) | 35 | 0 | Full | 2978 | Full |
| 2D12-mIgG1-D265A-L6-hIL-2 (N88H) | 36 | 1-3 | Full | >10,000 on graph, NC [a] | Inactive |
| 2D12-mIgG1-D265A-L6-hIL-2 (N88K) | 37 | 564-9557 | Partial, 40% | >10,000 on graph, NC [a] | Inactive |
| 2D12-mIgG1-D265A-L6-hIL-2 (Q126L) | 375 | 0-12 | Full | 118 | Full |
| 2D12-mIgG1-D265A-L6-hIL-2 (Q126E) | 376 | 0-3 | Full | 40 | Full |
| 2D12-mIgG1-D265A-L6-hIL-2 (F42K/F44K) | 16 | 44 | Full | >10,000 on graph, NC [a] | Inactive |
| 2D12-mIgG1-D265A-L6-hIL-2 (F42K/Y45R) | 17 | 1-2 | Full | 0-3 | Full |
| 2D12-mIgG1-D265A-L6-hIL-2 (F42K/V69R) | 18 | 1500 | Partial, 80% | 841 | Partial, 80% |
| 2D12-mIgG1-D265A-L6-hIL-2 (Y45R/V69R) | 19 | 1 | Full | 3 | Full |
| 2D12-mIgG1-D265A-L6-hIL-2 (D20A/D84A) | 38 | 1 | Full | >10,000 on graph, NC [a] | Inactive |
| 2D12-mIgG1-D265A-L6-hIL-2 (D20A/E15A) | 39 | 0 | Full | >10,000 on graph, NC [a] | Partial, 40% |
| 2D12-mIgG1-D265A-L6-hIL-2 (D20A/E95A) | 40 | 0 | Full | >10,000 [a] | Full |
| 2D12-mIgG1-D265A-L6-hIL-2 (D20A/N88A) | 41 | 6 | Partial, 60% | >10,000 on graph, NC [a] | Inactive |
| 2D12-mIgG1-D265A-L6-hIL-2 (D20A/S87A) | 42 | 0 | Full | >10,000 [a] | Full |
| 2D12-mIgG1-D265A-L6-hIL-2 (D84A/N88A) | 43 | 0 | Full | >10,000 on graph, NC [a] | Inactive |
| 2D12-mIgG1-D265A-L6-hIL-2 (E15A/N88A) | 44 | 0 | Full | 4201 | Partial, 80% |

TABLE 14-continued

Fold change from rhIL-2 and agonistic activity on 2D12-mIgG1-D265A-L6-hIL-2 or 2D12-hIgG1-L6-hIL-2 fusion proteins from Group 1 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 2D12-mIgG1-D265A-L6-hIL-2 (S87A/N88A) | 45 | 0 | Full | 1521 | Full |
| 2D12-mIgG1-D265A-L6-hIL-2 (F42K/F44K/Y45R) | 20 | NT | NT | 0 | Full |
| 2D12-mIgG1-D265A-L6-hIL-2 (F42A/Y45A/L72G) | 574 | 0-1 | Full | 0-3 | Full |
| 2D12-mIgG1-D265A-L6-hIL-2 (R38A/F42K/Y45R) | 21 | 1 | Full | 0 | Full |
| 2D12-mIgG1-D265A-L6-hIL-2 (R38E/F42K/Y45R) | 22 | 1-3 | Full | 0 | Full |
| 2D12-mIgG1-D265A-L6-hIL-2 (K43E/F42K/Y45R) | 23 | 0 | Full | 3 | Full |
| 2D12-mIgG1-D265A-L6-hIL-2 (K43T/F42K/Y45R) | 24 | 0 | Full | 3 | Full |
| 2D12-mIgG1-D265A-L6-hIL-2 (F42K/Y45R/E62A) | 25 | 1 | Full | 0-3 | Full |
| 2D12-mIgG1-D265A-L6-hIL-2 (P65R/F42K/Y45R) | 26 | 1 | Full | 0-2 | Full |
| 2D12-mIgG1-D265A-L6-hIL-2 (P65S/F42K/Y45R) | 27 | 1 | Full | 0-2 | Full |
| 2D12-mIgG1-D265A-L6-hIL-2 (V69A/F42K/Y45R) | 28 | 1 | Full | 0-4 | Full |
| 2D12-mIgG1-D265A-L6-hIL-2 (V69D/F42K/Y45R) | 29 | 1 | Full | 0-5 | Full |
| 2D12-mIgG1-D265A-L6-hIL-2 (V69R/F42K/Y45R) | 30 | 1-4 | Full | 0-6 | Full |

NT = Not Tested
NC = Not Calculated by GraphPad Prism 7
[a] = Fold change is an estimate only since a full four parameter logistic curve was not reached

TABLE 15

Fold change from rhIL-2 and agonistic activity on 1H3-hIgG1-L6-hIL-2 fusion proteins from Group 2 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1+ IL-2Rβ) |
|---|---|---|---|---|---|
| 1H3-hIgG1-L6-hIL-2 (R38A) | 46 | 0 | Full | 1 | Full |
| 1H3-hIgG1-L6-hIL-2 (R38D) | 47 | 3 | Full | 0 | Full |
| 1H3-hIgG1-L6-hIL-2 (R38E) | 48 | 7 | Full | 1 [a] | Full |
| 1H3-hIgG1-L6-hIL-2 (F42R) | 50 | 6 | Full | 0 [a] | Full |
| 1H3-hIgG1-L6-hIL-2 (F42D) | 52 | 10 | Full | 2 | Full |
| 1H3-hIgG1-L6-hIL-2 (K43A) | 54 | 1 [a] | Full | 2 | Full |
| 1H3-hIgG1-L6-hIL-2 (Y45R) | 60 | 4 | Full | 0 [a] | Full |
| 1H3-hIgG1-L6-hIL-2 (E61A) | 61 | 0 [a] | Full | 1 | Full |
| 1H3-hIgG1-L6-hIL-2 (E61R) | 62 | 1 | Full | 1 | Full |
| 1H3-hIgG1-L6-hIL-2 (E61K) | 63 | 1 | Full | 1 | Full |
| 1H3-hIgG1-L6-hIL-2 (E62A) | 64 | 1 | Full | 1 | Full |
| 1H3-hIgG1-L6-hIL-2 (E62R) | 65 | >10,000 on graph, NC [a] | Inactive | 209 | Partial, 60% |
| 1H3-hIgG1-L6-hIL-2 (E62K) | 66 | >10,000 [a] | Partial, 40-70% | 67-99 | Partial, 60% |
| 1H3-hIgG1-L6-hIL-2 (E62Y) | 67 | 1 | Full | 1 | Full |
| 1H3-hIgG1-L6-hIL-2 (E68K) | 70 | 0 | Full | 1 | Full |
| 1H3-hIgG1-L6-hIL-2 (E68R) | 71 | 1 | Full | 1 | Full |
| 1H3-hIgG1-L6-hIL-2 (L72R) | 74 | 3 | Full | 3 | Full |
| 1H3-hIgG1-L6-hIL-2 (L72D) | 76 | 2 | Full | 0 | Full |
| 1H3-hIgG1-L6-hIL-2 (L72H) | 77 | 1 | Full | 1 | Full |
| 1H3-hIgG1-L6-hIL-2 (R38D/E61R) | 79 | 36 | Full | 2 | Full |
| 1H3-hIgG1-L6-hIL-2 (R38D/E61R/K43E) | 80 | 27 | Full | 1 | Full |

TABLE 15-continued

Fold change from rhIL-2 and agonistic activity on 1H3-hIgG1-L6-hIL-2 fusion proteins from Group 2 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1+ IL-2Rβ) |
|---|---|---|---|---|---|
| 1H3-hIgG1-L6-hIL-2 (T3A/F42A/Y45A/L72G/C125A) | 81 | 142 | Full | 1-2 | Partial, 40%-Full |

NT = Not Tested
NC = Not Calculated by GraphPad Prism 7
$^a$ = Fold change is an estimate only since a full four parameter logistic curve was not reached

TABLE 16

Fold change from rhIL-2 and agonistic activity on 1H3-hIgG1-L6-hIL-2 fusion proteins from Group 3 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1+ IL-2Rβ) |
|---|---|---|---|---|---|
| 1H3-hIgG1-L6-hIL-2 (H16E) | 87 | 0 | Full | 34 | Full |
| 1H3-hIgG1-L6-hIL-2 (L19A) | 88 | NT | NT | 1 | Full |
| 1H3-hIgG1-L6-hIL-2 (D20I) | 89 | NT | NT | 8 $^a$ | Partial, 50% |
| 1H3-hIgG1-L6-hIL-2 (D20S) | 90 | 1 | Full | 201-304 | Partial, 80%-Full |
| 1H3-hIgG1-L6-hIL-2 (D20H) | 91 | 239 | Full | 986-6461 $^a$ | Partial, 50-70% |
| 1H3-hIgG1-L6-hIL-2 (D20W) | 93 | NT | NT | >10,000 on graph, NC $^a$ | Inactive |
| 1H3-hIgG1-L6-hIL-2 (D20Y) | 94 | 880-2097 $^a$ | Full | 383 | Full |
| 1H3-hIgG1-L6-hIL-2 (D20R) | 95 | NT | NT | 262-275 | Full |
| 1H3-hIgG1-L6-hIL-2 (D20F) | 96 | NT | NT | >10,000 on graph, NC $^a$ | Inactive |
| 1H3-hIgG1-L6-hIL-2 (D84A) | 98 | NT | NT | 21 | Full |
| 1H3-hIgG1-L6-hIL-2 (D84R) | 99 | 9 | Full | 269-455 | Partial, 80-90% |
| 1H3-hIgG1-L6-hIL-2 (D84K) | 100 | 4 | Full | 354-385 | Partial, 70%-Full |
| 1H3-hIgG1-L6-hIL-2 (N88Y) | 102 | NT | NT | >10,000 on graph, NC $^a$ | Inactive |
| 1H3-hIgG1-L6-hIL-2 (N88D) | 103 | 0 | Full | 115-137 | Partial, 70%-Full |
| 1H3-hIgG1-L6-hIL-2 (N88R) | 104 | 1-5 | Partial, 80%-Full | 959 | Partial, 80% |
| 1H3-hIgG1-L6-hIL-2 (N88E) | 105 | NT | NT | 1162 | Partial, 50% |
| 1H3-hIgG1-L6-hIL-2 (N88F) | 106 | NT | NT | >10,000 on graph, NC $^a$ | Inactive |
| 1H3-hIgG1-L6-hIL-2 (N88I) | 107 | NT | NT | >10,000 on graph, NC $^a$ | Inactive |
| 1H3-hIgG1-L6-hIL-2 (I92Y) | 109 | NT | NT | 1 | Full |
| 1H3-hIgG1-L6-hIL-2 (I92S) | 110 | NT | NT | 10 | Full |
| 1H3-hIgG1-L6-hIL-2 (I92R) | 112 | NT | NT | 13 | Full |
| 1H3-hIgG1-L6-hIL-2 (I92D) | 113 | 15-20 | Full | 609-1006 | Partial, 90%-Full |
| 1H3-hIgG1-L6-hIL-2 (E95R) | 116 | NT | NT | 8 | Full |
| 1H3-hIgG1-L6-hIL-2 (D20T) | 92 | 2 | Full | 124-149 | Full |
| 1H3-hIgG1-L6-hIL-2 (D20Y/H16E) | 118 | 5 | Full | 8076 $^a$ | Partial, 80% |

NT = Not Tested
NC = Not Calculated by GraphPad Prism 7
$^a$ = Fold change is an estimate only since a full four parameter logistic curve was not reached

TABLE 17

Fold change from rhIL-2 and agonistic activity on 1H3-hIgG1-L6-hIL-2 fusion proteins from Group 4 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hCD25(1-164)-L20-hIL-2 (E15A) | 82 | 14 | Partial, 90% | 13 | Partial, 70% |

TABLE 17-continued

Fold change from rhIL-2 and agonistic activity on 1H3-hIgG1-L6-hIL-2 fusion proteins from Group 4 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
| --- | --- | --- | --- | --- | --- |
| 1H3-hIgG1-L6-hCD25(1-164)-L20-hIL-2 (D20S) | 90 | 127 | Full | 8709 [a] | Partial, 50% |
| 1H3-hIgG1-L6-hCD25(1-164)-L20-hIL-2 (D20W) | 93 | >10,000 on graph, NC [a] | Inactive | >10,000 on graph, NC [a] | Inactive |
| 1H3-hIgG1-L6-hCD25(1-164)-L20-hIL-2 (D20Y) | 94 | >10,000 on graph, NC [a] | Partial, 50% | >10,000 on graph, NC [a] | Inactive |
| 1H3-hIgG1-L6-hCD25(1-164)-L20-hIL-2 (D84K) | 100 | 783 | Partial, 90% | 2051 [a] | Partial, 30% |
| 1H3-hIgG1-L6-hCD25(1-164)-L20-hIL-2 (S87A) | 101 | 19 | Partial, 90% | 20 | Partial, 90% |
| 1H3-hIgG1-L6-hCD25(1-164)-L20-hIL-2 (N88D) | 103 | 50 | Full | 3284 [a] | Partial, 90% |
| 1H3-hIgG1-L6-hCD25(1-164)-L20-hIL-2 (N88R) | 104 | 42 | Full | 6864 [a] | Partial, 50% |
| 1H3-hIgG1-L6-hCD25(1-164)-L20-hIL-2 (E95K) | 117 | 51 | Full | 164 | Partial, 80% |

NC = Not Calculated by GraphPad Prism 7
[a] = Fold change is an estimate only since a full four parameter logistic curve was not reached

TABLE 18

Fold change from rhIL-2 and agonistic activity on 1H3-hIgG1-L6-hIL-2 fusion proteins from Group 5 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
| --- | --- | --- | --- | --- | --- |
| 1H3-hIgG1-L6-hIL-2 (F42K/D20A) | 129 | >10,000 on graph, NC [a] | Partial, 20% | 3060 [a] | Full |
| 1H3-hIgG1-L6-hIL-2 (F42A/D20A) | 130 | >10,000 on graph, NC [a] | Full | 2081 [a] | Full |
| 1H3-hIgG1-L6-hIL-2 (R38P/D20A) | 141 | 86 | Full | 761 | Full |
| 1H3-hIgG1-L6-hIL-2 (R38S/D20A) | 142 | 140 | Full | 662 | Full |
| 1H3-hIgG1-L6-hIL-2 (R38V/D20A) | 146 | 11 | Full | 843 | Full |
| 1H3-hIgG1-L6-hIL-2 (D20A/R38E) | 149 | 1183-2016 | Partial, 70%-Full | >10,000 [a] | Partial, 80%-Full |
| 1H3-hIgG1-L6-hIL-2 (R38D/D20A) | 150 | 2262 [a] | Full | 680 | Full |
| 1H3-hIgG1-L6-hIL-2 (F42R/I92D) | 159 | >10,000 on graph, NC [a] | Partial, 30% | 1210 | Full |
| 1H3-hIgG1-L6-hIL-2 (F42H/I92D) | 160 | 288 [a] | Full | 242 [a] | Full |
| 1H3-hIgG1-L6-hIL-2 (F42A/I92D) | 161 | >10,000 on graph, NC [a] | Partial, 60% | 2275 | Partial, 80% |
| 1H3-hIgG1-L6-hIL-2 (R38D/I92D) | 170 | 746 [a] | Partial, 90% | 172 | Full |
| 1H3-hIgG1-L6-hIL-2 (R38E/I92D) | 171 | 1611 [a] | Full | 116 | Full |
| 1H3-hIgG1-L6-hIL-2 (R38E/D84R) | 175 | >10,000 on graph, NC [a] | Full | 147 | Full |
| 1H3-hIgG1-L6-hIL-2 (R38E/D84K) | 176 | >10,000 on graph, NC [a] | Partial, 70% | 315 | Full |
| 1H3-hIgG1-L6-hIL-2 (R38D/E61R/D20A) | 179 | >10,000 on graph, NC [a] | Partial, 50% | 984 | Full |
| 1H3-hIgG1-L6-hIL-2 (R38E/E61R/D20A) | 180 | >10,000 on graph, NC [a] | Full | 417 | Full |
| 1H3-hIgG1-L6-hIL-2 (R38Q/E61R/D20A) | 181 | >10,000 on graph, NC [a] | Partial, 80% | 803 | Full |
| 1H3-hIgG1-L6-hIL-2 (R38A/E61R/D20A) | 182 | >10,000 on graph, NC [a] | Partial, 60% | 1031 | Full |
| 1H3-hIgG1-L6-hIL-2 (D20A/E95A/R38A) | 183 | 42 | Partial, 70% | 537 | Partial, 80% |
| 1H3-hIgG1-L6-hIL-2 (D20A/E95A/R38D) | 184 | 5315 [a] | Partial, 50% | 492 | Partial, 80% |
| 1H3-hIgG1-L6-hIL-2 (D20A/E95A/R38E) | 185 | >10,000 on graph, NC [a] | Full | 439 | Partial, 90% |
| 1H3-hIgG1-L6-hIL-2 (D20A/E95A/R38Q) | 186 | 572 | Full | 859 | Partial, 80% |
| 1H3-hIgG1-L6-hIL-2 (D20A/E95A/F42R) | 187 | 2096 | Partial, 70% | 356 | Partial, 70% |
| 1H3-hIgG1-L6-hIL-2 (D20A/E95A/F42A) | 188 | 369 | Partial, 70% | 73 | Partial, 90% |
| 1H3-hIgG1-L6-hIL-2 (D20A/E95A/F42D) | 189 | >10,000 on graph, NC [a] | Inactive | >10,000 on graph, NC [a] | Inactive |
| 1H3-hIgG1-L6-hIL-2 (D20A/E95A/F42H) | 190 | 641 | Partial, 90% | 320 | Full |
| 1H3-hIgG1-L6-hIL-2 (D20A/E95A/F42K) | 191 | >10,000 on graph, NC [a] | Inactive | 272 | Partial, 80% |

TABLE 18-continued

Fold change from rhIL-2 and agonistic activity on 1H3-hIgG1-L6-hIL-2 fusion proteins from Group 5 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (D20A/E95A/K43E) | 193 | 80 | Partial, 90% | 1876 [a] | Partial, 70% |
| 1H3-hIgG1-L6-hIL-2 (D20A/E95A/Y45A) | 195 | 25 | Full | 82 | Partial, 90% |
| 1H3-hIgG1-L6-hIL-2 (D20A/E95A/Y45K) | 196 | >10,000 on graph, NC [a] | Partial, 20% | 383 | Partial, 60% |
| 1H3-hIgG1-L6-hIL-2 (D20A/E95A/Y45R) | 198 | >10,000 on graph, NC [a] | Inactive | 57 | Partial, 50% |
| 1H3-hIgG1-L6-hIL-2 (D20A/E95A/E61A) | 199 | 306 [a] | Partial, 80% | 702 | Partial, 80% |
| 1H3-hIgG1-L6-hIL-2 (D20A/E95A/E62A) | 200 | >10,000 on graph, NC [a] | Partial, 20% | 661 | Partial, 60% |
| 1H3-hIgG1-L6-hIL-2 (D20A/E95A/E62R) | 201 | >10,000 on graph, NC [a] | Inactive | >10,000 on graph, NC [a] | Inactive |
| 1H3-hIgG1-L6-hIL-2 (D20A/E95A/E62K) | 202 | >10,000 on graph, NC [a] | Inactive | >10,000 on graph, NC [a] | Inactive |
| 1H3-hIgG1-L6-hIL-2 (D20A/E95A/E62Y) | 203 | 721 | Partial, 40% | 982 [a] | Partial, 30% |
| 1H3-hIgG1-L6-hIL-2 (D20A/E95A/E68Y) | 204 | 11 | Full | 469 | Full |
| 1H3-hIgG1-L6-hIL-2 (D20A/E95A/E68A) | 205 | 6 | Partial, 50% | 535 | Partial, 80% |
| 1H3-hIgG1-L6-hIL-2 (D20A/E95A/E68L) | 206 | 15 | Full | 972 | Partial, 60% |
| 1H3-hIgG1-L6-hIL-2 (D20A/E95A/L72R) | 208 | 655 [a] | Partial, 50% | 316 | Partial, 40% |
| 1H3-hIgG1-L6-hIL-2 (D20A/E95A/L72D) | 210 | 5415 | Inactive | 125 | Partial, 90% |
| 1H3-hIgG1-L6-hIL-2 (D20A/E95A/L72H) | 211 | 583 [a] | Partial, 60% | 135 | Partial, 80% |
| 1H3-hIgG1-L6-hIL-2 (D20A/E95A/F42K/Y45R) | 214 | >10,000 on graph, NC [a] | Inactive | 58-209 | Partial, 40-80% |
| 1H3-hIgG1-L6-hIL-2 (F42K/Y45R/D20A/S87A) | 213 | 123 | Full | 0 | Full |
| 1H3-hIgG1-L6-hIL-2 (D20A/R38E/C125A) | 215 | >10,000 [a] | Partial, 30-90% | 2102 [a] | Partial, 80% |
| 1H3-hIgG1-L6-hIL-2 (T3A/D20A/R38E) | 216 | 2338-5870 | Partial, 80%-Full | 353-571 | Full |
| 1H3-hIgG1-L6-hIL-2 (T3A/D20A/R38E/C125A) | 217 | >10,000 [a] | Full | 1086 [a] | Partial, 80%-Full |
| 1H3-hIgG1-L6-hIL-2 (Δ1-3APT/D20A/R38E) | 218 | 4-16 | Full | 32 | Partial, 90% |
| 1H3-hIgG1-L6-hIL-2 (Δ1-3APT/D20A/R38E/C125A) | 219 | >10,000 [a] | Inactive-Partial, 50% | 993 [a] | Partial, 60% |
| 1H3-hIgG1-L6-hIL-2 (F42K/Y45R/Q126D) | 228 | >10,000 [a] | Partial, 50% | 597 | Partial, 80% |
| 1H3-hIgG1-L6-hIL-2 (D20A/E95A/Q126D) | 229 | 106 [a] | Inactive | >10,000 on graph, NC [a] | Inactive |

NC = Not Calculated by GraphPad Prism 7
[a] = Fold change is an estimate only since a full four parameter logistic curve was not reached

TABLE 19

Fold change from rhIL-2 and agonistic activity on 1H3-hIgG1-L6-hIL-2 fusion proteins from Group 6 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (D20A/E61R) | 230 | 3950 [a] | Partial, 10% | 278 | Partial, 50% |
| 1H3-hIgG1-L6-hIL-2 (D20A/F42N) | 247 | >10,000 [a] | Partial, 50% | 662 | Partial, 80% |
| 1H3-hIgG1-L6-hIL-2 (D20A/F42Q) | 248 | >10,000 on graph, NC [a] | Partial, 30% | 630 | Partial, 80% |
| 1H3-hIgG1-L6-hIL-2 (D20A/F42I) | 251 | 1307 [a] | Partial, 20% | 494 | Partial, 60% |
| 1H3-hIgG1-L6-hIL-2 (D20A/F42L) | 252 | 68 | Full | 533 | Partial, 60% |
| 1H3-hIgG1-L6-hIL-2 (D20A/F42M) | 253 | 53 | Full | 370 | Partial, 50% |
| 1H3-hIgG1-L6-hIL-2 (D20A/F42P) | 254 | 9374 [a] | Partial, 80% | 702 | Partial, 80% |
| 1H3-hIgG1-L6-hIL-2 (D20A/F42S) | 255 | 1286 | Partial, 70% | 687 | Partial, 70% |
| 1H3-hIgG1-L6-hIL-2 (D20A/F42T) | 256 | 1474 [a] | Partial, 10% | 622 | Partial, 80% |
| 1H3-hIgG1-L6-hIL-2 (D20A/F42W) | 257 | 414 [a] | Partial, 70% | 400 | Partial, 70% |
| 1H3-hIgG1-L6-hIL-2 (D20A/F42Y) | 258 | 322 | Partial, 70% | 545 | Partial, 70% |
| 1H3-hIgG1-L6-hIL-2 (D20A/F42V) | 259 | 5796 [a] | Partial, 30% | 579 | Partial, 80% |
| 1H3-hIgG1-L6-hIL-2 (D20A/Y45A) | 260 | 61 | Partial, 80% | 554 | Partial, 80% |
| 1H3-hIgG1-L6-hIL-2 (D20A/Y45N) | 261 | 31 | Full | 390 | Partial, 70% |
| 1H3-hIgG1-L6-hIL-2 (D20A/Y45D) | 262 | 363 | Partial, 60% | 729 | Partial, 70% |
| 1H3-hIgG1-L6-hIL-2 (D20A/Y45Q) | 263 | 730 [a] | Partial, 70% | 348 | Partial, 70% |
| 1H3-hIgG1-L6-hIL-2 (D20A/Y45E) | 264 | 1414 [a] | Partial, 60% | 486 | Partial, 70% |
| 1H3-hIgG1-L6-hIL-2 (D20A/Y45G) | 265 | 613 [a] | Partial, 80% | 392 | Partial, 60% |
| 1H3-hIgG1-L6-hIL-2 (D20A/Y45H) | 266 | 420 [a] | Partial, 70% | 427 | Partial, 60% |
| 1H3-hIgG1-L6-hIL-2 (D20A/Y45I) | 267 | 39 | Partial, 70% | 137 | Partial, 30% |
| 1H3-hIgG1-L6-hIL-2 (D20A/Y45L) | 268 | 11 | Full | 426 | Partial, 70% |

TABLE 19-continued

Fold change from rhIL-2 and agonistic activity on 1H3-hIgG1-L6-hIL-2 fusion proteins from Group 6 in a cell-based proliferation assay

| Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| 1H3-hIgG1-L6-hIL-2 (D20A/Y45M) | 269 | 107 | Full | 449 | Partial, 60% |
| 1H3-hIgG1-L6-hIL-2 (D20A/Y45F) | 270 | 25 | Partial, 90% | 272 | Partial, 50% |
| 1H3-hIgG1-L6-hIL-2 (D20A/Y45P) | 271 | 577 $^a$ | Full | 710 | Full |
| 1H3-hIgG1-L6-hIL-2 (I92D/F42Q) | 277 | 7227 $^a$ | Partial, 30% | 872 | Full |
| 1H3-hIgG1-L6-hIL-2 (I92D/F42I) | 280 | 4587 $^a$ | Partial, 10% | 3644 $^a$ | Full |
| 1H3-hIgG1-L6-hIL-2 (I92D/F42K) | 282 | >10,000 $^a$ | Partial, 20% | 848 $^a$ | Full |
| 1H3-hIgG1-L6-hIL-2 (I92D/F42T) | 286 | >10,000 $^a$ | Partial, 40% | 1068 $^a$ | Full |
| 1H3-hIgG1-L6-hIL-2 (I92D/F42W) | 287 | 405 $^a$ | Full | 3954 $^a$ | Full |
| 1H3-hIgG1-L6-hIL-2 (I92D/F42Y) | 288 | 58 | Full | 106 | Full |
| 1H3-hIgG1-L6-hIL-2 (I92D/F42V) | 289 | 1075 $^a$ | Partial, 60% | 343 | Full |
| 1H3-hIgG1-L6-hIL-2 (I92D/Y45A) | 290 | 15 | Full | 285 | Full |
| 1H3-hIgG1-L6-hIL-2 (I92D/Y45Q) | 293 | 53 | Full | 80 | Full |
| 1H3-hIgG1-L6-hIL-2 (I92D/Y45G) | 295 | 41 | Full | 91 | Full |
| 1H3-hIgG1-L6-hIL-2 (I92D/Y45M) | 299 | 7 | Full | 146 | Full |
| 1H3-hIgG1-L6-hIL-2 (I92D/Y45F) | 300 | 33 | Full | 1650 $^a$ | Full |
| 1H3-hIgG1-L6-hIL-2 (I92D/Y45S) | 302 | 20 | Full | 306 | Full |
| 1H3-hIgG1-L6-hIL-2 (R38E/D20H) | 306 | 13 | Inactive | 2945 | Partial, 40% |
| 1H3-hIgG1-L6-hIL-2 (R38E/D20S) | 307 | >10,000 on graph, NC $^a$ | Partial, 50% | 626 | Full |
| 1H3-hIgG1-L6-hIL-2 (F42A/N88R) | 308 | 8351 $^a$ | Partial, 70% | 1456 | Full |
| 1H3-hIgG1-L6-hIL-2 (F42A/N88D) | 309 | 1966 $^a$ | Full | 86 | Full |
| 1H3-hIgG1-L6-hIL-2 (R38E/I92K) | 334 | >10,000 $^a$ | Partial, 70% | 239 | Full |
| 1H3-hIgG1-L6-hIL-2 (R38E/I92P) | 337 | >10,000 on graph, NC $^a$ | Inactive | >10,000 on graph, NC $^a$ | Inactive |
| 1H3-hIgG1-L6-hIL-2 (R38E/H16E) | 343 | 658 $^a$ | Full | 58 | Full |
| 1H3-hIgG1-L6-hIL-2 (R38K/D20A) | 344 | 66 | Full | 369 | Partial, 70% |

NC = Not Calculated by GraphPad Prism 7
$^a$ = Fold change is an estimate only since a full four parameter logistic curve was not reached Example 6: Generation of Anti-hPD-1 Antibodies Several approaches were used to generate a variety of different anti-hPD-1 antibodies with desired properties.

In one approach, anti-hPD-1 human monoclonal antibodies were generated using transgenic chickens (OmniChicken™) that express human antibody genes (human light chain (VLCL or VKCK) and human VH) and the chicken constant regions of the heavy chain (Ching et al., mAbs 2018). Transgenic chickens were immunized with 100 µg of Fc-tagged human PD-1 protein (huPD-1-Fc) (SEQ ID NO: 380) every 14 days for 14 weeks. In another approach, transgenic chickens were genetically immunized six times with DNA encoding human PD-1 (SEQ ID NO: 347) followed by a final boost with 100 µg huPD-1-Fc (SEQ ID NO: 380). The serum immune response of each animal was monitored by ELISA against biotinylated human PD-1 on streptavidin coated plates.

Splenocytes were isolated from each immunized animal, tested for positive antibody clones using the Gel Encapsulated Microenvironment (GEM) assay (as described in Mettler Izquierdo, S., Varela, S., Park, M., Collarini, E. J., Lu, D., Pramanick, S., Rucker, J., Lopalco, L., Etches, R., & Harriman, W. (2016). High-efficiency antibody discovery achieved with multiplexed microscopy. *Microscopy (Oxford, England)*, 65 (4), 341-352) and screened against human PD-1 labelled beads. Positive clones were sequenced and variable regions of the heavy and light chains were cloned, assembled into a single chain variable fragment, and fused to the hinge and Fc regions of immunoglobulins (ScFv-Fc). These unique scFv-Fc fusion proteins were transiently expressed in Expi293 cells and supernatants were tested for binding activity by ELISA on plates coated with huPD-1-Fc (SEQ ID NO: 380) or cynomolgous-PD-1-Fc (SEQ ID NO: 381). In total, 102 unique anti-human PD-1 variable heavy and variable light pairings were identified using this method. 2H7-hIgG4 (SEQ ID NOs: 382-391, 424, and 425) and A2-hIgG4 (SEQ ID NOs: 402-411, 428, and 429) were among the antibodies identified in this approach.

Other approaches led to the identification of an anti-hPD-1 antibody denoted as C51E6-hIgG4, which was germline optimized to become the antibody designated C51E6-5-hIgG4 (SEQ ID NOs: 392-401, 426, 427), and humanized and further sequence optimized to become the antibody designated Abzlmod-hIgG4 (SEQ ID NOs: 449, 450).

The anti-PD-1 variable region sequences were expressed as human IgG4 kappa antibodies and were evaluated for the ability to bind to PD-1 expressing cells using flow cytometry as described in General Methods Protocol A. Antibodies to be tested were first screened for binding to human PD-1 using a Jurkat cell line expressing recombinant human PD-1 (Jurkat+hPD-1 cell line). Antibodies were serially diluted from a top concentration of 280 nM and Allophycocyanin-conjugated anti-human IgG secondary antibody was then added to cells for detection. Of 92 hits, 79 test anti-PD-1 antibodies had an $EC_{50}$ binding (by flow cytometry) of <30 nM. 2H7-hIgG4 (SEQ ID NOs: 382-391, 424, and 425), C51E6-5-hIgG4 (SEQ ID NOs: 392-401, 426, and 427), A2-hIgG4 (SEQ ID NOs: 402-411, 428, and 429), OMC.1.B6-hIgG4 (SEQ ID NOs: 438 and 439), OMC.1.D6-hIgG4 (SEQ ID NOs: 442 and 443), OMC.2.C6-hIgG4 (SEQ ID NOs: 440 and 441), 1H9-hIgG4 (SEQ ID NOs: 576 and 525), 1D5-hIgG4 (SEQ ID NOs: 577 and 527), and 2A3.H7-hIgG4 (SEQ ID NOs: 424 and 523) were among a group of antibodies identified as antibodies with medium to high affinity binding to hPD-1 using a Jurkat cell line expressing human PD-1 (SEQ ID NO: 346). The calculated $EC_{50}$ of binding to Jurkat cells which recombinantly expressed hPD-1 by flow cytometry in multiple experiments was 0.1-0.3 nM for 2H7-hIgG4, 1H9-hIgG4, 1D5-hIgG4, and 2A3.H7-hIgG4. The calculated $EC_{50}$ of binding to Jurkat cells expressing hPD-1 by flow for C51E6-5-hIgG4 was 2-4 nM, and 3-16 nM for A2-hIgG4, OMC.1.B6-hIgG4, OMC.1.D6-hIgG4, and OMC.2.C6-hIgG4. Binding was specific to hPD-1 since 2H7-hIgG4, C51E6-5-hIgG4, A2-hIgG4, 1H9-hIgG4, 1D5-hIgG4, 2A3.H7-hIgG4, OMC.1.B6-hIgG4, OMC.1.D6-hIgG4, and OMC.2.C6-hIgG4 antibody titrations did not bind the parental Jurkat cell line which did not express hPD-1 (data not shown).

Example 7: Characterization of Anti-hPD-1 Antibody Binding in the Presence of Anti-hPD-1 #1-mIgG2b-N297A and Anti-hPD-1 #2-mIgG2b-N297A Antibodies 2H7-hIgG4, C51E6-5-hIgG4, and A2-hIgG4 were assessed for binding competition to hPD-1 in the presence of anti-hPD-1 #1-mIgG2b-N297A and anti-hPD-1 #2-mIgG2b-N297A as described in General Methods Protocol B.

Figure 4B:
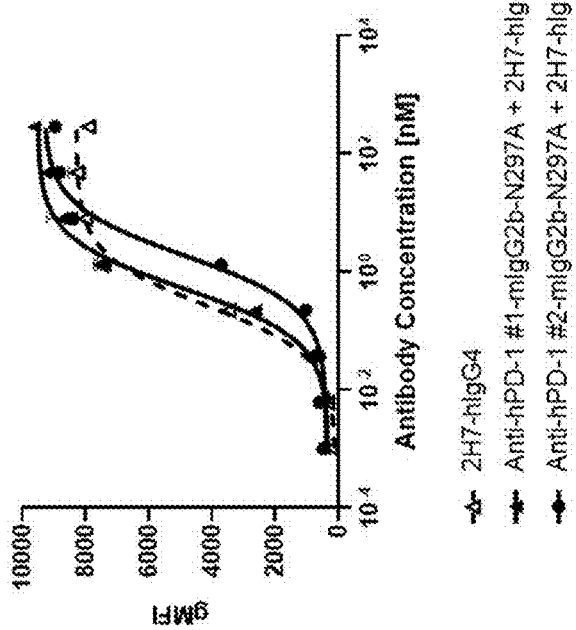
FIG. 4A, FIG. 4B, FIG. 4C, and FIG. 4D show the results of experiments analyzing the binding of the anti-hPD-1 antibodies 2H7-hIgG4, C51E6-5-hIgG4, and A2-hIgG4 to the human PD-1 receptor on Jurkat cells in the presence of saturating concentrations of anti-hPD-1 #1-mIgG2b-N297A and anti-hPD-1 #2-mIgG2b-N297A (10 μM) prior to exposure with anti-hPD-1 antibodies.
Figure 4A:
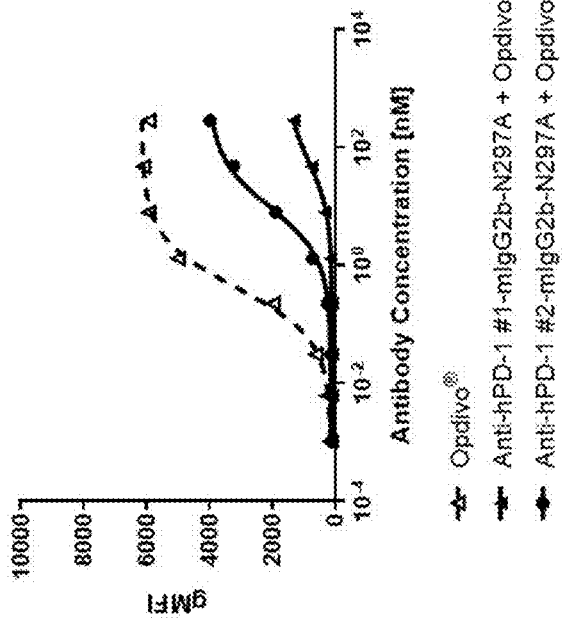
Figure 4D:
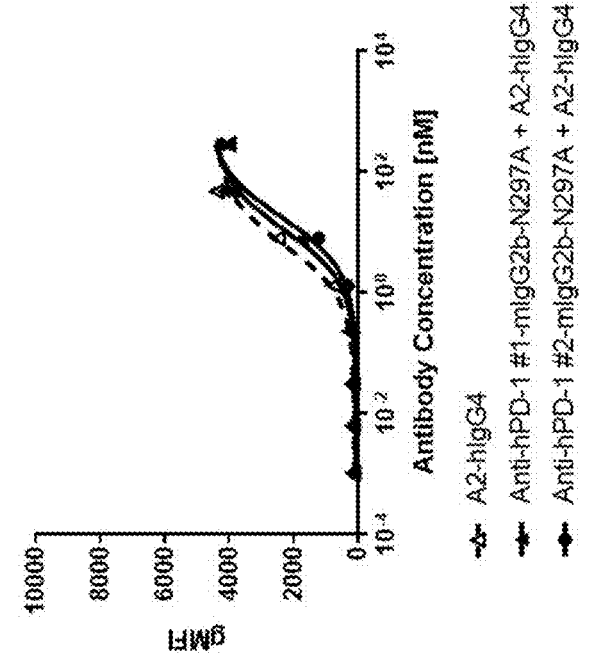
Figure 4C:
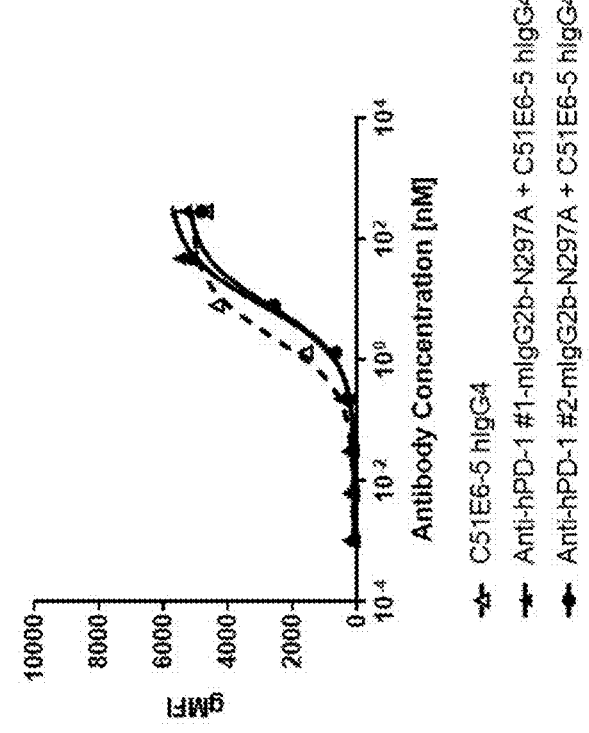

As a control, OPDIVO® (nivolumab) was titrated in the presence of saturating concentrations of 10 UM anti-hPD-1 #1-mIgG2b-N297A (FIG. 4A). The dose-titration curve in the presence of anti-hPD-1 #1-mIgG2b-N297A competitor was greatly reduced (100 to 1000-fold shift of the dose-titration curve to the right of the graph) when compared to the dose-titration curve of OPDIVO® without anti-hPD-1 #1-mIgG2b-N297A competitor. The addition of anti-hPD-1 #1-mIgG2b-N297A or anti-hPD-1 #2-mIgG2b-N297A at saturating concentrations (10 μM) prior to exposure with 2H7-hIgG4, C51E6-5-hIgG4, or A2-hIgG4 did not abrogate binding of 2H7-hIgG4, C51E6-5-hIgG4, or A2-hIgG4 to hPD-1 as illustrated by less than 10-fold shift in FIG. 4B-4D, suggesting that 2H7-hIgG4, C51E6-5-hIgG4 and A2-hIgG4 did not compete for binding to PD-1 in the presence of anti-hPD-1 #1-mIgG2b-N297A or anti-hPD-1 #2-mIgG2b-N297A.

Example 8: Characterization of Non-Antagonist hPD-1 Antibodies

Anti-hPD-1 antibodies 2H7-hIgG4, C51E6-5-hIgG4 and A2-hIgG4 were tested for PD-1 antagonist activity using an in vitro cell-based human PD-1/PD-L1 blockade bioassay as described in General Methods Protocol C. All antibodies except A2-hIgG4 were tested at 200 nM final concentration. A2-hIgG4 was tested at 500 nM final concentration.

None of the anti-hPD-1 antibodies 2H7-hIgG4, C51E6-5-hIgG4, A2-hIgG4, OMC.1.B6-hIgG4, OMC.1.D6-hIgG4, OMC.2.C6-hIgG4, 1H9-hIgG4, 1D5-hIgG4, and 2A3.H7-hIgG4 demonstrated hPD-1 antagonist activity, as all displayed luminescence levels of an average of 3000 relative luminescence units (RLU) and exhibited an RLU similar to the negative control KLH-C3-hIgG4 (data not shown). In contrast, the anti-hPD-1 #1, which is a known hPD-1 antagonist that blocks hPD-L1 (SEQ ID NO: 584) engagement with hPD-1, exhibited luminescence of above 14,000 RLU (data not shown).

Example 9: Anti-hPD-1-Attenuated hIL-2 Fusion Proteins Bind Jurkat Cells Expressing Human PD-1

In order to construct various antibody and antibody-attenuated hIL-2 fusion protein expression vectors, the corresponding polynucleotide encoding sequences of antibody, cytokines, cytokine receptors and linkers were generated and cloned into expression vectors. The antibodies or antibody fusion proteins were transiently expressed in Human Embryonic Kidney (HEK) 293 cells, then purified by affinity chromatography using Protein A- or Protein G-Sepharose. The purified proteins were concentrated and buffer-exchanged to phosphate buffered saline or phosphate buffered saline containing 100 mM L-arginine and 10 mM L-histidine using ultracentrifugal filtration, after which protein concentration was determined.

Figure 5:
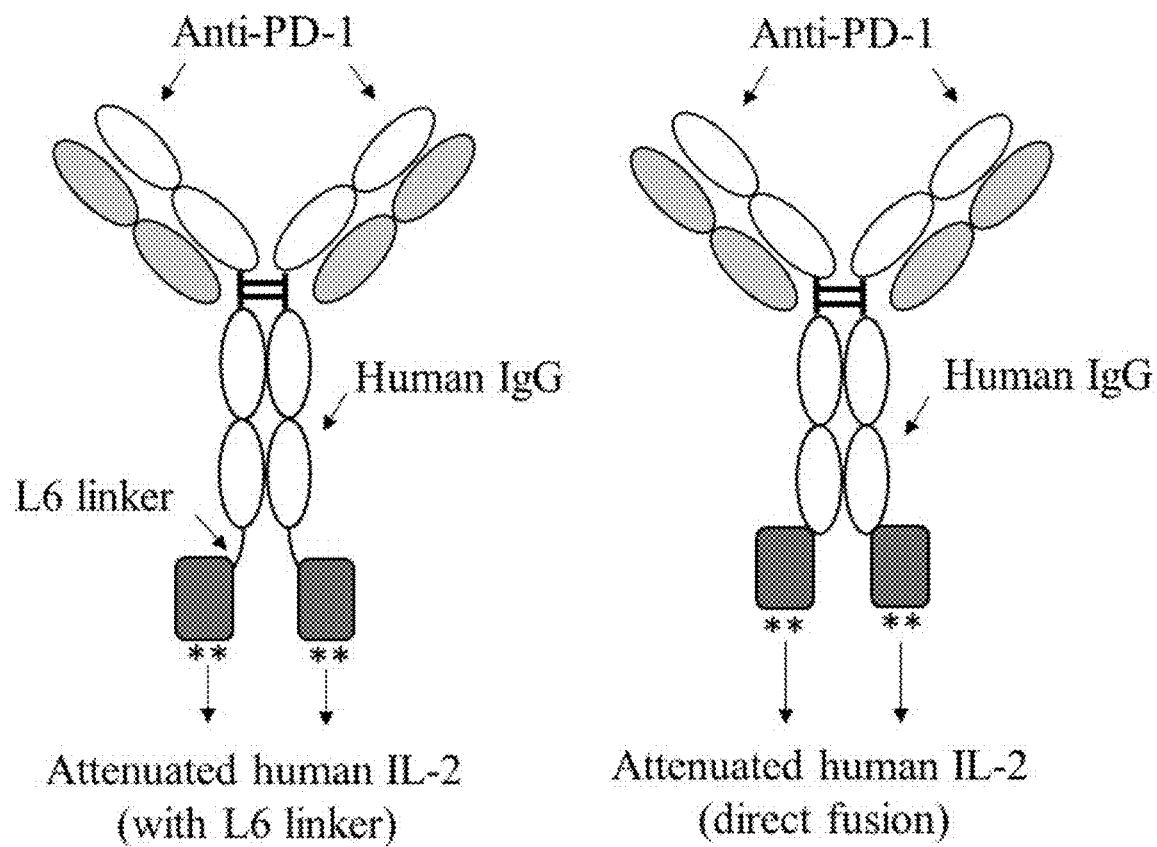
FIG. 5 illustrates exemplary anti-hPD-1-attenuated hIL-2 immunoconjugates either with an L6 linker (L6) (left) or direct fusion (df) (right). Anti-hPD-1 antibodies comprising either hIgG4 or hIgG1 Fc domains, with or without L235E (LE) or L235A/G237A (LAGA) modifications in the Fc domain, were fused to attenuated hIL-2 cytokines at the C-terminus of the antibody heavy chains. Various substitutions in the hIL-2 cytokine were introduced for potency attenuation.
Figure 6A:
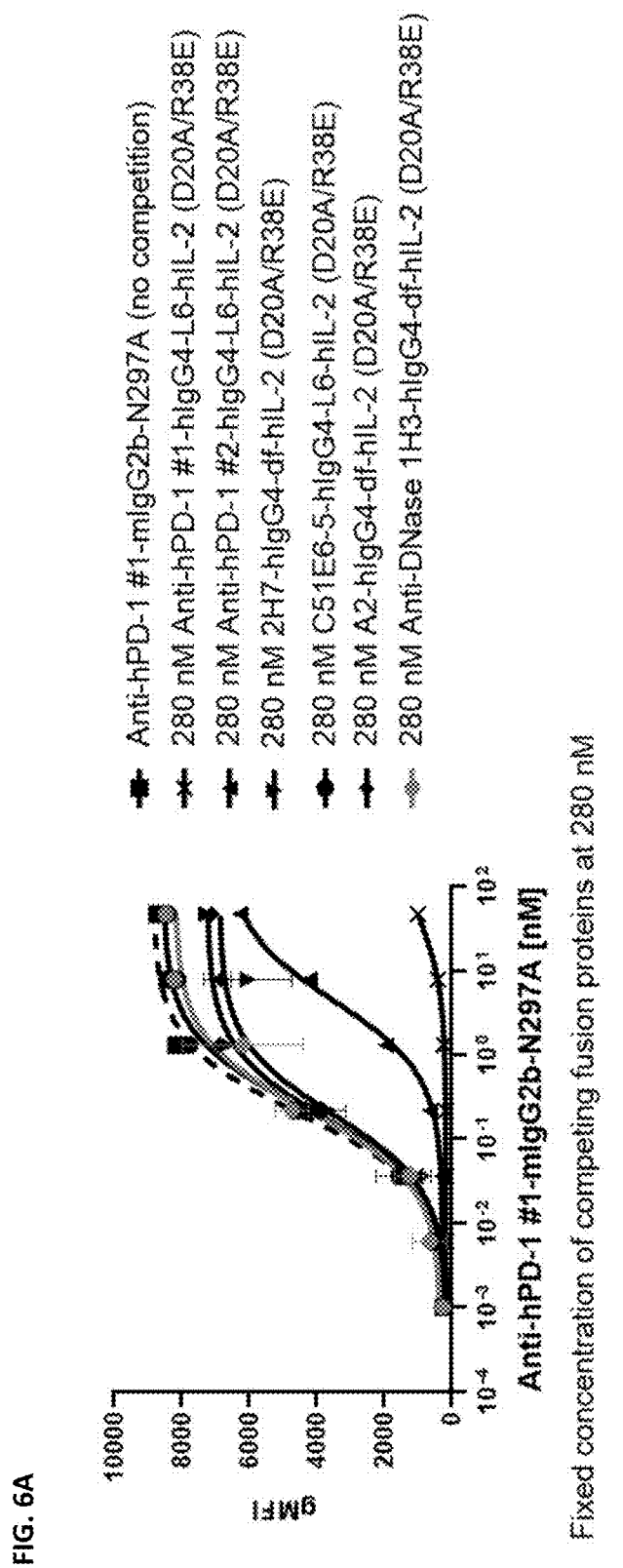
FIG. 6A and FIG. 6B show the results of competition assays demonstrating that anti-hPD-1 #1-mIgG2b-N297A (FIG. 6A) or anti-hPD-1 #2-mIgG2b-N297A (FIG. 6B) bind to anti-hPD-1 receptor on Jurkat cells in the presence of saturating concentrations of anti-hPD-1-attenuated hIL-2 immunoconjugates (280 nM).
Figure 6B:
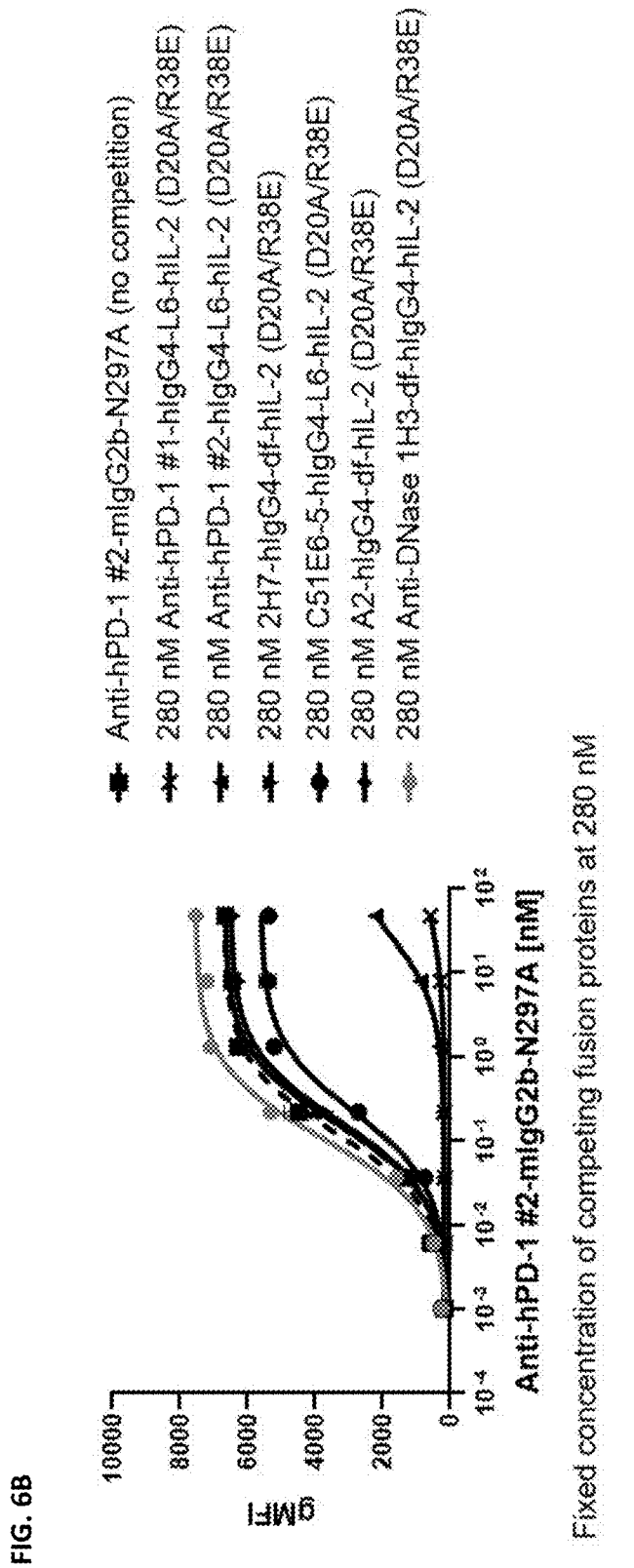

In some approaches, 2H7-hIgG4, C51E6-5-hIgG4, and A2-hIgG4 carrying an S228P hinge stabilization mutation were directly fused (df) to hIL-2 or fused to hIL-2 at the C-terminus of the immunoglobulin heavy chain using the L6 linker. An illustration of these anti-PD-1-attenuated hIL-2 fusion proteins is summarized in FIG. 5. Various constructs were generated with the substitutions in hIL-2 that attenuated hIL-2 activity as described in Example 2. Anti-hPD-1-attenuated hIL-2 fusion proteins listed in Table 20 were tested for binding to hPD-1 using the Jurkat cell line expressing hPD-1 as described in General Methods Protocol A. The variable region of 2H7-hIgG4 (SEQ ID NOs: 384 and 385) was further optimized, and the isotype was switched to a human IgG1with the effector function null substitutions L235A/G237A (LAGA, as described in WO1998/006248) to become H7-632-hIgG1-LAGA (SEQ ID NOs: 414 and 415). The optimized H7-632-hIgG1-LAGA was also directly fused (df) to a variant of hIL-2 with attenuated hIL-2 activity (hIL-2 T3A/D20A/R38E/C125A; SEQ ID NO: 217) to become H7-767 (SEQ ID NOs: 412-413, 415-423, 532) and both H7-632-hIgG1-LAGA and H7-767 were tested for binding to hPD-1 (Table 20). $EC_{50}$ values were calculated from the geometric mean fluorescent intensity (gMFI) across the titrated concentrations using GraphPad Prism 7 software.

The generation of anti-hPD-1-attenuated hIL-2 fusion proteins did not reduce binding to hPD-1, and the anti-hPD-1-attenuated hIL-2 fusion proteins were still able to bind to Jurkat cells expressing human PD-1. The calculated $EC_{50}$ of tested anti-hPD-1-attenuated hIL-2 fusion proteins in comparison to respective anti-hPD-1 antibody without the attenuated hIL-2 moiety is summarized in Table 20.

TABLE 20

Anti-hPD-1-attenuated hIL-2 fusion protein binding ($EC_{50}$) to hPD-1 expressing Jurkat cell line by flow cytometry

| Anti-hPD-1 Antibody | $EC_{50}$ (nM) | Corresponding Anti-hPD-1-hIL-2 Fusion Protein | $EC_{50}$ (nM) |
|---|---|---|---|
| Anti-hPD-1 #1 | 0.3586 | Anti-hPD-1 #1-hIgG4-L6-hIL-2 (D20A/R38E) | 0.5318 |
| C51E6-5-hIgG4 | 2.048 | C51E6-5-hIgG4-L6-hIL-2 (D20A/R38E) | 1.587 |
| OMC.1.B6-hIgG4 | 7.422 | OMC.1.B6-hIgG4-L6-hIL-2 (D20A/R38E) | 5.635 |
| OMC.2.C6-hIgG4 | 11.52 | OMC.2.C6-hIgG4-L6-hIL-2 (D20A/R38E) | 16.32 |
| OMC.1.D6-hIgG4 | 15.96 | OMC.1.D6-hIgG4-L6-hIL-2 (D20A/R38E) | 8.87 |

TABLE 20-continued

Anti-hPD-1-attenuated hIL-2 fusion protein binding ($EC_{50}$) to hPD-1 expressing Jurkat cell line by flow cytometry

| Anti-hPD-1 Antibody | $EC_{50}$ (nM) | Corresponding Anti-hPD-1-hIL-2 Fusion Protein | $EC_{50}$ (nM) |
|---|---|---|---|
| A2-hIgG4 | 5.968 | A2-hIgG4-df-hIL-2 (D20A/R38E) | 10.67 |
| D12-hIgG4 | 9.674 | D12-hIgG4-df-hIL-2 (D20A/R38E) | 17.09 |
| G12-hIgG4 | 5.36 | G12-hIgG4-df-hIL-2 (D20A/R38E) | 7.578 |
| 2H7-hIgG4 | 0.2769 | 2H7-hIgG4-df-hIL-2 (D20A/R38E) | 0.1946 |
| H7-632-hIgG1-LAGA | 0.115 | H7-767 | 0.218 |

The addition of the attenuated hIL-2 moiety on anti-hPD-1 antibodies did not abrogate binding to human PD-1 as demonstrated by a less than 2-fold increase in $EC_{50}$ binding of anti-hPD-1-hIL-2 fusion proteins to Jurkat+ hPD-1 cells in comparison to the anti-hPD-1 antibody without the attenuated hIL-2 moiety.

Example 10: Anti-hPD-1-Attenuated hIL-2 Fusion Proteins Bind hPD-1 in the Presence of Anti-hPD-1 #1 and Anti-hPD-1 #2 Antibodies Anti-hPD-1-attenuated hIL-2 fusion proteins were tested for binding to the hPD-1 receptor in the presence of anti-hPD-1 #1 and anti-hPD-1 #2 as described in General Methods Protocol B and Example 7. The converse experiment was also performed in which anti-hPD-1 #1-mIgG2b-N297A or anti-hPD-1 #2-mIgG2b-N297A was examined for binding to hPD-1 in the presence of saturating concentrations of test antibody-attenuated hIL-2 fusion proteins. In this format, Jurkat cells expressing hPD-1 were plated at 100,000 cells per well in FACS buffer, blocked with anti-human FcγR Blocking Reagent (Miltenyi) for 10 minutes at 4° C. and washed. Test antibody-attenuated hIL-2 fusion proteins 2H7-hIgG4-df-hIL-2 (D20A/R38E), C51E6-5-hIgG4-L6-hIL-2 (D20A/R38E), A2-hIgG4-df-hIL-2 (D20A/R38E), H7-767, and isotype control anti-DNase 1H3-hIgG4-df-hIL-2 (D20A/R38E) were diluted to 280 nM final concentration in 100 μL FACS buffer and incubated with Jurkat cells expressing hPD-1 cells for 1 hour on ice. Cells were washed and re-suspended in FACS buffer containing six-fold serial titrations of anti-hPD-1 #1-mIgG2b-N297A or anti-hPD-1 #2-mIgG2b-N297A starting at a maximum concentration of 50 nM for 1 hour on ice. Cells were washed and re-suspended in 1:100 dilution of Phycoerythrin-conjugated anti-mouse IgG light chain kappa monoclonal antibody for 45 minutes on ice. Cells were again washed and re-suspended in FACS buffer with 1:1000 dilution of Sytox Green (Thermo Fisher). Flow cytometry analysis was performed using the BD FACS Canto II (BD Biosciences) and gMFI calculated using FlowJo software version 10. $EC_{50}$ values were calculated from the gMFI of the Phycoerythrin signal across the titrated concentrations using GraphPad Prism 7 software.

The addition of the attenuated hIL-2 to anti-hPD-1 antibodies 2H7-hIgG4, C51E6-5-hIgG4, and A2-hIgG4 did not diminish the ability of the anti-hPD-1 proteins to bind to human PD-1 in the presence of anti-hPD-1 #1-mIgG2b-N297A or anti-hPD-1 #2-mIgG2b-N297A, similar to the results described in Example 7 (FIG. 16B-16D). H7-767 was also tested in this competition assay and FIG. 13B illustrates that H7-767 continues to bind to the hPD-1 receptor in the presence of anti-hPD-1-#1-mIgG2b-N297A or anti-hPD-1 #2-mIgG2b-N297A. In contrast, the binding of the positive control anti-hPD-1 #1 was substantially decreased in the presence of anti-hPD-1 #1-mIgG2b-N297A or anti-hPD-1 #2-mIgG2b-N297A (FIG. 16A, 13A).

FIG. 6A and FIG. 6B show that for the converse competition assay, anti-hPD-1 #1-mIgG2b-N297A (FIG. 6A) and anti-hPD-1 #2-mIgG2b-N297A (FIG. 6B) were still able to bind to hPD-1 on Jurkat cells in the presence of saturating (280 nM) anti-hPD-1-attenuated hIL-2 fusion proteins 2H7-hIgG4-df-hIL-2 (D20A/R38E), C51E6-5-hIgG4-df-hIL-2 (D20A/R38E) or A2-hIgG4-df-hIL-2 (D20A/R38E). These binding curves with saturating anti-hPD-1-attenuated hIL-2 fusion proteins prior to exposure with anti-hPD-1 fusion proteins overlapped with binding curves of anti-hPD-1 #1-mIgG2b-N297A (no competition) or anti-hPD-1 #2-mIgG2b-N297A (no competition). The binding curves also overlapped with a saturating negative control fusion protein, 1H3-hIgG4-df-hIL-2 (D20A/R38E) that did not bind to hPD-1.

Example 11: Anti-hPD-1-Attenuated hIL-2 Fusion Proteins Bind Recombinantly-Expressed Cynomolgus PD-1

Anti-hPD-1-attenuated hIL-2 fusion proteins were tested in flow cytometry for binding to cynomolgus PD-1 using a human Embryonic Kidney 293 cell line expressing the SV40 large T cell antigen (HEK-293T) that was transiently transfected to recombinantly express cynomolgus PD-1. For each transfection reaction, 2 million HEK-293T cells were transfected with 2 μg of pCMV6-hygro-HA-cyno-PD-1 (1-185) (SEQ ID NO: 448), a mammalian vector comprising the cynomolgus PD-1 extracellular domain tagged with a human influenza hemagglutinin and the sequence encoding for hygromycin resistance. Transfection was performed by electroporation. Transfected cells were blocked with human FcγR blocking reagent and stained with titrating amounts of anti-hPD-1-attenuated hIL-2 fusion proteins. Additionally, Phycoerythrin conjugated anti-hemagglutinin clone 15B12 was added to cells to stain for transfected cells and Allophycocyanin-conjugated anti-human IgG Fc secondary clone HP6017 (BioLegend Cat #409306) was added to cells to stain bound antibody. The cells were analyzed on the BD Canto II and FlowJo software version 10 was used to gate on live, transfected (hemagglutinin-positive) cells and to calculate gMFI of the Allophycocyanin signal. $EC_{50}$ values were calculated from the gMFI across the titrated concentrations using GraphPad Prism 7 software.

Anti-hPD-1-attenuated hIL-2 fusion proteins bound to cynomolgus PD-1-expressing HEK-293T cells in a similar fashion to the binding profile seen on Jurkat T cells expressing human PD-1 (FIG. 17). The $EC_{50}$ for binding to cynomolgus PD-1 expressing HEK-293T cells was 5 nM for 2H7-hIgG4-df-hIL-2 (D20A/R38E), 6 nM for C51E6-5-hIgG4-df-hIL-2 (D20A/R38E), and 11 nM for A2-hIgG4-df-hIL-2 (D20A/R38E). Anti-hPD-1 #1 and anti-hPD-1 #2 which were formatted as comparator anti-hPD-1-attenuated hIL-2 fusion proteins also bound to cynomolgus PD-1 with $EC_{50}$ values of 9 nM and 2 nM, respectively, suggesting that the addition of the attenuated hIL-2 moiety on the anti-hPD-1 antibodies did not abrogate binding to cynomolgus PD-1.

Example 12: Anti-hPD-1-Attenuated hIL-2 Fusion Proteins Bind Activated Primary Human and Cynomolgus PD-1

The binding of anti-hPD-1 antibodies and anti-hPD-1-attenuated hIL-2 fusion proteins on activated primary T cells expressing hPD-1 was examined by flow cytometry. To test if 2H7-hIgG4, C51E6-5-hIgG4, or A2-hIgG4 bound to native hPD-1, cryopreserved human peripheral blood mononuclear cells (PBMCs) were thawed and activated with 50 ng/ml phorbol 12-myristate 13-acetate (PMA) and 1 µg/mL ionomycin to up-regulate the hPD-1 receptor. Activated PBMCs were collected, blocked with 1:50 dilution of Human FcγR Blocking Reagent (Miltenyi) for 10 minutes at 4° C., and stained with titrated concentrations of anti-hPD-1 antibodies 2H7-hIgG4, C51E6-5-hIgG4, A2-hIgG4, anti-hPD-1 #1, and isotype control. Cells were then stained with 1:20 dilution of Allophycocyanin-conjugated anti-human IgG Fc to detect bound antibody. To delineate immune subsets, a cocktail of surface markers included anti-human CD3, anti-CD4, and anti-CD8 antibodies was used. In addition, a sample fraction was examined for cellular expression of hPD-1, hCD25, hCD122, and hCD132. Cells were analyzed on the BD Fortessa (BD Biosciences), FlowJo software version 10 was used to gate on T cell subsets then calculate gMFI of the allophycocyanin signal. $EC_{50}$ values were calculated from the gMFI across the titrated concentrations using GraphPad Prism 7 software. To test the binding of anti-hPD-1-hIL-2 fusion proteins, cryopreserved CD3+ T cells were activated with PMA/ionomycin and flow cytometry binding was performed identically as described above.

Human PD-1 antibody-attenuated hIL-2 fusion proteins were also tested for binding to activated cynomolgus T cells using flow cytometry. Cynomolgus PBMCs were activated with a mixture of 0.081 µM PMA and 1.34 µM ionomycin. 24 hours later, cells were stained using the same procedure as binding to human PD-1 primary cells described above except cynomolgus cross-reactive markers were used. FlowJo software version 10 was used to gate on live, $CD3^+CD4^+$ or $CD3^+CD8^+$ T cells and then to calculate gMFI of the Allophycocyanin signal. $EC_{50}$ values were calculated from the gMFI across the titrated concentrations of anti-hPD-1 antibodies or hPD-1 antibody-attenuated hIL-2 fusion proteins using GraphPad Prism 7 software.

In some variants tested, the attenuated hIL-2 also included the substitutions T3A and C125A, which remove a site for O-linked glycosylation and substitute away a free cysteine residue, respectively.

40-50% of $CD4^+$ T cells were PD-1$^+$ while 30-40% of $CD8^+$ T cells were PD-1$^+$ after PMA and ionomycin activation (data not shown). The calculated $EC_{50}$ for binding to activated human $CD3^+CD4^+$ T cells by flow cytometry was 0.1-0.7 nM for 2H7-hIgG4, 12 nM for C51E6-5-hIgG4, 30 nM for A2-hIgG4, and 0.04 nM for 2H7-hIgG4-df-hIL-2 (T3A/D20A/R38E/C125A). The $EC_{50}$ for binding to activated human $CD3^+CD8^+$ T cells was 0.1-0.8 nM for 2H7-hIgG4, 16 nM for C51E6-5-hIgG4, 22 nM for A2-hIgG4, and 0.03 nM for 2H7-hIgG4-df-hIL-2 (T3A/D20A/R38E/C125A). The $EC_{50}$ for binding to activated human $CD3^+$ $CD4^+$ T cells was 0.19 nM and activated human $CD3^+CD8^+$ T cells was 0.12 nM for H7-767. The $EC_{50}$ for binding to activated cynomolgus $CD3^+CD4+$ T cells was 0.09 nM for 2H7-hIgG4 and 0.04 nM for 2H7-hIgG4-df-hIL-2 (T3A/D20A/R38E/C125A). $EC_{50}$ for binding to activated cynomolgus $CD3^+CD8+$ T cells was 0.08 nM for 2H7-hIgG4 and 0.03 nM for 2H7-hIgG4-df-hIL-2 (T3A/D20A/R38E/C125A). The $EC_{50}$ for binding to activated cynomolgus $CD3^+CD4^+$ T cells was 0.26 nM and activated cynomolgus $CD3^+CD8^+$ T cells was 0.24 nM for H7-767. This data demonstrated that when the hPD-1 antibodies were converted to anti-hPD-1-attenuated hIL-2 fusion proteins, the calculated $EC_{50}$ value for binding to activated hPD-1 remained similar to the calculated $EC_{50}$ value of hPD-1 naked antibody binding to hPD-1. H7-767 and H7-632-hIgG1-LAGA anti-PD-1 naked antibody were tested for binding on primary non-activated human $CD4^+$ and $CD8^+$ T cells by flow cytometry. Frozen human $CD3^+$ T were thawed and flow cytometry performed as described above. Both H7-767 and H7-632-hIgG1-LAGA anti-PD-1 naked antibody did not bind non-activated human $CD4^+$ and $CD8^+$ T cells (data not shown).

Example 13: Quantification of Binding of Anti-hPD-1 Antibodies and Anti-hPD-1-Attenuated hIL-2 Fusion Proteins to Recombinant Human or Cynomolgus PD-1 by Surface Plasmon Resonance (SPR)

Surface plasmon resonance binding analysis was performed using a high-throughput SPR Carterra® LSA™ to determine binding affinities of anti-hPD-1 antibodies and anti-hPD-1-attenuated hIL-2 fusion proteins. Proteins were diluted to 2 or 10 µg/mL in 10 mM sodium acetate pH 4.5 containing 0.01% Tween-20 and coupled to a HC30M (Carterra Bio) chip using sulpho-N-hydroxysuccinimide/1-ethyl-3-(3-dimethylamino) propyl carbodiimide (sulpho-NHS/EDC) coupling chemistry and blocked with ethanolamine. A non-regenerative kinetic coupling process was used to determine binding kinetics to commercially sourced recombinant His-tagged human PD-1 and His-tagged cynomolgus PD-1 (Acro Biosystems).

Anti-hPD-1 antibodies and anti-hPD-1-attenuated hIL-2 fusion proteins were expressed with either a modified human IgG1 or a modified IgG4 isotype with a kappa light chain framework. Additional substitutions L235E, or L235A/G237A (LAGA, as described in Int'l Pub. No. WO1998/006248) (numbering based upon the EU numbering system) were introduced to the Fc region to abrogate effector functions of the immunoglobulin component.

The association constants ($k_a$), dissociation constants ($k_d$), and equilibrium constants ($K_D$) of various anti-hPD-1 antibodies and anti-hPD-1 antibody-attenuated hIL-2 fusion proteins binding to recombinant human or cynomolgus PD-1 proteins was determined from the titration curves and the Carterra Kinetics software. The maximal feasible SPR signal generated ($R_{max}$) and residual standard deviation (Res SD) was also calculated. The results from the kinetics screen are summarized in Table 21, and demonstrated that the addition of the attenuated hIL-2 moiety on anti-hPD-1 antibodies did not modulate PD-1 antibody binding to the human PD-1 or cynomolgus PD-1 antigens. In a separate experiment, H7-632-hIgG1-LAGA (SEQ ID NOs: 414 and 415) was measured by SPR and had a steady state equilibrium dissociation constant ($K_D$) of $1.23 \times 10^{-9}$M and H7-767 had a $K_D$=$1.93 \times 10^{-9}$M.

TABLE 21

Binding kinetics of anti-hPD-1 and anti-hPD-1-hIL-2 fusion proteins to recombinant human PD-1 and cynomolgus PD-1 by high-throughput SPR Carterra® LSA™

| | | Kinetics Summary | | | | | | | | |
|---|---|---|---|---|---|---|---|---|---|---|
| | | Human PD-1 | | | | | Cyno PD-1 | | | |
| | Name | $k_a$ (M-1 s-1) | $k_d$ (s-1) | $K_D$ (M) | Rmax | Res SD | $k_a$ (M-1 s-1) | $k_d$ (s-1) | $K_D$ (M) | Rmax | Res SD |
| Anti-hPD-1 Antibodies | 2H7-hIgG4-LE | 2.60E+05 | 8.20E-04 | 3.10E-09 | 146 | 8.5 | 1.40E+05 | 1.00E-03 | 7.10E-09 | 186 | 6.5 |
| | 2H7-hIgG4-LAGA | 1.70E+05 | 9.10E-04 | 5.30E-09 | 258 | 13 | 9.10E+04 | 1.10E-03 | 1.20E-08 | 295 | 11 |
| | Abz1mod-hIgG4 | 1.40E+05 | 6.00E-05 | 4.26E-10 | 123 | 8.1 | 1.70E+05 | 6.20E-04 | 3.70E-09 | 183 | 10 |
| | A2-hIgG4 | 3.70E+04 | 1.30E-03 | 3.60E-08 | 341 | 7.8 | 6.80E+04 | 4.00E-02 | 5.89E-07 | 238 | 4.8 |
| | OMC.1.B6-hIgG4 | 7.70E+04 | 4.00E-03 | 5.20E-08 | 241 | 6.8 | 8.80E+04 | 4.40E-03 | 5.10E-08 | 262 | 5.5 |
| | OMC.2.C6-hIgG4 | 5.70E+04 | 6.60E-04 | 1.20E-08 | 229 | 8.7 | 5.50E+04 | 7.40E-04 | 1.30E-08 | 268 | 8.9 |
| | OMC.1.D6-hIgG4 | 4.10E+04 | 1.70E-03 | 4.20E-08 | 263 | 5.1 | 5.80E+04 | 4.00E-02 | 6.94E-07 | 182 | 4 |
| | OMC476pH7-hIgG4 | 6.00E+04 | 1.10E-03 | 1.80E-08 | 225 | 8.9 | 7.80E+04 | 1.70E-02 | 2.21E-07 | 254 | 2.8 |
| | OMC476pB11-hIgG4 | 5.00E+04 | 1.50E-03 | 3.00E-08 | 221 | 7 | 8.00E+04 | 2.60E-02 | 3.21E-07 | 204 | 2.7 |
| | OMC476pG10-hIgG4 | 9.30E+04 | 4.10E-03 | 4.40E-08 | 256 | 4.9 | 1.20E+05 | 6.00E-02 | 4.87E-07 | 188 | 4.9 |
| | OMC476pH10-hIgG4 | 1.00E+05 | 6.50E-03 | 6.40E-08 | 63 | 1.8 | 1.20E+05 | 5.90E-02 | 4.80E-07 | 81 | 3.8 |
| | OMC476pE4-hIgG4 | 7.90E+04 | 8.80E-04 | 1.10E-08 | 216 | 9.6 | 1.00E+05 | 3.50E-02 | 3.31E-07 | 204 | 6.3 |
| | D12-hIgG4 | 5.70E+04 | 4.60E-04 | 8.10E-09 | 234 | 9.9 | 5.90E+04 | 1.60E-02 | 2.72E-07 | 297 | 2.4 |
| | G12-hIgG4 | 5.30E+04 | 2.60E-03 | 5.00E-08 | 477 | 8.5 | 8.60E+04 | 6.50E-02 | 7.54E-07 | 327 | 7.8 |
| | EH12.2H7-mIgG1* | 1.10E+05 | 2.20E-03 | 1.90E-08 | 309 | 5.2 | 8.60E+04 | 7.30E-03 | 8.50E-08 | 307 | 4.2 |
| | J105-mIgG1* | 6.20E+04 | 5.30E-03 | 8.60E-08 | 186 | 2.8 | 5.00E+04 | 6.60E-03 | 1.30E-09 | 92 | 1.2 |
| | MIH4-mIgG1* | 1.30E+05 | 1.40E-03 | 1.00E-08 | 117 | 3.8 | 1.30E+05 | 1.20E-01 | 8.91E-07 | 61 | 1.8 |
| | J110-hIgG1 | 1.00E+05 | 1.00E-03 | 1.00E-08 | 346 | 15 | 4.10E+04 | 5.00E-02 | 1.20E-09 | 228 | 8.2 |
| | OPDIVO® (nivolumab) | 1.70E+05 | 1.70E-03 | 1.00E-08 | 55 | 2.6 | 1.50E+05 | 9.50E-04 | 6.40E-09 | 75 | 3.2 |
| | KEYTRUDA® (pembrolizumab) | 2.90E+05 | 1.30E-03 | 4.50E-09 | 19 | 2.6 | 7.00E+05 | 4.00E-04 | 5.75E-07 | 53 | 3.7 |
| Anti-hPD-1-attenuated hIL-2 Fusion Proteins | 2H7-hIgG1-LAGA-hIL-2 (T3A/D20A/R38E/C125A) | 1.50E+05 | 8.30E-04 | 5.40E-09 | 420 | 28 | 8.80E+04 | 9.70E-04 | 1.10E-08 | 502 | 21 |
| | 2H7-hIgG4-LE-hIL-2 (T3A/D20A/R38E/C125A) | 1.90E+05 | 8.10E-04 | 4.30E-09 | 374 | 17 | 9.00E+04 | 1.00E-03 | 1.10E-08 | 449 | 15 |
| | 2H7-hIgG4-LAGA-hIL-2 (T3A/D20A/R38E/C125A) | 1.70E+05 | 8.20E-04 | 4.80E-09 | 359 | 22 | 9.60E+04 | 9.80E-04 | 1.00E-08 | 429 | 17 |
| | 2H7-hIgG1-LAGA-hIL-2 (T3A/R38E/192K/C125A) | 1.80E+05 | 7.80E-04 | 4.30E-09 | 417 | 25 | 9.10E+04 | 9.70E-04 | 1.10E-08 | 505 | 19 |
| | hIgG4-LE-hIL-2 (T3A/R38E/192K/C125A) | 1.90E+05 | 8.80E-04 | 4.70E-09 | 380 | 19 | 9.50E+04 | 1.10E-03 | 1.20E-08 | 429 | 17 |
| | 2H7-hIgG4-LAGA-hIL-2 (T3A/R38E/192K/C125A) | 2.20E+05 | 8.20E-04 | 3.70E-09 | 355 | 17 | 1.00E+05 | 1.10E-03 | 1.10E-08 | 418 | 16 |
| | 2H7-hIgG1-LAGA-hIL-2 (T3A/R38E/D84K/C125A) | 1.30E+05 | 8.10E-04 | 6.20E-09 | 458 | 29 | 7.60E+04 | 1.00E-03 | 1.30E-08 | 532 | 23 |
| | 2H7-hIgG4-LE-hIL-2 (T3A/R38E/D84K/C125A) | 2.00E+05 | 9.40E-04 | 4.70E-09 | 232 | 13 | 1.30E+05 | 1.10E-03 | 8.20E-09 | 262 | 10 |
| | 2H7 hIgG4LAGA-df-hIL-2 (T3A/R38E/D84K/C125A) | 1.70E+05 | 7.30E-04 | 4.40E-09 | 400 | 20 | 8.10E+04 | 1.00E-03 | 1.30E-08 | 482 | 20 |

*Commercially sourced, no sequence available

Example 14: Determining Whether Anti-hPD-1 Antibodies and Anti-hPD-1-Attenuated hIL-2 Fusion Proteins Compete with Anti-hPD-1 #1 and Anti-hPD-1 #2 for Binding to PD-1 by Surface Plasmon Resonance (SPR)

Anti-hPD-1 and anti-hPD-1-attenuated hIL-2 fusion proteins were assayed for competition with one another using a sandwich method. Antibodies and corresponding antibody-IL-2 cytokine-fusion proteins were immobilized to HC30M chips using amine coupling chemistry described in Example 13. Following kinetic analysis described in Example 13, 80 nM human PD-1 (Acro Biosystems, Cat #PD-1-H5221-100 µg) was injected into the whole array. Competing anti-hPD-1 and anti-hPD-1-attenuated hIL-2 fusion proteins (analyte) were diluted to 30 µg/mL and subsequently injected into the array and binding parameters were assessed using SPR. Assessment of all anti-hPD-1 and anti-hPD-1-hIL-2 fusion proteins was performed in duplicate. Some variants tested had a modified human IgG1 or IgG4 kappa light chain framework with additional L235E or L235A/G237A (LAGA) substitutions to abrogate effector function of the immunoglobulin.

The screening of pairs of anti-hPD-1 or anti-hPD-1-attenuated hIL-2 fusion proteins allowed the identification of two bins, shown in Table 22. Antibodies and fusion proteins from Group 1 were able to bind hPD-1 in the presence of all antibodies and fusion proteins from Group 2, but competed with all members of the same Group. Antibodies and fusion proteins from Group 2 were able to bind hPD-1 in the presence of all antibodies and fusion proteins from Group 1, but competed with all members of the same Group. None of the anti-hPD-1 listed in Group 1 in Table 22 competed with KEYTRUDA® and OPDIVO®.

TABLE 22

Groups 1 and 2 from anti-hPD-1 and anti-hPD-1-attenuated hIL-2 fusion protein binning screen by SPR

| Group 1 | Group 2 |
|---|---|
| Abz1mod-hIgG4 | KEYTRUDA® |
| OMC.1.B6-hIgG4 | OPDIVO® |
| OMC.1.D6-hIgG4 | Anti-hPD-1 clone |
| OMC.2.C6-hIgG4 | EH12.2H7-mIgG1* |
| OMC476pE4-hIgG4 | Anti-hPD-1 clone |

TABLE 22-continued

Groups 1 and 2 from anti-hPD-1 and anti-hPD-1-attenuated hIL-2 fusion protein binning screen by SPR

| Group 1 | Group 2 |
| --- | --- |
| OMC476pH7-hIgG4 | J105-mIgG1* |
| OMC476pB11-hIgG4 | |
| OMC476pH10-hIgG4 | |
| OMC476pG10-hIgG4 | |
| A2-hIgG4 | |
| D12-hIgG4 | |
| G12-hIgG4 | |
| 2H7-hIgG4-LE | |
| 2H7-hIgG4-LE-df-hIL-2 (T3A/D20A/R38E/C125A) | |
| 2H7-hIgG4-LAGA-df-hIL-2 (T3A/D20A/R38E/C125A) | |
| 2H7-hIgG1-LAGA-df-hIL-2 (T3A/D20A/R38E/C125A) | |
| 2H7-hIgG4-LE-df-hIL-2 (T3A/R38E/I92K/C125A) | |
| 2H7-hIgG4-LAGA-df-hIL-2 (T3A/R38E/I92K/C125A) | |
| 2H7-hIgG1-LAGA-df-hIL-2 (T3A/R38E/I92K/C125A) | |
| 2H7-hIgG4-LE-df-hIL-2 (T3A/R38E/D84K/C125A) | |
| 2H7-hIgG4-LAGA-df-hIL-2 (T3A/R38E/D84K/C125A) | |
| 2H7-hIgG1-LAGA-df-hIL-2 (T3A/R38E/D84K/C125A) | |
| Anti-PD-1 clone MIH4 mIgG1 | |
| Anti-PD-1 clone J110 hIgG1 | |

*Commercially sourced, no sequence available

Example 15: Antagonism of Anti-hPD-1-Attenuated hIL-2 Fusion Proteins to hPD-1 in the Presence of Anti-hPD-1 #1 and Anti-hPD-1 #2

Figure 15:
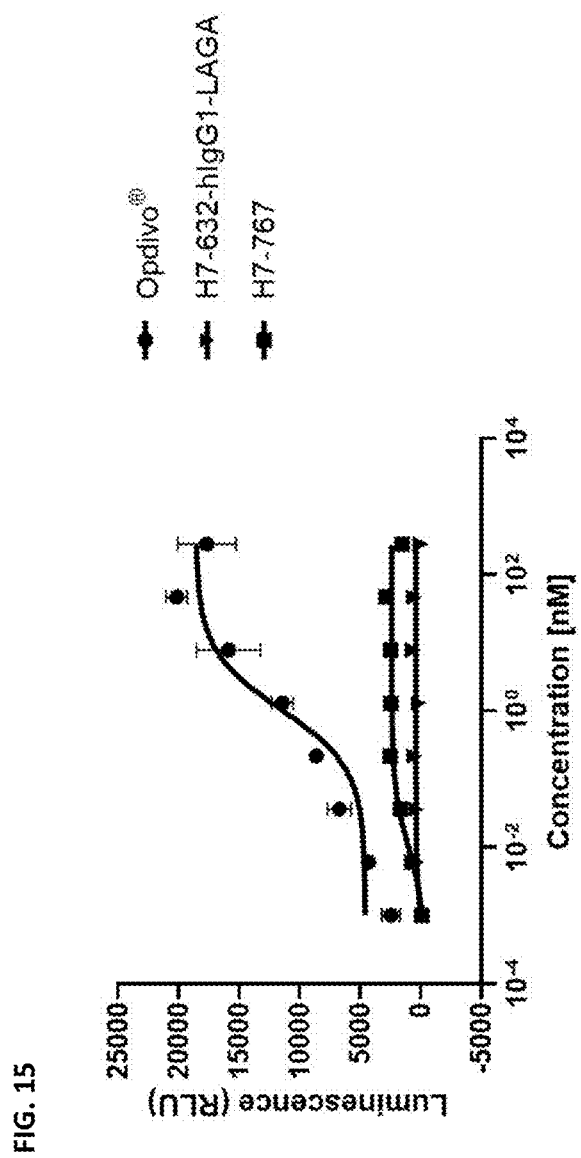
FIG. 15 demonstrates that H7-632-hIgG1-LAGA and H7-767 do not inhibit the binding of human PD-L1 to the human PD-1 receptor using an hPD-1/hPD-L1 Blockade Bioassay.
Figure 16B:
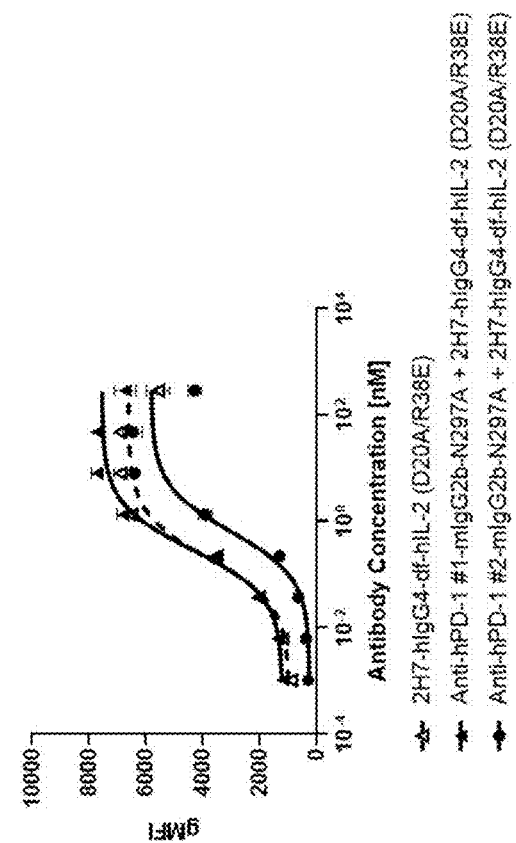
FIG. 16A, FIG. 16B, FIG. 16C, and FIG. 16D are graphs showing the binding of anti-hPD-1-attenuated hIL-2 immunoconjugates 2H7-hIgG4-df-hIL-2 (D20A/R38E), C51E6-5-hIgG4-df-hIL-2 (D20A/R38E), and A2-hIgG4-df-hIL-2 (D20A/R38E) to the human PD-1 receptor on Jurkat cells in the presence of saturating concentrations of anti-hPD-1 #1-mIgG2b-N297A and anti-hPD-1 #2-mIgG2b-N297A (10 µM) prior to exposure with anti-hPD-1-attenuated hIL-2 immunoconjugates, as assessed by flow cytometry.
Figure 16A:
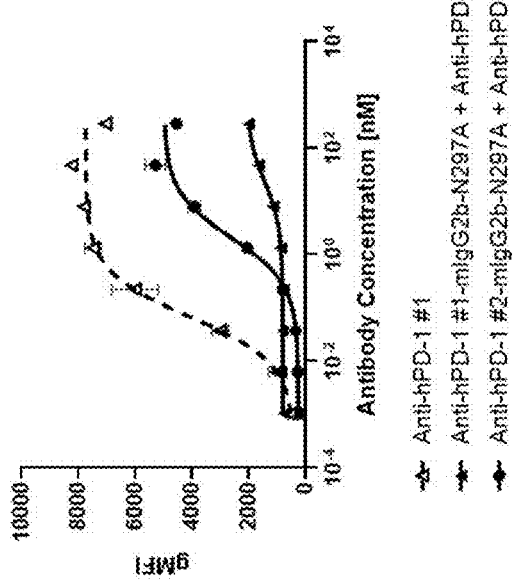
Figure 16D:
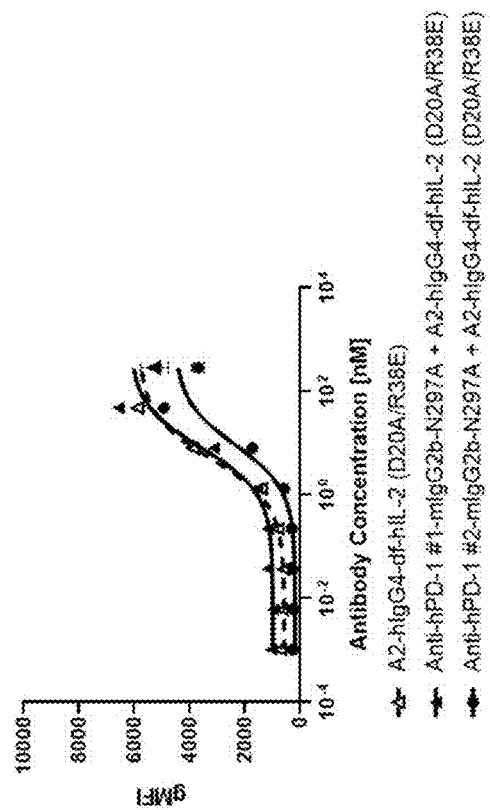
Figure 16C:
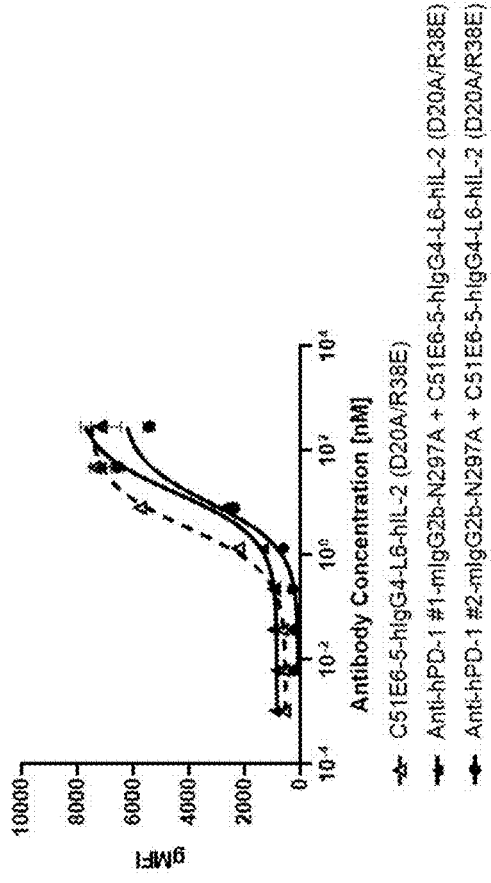
Figure 17:
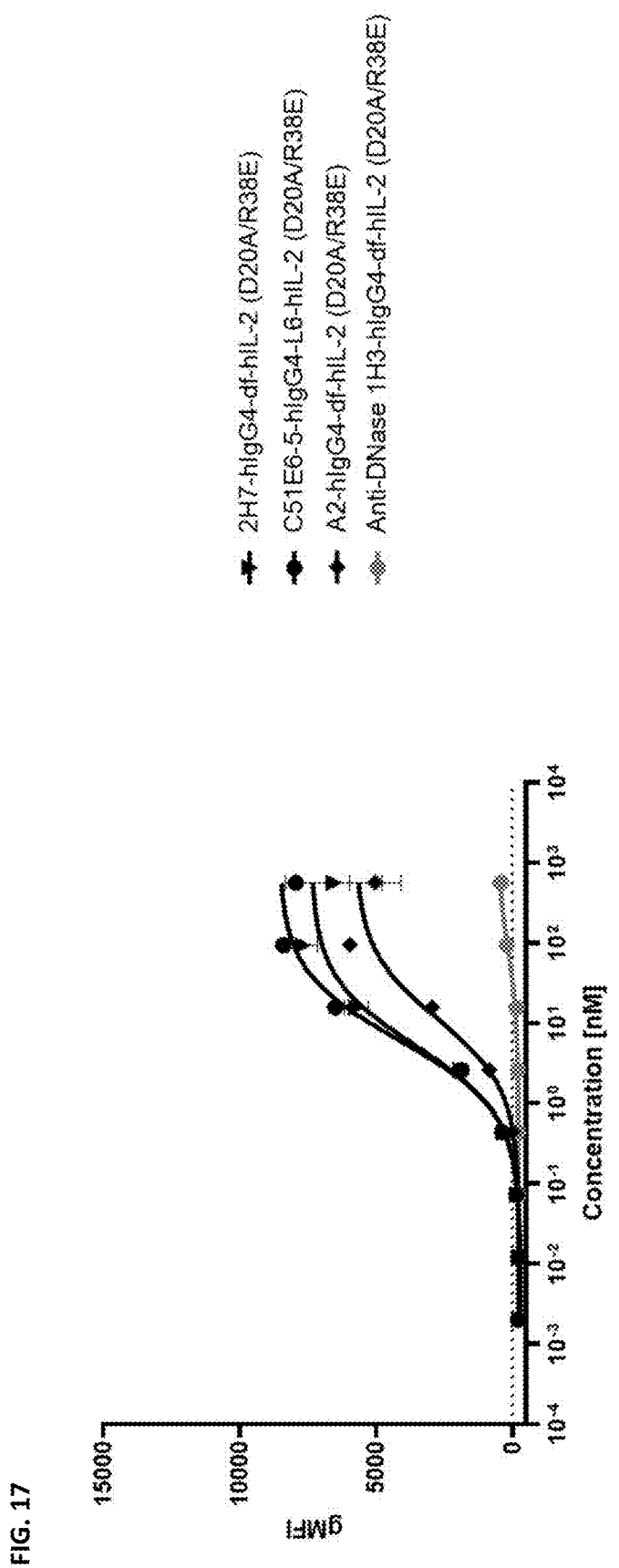
FIG. 17 is a graph showing the binding of 2H7-hIgG4-df-hIL-2 (D20A/R38E), C51E6-5-hIgG4-df-hIL-2 (D20A/R38E), A2-hIgG4-df-hIL-2 (D20A/R38E) and the irrelevant antibody control 1H3-hIgG4-df-hIL-2 (D20A/R38E) to HEK-293T cells recombinantly expressing cynomolgus PD-1, as assessed by flow cytometry.

Anti-hPD-1-attenuated hIL-2 fusion proteins were tested for antagonism of hPD-1. Characterization of anti-hPD-1-attenuated hIL-2 fusion proteins was performed according to General Methods Protocol C. FIG. 7 illustrates these results. When compared to the PD-1 antagonists KEYTRUDA® or OPDIVO®, 2H7-hIgG4-df-hIL-2 (D20A/R38E), C51E6-5-hIgG4-L6-hIL-2 (D20A/R38E), and A2-hIgG4-df-hIL-2 (D20A/R38E) were non-antagonistic to human PD-1, as demonstrated by the low level of detectable luminescence. H7-632-hIgG1-LAGA and H7-767 were also tested for antagonist activity as described in General Protocol C. FIG. 15 illustrates that H7-632-hIgG1-LAGA and H7-767 do not block hPD-L1 (SEQ ID NO: 584) from interacting with the hPD-1 receptor.

Figure 18A:
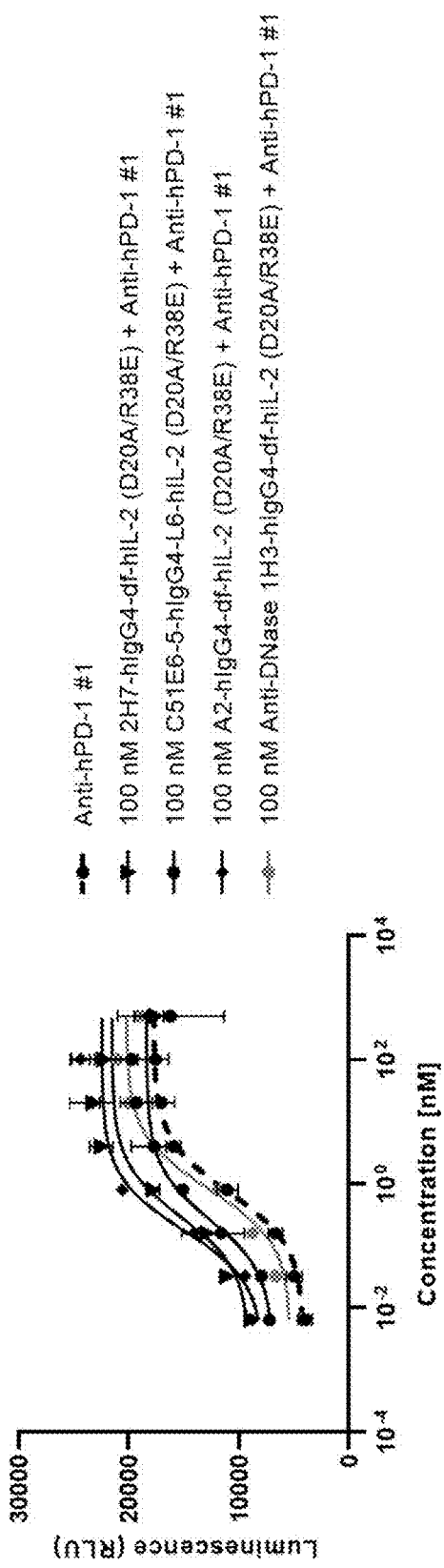
FIG. 18A, FIG. 18B, FIG. 18C, and FIG. 18D show the antagonist activity of anti-hPD-1-attenuated hIL-2 immunoconjugates 2H7-hIgG4-df-hIL-2 (D20A/R38E), C51E6-5-hIgG4-df-hIL-2 (D20A/R38E), and A2-hIgG4-df-hIL-2 (D20A/R38E) in the presence of anti-hPD-1 #1 or anti-hPD-1 #2.
Figure 18B:
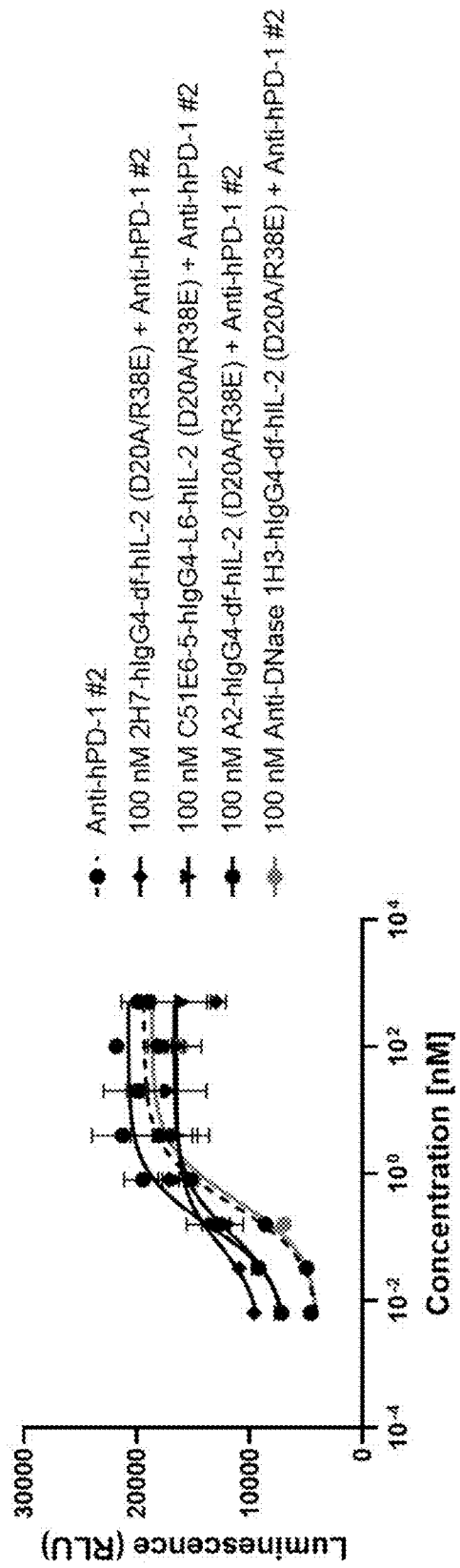

For competition assays using the cell-based co-culture assay described in General protocol C, a few modifications were performed. Samples of the anti-hPD-1-attenuated hIL-2 fusion proteins were diluted to a fixed concentration of 400 nM and 20 µL was added to 20 µL of titrated anti-hPD-1 #1 or anti-hPD-1 #2. The 40 µL mixture was added to CHO cells. Forty (40) µL of Jurkat PD-1 effector cells were overlayed on the mixture of CHO cells and anti-hPD-1-attenuated hIL-2 fusion proteins. In this competition assay, a final concentration of saturating 100 nM anti-hPD-1-attenuated hIL-2 fusion proteins was tested in combination with titrated anti-hPD-1 #1 or anti-hPD-1 #2. The rest of the assay was performed as described in General Protocol C. FIG. 18A and FIG. 18B demonstrate that the addition of 100 nM anti-hPD-1-attenuated hIL-2 fusion proteins did not compete with the blocking of titrated anti-hPD-1 #1 binding to hPD-L1 (SEQ ID NO: 584). Dose-titration curves of anti-hPD-1 #1 remained unchanged from curves without competitor antibody, suggesting that the presence of anti-hPD-1-attenuated hIL-2 fusion proteins did not compete with anti-hPD-1 #1 function even at high concentrations. In the presence of 100 nM 2H7-hIgG4-df-hIL-2 (D20A/R38E) and 100 nM C51E6-5-hIgG4-L6-hIL-2 (D20A/R38E), anti-hPD-1 #2 exhibited a 35% reduction in luminescence (RLU) at higher concentrations of anti-hPD-1 #2 (FIG. 18B) but it is unclear if this reduction was significant due to the extent of the standard deviation.

Figure 18C:
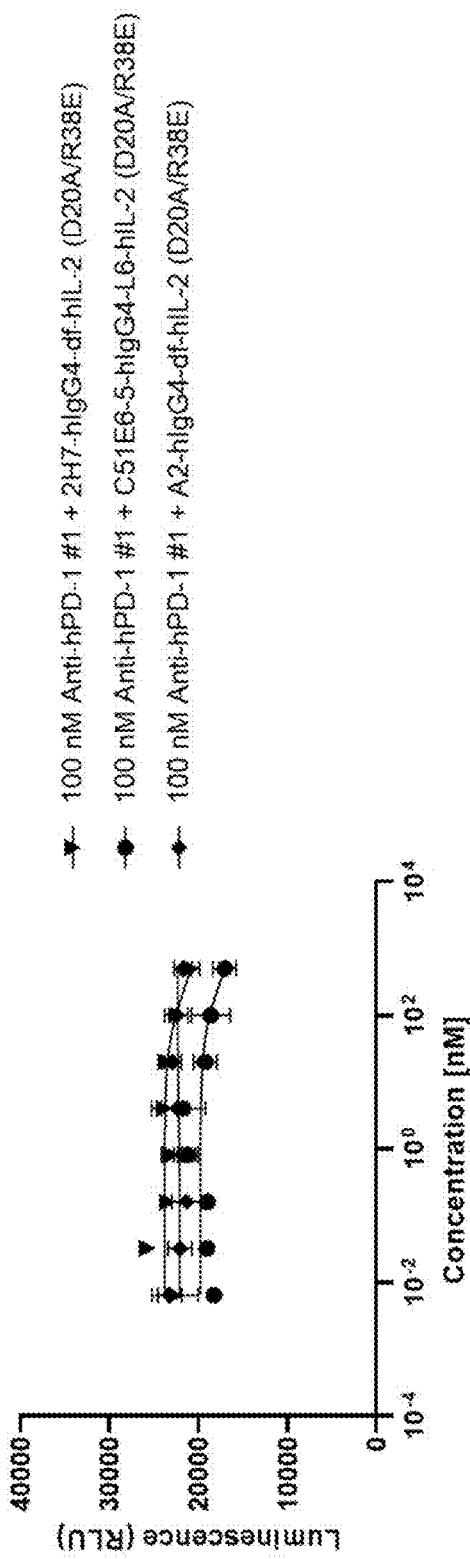
Figure 18D:
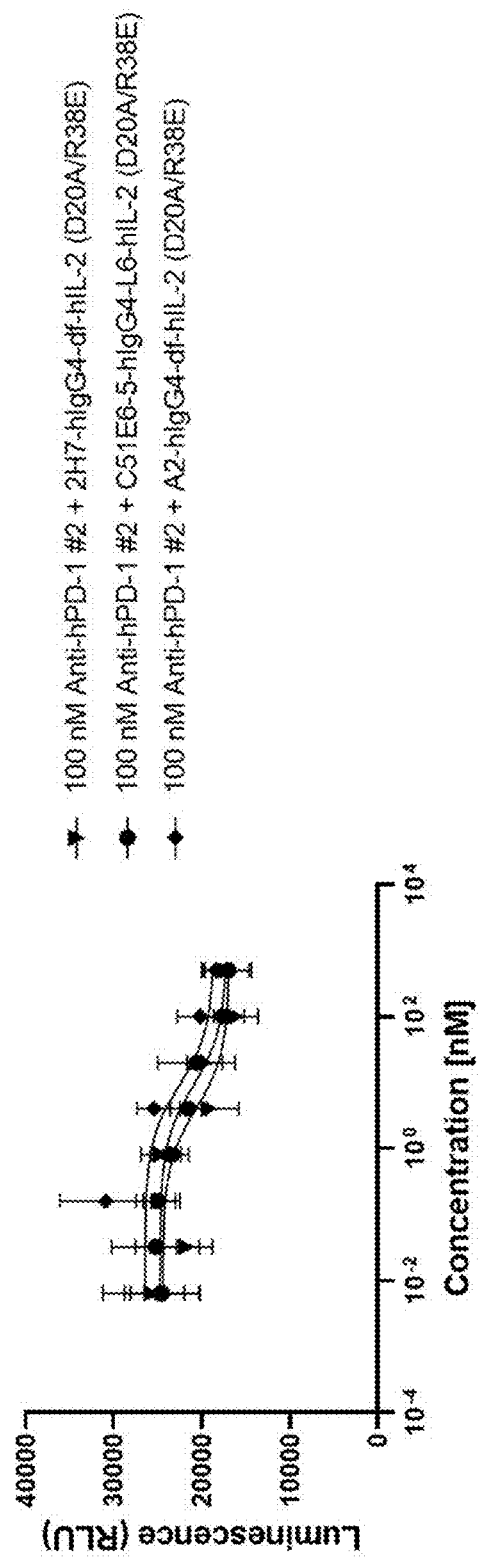

In the converse experiment, either anti-hPD-1 #1 or anti-hPD-1 #2 were diluted to a concentration of 400 nM and 20 µL was combined with 20 µL of titrated anti-hPD-1-attenuated hIL-2 fusion proteins. Anti-hPD-1-attenuated hIL-2 fusion proteins were serially titrated and the 40 µL mixture was added to CHO cells, then overlayed with 40 µL of Jurkat PD-1 Effector cells. The rest of the assay was performed as described in General Protocol C. FIG. 18C and FIG. 18D demonstrate that the addition of 100 nM anti-hPD-1 #1 (FIG. 18C) or 100 nM anti-hPD-1 #2 (FIG. 18D) do not impair the ability of the anti-hPD-1-attenuated hIL-2 fusion proteins to be antagonists. The observed flat curve above 18,000 relative luminescent units (RLU) indicated that there was no competition for antagonist activity and the anti-hPD-1-attenuated hIL-2 fusion proteins tested remained able to exhibit antagonist function even in the presence of anti-hPD-1 #1 or anti-hPD-1 #2.

Example 16: Testing Anti-hPD-1-Attenuated hIL-2 Fusion Proteins for Attenuation on the High-Affinity and Intermediate-Affinity hIL-2 Receptors with Cell-Based Proliferation Assays Anti-hPD-1-attenuated hIL-2 fusion proteins were evaluated for the level of attenuation of hIL-2 activity using the cell proliferation assays on NK-92 and TF1+IL-2Rβ cell lines as described in General Protocol E. Control fusion proteins included fusion proteins incorporating an anti-DNase I antibody (designated 1H3) with a human IgG4 or human IgG1 backbone directly fused to hIL-2 or with a linker (SEQ ID NO: 355) to demonstrate the effects of non-targeting attenuated hIL-2 fusion proteins. The hIL-2 sequence of these constructs contained substitutions for attenuated hIL-2 activity as described in Example 2. Full, partial, or no agonistic IL-2 activity (inactive) was also assessed similarly to Example 3. Some of the variants tested were expressed on a modified human IgG1 or IgG4 isotype with a kappa light chain, with additional L235E or L235A/G237A (LAGA) substitutions in the Fc region to abrogate immunoglobulin effector function. In some antibody-cytokine fusion proteins, the hIL-2 cytokine was fused to the C-terminus of the light chain (LC fusion).

The calculated $EC_{50}$ of each antibody-cytokine fusion protein was determined from relative luminescence units (RLU), and fold change $EC_{50}$ was calculated when compared with recombinant human IL-2 (rhIL-2). The fold change from rhIL-2 and agonistic activity is summarized in Table 23. Agonistic activity was measured as full, partial, or inactive as determined by the maximal luminescence of antibody-attenuated hIL-2 fusion proteins in comparison to the maximal luminescence of rhIL-2. Antibody-attenuated hIL-2 fusion proteins dose-titration curves that reached the maximal luminescence as the rhIL-2 were considered to be variants with full activity. Partial activity was calculated as a percentage of full activity using rhIL-2 maximal luminescence as 100%. Maximal RLU of antibody-attenuated hIL-2 fusion proteins with less than 10% of the rhIL-2 maximal RLU at the highest concentration of 1200 nM were considered to have no agonist activity or inactive. For some variants EC$_{50}$ values were estimated only since maximal luminescence was not reached, as annotated by an [a] in Table 23.

TABLE 23

Fold change from rhIL-2 and agonistic activity of antibody-attenuated hIL-2 fusion proteins on NK-92 (high-affinity IL-2R) and TF1 + IL-2Rβ (intermediate-affinity IL-2R) cell lines.

| | Variants | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|
| Non-Targeted Antibody-Attenuated hIL-2 Fusion Proteins | 1H3-hIgG4-df-hIL-2 (WT) | 0 [a] | Full | 0-1 | Full |
| | 1H3-hIgG4-L6-hIL-2 (WT) | 0 [a] | Full | 0-1 | Full |
| | 1H3-hIgG4-df-hIL-2 (WT) LC fusion | 0 [a] | Full | 24 | Full |
| | 1H3-hIgG4-L6-hIL-2 (WT) LC fusion | 0 [a] | Full | 2 | Full |
| | 1H3-hIgG4-L6-hIL-2 (D20Y) | >10,000 on graph, NC [a] | Inactive | >10,000 on graph, NC [a] | Inactive |
| | 1H3-hIgG4-df-hIL-2 (D20Y) | >10,000 on graph, NC [a] | Partial, 60% | >10,000 on graph, NC [a] | Inactive |
| | 1H3-hIgG1-df-hIL-2 (D20Y) | 8539 [a] | Partial, 90% | >10,000 on graph, NC [a] | Inactive |
| | 1H3-hIgG4-L6-hIL-2 (D20A/R38P) | >10,000 [a] | Partial, 80% | 4132 [a] | Full |
| | 1H3-hIgG4-L6-hIL-2 (D20A/R38S) | >10,000 on graph, NC [a] | Partial, 90% | 9225 [a] | Full |
| | 1H3-hIgG4-L6-hIL-2 (D20A/R38D) | 118 [a] | Partial, 90% | 8591 [a] | Partial, 90% |
| | 1H3-hIgG4-L6-hIL-2 (D20A/R38Q/E95A) | 153 | Full | 5738 [a] | Full |
| | 1H3-hIgG4-L6-hIL-2 (D20A/F42H/E95A) | >10,000 [a] | Full | 1368 [a] | Full |
| | 1H3-hIgG4-L6-hIL-2 (R38D/I92D) | 190 | Full | 437 | Full |
| | 1H3-hIgG4-L6-hIL-2 (R38E/I92D) | 377 [a] | Full | 296 | Full |
| | 1H3-hIgG4-L6-hIL-2 (F42H/I92D) | 794 [a] | Full | 393 | Full |
| | 1H3-hIgG4-df-hIL-2 (D20A/R38E) | 868 [a] | Partial, 90%-Full | >10,000 [a] | Partial, 70%-Full |
| | 1H3-hIgG4-L6-hIL-2 (D20A/R38E) | 177 [a] | Partial, 60-80% | >10,000 [a] | Partial, 70%-Full |
| | 1H3-hIgG4-L6-hIL-2 (T3A/D20A/R38E) | >10,000 on graph, NC [a] | Partial, 40% | >10,000 | Partial, 70% |
| | 1H3-hIgG4-L6-hIL-2 (D20A/R38E/C125A) | >10,000 [a] | Partial, 20% | 6436 | Partial, 40% |
| | 1H3-hIgG4-L6-hIL-2 (T3A/D20A/R38E/C125A) | >10,000 on graph, NC [a] | Partial, 20% | >10,000 | Full |
| | 1H3-hIgG1-L6-hIL-2 (D20A/R38E) | NT | NT | 250-372 | Full |
| | 1H3-hIgG1-L6-hIL-2 (T3A/D20A/R38E) | 392 | Partial, 80% | 186 | Partial, 60% |
| | 1H3-hIgG1-L6-hIL-2 (D20A/R38E/C125A) | 2346 [a] | Partial, 80% | 2157 [a] | Partial, 60% |
| | 1H3-hIgG4-df-hIL-2 (D20A/R38E) LC fusion | >10,000 on graph, NC [a] | Inactive | >10,000 on graph, NC [a] | Inactive |
| | 1H3-hIgG4-L6-hIL-2 (D20A/R38E) LC fusion | >10,000 on graph, NC [a] | Inactive | 2155 [a] | Partial, 30% |
| | 1H3-hIgG1-L6-hIL2 (H16A) | 0 | Full | 0 [a] | Full |
| | 1H3-hIgG1-L6-hIL2 (F42A) | 0 | Full | 0 [a] | Full |
| | 1H3-hIgG1-L6-hIL2 (H16A/F42A) | 1 | Full | 0 [a] | Full |
| Anti-hPD-1-Attenuated hIL-2 Fusion Proteins | A2-hIgG4-df-hIL-2 (D20A/R38E) | 811 [a] | Partial, 20-90% | >10,000 [a] | Partial, 60-80% |
| | D12-hIgG4-df-hIL-2 (D20A/R38E) | >10,000 on graph, NC [a] | Partial, 20% | >10,000 [a] | Partial, 40% |
| | G12-hIgG4-df-hIL-2 (D20A/R38E) | >10,000 [a] | Partial, 20% | >10,000 [a] | Partial, 50% |
| | OMC476pB11-hIgG4-df-hIL-2 (D20A/R38E) | >10,000 on graph, NC [a] | Partial, 70% | 36 | Full |
| | OMC476pE4-hIgG4-df-hIL-2 (D20A/R38E) | >10,000 on graph, NC [a] | Partial, 70% | 1619 | Full |
| | OMC476pG10-hIgG4-df-hIL-2 (D20A/R38E) | >10,000 [a] | Partial, 70% | NC [a] | Inactive |
| | OMC476pH10-hIgG4-df-hIL-2 (D20A/R38E) | >10,000 on graph, NC [a] | Partial, 70% | 3563 [a] | Partial, 80% |
| | A2-hIgG4-df-hIL-2 (D20A/F42A) | 284 | Full | 4323 [a] | Partial, 80% |
| | A2-hIgG4-df-hIL-2 (D20A/F42S) | 3542 | Full | 4052 [a] | Partial, 90% |
| | A2-hIgG4-df-hIL-2 (D20S/R38E) | NT | NT | 7035 [a] | Full |
| | A2-hIgG4-df-hIL-2 (F42A/N88R) | 6423 | Full | 3757 [a] | Partial, 90% |
| | A2-hIgG4-df-hIL-2 (F42I/I92D) | 9543 | Full | 5611 [a] | Partial, 90% |
| | A2-hIgG4-df-hIL-2 (F42Q/I92D) | 8572 | Full | 3363 [a] | Full |
| | A2-hIgG4-df-hIL-2 (F42T/I92D) | 2175 | Full | 5649 [a] | Full |
| | A2-hIgG4-df-hIL-2 (F42W/I92D) | 1239 | Full | 4409 [a] | Partial, 50% |
| | A2-hIgG4-df-hIL-2 (R38E/D84K) | 160-1503 | Full | 1158-1716 | Partial, 90% |
| | A2-hIgG4-df-hIL-2 (R38E/I92K) | 252-977 | Full | 864-1655 | Partial, 80%-Full |
| | C51E6-5-hIgG4-df-hIL-2 (D20A/R38E) | 4317 | Partial, 70% | >10,000 [a] | Partial, 60% |
| | C51E6-5-hIgG4-L6-hIL-2 (D20A/R38E) | NT | NT | >10,000 [a] | Partial, 80% |

TABLE 23-continued

Fold change from rhIL-2 and agonistic activity of antibody-attenuated hIL-2 fusion proteins on NK-92 (high-affinity IL-2R) and TF1 + IL-2Rβ (intermediate-affinity IL-2R) cell lines.

| Variants | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|
| C51E6-5-hIgG4-LE-df-hIL-2 (T3A/D20A/R38E/C125A) | 4326 | Partial, 80% | >10,000 $^a$ | Partial, 70% |
| C51E6-5-hIgG4-LAGA-df-hIL-2 (T3A/D20A/R38E/C125A) | 4336 | Partial, 60% | >10,000 on graph, NC $^a$ | Partial, 60% |
| OMC.1.B6-hIgG4-L6-hIL-2 (D20A/R38E) | NT | NT | 8460 $^a$ | Partial, 70% |
| OMC.1.D6-hIgG4-L6-hIL-2 (D20A/R38E) | NT | NT | >10,000 $^a$ | Partial, 70% |
| OMC.2.C6-hIgG4-L6-hIL-2 (D20A/R38E) | NT | NT | >10,000 $^a$ | Partial, 70% |
| 2A3.H7-hIgG4-df-hIL-2 (D20A/R38E) | NT | NT | 6603 $^a$ | Partial, 60% |
| 1H9-hIgG4-df-hIL-2 (D20A/R38E) | NT | NT | 9769 $^a$ | Partial, 90% |
| 1D5-hIgG4-df-hIL-2 (D20A/R38E) | NT | NT | 7420 $^a$ | Partial, 80% |
| 1D5-hIgG4-LE-df-hIL-2 (T3A/D20A/R38E/C125A) | NT | NT | NC $^a$ | Inactive |
| 1D5-hIgG4-LAGA-df-hIL-2 (T3A/D20A/R38E/C125A) | NT | NT | NC $^a$ | Partial, 20% |
| 2H7-hIgG1-df-hIL-2 (T3A/D20A/R38E/C125A) | 4839 $^a$ | Full | 2057 $^a$ | Full |
| 2H7-hIgG1-LE-df-hIL-2 (T3A/D20A/R38E/C125A) | 7727 $^a$ | Full | 6729 $^a$ | Partial, 80% |
| 2H7-hIgG1-LAGA-df-hIL-2 (T3A/D20A/R38E/C125A) | >10,000 $^a$ | Full | 3428 $^a$ | Partial, 50-60% |
| 2H7-hIgG4-df-hIL-2 (T3A/D20A/R38E/C125A) | 707-7206 $^a$ | Full | >10,000 $^a$ | Partial, 60%-Full |
| 2H7-hIgG4-LE-df-hIL-2 (T3A/D20A/R38E/C125A) | >10,000 | Full | >10,000 $^a$ | Partial, 50-60% |
| 2H7-hIgG4-LAGA-df-hIL-2 T3A/D20A/R38E/C125A) | >10,000 | Full | 7480 $^a$ | Partial, 40-50% |
| H7-767 | >10,000 $^a$ | Partial, Full | >10,000 $^a$ | Full |
| 2H7-hIgG1-df-hIL-2 (T3A/R38E/D84K/C125A) | 1500 | Partial, 90% | 140 $^a$ | Full |
| 2H7-hIgG1-LE-df-hIL-2 (T3A/R38E/D84K/C125A) | 1268 | Partial, 90% | 517 $^a$ | Full |
| 2H7-hIgG1-LAGA-df-hIL-2 (T3A/R38E/D84K/C125A) | 2157-4035 | Partial, 90%-Full | 774-1650 $^a$ | Full |
| 2H7-hIgG4-df-hIL-2 (T3A/R38E/D84K/C125A) | 1602 | Partial, 90% | >10,000 $^a$ | Full |
| 2H7-hIgG4-LE-df-hIL-2 (T3A/R38E/D84K/C125A) | 1675-5096 | Partial, 90% | 1281-2842 $^a$ | Full |
| 2H7-hIgG4-LAGA-df-hIL-2 (T3A/R38E/D84K/C125A) | 1596-5689 | Partial, 90%-Full | 1203-3515 $^a$ | Partial, 60-80% |
| 2H7-hIgG1-df-hIL-2 (T3A/R38E/I92K/C125A) | 370 | Full | 160 | Full |
| 2H7-hIgG1-LE-df-hIL-2 (T3A/R38E/I92K/C125A) | 319 | Full | 656 | Full |
| 2H7-hIgG1-LAGA-df-hIL-2 (T3A/R38E/I92K/C125A) | 406-1280 | Full | 514-1569 $^a$ | Full |
| 2H7-hIgG4-df-hIL-2 (T3A/R38E/I92K/C125A) | 520 | Full | 789-926 | Partial, 80%-Full |
| 2H7-hIgG4-LE-df-hIL-2 (T3A/R38E/I92K/C125A) | 610-1675 | Full | 474-2080 $^a$ | Full |
| 2H7-hIgG4-LAGA-df-hIL-2 (T3A/R38E/I92K/C125A) | 827-2888 | Full | 737-2845 $^a$ | Partial, 70%-Full |
| 2H7-hIgG1-LAGA-df-hIL2 (T3A/D20S/R38E/C125A) | 6689 | Full | 9711 $^a$ | Partial, 70% |
| 2H7-hIgG1-LAGA-df-hIL2 (T3A/R38E/D84F/C125A) | 6199 | Full | 3915 | Full |
| 2H7-hIgG1-LAGA-df-hIL2 (T3A/R38E/I92R/C125A) | 75 | Full | 89 | Full |
| 2H7-hIgG1-LAGA-df-hIL2 (T3A/R38E/I92E/C125A) | 118 | Full | 53 | Full |
| 2H7-hIgG1-LAGA-df-hIL2 (T3A/R38E/I92S/C125A) | 9 | Full | 30 | Full |
| 2H7-hIgG1-LAGA-df-hIL2 (T3A/R38E/I92D/C125A) | 2717 | Full | 3396 $^a$ | Partial, 80% |
| 2H7-hIgG1-LAGA-df-hIL2 (T3A/H16E/R38E/C125A) | 126 | Full | 122 | Full |

NT = Not Tested
NC = Not Calculated by GraphPad Prism 7
$^a$ = Fold change is an estimate only since a full four parameter logistic curve was not reached

Example 17: Rescue of IL-2 Activity of Anti-hPD-1-Attenuated hIL-2 Fusion Proteins on a Cell Line Expressing the Intermediate-Affinity hIL-2 Receptor and hPD-1

Anti-hPD-1-attenuated hIL-2 fusion proteins were evaluated for rescue of hIL-2 activity using a targeted cell line expressing hPD-1. Briefly, the TF1+IL-2Rβ cell line described in General Methods Protocol D was modified through lentiviral transduction to express the hPD-1 receptor (SEQ ID NO: 580). Flow cytometry with a Brilliant Blue 515 conjugated hPD-1 antibody (BD Biosciences Cat #565936) was used to detect hPD-1 expressing TF1+IL-2Rβ cells. Cells were sorted for low hPD-1 expression (less than $10^3$ intensity on the Brilliant Blue 515 fluorophore). The pool was sorted twice more to collect cells that approximated hPD-1 expression levels on activated primary cells. This cell line (TF1+IL-2Rβ+hPD-1) was expanded and frozen in aliquots for the cell-based proliferation assays. Proliferation assays were performed as described in General Methods Protocol E with an incubation period of 3 days. Some variants tested had a modified human IgG1 or IgG4 kappa light chain framework with additional L235E or L235A/G237A (LAGA) substitutions to abrogate effector function of the immunoglobulin.

Table 24 summarizes the results from the proliferation assays on the targeted TF1+IL-2Rβ+hPD-1 cell line. Agonistic activity was measured as full, partial, or inactive as determined by the maximal luminescence of antibody-attenuated hIL-2 fusion proteins in comparison to the maximal luminescence of rhIL-2. Antibody-attenuated hIL-2 fusion protein dose-titration curves that reached the maximal luminescence as the rhIL-2 were considered to be variants with full activity. Partial activity was calculated as a percentage of full activity using rhIL-2 maximal luminescence as 100%. Maximal RLU of antibody-attenuated hIL-2 fusion proteins with less than 10% of the rhIL-2 maximal RLU at the highest concentration of 1200 nM were considered to have no agonist activity or inactive. For some variants, $EC_{50}$ values were estimates only since a full curve was not reached. Many examples of anti-hPD-1-hIL-2 fusion proteins with attenuated hIL-2 showed rescued hIL-2 activity on the targeted cell line where the non-targeting antibody controls (denoted with 1H3) demonstrated no rescue of hIL-2 activity. Full rescue was illustrated by the reduction of fold-change from rhIL-2 to a value of 0 or 1.

TABLE 24

Fold change from rhIL-2 and agonistic activity of antibody-hIL-2 fusion proteins on TF1 + IL-2Rβ + hPD-1 cell line (human PD-1 expressing cell line with intermediate-affinity IL-2R).

| | Variants | Fold decrease from rhIL-2 (TF1 + IL-2Rβ + hPD-1) | Agonistic Activity (TF1 + IL-2Rβ + hPD-1) |
|---|---|---|---|
| Non-Targeted Antibody-Attenuated hIL-2 Fusion Proteins | 1H3-hIgG4-df-hIL-2 (WT) | 1 | Full |
| | 1H3-hIgG4-L6-hIL-2 (WT) | 1 | Full |
| | 1H3-hIgG4-L6-hIL-2 (D20Y) | NC [a] | Inactive |
| | 1H3-hIgG4-df-hIL-2 (D20Y) | NC [a] | Inactive |
| | 1H3-hIgG4-L6-hIL-2 (D20A/R38P) | 3074 [a] | Partial, 80% |
| | 1H3-hIgG4-L6-hIL-2 (D20A/R38S) | 4482 [a] | Partial, 80% |
| | 1H3-hIgG4-L6-hIL-2 (D20A/R38D) | 2964 [a] | Partial, 60% |
| | 1H3-hIgG4-L6-hIL-2 (D20A/R38Q/E95A) | 3538 [a] | Partial, 80% |
| | 1H3-hIgG4-L6-hIL-2 (D20A/F42H/E95A) | 657 [a] | Partial, 70% |
| | 1H3-hIgG4-L6-hIL-2 (R38D/I92D) | 1428 [a] | Full |
| | 1H3-hIgG4-L6-hIL-2 (R38E/I92D) | 1887 [a] | Full |
| | 1H3-hIgG4-L6-hIL-2 (F42H/I92D) | 2024 [a] | Full |
| | 1H3-hIgG4-df-hIL-2 (D20A/R38E) | 307-3628 [a] | Partial, 70%-Full |
| | 1H3-hIgG4-L6-hIL-2 (D20A/R38E) | 4883-5226 | Partial, 70%-Full |
| | 1H3-hIgG4-L6-hIL-2 (T3A/D20A/R38E) | 9167 [a] | Partial, 80% |
| | 1H3-hIgG4-L6-hIL-2 (D20A/R38E/C125A) | 4714 | Partial, 60% |
| | 1H3-hIgG4-L6-hIL-2 (T3A/D20A/R38E/C125A) | 4626 | Partial, 60% |
| | 1H3-hIgG1-L6-hIL-2 (D20A/R38E) | 297 | Full |
| | 1H3-hIgG1-L6-hIL-2 (T3A/D20A/R38E) | 513 | Partial, 80% |
| | 1H3-hIgG1-L6-hIL-2 (D20A/R38E/C125A) | 3342 | Partial, 80% |
| | 1H3-hIgG1-L6-hIL-2 (T3A/D20A/R38E/C125A) | 1081 | Partial, 90% |
| | 1H3-hIgG1-LAGA-df-hIL-2 (T3A/D20A/R38E/C125A) | 6459 | Full |
| | 1H3-hIgG1-L6-hIL-2 (H16A) | 4 [a] | Full |
| | 1H3-hIgG1-L6-hIL-2 (F42A) | 0 [a] | Full |
| | 1H3-hIgG1-L6-hIL-2 (H16A/F42A) | 2 [a] | Full |
| | 1H3-hIgG1-L6-hIL-2 (D20T) | 75 [a] | Full |
| | 1H3-hIgG1-L6-hIL-2 (T3A/F42A/Y45A/L72G/C125A) | 2 [a] | Full |

TABLE 24-continued

Fold change from rhIL-2 and agonistic activity of antibody-hIL-2 fusion proteins on TF1 + IL-2Rβ + hPD-1 cell line (human PD-1 expressing cell line with intermediate-affinity IL-2R).

| | Variants | Fold decrease from rhIL-2 (TF1 + IL-2Rβ + hPD-1) | Agonistic Activity (TF1 + IL-2Rβ + hPD-1) |
|---|---|---|---|
| Anti-hPD-1-Attenuated hIL-2 Fusion Proteins | A2-hIgG4-df-hIL-2 (D20A/R38E) | 0-1 [a] | Full |
| | D12-hIgG4-df-hIL-2 (D20A/R38E) | 1 [a] | Full |
| | G12-hIgG4-df-hIL-2 (D20A/R38E) | 1 [a] | Full |
| | OMC476pB11-hIgG4-df-hIL-2 (D20A/R38E) | 0 [a] | Full |
| | OMC476pE4-hIgG4-df-hIL-2 (D20A/R38E) | 2 [a] | Full |
| | OMC476pG10-hIgG4-df-hIL-2 (D20A/R38E) | 0 [a] | Full |
| | OMC476pH10-hIgG4-df-hIL-2 (D20A/R38E) | 1 [a] | Full |
| | A2-hIgG4-df-hIL-2 (D20A/F42A) | 2 [a] | Full |
| | A2-hIgG4-df-hIL-2 (D20A/F42S) | 1 [a] | Full |
| | A2-hIgG4-df-hIL-2 (D20S/R38E) | 0 [a] | Full |
| | A2-hIgG4-df-hIL-2 (F42A/N88R) | 0 [a] | Full |
| | A2-hIgG4-df-hIL-2 (F42I/I92D) | 9 [a] | Full |
| | A2-hIgG4-df-hIL-2 (F42Q/I92D) | 5 [a] | Full |
| | A2-hIgG4-df-hIL-2 (F42T/I92D) | 1 [a] | Full |
| | A2-hIgG4-df-hIL-2 (F42W/I92D) | 4 [a] | Full |
| | A2-hIgG4-df-hIL-2 (R38E/D84K) | 0-1 [a] | Full |
| | A2-hIgG4-df-hIL-2 (R38E/I92K) | 0-1 [a] | Full |
| | C51E6-5-hIgG4-df-hIL-2 (D20A/R38E) | 0-1 [a] | Partial, 70%-Full |
| | C51E6-5-hIgG4-L6-hIL-2 (D20A/R38E) | 1 [a] | Partial, 90% |
| | C51E6-5-hIgG4-LE-df-hIL-2 (T3A/D20A/R38E/C125A) | 1 [a] | Full |
| | C51E6-5-hIgG4-LAGA-df-hIL-2 (T3A/D20A/R38E/C125A) | 0 [a] | Full |
| | OMC.1.B6-hIgG4-L6-hIL-2 (D20A/R38E) | 0 [a] | Partial, 60% |
| | OMC.1.D6-hIgG4-L6-hIL-2 (D20A/R38E) | 0 [a] | Partial, 90% |
| | OMC.2.C6-hIgG4-L6-hIL-2 (D20A/R38E) | 0 [a] | Partial, 60% |
| | 2A3.H7-hIgG4-df-hIL-2 (D20A/R38E) | 0 [a] | Full |
| | 1H9-hIgG4-df-hIL-2 (D20A/R38E) | 0 [a] | Full |
| | 1D5-hIgG4-df-hIL-2 (D20A/R38E) | 1 [a] | Full |
| | 2H7-hIgG1-df-hIL-2 (T3A/D20A/R38E/C125A) | 1 [a] | Full |
| | 2H7-hIgG1-LE-df-hIL-2 (T3A/D20A/R38E/C125A) | 0 | Full |
| | 2H7-hIgG1-LAGA-df-hIL-2 (T3A/D20A/R38E/C125A) | 1 [a] | Full |
| | 2H7-hIgG4-df-hIL-2 (T3A/D20A/R38E/C125A) | 1 [a] | Full |
| | 2H7-hIgG4-LE-df-hIL-2 (T3A/D20A/R38E/C125A) | 1-4 [a] | Full |
| | 2H7-hIgG4-LAGA-df-hIL-2 (T3A/D20A/R38E/C125A) | 1 [a] | Full |
| | H7-767 | 0-1 [a] | Full |
| | 2H7-hIgG1-df-hIL-2 (T3A/R38E/D84K/C125A) | 2 [a] | Full |
| | 2H7-hIgG1-LE-df-hIL-2 (T3A/R38E/D84K/C125A) | 1 [a] | Full |
| | 2H7-hIgG1-LAGA-df-hIL-2 (T3A/R38E/D84K/C125A) | 1 [a] | Full |
| | 2H7-hIgG4-df-hIL-2 (T3A/R38E/D84K/C125A) | 1 [a] | Full |
| | 2H7-hIgG4-LE-df-hIL-2 (T3A/R38E/D84K/C125A) | 0-2 [a] | Full |
| | 2H7-hIgG4-LAGA-df-hIL-2 (T3A/R38E/D84K/C125A) | 1-3 [a] | Full |
| | 2H7-hIgG1-df-hIL-2 (T3A/R38E/I92K/C125A) | 1 [a] | Full |
| | 2H7-hIgG1-LE-df-hIL-2 (T3A/R38E/I92K/C125A) | 1 [a] | Full |
| | 2H7-hIgG1-LAGA-df-hIL-2 (T3A/R38E/I92K/C125A) | 1-2 [a] | Full |

TABLE 24-continued

Fold change from rhIL-2 and agonistic activity of antibody-hIL-2 fusion proteins on TF1 + IL-2Rβ + hPD-1 cell line (human PD-1 expressing cell line with intermediate-affinity IL-2R).

| Variants | Fold decrease from rhIL-2 (TF1 + IL-2Rβ + hPD-1) | Agonistic Activity (TF1 + IL-2Rβ + hPD-1) |
|---|---|---|
| 2H7-hIgG4-df-hIL-2 (T3A/R38E/I92K/C125A) | 1 [a] | Full |
| 2H7-hIgG4-LE-df-hIL-2 (T3A/R38E/I92K/C125A) | 1 [a] | Full |
| 2H7-hIgG4-LAGA-df-hIL-2 (T3A/R38E/I92K/C125A) | 1 [a] | Full |
| 2H7-hIgG1-LAGA-df-hIL2 (T3A/D20S/R38E/C125A) | Not Attenuated on graph; NC [a] | Full |
| 2H7-hIgG1-LAGA-df-hIL2 (T3A/R38E/D84F/C125A) | 0 [a] | Full |
| 2H7-hIgG1-LAGA-df-hIL2 (T3A/R38E/I92R/C125A) | 0 [a] | Full |
| 2H7-hIgG1-LAGA-df-hIL2 (T3A/R38E/I92E/C125A) | 2 [a] | Full |
| 2H7-hIgG1-LAGA-df-hIL2 (T3A/R38E/I92S/C125A) | Not Attenuated on graph; NC [a] | Full |
| 2H7-hIgG1-LAGA-df-hIL2 (T3A/R38E/C125A) | 0 [a] | Full |
| 2H7-hIgG1-LAGA-df-hIL2 (T3A/H16E/R38E/C125A) | >10,000 [a] | Full |

NC = Not Calculated by GraphPad Prism 7
[a] = Fold change is an estimate only since a full four parameter logistic curve was not reached Example 18: Evaluation of Surrogate Anti-hPD-1-Attenuated hIL-2 Fusion Proteins that Block or do not Block Mouse PD-L1 in an In Vivo Murine Colon Adenocarcinoma (MC38) Model Since there are no accepted models to explore in vivo efficacy of oncology therapeutics in primates, a surrogate anti-mPD-1-attenuated hIL-2 fusion protein was generated and tested in a syngeneic murine tumor model. This MC38 colon adenocarcinoma model is routinely used to test efficacy of immuno-oncology therapeutics. To explore the in vivo effect of the anti-PD-1-attenuated hIL-2 fusion protein, a surrogate anti-mouse PD-1 antibody designated RMP1-14 (known to block mouse PD-L1 binding) and RMP1-30 (described as a mouse PD-L1 non-blocker) was fused to an attenuated hIL-2 at the C-terminus of the mouse IgG2b-N297A heavy chain and tested in an MC38 colon adenocarcinoma model. The hIL-2 moiety included the substitutions F42K, Y45R, and V69R that were tested on an IL-2 dependent mouse T lymphoblast cell line (CTLL-2) and that were demonstrated to be attenuated for mouse IL-2 activity. Human IL-2 can stimulate proliferation of mouse T cells at similar concentrations, however the same substitutions that attenuate activity on human IL-2 dependent cell lines do not attenuate activity on the CTLL-2 cell line (data not shown). As such, the F42K/Y45R/V69R substitutions were used in hIL-2 as a surrogate since they demonstrated attenuated IL-2 activity on mouse cell lines. Sequences comprising the heavy and light chain variable region sequences of anti-mouse PD-1 antibodies RMP1-14 and RMP1-30 (as described in Matsumoto K et al., J Immunol. 2004 Feb. 15; 172 (4): 2530-41) were also formatted onto a murine IgG2b-N297A background to generate anti-mPD-1 RMP1-14 mIgG2b-N297A (SEQ ID NOs: 564 and 566) and anti-mPD-1 RMP1-30 mIgG2b-N297A (SEQ ID NOs: 567 and 568). The mouse IgG2b isotype with an N297A substitution is the murine equivalent of an Fc isotype that abrogates Fc immune effector function. Surrogate antibodies and anti-body-attenuated hIL-2 fusion proteins were produced, expressed and Protein-A purified using standard techniques.

In this murine tumor model, ten week old female C57BL/6NCrl (Charles River) mice were injected into the right flank with $5 \times 10^5$ MC38 colorectal carcinoma cells. When tumors reached 80-120 mm$^3$. mice were sorted into cohorts (10 mice/group) and treatment began on day 1 of study. Anti-mPD-1 RMP1-14 mIgG2b-N297A. anti-mPD-1 RMP1-30 mIgG2b-N297A. anti-mPD-1 RMP1-14 mIgG2b-N297A-L6-hIL-2 (F42K/Y45R/V69R) (SEQ ID NOs: 565 and 566), and anti-mPD-1 RMP1-30 mIgG2b-N297A-L6-hIL-2 (F42K/Y45R/V69R) (SEQ ID NOs: 568 and 569) were dosed intraperitoneally at 5 mg/kg twice weekly for 4 weeks along with vehicle control (phosphate-buffered saline). Tumor size was measured with calipers twice weekly using the formula (w$^2 \times$L)/2 where w=width and L=length for the duration of the study. The study endpoint was a tumor volume of 1000 mm$^3$ or survival at day 50, whichever came first.

FIG. 8 demonstrates that although the administration of anti-mPD-1 RMP1-14-mIgG2b-N297A or anti-mPD-1 RMP1-30-mIgG2b-N297A antibodies alone did not promote significant efficacy relative to treatment with vehicle control, the administration of anti-mPD-1 RMP1-14 mIgG2b-N297A-L6-hIL-2 (F42K/Y45R/V69R) or anti-mPD-1 RMP1-30 mIgG2b-N297A-L6-hIL-2 (F42K/Y45R/V69R) anti-PD-1-attenuated hIL-2 fusion proteins was associated with 90% and 100% complete tumor regressions respectively. These data demonstrate that the anti-tumor efficacy mediated by anti-mPD-1-hIL-2 (F42K/Y45R/V69R) fusion proteins does not require PD-1 checkpoint blockade and that efficacy is dependent on hIL-2 activity. The data further demonstrate that antibody mediated targeting of PD-1 expressing T cells is sufficient to promote potent anti-tumor efficacy in the MC38 tumor model.

Example 19: Surrogate Anti-hPD-1-Attenuated hIL-2 Fusion Protein Expands Effector Memory CD8+ T Cells in an In Vivo Murine Colon Adenocarcinoma Model To understand the mechanism-of-action of the surrogate anti-hPD-1-attenuated hIL-2 fusion protein in vivo, a similar in vivo experiment to Example 18 was performed, followed by immunophenotyping of the resultant T cell populations in tumors, blood, spleens and lymph nodes after three doses. Ten week old female C57BL/6NCrl (Charles River) mice were subcutaneously implanted with the 5×10$^5$ murine MC38 colon adenocarcinoma cancer tumor cells into the right flank and tumors were monitored for growth. Animals with tumors between 150-260 mm$^3$ were divided between four groups with 10 mice per group for the study. After 21 days post-implantation, animals were dosed intraperitoneally with 0.2 mL/dose phosphate buffered saline (PBS) for the vehicle control, 5 mg/kg anti-KLH-C3-mIgG2b-N297A-L6-hIL-2 (F42K/Y45R/V69R), 5 mg/kg anti-mPD-1 RMP1-30 mIgG2b-N297A, or 5 mg/kg anti-mPD-1 RMP1-30 mIgG2b-N297A-L6-hIL-2 (F42K/Y45R/V69R) on days 1, 4 and 8. On day 9, tumors, spleens and inguinal lymph nodes were harvested from all mice and processed into single cell suspensions for subsequent flow cytometry analysis.

Figure 9A:
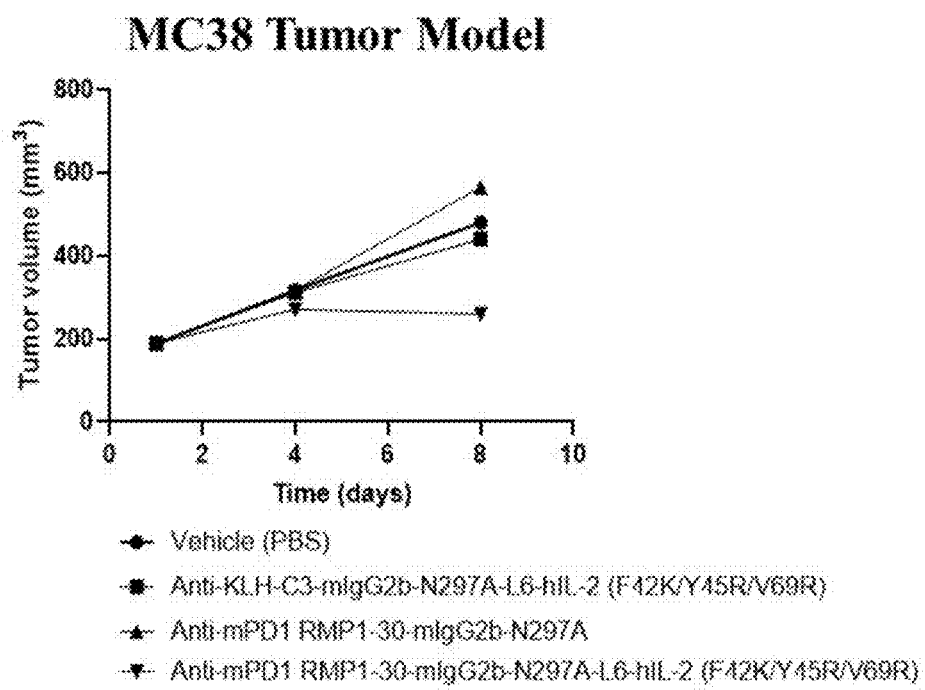
Figure 9B:
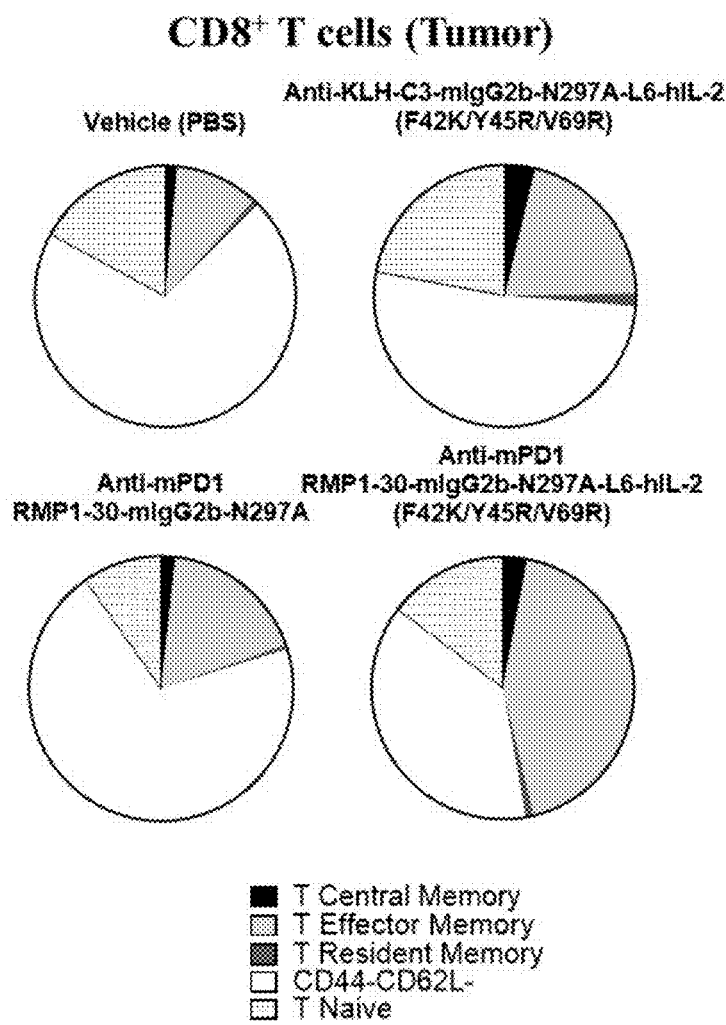

FIG. 9A charts the tumor volume growth (mm$^3$) over 9 days from the first dose on day 1 where each point represents a mean of 10 mice. By day 8, anti-mPD-1 RMP1-30 mIgG2b-N297A-L6-hIL-2 (F42K/Y45R/V69R) had a reduction in tumor volume compared to other treatment groups. FIG. 9B summarizes the contribution of various CD8$^+$ T cell subsets in the tumor of each treatment group in which T Central Memory were phenotyped as CD45$^+$CD3$^+$CD4$^-$CD8$^+$CD44$^+$CD127$^+$CD69$^-$CD103$^-$. T Effector Memory were CD45$^+$CD3$^+$CD4$^-$CD8$^+$CD44$^+$CD127$^+$CD69$^+$CD103$^-$CD62L$^-$. T Resident Memory were CD45$^+$CD3$^+$CD4$^+$CD8$^+$CD44$^+$CD127$^+$CD69$^+$CD103$^+$, CD44$^+$CD62L$^-$ T cells were CD45$^+$CD3$^+$CD4$^-$CD8$^+$CD44$^+$CD62L$^-$ and T Naïve were CD45$^+$CD3$^+$CD4$^+$CD8$^+$CD44$^-$CD62L$^+$. In comparison to other treatment groups, there was expansion of the CD8$^+$ T Effector Memory subset in the anti-mPD-1 RMP1-30 mIgG2b-N297A-L6-hIL-2 (F42K/Y45R/V69R) treated mice as indicated in the increase of the light grey slice of FIG. 9B. This was also illustrated in FIG. 9C in absolute counts (cells/μL) within the MC38 dissected tumor. Furthermore, within the tumor, there was a decrease in the absolute counts (cells/μL) of Regulatory T cells defined as expressing CD45$^+$CD3$^+$CD4$^+$CD8$^+$CD25$^+$FoxP3$^+$ markers.

The expansion of CD8$^+$ T Effector Memory and decrease in Regulatory T cells has been associated with effective immunotherapy in both mice and humans.

Example 20: Anti-hPD-1-Attenuated hIL-2 Fusion Proteins are Active In Vivo in an NCG-PBMC Model Engrafting human immune cells into NOD-Prkdc$^{em2Cd52}$IL-2rg$^{em26Cd22}$/NjuCrl (NCG) mice that lack functional T, B, and NK cells has been a valuable tool for evaluating efficacy of therapeutics hypothesized to stimulate human T cells. In this model, if the therapeutic activates human T cells, there would be a resulting expansion of T cells and accelerated graft-versus-host disease (GvHD).

Three independent donors for human peripheral mononuclear cell (hPBMC) engraftment were evaluated over a 4 week period for engraftment kinetics as well as expression of human PD-1 and human IL-2 receptors on T cells. Of the three donors tested. the donor that induced the most T cells with an intermediate window for GvHD was chosen. 1.5× 10$^7$ hPBMCs were intravenously injected into NCG mice and divided into 8 groups of 8-16 mice. On days 7, 10, and 14, mice were intraperitoneally injected with three doses of 2H7-hIgG1-LAGA-df-hIL-2 (T3A/D20A/R38E/C125A) (SEQ ID NOs: 471, 425) (2.5 mg/kg, 5 mg/kg, or 10 mg/kg), 1H3-hIgG1-LAGA-df-hIL-2 (T3A/D20A/R38E/C125A) (SEQ ID NOs: 546, 374) (5 mg/kg or 10 mg/kg), 1H3-hIgG1-LAGA-df-hIL-2 (T3A/C125A) (SEQ ID NOs: 563, 374) (10 mg/kg), or 2H7-hIgG1-LAGA-df-hIL-2 (T3A/R38E/192K/C125A) (SEQ ID NOs: 474, 425) (5 mg/kg). The anti-DNase fusion protein both as a wild-type hIL-2 (1H3-hIgG1-LAGA-df-hIL-2 (T3A/C125A)) and with the attenuated hIL-2 moiety (1H3-hIgG1-LAGA-df-hIL-2 (T3A/D20A/R38E/C125A)) was used as a non-targeting antibody control. Although the 1H3-hIgG1-LAGA-df-hIL-2 (T3A/C125A) fusion protein had no changes in the hIL-2 moiety which reduce hIL-2 activity, it did comprise the T3A and C125A substitutions to remove the predicted O-linked glycosylation site on human IL-2 (see for example Int'l Pub. No. WO2012/107417) and unpaired cysteine residue (see for example Int'l Pub. No. WO2018/184964), respectively. These substitutions have not demonstrated reduced hIL-2 potency in the clinic. On Day 21, blood, spleen, and lungs were harvested in which blood and spleens were processed for flow cytometry immunophenotyping while lungs were weighed.

After 21 days, flow cytometry immunophenotyping was performed on the blood and spleens of animals. Table 25 summarizes the markers used to delineate human T cell populations for subsequent analysis.

TABLE 25

Phenotypic markers to define human T cell subsets in NCG-PBMC mice

| Cell Population | Phenotypic Markers |
| --- | --- |
| Pan T cells | CD3+ |
| CD8+ Naïve | CD3+CD4−CD8+CD45RO−CCR7+ |
| CD8+ Effector | CD3+CD4−CD8+CD45RO−CCR7− |
| CD8+ Effector Memory | CD3+CD4−CD8+CD45RO+CCR7− |
| CD8+ Central Memory | CD3+CD4−CD8+CD45RO+CCR7+ |
| CD4+ Naïve | CD3+CD4+CD8−CD45RO−CCR7+ |
| CD4+ Effector | CD3+CD4+CD8−CD45RO−CCR7− |
| CD4+ Effector Memory | CD3+CD4+CD8−CD45RO+CCR7− |
| CD4+ Central Memory | CD3+CD4+CD8−CD45RO+CCR7+ |
| Regulatory T cells | CD3+CD4+CD8−CD25+Foxp3+ |
| NK Cells | CD3−CD56+ |

Figure 10:
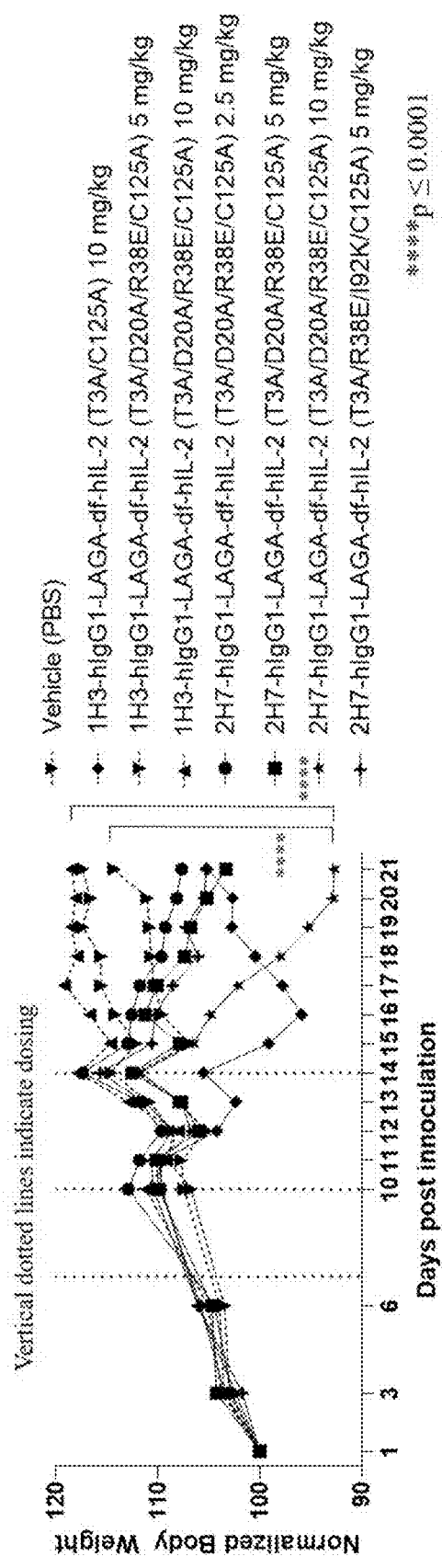
FIG. 10 shows the results from an experiment analyzing the acceleration of Graft vs Host Disease in NOD-Prkdc$^{em26Cd52}$IL-2rg$^{em26Cd22}$/NjuCrl (NCG) mice exposed to anti-hPD-1-attenuated hIL-2 immunoconjugates, as demonstrated by significant body weight decrease in an NCG-PBMC model.

Body weight was measured for 21 days and normalized to day 1 for each individual animal as an assessment of graft-versus-host disease (GvHD) as illustrated in FIG. 10. Accelerated GvHD was observed in the 2H7-hIgG1-LAGA-df-hIL-2 (T3A/D20A/R38E/C125A) treated mice at 10 mg/kg. A small decrease in body weight was also observed in the 2H7-hIgG1-LAGA-df-hIL-2 (T3A/D20A/R38E/C125A) treated mice at 2.5 mg/kg, 5 mg/kg, and 2H7-hIgG1-LAGA-df-hIL-2 (T3A/R38E/192K/C125A) at 5 mg/kg. Although body weight loss was seen in the 1H3-hIgG1-LAGA-df-hIL-2 (T3A/C125A), it was not sustained.

The flow cytometry analysis correlated with the accelerated graft-versus-host disease (GvHD) observed. Using the phenotypic markers for human T cell subset delineation provided in Table 25, flow cytometry analysis of peripheral blood demonstrated only a minor expansion of CD3$^+$, CD4$^+$, and CD8$^+$ T cell subsets (as quantified by a fold change from vehicle control of between 10-fold to 50-fold for CD3+ T cells) in mice treated with 2H7-hIgG1-LAGA-df-hIL-2 (T3A/D20A/R38E/C125A) at 2.5 mg/kg and 5 mg/kg, and mice treated with 1H3-hIgG1-LAGA-df-hIL-2 (T3A/C125A) at 10 mg/kg. Furthermore, CD3$^+$, CD4$^+$, and CD8$^+$ T cell subsets were greatly expanded (fold change from vehicle control was greater than 50-fold for CD3$^+$ T cells) in the peripheral blood of mice treated with 2H7-hIgG1-LAGA-df-hIL-2 (T3A/D20A/R38E/C125A) at 10 mg/kg. Table 26 summarizes the expanded human T cell subsets.

TABLE 26

Expansion of human CD3$^+$, CD4$^+$, and CD8$^+$ T cell subsets in NCG-PBMC mice

| Agent | Fold Change in numbers (Blood) | | |
| --- | --- | --- | --- |
| | CD3$^+$ T cells | CD4$^+$ T cells | CD8$^+$ T cells |
| Vehicle (PBS) | 1 | 1 | 1 |
| 1H3-hIgG1-LAGA-df-hIL-2 (T3A/C125A) 10 mg/kg | 22.76 | 27.73 | 16.13 |
| 1H3-hIgG1-LAGA-df-hIL-2 (T3A/D20A/R38E/C125A) 5 mg/kg | 1.94 | 2.12 | 1.74 |
| 1H3-hIgG1-LAGA-df-hIL-2 (T3A/D20A/R38E/C125A) 10 mg/kg | 0.56 | 0.56 | 0.57 |
| 2H7-hIgG1-LAGA-df-hIL-2 (T3A/D20A/R38E/C125A) 2.5 mg/kg | 24.57 | 32.4 | 14.4 |
| 2H7-hIgG1-LAGA-df-hIL-2 (T3A/D20A/R38E/C125A) 5 mg/kg | 53.03 | 70.74 | 22.86 |
| 2H7-hIgG1-LAGA-df-hIL-2 (T3A/D20A/R38E/C125A) 10 mg/kg | 203.3 | 296.94 | 58.82 |
| 2H7-hIgG1-LAGA-df-hIL-2 (T3A/R38E/I92K/C125A) 5 mg/kg | 31.79 | 48.76 | 8.79 |

N/A = Not Applicable

Figures 11A, 11B:
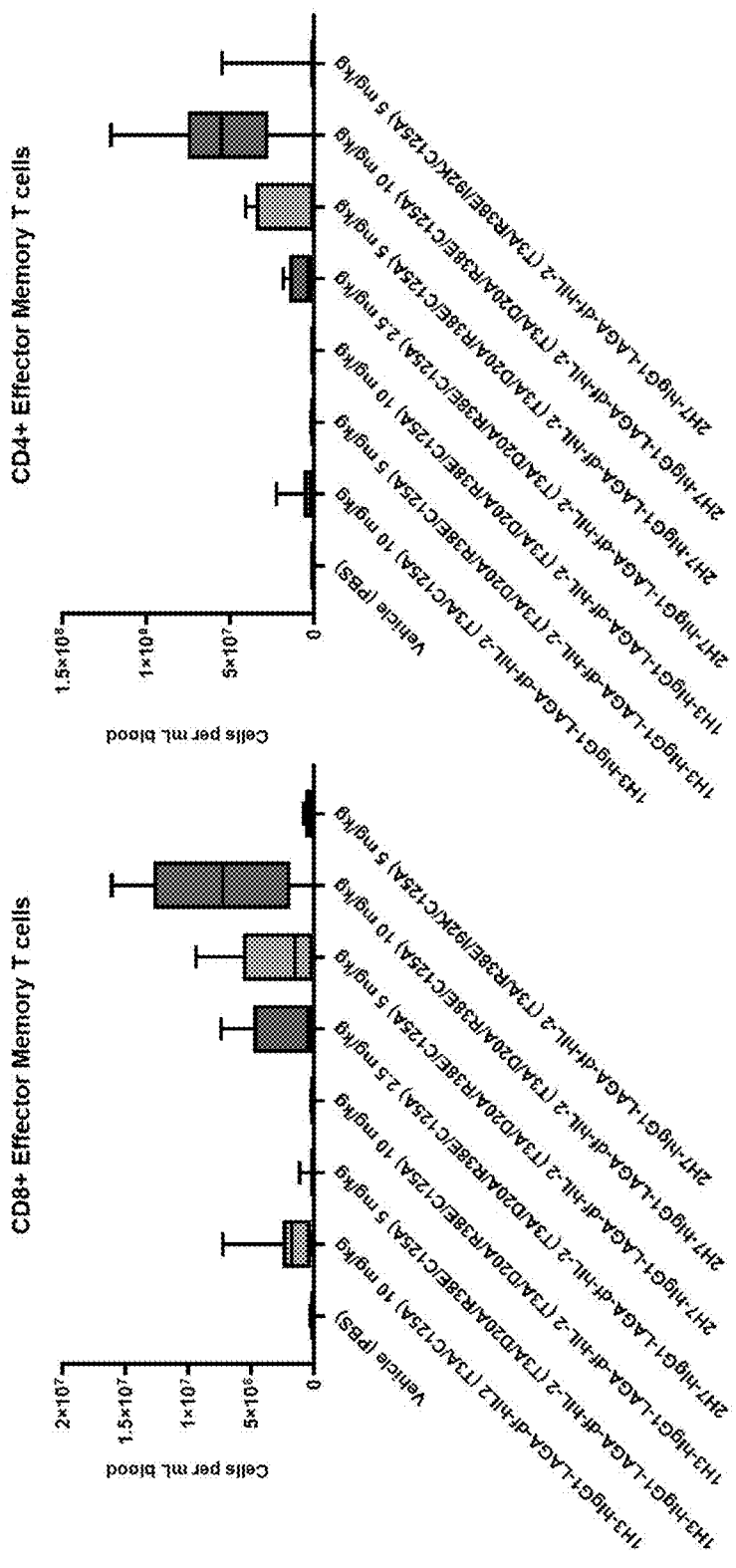
FIG. 11A and FIG. 11B show the results of an experiment analyzing the dose-dependent expansion of cells/mL of blood CD8$^+$ Effector Memory T cells (FIG. 11A) and CD4$^+$ Effector Memory T cells (FIG. 11B) of NOD-Prkdc$^{em26cd2}$IL-2rg$^{em26Cd22}$/NjuCrl (NCG) mice treated with 2H7-hIgG1-LAGA-df-hIL-2 (T3A/D20A/R38E/C125A) in the NCG-PBMC model.

In addition to evaluating CD3$^+$, CD4$^+$, and CD8$^+$ T cells between treatment groups, the memory and naïve subsets for CD4$^+$ and CD8$^+$ T cell subsets were also assessed. The phenotypic markers used for delineation of Naïve, Effector, Effector Memory and Central Memory for both CD4$^+$ and CD8$^+$ T cell is summarized in Table 25. There were no changes in Naïve, Effector or Central Memory T cells between treatment groups (data not shown). However, mice treated with 2H7-hIgG1-LAGA-df-hIL-2 (T3A/D20A/R38E/C125A) at 10 mg/kg had greatly expanded CD4$^+$ and CD8$^+$ Effector Memory (EM) T cells in the peripheral blood with an average cell number per milliliter greater than 5 million for CD8$^+$ T cells and greater than 50 million for CD4$^+$ T cells (FIGS. 11A and 11B). Box-and-whisker plots were graphed with the box around the first and third quartile, the horizontal line as the median, and lines indicated the minimum and maximum points. There was moderate expansion of CD8$^+$ Effector Memory (EM) T cells defined as an average cell number per million between 1 to 5 million per milliliter for animals treated with 2H7-hIgG1-LAGA-df-hIL-2 (T3A/D20A/R38E/C125A) at 2.5 mg/kg and 5 mg/kg as well as for 1H3-hIgG1-LAGA-df-hIL-2 (T3A/C125A). There was moderate expansion of CD4$^+$ Effector Memory (EM) T cells between 6 to 13 million per milliliter for CD4$^+$ T cells in the mice treated with 2H7-hIgG1-LAGA-df-hIL-2 (T3A/D20A/R38E/C125A) at 2.5 mg/kg and 5 mg/kg.

Figure 12:
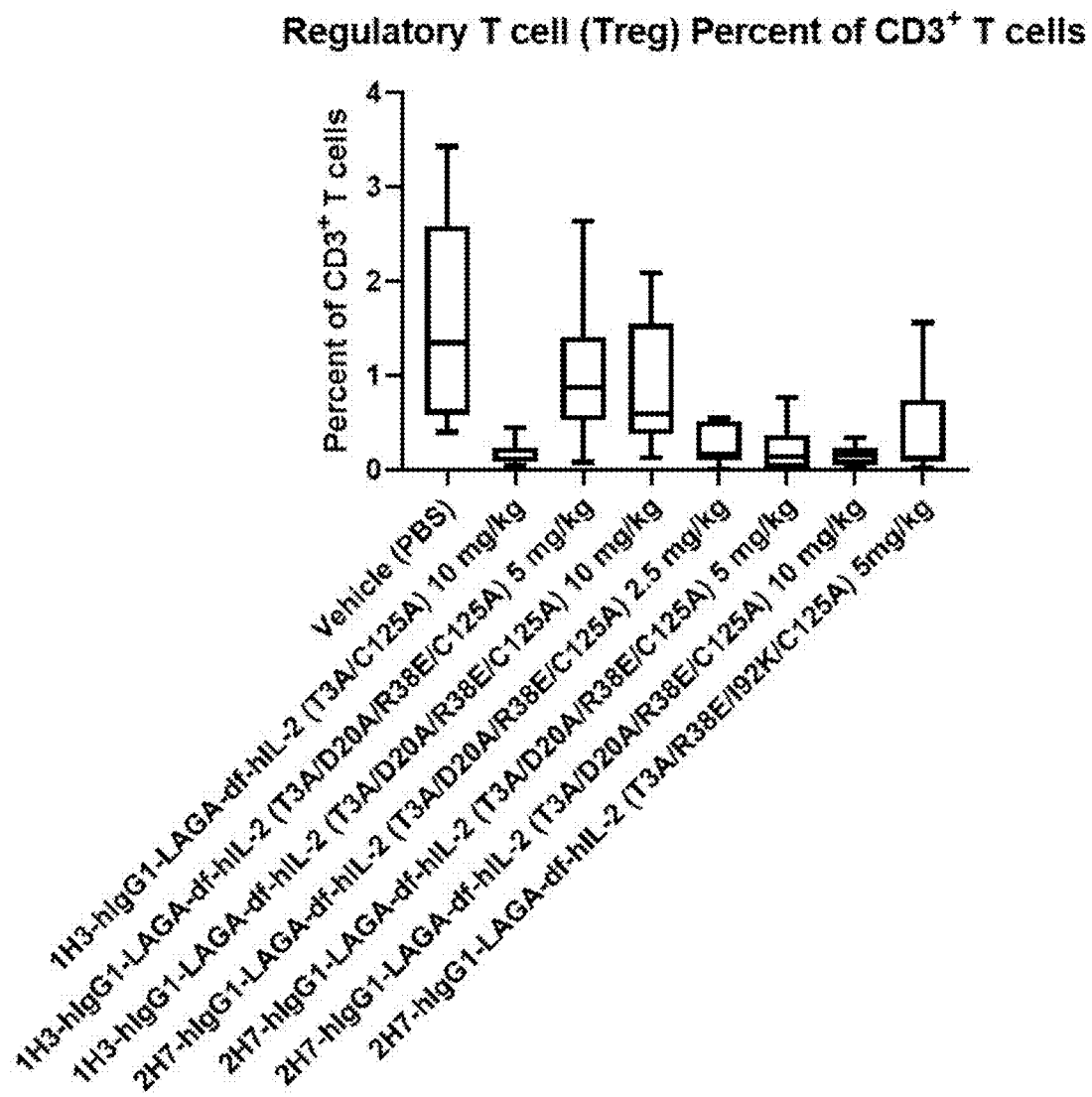
FIG. 12 shows a decrease in cells/mL of blood regulatory T cells of NOD-Prkdc$^{em26Cd52}$IL-2rg$^{em26Cd22}$/NjuCrl (NCG) mice treated with 2H7-hIgG1-LAGA-df-hIL-2 (T3A/D20A/R38E/C125A) in the NCG-PBMC model.
Figure 13B:
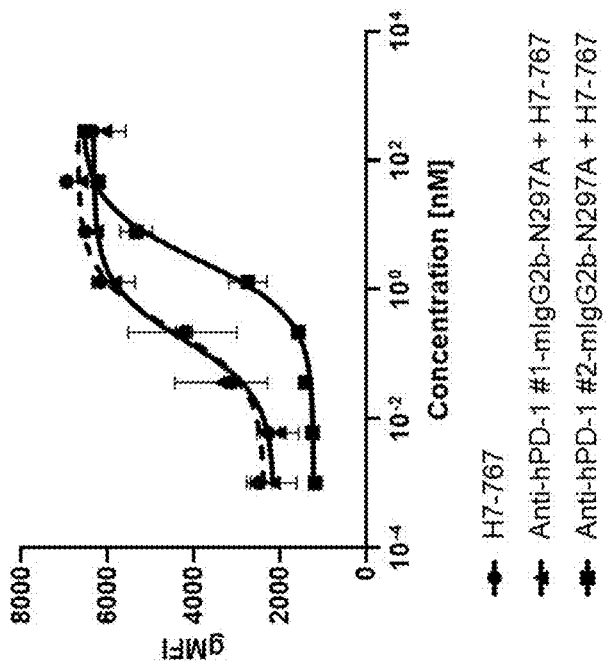
FIG. 13A and FIG. 13B show that H7-632-hIgG1-LAGA-df-hIL-2 (T3A/D20A/R38E/C125A) (designated "H7-767") (FIG. 13B) continues to bind to the human PD-1 receptor on Jurkat cells in the presence of saturating concentrations of anti-hPD-1 #1-mIgG2b-N297A and anti-hPD-1 #2-mIgG2b-N297A (10 µM) prior to exposure.
Figure 13A:
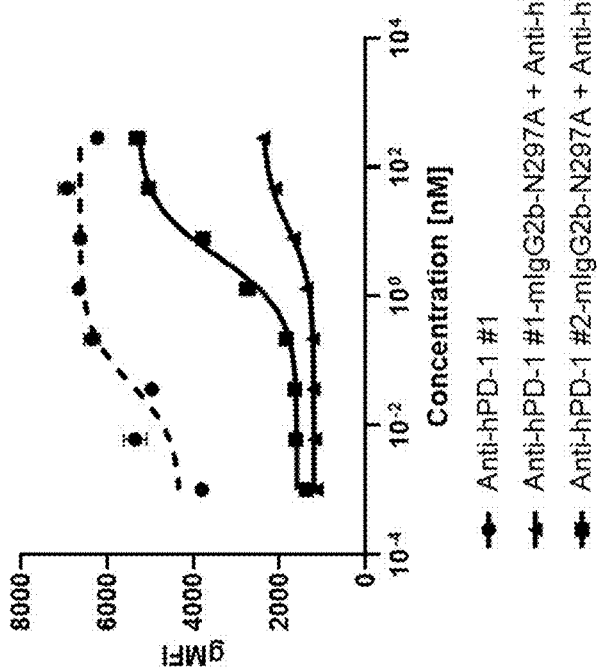
Figure 14B:
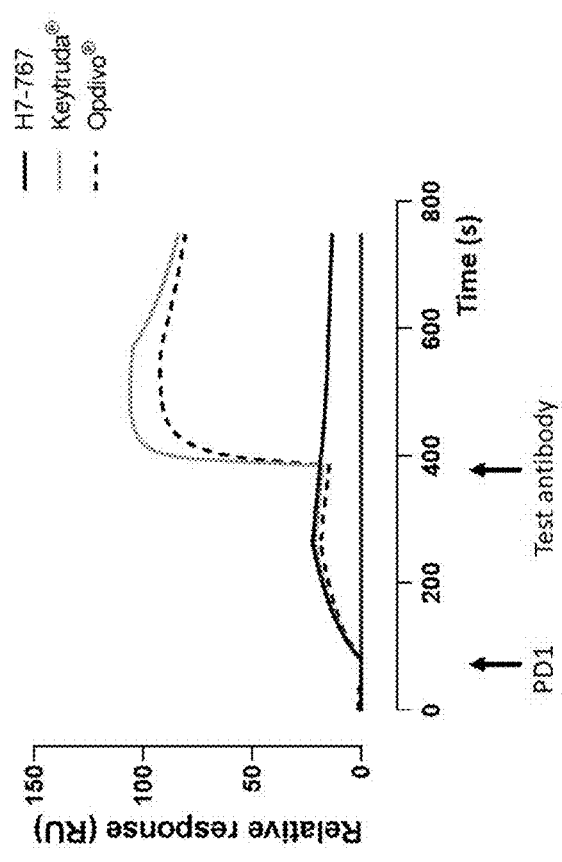
FIG. 14A and FIG. 14B are graphs showing the binding of recombinant human PD-1 captured by H7-767 immobilized to a CM5 sensor chip followed by binding of either (FIG. 14A) H7-767, KEYTRUDA®, or OPDIVO® or (FIG. 14B) PD-L1 or PD-L2, as evaluated by surface plasmon resonance (SPR).
Figure 14A:
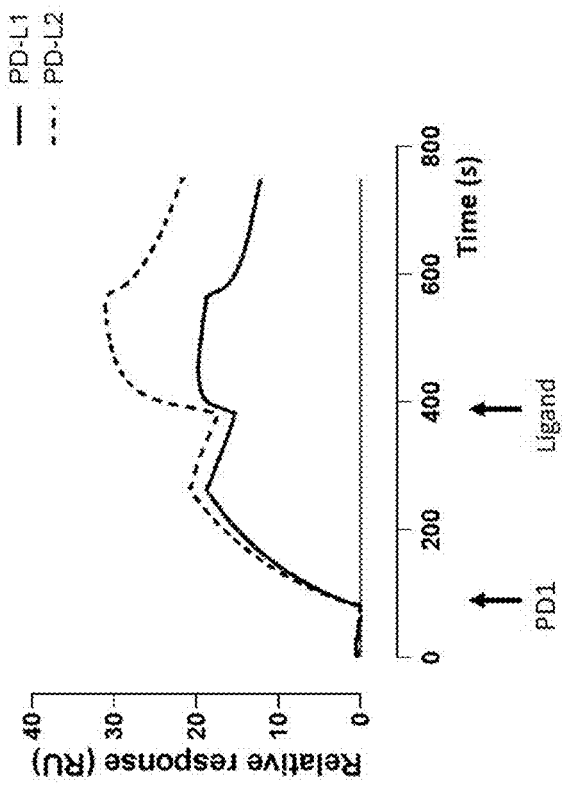

In addition to stimulating effector T cells, IL-2 has been described to stimulate NK cells and regulatory T cells (Tregs) and since Tregs express high levels of CD25 and NK cells express CD122, these immune cell types were also evaluated. FIG. 12 illustrates that animals treated with 2H7-hIgG1-LAGA-df-hIL-2 (T3A/D20A/R38E/C125A) at the highest dose of 10 mg/kg did not expand human regulatory T cells and instead had the lowest percent of regulatory T cells (as phenotypically defined in Table 25) in the peripheral blood of animals. There was a dose-dependent decrease of human regulatory T cells and in comparison to vehicle control that had an average of 1.6% human CD3$^+$ T cells that were Tregs, 2H7-hIgG1-LAGA-df-hIL-2 (T3A/D20A/R38E/C125A) at 10 mg/kg had an average of 0.16% human CD3$^+$ T cells that were Tregs. There were no changes in the percentage of human NK cells in peripheral blood (phenotype defined in Table 25) in all treatment groups in comparison to vehicle control (data not shown).

Example 21: Non-Clinical Safety Profile of Anti-hPD-1-Attenuated hIL-2 Fusion Proteins Cynomolgus monkeys previously have been used to evaluate the toxicity of unmodified IL-2. Lethality was observed in cynomolgus monkeys at exogenous recombinant IL-2 doses as low as 50 μg/kg/day. Since the binding of H7-767 to cynomolgus monkey hPD-1 on primary activated PBMCs was confirmed by flow cytometry (Example 12), a single-dose study for preliminary safety assessment was performed with both a variant of H7-767 (H7-02-hIgG1-LAGA-df-hIL-2 (T3A/D20A/R38E/C125A) (SEQ ID NOs: 582 and 583) and H7-767. H7-02-hIgG1-LAGA-df-hIL-2 (T3A/D20A/R38E/C125A) was delivered by 15 minute iv infusion to 8 monkeys at 1 mg/kg (4 animals) or 10 mg/kg (4 animals). Sampling at time-points up to 360 hours following infusion was performed. No adverse effects, gross toxicities, body weight loss, or lethality was observed (data not shown). A follow-up single-dose study using H7-767 was performed at higher doses of 5 mg/kg and 50 mg/kg similar to the first study, with sampling at time-points up to 360 hours post-infusion. Again, no adverse effects, gross toxicities, body weight loss or lethality was observed (data not shown).

Example 22: Attenuation of IL-2 Activity of Modified hIL-2 Proteins

The attenuation of IL-2 activity of modified hIL-2 proteins comprising a substitution at amino acid position 20 (D20) and a substitution at amino acid position 38 (R38) was tested in proliferation assays in both the NK-92 and TF1+ IL-2Rβ cell lines as described in Example 5 above. The modified hIL-2 proteins were grouped into 7 groups (1 to 7) based upon the maximal agonist activity of the modified hIL-2 protein and the level of attenuation of potency on both the intermediate and high-affinity receptors (Table 27) relative to non-modified recombinant hIL-2. The criteria used for grouping the modified hIL-2 proteins was:
  Group 1: Variants with the highest attenuation (i.e., >10,000-fold) and at least about 80% activity on the intermediate-affinity receptor but also had high attenuation and at least about 70% activity on the high-affinity receptor.

Group 2: Variants with at least about 70% activity and >1,000-fold attenuation on the intermediate-affinity receptor, and about 20% activity to about 30% activity on the high-affinity receptor.

Group 3: Variants with about 50% activity to about 70% activity and >1,000-fold attenuation on the intermediate-affinity receptor, and about 20% activity on the high-affinity receptor.

Group 4: Variants with at least about 70% activity but only >500-fold attenuation on the intermediate-affinity receptor, and about 50% activity on the high-affinity receptor.

Group 5: Variants with at least about 70% activity on both receptors but >10-fold to >300-fold attenuation on the intermediate-affinity receptor in descending order and 70-fold to 1500-fold attenuation on the high-affinity receptor also in descending order.

Group 6: Variants with only about 30% activity and >2,500-fold attenuation on the intermediate-affinity receptor, and no activity on the high-affinity receptor.

Group 7: Variants with no activity on both the intermediate-affinity receptor and high-affinity receptor.

TABLE 27

Fold change from rhIL-2 and agonistic activity of modified hIL-2 proteins comprising a substitution at amino acid position 20 (D20) and a substitution at amino acid position 38 (R38) in a cell-based proliferation assay

| | Variants | SEQ ID NO of hIL-2 variant | Fold change from rhIL-2 (NK-92) | Agonistic Activity (NK-92) | Fold change from rhIL-2 (TF1 + IL-2Rβ) | Agonistic Activity (TF1 + IL-2Rβ) |
|---|---|---|---|---|---|---|
| Group 1 | 1H3-hIgG1-L6-hIL-2 (D20A/R38E) | 149 | 1183-2016 | at least about 70% | >10,000 [a] | at least about 80% |
| Group 2 | 1H3-hIgG1-L6-hIL-2 (D20Q/R38E) | 608 | >10,000 [a] | about 30% | 6665 | at least about 70% |
| Group 2 | 1H3-hIgG1-L6-hIL-2 (D20M/R38E) | 614 | >10,000 [a] | about 30% | 2607 | at least about 70% |
| Group 2 | 1H3-hIgG1-L6-hIL-2 (D20I/R38E) | 611 | >10,000 [a] | about 20% | 1782 | at least about 70% |
| Group 3 | 1H3-hIgG1-L6-hIL-2 (D20V/R38E) | 620 | >10,000 on graph, NC [a] | about 20% | 1849 | about 50% |
| Group 4 | 1H3-hIgG1-L6-hIL-2 (D20S/R38E) | 307 | >10,000 on graph, NC [a] | about 50% | 626 | at least about 70% |
| Group 5 | 1H3-hIgG1-L6-hIL-2 (D20N/R38E) | 607 | 1521 | at least about 70% | 378 | at least about 70% |
| Group 5 | 1H3-hIgG1-L6-hIL-2 (D20G/R38E) | 610 | 1288 | at least about 70% | 212 | at least about 70% |
| Group 5 | 1H3-hIgG1-L6-hIL-2 (D20T/R38E) | 617 | 524 | at least about 70% | 75 | at least about 70% |
| Group 5 | 1H3-hIgG1-L6-hIL-2 (D20E/R38E) | 609 | 77 | at least about 70% | 12 | at least about 70% |
| Group 6 | 1H3-hIgG1-L6-hIL-2 (D20H/R38E) | 306 | No activity | No activity | 2945 | about 30% |
| Group 7 | 1H3-hIgG1-L6-hIL-2 (D20L/R38E) | 612 | >10,000 [a] | No activity | >10,000 [a] | No activity |
| Group 7 | 1H3-hIgG1-L6-hIL-2 (D20K/R38E) | 613 | No activity | No activity | 544 | No activity |
| Group 7 | 1H3-hIgG1-L6-hIL-2 (D20F/R38E) | 615 | >10,000 [a] | No activity | >10,000 [a] | No activity |
| Group 7 | 1H3-hIgG1-L6-hIL-2 (D20P/R38E) | 616 | >10,000 [a] | No activity | >10,000 [a] | No activity |
| Group 7 | 1H3-hIgG1-L6-hIL-2 (D20W/R38E) | 618 | >10,000 [a] | No activity | >10,000 [a] | No activity |
| Group 7 | 1H3-hIgG1-L6-hIL-2 (D20Y/R38E) | 619 | >10,000 [a] | No activity | 1 | No activity |
| Group 7 | 1H3-hIgG1-L6-hIL-2 (D20R/R38E) | 606 | >10,000 [a] | No activity | >10,000 [a] | No activity |

Example 23: Activity of Surrogate Fusion Protein in a Murine MC38 Colo-Rectal Tumor Model Ten week old female C57BL/6NCrl mice were injected into the right flank with $5 \times 10^5$ syngeneic MC38 colorectal carcinoma cells. When tumors reached 80-120 mm$^3$, mice were sorted into cohorts (10 mice/group) and treatment began on day 1 of study. All agents except hIL-2 were dosed intraperitoneally at 5 mg/kg twice weekly for 4 weeks, starting on day 1. hIL-2 was dosed intraperitoneally at 36,000 International Units once a day from days 1-5. Tumor size was measured with calipers twice weekly for the duration of the study. The study endpoint was a tumor volume of 1000 mm$^3$ or survival at day 50 or progression free survival at day 70, whichever came first.

All test agents including antibody molecules and antibody-hIL-2 fusion proteins were generated using a mouse IgG2b Fc region with a single N297A amino-acid substitution at position 297, which prevents glycosylation of the Fc region and significantly reduces any Fc region-mediated immune effector function, thereby preventing cellular depletion in vivo. Anti-mPD-1 RMP1-14 is a monoclonal antibody antagonist of the mouse PD-1 receptor (Matsumoto, J Immunol 172:2530-2541, 2004). Anti-mPD-1 RMP1-14-hIL-2 F42K/Y45R/V69R is a bi-functional fusion protein consisting of the monoclonal RMP1-14 antibody antagonist of the mouse PD-1 receptor fused at its C-terminus via a flexible six amino-acid glycine/serine linker to hIL-2 F42K/Y45R/V69R (SEQ ID NO: 621) that is a reduced potency IL-2 variant. This molecule was designed to target a reduced potency hIL-2 variant directly to PD-1 expressing T cells in vivo in mice. Anti-KLH-hIL-2 F42K, Y45R, V69R is a control fusion protein consisting of an isotype control monoclonal antibody recognizing a non-mammalian antigen (keyhole limpet hemocyanin, KLH) fused at its C-terminus via a flexible six amino-acid glycine/serine linker to hIL-2 F42K, Y45R, V69R that is a reduced potency IL-2 variant.

Figure 19:
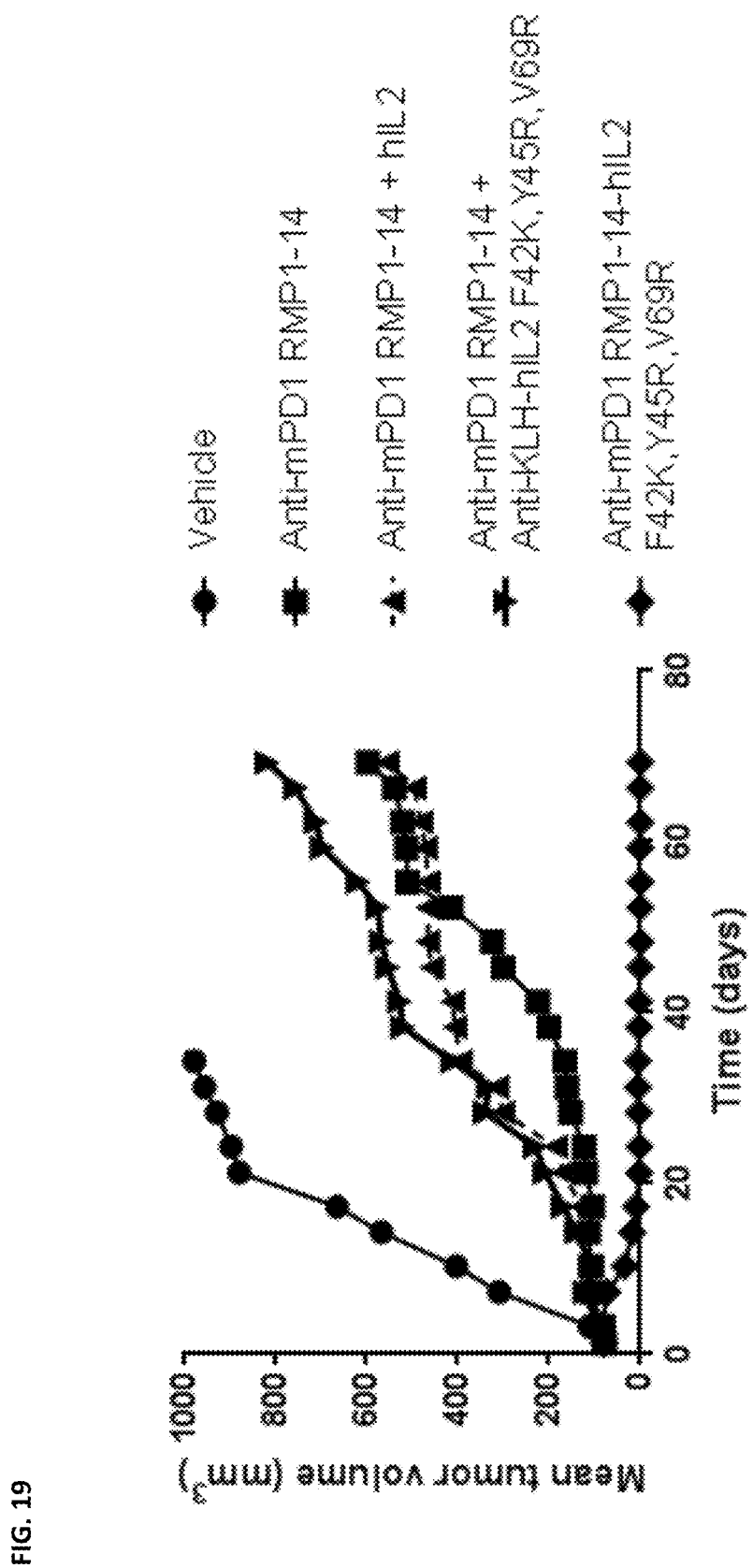
FIG. 19 shows the effect of the administration of various test agents including a surrogate anti-mouse PD-1/attenuated IL-2 immunoconjugate on the growth of established subcutaneous MC38 syngeneic tumors in C57BL/6 mice. Each growth curve represents the mean tumor volume of ten mice per treatment group.

Results are presented in FIG. 19. The MC38 colo-rectal tumor model is particularly responsive to antibody mediated PD-1 receptor inhibition. Although tumors growing in vehicle-treated mice rapidly reached study endpoint, 50% of mice treated with anti-mPD-1 RMP1-14 experienced complete tumor regression. In contrast, 100% of mice treated with an anti-mPD-1 RMP1-14-hIL-2 F42K, Y45R, V69R fusion protein experienced durable, long-term tumor regression. Mice treated with various combinations of the individual components of anti-mPD-1 RMP1-14-hIL-2 F42K, Y45R, V69R fusion protein, including either anti-mPD-1 RMP1-14 combined with hIL-2 free cytokine (administered at a dose and regimen equivalent to a therapeutic dose in humans) or anti-mPD-1 RMP1-14 combined with a non-targeted anti-KLH-hIL-2 F42K, Y45R, V69R fusion protein did not recapitulate the efficacy seen with anti-mPD-1 RMP1-14-hIL-2 F42K, Y45R, V69R. These data demonstrate that targeting a reduced potency hIL-2 to PD-1 expressing cells significantly improves anti-tumor efficacy relative to an anti-PD-1 receptor antagonist and that the activity of the fusion protein is not due to the additive effects of the molecule's individual components.

Example 24: Evaluation of Protective Anti-Tumor Immunity Induced by Surrogate Anti-mPD-1 RMP1-14-hIL-2 F42K, Y45R, V69R in the MC38 Colo-Rectal Tumor Model Mice that had undergone a complete tumor regression in the primary tumor study described in Example 23 and that had survived to day 50 were subjected to a secondary tumor challenge without any additional drug therapy. For tumor re-challenge, mice were implanted on the left flank contralateral to the location of the primary tumor with $5 \times 10^5$ MC38 tumor cells. As a control group, 10 age-matched tumor naïve mice were also implanted with MC38 tumor cells.

Figure 20:
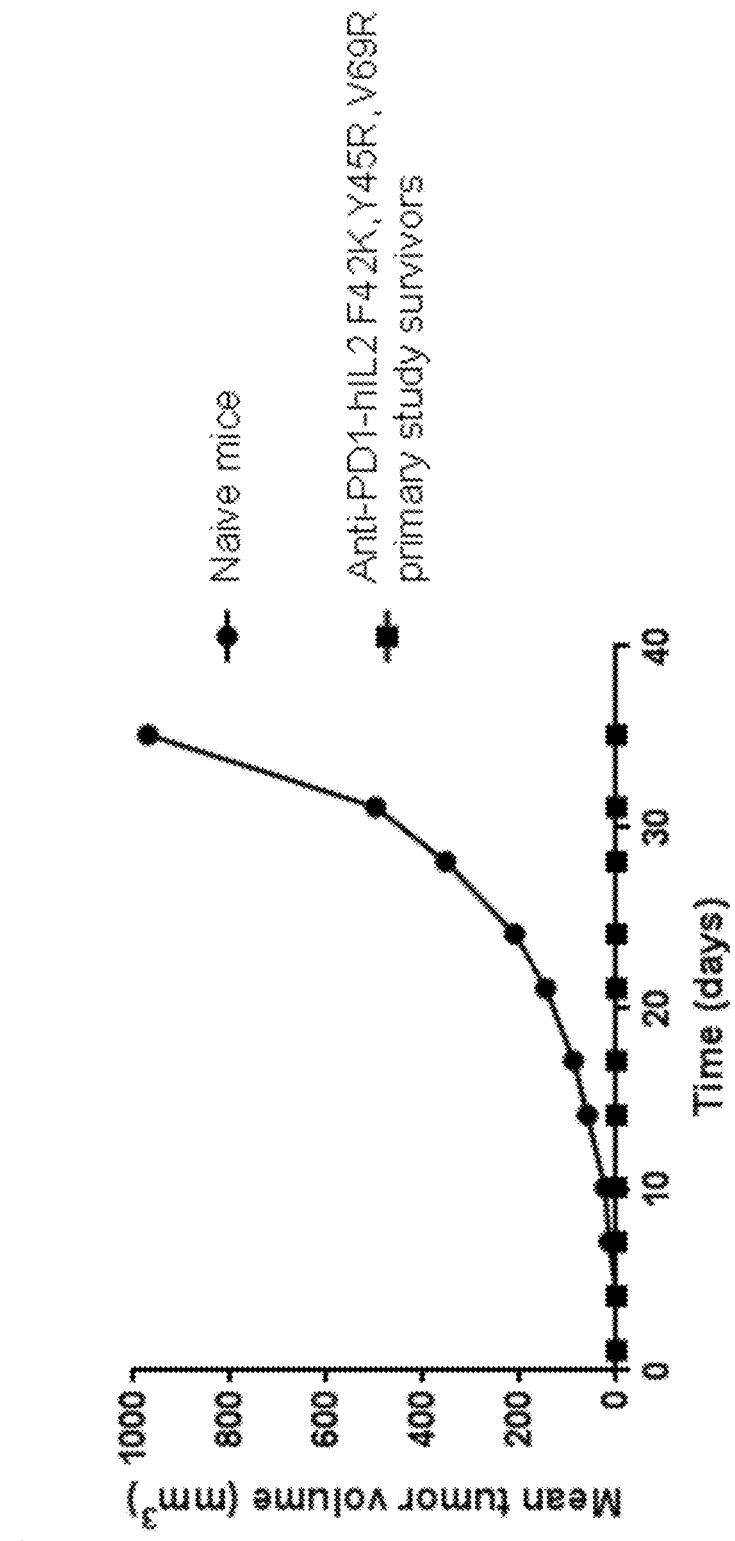
FIG. 20 shows the ability of MC38 tumor cells to grow in tumor naïve mice compared to mice from the MC38 primary tumor study illustrated in FIG. 19 that were previously dosed with anti-mPD-1-hIL-2 F42K/Y45R/V69R and which had demonstrated complete long-term regression of the established primary tumor. Animals from both cohorts (10 mice per group) were subcutaneously implanted with 5×10$^5$ MC38 tumor cells on the left flank contralateral to the location of the primary tumor. Mice previously exposed to the surrogate agent anti-mPD-1-hIL-2 F42K/Y45R/V69R demonstrated no tumor growth as they had developed a sustained immunity, whilst corresponding naïve mice controls demonstrated the typical growth of tumors in their flanks.

FIG. 20 shows that all mice that had previously undergone a complete tumor regression in a prior primary tumor study and had survived to day 50 after treatment with anti-mPD-1 RMP1-14-hIL-2 F42K, Y45R, V69R were completely protected from secondary tumor development. In contrast, all tumor-naïve mice implanted with MC38 tumor cells went on to develop tumors that rapidly reached study endpoint of tumor volume of 100 mm$^3$. The development of protective anti-tumor immunity in the absence of continued drug therapy suggests that anti-mPD-1 RMP1-14-hIL-2 F42K, Y45R, V69R induced an anti-tumor memory T cell response.

Those skilled in the art will appreciate that numerous changes and modifications can be made to the preferred embodiments disclosed herein and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 28

Exemplary Antibodies

| Antibody Name | Heavy chain | Light chain |
| --- | --- | --- |
| Anti-hPD-1 #1-mIgG2b-N297A | Anti-hPD-1 #1-mIgG2b-N297A HC (SEQ ID NO: 348) | Anti-hPD-1 #1-mKappa LC (SEQ ID NO: 349) |
| Anti-hPD-1 #2-mIgG2b-N297A | Anti-hPD-1 #2-mIgG2b-N297A HC (SEQ ID NO: 350) | Anti-hPD-1 #2-mKappa LC (SEQ ID NO: 351) |
| hIL-2 Nterm light chain df | 1H3-hIgG1 HC (SEQ ID NO: 379) | hIL-2-df-1H3-hkappa LC (SEQ ID NO: 356) |
| hIL-2 Nterm light chain L6 fusion | 1H3-hIgG1 HC (SEQ ID NO: 379) | hIL-2-L6-1H3-hkappa LC (SEQ ID NO: 357) |
| hIL-2 Nterm heavy chain df | hIL-2-df-1H3-hIgG1 HC (SEQ ID NO: 358) | 1H3-hKappa LC (SEQ ID NO: 374) |
| hIL-2 Nterm heavy chain L6 fusion | hIL-2-L6-1H3-hIgG1 HC (SEQ ID NO: 359) | 1H3-hKappa LC (SEQ ID NO: 374) |
| hIL-2 Cterm heavy chain df | 1H3-hIgG1-df-hIL-2 HC (SEQ ID NO: 360) | 1H3-hKappa LC (SEQ ID NO: 374) |
| hIL-2 Cterm heavy chain L6 fusion | 1H3-hIgG1-L6-hIL-2 HC (SEQ ID NO: 361) | 1H3-hKappa LC (SEQ ID NO: 374) |

TABLE 28-continued

Exemplary Antibodies

| Antibody Name | Heavy chain | Light chain |
| --- | --- | --- |
| hIL-2 Cterm light chain df | 1H3-hIgG1 HC (SEQ ID NO: 379) | 1H3-hKappa-df-hIL-2 (WT) LC (SEQ ID NO: 362) |
| hIL-2 Cterm light chain L6 fusion | 1H3-hIgG1 HC (SEQ ID NO: 379) | 1H3-hKappa-L6-hIL-2 (WT) LC (SEQ ID NO: 363) |
| hCD25-L20-hIL-2 Nterm heavy chain df | hCD25-L20-hIL-2-df-1H3-hIgG1 HC (SEQ ID NO: 365) | 1H3-hKappa LC (SEQ ID NO: 374) |
| hCD25-L20-hIL-2 Nterm heavy chain L6 fusion | hCD25-L20-hIL-2-L6-1H3-hIgG1 HC (SEQ ID NO: 366) | 1H3-hKappa LC (SEQ ID NO: 374) |
| hCD25-L20-hIL-2 Nterm light chain df | 1H3-hIgG1 HC (SEQ ID NO: 379) | hCD25-L20-hIL-2-df-1H3-hKappa LC (SEQ ID NO: 367) |
| hCD25-L20-hIL-2 Nterm light chain L6 fusion | 1H3-hIgG1 HC (SEQ ID NO: 379) | hCD25-L20-hIL-2-L6-1H3-hKappa LC (SEQ ID NO: 368) |
| hCD25-L20-hIL-2 Cterm heavy chain df | 1H3-hIgG1-df-hCD25-L20-hIL-2 HC (SEQ ID NO: 369) | 1H3-hKappa LC (SEQ ID NO: 374) |
| hCD25-L20-hIL-2 Cterm heavy chain L6 fusion | 1H3-hIgG1-L6-hCD25-L20-hIL-2 HC (SEQ ID NO: 370) | 1H3-hKappa LC (SEQ ID NO: 374) |
| hCD25-L20-hIL-2 Cterm light chain df | 1H3-hIgG1 HC (SEQ ID NO: 379) | 1H3-hKappa-df-hCD25-L20-hIL-2 LC (SEQ ID NO: 371) |
| hCD25-L20-hIL-2 Cterm light chain L6 fusion | 1H3-hIgG1 HC (SEQ ID NO: 379) | 1H3-hKappa-L6-hCD25-L20-hIL-2 LC (SEQ ID NO: 372) |
| 2D12-mIgG1-D265A-L6-hIL-2 | 2D12-mIgG1-D265A-L6-hIL-2 HC (SEQ ID NO: 375) | 2D12-mKappa LC (SEQ ID NO: 376) |
| 2H7-hIgG4 | 2H7-hIgG4 HC (SEQ ID NO: 424) | 2H7-hKappa LC (SEQ ID NO: 425) |
| C51E6-5-hIgG4 | C51E6-5-hIgG4 HC (SEQ ID NO: 426) | C51E6-5-hKappa LC (SEQ ID NO: 427) |
| A2-hIgG4 | A2-hIgG4 HC (SEQ ID NO: 428) | A2-hLambda LC (SEQ ID NO: 429) |
| H7-632-hIgG1-LAGA | H7-632 HC (SEQ ID NO: 414) | H7-632 LC (SEQ ID NO: 415) |
| 2H7-hIgG4-df-hIL-2 (D20A/R38E) | 2H7-hIgG4-df-hIL-2 (D20A/R38E) HC (SEQ ID NO: 430) | 2H7-hKappa LC (SEQ ID NO: 425) |
| C51E6-5-hIgG4-L6-hIL-2 (D20A/R38E) | C51E6-5-hIgG4-L6-hIL-2 (D20A/R38E) HC (SEQ ID NO: 432) | C51E6-5-hKappa LC (SEQ ID NO: 427) |
| A2-hIgG4-df-hIL-2 (D20A/R38E) | A2-hIgG4-df-hIL-2 (D20A/R38E) HC (SEQ ID NO: 433) | A2-hLambda LC (SEQ ID NO: 429) |
| 1H3-hIgG4-df-hIL-2 (D20A/R38E) | 1H3-hIgG4-df-hIL-2 (D20A/R38E) HC (SEQ ID NO: 434) | 1H3-hKappa LC (SEQ ID NO: 374) |
| 2H7-hIgG4-df-hIL-2 (T3A/D20A/R38E/C125A) | 2H7-hIgG4-df-hIL-2 (T3A/D20A/R38E/C125A) HC (SEQ ID NO: 435) | 2H7-hKappa LC (SEQ ID NO: 425) |
| OMC.1.B6-hIgG4 | OMC.1.B6-hIgG4 HC (SEQ ID NO: 438) | OMC.1.B6-hLambda LC (SEQ ID NO: 439) |
| OMC.2.C6-hIgG4 | OMC.2.C6-hIgG4 HC (SEQ ID NO: 440) | OMC.2.C6-hLambda LC (SEQ ID NO: 441) |
| OMC.1.D6-hIgG4 | OMC.1.D6-hIgG4 HC (SEQ ID NO: 442) | OMC.1.D6-hLambda LC (SEQ ID NO: 443) |
| D12-hIgG4 | D12-hIgG4 HC (SEQ ID NO: 444) | D12-hLambda LC (SEQ ID NO: 445) |
| G12-hIgG4 | G12-hIgG4 HC (SEQ ID NO: 446) | G12-hLambda LC (SEQ ID NO: 447) |
| Abz1mod-hIgG4 | Abz1mod-hIgG4 HC (SEQ ID NO: 449) | Abz1mod-hKappa LC (SEQ ID NO: 450) |
| Anti-hPD-1 #1-hIgG4-L6-hIL-2 (D20A/R38E) | Anti-hPD-1 #1-hIgG4-L6-hIL-2 (D20A/R38E) (SEQ ID NO: 451) | Anti-hPD-1 #1-hKappa (SEQ ID NO: 452) |
| OMC.1.B6-hIgG4-L6-hIL-2 (D20A/R38E) | OMC.1.B6-hIgG4-L6-hIL-2 (D20A/R38E) HC (SEQ ID NO: 453) | OMC.1.B6-hLambda LC (SEQ ID NO: 439) |
| OMC.2.C6-hIgG4-L6-hIL-2 (D20A/R38E) | OMC.2.C6-hIgG4-L6-hIL-2 (D20A/R38E) HC (SEQ ID NO: 454) | OMC.2.C6-hLambda LC (SEQ ID NO: 441) |
| OMC.1.D6-hIgG4-L6-hIL-2 (D20A/R38E) | OMC.1.D6-hIgG4-L6-hIL-2 (D20A/R38E) HC (SEQ ID NO: 455) | OMC.1.D6-hLambda LC (SEQ ID NO: 443) |
| D12-hIgG4-df-hIL-2 (D20A/R38E) | D12-hIgG4-df-hIL-2 (D20A/R38E) HC (SEQ ID NO: 456) | D12-hLambda LC (SEQ ID NO: 445) |
| G12-hIgG4-df-hIL-2 (D20A/R38E) | G12-hIgG4-df-hIL-2 (D20A/R38E) HC (SEQ ID NO: 457) | G12-hLambda LC (SEQ ID NO: 447) |
| 2H7-hIgG4-LE | 2H7-hIgG4-LE HC (SEQ ID NO: 458) | 2H7-hKappa LC (SEQ ID NO: 425) |
| 2H7-hIgG4-LAGA | 2H7-hIgG4-LAGA HC (SEQ ID NO: 459) | 2H7-hKappa LC (SEQ ID NO: 425) |
| OMC476pH7-hIgG4 | OMC476pH7-hIgG4 HC (SEQ ID NO: 461) | OMC476pB11.H7 LC (SEQ ID NO: 462) |
| OMC476pB11-hIgG4 | OMC476pB11-hIgG4 HC (SEQ ID NO: 463) | OMC476pB11.H7 LC (SEQ ID NO: 462) |
| OMC476pG10-hIgG4 | OMC476pG10-hIgG4 HC (SEQ ID NO: 464) | OMC476pG10.H10 LC (SEQ ID NO: 466) |
| OMC476pH10-hIgG4 | OMC476pH10-hIgG4 HC (SEQ ID NO: 465) | OMC476pG10.H10 LC (SEQ ID NO: 466) |
| OMC476pE4-hIgG4 | OMC476pE4-hIgG4 HC (SEQ ID NO: 467) | OMC476pE4 LC (SEQ ID NO: 468) |
| J110-hIgG1 | J110-hIgG1 HC (SEQ ID NO: 469) | J110-hKappa LC (SEQ ID NO: 470) |
| 2H7-hIgG1-LAGA-df-hIL-2 (T3A/D20A/R38E/C125A) | 2H7-hIgG1-LAGA-df-hIL-2 (T3A/D20A/R38E/C125A) HC (SEQ ID NO: 471) | 2H7-hKappa LC (SEQ ID NO: 425) |

TABLE 28-continued

Exemplary Antibodies

| Antibody Name | Heavy chain | Light chain |
|---|---|---|
| 2H7-hIgG4-LE-df-hIL-2 (T3A/D20A/R38E/C125A) | 2H7-hIgG4-LE-df-hIL-2 (T3A/D20A/R38E/C125A) HC (SEQ ID NO: 472) | 2H7-hKappa LC (SEQ ID NO: 425) |
| 2H7-hIgG4-LAGA-df-hIL-2 (T3A/D20A/R38E/C125A) | 2H7-hIgG4-LAGA-df-hIL-2 (T3A/D20A/R38E/C125A) HC (SEQ ID NO: 473) | 2H7-hKappa LC (SEQ ID NO: 425) |
| 2H7-hIgG1-LAGA-df-hIL-2 (T3A/R38E/I92K/C125A) | 2H7-hIgG1-LAGA-df-hIL-2 (T3A/R38E/I92K/C125A) HC (SEQ ID NO: 474) | 2H7-hKappa LC (SEQ ID NO: 425) |
| hIgG4-LE-df-hIL-2 (T3A/R38E/I92K/C125A) | hIgG4-LE-df-hIL-2 (T3A/R38E/I92K/C125A) HC (SEQ ID NO: 475) | 2H7-hKappa LC (SEQ ID NO: 425) |
| 2H7-hIgG4-LAGA-df-hIL-2 (T3A/R38E/I92K/C125A) | 2H7-hIgG4-LAGA-df-hIL-2 (T3A/R38E/I92K/C125A) HC (SEQ ID NO: 476) | 2H7-hKappa LC (SEQ ID NO: 425) |
| 2H7-hIgG1-LAGA-df-hIL-2 (T3A/R38E/D84K/C125A) | 2H7-hIgG1-LAGA-df-hIL-2 (T3A/R38E/D84K/C125A) HC (SEQ ID NO: 477) | 2H7-hKappa LC (SEQ ID NO: 425) |
| 2H7-hIgG4-LE-df-hIL-2 (T3A/R38E/D84K/C125A) | 2H7-hIgG4-LE-df-hIL-2 (T3A/R38E/D84K/C125A) HC (SEQ ID NO: 478) | 2H7-hKappa LC (SEQ ID NO: 425) |
| 2H7-hIgG4-LAGA-df-hIL-2 (T3A/R38E/D84K/C125A) | 2H7-hIgG4-LAGA-df-hIL-2 (T3A/R38E/D84K/C125A) HC (SEQ ID NO: 479) | 2H7-hKappa LC (SEQ ID NO: 425) |
| 1H3-hIgG4-df-hIL-2 (WT) | 1H3-hIgG4-df-hIL-2 (WT) HC (SEQ ID NO: 480) | 1H3-hKappa LC (SEQ ID NO: 374) |
| 1H3-hIgG4-L6-hIL-2 (WT) | 1H3-hIgG4-L6-hIL-2 (WT) HC (SEQ ID NO: 481) | 1H3-hKappa LC (SEQ ID NO: 374) |
| 1H3-hIgG4-df-hIL-2 (WT) LC fusion | 1H3-hIgG4 HC (SEQ ID NO: 482) | 1H3-hKappa-df-hIL-2 (WT) LC (SEQ ID NO: 362) |
| 1H3-hIgG4-L6-hIL-2 (WT) LC fusion | 1H3-hIgG4 HC (SEQ ID NO: 482) | 1H3-hKappa-L6-hIL-2 (WT) LC (SEQ ID NO: 363) |
| 1H3-hIgG4-L6-hIL-2 (D20Y) | 1H3-hIgG4-L6-hIL-2 (D20Y) HC (SEQ ID NO: 485) | 1H3-hKappa LC (SEQ ID NO: 374) |
| 1H3-hIgG4-df-hIL-2 (D20Y) | 1H3-hIgG4-df-hIL-2 (D20Y) HC (SEQ ID NO: 486) | 1H3-hKappa LC (SEQ ID NO: 374) |
| 1H3-hIgG1-df-hIL-2 (D20Y) | 1H3-hIgG1-df-hIL-2 (D20Y) HC (SEQ ID NO: 487) | 1H3-hKappa LC (SEQ ID NO: 374) |
| 1H3-hIgG4-L6-hIL-2 (D20A/R38P) | 1H3-hIgG4-L6-hIL-2 (D20A/R38P) HC (SEQ ID NO: 488) | 1H3-hKappa LC (SEQ ID NO: 374) |
| 1H3-hIgG4-L6-hIL-2 (D20A/R38S) | 1H3-hIgG4-L6-hIL-2 (D20A/R38S) HC (SEQ ID NO: 489) | 1H3-hKappa LC (SEQ ID NO: 374) |
| 1H3-hIgG4-L6-hIL-2 (D20A/R38D) | 1H3-hIgG4-L6-hIL-2 (D20A/R38D) HC (SEQ ID NO: 490) | 1H3-hKappa LC (SEQ ID NO: 374) |
| 1H3-hIgG4-L6-hIL-2 (D20A/R38Q/E95A) | 1H3-hIgG4-L6-hIL-2 (D20A/R38Q/E95A) HC (SEQ ID NO: 491) | 1H3-hKappa LC (SEQ ID NO: 374) |
| 1H3-hIgG4-L6-hIL-2 (D20A/F42H/E95A) | 1H3-hIgG4-L6-hIL-2 (D20A/F42H/E95A) HC (SEQ ID NO: 492) | 1H3-hKappa LC (SEQ ID NO: 374) |
| 1H3-hIgG4-L6-hIL-2 (R38D/I92D) | 1H3-hIgG4-L6-hIL-2 (R38D/I92D) HC (SEQ ID NO: 493) | 1H3-hKappa LC (SEQ ID NO: 374) |
| 1H3-hIgG4-L6-hIL-2 (R38E/I92D) | 1H3-hIgG4-L6-hIL-2 (R38E/I92D) HC (SEQ ID NO: 494) | 1H3-hKappa LC (SEQ ID NO: 374) |
| 1H3-hIgG4-L6-hIL-2 (F42H/I92D) | 1H3-hIgG4-L6-hIL-2 (F42H/I92D) HC (SEQ ID NO: 495) | 1H3-hKappa LC (SEQ ID NO: 374) |
| 1H3-hIgG4-L6-hIL-2 (D20A/R38E) | 1H3-hIgG4-L6-hIL-2 (D20A/R38E) HC (SEQ ID NO: 496) | 1H3-hKappa LC (SEQ ID NO: 374) |
| 1H3-hIgG4-L6-hIL-2 (T3A/D20A/R38E) | 1H3-hIgG4-L6-hIL-2 (T3A/D20A/R38E) HC (SEQ ID NO: 497) | 1H3-hKappa LC (SEQ ID NO: 374) |
| 1H3-hIgG4-L6-hIL-2 (D20A/R38E/C125A) | 1H3-hIgG4-L6-hIL-2 (D20A/R38E/C125A) HC (SEQ ID NO: 498) | 1H3-hKappa LC (SEQ ID NO: 374) |
| 1H3-hIgG4-L6-hIL-2 (T3A/D20A/R38E/C125A) | 1H3-hIgG4-L6-hIL-2 (T3A/D20A/R38E/C125A) HC (SEQ ID NO: 499) | 1H3-hKappa LC (SEQ ID NO: 374) |
| 1H3-hIgG1-L6-hIL-2 (D20A/R38E) | 1H3-hIgG1-L6-hIL-2 (D20A/R38E) HC (SEQ ID NO: 500) | 1H3-hKappa LC (SEQ ID NO: 374) |
| 1H3-hIgG1-L6-hIL-2 (T3A/D20A/R38E) | 1H3-hIgG1-L6-hIL-2 (T3A/D20A/R38E) HC (SEQ ID NO: 501) | 1H3-hKappa LC (SEQ ID NO: 374) |
| 1H3-hIgG1-L6-hIL-2 (D20A/R38E/C125A) | 1H3-hIgG1-L6-hIL-2 (D20A/R38E/C125A) HC (SEQ ID NO: 502) | 1H3-hKappa LC (SEQ ID NO: 374) |
| 1H3-hIgG4-df-hIL-2 (D20A/R38E) LC fusion | 1H3-hIgG4 HC (SEQ ID NO: 482) | 1H3-hKappa-df-hIL-2 (D20A/R38E) LC (SEQ ID NO: 503) |

TABLE 28-continued

Exemplary Antibodies

| Antibody Name | Heavy chain | Light chain |
| --- | --- | --- |
| 1H3-hIgG4-L6-hIL-2 (D20A/R38E) LC fusion | 1H3-hIgG4 HC (SEQ ID NO: 482) | 1H3-hKappa-L6-hIL-2 (D20A/R38E) LC (SEQ ID NO: 504) |
| OMC476pB11-hIgG4-df-hIL-2 (D20A/R38E) | OMC476pB11-hIgG4-df-hIL-2 (D20A/R38E) HC (SEQ ID NO: 505) | OMC476pB11.H7 LC (SEQ ID NO: 462) |
| OMC476pE4-hIgG4-df-hIL-2 (D20A/R38E) | OMC476pE4-hIgG4-df-hIL-2 (D20A/R38E) HC (SEQ ID NO: 506) | OMC476pE4 LC (SEQ ID NO: 468) |
| OMC476pG10-hIgG4-df-hIL-2 (D20A/R38E) | OMC476pG10-hIgG4-df-hIL-2 (D20A/R38E) HC (SEQ ID NO: 507) | OMC476pG10.H10 LC (SEQ ID NO: 466) |
| OMC476pH10-hIgG4-df-hIL-2 (D20A/R38E) | OMC476pH10-hIgG4-df-hIL-2 (D20A/R38E) HC (SEQ ID NO: 508) | OMC476pG10.H10 LC (SEQ ID NO: 466) |
| A2-hIgG4-df-hIL-2 (D20A/F42A) | A2-hIgG4-df-hIL-2 (D20A/F42A) HC (SEQ ID NO: 509) | A2-hLambda LC (SEQ ID NO: 429) |
| A2-hIgG4-df-hIL-2 (D20A/F42S) | A2-hIgG4-df-hIL-2 (D20A/F42S) HC (SEQ ID NO: 510) | A2-hLambda LC (SEQ ID NO: 429) |
| A2-hIgG4-df-hIL-2 (D20S/R38E) | A2-hIgG4-df-hIL-2 (D20S/R38E) HC (SEQ ID NO: 511) | A2-hLambda LC (SEQ ID NO: 429) |
| A2-hIgG4-df-hIL-2 (F42A/N88R) | A2-hIgG4-df-hIL-2 (F42A/N88R) HC (SEQ ID NO: 512) | A2-hLambda LC (SEQ ID NO: 429) |
| A2-hIgG4-df-hIL-2 (F42I/I92D) | A2-hIgG4-df-hIL-2 (F42I/I92D) HC (SEQ ID NO: 513) | A2-hLambda LC (SEQ ID NO: 429) |
| A2-hIgG4-df-hIL-2 (F42Q/I92D) | A2-hIgG4-df-hIL-2 (F42Q/I92D) HC (SEQ ID NO: 514) | A2-hLambda LC (SEQ ID NO: 429) |
| A2-hIgG4-df-hIL-2 (F42T/I92D) | A2-hIgG4-df-hIL-2 (F42T/I92D) HC (SEQ ID NO: 515) | A2-hLambda LC (SEQ ID NO: 429) |
| A2-hIgG4-df-hIL-2 (F42W/I92D) | A2-hIgG4-df-hIL-2 (F42W/I92D) HC (SEQ ID NO: 516) | A2-hLambda LC (SEQ ID NO: 429) |
| A2-hIgG4-df-hIL-2 (R38E/D84K) | A2-hIgG4-df-hIL-2 (R38E/D84K) HC (SEQ ID NO: 517) | A2-hLambda LC (SEQ ID NO: 429) |
| A2-hIgG4-df-hIL-2 (R38E/I92K) | A2-hIgG4-df-hIL-2 (R38E/I92K) HC (SEQ ID NO: 518) | A2-hLambda LC (SEQ ID NO: 429) |
| C51E6-5-hIgG4-df-hIL-2 (D20A/R38E) | C51E6-5-hIgG4-df-hIL-2 (D20A/R38E) HC (SEQ ID NO: 519) | C51E6-5-hKappa LC (SEQ ID NO: 427) |
| C51E6-5-hIgG4-LE-df-hIL-2 (T3A/D20A/R38E/C125A) | C51E6-5-hIgG4-LE-df-hIL-2 (T3A/D20A/R38E/C125A) HC (SEQ ID NO: 520) | C51E6-5-hKappa LC (SEQ ID NO: 427) |
| C51E6-5-hIgG4-LAGA-df-hIL-2 (T3A/D20A/R38E/C125A) | C51E6-5-hIgG4-LAGA-df-hIL-2 (D20A/R38E) HC (SEQ ID NO: 521) | C51E6-5-hKappa LC (SEQ ID NO: 427) |
| 2A3.H7-hIgG4-df-hIL-2 (D20A/R38E) | 2H7-hIgG4-df-hIL-2 (D20A/R38E) HC (SEQ ID NO: 430) | 2A3-hKappa LC (SEQ ID NO: 523) |
| 1H9-hIgG4-df-hIL-2 (D20A/R38E) | 1H9-hIgG4-df-hIL-2 (D20A/R38E) HC (SEQ ID NO: 524) | 1H9-hKappa LC (SEQ ID NO: 525) |
| 1D5-hIgG4-df-hIL-2 (D20A/R38E) | 1D5-hIgG4-df-hIL-2 (D20A/R38E) HC (SEQ ID NO: 526) | 1D5-hKappa LC (SEQ ID NO: 527) |
| 1D5-hIgG4-LE-df-hIL-2 (T3A/D20A/R38E/C125A) | 1D5-hIgG4-LE-df-hIL-2 (T3A/D20A/R38E/C125A) HC (SEQ ID NO: 528) | 1D5-hKappa LC (SEQ ID NO: 527) |
| 1D5-hIgG4-LAGA-df-hIL-2 (T3A/D20A/R38E/C125A) | 1D5-hIgG4-LAGA-df-hIL-2 (T3A/D20A/R38E/C125A) HC (SEQ ID NO: 529) | 1D5-hKappa LC (SEQ ID NO: 527) |
| 2H7-hIgG1-df-hIL-2 (T3A/D20A/R38E/C125A) | 2H7-hIgG1-df-hIL-2 (T3A/D20A/R38E/C125A) HC (SEQ ID NO: 530) | 2H7-hKappa LC (SEQ ID NO: 425) |
| 2H7-hIgG1-LE-df-hIL-2 (T3A/D20A/R38E/C125A) | 2H7-hIgG1-LE-df-hIL-2 (T3A/D20A/R38E/C125A) HC (SEQ ID NO: 531) | 2H7-hKappa LC (SEQ ID NO: 425) |
| 2H7-hIgG1-LE-df-hIL-2 (T3A/R38E/D84K/C125A) | 2H7-hIgG1-LE-df-hIL-2 (T3A/R38E/D84K/C125A) HC (SEQ ID NO: 533) | 2H7-hKappa LC (SEQ ID NO: 425) |
| 2H7-hIgG4-df-hIL-2 (T3A/R38E/D84K/C125A) | 2H7-hIgG4-df-hIL-2 (T3A/R38E/D84K/C125A) HC (SEQ ID NO: 534) | 2H7-hKappa LC (SEQ ID NO: 425) |
| 2H7-hIgG1-df-hIL-2 (T3A/R38E/I92K/C125A) | 2H7-hIgG1-df-hIL-2 (T3A/R38E/I92K/C125A) HC (SEQ ID NO: 535) | 2H7-hKappa LC (SEQ ID NO: 425) |
| 2H7-hIgG1-LE-df-hIL-2 (T3A/R38E/I92K/C125A) | 2H7-hIgG1-LE-df-hIL-2 (T3A/R38E/I92K/C125A) HC (SEQ ID NO: 536) | 2H7-hKappa LC (SEQ ID NO: 425) |
| 2H7-hIgG4-df-hIL-2 (T3A/R38E/I92K/C125A) | 2H7-hIgG4-df-hIL-2 (T3A/R38E/I92K/C125A) HC (SEQ ID NO: 537) | 2H7-hKappa LC (SEQ ID NO: 425) |
| 2H7-hIgG1-LAGA-df-hIL2 (T3A/D20S/R38E/C125A) | 2H7-hIgG1-LAGA-df-hIL2 (T3A/D20S/R38E/C125A) HC (SEQ ID NO: 538) | 2H7-hKappa LC (SEQ ID NO: 425) |
| 2H7-hIgG1-LAGA-df-hIL2 (T3A/R38E/D84F/C125A) | 2H7-hIgG1-LAGA-df-hIL2 (T3A/R38E/D84F/C125A) HC (SEQ ID NO: 539) | 2H7-hKappa LC (SEQ ID NO: 425) |

TABLE 28-continued

Exemplary Antibodies

| Antibody Name | Heavy chain | Light chain |
|---|---|---|
| 2H7-hIgG1-LAGA-df-hIL2 (T3A/R38E/I92R/C125A) | 2H7-hIgG1-LAGA-df-hIL2 (T3A/R38E/I92R/C125A) HC (SEQ ID NO: 540) | 2H7-hKappa LC (SEQ ID NO: 425) |
| 2H7-hIgG1-LAGA-df-hIL2 (T3A/R38E/I92E/C125A) | 2H7-hIgG1-LAGA-df-hIL2 (T3A/R38E/I92E/C125A) HC (SEQ ID NO: 541) | 2H7-hKappa LC (SEQ ID NO: 425) |
| 2H7-hIgG1-LAGA-df-hIL2 (T3A/R38E/I92S/C125A) | 2H7-hIgG1-LAGA-df-hIL2 (T3A/R38E/I92S/C125A) HC (SEQ ID NO: 542) | 2H7-hKappa LC (SEQ ID NO: 425) |
| 2H7-hIgG1-LAGA-df-hIL2 (T3A/R38E/I92D/C125A) | 2H7-hIgG1-LAGA-df-hIL2 (T3A/R38E/I92D/C125A) HC (SEQ ID NO: 543) | 2H7-hKappa LC (SEQ ID NO: 425) |
| 2H7-hIgG1-LAGA-df-hIL2 (T3A/H16E/R38E/C125A) | 2H7-hIgG1-LAGA-df-hIL2 (T3A/H16E/R38E/C125A) HC (SEQ ID NO: 544) | 2H7-hKappa LC (SEQ ID NO: 425) |
| 1H3-hIgG1-L6-hIL-2 (T3A/D20A/R38E/C125A) | 1H3-hIgG1-L6-hIL-2 (T3A/D20A/R38E/C125A) HC (SEQ ID NO: 545) | 1H3-hKappa LC (SEQ ID NO: 374) |
| 1H3-hIgG1-LAGA-df-hIL-2 (T3A/D20A/R38E/C125A) | 1H3-hIgG1-LAGA-df-hIL-2 (T3A/D20A/R38E/C125A) HC (SEQ ID NO: 546) | 1H3-hKappa LC (SEQ ID NO: 374) |
| C51E6-5-hIgG4/k-LE | C51E6-5-hIgG4/k-LE HC (SEQ ID NO: 547) | C51E6-5-hKappa LC (SEQ ID NO: 427) |
| C51E6-5-hIgG4/k-LAGA | C51E6-5-hIgG4/k-LAGA HC (SEQ ID NO: 548) | C51E6-5-hKappa LC (SEQ ID NO: 427) |
| C51E6-5-hIgG4/k-LEPG | C51E6-5-hIgG4/k-LEPG HC (SEQ ID NO: 549) | C51E6-5-hKappa LC (SEQ ID NO: 427) |
| C51E6-5-hIgG4/k-df-hIL-2 (T3A/D20A/R38E/C125A) | C51E6-5-hIgG4/k-df-hIL-2 (T3A/D20A/R38E/C125A) HC (SEQ ID NO: 550) | C51E6-5-hKappa LC (SEQ ID NO: 427) |
| C51E6-5-hIgG4/k-LEPG-hIL-2 (T3A/D20A/R38E/C125A) | C51E6-5-hIgG4/k-LEPG-hIL-2 (T3A/D20A/R38E/C125A) HC (SEQ ID NO: 551) | C51E6-5-hKappa LC (SEQ ID NO: 427) |
| A2-hIgG4/k-LE | A2-hIgG4/k-LE HC (SEQ ID NO: 552) | A2-hLambda LC (SEQ ID NO: 429) |
| A2-hIgG4/k-LAGA | A2-hIgG4/k-LAGA HC (SEQ ID NO: 553) | A2-hLambda LC (SEQ ID NO: 429) |
| A2-hIgG4/k-LEPG | A2-hIgG4/k-LEPG HC (SEQ ID NO: 554) | A2-hLambda LC (SEQ ID NO: 429) |
| A2-hIgG4/k-df-hIL-2 (T3A/D20A/R38E/C125A) | A2-hIgG4/k-df-hIL-2 (T3A/D20A/R38E/C125A) HC (SEQ ID NO: 555) | A2-hLambda LC (SEQ ID NO: 429) |
| A2-hIgG4/k-LE-df-hIL-2 (T3A/D20A/R38E/C125A) | A2-hIgG4/k-LE-df-hIL-2 (T3A/D20A/R38E/C125A) HC (SEQ ID NO: 556) | A2-hLambda LC (SEQ ID NO: 429) |
| A2-hIgG4/k-LAGA-df-hIL-2 (T3A/D20A/R38E/C125A) | A2-hIgG4/k-LAGA-df-hIL-2 (T3A/D20A/R38E/C125A) HC (SEQ ID NO: 557) | A2-hLambda LC (SEQ ID NO: 429) |
| A2-hIgG4/k-LEPG-df-hIL-2 (T3A/D20A/R38E/C125A) | A2-hIgG4/k-LEPG-df-hIL-2 (T3A/D20A/R38E/C125A) HC (SEQ ID NO: 558) | A2-hLambda LC (SEQ ID NO: 429) |
| Anti-CD20-hIgG1/k | Anti-CD20-hIgG1/k HC (SEQ ID NO: 560) | Anti-CD20-hKappa LC (SEQ ID NO: 562) |
| Anti-CD20-hIgG1/k-LAGA | Anti-CD20-hIgG1/k-LAGA HC (SEQ ID NO: 561) | Anti-CD20-hKappa LC (SEQ ID NO: 562) |
| 1H3-hIgG1-LAGA-df-hIL-2 (T3A/C125A) | 1H3-hIgG1-LAGA-df-hIL-2 T3A/C125A) HC (SEQ ID NO: 563) | 1H3-hKappa LC (SEQ ID NO: 374) |
| anti-mPD-1 RMP1-14 mIgG2b-N297A | anti-mPD-1 RMP1-14 mIgG2b-N297A HC (SEQ ID NO: 564) | anti-mPD-1 RMP1-14 mKappa LC (SEQ ID NO: 566) |
| anti-mPD-1 RMP1-14 mIgG2b-N297A-L6-hIL-2 (F42K/Y45R/V69R) | anti-mPD-1 RMP1-14 mIgG2b-N297A-L6-hIL-2(F42K/Y45R/V69R) HC (SEQ ID NO: 565) | anti-mPD-1 RMP1-14 mKappa LC (SEQ ID NO: 566) |
| anti-mPD-1 RMP1-30 mIgG2b-N297A | anti-mPD-1 RMP1-30 mIgG2b-N297A HC (SEQ ID NO: 567) | anti-mPD-1 RMP1-30 mKappa LC (SEQ ID NO: 568) |
| anti-mPD-1 RMP1-30 mIgG2b-N297A-L6-hIL-2 (F42K/Y45R/V69R) | anti-mPD-1 RMP1-30 mIgG2b-N297A-L6-hIL-2 (F42K/Y45R/V69R) HC (SEQ ID NO: 569) | anti-mPD-1 RMP1-30 mKappa LC (SEQ ID NO: 568) |
| anti-KLH-C3-mIgG2b-N297A-L6-hIL-2 (F42K/Y45R/V69R) | anti-KLH-C3-mIgG2b-N297A-L6-hIL-2 (F42K/Y45R/V69R) HC (SEQ ID NO: 570) | KLH-C3-mKappa LC (SEQ ID NO: 571) |
| 2D12-hIgG1-L6-hIL-2 | 2D12-hIgG1-L6-hIL-2 HC (SEQ ID NO: 572) | 2D12-hKappa LC (SEQ ID NO: 573) |

TABLE 28-continued

Exemplary Antibodies

| Antibody Name | Heavy chain | Light chain |
| --- | --- | --- |
| 1H9-hIgG4 | 1H9-hIgG4 HC (SEQ ID NO: 576) | 1H9-hKappa LC (SEQ ID NO: 525) |
| 1D5-hIgG4 | 1D5-hIgG4 HC (SEQ ID NO: 577) | 1D5-hKappa LC (SEQ ID NO: 527) |
| 2A3.H7-hIgG4 | 2H7-hIgG4 HC (SEQ ID NO: 424) | 2A3-hKappa LC (SEQ ID NO: 523) |
| H7-02-hIgG1-LAGA-df-hIL-2 (T3A/D20A/R38E/C125A) | H7-02-hIgG1-LAGA-df-hIL-2 (T3A/D20A/R38E/C125A) HC (SEQ ID NO: 582) | H7-02-hKappa LC (SEQ ID NO: 583) |
| KLH-C3-hIgG4 | KLH-C3-hIgG4 HC (SEQ ID NO: 585) | KLH-C3-hKappa LC (SEQ ID NO: 586) |
| 1H3-hIgG1-L6-hCD25(1-164)-L20-hIL-2 (E15A) | 1H3-hIgG1-L6-hCD25(1-164)-L20-hIL-2 (E15A) HC (SEQ ID NO: 587) | 1H3-hkappa LC (SEQ ID NO: 374) |
| 1H3-hIgG1-L6-hCD25(1-164)-L20-hIL-2 (D20I) | 1H3-hIgG1-L6-hCD25(1-164)-L20-hIL-2 (D20I) HC (SEQ ID NO: 588) | 1H3-hkappa LC (SEQ ID NO: 374) |
| 1H3-hIgG1-L6-hCD25(1-164)-L20-hIL-2 (D20S) | 1H3-hIgG1-L6-hCD25(1-164)-L20-hIL-2 (D20S) HC (SEQ ID NO: 589) | 1H3-hkappa LC (SEQ ID NO: 374) |
| 1H3-hIgG1-L6-hCD25(1-164)-L20-hIL-2 (D20H) | 1H3-hIgG1-L6-hCD25(1-164)-L20-hIL-2 (D20H) HC (SEQ ID NO: 590) | 1H3-hkappa LC (SEQ ID NO: 374) |
| 1H3-hIgG1-L6-hCD25(1-164)-L20-hIL-2 (D20W) | 1H3-hIgG1-L6-hCD25(1-164)-L20-hIL-2 (D20W) HC (SEQ ID NO: 591) | 1H3-hkappa LC (SEQ ID NO: 374) |
| 1H3-hIgG1-L6-hCD25(1-164)-L20-hIL-2 (D20Y) | 1H3-hIgG1-L6-hCD25(1-164)-L20-hIL-2 (D20Y) HC (SEQ ID NO: 592) | 1H3-hkappa LC (SEQ ID NO: 374) |
| 1H3-hIgG1-L6-hCD25(1-164)-L20-hIL-2 (D20R) | 1H3-hIgG1-L6-hCD25(1-164)-L20-hIL-2 (D20R) HC (SEQ ID NO: 593) | 1H3-hkappa LC (SEQ ID NO: 374) |
| 1H3-hIgG1-L6-hCD25(1-164)-L20-hIL-2 (D20F) | 1H3-hIgG1-L6-hCD25(1-164)-L20-hIL-2 (D20F) HC (SEQ ID NO: 594) | 1H3-hkappa LC (SEQ ID NO: 374) |
| 1H3-hIgG1-L6-hCD25(1-164)-L20-hIL-2 (D84K) | 1H3-hIgG1-L6-hCD25(1-164)-L20-hIL-2 (D84K) HC (SEQ ID NO: 595) | 1H3-hkappa LC (SEQ ID NO: 374) |
| 1H3-hIgG1-L6-hCD25(1-164)-L20-hIL-2 (S87A) | 1H3-hIgG1-L6-hCD25(1-164)-L20-hIL-2 (S87A) HC (SEQ ID NO: 596) | 1H3-hkappa LC (SEQ ID NO: 374) |
| 1H3-hIgG1-L6-hCD25(1-164)-L20-hIL-2 (N88Y) | 1H3-hIgG1-L6-hCD25(1-164)-L20-hIL-2 (N88Y) HC (SEQ ID NO: 597) | 1H3-hkappa LC (SEQ ID NO: 374) |
| 1H3-hIgG1-L6-hCD25(1-164)-L20-hIL-2 (N88D) | 1H3-hIgG1-L6-hCD25(1-164)-L20-hIL-2 (N88D) HC (SEQ ID NO: 598) | 1H3-hkappa LC (SEQ ID NO: 374) |
| 1H3-hIgG1-L6-hCD25(1-164)-L20-hIL-2 (N88R) | 1H3-hIgG1-L6-hCD25(1-164)-L20-hIL-2 (N88R) HC (SEQ ID NO: 599) | 1H3-hkappa LC (SEQ ID NO: 374) |
| 1H3-hIgG1-L6-hCD25(1-164)-L20-hIL-2 (N88E) | 1H3-hIgG1-L6-hCD25(1-164)-L20-hIL-2 (N88E) HC (SEQ ID NO: 600) | 1H3-hkappa LC (SEQ ID NO: 374) |
| 1H3-hIgG1-L6-hCD25(1-164)-L20-hIL-2 (N88F) | 1H3-hIgG1-L6-hCD25(1-164)-L20-hIL-2 (N88F) HC (SEQ ID NO: 601) | 1H3-hkappa LC (SEQ ID NO: 374) |
| 1H3-hIgG1-L6-hCD25(1-164)-L20-hIL-2 (N88I) | 1H3-hIgG1-L6-hCD25(1-164)-L20-hIL-2 (N88I) HC (SEQ ID NO: 602) | 1H3-hkappa LC (SEQ ID NO: 374) |
| 1H3-hIgG1-L6-hCD25(1-164)-L20-hIL-2 (I92A) | 1H3-hIgG1-L6-hCD25(1-164)-L20-hIL-2 (I92A) HC (SEQ ID NO: 603) | 1H3-hkappa LC (SEQ ID NO: 374) |
| 1H3-hIgG1-L6-hCD25(1-164)-L20-hIL-2 (E95A) | 1H3-hIgG1-L6-hCD25(1-164)-L20-hIL-2 (E95A) HC (SEQ ID NO: 604) | 1H3-hkappa LC (SEQ ID NO: 374) |
| 1H3-hIgG1-L6-hCD25(1-164)-L20-hIL-2 (E95K) | 1H3-hIgG1-L6-hCD25(1-164)-L20-hIL-2 (E95K) HC (SEQ ID NO: 605) | 1H3-hkappa LC (SEQ ID NO: 374) |
| H7-02-hIgG4 | H7-02-hIgG4 HC (SEQ ID NO: 373) | H7-02 hKappa LC (SEQ ID NO: 607) |
| H7-632-hIgG1-LAGA-df-hIL-2 (T3A/C125A) | H7-632-hIgG1-LAGA-df-hIL-2 (T3A/C125A) HC (SEQ ID NO: 431) | H7-632 LC (SEQ ID NO: 415) |
| 1H3-hIgG1-LAGA-L6-hIL-2 (T3A/D20A/R38E/C125A) | 1H3-hIgG1-LAGA-L6-hIL-2 (T3A/D20A/R38E/C125A) (SEQ ID NO: 522) | 1H3-hKappa LC (SEQ ID NO: 374) |
| 1H3-hIgG1 | 1H3-hIgG1 HC (SEQ ID NO: 379) | 1H3-hKappa LC (SEQ ID NO: 374) |
| H7-767 | H7-767 HC (SEQ ID NO: 532) | H7-632 LC (SEQ ID NO: 415) |
| Anti-hPD-1 #1 | Anti-hPD-1 #1 HC (SEQ ID NO: 559) | Anti-hPD-1#1-hKappa (SEQ ID NO: 452) |
| Anti-hPD-1 #2 | Anti-hPD-1 #2 HC (SEQ ID NO: 578) | Anti-hPD-1 #2 LC (SEQ ID NO: 579) |
| 2H7-hIgG4-LE-df-hIL-2 (T3A/R38E/I92K/C125A) | 2H7-hIgG4-LE-df-hIL-2 (T3A/R38E/I92K/C125A) HC (SEQ ID NO: 475) | 2H7-hKappa LC (SEQ ID NO: 425) |

TABLE 29

Sequences

| SEQ ID NO: | Name | Sequence |
| --- | --- | --- |
| 1 | hIL-2 F42K | APTSSSTKKTQLQLEHLLLDLQMILNGINNYKNPKLTRMLTKKFYMPKKATELKHLQCLEEELKPLEEV LNLAQSKNFHLRPRDLISNINVIVLELKGSETTFMCEYADETATIVEFLNRWITFCQSIISTLT |
| 2 | hIL-2 V69A | APTSSSTKKTQLQLEHLLLDLQMILNGINNYKNPKLTRMLTFKFYMPKKATELKHLQCLEEELKPLEEA LNLAQSKNFHLRPRDLISNINVIVLELKGSETTEMCEYADETATIVEFLNRWITFCQSIISTLT |

TABLE 29-continued

Sequences

| SEQ ID NO: | Name | Sequence |
|---|---|---|
| 3 | hIL-2 V69E | APTSSSTKKTQLQLEHLLLDLQMILNGINNYKNPKLTRMLTFKFYMPKKATELKHLQCLEEELKPLEEE<br>LNLAQSKNFHLRPRDLISNINVIVLELKGSETTFMCEYADETATIVEFLNRWITFCQSIISTLT |
| 4 | hIL-2 V69F | APTSSSTKKTQLQLEHLLLDLQMILNGINNYKNPKLTRMLTFKFYMPKKATELKHLQCLEEELKPLEEF<br>LNLAQSKNFHLRPRDLISNINVIVLELKGSETTFMCEYADETATIVEFLNRWITFCQSIISTLT |
| 5 | hIL-2 V69G | APTSSSTKKTQLQLEHLLLDLQMILNGINNYKNPKLTRMLTFKFYMPKKATELKHLQCLEEELKPLEEG<br>LNLAQSKNFHLRPRDLISNINVIVLELKGSETTFMCEYADETATIVEFLNRWITFCQSIISTLT |
| 6 | hIL-2 V69H | APTSSSTKKTQLQLEHLLLDLQMILNGINNYKNPKLTRMLTFKFYMPKKATELKHLQCLEEELKPLEEH<br>LNLAQSKNFHLRPRDLISNINVIVLELKGSETTFMCEYADETATIVEFLNRWITFCQSIISTLT |
| 7 | hIL-2 V69I | APTSSSTKKTQLQLEHLLLDLQMILNGINNYKNPKLTRMLTFKFYMPKKATELKHLQCLEEELKPLEEI<br>LNLAQSKNFHLRPRDLISNINVIVLELKGSETTFMCEYADETATIVEFLNRWITFCQSIISTLT |
| 8 | hIL-2 V69K | APTSSSTKKTQLQLEHLLLDLQMILNGINNYKNPKLTRMLTFKFYMPKKATELKHLQCLEEELKPLEEK<br>LNLAQSKNFHLRPRDLISNINVIVLELKGSETTFMCEYADETATIVEFLNRWITFCQSIISTLT |
| 9 | hIL-2 V69L | APTSSSTKKTQLQLEHLLLDLQMILNGINNYKNPKLTRMLTFKFYMPKKATELKHLQCLEEELKPLEEL<br>LNLAQSKNFHLRPRDLISNINVIVLELKGSETTFMCEYADETATIVEFLNRWITFCQSIISTLT |
| 10 | hIL-2 V69M | APTSSSTKKTQLQLEHLLLDLQMILNGINNYKNPKLTRMLTFKFYMPKKATELKHLQCLEEELKPLEEM<br>LNLAQSKNFHLRPRDLISNINVIVLELKGSETTFMCEYADETATIVEFLNRWITFCQSIISTLT |
| 11 | hIL-2 V69Q | APTSSSTKKTQLQLEHLLLDLQMILNGINNYKNPKLTRMLTFKFYMPKKATELKHLQCLEEELKPLEEQ<br>LNLAQSKNFHLRPRDLISNINVIVLELKGSETTFMCEYADETATIVEFLNRWITFCQSIISTLT |
| 12 | hIL-2 V69S | APTSSSTKKTQLQLEHLLLDLQMILNGINNYKNPKLTRMLTFKFYMPKKATELKHLQCLEEELKPLEES<br>LNLAQSKNFHLRPRDLISNINVIVLELKGSETTFMCEYADETATIVEFLNRWITFCQSIISTLT |
| 13 | hIL-2 V69T | APTSSSTKKTQLQLEHLLLDLQMILNGINNYKNPKLTRMLTFKFYMPKKATELKHLQCLEEELKPLEET<br>LNLAQSKNFHLRPRDLISNINVIVLELKGSETTFMCEYADETATIVEFLNRWITFCQSIISTLT |
| 14 | hIL-2 V69W | APTSSSTKKTQLQLEHLLLDLQMILNGINNYKNPKLTRMLTFKFYMPKKATELKHLQCLEEELKPLEEW<br>LNLAQSKNFHLRPRDLISNINVIVLELKGSETTFMCEYADETATIVEFLNRWITFCQSIISTLT |
| 15 | hIL-2 V69Y | APTSSSTKKTQLQLEHLLLDLQMILNGINNYKNPKLTRMLTFKFYMPKKATELKHLQCLEEELKPLEEY<br>LNLAQSKNFHLRPRDLISNINVIVLELKGSETTFMCEYADETATIVEFLNRWITFCQSIISTLT |
| 16 | hIL-2 F42K/F44K | APTSSSTKKTQLQLEHLLLDLQMILNGINNYKNPKLTRMLTKKYMPKKATELKHLQCLEEELKPLEEV<br>LNLAQSKNFHLRPRDLISNINVIVLELKGSETTFMCEYADETATIVEFLNRWITFCQSIISTLT |
| 17 | hIL-2 F44K/Y45R | APTSSSTKKTQLQLEHLLLDLQMILNGINNYKNPKLTRMLTFKKRMPKKATELKHLQCLEEELKPLEEV<br>LNLAQSKNFHLRPRDLISNINVIVLELKGSETTFMCEYADETATIVEFLNRWITFCQSIISTLT |
| 18 | hIL-2 F42K/V69R | APTSSSTKKTQLQLEHLLLDLQMILNGINNYKNPKLTRMLTKKYMPKKATELKHLQCLEEELKPLEER<br>LNLAQSKNFHLRPRDLISNINVIVLELKGSETTFMCEYADETATIVEFLNRWITFCQSIISTLT |
| 19 | hIL-2 Y45R/V69R | APTSSSTKKTQLQLEHLLLDLQMILNGINNYKNPKLTRMLTFKFRMPKKATELKHLQCLEEELKPLEER<br>LNLAQSKNFHLRPRDLISNINVIVLELKGSETTFMCEYADETATIVEFLNRWITFCQSIISTLT |
| 20 | hIL-2 F42K/F44K/Y45R | APTSSSTKKTQLQLEHLLLDLQMILNGINNYKNPKLTRMLTKKKRMPKKATELKHLQCLEEELKPLEEV<br>LNLAQSKNFHLRPRDLISNINVIVLELKGSETTFMCEYADETATIVEFLNRWITFCQSIISTLT |
| 21 | hIL-2 R38A/F42K/Y45R | APTSSSTKKTQLQLEHLLLDLQMILNGINNYKNPKLTAMLTKKERMPKKATELKHLQCLEEELKPLEEV<br>LNLAQSKNFHLRPRDLISNINVIVLELKGSETTFMCEYADETATIVEFLNRWITFCQSIISTLT |
| 22 | hIL-2 R38E/F42K/Y45R | APTSSSTKKTQLQLEHLLLDLQMILNGINNYKNPKLTEMLTKKERMPKKATELKHLQCLEEELKPLEEV<br>LNLAQSKNFHLRPRDLISNINVIVLELKGSETTFMCEYADETATIVEFLNRWITFCQSIISTLT |
| 23 | hIL-2 K43E/F42K/Y45R | APTSSSTKKTQLQLEHLLLDLQMILNGINNYKNPKLTRMLTKEFRMPKKATELKHLQCLEEELKPLEEV<br>LNLAQSKNFHLRPRDLISNINVIVLELKGSETTFMCEYADETATIVEFLNRWITFCQSIISTLT |
| 24 | hIL-2 K43T/F42K/Y45R | APTSSSTKKTQLQLEHLLLDLQMILNGINNYKNPKLTRMLTKTERMPKKATELKHLQCLEEELKPLEEV<br>LNLAQSKNFHLRPRDLISNINVIVLELKGSETTFMCEYADETATIVEFLNRWITFCQSIISTLT |
| 25 | hIL-2 F42K/Y45R/E62A | APTSSSTKKTQLQLEHLLLDLQMILNGINNYKNPKLTRMLTKKERMPKKATELKHLQCLEEALKPLEEV<br>LNLAQSKNFHLRPRDLISNINVIVLELKGSETTFMCEYADETATIVEFLNRWITFCQSIISTLT |
| 26 | hIL-2 P65R/F42K/Y45R | APTSSSTKKTQLQLEHLLLDLQMILNGINNYKNPKLTRMLTKKERMPKKATELKHLQCLEEELKRLEEV<br>LNLAQSKNFHLRPRDLISNINVIVLELKGSETTFMCEYADETATIVEFLNRWITFCQSIISTLT |
| 27 | hIL-2 P65S/F42K/Y45R | APTSSSTKKTQLQLEHLLLDLQMILNGINNYKNPKLTRMLTKKFRMPKKATELKHLQCLEEELKSLEEV<br>LNLAQSKNFHLRPRDLISNINVIVLELKGSETTFMCEYADETATIVEFLNRWITFCQSIISTLT |

TABLE 29-continued

Sequences

| SEQ ID NO: | Name | Sequence |
|---|---|---|
| 28 | hIL-2 V69A/F42K/Y45R | APTSSSTKKTQLQLEHLLLDLQMILNGINNYKNPKLTRMLTKKERMPKKATELKHLQCLEEELKPLEEA LNLAQSKNFHLRPRDLISNINVIVLELKGSETTEMCEYADETATIVEFLNRWITFCQSIISTLT |
| 29 | hIL-2 V69D/F42K/Y45R | APTSSSTKKTQLQLEHLLLDLQMILNGINNYKNPKLTRMLTKKERMPKKATELKHLQCLEEELKPLEED LNLAQSKNFHLRPRDLISNINVIVLELKGSETTEMCEYADETATIVEFLNRWITFCQSIISTLT |
| 30 | hIL-2 V69R/F42K/Y45R | APTSSSTKKTQLQLEHLLLDLQMILNGINNYKNPKLTRMLTKKERMPKKATELKHLQCLEEELKPLEER LNLAQSKNFHLRPRDLISNINVIVLELKGSETTEMCEYADETATIVEFLNRWITFCQSIISTLT |
| 31 | hIL-2 D20A | APTSSSTKKTQLQLEHLLLALQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 32 | hIL-2 D20N | APTSSSTKKTQLQLEHLLLNLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 33 | hIL-2 D20K | APTSSSTKKTQLQLEHLLLKLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 34 | hIL-2 N88A | APTSSSTKKTQLQLEHLLLDLQMILNGINNYKNPKLTRMLTFKFYMPKKATELKHLQCLEEELKPLEEV LNLAQSKNFHLRPRDLISAINVIVLELKGSETTFMCEYADETATIVEFLNRWITFCQSIISTLT |
| 35 | hIL-2 N88G | APTSSSTKKTQLQLEHLLLDLQMILNGINNYKNPKLTRMLTFKFYMPKKATELKHLQCLEEELKPLEEV LNLAQSKNFHLRPRDLISGINVIVLELKGSETTFMCEYADETATIVEFLNRWITFCQSIISTLT |
| 36 | hIL-2 N88H | APTSSSTKKTQLQLEHLLLDLQMILNGINNYKNPKLTRMLTFKFYMPKKATELKHLQCLEEELKPLEEV LNLAQSKNFHLRPRDLISHINVIVLELKGSETTFMCEYADETATIVEFLNRWITFCQSIISTLT |
| 37 | hIL-2 N88K | APTSSSTKKTQLQLEHLLLDLQMILNGINNYKNPKLTRMLTFKFYMPKKATELKHLQCLEEELKPLEEV LNLAQSKNFHLRPRDLISKINVIVLELKGSETTFMCEYADETATIVEFLNRWITFCQSIISTLT |
| 38 | hIL-2 D20A/D84A | APTSSSTKKTQLQLEHLLLALQMILNGINNYKNPKLTRMLTFKFYMPKKATELKHLQCLEEELKPLEEV LNLAQSKNFHLRPRALISNINVIVLELKGSETTEMCEYADETATIVEFLNRWITFCQSIISTLT |
| 39 | hIL-2 D20A/E15A | APTSSSTKKTQLQLAHLLLALQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 40 | hIL-2 D20A/E95A | APTSSSTKKTQLQLEHLLLALQMILNGINNYKNPKLTRMLTFKFYMPKKATELKHLQCLEEELKPLEEV LNLAQSKNFHLRPRDLISNINVIVLALKGSETTFMCEYADETATIVEFLNRWITFCQSIISTLT |
| 41 | hIL-2 D20A/N88A | APTSSSTKKTQLQLEHLLLALQMILNGINNYKNPKLTRMLTFKFYMPKKATELKHLQCLEEELKPLEEV LNLAQSKNFHLRPRDLISAINVIVLELKGSETTEMCEYADETATIVEFLNRWITFCQSIISTLT |
| 42 | hIL-2 D20A/S87A | APTSSSTKKTQLQLEHLLLALQMILNGINNYKNPKLTRMLTFKFYMPKKATELKHLQCLEEELKPLEEV LNLAQSKNFHLRPRDLIANINVIVLELKGSETTFMCEYADETATIVEFLNRWITFCQSIISTLT |
| 43 | hIL-2 D84A/N88A | APTSSSTKKTQLQLEHLLLDLQMILNGINNYKNPKLTRMLTFKFYMPKKATELKHLQCLEEELKPLEEV LNLAQSKNFHLRPRALISAINVIVLELKGSETTEMCEYADETATIVEFLNRWITFCQSIISTLT |
| 44 | hIL-2 E15A/N88A | APTSSSTKKTQLQLAHLLLDLQMILNGINNYKNPKLTRMLTFKFYMPKKATELKHLQCLEEELKPLEEV LNLAQSKNFHLRPRDLISAINVIVLELKGSETTEMCEYADETATIVEFLNRWITFCQSIISTLT |
| 45 | hIL-2 S87A/N88A | APTSSSTKKTQLQLEHLLLDLQMILNGINNYKNPKLTRMLTFKFYMPKKATELKHLQCLEEELKPLEEV LNLAQSKNFHLRPRDLIAAINVIVLELKGSETTFMCEYADETATIVEFLNRWITFCQSIISTLT |
| 46 | hIL-2 R38A | APTSSSTKKTQLQLEHLLLDLQMILNGINNYKNPKLTAMLTFKFYMPKKATELKHLQCLEEELKPLEEV LNLAQSKNFHLRPRDLISNINVIVLELKGSETTEMCEYADETATIVEFLNRWITFCQSIISTLT |
| 47 | hIL-2 R38D | APTSSSTKKTQLQLEHLLLDLQMILNGINNYKNPKLTDMLTFKFYMPKKATELKHLQCLEEELKPLEEV LNLAQSKNFHLRPRDLISNINVIVLELKGSETTEMCEYADETATIVEFLNRWITFCQSIISTLT |
| 48 | hIL-2 R38E | APTSSSTKKTQLQLEHLLLDLQMILNGINNYKNPKLTEMLTFKFYMPKKATELKHLQCLEEELKPLEEV LNLAQSKNFHLRPRDLISNINVIVLELKGSETTEMCEYADETATIVEFLNRWITFCQSIISTLT |
| 49 | hIL-2 R38Q | APTSSSTKKTQLQLEHLLLDLQMILNGINNYKNPKLTQMLTFKFYMPKKATELKHLQCLEEELKPLEEV LNLAQSKNFHLRPRDLISNINVIVLELKGSETTEMCEYADETATIVEFLNRWITFCQSIISTLT |
| 50 | hIL-2 F42R | APTSSSTKKTQLQLEHLLLDLQMILNGINNYKNPKLTRMLTRKFYMPKKATELKHLQCLEEELKPLEEV LNLAQSKNFHLRPRDLISNINVIVLELKGSETTEMCEYADETATIVEFLNRWITFCQSIISTLT |
| 51 | hIL-2 F42A | APTSSSTKKTQLQLEHLLLDLQMILNGINNYKNPKLTRMLTAKFYMPKKATELKHLQCLEEELKPLEEV LNLAQSKNFHLRPRDLISNINVIVLELKGSETTEMCEYADETATIVEFLNRWITFCQSIISTLT |
| 52 | hIL-2 F42D | APTSSSTKKTQLQLEHLLLDLQMILNGINNYKNPKLTRMLTDKFYMPKKATELKHLQCLEEELKPLEEV LNLAQSKNFHLRPRDLISNINVIVLELKGSETTEMCEYADETATIVEFLNRWITFCQSIISTLT |

TABLE 29-continued

Sequences

| SEQ ID NO: | Name | Sequence |
|---|---|---|
| 53 | hIL-2 F42H | APTSSSTKKTQLQLEHLLLDLQMILNGINNYKNPKLTRMLTHKFYMPKKATELKHLQCLEEELKPLEEV<br>LNLAQSKNFHLRPRDLISNINVIVLELKGSETTFMCEYADETATIVEFLNRWITFCQSIISTLT |
| 54 | hIL-2 K43A | APTSSSTKKTQLQLEHLLLDLQMILNGINNYKNPKLTRMLTFAYMPKKATELKHLQCLEEELKPLEEV<br>LNLAQSKNFHLRPRDLISNINVIVLELKGSETTFMCEYADETATIVEFLNRWITFCQSIISTLT |
| 55 | hIL-2 K43E | APTSSSTKKTQLQLEHLLLDLQMILNGINNYKNPKLTRMLTFEYMPKKATELKHLQCLEEELKPLEEV<br>LNLAQSKNFHLRPRDLISNINVIVLELKGSETTFMCEYADETATIVEFLNRWITFCQSIISTLT |
| 56 | hIL-2 K43Q | APTSSSTKKTQLQLEHLLLDLQMILNGINNYKNPKLTRMLTFQYMPKKATELKHLQCLEEELKPLEEV<br>LNLAQSKNFHLRPRDLISNINVIVLELKGSETTFMCEYADETATIVEFLNRWITFCQSIISTLT |
| 57 | hIL-2 Y45A | APTSSSTKKTQLQLEHLLLDLQMILNGINNYKNPKLTRMLTFKFAMPKKATELKHLQCLEEELKPLEEV<br>LNLAQSKNFHLRPRDLISNINVIVLELKGSETTFMCEYADETATIVEFLNRWITFCQSIISTLT |
| 58 | hIL-2 Y45K | APTSSSTKKTQLQLEHLLLDLQMILNGINNYKNPKLTRMLTFKFKMPKKATELKHLQCLEEELKPLEEV<br>LNLAQSKNFHLRPRDLISNINVIVLELKGSETTFMCEYADETATIVEFLNRWITFCQSIISTLT |
| 59 | hIL-2 Y45S | APTSSSTKKTQLQLEHLLLDLQMILNGINNYKNPKLTRMLTFKFSMPKKATELKHLQCLEEELKPLEEV<br>LNLAQSKNFHLRPRDLISNINVIVLELKGSETTFMCEYADETATIVEFLNRWITFCQSIISTLT |
| 60 | hIL-2 Y45R | APTSSSTKKTQLQLEHLLLDLQMILNGINNYKNPKLTRMLTFKFRMPKKATELKHLQCLEEELKPLEEV<br>LNLAQSKNFHLRPRDLISNINVIVLELKGSETTFMCEYADETATIVEFLNRWITFCQSIISTLT |
| 61 | hIL-2 E61A | APTSSSTKKTQLQLEHLLLDLQMILNGINNYKNPKLTRMLTFKFYMPKKATELKHLQCLEAELKPLEEV<br>LNLAQSKNFHLRPRDLISNINVIVLELKGSETTFMCEYADETATIVEFLNRWITFCQSIISTLT |
| 62 | hIL-2 E61R | APTSSSTKKTQLQLEHLLLDLQMILNGINNYKNPKLTRMLTFKFYMPKKATELKHLQCLERELKPLEEV<br>LNLAQSKNFHLRPRDLISNINVIVLELKGSETTFMCEYADETATIVEFLNRWITFCQSIISTLT |
| 63 | hIL-2 E61K | APTSSSTKKTQLQLEHLLLDLQMILNGINNYKNPKLTRMLTFKFYMPKKATELKHLQCLEKELKPLEEV<br>LNLAQSKNFHLRPRDLISNINVIVLELKGSETTFMCEYADETATIVEFLNRWITFCQSIISTLT |
| 64 | hIL-2 E62A | APTSSSTKKTQLQLEHLLLDLQMILNGINNYKNPKLTRMLTFKFYMPKKATELKHLQCLEEALKPLEEV<br>LNLAQSKNFHLRPRDLISNINVIVLELKGSETTFMCEYADETATIVEFLNRWITFCQSIISTLT |
| 65 | hIL-2 E62R | APTSSSTKKTQLQLEHLLLDLQMILNGINNYKNPKLTRMLTFKFYMPKKATELKHLQCLEERLKPLEEV<br>LNLAQSKNFHLRPRDLISNINVIVLELKGSETTFMCEYADETATIVEFLNRWITFCQSIISTLT |
| 66 | hIL-2 E62K | APTSSSTKKTQLQLEHLLLDLQMILNGINNYKNPKLTRMLTFKFYMPKKATELKHLQCLEEKLKPLEEV<br>LNLAQSKNFHLRPRDLISNINVIVLELKGSETTFMCEYADETATIVEFLNRWITFCQSIISTLT |
| 67 | hIL-2 E62Y | APTSSSTKKTQLQLEHLLLDLQMILNGINNYKNPKLTRMLTFKFYMPKKATELKHLQCLEEYLKPLEEV<br>LNLAQSKNFHLRPRDLISNINVIVLELKGSETTFMCEYADETATIVEFLNRWITFCQSIISTLT |
| 68 | hIL-2 E68Y | APTSSSTKKTQLQLEHLLLDLQMILNGINNYKNPKLTRMLTFKFYMPKKATELKHLQCLEEELKPLEYV<br>LNLAQSKNFHLRPRDLISNINVIVLELKGSETTFMCEYADETATIVEFLNRWITFCQSIISTLT |
| 69 | hIL-2 E68A | APTSSSTKKTQLQLEHLLLDLQMILNGINNYKNPKLTRMLTFKFYMPKKATELKHLQCLEEELKPLEAV<br>LNLAQSKNFHLRPRDLISNINVIVLELKGSETTFMCEYADETATIVEFLNRWITFCQSIISTLT |
| 70 | hIL-2 E68K | APTSSSTKKTQLQLEHLLLDLQMILNGINNYKNPKLTRMLTFKFYMPKKATELKHLQCLEEELKPLEKV<br>LNLAQSKNFHLRPRDLISNINVIVLELKGSETTFMCEYADETATIVEFLNRWITFCQSIISTLT |
| 71 | hIL-2 E68R | APTSSSTKKTQLQLEHLLLDLQMILNGINNYKNPKLTRMLTFKFYMPKKATELKHLQCLEEELKPLERV<br>LNLAQSKNFHLRPRDLISNINVIVLELKGSETTFMCEYADETATIVEFLNRWITFCQSIISTLT |
| 72 | hIL-2 E68L | APTSSSTKKTQLQLEHLLLDLQMILNGINNYKNPKLTRMLTFKFYMPKKATELKHLQCLEEELKPLELV<br>LNLAQSKNFHLRPRDLISNINVIVLELKGSETTFMCEYADETATIVEFLNRWITFCQSIISTLT |
| 73 | hIL-2 L72Y | APTSSSTKKTQLQLEHLLLDLQMILNGINNYKNPKLTRMLTFKFYMPKKATELKHLQCLEEELKPLEEV<br>LNYAQSKNFHLRPRDLISNINVIVLELKGSETTFMCEYADETATIVEFLNRWITFCQSIISTLT |
| 74 | hIL-2 L72R | APTSSSTKKTQLQLEHLLLDLQMILNGINNYKNPKLTRMLTFKFYMPKKATELKHLQCLEEELKPLEEV<br>LNRAQSKNFHLRPRDLISNINVIVLELKGSETTFMCEYADETATIVEFLNRWITFCQSIISTLT |
| 75 | hIL-2 L72A | APTSSSTKKTQLQLEHLLLDLQMILNGINNYKNPKLTRMLTFKFYMPKKATELKHLQCLEEELKPLEEV<br>LNAAQSKNFHLRPRDLISNINVIVLELKGSETTFMCEYADETATIVEFLNRWITFCQSIISTLT |
| 76 | hIL-2 L72D | APTSSSTKKTQLQLEHLLLDLQMILNGINNYKNPKLTRMLTFKFYMPKKATELKHLQCLEEELKPLEEV<br>LNDAQSKNFHLRPRDLISNINVIVLELKGSETTFMCEYADETATIVEFLNRWITFCQSIISTLT |
| 77 | hIL-2 L72H | APTSSSTKKTQLQLEHLLLDLQMILNGINNYKNPKLTRMLTFKFYMPKKATELKHLQCLEEELKPLEEV<br>LNHAQSKNFHLRPRDLISNINVIVLELKGSETTFMCEYADETATIVEFLNRWITFCQSIISTLT |

TABLE 29-continued

Sequences

| SEQ ID NO: | Name | Sequence |
|---|---|---|
| 78 | hIL-2 L72F | APTSSSTKKTQLQLEHLLLDLQMILNGINNYKNPKLTRMLTFKFYMPKKATELKHLQCLEEELKPLEEV<br>LNFAQSKNFHLRPRDLISNINVIVLELKGSETTFMCEYADETATIVEFLNRWITFCQSIISTLT |
| 79 | hIL-2 R38D/E61R | APTSSSTKKTQLQLEHLLLDLQMILNGINNYKNPKLTDMLTFKFYMPKKATELKHLQCLERELKPLEEV<br>LNLAQSKNFHLRPRDLISNINVIVLELKGSETTEMCEYADETATIVEFLNRWITFCQSIISTLT |
| 80 | hIL-2 R38D/E61R/K43E | APTSSSTKKTQLQLEHLLLDLQMILNGINNYKNPKLTDMLTFEYMPKKATELKHLQCLERELKPLEEV<br>LNLAQSKNFHLRPRDLISNINVIVLELKGSETTEMCEYADETATIVEFLNRWITFCQSIISTLT |
| 81 | hIL-2 T3A/F42A/Y45A/L72G/C125A | APASSSTKKTQLQLEHLLLDLQMILNGINNYKNPKLTRMLTAKFAMPKKATELKHLQCLEEELKPLEEV<br>LNGAQSKNFHLRPRDLISNINVIVLELKGSETTFMCEYADETATIVEFLNRWITFAQSIISTLT |
| 82 | hIL-2 E15A | APTSSSTKKTQLQLAHLLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 83 | hIL-2 E15R | APTSSSTKKTQLQLRHLLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 84 | hIL-2 E15K | APTSSSTKKTQLQLKHLLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 85 | hIL-2 H16A | APTSSSTKKTQLQLEALLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 86 | hIL-2 H16Y | APTSSSTKKTQLQLEYLLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 87 | hIL-2 H16E | APTSSSTKKTQLQLEELLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 88 | hIL-2 L19A | APTSSSTKKTQLQLEHLLADLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 89 | hIL-2 D20I | APTSSSTKKTQLQLEHLLLILQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 90 | hIL-2 D20S | APTSSSTKKTQLQLEHLLLSLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 91 | hIL-2 D20H | APTSSSTKKTQLQLEHLLLHLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 92 | hIL-2 D20T | APTSSSTKKTQLQLEHLLLTLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 93 | hIL-2 D20W | APTSSSTKKTQLQLEHLLLWLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 94 | hIL-2 D20Y | APTSSSTKKTQLQLEHLLLYLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 95 | hIL-2 D20R | APTSSSTKKTQLQLEHLLLRLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 96 | hIL-2 D20F | APTSSSTKKTQLQLEHLLLFLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 97 | hIL-2 R81A | APTSSSTKKTQLQLEHLLLDLQMILNGINNYKNPKLTRMLTFKFYMPKKATELKHLQCLEEELKPLEEV<br>LNLAQSKNFHLAPRDLISNINVIVLELKGSETTFMCEYADETATIVEFLNRWITFCQSIISTLT |
| 98 | hIL-2 D84A | APTSSSTKKTQLQLEHLLLDLQMILNGINNYKNPKLTRMLTFKFYMPKKATELKHLQCLEEELKPLEEV<br>LNLAQSKNFHLRPRALISNINVIVLELKGSETTFMCEYADETATIVEFLNRWITFCQSIISTLT |
| 99 | hIL-2 D84R | APTSSSTKKTQLQLEHLLLDLQMILNGINNYKNPKLTRMLTEKYMPKKATELKHLQCLEEELKPLEEV<br>LNLAQSKNFHLRPRRLISNINVIVLELKGSETTEMCEYADETATIVEFLNRWITFCQSIISTLT |
| 100 | hIL-2 D84K | APTSSSTKKTQLQLEHLLLDLQMILNGINNYKNPKLTRMLTFKFYMPKKATELKHLQCLEEELKPLEEV<br>LNLAQSKNFHLRPRKLISNINVIVLELKGSETTEMCEYADETATIVEFLNRWITFCQSIISTLT |
| 101 | hIL-2 S87A | APTSSSTKKTQLQLEHLLLDLQMILNGINNYKNPKLTRMLTFKFYMPKKATELKHLQCLEEELKPLEEV<br>LNLAQSKNFHLRPRDLIANINVIVLELKGSETTFMCEYADETATIVEFLNRWITFCQSIISTLT |
| 102 | hIL-2 N88Y | APTSSSTKKTQLQLEHLLLDLQMILNGINNYKNPKLTRMLTFKFYMPKKATELKHLQCLEEELKPLEEV<br>LNLAQSKNFHLRPRDLISYINVIVLELKGSETTFMCEYADETATIVEFLNRWITFCQSIISTLT |

TABLE 29-continued

Sequences

| SEQ ID NO: | Name | Sequence |
|---|---|---|
| 103 | hIL-2 N88D | APTSSSTKKTQLQLEHLLLDLQMILNGINNYKNPKLTRMLTFKFYMPKKATELKHLQCLEEELKPLEEV LNLAQSKNFHLRPRDLISDINVIVLELKGSETTFMCEYADETATIVEFLNRWITFCQSIISTLT |
| 104 | hIL-2 N88R | APTSSSTKKTQLQLEHLLLDLQMILNGINNYKNPKLTRMLTFKFYMPKKATELKHLQCLEEELKPLEEV LNLAQSKNFHLRPRDLISRINVIVLELKGSETTFMCEYADETATIVEFLNRWITFCQSIISTLT |
| 105 | hIL-2 N88E | APTSSSTKKTQLQLEHLLLDLQMILNGINNYKNPKLTRMLTFKFYMPKKATELKHLQCLEEELKPLEEV LNLAQSKNFHLRPRDLISEINVIVLELKGSETTEMCEYADETATIVEFLNRWITFCQSIISTLT |
| 106 | hIL-2 N88F | APTSSSTKKTQLQLEHLLLDLQMILNGINNYKNPKLTRMLTFKFYMPKKATELKHLQCLEEELKPLEEV LNLAQSKNFHLRPRDLISFINVIVLELKGSETTFMCEYADETATIVEFLNRWITFCQSIISTLT |
| 107 | hIL-2 N88I | APTSSSTKKTQLQLEHLLLDLQMILNGINNYKNPKLTRMLTFKFYMPKKATELKHLQCLEEELKPLEEV LNLAQSKNFHLRPRDLISIINVIVLELKGSETTFMCEYADETATIVEFLNRWITFCQSIISTLT |
| 108 | hIL-2 I92A | APTSSSTKKTQLQLEHLLLDLQMILNGINNYKNPKLTRMLTFKFYMPKKATELKHLQCLEEELKPLEEV LNLAQSKNFHLRPRDLISNINVAVLELKGSETTFMCEYADETATIVEFLNRWITFCQSIISTLT |
| 109 | hIL-2 I92Y | APTSSSTKKTQLQLEHLLLDLQMILNGINNYKNPKLTRMLTFKFYMPKKATELKHLQCLEEELKPLEEV LNLAQSKNFHLRPRDLISNINVYVLELKGSETTFMCEYADETATIVEFLNRWITFCQSIISTLT |
| 110 | hIL-2 I92S | APTSSSTKKTQLQLEHLLLDLQMILNGINNYKNPKLTRMLTFKFYMPKKATELKHLQCLEEELKPLEEV LNLAQSKNFHLRPRDLISNINVSVLELKGSETTFMCEYADETATIVEFLNRWITFCQSIISTLT |
| 111 | hIL-2 I92F | APTSSSTKKTQLQLEHLLLDLQMILNGINNYKNPKLTRMLTFKFYMPKKATELKHLQCLEEELKPLEEV LNLAQSKNFHLRPRDLISNINVFVLELKGSETTEMCEYADETATIVEFLNRWITFCQSIISTLT |
| 112 | hIL-2 I92R | APTSSSTKKTQLQLEHLLLDLQMILNGINNYKNPKLTRMLTFKFYMPKKATELKHLQCLEEELKPLEEV LNLAQSKNFHLRPRDLISNINVRVLELKGSETTFMCEYADETATIVEFLNRWITFCQSIISTLT |
| 113 | hIL-2 I92D | APTSSSTKKTQLQLEHLLLDLQMILNGINNYKNPKLTRMLTFKFYMPKKATELKHLQCLEEELKPLEEV LNLAQSKNFHLRPRDLISNINVDVLELKGSETTFMCEYADETATIVEFLNRWITFCQSIISTLT |
| 114 | hIL-2 I92E | APTSSSTKKTQLQLEHLLLDLQMILNGINNYKNPKLTRMLTFKFYMPKKATELKHLQCLEEELKPLEEV LNLAQSKNFHLRPRDLISNINVEVLELKGSETTEMCEYADETATIVEFLNRWITFCQSIISTLT |
| 115 | hIL-2 E95A | APTSSSTKKTQLQLEHLLLDLQMILNGINNYKNPKLTRMLTFKFYMPKKATELKHLQCLEEELKPLEEV LNLAQSKNFHLRPRDLISNINVIVLALKGSETTFMCEYADETATIVEFLNRWITFCQSIISTLT |
| 116 | hIL-2 E95R | APTSSSTKKTQLQLEHLLLDLQMILNGINNYKNPKLTRMLTFKFYMPKKATELKHLQCLEEELKPLEEV LNLAQSKNFHLRPRDLISNINVIVLRLKGSETTFMCEYADETATIVEFLNRWITFCQSIISTLT |
| 117 | hIL-2 E95K | APTSSSTKKTQLQLEHLLLDLQMILNGINNYKNPKLTRMLTFKFYMPKKATELKHLQCLEEELKPLEEV LNLAQSKNFHLRPRDLISNINVIVLKLKGSETTEMCEYADETATIVEFLNRWITFCQSIISTLT |
| 118 | hIL-2 D20Y/H16E | APTSSSTKKTQLQLEELLLYLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 119 | hIL-2 D20Y/H16A | APTSSSTKKTQLQLEALLLYLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 120 | hIL-2 D20Y/H16Y | APTSSSTKKTQLQLEYLLLYLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT |
| 121 | hIL-2 D20Y/I92A | APTSSSTKKTQLQLEHLLLYLQMILNGINNYKNPKLTRMLTFKFYMPKKATELKHLQCLEEELKPLEEV LNLAQSKNFHLRPRDLISNINVAVLELKGSETTEMCEYADETATIVEFLNRWITFCQSIISTLT |
| 122 | hIL-2 D20Y/I92S | APTSSSTKKTQLQLEHLLLYLQMILNGINNYKNPKLTRMLTFKFYMPKKATELKHLQCLEEELKPLEEV LNLAQSKNFHLRPRDLISNINVSVLELKGSETTEMCEYADETATIVEFLNRWITFCQSIISTLT |
| 123 | hIL-2 D20Y/I92R | APTSSSTKKTQLQLEHLLLYLQMILNGINNYKNPKLTRMLTFKFYMPKKATELKHLQCLEEELKPLEEV LNLAQSKNFHLRPRDLISNINVRVLELKGSETTEMCEYADETATIVEFLNRWITFCQSIISTLT |
| 124 | hIL-2 D20Y/E95R | APTSSSTKKTQLQLEHLLLYLQMILNGINNYKNPKLTRMLTFKFYMPKKATELKHLQCLEEELKPLEEV LNLAQSKNFHLRPRDLISNINVIVLRLKGSETTEMCEYADETATIVEFLNRWITFCQSIISTLT |
| 125 | hIL-2 D20Y/E95A | APTSSSTKKTQLQLEHLLLYLQMILNGINNYKNPKLTRMLTFKFYMPKKATELKHLQCLEEELKPLEEV LNLAQSKNFHLRPRDLISNINVIVLALKGSETTEMCEYADETATIVEFLNRWITFCQSIISTLT |
| 126 | hCD25 (1-164) | ELCDDDPPEIPHATFKAMAYKEGTMLNCECKRGERRIKSGSLYMLCTGNSSHSSWDNQCQCTSSATRNT TKQVTPQPEEQKERKTTEMQSPMQPVDQASLPGHCREPPPWENEATERIYHFVVGQMVYYQCVQGYRAL HRGPAESVCKMTHGKTRWTQPQLICT |

TABLE 29-continued

Sequences

| SEQ ID NO: | Name | Sequence |
|---|---|---|
| 127 | hIL-2 F42D/D20A | APTSSSTKKTQLQLEHLLLALQMILNGINNYKNPKLTRMLTDKFYMPKKATELKHLQCLEEELKPLEEV<br>LNLAQSKNFHLRPRDLISNINVIVLELKGSETTEMCEYADETATIVEFLNRWITFCQSIISTLT |
| 128 | hIL-2 F42R/D20A | APTSSSTKKTQLQLEHLLLALQMILNGINNYKNPKLTRMLTRKFYMPKKATELKHLQCLEEELKPLEEV<br>LNLAQSKNFHLRPRDLISNINVIVLELKGSETTEMCEYADETATIVEFLNRWITFCQSIISTLT |
| 129 | hIL-2 F42K/D20A | APTSSSTKKTQLQLEHLLLALQMILNGINNYKNPKLTRMLTKKFYMPKKATELKHLQCLEEELKPLEEV<br>LNLAQSKNFHLRPRDLISNINVIVLELKGSETTFMCEYADETATIVEFLNRWITFCQSIISTLT |
| 130 | hIL-2 F42A/D20A | APTSSSTKKTQLQLEHLLLALQMILNGINNYKNPKLTRMLTAKFYMPKKATELKHLQCLEEELKPLEEV<br>LNLAQSKNFHLRPRDLISNINVIVLELKGSETTFMCEYADETATIVEFLNRWITFCQSIISTLT |
| 131 | hIL-2 F42H/D20A | APTSSSTKKTQLQLEHLLLALQMILNGINNYKNPKLTRMLTHKFYMPKKATELKHLQCLEEELKPLEEV<br>LNLAQSKNFHLRPRDLISNINVIVLELKGSETTFMCEYADETATIVEFLNRWITFCQSIISTLT |
| 132 | hIL-2 Y45R/D20A | APTSSSTKKTQLQLEHLLLALQMILNGINNYKNPKLTRMLTFKFRMPKKATELKHLQCLEEELKPLEEV<br>LNLAQSKNFHLRPRDLISNINVIVLELKGSETTFMCEYADETATIVEFLNRWITFCQSIISTLT |
| 133 | hIL-2 Y45K/D20A | APTSSSTKKTQLQLEHLLLALQMILNGINNYKNPKLTRMLTFKFKMPKKATELKHLQCLEEELKPLEEV<br>LNLAQSKNFHLRPRDLISNINVIVLELKGSETTFMCEYADETATIVEFLNRWITFCQSIISTLT |
| 134 | hIL-2 R38N/D20A | APTSSSTKKTQLQLEHLLLALQMILNGINNYKNPKLTNMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 135 | hIL-2 R38G/D20A | APTSSSTKKTQLQLEHLLLALQMILNGINNYKNPKLTGMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 136 | hIL-2 R38H/D20A | APTSSSTKKTQLQLEHLLLALQMILNGINNYKNPKLTHMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 137 | hIL-2 R38I/D20A | APTSSSTKKTQLQLEHLLLALQMILNGINNYKNPKLTIMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 138 | hIL-2 R38L/D20A | APTSSSTKKTQLQLEHLLLALQMILNGINNYKNPKLTLMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 139 | hIL-2 R38M/D20A | APTSSSTKKTQLQLEHLLLALQMILNGINNYKNPKLTMMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 140 | hIL-2 R38F/D20A | APTSSSTKKTQLQLEHLLLALQMILNGINNYKNPKLTFMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 141 | hIL-2 R38P/D20A | APTSSSTKKTQLQLEHLLLALQMILNGINNYKNPKLTPMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 142 | hIL-2 R38S/D20A | APTSSSTKKTQLQLEHLLLALQMILNGINNYKNPKLTSMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 143 | hIL-2 R38T/D20A | APTSSSTKKTQLQLEHLLLALQMILNGINNYKNPKLTTMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 144 | hIL-2 R38W/D20A | APTSSSTKKTQLQLEHLLLALQMILNGINNYKNPKLTWMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 145 | hIL-2 R38Y/D20A | APTSSSTKKTQLQLEHLLLALQMILNGINNYKNPKLTYMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 146 | hIL-2 R38V/D20A | APTSSSTKKTQLQLEHLLLALQMILNGINNYKNPKLTVMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 147 | hIL-2 R38A/D20A | APTSSSTKKTQLQLEHLLLALQMILNGINNYKNPKLTAMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 148 | hIL-2 R38Q/D20A | APTSSSTKKTQLQLEHLLLALQMILNGINNYKNPKLTQMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 149 | hIL-2 D20A/R38E | APTSSSTKKTQLQLEHLLLALQMILNGINNYKNPKLTEMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 150 | hIL-2 R38D/D20A | APTSSSTKKTQLQLEHLLLALQMILNGINNYKNPKLTDMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 151 | hIL-2 K43E/D20A | APTSSSTKKTQLQLEHLLLALQMILNGINNYKNPKLTRMLTFEFYMPKKATELKHLQCLEEELKPLEEV<br>LNLAQSKNFHLRPRDLISNINVIVLELKGSETTFMCEYADETATIVEFLNRWITFCQSIISTLT |

TABLE 29-continued

Sequences

| SEQ ID NO: | Name | Sequence |
|---|---|---|
| 152 | hIL-2 E61A/D20A | APTSSSTKKTQLQLEHLLLALQMILNGINNYKNPKLTRMLTFKFYMPKKATELKHLQCLEAELKPLEEV LNLAQSKNFHLRPRDLISNINVIVLELKGSETTEMCEYADETATIVEFLNRWITFCQSIISTLT |
| 153 | hIL-2 E62A/D20A | APTSSSTKKTQLQLEHLLLALQMILNGINNYKNPKLTRMLTFKFYMPKKATELKHLQCLEEALKPLEEV LNLAQSKNFHLRPRDLISNINVIVLELKGSETTEMCEYADETATIVEFLNRWITFCQSIISTLT |
| 154 | hIL-2 E62Y/D20A | APTSSSTKKTQLQLEHLLLALQMILNGINNYKNPKLTRMLTFKFYMPKKATELKHLQCLEEYLKPLEEV LNLAQSKNFHLRPRDLISNINVIVLELKGSETTFMCEYADETATIVEFLNRWITFCQSIISTLT |
| 155 | hIL-2 L72D/D20A | APTSSSTKKTQLQLEHLLLALQMILNGINNYKNPKLTRMLTFKFYMPKKATELKHLQCLEEELKPLEEV LNDAQSKNFHLRPRDLISNINVIVLELKGSETTFMCEYADETATIVEFLNRWITFCQSIISTLT |
| 156 | hIL-2 L72H/D20A | APTSSSTKKTQLQLEHLLLALQMILNGINNYKNPKLTRMLTFKFYMPKKATELKHLQCLEEELKPLEEV LNHAQSKNFHLRPRDLISNINVIVLELKGSETTFMCEYADETATIVEFLNRWITFCQSIISTLT |
| 157 | hIL-2 L72R/D20A | APTSSSTKKTQLQLEHLLLALQMILNGINNYKNPKLTRMLTFKFYMPKKATELKHLQCLEEELKPLEEV LNRAQSKNFHLRPRDLISNINVIVLELKGSETTFMCEYADETATIVEFLNRWITFCQSIISTLT |
| 158 | hIL-2 F42D/I92D | APTSSSTKKTQLQLEHLLLDLQMILNGINNYKNPKLTRMLTDKFYMPKKATELKHLQCLEEELKPLEEV LNLAQSKNFHLRPRDLISNINVDVLELKGSETTFMCEYADETATIVEFLNRWITFCQSIISTLT |
| 159 | hIL-2 F42R/I92D | APTSSSTKKTQLQLEHLLLDLQMILNGINNYKNPKLTRMLTRKFYMPKKATELKHLQCLEEELKPLEEV LNLAQSKNFHLRPRDLISNINVDVLELKGSETTFMCEYADETATIVEFLNRWITFCQSIISTLT |
| 160 | hIL-2 F42H/I92D | APTSSSTKKTQLQLEHLLLDLQMILNGINNYKNPKLTRMLTHKFYMPKKATELKHLQCLEEELKPLEEV LNLAQSKNFHLRPRDLISNINVDVLELKGSETTFMCEYADETATIVEFLNRWITFCQSIISTLT |
| 161 | hIL-2 F42A/I92D | APTSSSTKKTQLQLEHLLLDLQMILNGINNYKNPKLTRMLTAKFYMPKKATELKHLQCLEEELKPLEEV LNLAQSKNFHLRPRDLISNINVDVLELKGSETTFMCEYADETATIVEFLNRWITFCQSIISTLT |
| 162 | hIL-2 K43E/I92D | APTSSSTKKTQLQLEHLLLDLQMILNGINNYKNPKLTRMLTFEYMPKKATELKHLQCLEEELKPLEEV LNLAQSKNFHLRPRDLISNINVDVLELKGSETTFMCEYADETATIVEFLNRWITFCQSIISTLT |
| 163 | hIL-2 Y45R/I92D | APTSSSTKKTQLQLEHLLLDLQMILNGINNYKNPKLTRMLTFKFRMPKKATELKHLQCLEEELKPLEEV LNLAQSKNFHLRPRDLISNINVDVLELKGSETTFMCEYADETATIVEFLNRWITFCQSIISTLT |
| 164 | hIL-2 Y45K/I92 | APTSSSTKKTQLQLEHLLLDLQMILNGINNYKNPKLTRMLTFKFKMPKKATELKHLQCLEEELKPLEEV LNLAQSKNFHLRPRDLISNINVDVLELKGSETTFMCEYADETATIVEFLNRWITFCQSIISTLT |
| 165 | hIL-2 E62A/I92D | APTSSSTKKTQLQLEHLLLDLQMILNGINNYKNPKLTRMLTFKFYMPKKATELKHLQCLEEALKPLEEV LNLAQSKNFHLRPRDLISNINVDVLELKGSETTFMCEYADETATIVEFLNRWITFCQSIISTLT |
| 166 | hIL-2 E62Y/I92D | APTSSSTKKTQLQLEHLLLDLQMILNGINNYKNPKLTRMLTFKFYMPKKATELKHLQCLEEYLKPLEEV LNLAQSKNFHLRPRDLISNINVDVLELKGSETTFMCEYADETATIVEFLNRWITFCQSIISTLT |
| 167 | hIL-2 L72D/I92D | APTSSSTKKTQLQLEHLLLDLQMILNGINNYKNPKLTRMLTFKFYMPKKATELKHLQCLEEELKPLEEV LNDAQSKNFHLRPRDLISNINVDVLELKGSETTFMCEYADETATIVEFLNRWITFCQSIISTLT |
| 168 | hIL-2 L72H/I92D | APTSSSTKKTQLQLEHLLLDLQMILNGINNYKNPKLTRMLTFKFYMPKKATELKHLQCLEEELKPLEEV LNHAQSKNFHLRPRDLISNINVDVLELKGSETTFMCEYADETATIVEFLNRWITFCQSIISTLT |
| 169 | hIL-2 L72R/I92D | APTSSSTKKTQLQLEHLLLDLQMILNGINNYKNPKLTRMLTFKFYMPKKATELKHLQCLEEELKPLEEV LNRAQSKNFHLRPRDLISNINVDVLELKGSETTFMCEYADETATIVEFLNRWITFCQSIISTLT |
| 170 | hIL-2 R38D/I92D | APTSSSTKKTQLQLEHLLLDLQMILNGINNYKNPKLTDMLTFKFYMPKKATELKHLQCLEEELKPLEEV LNLAQSKNFHLRPRDLISNINVDVLELKGSETTFMCEYADETATIVEFLNRWITFCQSIISTLT |
| 171 | hIL-2 R38E/I92D | APTSSSTKKTQLQLEHLLLDLQMILNGINNYKNPKLTEMLTFKFYMPKKATELKHLQCLEEELKPLEEV LNLAQSKNFHLRPRDLISNINVDVLELKGSETTFMCEYADETATIVEFLNRWITFCQSIISTLT |
| 172 | hIL-2 R38Q/I92D | APTSSSTKKTQLQLEHLLLDLQMILNGINNYKNPKLTQMLTFKFYMPKKATELKHLQCLEEELKPLEEV LNLAQSKNFHLRPRDLISNINVDVLELKGSETTFMCEYADETATIVEFLNRWITFCQSIISTLT |
| 173 | hIL-2 R38A/I92D | APTSSSTKKTQLQLEHLLLDLQMILNGINNYKNPKLTAMLTFKFYMPKKATELKHLQCLEEELKPLEEV LNLAQSKNFHLRPRDLISNINVDVLELKGSETTFMCEYADETATIVEFLNRWITFCQSIISTLT |
| 174 | hIL-2 R38E/N88R | APTSSSTKKTQLQLEHLLLDLQMILNGINNYKNPKLTEMLTFKFYMPKKATELKHLQCLEEELKPLEEV LNLAQSKNFHLRPRDLISRINVIVLELKGSETTFMCEYADETATIVEFLNRWITFCQSIISTLT |
| 175 | hIL-2 R38E/D84R | APTSSSTKKTQLQLEHLLLDLQMILNGINNYKNPKLTEMLTFKFYMPKKATELKHLQCLEEELKPLEEV LNLAQSKNFHLRPRRLISNINVIVLELKGSETTFMCEYADETATIVEFLNRWITFCQSIISTLT |
| 176 | hIL-2 R38E/D84K | APTSSSTKKTQLQLEHLLLDLQMILNGINNYKNPKLTEMLTFKFYMPKKATELKHLQCLEEELKPLEEV LNLAQSKNFHLRPRKLISNINVIVLELKGSETTFMCEYADETATIVEFLNRWITFCQSIISTLT |

TABLE 29-continued

Sequences

| SEQ ID NO: | Name | Sequence |
|---|---|---|
| 177 | hIL-2 F42A/Y45R/D20A | APTSSSTKKTQLQLEHLLLALQMILNGINNYKNPKLTRMLTAKFRMPKKATELKHLQCLEEELKPLEEVLNLAQSKNFHLRPRDLISNINVIVLELKGSETTFMCEYADETATIVEFLNRWITFCQSIISTLT |
| 178 | hIL-2 F42H/Y45R/D20A | APTSSSTKKTQLQLEHLLLALQMILNGINNYKNPKLTRMLTHKFRMPKKATELKHLQCLEEELKPLEEVLNLAQSKNFHLRPRDLISNINVIVLELKGSETTFMCEYADETATIVEFLNRWITFCQSIISTLT |
| 179 | hIL-2 R38D/E61R/D20A | APTSSSTKKTQLQLEHLLLALQMILNGINNYKNPKLTDMLTFKFYMPKKATELKHLQCLERELKPLEEVLNLAQSKNFHLRPRDLISNINVIVLELKGSETTFMCEYADETATIVEFLNRWITFCQSIISTLT |
| 180 | hIL-2 R38E/E61R/D20A | APTSSSTKKTQLQLEHLLLALQMILNGINNYKNPKLTEMLTFKFYMPKKATELKHLQCLERELKPLEEVLNLAQSKNFHLRPRDLISNINVIVLELKGSETTFMCEYADETATIVEFLNRWITFCQSIISTLT |
| 181 | hIL-2 R38Q/E61R/D20A | APTSSSTKKTQLQLEHLLLALQMILNGINNYKNPKLTQMLTFKFYMPKKATELKHLQCLERELKPLEEVLNLAQSKNFHLRPRDLISNINVIVLELKGSETTFMCEYADETATIVEFLNRWITFCQSIISTLT |
| 182 | hIL-2 R38A/E61R/D20A | APTSSSTKKTQLQLEHLLLALQMILNGINNYKNPKLTAMLTFKFYMPKKATELKHLQCLERELKPLEEVLNLAQSKNFHLRPRDLISNINVIVLELKGSETTFMCEYADETATIVEFLNRWITFCQSIISTLT |
| 183 | hIL-2 R38A/D20A/E95A | APTSSSTKKTQLQLEHLLLALQMILNGINNYKNPKLTAMLTFKFYMPKKATELKHLQCLEEELKPLEEVLNLAQSKNFHLRPRDLISNINVIVLALKGSETTFMCEYADETATIVEFLNRWITFCQSIISTLT |
| 184 | hIL-2 D20A/E95A/R38D | APTSSSTKKTQLQLEHLLLALQMILNGINNYKNPKLTDMLTFKFYMPKKATELKHLQCLEEELKPLEEVLNLAQSKNFHLRPRDLISNINVIVLALKGSETTFMCEYADETATIVEFLNRWITFCQSIISTLT |
| 185 | hIL-2 D20A/E95A/R38E | APTSSSTKKTQLQLEHLLLALQMILNGINNYKNPKLTEMLTFKFYMPKKATELKHLQCLEEELKPLEEVLNLAQSKNFHLRPRDLISNINVIVLALKGSETTFMCEYADETATIVEFLNRWITFCQSIISTLT |
| 186 | hIL-2 D20A/E95A/R38Q | APTSSSTKKTQLQLEHLLLALQMILNGINNYKNPKLTQMLTFKFYMPKKATELKHLQCLEEELKPLEEVLNLAQSKNFHLRPRDLISNINVIVLALKGSETTFMCEYADETATIVEFLNRWITFCQSIISTLT |
| 187 | hIL-2 D20A/E95A/F42R | APTSSSTKKTQLQLEHLLLALQMILNGINNYKNPKLTRMLTRKFYMPKKATELKHLQCLEEELKPLEEVLNLAQSKNFHLRPRDLISNINVIVLALKGSETTFMCEYADETATIVEFLNRWITFCQSIISTLT |
| 188 | hIL-2 D20A/E95A/F42A | APTSSSTKKTQLQLEHLLLALQMILNGINNYKNPKLTRMLTAKFYMPKKATELKHLQCLEEELKPLEEVLNLAQSKNFHLRPRDLISNINVIVLALKGSETTFMCEYADETATIVEFLNRWITFCQSIISTLT |
| 189 | hIL-2 D20A/E95A/F42D | APTSSSTKKTQLQLEHLLLALQMILNGINNYKNPKLTRMLTDKFYMPKKATELKHLQCLEEELKPLEEVLNLAQSKNFHLRPRDLISNINVIVLALKGSETTFMCEYADETATIVEFLNRWITFCQSIISTLT |
| 190 | hIL-2 D20A/E95A/F42H | APTSSSTKKTQLQLEHLLLALQMILNGINNYKNPKLTRMLTHKFYMPKKATELKHLQCLEEELKPLEEVLNLAQSKNFHLRPRDLISNINVIVLALKGSETTFMCEYADETATIVEFLNRWITFCQSIISTLT |
| 191 | hIL-2 D20A/E95A/F42K | APTSSSTKKTQLQLEHLLLALQMILNGINNYKNPKLTRMLTKKFYMPKKATELKHLQCLEEELKPLEEVLNLAQSKNFHLRPRDLISNINVIVLALKGSETTFMCEYADETATIVEFLNRWITFCQSIISTLT |
| 192 | hIL-2 D20A/E95A/K43A | APTSSSTKKTQLQLEHLLLALQMILNGINNYKNPKLTRMLTFAYMPKKATELKHLQCLEEELKPLEEVLNLAQSKNFHLRPRDLISNINVIVLALKGSETTFMCEYADETATIVEFLNRWITFCQSIISTLT |
| 193 | hIL-2 D20A/E95A/K43E | APTSSSTKKTQLQLEHLLLALQMILNGINNYKNPKLTRMLTFEYMPKKATELKHLQCLEEELKPLEEVLNLAQSKNFHLRPRDLISNINVIVLALKGSETTFMCEYADETATIVEFLNRWITFCQSIISTLT |
| 194 | hIL-2 D20A/E95A/K43Q | APTSSSTKKTQLQLEHLLLALQMILNGINNYKNPKLTRMLTFQYMPKKATELKHLQCLEEELKPLEEVLNLAQSKNFHLRPRDLISNINVIVLALKGSETTFMCEYADETATIVEFLNRWITFCQSIISTLT |
| 195 | hIL-2 D20A/E95A/Y45A | APTSSSTKKTQLQLEHLLLALQMILNGINNYKNPKLTRMLTFKAMPKKATELKHLQCLEEELKPLEEVLNLAQSKNFHLRPRDLISNINVIVLALKGSETTFMCEYADETATIVEFLNRWITFCQSIISTLT |
| 196 | hIL-2 D20A/E95A/Y45K | APTSSSTKKTQLQLEHLLLALQMILNGINNYKNPKLTRMLTFKKMPKKATELKHLQCLEEELKPLEEVLNLAQSKNFHLRPRDLISNINVIVLALKGSETTFMCEYADETATIVEFLNRWITFCQSIISTLT |
| 197 | hIL-2 D20A/E95A/45S | APTSSSTKKTQLQLEHLLLALQMILNGINNYKNPKLTRMLTFKESMPKKATELKHLQCLEEELKPLEEVLNLAQSKNFHLRPRDLISNINVIVLALKGSETTFMCEYADETATIVEFLNRWITFCQSIISTLT |
| 198 | hIL-2 D20A/E95A/Y45R | APTSSSTKKTQLQLEHLLLALQMILNGINNYKNPKLTRMLTFKFRMPKKATELKHLQCLEEELKPLEEVLNLAQSKNFHLRPRDLISNINVIVLALKGSETTFMCEYADETATIVEFLNRWITFCQSIISTLT |

TABLE 29-continued

Sequences

| SEQ ID NO: | Name | Sequence |
|---|---|---|
| 199 | hIL-2 D20A/E95A/E61A | APTSSSTKKTQLQLEHLLLALQMILNGINNYKNPKLTRMLTFKFYMPKKATELKHLQCLEAELKPLEEV LNLAQSKNFHLRPRDLISNINVIVLALKGSETTFMCEYADETATIVEFLNRWITFCQSIISTLT |
| 200 | hIL-2 D20A/E95A/E62A | APTSSSTKKTQLQLEHLLLALQMILNGINNYKNPKLTRMLTFKFYMPKKATELKHLQCLEEALKPLEEV LNLAQSKNFHLRPRDLISNINVIVLALKGSETTEMCEYADETATIVEFLNRWITFCQSIISTLT |
| 201 | hIL-2 D20A/E95A/E62R | APTSSSTKKTQLQLEHLLLALQMILNGINNYKNPKLTRMLTFKFYMPKKATELKHLQCLEERLKPLEEV LNLAQSKNFHLRPRDLISNINVIVLALKGSETTEMCEYADETATIVEFLNRWITFCQSIISTLT |
| 202 | hIL-2 D20A/E95A/E62K | APTSSSTKKTQLQLEHLLLALQMILNGINNYKNPKLTRMLTFKFYMPKKATELKHLQCLEEKLKPLEEV LNLAQSKNFHLRPRDLISNINVIVLALKGSETTEMCEYADETATIVEFLNRWITFCQSIISTLT |
| 203 | hIL-2 D20A/E95A/E62Y | APTSSSTKKTQLQLEHLLLALQMILNGINNYKNPKLTRMLTFKFYMPKKATELKHLQCLEEYLKPLEEV LNLAQSKNFHLRPRDLISNINVIVLALKGSETTEMCEYADETATIVEFLNRWITFCQSIISTLT |
| 204 | hIL-2 D20A/E95A/E68Y | APTSSSTKKTQLQLEHLLLALQMILNGINNYKNPKLTRMLTFKFYMPKKATELKHLQCLEEELKPLEYV LNLAQSKNFHLRPRDLISNINVIVLALKGSETTEMCEYADETATIVEFLNRWITFCQSIISTLT |
| 205 | hIL-2 D20A/E95A/E68A | APTSSSTKKTQLQLEHLLLALQMILNGINNYKNPKLTRMLTFKFYMPKKATELKHLQCLEEELKPLEAV LNLAQSKNFHLRPRDLISNINVIVLALKGSETTEMCEYADETATIVEFLNRWITFCQSIISTLT |
| 206 | hIL-2 D20A/E95A/E68L | APTSSSTKKTQLQLEHLLLALQMILNGINNYKNPKLTRMLTFKFYMPKKATELKHLQCLEEELKPLELV LNLAQSKNFHLRPRDLISNINVIVLALKGSETTEMCEYADETATIVEFLNRWITFCQSIISTLT |
| 207 | hIL-2 D20A/E95A/L72Y | APTSSSTKKTQLQLEHLLLALQMILNGINNYKNPKLTRMLTFKFYMPKKATELKHLQCLEEELKPLEEV LNYAQSKNFHLRPRDLISNINVIVLALKGSETTEMCEYADETATIVEFLNRWITFCQSIISTLT |
| 208 | hIL-2 D20A/E95A/L72R | APTSSSTKKTQLQLEHLLLALQMILNGINNYKNPKLTRMLTFKFYMPKKATELKHLQCLEEELKPLEEV LNRAQSKNFHLRPRDLISNINVIVLALKGSETTEMCEYADETATIVEFLNRWITFCQSIISTLT |
| 209 | hIL-2 D20A/E95A/L72A | APTSSSTKKTQLQLEHLLLALQMILNGINNYKNPKLTRMLTFKFYMPKKATELKHLQCLEEELKPLEEV LNAAQSKNFHLRPRDLISNINVIVLALKGSETTEMCEYADETATIVEFLNRWITFCQSIISTLT |
| 210 | hIL-2 D20A/E95A/L72D | APTSSSTKKTQLQLEHLLLALQMILNGINNYKNPKLTRMLTFKFYMPKKATELKHLQCLEEELKPLEEV LNDAQSKNFHLRPRDLISNINVIVLALKGSETTEMCEYADETATIVEFLNRWITFCQSIISTLT |
| 211 | hIL-2 D20A/E95A/L72H | APTSSSTKKTQLQLEHLLLALQMILNGINNYKNPKLTRMLTFKFYMPKKATELKHLQCLEEELKPLEEV LNHAQSKNFHLRPRDLISNINVIVLALKGSETTEMCEYADETATIVEFLNRWITFCQSIISTLT |
| 212 | hIL-2 D20A/E95A/L72F | APTSSSTKKTQLQLEHLLLALQMILNGINNYKNPKLTRMLTFKFYMPKKATELKHLQCLEEELKPLEEV LNFAQSKNFHLRPRDLISNINVIVLALKGSETTEMCEYADETATIVEFLNRWITFCQSIISTLT |
| 213 | hIL-2 F42K/Y45R/D20A/S87A | APTSSSTKKTQLQLEHLLLALQMILNGINNYKNPKLTRMLTKKFRMPKKATELKHLQCLEEELKPLEEV LNLAQSKNFHLRPRDLIANINVIVLELKGSETTEMCEYADETATIVEFLNRWITFCQSIISTLT |
| 214 | hIL-2 F42K/Y45R/D20A/E95A | APTSSSTKKTQLQLEHLLLALQMILNGINNYKNPKLTRMLTKKERMPKKATELKHLQCLEEELKPLEEV LNLAQSKNFHLRPRDLISNINVIVLALKGSETTEMCEYADETATIVEFLNRWITFCQSIISTLT |
| 215 | hIL-2 D20A/R38E/C125A | APTSSSTKKTQLQLEHLLLALQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFAQSIISTLT |
| 216 | hIL-2 T3A/D20A/R38E | APASSSTKKTQLQLEHLLLALQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 217 | hIL-2 T3A/D20A/R38E/C125A (IL-2-AAEA) | APASSSTKKTQLQLEHLLLALQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFAQSIISTLT |

TABLE 29-continued

Sequences

| SEQ ID NO: | Name | Sequence |
|---|---|---|
| 218 | hIL-2 Δ1-3APT/D20A/R38E | SSSTKKTQLQLEHLLLALQMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCQSIISTLT |
| 219 | hIL-2 Δ1-3APT/D20A/R38E/C125A | SSSTKKTQLQLEHLLLALQMILNGINNYKNPKLTEMLTFKFYMPKKATELKHLQCLEEELKPLEEVLNLAQSKNFHLRPRDLISNINVIVLELKGSETTEMCEYADETATIVEFLNRWITFAQSIISTLT |
| 220 | hIL-2 R38E/Q22A | APTSSSTKKTQLQLEHLLLDLAMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCQSIISTLT |
| 221 | hIL-2 R38E/T123A | APTSSSTKKTQLQLEHLLLDLQMILNGINNYKNPKLTEMLTFKFYMPKKATELKHLQCLEEELKPLEEVLNLAQSKNFHLRPRDLISNINVIVLELKGSETTFMCEYADETATIVEFLNRWIAFCQSIISTLT |
| 222 | hIL-2 R38E/I129A | APTSSSTKKTQLQLEHLLLDLQMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCQSIASTLT |
| 223 | hIL-2 R38E/S130A | APTSSSTKKTQLQLEHLLLDLQMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCQSIIATLT |
| 224 | hIL-2 R38E/Q126A | APTSSSTKKTQLQLEHLLLDLQMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCASIISTLT |
| 225 | hIL-2 R38E/Q126D | APTSSSTKKTQLQLEHLLLDLQMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCDSIISTLT |
| 226 | hIL-2 R38E/Q126V | APTSSSTKKTQLQLEHLLLDLQMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCVSIISTLT |
| 227 | hIL-2 R38E/Q22A/S130A | APTSSSTKKTQLQLEHLLLDLAMILNGINNYKNPKLTEMLTFKFYMPKKATELKHLQCLEEELKPLEEVLNLAQSKNFHLRPRDLISNINVIVLELKGSETTFMCEYADETATIVEFLNRWITFCQSIIATLT |
| 228 | hIL-2 F42K/Y45R/Q126D | APTSSSTKKTQLQLEHLLLDLQMILNGINNYKNPKLTRMLTKKFRMPKKATELKHLQCLEEELKPLEEVLNLAQSKNFHLRPRDLISNINVIVLELKGSETTFMCEYADETATIVEFLNRWITFCDSIISTLT |
| 229 | hIL-2 D20A/E95A/Q126D | APTSSSTKKTQLQLEHLLLALQMILNGINNYKNPKLTRMLTFKFYMPKKATELKHLQCLEEELKPLEEVLNLAQSKNFHLRPRDLISNINVIVLALKGSETTFMCEYADETATIVEFLNRWITFCDSIISTLT |
| 230 | hIL-2 D20A/E61R | APTSSSTKKTQLQLEHLLLALQMILNGINNYKNPKLTRMLTFKFYMPKKATELKHLQCLERELKPLEEVLNLAQSKNFHLRPRDLISNINVIVLELKGSETTFMCEYADETATIVEFLNRWITFCQSIISTLT |
| 231 | hIL-2 D20A/E61N | APTSSSTKKTQLQLEHLLLALQMILNGINNYKNPKLTRMLTFKFYMPKKATELKHLQCLENELKPLEEVLNLAQSKNFHLRPRDLISNINVIVLELKGSETTFMCEYADETATIVEFLNRWITFCQSIISTLT |
| 232 | hIL-2 D20A/E61D | APTSSSTKKTQLQLEHLLLALQMILNGINNYKNPKLTRMLTFKFYMPKKATELKHLQCLEDELKPLEEVLNLAQSKNFHLRPRDLISNINVIVLELKGSETTFMCEYADETATIVEFLNRWITFCQSIISTLT |
| 233 | hIL-2 D20A/E61Q | APTSSSTKKTQLQLEHLLLALQMILNGINNYKNPKLTRMLTFKFYMPKKATELKHLQCLEQELKPLEEVLNLAQSKNFHLRPRDLISNINVIVLELKGSETTFMCEYADETATIVEFLNRWITFCQSIISTLT |
| 234 | hIL-2 D20A/E61G | APTSSSTKKTQLQLEHLLLALQMILNGINNYKNPKLTRMLTFKFYMPKKATELKHLQCLEGELKPLEEVLNLAQSKNFHLRPRDLISNINVIVLELKGSETTFMCEYADETATIVEFLNRWITFCQSIISTLT |
| 235 | hIL-2 D20A/E61H | APTSSSTKKTQLQLEHLLLALQMILNGINNYKNPKLTRMLTFKFYMPKKATELKHLQCLEHELKPLEEVLNLAQSKNFHLRPRDLISNINVIVLELKGSETTFMCEYADETATIVEFLNRWITFCQSIISTLT |
| 236 | hIL-2 D20A/E61I | APTSSSTKKTQLQLEHLLLALQMILNGINNYKNPKLTRMLTFKFYMPKKATELKHLQCLEIELKPLEEVLNLAQSKNFHLRPRDLISNINVIVLELKGSETTFMCEYADETATIVEFLNRWITFCQSIISTLT |
| 237 | hIL-2 D20A/E61L | APTSSSTKKTQLQLEHLLLALQMILNGINNYKNPKLTRMLTFKFYMPKKATELKHLQCLELELKPLEEVLNLAQSKNFHLRPRDLISNINVIVLELKGSETTFMCEYADETATIVEFLNRWITFCQSIISTLT |
| 238 | hIL-2 D20A/E61K | APTSSSTKKTQLQLEHLLLALQMILNGINNYKNPKLTRMLTFKFYMPKKATELKHLQCLEKELKPLEEVLNLAQSKNFHLRPRDLISNINVIVLELKGSETTFMCEYADETATIVEFLNRWITFCQSIISTLT |
| 239 | hIL-2 D20A/E61M | APTSSSTKKTQLQLEHLLLALQMILNGINNYKNPKLTRMLTFKFYMPKKATELKHLQCLEMELKPLEEVLNLAQSKNFHLRPRDLISNINVIVLELKGSETTFMCEYADETATIVEFLNRWITFCQSIISTLT |
| 240 | hIL-2 D20A/E61F | APTSSSTKKTQLQLEHLLLALQMILNGINNYKNPKLTRMLTFKFYMPKKATELKHLQCLEFELKPLEEVLNLAQSKNFHLRPRDLISNINVIVLELKGSETTFMCEYADETATIVEFLNRWITFCQSIISTLT |

TABLE 29-continued

Sequences

| SEQ ID NO: | Name | Sequence |
|---|---|---|
| 241 | hIL-2 D20A/E61P | APTSSSTKKTQLQLEHLLLALQMILNGINNYKNPKLTRMLTFKFYMPKKATELKHLQCLEPELKPLEEVLNLAQSKNFHLRPRDLISNINVIVLELKGSETTFMCEYADETATIVEFLNRWITFCQSIISTLT |
| 242 | hIL-2 D20A/E61S | APTSSSTKKTQLQLEHLLLALQMILNGINNYKNPKLTRMLTFKFYMPKKATELKHLQCLESELKPLEEVLNLAQSKNFHLRPRDLISNINVIVLELKGSETTFMCEYADETATIVEFLNRWITFCQSIISTLT |
| 243 | hIL-2 D20A/E61T | APTSSSTKKTQLQLEHLLLALQMILNGINNYKNPKLTRMLTFKFYMPKKATELKHLQCLETELKPLEEVLNLAQSKNFHLRPRDLISNINVIVLELKGSETTFMCEYADETATIVEFLNRWITFCQSIISTLT |
| 244 | hIL-2 D20A/E61W | APTSSSTKKTQLQLEHLLLALQMILNGINNYKNPKLTRMLTFKFYMPKKATELKHLQCLEWELKPLEEVLNLAQSKNFHLRPRDLISNINVIVLELKGSETTFMCEYADETATIVEFLNRWITFCQSIISTLT |
| 245 | hIL-2 D20A/E61Y | APTSSSTKKTQLQLEHLLLALQMILNGINNYKNPKLTRMLTFKFYMPKKATELKHLQCLEYELKPLEEVLNLAQSKNFHLRPRDLISNINVIVLELKGSETTFMCEYADETATIVEFLNRWITFCQSIISTLT |
| 246 | hIL-2 D20A/E61V | APTSSSTKKTQLQLEHLLLALQMILNGINNYKNPKLTRMLTFKFYMPKKATELKHLQCLEVELKPLEEVLNLAQSKNFHLRPRDLISNINVIVLELKGSETTFMCEYADETATIVEFLNRWITFCQSIISTLT |
| 247 | hIL-2 D20A/F42N | APTSSSTKKTQLQLEHLLLALQMILNGINNYKNPKLTRMLTNKFYMPKKATELKHLQCLEEELKPLEEVLNLAQSKNFHLRPRDLISNINVIVLELKGSETTEMCEYADETATIVEFLNRWITFCQSIISTLT |
| 248 | hIL-2 D20A/F42Q | APTSSSTKKTQLQLEHLLLALQMILNGINNYKNPKLTRMLTQKFYMPKKATELKHLQCLEEELKPLEEVLNLAQSKNFHLRPRDLISNINVIVLELKGSETTEMCEYADETATIVEFLNRWITFCQSIISTLT |
| 249 | hIL-2 D20A/F42E | APTSSSTKKTQLQLEHLLLALQMILNGINNYKNPKLTRMLTEKFYMPKKATELKHLQCLEEELKPLEEVLNLAQSKNFHLRPRDLISNINVIVLELKGSETTEMCEYADETATIVEFLNRWITFCQSIISTLT |
| 250 | hIL-2 D20A/F42G | APTSSSTKKTQLQLEHLLLALQMILNGINNYKNPKLTRMLTGKFYMPKKATELKHLQCLEEELKPLEEVLNLAQSKNFHLRPRDLISNINVIVLELKGSETTEMCEYADETATIVEFLNRWITFCQSIISTLT |
| 251 | hIL-2 D20A/F42I | APTSSSTKKTQLQLEHLLLALQMILNGINNYKNPKLTRMLTIKFYMPKKATELKHLQCLEEELKPLEEVLNLAQSKNFHLRPRDLISNINVIVLELKGSETTEMCEYADETATIVEFLNRWITFCQSIISTLT |
| 252 | hIL-2 D20A/F42L | APTSSSTKKTQLQLEHLLLALQMILNGINNYKNPKLTRMLTLKFYMPKKATELKHLQCLEEELKPLEEVLNLAQSKNFHLRPRDLISNINVIVLELKGSETTEMCEYADETATIVEFLNRWITFCQSIISTLT |
| 253 | hIL-2 D20A/F42M | APTSSSTKKTQLQLEHLLLALQMILNGINNYKNPKLTRMLTMKFYMPKKATELKHLQCLEEELKPLEEVLNLAQSKNFHLRPRDLISNINVIVLELKGSETTEMCEYADETATIVEFLNRWITFCQSIISTLT |
| 254 | hIL-2 D20A/F42P | APTSSSTKKTQLQLEHLLLALQMILNGINNYKNPKLTRMLTPKFYMPKKATELKHLQCLEEELKPLEEVLNLAQSKNFHLRPRDLISNINVIVLELKGSETTEMCEYADETATIVEFLNRWITFCQSIISTLT |
| 255 | hIL-2 D20A/F42S | APTSSSTKKTQLQLEHLLLALQMILNGINNYKNPKLTRMLTSKFYMPKKATELKHLQCLEEELKPLEEVLNLAQSKNFHLRPRDLISNINVIVLELKGSETTEMCEYADETATIVEFLNRWITFCQSIISTLT |
| 256 | hIL-2 D20A/F42T | APTSSSTKKTQLQLEHLLLALQMILNGINNYKNPKLTRMLTTKFYMPKKATELKHLQCLEEELKPLEEVLNLAQSKNFHLRPRDLISNINVIVLELKGSETTEMCEYADETATIVEFLNRWITFCQSIISTLT |
| 257 | hIL-2 D20A/F42W | APTSSSTKKTQLQLEHLLLALQMILNGINNYKNPKLTRMLTWKFYMPKKATELKHLQCLEEELKPLEEVLNLAQSKNFHLRPRDLISNINVIVLELKGSETTEMCEYADETATIVEFLNRWITFCQSIISTLT |
| 258 | hIL-2 D20A/F42Y | APTSSSTKKTQLQLEHLLLALQMILNGINNYKNPKLTRMLTYKFYMPKKATELKHLQCLEEELKPLEEVLNLAQSKNFHLRPRDLISNINVIVLELKGSETTEMCEYADETATIVEFLNRWITFCQSIISTLT |
| 259 | hIL-2 D20A/F42V | APTSSSTKKTQLQLEHLLLALQMILNGINNYKNPKLTRMLTVKFYMPKKATELKHLQCLEEELKPLEEVLNLAQSKNFHLRPRDLISNINVIVLELKGSETTEMCEYADETATIVEFLNRWITFCQSIISTLT |
| 260 | hIL-2 D20A/Y45A | APTSSSTKKTQLQLEHLLLALQMILNGINNYKNPKLTRMLTFKFAMPKKATELKHLQCLEEELKPLEEVLNLAQSKNFHLRPRDLISNINVIVLELKGSETTEMCEYADETATIVEFLNRWITFCQSIISTLT |
| 261 | hIL-2 D20A/Y45N | APTSSSTKKTQLQLEHLLLALQMILNGINNYKNPKLTRMLTFKFNMPKKATELKHLQCLEEELKPLEEVLNLAQSKNFHLRPRDLISNINVIVLELKGSETTEMCEYADETATIVEFLNRWITFCQSIISTLT |
| 262 | hIL-2 D20A/Y45D | APTSSSTKKTQLQLEHLLLALQMILNGINNYKNPKLTRMLTFKFDMPKKATELKHLQCLEEELKPLEEVLNLAQSKNFHLRPRDLISNINVIVLELKGSETTEMCEYADETATIVEFLNRWITFCQSIISTLT |
| 263 | hIL-2 D20A/Y45Q | APTSSSTKKTQLQLEHLLLALQMILNGINNYKNPKLTRMLTFKFQMPKKATELKHLQCLEEELKPLEEVLNLAQSKNFHLRPRDLISNINVIVLELKGSETTEMCEYADETATIVEFLNRWITFCQSIISTLT |
| 264 | hIL-2 D20A/Y45E | APTSSSTKKTQLQLEHLLLALQMILNGINNYKNPKLTRMLTFKFEMPKKATELKHLQCLEEELKPLEEVLNLAQSKNFHLRPRDLISNINVIVLELKGSETTEMCEYADETATIVEFLNRWITFCQSIISTLT |
| 265 | hIL-2 D20A/Y45G | APTSSSTKKTQLQLEHLLLALQMILNGINNYKNPKLTRMLTFKFGMPKKATELKHLQCLEEELKPLEEVLNLAQSKNFHLRPRDLISNINVIVLELKGSETTEMCEYADETATIVEFLNRWITFCQSIISTLT |

TABLE 29-continued

Sequences

| SEQ ID NO: | Name | Sequence |
|---|---|---|
| 266 | hIL-2 D20A/Y45H | APTSSSTKKTQLQLEHLLLALQMILNGINNYKNPKLTRMLTFKFHMPKKATELKHLQCLEEELKPLEEV<br>LNLAQSKNFHLRPRDLISNINVIVLELKGSETTFMCEYADETATIVEFLNRWITFCQSIISTLT |
| 267 | hIL-2 D20A/Y45I | APTSSSTKKTQLQLEHLLLALQMILNGINNYKNPKLTRMLTFKFIMPKKATELKHLQCLEEELKPLEEV<br>LNLAQSKNFHLRPRDLISNINVIVLELKGSETTFMCEYADETATIVEFLNRWITFCQSIISTLT |
| 268 | hIL-2 D20A/Y45L | APTSSSTKKTQLQLEHLLLALQMILNGINNYKNPKLTRMLTFKFLMPKKATELKHLQCLEEELKPLEEV<br>LNLAQSKNFHLRPRDLISNINVIVLELKGSETTFMCEYADETATIVEFLNRWITFCQSIISTLT |
| 269 | hIL-2 D20A/Y45M | APTSSSTKKTQLQLEHLLLALQMILNGINNYKNPKLTRMLTFKFMMPKKATELKHLQCLEEELKPLEEV<br>LNLAQSKNFHLRPRDLISNINVIVLELKGSETTFMCEYADETATIVEFLNRWITFCQSIISTLT |
| 270 | hIL-2 D20A/Y45F | APTSSSTKKTQLQLEHLLLALQMILNGINNYKNPKLTRMLTFKFFMPKKATELKHLQCLEEELKPLEEV<br>LNLAQSKNFHLRPRDLISNINVIVLELKGSETTFMCEYADETATIVEFLNRWITFCQSIISTLT |
| 271 | hIL-2 D20A/Y45P | APTSSSTKKTQLQLEHLLLALQMILNGINNYKNPKLTRMLTFKFPMPKKATELKHLQCLEEELKPLEEV<br>LNLAQSKNFHLRPRDLISNINVIVLELKGSETTFMCEYADETATIVEFLNRWITFCQSIISTLT |
| 272 | hIL-2 D20A/Y45S | APTSSSTKKTQLQLEHLLLALQMILNGINNYKNPKLTRMLTFKFSMPKKATELKHLQCLEEELKPLEEV<br>LNLAQSKNFHLRPRDLISNINVIVLELKGSETTFMCEYADETATIVEFLNRWITFCQSIISTLT |
| 273 | hIL-2 D20A/Y45T | APTSSSTKKTQLQLEHLLLALQMILNGINNYKNPKLTRMLTFKFTMPKKATELKHLQCLEEELKPLEEV<br>LNLAQSKNFHLRPRDLISNINVIVLELKGSETTFMCEYADETATIVEFLNRWITFCQSIISTLT |
| 274 | hIL-2 D20A/Y45W | APTSSSTKKTQLQLEHLLLALQMILNGINNYKNPKLTRMLTFKFWMPKKATELKHLQCLEEELKPLEEV<br>LNLAQSKNFHLRPRDLISNINVIVLELKGSETTFMCEYADETATIVEFLNRWITFCQSIISTLT |
| 275 | hIL-2 D20A/Y45V | APTSSSTKKTQLQLEHLLLALQMILNGINNYKNPKLTRMLTFKFVMPKKATELKHLQCLEEELKPLEEV<br>LNLAQSKNFHLRPRDLISNINVIVLELKGSETTFMCEYADETATIVEFLNRWITFCQSIISTLT |
| 276 | hIL-2 I92D/F42N | APTSSSTKKTQLQLEHLLLDLQMILNGINNYKNPKLTRMLTNKFYMPKKATELKHLQCLEEELKPLEEV<br>LNLAQSKNFHLRPRDLISNINVDVLELKGSETTFMCEYADETATIVEFLNRWITFCQSIISTLT |
| 277 | hIL-2 I92D/F42Q | APTSSSTKKTQLQLEHLLLDLQMILNGINNYKNPKLTRMLTQKFYMPKKATELKHLQCLEEELKPLEEV<br>LNLAQSKNFHLRPRDLISNINVDVLELKGSETTFMCEYADETATIVEFLNRWITFCQSIISTLT |
| 278 | hIL-2 I92D/F42E | APTSSSTKKTQLQLEHLLLDLQMILNGINNYKNPKLTRMLTEKFYMPKKATELKHLQCLEEELKPLEEV<br>LNLAQSKNFHLRPRDLISNINVDVLELKGSETTFMCEYADETATIVEFLNRWITFCQSIISTLT |
| 279 | hIL-2 I92D/F42G | APTSSSTKKTQLQLEHLLLDLQMILNGINNYKNPKLTRMLTGKFYMPKKATELKHLQCLEEELKPLEEV<br>LNLAQSKNFHLRPRDLISNINVDVLELKGSETTFMCEYADETATIVEFLNRWITFCQSIISTLT |
| 280 | hIL-2 I92D/F42I | APTSSSTKKTQLQLEHLLLDLQMILNGINNYKNPKLTRMLTIKFYMPKKATELKHLQCLEEELKPLEEV<br>LNLAQSKNFHLRPRDLISNINVDVLELKGSETTFMCEYADETATIVEFLNRWITFCQSIISTLT |
| 281 | hIL-2 I92D/F42L | APTSSSTKKTQLQLEHLLLDLQMILNGINNYKNPKLTRMLTLKFYMPKKATELKHLQCLEEELKPLEEV<br>LNLAQSKNFHLRPRDLISNINVDVLELKGSETTFMCEYADETATIVEFLNRWITFCQSIISTLT |
| 282 | hIL-2 I92D/F42K | APTSSSTKKTQLQLEHLLLDLQMILNGINNYKNPKLTRMLTKKFYMPKKATELKHLQCLEEELKPLEEV<br>LNLAQSKNFHLRPRDLISNINVDVLELKGSETTFMCEYADETATIVEFLNRWITFCQSIISTLT |
| 283 | hIL-2 I92D/F42M | APTSSSTKKTQLQLEHLLLDLQMILNGINNYKNPKLTRMLTMKFYMPKKATELKHLQCLEEELKPLEEV<br>LNLAQSKNFHLRPRDLISNINVDVLELKGSETTFMCEYADETATIVEFLNRWITFCQSIISTLT |
| 284 | hIL-2 I92D/F42P | APTSSSTKKTQLQLEHLLLDLQMILNGINNYKNPKLTRMLTPKFYMPKKATELKHLQCLEEELKPLEEV<br>LNLAQSKNFHLRPRDLISNINVDVLELKGSETTFMCEYADETATIVEFLNRWITFCQSIISTLT |
| 285 | hIL-2 I92D/F42S | APTSSSTKKTQLQLEHLLLDLQMILNGINNYKNPKLTRMLTSKFYMPKKATELKHLQCLEEELKPLEEV<br>LNLAQSKNFHLRPRDLISNINVDVLELKGSETTFMCEYADETATIVEFLNRWITFCQSIISTLT |
| 286 | hIL-2 I92D/F42T | APTSSSTKKTQLQLEHLLLDLQMILNGINNYKNPKLTRMLTTKFYMPKKATELKHLQCLEEELKPLEEV<br>LNLAQSKNFHLRPRDLISNINVDVLELKGSETTFMCEYADETATIVEFLNRWITFCQSIISTLT |
| 287 | hIL-2 I92D/F42W | APTSSSTKKTQLQLEHLLLDLQMILNGINNYKNPKLTRMLTWKFYMPKKATELKHLQCLEEELKPLEEV<br>LNLAQSKNFHLRPRDLISNINVDVLELKGSETTFMCEYADETATIVEFLNRWITFCQSIISTLT |
| 288 | hIL-2 I92D/F42Y | APTSSSTKKTQLQLEHLLLDLQMILNGINNYKNPKLTRMLTYKFYMPKKATELKHLQCLEEELKPLEEV<br>LNLAQSKNFHLRPRDLISNINVDVLELKGSETTFMCEYADETATIVEFLNRWITFCQSIISTLT |
| 289 | hIL-2 I92D/F42V | APTSSSTKKTQLQLEHLLLDLQMILNGINNYKNPKLTRMLTVKFYMPKKATELKHLQCLEEELKPLEEV<br>LNLAQSKNFHLRPRDLISNINVDVLELKGSETTFMCEYADETATIVEFLNRWITFCQSIISTLT |
| 290 | hIL-2 I92D/Y45A | APTSSSTKKTQLQLEHLLLDLQMILNGINNYKNPKLTRMLTFKFAMPKKATELKHLQCLEEELKPLEEV<br>LNLAQSKNFHLRPRDLISNINVDVLELKGSETTFMCEYADETATIVEFLNRWITFCQSIISTLT |

TABLE 29-continued

Sequences

| SEQ ID NO: | Name | Sequence |
|---|---|---|
| 291 | hIL-2 I92D/Y45N | APTSSSTKKTQLQLEHLLLDLQMILNGINNYKNPKLTRMLTFKENMPKKATELKHLQCLEEELKPLEEV<br>LNLAQSKNFHLRPRDLISNINVDVLELKGSETTFMCEYADETATIVEFLNRWITFCQSIISTLT |
| 292 | hIL-2 I92D/Y45D | APTSSSTKKTQLQLEHLLLDLQMILNGINNYKNPKLTRMLTFKEDMPKKATELKHLQCLEEELKPLEEV<br>LNLAQSKNFHLRPRDLISNINVDVLELKGSETTFMCEYADETATIVEFLNRWITFCQSIISTLT |
| 293 | hIL-2 I92D/Y45Q | APTSSSTKKTQLQLEHLLLDLQMILNGINNYKNPKLTRMLTFKFQMPKKATELKHLQCLEEELKPLEEV<br>LNLAQSKNFHLRPRDLISNINVDVLELKGSETTFMCEYADETATIVEFLNRWITFCQSIISTLT |
| 294 | hIL-2 I92D/Y45E | APTSSSTKKTQLQLEHLLLDLQMILNGINNYKNPKLTRMLTFKFEMPKKATELKHLQCLEEELKPLEEV<br>LNLAQSKNFHLRPRDLISNINVDVLELKGSETTFMCEYADETATIVEFLNRWITFCQSIISTLT |
| 295 | hIL-2 I92D/Y45G | APTSSSTKKTQLQLEHLLLDLQMILNGINNYKNPKLTRMLTFKFGMPKKATELKHLQCLEEELKPLEEV<br>LNLAQSKNFHLRPRDLISNINVDVLELKGSETTFMCEYADETATIVEFLNRWITFCQSIISTLT |
| 296 | hIL-2 I92D/Y45H | APTSSSTKKTQLQLEHLLLDLQMILNGINNYKNPKLTRMLTFKFHMPKKATELKHLQCLEEELKPLEEV<br>LNLAQSKNFHLRPRDLISNINVDVLELKGSETTFMCEYADETATIVEFLNRWITFCQSIISTLT |
| 297 | hIL-2 I92D/Y45I | APTSSSTKKTQLQLEHLLLDLQMILNGINNYKNPKLTRMLTFKFIMPKKATELKHLQCLEEELKPLEEV<br>LNLAQSKNFHLRPRDLISNINVDVLELKGSETTFMCEYADETATIVEFLNRWITFCQSIISTLT |
| 298 | hIL-2 I92D/Y45L | APTSSSTKKTQLQLEHLLLDLQMILNGINNYKNPKLTRMLTEKELMPKKATELKHLQCLEEELKPLEEV<br>LNLAQSKNFHLRPRDLISNINVDVLELKGSETTFMCEYADETATIVEFLNRWITFCQSIISTLT |
| 299 | hIL-2 I92D/Y45M | APTSSSTKKTQLQLEHLLLDLQMILNGINNYKNPKLTRMLTFKEMMPKKATELKHLQCLEEELKPLEEV<br>LNLAQSKNFHLRPRDLISNINVDVLELKGSETTFMCEYADETATIVEFLNRWITFCQSIISTLT |
| 300 | hIL-2 I92D/Y45F | APTSSSTKKTQLQLEHLLLDLQMILNGINNYKNPKLTRMLTFKFFMPKKATELKHLQCLEEELKPLEEV<br>LNLAQSKNFHLRPRDLISNINVDVLELKGSETTFMCEYADETATIVEFLNRWITFCQSIISTLT |
| 301 | hIL-2 I92D/Y45P | APTSSSTKKTQLQLEHLLLDLQMILNGINNYKNPKLTRMLTFKFPMPKKATELKHLQCLEEELKPLEEV<br>LNLAQSKNFHLRPRDLISNINVDVLELKGSETTFMCEYADETATIVEFLNRWITFCQSIISTLT |
| 302 | hIL-2 I92D/Y45S | APTSSSTKKTQLQLEHLLLDLQMILNGINNYKNPKLTRMLTEKESMPKKATELKHLQCLEEELKPLEEV<br>LNLAQSKNFHLRPRDLISNINVDVLELKGSETTFMCEYADETATIVEFLNRWITFCQSIISTLT |
| 303 | hIL-2 I92D/Y45T | APTSSSTKKTQLQLEHLLLDLQMILNGINNYKNPKLTRMLTFKFTMPKKATELKHLQCLEEELKPLEEV<br>LNLAQSKNFHLRPRDLISNINVDVLELKGSETTFMCEYADETATIVEFLNRWITFCQSIISTLT |
| 304 | hIL-2 I92D/Y45W | APTSSSTKKTQLQLEHLLLDLQMILNGINNYKNPKLTRMLTFKFWMPKKATELKHLQCLEEELKPLEEV<br>LNLAQSKNFHLRPRDLISNINVDVLELKGSETTFMCEYADETATIVEFLNRWITFCQSIISTLT |
| 305 | hIL-2 I92D/Y45V | APTSSSTKKTQLQLEHLLLDLQMILNGINNYKNPKLTRMLTFKFVMPKKATELKHLQCLEEELKPLEEV<br>LNLAQSKNFHLRPRDLISNINVDVLELKGSETTFMCEYADETATIVEFLNRWITFCQSIISTLT |
| 306 | hIL-2 R38E/D20H | APTSSSTKKTQLQLEHLLLHLQMILNGINNYKNPKLTEMLTFKYMPKKATELKHLQCLEEELKPLEEV<br>LNLAQSKNFHLRPRDLISNINVIVLELKGSETTFMCEYADETATIVEFLNRWITFCQSIISTLT |
| 307 | hIL-2 R38E/D20S | APTSSSTKKTQLQLEHLLLSLQMILNGINNYKNPKLTEMLTFKYMPKKATELKHLQCLEEELKPLEEV<br>LNLAQSKNFHLRPRDLISNINVIVLELKGSETTFMCEYADETATIVEFLNRWITFCQSIISTLT |
| 308 | hIL-2 F42A/N88R | APTSSSTKKTQLQLEHLLLDLQMILNGINNYKNPKLTRMLTAKYMPKKATELKHLQCLEEELKPLEEV<br>LNLAQSKNFHLRPRDLISRINVIVLELKGSETTFMCEYADETATIVEFLNRWITFCQSIISTLT |
| 309 | hIL-2 F42A/N88D | APTSSSTKKTQLQLEHLLLDLQMILNGINNYKNPKLTRMLTAKYMPKKATELKHLQCLEEELKPLEEV<br>LNLAQSKNFHLRPRDLISDINVIVLELKGSETTFMCEYADETATIVEFLNRWITFCQSIISTLT |
| 310 | hIL-2 R38E/D84A | APTSSSTKKTQLQLEHLLLDLQMILNGINNYKNPKLTEMLTFKYMPKKATELKHLQCLEEELKPLEEV<br>LNLAQSKNFHLRPRALISNINVIVLELKGSETTFMCEYADETATIVEFLNRWITFCQSIISTLT |
| 311 | hIL-2 R38E/D84N | APTSSSTKKTQLQLEHLLLDLQMILNGINNYKNPKLTEMLTFKYMPKKATELKHLQCLEEELKPLEEV<br>LNLAQSKNFHLRPRNLISNINVIVLELKGSETTFMCEYADETATIVEFLNRWITFCQSIISTLT |
| 312 | hIL-2 R38E/D84Q | APTSSSTKKTQLQLEHLLLDLQMILNGINNYKNPKLTEMLTFKYMPKKATELKHLQCLEEELKPLEEV<br>LNLAQSKNFHLRPRQLISNINVIVLELKGSETTFMCEYADETATIVEFLNRWITFCQSIISTLT |
| 313 | hIL-2 R38E/D84E | APTSSSTKKTQLQLEHLLLDLQMILNGINNYKNPKLTEMLTFKFYMPKKATELKHLQCLEEELKPLEEV<br>LNLAQSKNFHLRPRELISNINVIVLELKGSETTFMCEYADETATIVEFLNRWITFCQSIISTLT |
| 314 | hIL-2 R38E/D84G | APTSSSTKKTQLQLEHLLLDLQMILNGINNYKNPKLTEMLTFKYMPKKATELKHLQCLEEELKPLEEV<br>LNLAQSKNFHLRPRGLISNINVIVLELKGSETTFMCEYADETATIVEFLNRWITFCQSIISTLT |
| 315 | hIL-2 R38E/D84H | APTSSSTKKTQLQLEHLLLDLQMILNGINNYKNPKLTEMLTFKYMPKKATELKHLQCLEEELKPLEEV<br>LNLAQSKNFHLRPRHLISNINVIVLELKGSETTFMCEYADETATIVEFLNRWITFCQSIISTLT |

TABLE 29-continued

Sequences

| SEQ ID NO: | Name | Sequence |
|---|---|---|
| 316 | hIL-2 R38E/D84I | APTSSSTKKTQLQLEHLLLDLQMILNGINNYKNPKLTEMLTFKFYMPKKATELKHLQCLEEELKPLEEV LNLAQSKNFHLRPRILISNINVIVLELKGSETTFMCEYADETATIVEFLNRWITFCQSIISTLT |
| 317 | hIL-2 R38E/D84L | APTSSSTKKTQLQLEHLLLDLQMILNGINNYKNPKLTEMLTFKFYMPKKATELKHLQCLEEELKPLEEV LNLAQSKNFHLRPRLLISNINVIVLELKGSETTFMCEYADETATIVEFLNRWITFCQSIISTLT |
| 318 | hIL-2 R38E/D84M | APTSSSTKKTQLQLEHLLLDLQMILNGINNYKNPKLTEMLTFKFYMPKKATELKHLQCLEEELKPLEEV LNLAQSKNFHLRPRMLISNINVIVLELKGSETTFMCEYADETATIVEFLNRWITFCQSIISTLT |
| 319 | hIL-2 R38E/D84F | APTSSSTKKTQLQLEHLLLDLQMILNGINNYKNPKLTEMLTFKFYMPKKATELKHLQCLEEELKPLEEV LNLAQSKNFHLRPRFLISNINVIVLELKGSETTFMCEYADETATIVEFLNRWITFCQSIISTLT |
| 320 | hIL-2 R38E/D84P | APTSSSTKKTQLQLEHLLLDLQMILNGINNYKNPKLTEMLTFKFYMPKKATELKHLQCLEEELKPLEEV LNLAQSKNFHLRPRPLISNINVIVLELKGSETTFMCEYADETATIVEFLNRWITFCQSIISTLT |
| 321 | hIL-2 R38E/D84S | APTSSSTKKTQLQLEHLLLDLQMILNGINNYKNPKLTEMLTFKFYMPKKATELKHLQCLEEELKPLEEV LNLAQSKNFHLRPRSLISNINVIVLELKGSETTFMCEYADETATIVEFLNRWITFCQSIISTLT |
| 322 | hIL-2 R38E/D84T | APTSSSTKKTQLQLEHLLLDLQMILNGINNYKNPKLTEMLTFKFYMPKKATELKHLQCLEEELKPLEEV LNLAQSKNFHLRPRTLISNINVIVLELKGSETTFMCEYADETATIVEFLNRWITFCQSIISTLT |
| 323 | hIL-2 R38E/D84W | APTSSSTKKTQLQLEHLLLDLQMILNGINNYKNPKLTEMLTFKFYMPKKATELKHLQCLEEELKPLEEV LNLAQSKNFHLRPRWLISNINVIVLELKGSETTFMCEYADETATIVEFLNRWITFCQSIISTLT |
| 324 | hIL-2 R38E/D84Y | APTSSSTKKTQLQLEHLLLDLQMILNGINNYKNPKLTEMLTFKFYMPKKATELKHLQCLEEELKPLEEV LNLAQSKNFHLRPRYLISNINVIVLELKGSETTFMCEYADETATIVEFLNRWITFCQSIISTLT |
| 325 | hIL-2 R38E/D84V | APTSSSTKKTQLQLEHLLLDLQMILNGINNYKNPKLTEMLTFKFYMPKKATELKHLQCLEEELKPLEEV LNLAQSKNFHLRPRVLISNINVIVLELKGSETTFMCEYADETATIVEFLNRWITFCQSIISTLT |
| 326 | hIL-2 R38E/I92A | APTSSSTKKTQLQLEHLLLDLQMILNGINNYKNPKLTEMLTFKFYMPKKATELKHLQCLEEELKPLEEV LNLAQSKNFHLRPRDLISNINVAVLELKGSETTFMCEYADETATIVEFLNRWITFCQSIISTLT |
| 327 | hIL-2 R38E/I92R | APTSSSTKKTQLQLEHLLLDLQMILNGINNYKNPKLTEMLTFKFYMPKKATELKHLQCLEEELKPLEEV LNLAQSKNFHLRPRDLISNINVRVLELKGSETTFMCEYADETATIVEFLNRWITFCQSIISTLT |
| 328 | hIL-2 R38E/I92N | APTSSSTKKTQLQLEHLLLDLQMILNGINNYKNPKLTEMLTFKFYMPKKATELKHLQCLEEELKPLEEV LNLAQSKNFHLRPRDLISNINVNVLELKGSETTFMCEYADETATIVEFLNRWITFCQSIISTLT |
| 329 | hIL-2 R38E/I92Q | APTSSSTKKTQLQLEHLLLDLQMILNGINNYKNPKLTEMLTFKFYMPKKATELKHLQCLEEELKPLEEV LNLAQSKNFHLRPRDLISNINVQVLELKGSETTFMCEYADETATIVEFLNRWITFCQSIISTLT |
| 330 | hIL-2 R38E/I92E | APTSSSTKKTQLQLEHLLLDLQMILNGINNYKNPKLTEMLTFKFYMPKKATELKHLQCLEEELKPLEEV LNLAQSKNFHLRPRDLISNINVEVLELKGSETTFMCEYADETATIVEFLNRWITFCQSIISTLT |
| 331 | hIL-2 R38E/I92G | APTSSSTKKTQLQLEHLLLDLQMILNGINNYKNPKLTEMLTFKFYMPKKATELKHLQCLEEELKPLEEV LNLAQSKNFHLRPRDLISNINVGVLELKGSETTFMCEYADETATIVEFLNRWITFCQSIISTLT |
| 332 | hIL-2 R38E/I92H | APTSSSTKKTQLQLEHLLLDLQMILNGINNYKNPKLTEMLTFKFYMPKKATELKHLQCLEEELKPLEEV LNLAQSKNFHLRPRDLISNINVHVLELKGSETTFMCEYADETATIVEFLNRWITFCQSIISTLT |
| 333 | hIL-2 R38E/I92L | APTSSSTKKTQLQLEHLLLDLQMILNGINNYKNPKLTEMLTFKFYMPKKATELKHLQCLEEELKPLEEV LNLAQSKNFHLRPRDLISNINVLVLELKGSETTFMCEYADETATIVEFLNRWITFCQSIISTLT |
| 334 | hIL-2 R38E/I92K | APTSSSTKKTQLQLEHLLLDLQMILNGINNYKNPKLTEMLTFKFYMPKKATELKHLQCLEEELKPLEEV LNLAQSKNFHLRPRDLISNINVKVLELKGSETTFMCEYADETATIVEFLNRWITFCQSIISTLT |
| 335 | hIL-2 R38E/I92M | APTSSSTKKTQLQLEHLLLDLQMILNGINNYKNPKLTEMLTFKFYMPKKATELKHLQCLEEELKPLEEV LNLAQSKNFHLRPRDLISNINVMVLELKGSETTFMCEYADETATIVEFLNRWITFCQSIISTLT |
| 336 | hIL-2 R38E/I92F | APTSSSTKKTQLQLEHLLLDLQMILNGINNYKNPKLTEMLTFKFYMPKKATELKHLQCLEEELKPLEEV LNLAQSKNFHLRPRDLISNINVFVLELKGSETTFMCEYADETATIVEFLNRWITFCQSIISTLT |
| 337 | hIL-2 R38E/I92P | APTSSSTKKTQLQLEHLLLDLQMILNGINNYKNPKLTEMLTFKFYMPKKATELKHLQCLEEELKPLEEV LNLAQSKNFHLRPRDLISNINVPVLELKGSETTFMCEYADETATIVEFLNRWITFCQSIISTLT |
| 338 | hIL-2 R38E/I92S | APTSSSTKKTQLQLEHLLLDLQMILNGINNYKNPKLTEMLTFKFYMPKKATELKHLQCLEEELKPLEEV LNLAQSKNFHLRPRDLISNINVSVLELKGSETTFMCEYADETATIVEFLNRWITFCQSIISTLT |
| 339 | hIL-2 R38E/I92T | APTSSSTKKTQLQLEHLLLDLQMILNGINNYKNPKLTEMLTFKFYMPKKATELKHLQCLEEELKPLEEV LNLAQSKNFHLRPRDLISNINVTVLELKGSETTFMCEYADETATIVEFLNRWITFCQSIISTLT |
| 340 | hIL-2 R38E/I92W | APTSSSTKKTQLQLEHLLLDLQMILNGINNYKNPKLTEMLTFKFYMPKKATELKHLQCLEEELKPLEEV LNLAQSKNFHLRPRDLISNINVWVLELKGSETTFMCEYADETATIVEFLNRWITFCQSIISTLT |

TABLE 29-continued

Sequences

| SEQ ID NO: | Name | Sequence |
|---|---|---|
| 341 | hIL-2 R38E/I92Y | APTSSSTKKTQLQLEHLLLDLQMILNGINNYKNPKLTEMLTFKFYMPKKATELKHLQCLEEELKPLEEV<br>LNLAQSKNFHLRPRDLISNINVYVLELKGSETTFMCEYADETATIVEFLNRWITFCQSIISTLT |
| 342 | hIL-2 R38E/I92V | APTSSSTKKTQLQLEHLLLDLQMILNGINNYKNPKLTEMLTFKFYMPKKATELKHLQCLEEELKPLEEV<br>LNLAQSKNFHLRPRDLISNINVVVLELKGSETTFMCEYADETATIVEFLNRWITFCQSIISTLT |
| 343 | hIL-2 R38E/H16E | APTSSSTKKTQLQLEELLLDLQMILNGINNYKNPKLTEMLTFKFYMPKKATELKHLQCLEEELKPLEEV<br>LNLAQSKNFHLRPRDLISNINVIVLELKGSETTEMCEYADETATIVEFLNRWITFCQSIISTLT |
| 344 | hIL-2 R38K/D20A | APTSSSTKKTQLQLEHLLLALQMILNGINNYKNPKLTKMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 345 | WT hIL-2 | APTSSSTKKTQLQLEHLLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFCQSIISTLT |
| 346 | Human PD-1 | PGWFLDSPDRPWNPPTESPALLVVTEGDNATFTCSFSNTSESFVLNWYRMSPSNQTDKLAAFPEDRSQP<br>GQDCRFRVTQLPNGRDFHMSVVRARRNDSGTYLCGAISLAPKAQIKESLRAELRVTERRAEVPTAHPSP<br>SPRPAGQFQTLVVGVVGGLLGSLVLLVWVLAVICSRAARGTIGARRTGQPLKEDPSAVPVESVDYGELD<br>FQWREKTPEPPVPCVPEQTEYATIVFPSGMGTSSPARRGSADGPRSAQPLRPEDGHCSWPL |
| 347 | Human PD-1 | CCAGGATGGTTCTTAGACTCCCCAGACAGGCCCTGGAACCCCCCACCTTCTCCCCAGCCCTGCTCGTG<br>GTGACCGAAGGGGACAACGCCACCTTCACCTGCAGCTTCTCCAACACATCGGAGAGCTTCGTGCTAAAC<br>TGGTACCGCATGAGCCCCAGCAACCAGACGGACAAGCTGGCCGCCTTCCCCGAGGACCGCAGCCAGCCC<br>GGCCAGGACTGCCGCTTCCGTGTCACACAACTGCCCAACGGGCGTGACTTCCACATGAGCGTGGTCAGG<br>GCCCGGCGCAATGACAGCGGCACCTACCTCTGTGGGGCCATCTCCCTGGCCCCCAAGGCGCAGATCAAA<br>GAGAGCCTGCGGGCAGAGCTCAGGGTGACAGAGAGAAGGGCAGAAGTGCCCACAGCCCACCCCAGCCCC<br>TCACCCAGGCCAGCCGGCCAGTTCCAAACCCTGGTGGTTGGTGTCGTGGGCGGCCTGCTGGGCAGCCTG<br>GTGCTGCTAGTCTGGGTCCTGGCCGTCATCTGCTCCCGGGCCGCACGAGGGACAATAGGAGCCAGGCGC<br>ACCGGCCAGCCCCTGAAGGAGGACCCCTCAGCCGTGCCTGTGTTCTCTGTGGACTATGGGGAGCTGGAT<br>TTCCAGTGGCGAGAGAAGACCCCGGAGCCCCCCGTGCCCTGTGTCCCTGAGCAGACGGAGTATGCCACC<br>ATTGTCTTTCCTAGCGGAATGGGCACCTCATCCCCCGCCCGCAGGGGCTCAGCTGACGCCCTCGGAGT<br>GCCCAGCCACTGAGGCCTGAGGATGGACACTGCTCTTGGCCCCTC |
| 348 | Anti-hPD-1 #1-mIgG2b-N297A HC | QVQLVESGGGVVQPGRSLRLDCKASGITFSNSGMHWVRQAPGKGLEWVAVIWYDGSKRYYADSVKGRFT<br>ISRDNSKNTLFLQMNSLRAEDTAVYYCATNDDYWGQGTLVTVSSAKTTPPSVYPLAPGCGDTTGSSVTL<br>GCLVKGYFPESVTVTWNSGSLSSSVHTFPALLQSGLYTMSSSVTVPSSTWPSQTVTCSVAHPASSTTVD<br>KKLEPSGPISTINPCPPCKECHKCPAPNLEGGPSVFIFPPNIKDVLMISLTPKVTCVVVDVSEDDPDVQ<br>ISWFVNNVEVHTAQTQTHREDYASTIRVVSTLPIQHQDWMSGKEFKCKVNNKDLPSPIERTISKIKGLV<br>RAPQVYILPPPAEQLSRKDVSLTCLVVGFNPGDISVEWTSNGHTEENYKDTAPVLDSDGSYFIYSKLNM<br>KTSKWEKTDSFSCNVRHEGLKNYYLKKTISRSPGK |
| 349 | Anti-hPD-1 #1-mKappa LC | EIVLTQSPATLSLSPGERATLSCRASQSVSSYLAWYQQKPGQAPRLLIYDASNRATGIPARFSGSGSGT<br>DFTLTISSLEPEDFAVYYCQQSSNWPRTFGQGTKVEIKRADAAPTVSIFPPSSEQLTSGGASVVCFLNN<br>FYPKDINVKWKIDGSERQNGVLNSWTDQDSKDSTYSMSSTLTLTKDEYERHNSYTCEATHKTSTSPIVK<br>SENRNEC |
| 350 | Anti-hPD-1 #2-mIgG2b-N297A HC | QVQLVQSGVEVKKPGASVKVSCKASGYTFTNYYMYWVRQAPGQGLEWMGGINPSNGGTNENEKEKNRVT<br>LTTDSSTTTAYMELKSLQFDDTAVYYCARRDYRFDMGFDYWGQGTTVTVSSAKTTPPSVYPLAPGCGDT<br>TGSSVTLGCLVKGYFPESVTVTWNSGSLSSSVHTFPALLQSGLYTMSSSVTVPSSTWPSQTVTCSVAHP<br>ASSTTVDKKLEPSGPISTINPCPPCKECHKCPAPNLEGGPSVFIFPPNIKDVLMISLTPKVTCVVVDVS<br>EDDPDVQISWFVNNVEVHTAQTQTHREDYASTIRVVSTLPIQHQDWMSGKEFKCKVNNKDLPSPIERTI<br>SKIKGLVRAPQVYILPPPAEQLSRKDVSLTCLVVGFNPGDISVEWTSNGHTEENYKDTAPVLDSDGSYF<br>IYSKLNMKTSKWEKTDSFSCNVRHEGLKNYYLKKTISRSPGK |
| 351 | Anti-hPD-1 #2-mKappa LC | EIVLTQSPATLSLSPGERATLSCRASKGVSTSGYSYLHWYQQKPGQAPRLLIYLASYLESGVPARESGS<br>GSGTDFTLTISSLEPEDFAVYYCQHSRDLPLTFGGGTKVEIKRADAAPTVSIFPPSSEQLTSGGASVVC<br>FLNNFYPKDINVKWKIDGSERQNGVLNSWTDQDSKDSTYSMSSTLTLTKDEYERHNSYTCEATHKTSTS<br>PIVKSENRNEC |
| 352 | IL-2Rγ | LNTTILTPNGNEDTTADFFLTTMPTDSLSVSTLPLPEVQCFVENVEYMNCTWNSSSEPQPTNLTLHYWY<br>KNSDNDKVQKCSHYLFSEEITSGCQLQKKEIHLYQTFVVQLQDPREPRRQATQMKLQNLVIPWAPENL<br>TLHKLSESQLELNWNNRFLNHCLEHLVQYRTDWDHSWTEQSVDYRHKESLPSVDGQKRYTERVRSRENP<br>LCGSAQHWSEWSHPIHWGSNTSKENPFLFALEAVVISVGSMGLIISLLCVYFWLERTMPRIPTLKNLED<br>LVTEYHGNESAWSGVSKGLAESLQPDYSERLCLVSEIPPKGGALGEGPGASPCNQHSPYWAPPCYTLKP<br>ET |
| 353 | human CD122 (IL-2Rβ) | AVNGTSQFTCFYNSRANISCVWSQDGALQDTSCQVHAWPDRRRWNQTCELLPVSQASWACNLILGAPDS<br>QKLTTVDIVTLRVLCREGVRWRVMAIQDFKPFENLRLMAPISLQVVHVETHRCNISWEISQASHYFERH<br>LEFEARTLSPGHTWEEAPLLTLKQKQEWICLETLTPDTQYEFQVRVKPLQGEFTTWSPWSQPLAFRTKP<br>AALGKDTIPWLGHLLVGLSGAFGFIILVLLINCRNTGPWLKKVLKCNTPDPSKFFSQLSSEHGGDVQK<br>WLSSPFPSSSESPGGLAPEISPLEVLERDKVTQLLLQQDKVPEPASLSSNHSLTSCFTNQGYFFFHLPD<br>ALEIEACQVYFTYDPYSEEDPDEGVAGAPTGSSPQPLQPLSGEDDAYCTFPSRDDLLLESPSLLGGPSP<br>PSTAPGGSGAGEERMPPSLQERVPRDWDPQPLGPPTPGVPDLVDFQPPPELVLREAGEEVPDAGPREGV<br>SFPWSRPPGQGEFRALNARLPLNTDAYLSLQELQGQDPTHLV |

TABLE 29-continued

Sequences

| SEQ ID NO: | Name | Sequence |
|---|---|---|
| 354 | IL-2Rα | ELCDDDPPEIPHATFKAMAYKEGTMLNCECKRGFRRIKSGSLYMLCTGNSSHSSWDNQCQCTSSATRNT TKQVTPQPEEQKERKTTEMQSPMQPVDQASLPGHCREPPPWENEATERIYHFVVGQMVYYQCVQGYRAL HRGPAESVCKMTHGKTRWTQPQLICTGEMETSQFPPGEEKPQASPEGRPESETSCLVTTTDFQIQTEMAA TMETSIFTTEYQVAVAGCVELLISVLLLSGLTWQRRQRKSRRTI |
| 355 | L6 linker amino acid | SGGGGS |
| 356 | hIL-2-df-1H3-hkappa LC hIL-2 in italics | *APTSSSTKKTQLQLEHLLLDLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT*DTVLT QSPALAVSPGERVTISCRASESVRTGVHWYQQKPGQQPKLLIYGASNLESGVPARFSGSGSGTDFTLTI DPVEADDTATYFCQQSWNDPFTGSGTKLEIKRTVAAPSVFIFPPSDEQLKSGTASVVCLLNNFYPREA KVQWKVDNALQSGNSQESVTEQDSKDSTYSLSSTLTLSKADYEKHKVYACEVTHQGLSSPVTKSENRGE C |
| 357 | hIL-2-L6-1H3-hKappa LC Linker in dashed underline hIL-2 in italics | *APTSSSTKKTQLQLEHLLLDLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCQSIISTLT*<u>SGGGG S</u>DTVLTQSPALAVSPGERVTISCRASESVRTGVHWYQQKPGQQPKLLIYGASNLESGVPARFSGSGSGT DFTLTIDPVEADDTATYFCQQSWNDPFTGSGTKLEIKRTVAAPSVFIFPPSDEQLKSGTASVVCLLNN FYPREAKVQWKVDNALQSGNSQESVTEQDSKDSTYSLSSTLTLSKADYEKHKVYACEVTHQGLSSPVTK SENRGEC |
| 358 | hIL-2-df-1H3-hIgG1 HC hIL-2 in italics | *APTSSSTKKTQLQLEHLLLDLQMILNGINNYKNPKLTRMLTEKFYMPKKATELKHLQCLEEELKPLEEV LNLAQSKNFHLRPRDLISNINVIVLELKGSETTEMCEYADETATIVEFLNRWITFCQSIISTLT*EVQLV ESGGGLVQPGRSLKLSCAVSGFTFSDYAMAWVRQAPKKGLEWVATISYDGSRTYYRDSVKGRFTISRDN AKITLYLQMDSLRSEDTATYYCARHGSGYFDYWGQGVMVTVSSASTKGPSVFPLAPSSKSTSGGTAALG CLVKDYFPEPVTVSWNSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTVDKSRWQQ GNVFSCSVMHEALHNHYTQKSLSLSPGK |
| 359 | hIL-2-L6-1H3-hIgG1 HC Linker in dashed underline hIL-2 in italics | *APTSSSTKKTQLQLEHLLLDLQMILNGINNYKNPKLTRMLTEKFYMPKKATELKHLQCLEEELKPLEEV HRGPAESVCKMTHGKTRWTQPQLICTS*<u>GGGGSGGGGSGGGGSGGGS</u>*APTSSSTKKTQLQLEHLLLDLQM TISRDNAKITLYLQMDSLRSEDTATYYCARHGSGYFDYWGQGVMVTVSSASTKGPSVFPLAPSSKSTSG GTAALGCLVKDYFPEPVTVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEVTCVVVDVSHEDPEVKE NWYVDGVEVHNAKTKPREEQYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPPVLDSDGSFFLYSKLTVD KSRWQQGNVFSCSVMHEALHNHYTQKSLSLSPGK |
| 360 | 1H3-hIgG1-df-hIL-2 HC hIL-2 in italics | EVQLVESGGGLVQPGRSLKLSCAVSGFTESDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGK*APTSSSTKKTQLQLEHLLLDLQMILNGINNYKNPKL TRMLTFKFYMPKKATELKHLQCLEEELKPLEEVLNLAQSKNFHLRPRDLISNINVIVLELKGSETTEMC EYADETATIVEFLNRWITFCQSIISTLT* |
| 361 | 1H3-hIgG1-L6-hIL-2 HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGK<u>SGGGGS</u>*APTSSSTKKTQLQLEHLLLDLQMILNGINN YKNPKLTRMLTFKFYMPKKATELKHLQCLEEELKPLEEVLNLAQSKNFHLRPRDLISNINVIVLELKGS ETTEMCEYADETATIVEFLNRWITFCQSIISTLT* |
| 362 | 1H3-hKappa-df-hIL-2 (WT) LC hIL-2 in italics | DTVLTQSPALAVSPGERVTISCRASESVRTGVHWYQQKPGQQPKLLIYGASNLESGVPARFSGSGSGTD FTLTIDPVEADDTATYFCQQSWNDPFTGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGEC*APTSSSTKKTQLQLEHLLLDLQMILNGINNYKNPKLTRMLTEKFYMPKKATELKHLQCLEEEL KPLEEVLNLAQSKNFHLRPRDLISNINVIVLELKGSETTEMCEYADETATIVEFLNRWITFCQSIISTL T* |

TABLE 29-continued

Sequences

| SEQ ID NO: | Name | Sequence |
|---|---|---|
| 363 | 1H3-hKappa-L6-hIL-2 (WT) LC Linker in dashed underline hIL-2 in italics | DTVLTQSPALAVSPGERVTISCRASESVRTGVHWYQQKPGQQPKLLIYGASNLESGVPARFSGSGSGTD FTLTIDPVEADDTATYFCQQSWNDPFTGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGEC<u>SGGGGS</u>*APTSSSTKKTQLQLEHLLLDLQMILNGINNYKNPKLTRMLTFKFYMPKKATELKHLQ CLEEELKPLEEVLNLAQSKNFHLRPRDLISNINVIVLELKGSETTEMCEYADETATIVEFLNRWITECQ SIISTLT* |
| 364 | L20 linker | SGGGGSGGGGSGGGGSGGGS |
| 365 | hCD25-L20-hIL-2-df-1H3-hIgG1 HC Linker in dashed underline hIL-2 in italics | ELCDDDPPEIPHATFKAMAYKEGTMLNCECKRGFRRIKSGSLYMLCTGNSSHSSWDNQCQCTSSATRNT TKQVTPQPEEQKERKTTEMQSPMQPVDQASLPGHCREPPPWENEATERIYHFVVGQMVYYQCVQGYRAL HRGPAESVCKMTHGKTRWTQPQLICT<u>SGGGGSGGGGSGGGGSGGGS</u>*APTSSSTKKTQLQLEHLLLDLQM ILNGINNYKNPKLTRMLTFKFYMPKKATELKHLQCLEEELKPLEEVLNLAQSKNFHLRPRDLISNINVI VLELKGSETTEMCEYADETATIVEFLNRWITFCQSIISTLT*EVQLVESGGGLVQPGRSLKLSCAVSGFT FSDYAMAWVRQAPKKGLEWVATISYDGSRTYYRDSVKGRFTISRDNAKITLYLQMDSLRSEDTATYYCA RHGSGYFDYWGQGVMVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFSCSVMHEALHNHYTQKSLS LSPGK |
| 366 | hCD25-L20-hIL-2-L6-1H3-hIgG1 HC Linkers in dashed underline hIL-2 in italics | ELCDDDPPEIPHATFKAMAYKEGTMLNCECKRGFRRIKSGSLYMLCTGNSSHSSWDNQCQCTSSATRNT TKQVTPQPEEQKERKTTEMQSPMQPVDQASLPGHCREPPPWENEATERIYHFVVGQMVYYQCVQGYRAL HRGPAESVCKMTHGKTRWTQPQLICT<u>SGGGGSGGGGSGGGGSGGGS</u>*APTSSSTKKTQLQLEHLLLDLQM ILNGINNYKNPKLTRMLTFKFYMPKKATELKHLQCLEEELKPLEEVLNLAQSKNFHLRPRDLISNINVI VLELKGSETTEMCEYADETATIVEFLNRWITFCQSIISTLT*<u>SGGGGS</u>EVQLVESGGGLVQPGRSLKLSC AVSGFTFSDYAMAWVRQAPKKGLEWVATISYDGSRTYYRDSVKGRFTISRDNAKITLYLQMDSLRSEDT ATYYCARHGSGYFDYWGQGVMVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRWQQGNVFSCSVMHEALHNHY TQKSLSLSPGK |
| 367 | hCD25-L20-hIL-2-df-1H3-hKappa LC Linker in dashed underline hIL-2 in italics | ELCDDDPPEIPHATFKAMAYKEGTMLNCECKRGERRIKSGSLYMLCTGNSSHSSWDNQCQCTSSATRNT TKQVTPQPEEQKERKTTEMQSPMQPVDQASLPGHCREPPPWENEATERIYHFVVGQMVYYQCVQGYRAL HRGPAESVCKMTHGKTRWTQPQLICT<u>SGGGGSGGGGSGGGGSGGGS</u>*APTSSSTKKTQLQLEHLLLDLQM ILNGINNYKNPKLTRMLTEKFYMPKKATELKHLQCLEEELKPLEEVLNLAQSKNFHLRPRDLISNINVI VLELKGSETTEMCEYADETATIVEFLNRWITFCQSIISTLT*DTVLTQSPALAVSPGERVTISCRASESV RTGVHWYQQKPGQQPKLLIYGASNLESGVPARESGSGSGTDFTLTIDPVEADDTATYFCQQSWNDPFTE GSGTKLEIKRTVAAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSENRGEC |
| 368 | hCD25-L20-hIL-2-L6-1H3-hKappa LC Linkers in dashed underline hIL-2 in italics | ELCDDDPPEIPHATFKAMAYKEGTMLNCECKRGFRRIKSGSLYMLCTGNSSHSSWDNQCQCTSSATRNT TKQVTPQPEEQKERKTTEMQSPMQPVDQASLPGHCREPPPWENEATERIYHFVVGQMVYYQCVQGYRAL HRGPAESVCKMTHGKTRWTQPQLICT<u>SGGGGSGGGGSGGGGSGGGS</u>*APTSSSTKKTQLQLEHLLLDLQM ILNGINNYKNPKLTRMLTFKFYMPKKATELKHLQCLEEELKPLEEVLNLAQSKNFHLRPRDLISNINVI VLELKGSETTEMCEYADETATIVEFLNRWITFCQSIISTLT*<u>SGGGGS</u>DTVLTQSPALAVSPGERVTISC RASESVRTGVHWYQQKPGQQPKLLIYGASNLESGVPARFSGSGSGTDFTLTIDPVEADDTATYFCQQSW NDPFTGSGTKLEIKRTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSENRGEC |
| 369 | 1H3-hIgG1-df - hCD25-L20-hIL-2 HC Linker in dashed underline hIL-2 in italics | EVQLVESGGGLVQPGRSLKLSCAVSGFTFSDYAMAWVRQAPKKGLEWVATISYDGSRTYYRDSVKGRET ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKELCDDDPPEIPHATFKAMAYKEGTMLNCECKRGERR IKSGSLYMLCTGNSSHSSWDNQCQCTSSATRNTTKQVTPQPEEQKERKTTEMQSPMQPVDQASLPGHCR EPPPWENEATERIYHFVVGQMVYYQCVQGYRALHRGPAESVCKMTHGKTRWTQPQLICT<u>SGGGGSGGGG SGGGGSGGGS</u>*APTSSSTKKTQLQLEHLLLDLQMILNGINNYKNPKLTRMLTEKFYMPKKATELKHLQCL EEELKPLEEVLNLAQSKNFHLRPRDLISNINVIVLELKGSETTEMCEYADETATIVEFLNRWITFCQSI ISTLT* |

TABLE 29-continued

Sequences

| SEQ ID NO: | Name | Sequence |
|---|---|---|
| 370 | 1H3-hIgG1-L6-hCD25-L20-hIL-2 HC Linkers in dashed underline hIL-2 in italics | EVQLVESGGGLVQPGRSLKLSCAVSGFTFSDYAMAWVRQAPKKGLEWVATISYDGSRTYYRDSVKGRET ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKS<u>GGGGS</u>*ELCDDDPPEIPHATFKAMAYKEGTMLNCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTS<u>GGG GSGGGGSGGGGSGGGS</u>APTSSSTKKTQLQLEHLLLDLQMILNGINNYKNPKLTRMLTFKFYMPKKATEL KHLQCLEEELKPLEEVLNLAQSKNFHLRPRDLISNINVIVLELKGSETTEMCEYADETATIVEFLNRWI TFCQSIISTLT* |
| 371 | 1H3-hKappa-df-hCD25-L20-hIL-2 LC Linker in dashed underline hIL-2 in italics | DTVLTQSPALAVSPGERVTISCRASESVRTGVHWYQQKPGQQPKLLIYGASNLESGVPARFSGSGSGTD FTLTIDPVEADDTATYFCQQSWNDPPFTFGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGECELCDDDPPEIPHATFKAMAYKEGTMLNCECKRGERRIKSGSLYMLCTGNSSHSSWDNQCQCTS SATRNTTKQVTPQPEEQKERKTTEMQSPMQPVDQASLPGHCREPPPWENEATERIYHFVVGQMVYYQCV QGYRALHRGPAESVCKMTHGKTRWTQPQLICTS<u>GGGGSGGGGSGGGGSGGGS</u>*APTSSSTKKTQLQLEHL LLDLQMILNGINNYKNPKLTRMLTFKFYMPKKATELKHLQCLEEELKPLEEVLNLAQSKNFHLRPRDLI SNINVIVLELKGSETTEMCEYADETATIVEFLNRWITFCQSIISTLT* |
| 372 | 1H3-hKappa-L6-hCD25-L20-hIL-2 LC Linkers in dashed underline hIL-2 in italics | DTVLTQSPALAVSPGERVTISCRASESVRTGVHWYQQKPGQQPKLLIYGASNLESGVPARFSGSGSGTD FTLTIDPVEADDTATYFCQQSWNDPPFTFGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGEC<u>SGGGGS</u>ELCDDDPPEIPHATFKAMAYKEGTMLNCECKRGERRIKSGSLYMLCTGNSSHSSWDN QCQCTSSATRNTTKQVTPQPEEQKERKTTEMQSPMQPVDQASLPGHCREPPPWENEATERIYHFVVGQM VYYQCVQGYRALHRGPAESVCKMTHGKTRWTQPQLICTS<u>GGGGSGGGGSGGGGSGGGS</u>*APTSSSTKKTQ LQLEHLLLDLQMILNGINNYKNPKLTRMLTEKFYMPKKATELKHLQCLEEELKPLEEVLNLAQSKNEHL RPRDLISNINVIVLELKGSETTEMCEYADETATIVEFLNRWITFCQSIISTLT* |
| 373 | H7-02-hIgG4 HC | EVQLLESGGGLVQPGGSLRLSCAASGFTFKSYAMTWVRQAPGKGLEWVSAIVYSGGSTYYADSVKGRET ISRDNSKNTLYLQMNSLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWINGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 374 | 1H3-hkappa LC | DTVLTQSPALAVSPGERVTISCRASESVRTGVHWYQQKPGQQPKLLIYGASNLESGVPARFSGSGSGTD FTLTIDPVEADDTATYFCQQSWNDPPFTFGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGEC |
| 375 | 2D12-mIgG1-D265A-L6-hIL-2 HC | EVQLQQSGPELVKPGASVKISCKTSGYTFTEYTMHWVKQSHGKSLEWIGGINPNNGGTTYNQKFKGKAT LTVDKSSSTAYMELRSLTSQDSAVYYCARDYYRGHYYAMDYWGQGTSVTVSSAKTTPPSVYPLAPGSA AQTNSMVTLGCLVKGYFPEPVTVTWNSGSLSSGVHTFPAVLQSDLYTLSSSVTVPSSTWPSETVTCNVA HPASSTKVDKKIVPRDCGCKPCICTVPEVSSVFIFPPKPKDVLTITLTPKVTCVVVAISKDDPEVQFSW FVDDVEVHTAQTQPREEQFNSTFRSVSELPIMHQDWLNGKEFKCRVNSAAFPAPIEKTISKTKGRPKAP QVYTIPPPKEQMAKDKVSLTCMITDFFPEDITVEWQWNGQPAENYKNTQPIMDTDGSYFVYSKLNVQKS NWEAGNTFTCSVLHEGLHNHHTEKSLSHSPGKSGGGGS*APTSSSTKKTQLQLEHLLLDLQMILNGINNY KNPKLTRMLTFKFYMPKKATELKHLQCLEEELKPLEEVLNLAQSKNFHLRPRDLISNINVIVLELKGSE TTFMCEYADETATIVEFLNRWITFCQSIISTLT* |
| 376 | 2D12-mkappa LC | QIVLTQSPAIMSASPGEKVTMTCSVSSSVREMHWYQQKSGTSPKRWIYDTSKLASGVPARFSGSGSGTS YSLTISSMEAEDAATYYCQQWSSNPPTFGGGTKLKIKRADAAPTVSIFPPSSEQLTSGGASVVCFLNNF YPKDINVKWKIDGSERQNGVLNSWTDQDSKDSTYSMSSTLTLTKDEYERHNSYTCEATHKTSTSPIVKS FNRNEC |
| 377 | hIL-2 Q126L | APTSSSTKKTQLQLEHLLLDLQMILNGINNYKNPKLTRMLTFKFYMPKKATELKHLQCLEEELKPLEEV LNLAQSKNFHLRPRDLISNINVIVLELKGSETTEMCEYADETATIVEFLNRWITFCLSIISTLT |
| 378 | hIL-2 Q126E | APTSSSTKKTQLQLEHLLLDLQMILNGINNYKNPKLTRMLTFKFYMPKKATELKHLQCLEEELKPLEEV LNLAQSKNFHLRPRDLISNINVIVLELKGSETTFMCEYADETATIVEFLNRWITFCESIISTLT |
| 379 | 1H3-hIgG1 HC | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKFN |

TABLE 29-continued

Sequences

| SEQ ID NO: | Name | Sequence |
|---|---|---|
| | | WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGK |
| 380 | huPD-1-Fc | MQIPQAPWPVVWAVLQLGWRPGWELDSPDRPWNPPTESPALLVVTEGDNATFTCSESNTSESFVLNWYR<br>MSPSNQTDKLAAFPEDRSQPGQDCRFRVTQLPNGRDFHMSVVRARRNDSGTYLCGAISLAPKAQIKESL<br>RAELRVTERRAEVPTAHPSPSPRPAGQFQIEGRMDPKSCDKTHTCPPCPAPELLGGPSVELFPPKPKDT<br>LMISRTPEVTCVVVDVSHEDPEVKENWYVDGVEVHNAKTKPREEQYNSTYRVVSVLTVLHQDWLNGKEY<br>KCKVSNKALPAPIEKTISKAKGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYTQKSLSLSPGK |
| 381 | cynomolgous-<br>PD-1-Fc | MQIPQAPWPVVWAVLQLGWRPGWFLESPDRPWNAPTFSPALLLVTEGDNATFTCSFSNASESFVLNWYR<br>MSPSNQTDKLAAFPEDRSQPGQDCRERVTRLPNGRDFHMSVVRARRNDSGTYLCGAISLAPKAQIKESL<br>RAELRVTERRAEVPTAHPSPSPRPAGQFQIEGRMDPKSCDKTHTCPPCPAPELLGGPSVFLFPPKPKDT<br>LMISRTPEVTCVVVDVSHEDPEVKENWYVDGVEVHNAKTKPREEQYNSTYRVVSVLTVLHQDWLNGKEY<br>KCKVSNKALPAPIEKTISKAKGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYTQKSLSLSPGK |
| 382 | 2H7 VH | GAGGTGCAGCTGCTGGAAAGCGGCGGCGGACTGGTGCAGCCTGGAGGCAGCCTGCGGCTGTCTTGTGCC<br>GCTTCTGGCTTCACCTTCAAGGACTACTGCATGACCTGGGTCCAGGCCCCTGGCAAGGGCCTCGAG<br>TGGGTGTCCGCCATCGTGTACAGCGGCGGGTCAACATACTACGCCGACAGCGTGAAGGGCAGATTCACA<br>ATCAGCAGAGATAACAGCAAGAACACCCTGTACCTGCAGATGAACAACCTGAGAGCTGAAGATACCGCC<br>GTGTACTACTGCGCCAAGTACACCAGAGCCAGCTACTTCTACGACGCCATGGACGTGTGGGGCCAGGGC<br>ACCACCGTGACAGTGTCCTCAT |
| 383 | 2H7 VL | GAGATCGTGCTGACCCAGTCTCCTGGCACCCTGAGCCTGAGCCCTGGCGAGAGAGCTACACTGTCATGC<br>AGAGCCTCTCAGAGCATCGGCAAGAGCTTCCTGGCCTGGTACCAGCAAAAGCCTGGACAGGCCCCTAGA<br>CTGCTGATCTACGACGCCAGCACCAGAGCCGCTGATATCCCCGCCAGATTCAGCGGATCTGGCAGCGGC<br>ACTGATTTCACCCTCACCATCAGCAGCCTGGAACCCGAGGACTTCGCCGTGTACTACTGCCAGCAGTAC<br>TACGACTGGCCCCCCCTGTCTTTTGGCGGAGGCACAAAGGTGGAAATCAAG |
| 384 | 2H7 VH | EVQLLESGGGLVQPGGSLRLSCAASGFTFKDYCMTWVRQAPGKGLEWVSAIVYSGGSTYYADSVKGRFT<br>ISRDNSKNTLYLQMNNLRAEDTAVYYCAKYTRASYFYDAMDVWGQGTTVTSS |
| 385 | 2H7 VL | EIVLTQSPGTLSLSPGERATLSCRASQSIGKSFLAWYQQKPGQAPRLLIYDASTRAADIPARFSGSGSG<br>TDFTLTISSLEPEDFAVYYCQQYYDWPPLSFGGGTKVEIK |
| 386 | 2H7 HCDR1 | GFTFKDYCMT |
| 387 | 2H7 HCDR2 | AIVYSGGSTYYADSVKG |
| 388 | 2H7 HCDR3 | YTRASYFYDAMDV |
| 389 | 2H7 LCDR1 | RASQSIGKSFLA |
| 390 | 2H7 LCDR2 | DASTRAA |
| 391 | 2H7 LCDR3 | QQYYDWPPLS |
| 392 | C51E6-5 VH | CAGGTTCAGCTGGTTCAGTCTGGCAGCGAGCTGAAGAAACCTGGCGCCTCTGTGAAGGTGTCCTGCAAG<br>GCCTCTGGCTACAGCCTGTACGGCACCTCTATGCACTGGGTCCGACAGGCTCCAGGACAGGGACTTGAG<br>TGGATGGGCTACATCAGCCCCTTTACCGGCAGAGCCACATACGCCCAGGGCTTCACAGGCAGATTCGTG<br>TTCAGCCTGGACACCAGCGTGTCCACAGCCTACCTGCAGATCAGCTCTCTGAAGGCCGAGGACACCGCC<br>GTGTACTACTGCGCCAGAGACTACGACTACCGGTACTACTATGCCATGGACTACTGGGGCCAGGGCACC<br>ACAGTTACAGTGTCCTCA |
| 393 | C51E6-5 VL | GAAATTGTGCTGACACAGAGCCCCGACTTCCAGAGCGTGACCCCTAAAGAAAAAGTGACCATCACCTGT<br>ACCGCCAGCGAGTCCGTGCCTCCTCAGTTCCTGCATTGGTATCAGCAGAAGCCCGATCAGAGCCCCAAG<br>CTGCTGATCTACGCCAGCAGAGAAAGAGCCAGCGGCGTCCCAAGCAGATTTTCTGGCTCTGGCAGCGGC<br>ACCGACTTCACCCTGACAATCAATAGCCTGGAAGCCGAGGACGCCGCCACCTACTACTGCCACCAGTTT<br>CACAGAAGCCCTCTGACCTTTGGCGGAGGCACCAAGCTGGAAATCAAG |
| 394 | C51E6-5 VH | QVQLVQSGSELKKPGASVKVSCKASGYSLYGTSMHWVRQAPGQGLEWMGYISPFTGRATYAQGFTGRFV<br>FSLDTSVSTAYLQISSLKAEDTAVYYCARDYDYRYYYAMDYWGQGTTVTSS |
| 395 | C51E6-5 VL | EIVLTQSPDFQSVTPKEKVTITCTASESVPPQFLHWYQQKPDQSPKLLIYASRERASGVPSRESGSGSG<br>TDFTLTINSLEAEDAATYYCHQFHRSPLTFGGGTKLEIK |
| 396 | C51E6-5 HCDR1 | GYSLYGTSMH |
| 397 | C51E6-5 HCDR2 | YISPFTGRATYAQGFTG |
| 398 | C51E6-5 HCDR3 | DYDYRYYYAMDY |
| 399 | C51E6-5 LCDR1 | TASESVPPQFLH |

TABLE 29-continued

Sequences

| SEQ ID NO: | Name | Sequence |
| --- | --- | --- |
| 400 | C51E6-5 LCDR2 | ASRERAS |
| 401 | C51E6-5 LCDR3 | HQFHRSPLT |
| 402 | A2 VH | GACGTGCAGCTGGTGGAAAGCGGCGGAGGCCTGGTCCAGCCCGGCGGCTCTCTGAGACTGAGCTGCGCC<br>GCCAGCGGCTTCACCTTCGACATCAGCGCCATGAGCTGGGTGCGGCAGGCCCCTGGCAAGGGCCTGGAA<br>TGGGTCAGCACAATCAGCGGATCTGCCTACAGCACCTACTACGCCGACAGCGTGAAGGGCAGATTCACC<br>ATCTCAAGAGATAACAGCAAGAGCACCCTGTACCTGCAGATGAACAGCCTGCGGGCCGAGGACACCGCC<br>GTGTACTACTGCGCCAGAGAGATCTTCAGCGACTACTGGGGCTTGGGCACCCTGGTGACAGTGTCCTCA |
| 403 | A2 VL | CAAAGCGTGCTGACACAGCCCCCCAGCGCTTCTGGCACCCCTGGCCAGAGAGTGACCATCTCATGCAGC<br>GGGTCAACAAGCAACATCGGCAGAGAGAGCGTGTACTGGTACCAGCAGCTGCCTGGAACCGCCCCTAAG<br>CTGCTGATCTACAGCAACGTGCAGCGGCCTAGCGGCGCCCCTAACAGATTCAGCGGCAGCAAGAGCGGC<br>ACCAGCGCCAGCCTGGCCATCAGCGGCCTGCAGAGCGAGGACGAGGCCGACTACTACTGCGGCACATGG<br>GACGACAGCCTGAACGGCTGGGTGTTCGGCGGCGGAACTAAGCTGACCGTCCTA |
| 404 | A2 VH | DVQLVESGGGLVQPGGSLRLSCAASGFTFDISAMSWVRQAPGKGLEWVSTISGSAYSTYYADSVKGRFT<br>ISRDNSKSTLYLQMNSLRAEDTAVYYCAREIFSDYWGLGTLVTVSS |
| 405 | A2 VL<br>(OMC479p1.A2VL) | QSVLTQPPSASGTPGQRVTISCSGSTSNIGRESVYWYQQLPGTAPKLLIYSNVQRPSGAPNRESGSKSG<br>TSASLAISGLQSEDEADYYCGTWDDSLNGWVFGGGTKLTVL |
| 406 | A2 HCDR1 | GFTFDISAMS |
| 407 | A2 HCDR2 | TISGSAYSTYYADSVKG |
| 408 | A2 HCDR3 | EIFSDY |
| 409 | A2 LCDR1 | SGSTSNIGRESVY |
| 410 | A2 LCDR2 | SNVQRPS |
| 411 | A2 LCDR3 | GTWDDSLNGWV |
| 412 | H7-767 HC | GAGGTGCAGCTGCTGGAAAGCGGCGGCGGCCTCGTGCAGCCTGGCGGATCTCTGCGGCTGAGCTGTGCT<br>GCCAGCGGCTTCACATTTAAATCCTACGCCATGCACTGGGTTAGACAAGCCCCCGGAAAGGGCCTGGAA<br>TGGGTGTCCGCCATCGTCTACAGCGGCGGATCTACATACTACGCCGACAGCGTGAAGGGCCGGTTCACC<br>ATCAGCAGAGATAATAGCAAGAACACCCTGTACCTGCAGATGAACAGCCTGAGAGCCGAGGACACCGCC<br>GTGTACTACTGCGCCAAGTACGACAGAGCTTCTTATTTCTACGATGCCATGGACGTGTGGGGCCAGGGC<br>ACCACCGTGACAGTGTCCTCAGCTAGCACCAAGGGCCCTAGCGTGTTTCCACTGGCCCCTAGCTCTAAA<br>AGCACAAGCGGCGGAACCGCCGCTCTGGGTTGTCTGGTGAAGGACTACTTCCCTGAGCCTGTGACCGTC<br>AGCTGGAACAGCGGCGCCCTGACCAGCGGCGTTCACACATTCCCCGCTGTGCTGCAGAGCTCTGGGCTG<br>TACAGCCTGAGCAGCGTGGTGACCGTGCCTTCTTCTTCTCTGGGCACACAAACATACATCTGCAACGTG<br>AACCACAAGCCCAGTAATACCAAAGTGGATAAGAAGGTGGAACCTAAGTCTTGCGACAAGACCCACACC<br>TGTCCTCCGTGCCCTGCTCCTGAACTGgctGGAgctCCCAGCGTGTTCCTGTTCCCCCCCAAACCTAAA<br>GACACCCTGATGATCAGCCGGACCCCTGAGGTGACCTGCGTGGTCGTCGACGTGTCCCACGAAGATCCT<br>GAGGTGAAGTTCAACTGGTACGTGGACGGCGTGGAAGTGCATAATGCCAAGACAAAGCCTAGAGAGGAA<br>CAGTACAACAGCACCTATAGAGTGGTGTCCGTGCTGACAGTGCTGCACCAGGACTGGCTGAACGGCAAG<br>GAATACAAGTGCAAGGTGTCCAACAAGGCCCTCCCCGCCCCTATCGAGAAGACCATCAGCAAGGCAAAG<br>GGCCAACCTAGAGAGCCCCAGGTGTACACCCTGCCTCCAAGCAGAGATGAGCTGACCAAGAACCAGGTT<br>AGCCTGACTTGTCTGGTGAAAGGCTTCTACCCCTCCGATATCGCCGTGGAATGGGAGAGCAACGGCCAG<br>CCTGAGAACAACTACAAGACCACACCTCCAGTGCTGGACAGCGACGGCAGCTTCTTCCTGTATAGCAAG<br>CTGACAGTGGACAAGAGCAGATGGCAGCAGGGCAACGTGTTCAGCTGCAGCGTCATGCACGAGGCCCTG<br>CACAACCACTACACCCAGAAGTCTCTGAGCCTGAGCCCTGGAAAGGCCCCTGCTTCTAGCAGCACCAAG<br>AAGACCCAGCTGCAGCTGGAACACCTGCTGCTGGCCCTGCAGATGATCCTGAACGGCATCAACAACTAC<br>AAGAACCCCAAGCTGACCGAGATGCTGACATTTAAGTTCTACATGCCTAAGAAAGCCACCGAGCTGAAG<br>CACCTGCAATGTCTGGAAGAAGAGCTGAAACCTCTGGAAGAGGTGCTGAATCTGGCTCAGTCAAAGAAC<br>TTCCACCTTAGACCTAGAGATCTGATCAGCAACATCAACGTGATCGTGCTGGAACTGAAGGGCAGCGAG<br>ACGACCTTCATGTGCGAGTACGCCGACGAGACAGCCACAATCGTGGAGTTCCTGAACAGATGGATCACC<br>TTCGCCCAGAGCATCATCTCCACCCTGACC |
| 413 | H7-767 LC | GAGATCGTGCTGACCCAGTCCCCAGGCACACTGAGCCTGAGCCCCGGCGAGCGGGCCACCCTGAGCTGT<br>AGAGCTAGCCAGAGCATCTCCAGCAGCTTCCTGGCCTGGTACCAGCAGAAACCTGGCCAGGCCCCTAGA<br>CTGCTGATCTACGACGCCTCTGATAGAGCTACAGGCATCCCCGACCGGTTCAGCGGCAGCGGATCTGGC<br>ACCGACTTCACCCTGACCATCAGCAGACTCGAGCCTGAAGATTTCGCCGTGTACTACTGCCAGCAATAC<br>TATGACTGGCCTCCTCTGTTTTTGGCGGCGGAACAAAGGTGGAAATTAAGCGTACGGTGGCGGCGCCC<br>AGCGTGTTCATCTTCCCACCCAGCGACGAGCAGCTGAAGTCCGGCACAGCCAGCGTGGTGTGCCTGCTG<br>AACAACTTCTACCCCCGCGAGGCCAAGGTGCAGTGGAAGGTGGACAACGCCCTGCAGAGCGGCAACAGC<br>CAGGAAAGCGTGACCGAGCAGGACAGCAAGGACTCCACCTACAGCCTGAGCAGCACCCTGACCCTGAGC<br>AAGGCCGACTACGAGAAGCACAAGGTGTACGCCTGCGAAGTGACCCACCAGGGCCTGTCCAGCCCCGTG<br>ACCAAGAGCTTCAACCGGGGCGAGTGC |

TABLE 29-continued

Sequences

| SEQ ID NO: | Name | Sequence |
|---|---|---|
| 414 | H7-632 HC CDRs solid underlined Constant region dashed underlined | EVQLLESGGGLVQPGGSLRLSCAASGFTFKSYAMHWVRQAPGKGLEWVSAIVYSGGSTYYADSVKGRFT ISRDNSKNTLYLQMNSLRAEDTAVYYCAKYDRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVELFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPG |
| 415 | H7-632 LC CDRs solid underlined Constant region dashed underlined | EIVLTQSPGTLSLSPGERATLSCRASQSISSSFLAWYQQKPGQAPRLLIYDASDRATGIPDRESGSGSG TDFTLTISRLEPEDFAVYYCQQYYDWPPLSFGGGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSSPV KSRWQEGNVFSCSVMHEALHNHYTQKSLSLSLGKSGGGGSAPTSSSTKKTQLQLEHLLLALQMILNGIN |
| 416 | H7-632 VH | EVQLLESGGGLVQPGGSLRLSCAASGFTFKSYAMHWVRQAPGKGLEWVSAIVYSGGSTYYADSVKGRFT ISRDNSKNTLYLQMNSLRAEDTAVYYCAKYDRASYFYDAMDVWGQGTTVTVSS |
| 417 | H7-632 VL | EIVLTQSPGTLSLSPGERATLSCRASQSISSSFLAWYQQKPGQAPRLLIYDASDRATGIPDRESGSGSG TDFTLTISRLEPEDFAVYYCQQYYDWPPLSFGGGTKVEIK |
| 418 | H7-632 HCDR1 | GFTFKSYAMH |
| 419 | H7-632 HCDR2 | AIVYSGGSTYYADSVKG |
| 420 | H7-632 HCDR3 | YDRASYFYDAMDV |
| 421 | H7-632 LCDR1 | RASQSISSSFLA |
| 422 | H7-632 LCDR2 | DASDRAT |
| 423 | H7-632 LCDR3 | QQYYDWPPLS |
| 424 | 2H7-hIgG4 HC | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVEPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 425 | 2H7-hkappa LC | EIVLTQSPGTLSLSPGERATLSCRASQSIGKSFLAWYQQKPGQAPRLLIYDASTRAADIPARESGSGSG TDFTLTISSLEPEDFAVYYCQQYYDWPPLSFGGGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSSPV TKSENRGEC |
| 426 | C51E6-5-hIgG4 HC | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDRYYYAMDYWGQGTTVTVSSASTKGPSVEPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLG |
| 427 | C51E6-5-hKappa LC | EIVLTQSPDFQSVTPKEKVTITCTASESVPPQFLHWYQQKPDQSPKLLIYASRERASGVPSRESGSGSG TDFTLTINSLEAEDAATYYCHQFHRSPLTFGGGTKLEIKRTVAAPSVFIFPPSDEQLKSGTASVVCLLN NFYPREAKVQWKVDNALQSGNSQESVTEQDSKDSTYSLSSTLTLSKADYEKHKVYACEVTHQGLSSPVT KSENRGEC |
| 428 | A2-hIgG4 HC | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVELFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |

TABLE 29-continued

Sequences

| SEQ ID NO: | Name | Sequence |
|---|---|---|
| 429 | A2-hLambda LC | QSVLTQPPSASGTPGQRVTISCSGSTSNIGRESVYWYQQLPGTAPKLLIYSNVQRPSGAPNRESGSKSG<br>TSASLAISGLQSEDEADYYCGTWDDSLNGWVFGGGTKLTVLGQPKAAPSVTLEPPSSEELQANKATLVC<br>LISDFYPGAVTVAWKADSSPVKAGVETTTPSKQSNNKYAASSYLSLTPEQWKSHRSYSCQVTHEGSTVE<br>KTVAPTECS |
| 430 | 2H7-hIgG4-df-hIL-2 (D20A/R38E) HC hIL-2 in italics | EVQLLESGGGLVQPGGSLRLSCAASGFTFKDYCMTWVRQAPGKGLEWVSAIVYSGGSTYYADSVKGRFT<br>ISRDNSKNTLYLQMNNLRAEDTAVYYCAKYTRASYFYDAMDVWGQGTTVTVSSASTKGPSVFPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFLGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTV<br>DKSRWQEGNVFSCSVMHEALHNHYTQKSLSLSLGK*APTSSSTKKTQLQLEHLLLALQMILNGINNYKNP*<br>*KLTEMLTFKFYMPKKATELKHLQCLEEELKPLEEVINLAQSKNFHLRPRDLISNINVIVLELKGSETTE*<br>*MCEYADETATIVEFLNRWITFCQSIISTLT* |
| 431 | H7-632-hIgG1-LAGA-df-hIL-2 (T3A/C125A) HC | EVQLLESGGGLVQPGGSLRLSCAASGFTFKSYAMHWVRQAPGKGLEWVSAIVYSGGSTYYADSVKGRFT<br>ISRDNSKNTLYLQMNSLRAEDTAVYYCAKYDRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVFLFPPKPKDTLMISRTPEVTCVVVDVSHEDP<br>EVKFNWYVDGVEVHNAKTKPREEQYNSTYRVVSVLTVLHQDWINGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGKAPASSSTKKTQLQLEHLLLDLQMIINGINNY<br>KNPKLTRMLTFKFYMPKKATELKHLQCLEEELKPLEEVINLAQSKNFHERPRDLISNINVIVLELKGSE<br>ITEMCEYADETATIVEFLNRWITFAQSIISTLT |
| 432 | C51E6-5-hIgG4-L6-hIL-2 (D20A/R38E) HC Linker in dashed underline hIL-2 in italics | QVQLVQSGSELKKPGASVKVSCKASGYSLYGTSMHWVRQAPGQGLEWMGYISPFTGRATYAQGFTGRFV<br>FSLDTSVSTAYLQISSLKAEDTAVYYCARDYDYRYYYAMDYWGQGTTVTVSSASTKGPSVFPLAPCSRS<br>TSESTAALGCLVKDYFPEPVTVSWNSGALTSGVHTFPAVLQSSGLYSLSSVVTVPSSSLGTKTYTCNVD<br>HKPSNTKVDKRVESKYGPPCPPCPAPEFLGGPSVFLFPPKPKDTLMISRTPEVTCVVVDVSQEDPEVQF<br>NWYVDGVEVHNAKTKPREEQFNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKTTPPVLDSDGSFFLYSRLTVD<br>KSRWQEGNVFSCSVMHEALHNHYTQKSLSLSLGKSGGGGS*APTSSSTKKTQLQLEHLLLALQMILNGIN*<br>-------<br>*NYKNPKLTEMLTFKFYMPKKATELKHLQCLEEELKPLEEVINLAQSKNFHLRPRDLISNINVIVLELKG*<br>*SETTEMCEYADETATIVEFLNRWITFCQSIISTLT* |
| 433 | A2-hIgG4-df-hIL-2 (D20A/R38E) HC hIL-2 in italics | DVQLVESGGGLVQPGGSLRLSCAASGFTFDISAMSWVRQAPGKGLEWVSTISGSAYSTYYADSVKGRFT<br>ISRDNSKSTLYLQMNSLRAEDTAVYYCAREIFSDYWGLGTLVTVSSASTKGPSVFPLAPCSRSTSESTA<br>ALGCLVKDYFPEPVTVSWNSGALTSGVHTFPAVLQSSGLYSLSSVVTVPSSSLGTKTYTCNVDHKPSNT<br>KVDKRVESKYGPPCPPCPAPEFLGGPSVFLFPPKPKDTLMISRTPEVTCVVVDVSQEDPEVQFNWYVDG<br>VEVHNAKTKPREEQFNSTYRVVSVLTVLHQDWLNGKEYKCKVSNKGLPSSIEKTISKAKGQPREPQVYT<br>LPPSQEEMTKNQVSLTCLVKGFYPSDIAVEWESNGQPENNYKTTPPVLDSDGSFFLYSRLTVDKSRWQE<br>GNVFSCSVMHEALHNHYTQKSLSLSLGK*APTSSSTKKTQLQLEHLLLALQMILNGINNYKNPKLTEMLT*<br>*FKFYMPKKATELKHLQCLEEELKPLEEVINLAQSKNFHLRPRDLISNINVIVLELKGSETTEMCEYADE*<br>*TATIVEFLNRWITFCQSIISTLT* |
| 434 | 1H3-hIgG4-df-hIL-2 (D20A/R38E) HC hIL-2 in italics | EVQLVESGGGLVQPGRSLKLSCAVSGFTFSDYAMAWVRQAPKKGLEWVATISYDGSRTYYRDSVKGRET<br>ISRDNAKITLYLMDSLRSEDTATYYCARHGSGYFDYWGQGVMVTVSSASTKGPSVFPLAPCSRSTSES<br>TAALGCLVKDYFPEPVTVSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFFLYSRLTVDKSRW<br>QEGNVFSCSVMHEALHNHYTQKSLSLSLGK*APTSSSTKKTQLQLEHLLLALQMILNGINNYKNPKLTEM*<br>*LTFKFYMPKKATELKHLQCLEEELKPLEEVINLAQSKNFHLRPRDLISNINVIVLELKGSETTEMCEYA*<br>*DETATIVEFLNRWITFCQSIISTLT* |
| 435 | 2H7-hIgG4-df-hIL-2 (T3A/D20A/R38E/C125A) HC hIL-2 in italics | EVQLLESGGGLVQPGGSLRLSCAASGFTFKDYCMTWVRQAPGKGLEWVSAIVYSGGSTYYADSVKGRFT<br>ISRDNSKNTLYLQMNNLRAEDTAVYYCAKYTRASYFYDAMDVWGQGTTVTVSSASTKGPSVEPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFLGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTV<br>DKSRWQEGNVFSCSVMHEALHNHYTQKSLSLSLGK*APASSSTKKTQLQLEHLLLALQMILNGINNYKNP*<br>*KLTEMLTFKFYMPKKATELKHLQCLEEELKPLEEVINLAQSKNFHLRPRDLISNINVIVLELKGSETTE*<br>*MCEYADETATIVEFLNRWITFAQSIISTLT* |
| 436 | hPD-1 extracellular domain | CCAGGATGGTTCTTAGACTCCCCAGACAGGCCCTGGAACCCCCCACCTTCTCCCCAGCCCTGCTCGTG<br>GTGACCGAAGGGGACAACGCCACCTTCACCTGCAGCTTCTCCAACACATCGGAGAGCTTCGTGCTAAAC<br>TGGTACCGCATGAGCCCCAGCAACCAGACGGACAAGCTGGCCGCCTTCCCCGAGGACCGCAGCCAGCC<br>GGCCAGGACTGCCGCTTCCGTGTCACACAACTGCCCAACGGGCGTGACTTCCACATGAGCGGTCAGG<br>GCCCGGCGCAATGACAGCGGCACCTACCTCTGTGGGGCATCTCCCTGGCCCCCAAGGCGCAGATCAAA<br>GAGAGCCTGCGGGCAGAGCTCAGGGTGACAGAGAGAAGGGCAGAAGTGCCCACAGCCCACCCCAGCCCC<br>TCACCCAGGCCAGCCGGCCAGTTCCAA |

TABLE 29-continued

Sequences

| SEQ ID NO: | Name | Sequence |
|---|---|---|
| 437 | hPD-1 extracellular domain HC | PGWFLDSPDRPWNPPTFSPALLVVTEGDNATFTCSFSNTSESFVLNWYRMSPSNQTDKLAAFPEDRSQP GQDCRFRVTQLPNGRDFHMSVVRARRNDSGTYLCGAISLAPKAQIKESLRAELRVTERRAEVPTAHPSP SPRPAGQFQ |
| 438 | OMC.1.B6-hIgG4 HC | EVQLLESGGGLVQPGGSLRLSCAASGFTESSNYMSWVRQAPGKGLEWVSAISSSGGTIFYADSVKGRFT ISRDNSKNTLYLQMNSLRAEDTAVYYCAKHKWNAVYYDGMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 439 | OMC.1.B6-hLambda LC | QSVLTQPPSASGTPGQRVTISCSGSNSNIGRNLVNWYQQLPGTAPKLLIYTIDQRPSGVPDRESGSKSG TSASLVISGLQSEDEADYYCAAWDGSLNAWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 440 | OMC.2.C6-hIgG4 HC | EVQLLESGGGLVQPGGSLRLSCTASGFTESSYEMQWVRQAPGKGLEWVLGITSSSSHIFYADSVKGRET VSRDNSKNTLYLQMNSLRAEDTAVYYCTKDLNSYYGLDVWGQGTTVTVSSASTKGPSVFPLAPCSRSTS ESTAALGCLVKDYFPEPVTVSWNSGALTSGVHTFPAVLQSSGLYSLSSVVTVPSSSLGTKTYTCNVDHK PSNTKVDKRVESKYGPPCPPCPAPEFLGGPSVFLFPPKPKDTLMISRTPEVTCVVVDVSQEDPEVQENW YVDGVEVHNAKTKPREEQFNSTYRVVSVLTVLHQDWLNGKEYKCKVSNKGLPSSIEKTISKAKGQPREP QVYTLPPSQEEMTKNQVSLTCLVKGFYPSDIAVEWESNGQPENNYKTTPPVLDSDGSFFLYSRLTVDKS RWQEGNVFSCSVMHEALHNHYTQKSLSLSLG |
| 441 | OMC.2.C6-hLambda LC | QSVMTQPPSASGTPGQRVTISCSGSTSNLGNNYVSWYQHLPGTAPKLLIYGNDQRPSGVPDRESGSKSG TSASLAISGLQSDDEADYYCSSWDASLNVWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 442 | OMC.1.D6-hIgG4 HC | EVQLLESGGGLVQPGGSLRLSCAASGFTFSDYYMSWVRQAPGKGLEWVSAISSSGGTIFYADSVKGRFI ISRDNSKNTLYLQMNSLRAEDTAVYYCAKHKWNDVYYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 443 | OMC.1.D6-hLambda LC | QSVLTQPPSASGTPGQRVTISCSGSNSNIGRNLVNWYQQLPGTAPKLLIYTVDQRPSGVPDRESGSKSG TSASLAISGLASEDEADYYCAAWDSSLNSWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 444 | D12-hIgG4 HC | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVELFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 445 | D12-hLambda LC | QSVLTQPPSASGTPGQRVTISCSGNTSNIGRESVYWYQQLPGTAPKLLIYSNVQRPSGVPDRESGSKSG TSASLAISGLQSEDEADYYCGTWDDSLNGWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 446 | G12-hIgG4 HC | DSLVESGGGLVQPGGSLRLSCAASGFTFDISAMSWVRQAPGKGLEWVSTISGSAYSTYYADSVKGRFTI SRDNSKSTLYLQMNSLRAEDTAVYYCAREIFSDYWGLGTLVTVSSASTKGPSVFPLAPCSRSTSESTAA LGCLVKDYFPEPVTVSWNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTISKAKGQPREPQVYTL PPSQEEMTKNQVSLTCLVKGFYPSDIAVEWESNGQPENNYKTTPPVLDSDGSFFLYSRLTVDKSRWQEG NVFSCSVMHEALHNHYTQKSLSLSLG |
| 447 | G12-hLambda LC | QSVLTQPPSASGTPGQRVTISCSGSTSNIGRESVYWYQQLPGTAPKLLIYLNSQRPSGVPDRESGSKSG TSASLAISGLQSEDVADYYCGTWDDSLNGWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 448 | pCMV6-hygro-HA-cyno-PD-1 (1-185) | aacaaaatattaacgcttacaatttccattcgccattcaggctgcgcaactgttgggaagggcgatcgg tgcgggcctcttcgctattacgccagctggcgaaaggggatgtgctgcaaggcgattaagttgggtaa cgccagggttttcccagtcacgacgttgtaaaacgacggccagtgccaagctgatctatacattgaatc aatattggcaattagccatattagtcattggttatatagcataaatcaatattggctattggccattgc atacgttgtatctatatcataatatgtacatttatattggctcatgtccaatatgaccgccatgttgac attgattattgactagttattaatagtaatcaattacggggtcattagttcatagcccatatatggagt |

TABLE 29-continued

Sequences

| SEQ ID NO: | Name | Sequence |
|---|---|---|
| | | tccgcgttacataacttacggtaaatggcccgcctggctgaccgcccaacgaccccgcccattgacgt |
| | | caataatgacgtatgttcccatagtaacgccaatagggactttccattgacgtcaatgggtggagtatt |
| | | tacggtaaactgcccacttggcagtacatcaagtgtatcatatgccaagtccgcccctattgacgtca |
| | | atgacggtaaatggcccgcctggcattatgcccagtacatgaccttacgggactttcctacttggcagt |
| | | acatctacgtattagtcatcgctattaccatggtgatgcggttttggcagtacaccaatgggcgtggat |
| | | agcggtttgactcacggggatttccaagtctccaccccattgacgtcaatgggagtttgttttggcacc |
| | | aaaatcaacgggactttccaaaatgtcgtaataaccccgccccgttgacgcaaatgggcggtaggcgtg |
| | | tacggtgggaggtctatataagcagagctcgtttagtgaaccgtcagaattttgtaatacgactcacta |
| | | tagggcggccgggaattcgtcgactggatccggtaccgaggagatctgccgccgcgatcgccggcgcgc |
| | | cagatctcaagcttatggacatgcgggtgccagcacaacttctcggattactattgttatggctgcgag |
| | | gtgcgcgctgttatccttacgacgtgcctgactacgcccaggatggttcttagagtccccagacaggc |
| | | cctggaacgccccccaccttctccccagccctgctcctggtgaccgaaggggacaacgccaccttcacct |
| | | gcagcttctccaacgcatcggagagcttcgtgctaaactggtacaggatgagcccagcaaccagacgg |
| | | acaagctggccgccttccccgaggaccgcagccagcccggccaggactgccgcttccgtgtcacacgcc |
| | | tgcccaacgggcgtgacttccacatgagcgtggtcagggcccggcgcaatgacagcggcacctacctct |
| | | gtgggccatctccctggcccccaaggcgcagatcaaggagagcctgcgggcagagctcagggtgacag |
| | | agaagggcagaagtgcccacagcccacccagccccctcacccaggccagccggccagttccaagccc |
| | | tggtggttggtgtcgtgggcggcctgctgggcagcctggtgctgctagtctgggtcctggccgtcatct |
| | | gctcccgcgccgcacaagggacaatagaagcaggcgcacctgacgcgttaagcggccgcactcgaggt |
| | | ttaaacggccggccgcggtcatagctgtttcctgaacagatcccgggtggcatccctgtgacccctccc |
| | | cagtgcctctcctggccctggaagttgccactccagtgcccaccagccttgtcctaataaaattaagtt |
| | | gcatcattttgtctgactaggtgtccttctataatattatggggtggaggggggtggtatggagcaagg |
| | | ggcaagttgggaagacaacctgtagggcctgcggggtctattgggaaccaagctggagtgcagtggcac |
| | | aatcttggctcactgcaatctccgcctcctgggttcaagcgattctcctgcctcagcctcccgagttgt |
| | | tgggattccaggcatgcatgaccaggctcagctaattttttgttttttggtagagacgggggtttcacca |
| | | tattggccaggctggtctccaactcctaatctcaggtgatctacccaccttggcctcccaaattgctgg |
| | | gattacaggcgtgaaccactgctcccttccctgtccttctgattttaaaataactataccagcaggagg |
| | | acgtccagacacagcataggctacctggccatgcccaaccggtgggacatttgagttgcttgcttggca |
| | | ctgtcctctcatgcgttgggtccactcagtagatgcctgttgaattgggtacgcggccagcttggctgt |
| | | ggaatgtgtgtcagttagggtgtggaaagtccccaggctccccagcaggcagaagtatgcaaagcatgc |
| | | atctcaattagtcagcaaccaggtgtggaaagtccccaggctcccagcaggcagaagtatgcaaagca |
| | | tgcatctcaattagtcagcaaccatagtcccgcccctaactccgcccatcccgcccctaactccgccca |
| | | gttccgcccattctccgccccatggctgactaattttttatttatgcagaggccgaggccgcctcgg |
| | | cctctgagctattccagaagtagtgaggaggcttttttggaggcctaggcttttgcaaaaagctcccgg |
| | | gagcttgtatatccatttttcggatctgatcaagagacacgtacgaccatgaaaaagcctgaactcaccg |
| | | cgacgtctgttgagaagtttctgatcgaaaagttcgacagcgtctccgacctgatgcagctctcggagg |
| | | gcgaagaatctcgtgctttcagcttcgatgtaggagggcgtggatatgtcctgcgggtaaatagctgcg |
| | | ccgatggtttctacaaagatcgttatgtttatcggcactttgcatcggccgcgctcccgattccgaag |
| | | tgcttgacattggggaatttagcgagagcctgacctattgcatctcccgccgtgcacagggtgtcacgt |
| | | tgcaagacctgcctgaaaccgaactgcccgctgttctgcaaccggtcgcggaggccatggatgcaatcg |
| | | ctgcggccgatcttagccagacgagcgggttcggtccattgcgaccgcaaggaatcggtcaatacacta |
| | | catggcgtgatttcatatgcgcgattgctgatccccatgtgtatcactggcaaactgtgatgacgaca |
| | | ccgtcagtgcgtccgtcgcgcaggctctcgatgagctgatgctttgggccgaggactgccccgaagtcc |
| | | ggcacctcgtgcacgcggatttcggctccaacaatgtcctgacggacaatggccgcataacagcggtca |
| | | ttgactggagcgaggcgatgttcggggattcccaatacgaggtcgccaacatcttcttctggaggccgt |
| | | ggttggcttgtatggagcagcagacgcgctacttcgagcggaggcatccggagcttgcaggatcgccgc |
| | | ggctccgggcgtatatgctccgcattggtcttgaccaactctatcagagcttggttgacggcaatttcg |
| | | atgatgcagcttgggcgcagggtcgatgcgacgcaatcgtccgatccggagccgggactgtcgggcgta |
| | | cacaaatcgcccgcagaagcgcggccgtctggaccgatggctgtgtagaagtactcgccgatagtggaa |
| | | accgacgccccagcactcgtccgagggcaaaggaatagctgcagcgggactctggggttcgaaatgacc |
| | | gaccaagcgacgcccaacctgccatcacgagatttcgattccaccgccgccttctatgaaaggttgggc |
| | | ttcggaatcgttttccgggacgccggctggatgatcctccagcgcggggatctcatgctggagttcttc |
| | | gcccaccccaacttgtttattgcagcttataatggttacaaataaagcaatagcatcacaaatttcaca |
| | | aataaagcatttttttcactgcattctagttgtggtttgtccaaactcatcaatgtatcttatcatgtc |
| | | tgtataccgtcgacctctagctagagcttggcgtaatcatggtcatagctgtttcctgtgtgaaattgt |
| | | tatccgctcacaattccacacaacatacgagccggaagcataaagtgtaaagcctggggtgcctaatga |
| | | gtgagctaactcacattaattgcgttgcgctcactgcccgctttccagtcgggaaacctgtcgtgccag |
| | | ctgcattaatgaatcggccaacgcggggagaggcggtttgcgtattgggcgctcttccgcttcctcg |
| | | ctcactgactcgctgcgctcggtcgttcggctgcggcgagcggtatcagctcactcaaaggcggtaata |
| | | cggttatccacagaatcaggggataacgcaggaaagaacatgtgagcaaaaggccagcaaaaggccagg |
| | | aaccgtaaaaaggccgcgttgctggcgtttttccataggctccgcccccctgacgagcatcacaaaaat |
| | | cgacgctcaagtcagaggtggcgaaacccgacaggactataaagataccaggcgtttccccctggaagc |
| | | tccctcgtgcgctctcctgttccgaccctgccgcttaccggatacctgtccgcctttctcccttcggga |
| | | agcgtggcgctttctcatagctcacgctgtaggtatctcagttcggtgtaggtcgttcgctccaagctg |
| | | ggctgtgtgcacgaaccccccgttcagcccgaccgctgcgccttatccggtaactatcgtcttgagtcc |
| | | aacccggtaagacacgacttatcgccactggcagcagccactggtaacaggattagcagagcgaggtat |
| | | gtaggcggtgctacagagttcttgaagtggtggcctaactacggctacactagaagaacagtatttggt |
| | | atctgcgctctgctgaagccagttaccttcggaaaaagagttggtagctcttgatccggcaaacaaacc |
| | | accgctggtagcggtggtttttttgtttgcaagcagcagattacgcgcagaaaaaaaggatctcaagaa |
| | | gatcctttgatcttttctacggggtctgacgctcagtggaacgaaaactcacgttaagggattttggtc |
| | | atgagattatcaaaaaggatcttcacctagatccttttaaattaaaaatgaagttttaaatcaatctaa |
| | | agtatatatgagtaaacttggtctgacagttaccaatgcttaatcagtgaggcacctatctcagcgatc |
| | | tgtctatttcgttcatccatagttgcctgactccccgtcgtgtagataactacgatacgggagggctta |
| | | ccatctggccccagtgctgcaatgataccgcgagacccacgctcaccggctccagatttatcagcaata |
| | | aaccagccagccggaagggccgagcgcagaagtggtcctgcaactttatccgcctccatccagtctatt |

TABLE 29-continued

Sequences

| SEQ ID NO: | Name | Sequence |
|---|---|---|
| | | aattgttgccgggaagctagagtaagtagttcgccagttaatagtttgcgcaacgttgttgccattgct<br>acaggcatcgtggtgtcacgctcgtcgtttggtatggcttcattcagctccggttcccaacgatcaagg<br>cgagttacatgatccccatgttgtgcaaaaaagcggttagctccttcggtcctccgatcgttgtcaga<br>agtaagttggccgcagtgttatcactcatggttatggcagcactgcataattctcttactgtcatgcca<br>tccgtaagatgcttttctgtgactggtgagtactcaaccaagtcattctgagaatagtgtatgcggcga<br>ccgagttgctcttgcccggcgtcaatacgggataataccgcgccacatagcagaactttaaaagtgctc<br>atcattggaaaacgttcttcggggcgaaaactctcaaggatcttaccgctgttgagatccagttcgatg<br>taacccactcgtgcacccaactgatcttcagcatcttttactttcaccagcgtttctgggtgagcaaaa<br>acaggaaggcaaaatgccgcaaaaaagggaataagggcgacacggaaatgttgaatactcatactcttc<br>cttttcaatattattgaagcatttatcagggttattgtctcatgagcggatacatatttgaatgtatt<br>tagaaaaataaacaatagggggttccgcgcacatttccccgaaaagtgccacctgacgcgccctgtagc<br>ggcgcattaagcgcggcgggtgtggtggttacgcgcagcgtgaccgctacacttgccagcgccctagcg<br>cccgctcctttcgctttcttcccttcctttctcgccacgttcgccggctttccccgtcaagctctaaat<br>cggggggctccctttagggttccgatttagtgctttacggcacctcgaccccaaaaaacttgattagggt<br>gatggttcacgtagtgggccatcgccctgatagacggtttttcgccctttgacgttggagtccacgttc<br>tttaatagtggactcttgttccaaactggaacaacactcaaccctatctcggtctattctttgattta<br>taagggattttgccgatttcggcctattggttaaaaaatgagctgatttaacaaaaatttaacgcgaat<br>ttt |
| 449 | Abz1mod-hIgG4 HC | QVQLVQSGSELKKPGASVKVSCKASGYTFTSYAMHWVRQAPGQGLEWMGYISPFTGRATYAQGFTGREV<br>FSLDTSVSTAYLQISSLKAEDTAVYYCARDYDRYYYAMDYWGQGTTVTVSSASTKGPSVFPLAPCSRS<br>TSESTAALGCLVKDYFPEPVTVSWNSGALTSGVHTFPAVLQSSGLYSLSSVVTVPSSSLGTKTYTCNVD<br>HKPSNTKVDKRVESKYGPPCPPCPAPEFLGGPSVFLFPPKPKDTLMISRTPEVTCVVVDVSQEDPEVQF<br>NWYVDGVEVHNAKTKPREEQFNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKTTPPVLDSDGSFFLYSRLTVD<br>KSRWQEGNVFSCSVMHEALHNHYTQKSLSLSLG |
| 450 | Abz1mod-hKappa LC | EIVLTQSPDFQSVTPKEKVTITCRASQSIPPQFLHWYQQKPDQSPKLLIKAASQRASGVPSRESGSGSG<br>TDFTLTINSLEAEDAATYYCHQFHSSPLTFGGGTKLEIKRTVAAPSVFIFPPSDEQLKSGTASVVCLLN<br>NFYPREAKVQWKVDNALQSGNSQESVTEQDSKDSTYSLSSTLTLSKADYEKHKVYACEVTHQGLSSPVT<br>KSENRGEC |
| 451 | Anti-hPD-1 #1-hIgG4-L6-hIL-2 (D20A/R38E) HC Linker in dashed underline hIL-2 in italics | QVQLVESGGGVVQPGRSLRLDCKASGITFSNSGMHWVRQAPGKGLEWVAVIWYDGSKRYYADSVKGRET<br>ISRDNSKNTLFLQMNSLRAEDTAVYYCATNDDYWGQGTLVTVSSASTKGPSVEPLAPCSRSTSESTAAL<br>GCLVKDYFPEPVTVSWNSGALTSGVHTFPAVLQSSGLYSLSSVVTVPSSSLGTKTYTCNVDHKPSNTKV<br>DKRVESKYGPPCPPCPAPEFLGGPSVFLFPPKPKDTLMISRTPEVTCVVVDVSQEDPEVQFNWYVDGVE<br>VHNAKTKPREEQFNSTYRVVSVLTVLHQDWLNGKEYKCKVSNKGLPSSIEKTISKAKGQPREPQVYTLP<br>PSQEEMTKNQVSLTCLVKGFYPSDIAVEWESNGQPENNYKTTPPVLDSDGSFFLYSRLTVDKSRWQEGN<br>KSRWQEGNVFSCSVMHEALHNHYTQKSLSLSLGK<u>SGGGGS</u>*APTSSSTKKTQLQLEHLLLALQMILNGIN*<br>*EMLTFKFYMPKKATELKHLQCLEEELKPLEEVLNLAQSKNFHLRPRDLISNINVIVLELKGSETTEMCE*<br>*YADETATIVEFLNRWITFCQSIISTLT* |
| 452 | Anti-hPD-1 #1-hKappa LC | EIVLTQSPATLSLSPGERATLSCRASQSVSSYLAWYQQKPGQAPRLLIYDASNRATGIPARESGSGSGT<br>DFTLTISSLEPEDFAVYYCQQSSNWPRTFGQGTKVEIKRTVAAPSVFIFPPSDEQLKSGTASVVCLLNN<br>FYPREAKVQWKVDNALQSGNSQESVTEQDSKDSTYSLSSTLTLSKADYEKHKVYACEVTHQGLSSPVTK<br>SENRGEC |
| 453 | OMC.1.B6-hIgG4-L6-hIL-2 (D20A/R38E) HC Linker in dashed underline hIL-2 in italics | EVQLLESGGGLVQPGGSLRLSCAASGFTESSNYMSWVRQAPGKGLEWVSAISSSGGTIFYADSVKGRET<br>ISRDNSKNTLYLQMNSLRAEDTAVYYCAKHKWNAVYYDGMDVWGQGTTVTVSSASTKGPSVFPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFLGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTV<br>VFSCSVMHEALHNHYTQKSLSLSLGK<u>SGGGGS</u>*APTSSSTKKTQLQLEHLLLALQMILNGINNYKNPKLT*<br>*NNYKNPKLTEMLTFKFYMPKKATELKHLQCLEEELKPLEEVLNLAQSKNFHLRPRDLISNINVIVLELK*<br>*GSETTEMCEYADETATIVEFLNRWITFCQSIISTLT* |
| 454 | OMC.2.C6-hIgG4-L6-hIL-2 (D20A/R38E) HC Linker in dashed underline hIL-2 in italics | EVQLLESGGGLVQPGGSLRLSCTASGFTSSYEMQWVRQAPGKGLEWVLGITSSSSHIFYADSVKGRET<br>VSRDNSKNTLYLQMNSLRAEDTAVYYCTKDLNSYYGLDVWGQGTTVTVSSASTKGPSVEPLAPCSRSTS<br>ESTAALGCLVKDYFPEPVTVSWNSGALTSGVHTFPAVLQSSGLYSLSSVVTVPSSSLGTKTYTCNVDHK<br>PSNTKVDKRVESKYGPPCPPCPAPEFLGGPSVFLFPPKPKDTLMISRTPEVTCVVVDVSQEDPEVQENW<br>YVDGVEVHNAKTKPREEQFNSTYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTPPVLDSDGSFFLYSRLTVDKS<br>RWQEGNVFSCSVMHEALHNHYTQKSLSLSLGK<u>SGGGGS</u>*APTSSSTKKTQLQLEHLLLALQMILNGINNY*<br>*KNPKLTEMLTFKFYMPKKATELKHLQCLEEELKPLEEVLNLAQSKNFHLRPRDLISNINVIVLELKGSE*<br>*TTFMCEYADETATIVEFLNRWITFCQSIISTLT* |
| 455 | OMC.1.D6-hIgG4-L6-hIL-2 (D20A/R38E) HC Linker in dashed | EVQLLESGGGLVQPGGSLRLSCAASGFTSDYYMSWVRQAPGKGLEWVSAISSSGGTIFYADSVKGRFI<br>ISRDNSKNTLYLQMNSLRAEDTAVYYCAKHKWNDVYYDAMDVWGQGTTVTVSSASTKGPSVFPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFLGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP |

TABLE 29-continued

Sequences

| SEQ ID NO: | Name | Sequence |
|---|---|---|
| | underline hIL-2 in italics | REPQVYTLPPSQEEMTKNQVSLTCLVKGFYPSDIAVEWESNGQPENNYKTTPPVLDSDGSFFLYSRLTV RWQEGNVFSCSVMHEALHNHYTQKSLSLSLGK<u>GGGGS</u>*APTSSSTKKTQLQLEHLLLALQMILNGINNY NNYKNPKLTEMLTFKFYMPKKATELKHLQCLEEELKPLEEVLNLAQSKNFHLRPRDLISNINVIVLELK GSETTEMCEYADETATIVEFLNRWITFCQSIISTLT* |
| 456 | D12-hIgG4-df-hIL-2 (D20A/R38E) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVEPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLALQMILNGINNYKNPKLTEMLT FKFYMPKKATELKHLQCLEEELKPLEEVLNLAQSKNFHLRPRDLISNINVIVLELKGSETTEMCEYADE TATIVEFLNRWITFCQSIISTLT* |
| 457 | G12-hIgG4-df-hIL-2 (D20A/R38E) HC hIL-2 in italics | DSLVESGGGLVQPGGSLRLSCAASGFTFDISAMSWVRQAPGKGLEWVSTISGSAYSTYYADSVKGRFTI SRDNSKSTLYLQMNSLRAEDTAVYYCAREIFSDYWGLGTLVTVSSASTKGPSVFPLAPCSRSTSESTAA LGCLVKDYFPEPVTVSWNSGALTSGVHTFPAVLQSSGLYSLSSVVTVPSSSLGTKTYTCNVDHKPSNTK VDKRVESKYGPPCPPCPAPEFLGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTISKAKGQPREPQVYTL PPSQEEMTKNQVSLTCLVKGFYPSDIAVEWESNGQPENNYKTTPPVLDSDGSFFLYSRLTVDKSRWQEG NVFSCSVMHEALHNHYTQKSLSLSLGK*APTSSSTKKTQLQLEHLLLALQMILNGINNYKNPKLTEMLTE KFYMPKKATELKHLQCLEEELKPLEEVLNLAQSKNFHLRPRDLISNINVIVLELKGSETTEMCEYADET ATIVEFLNRWITFCQSIISTLT* |
| 458 | 2H7-hIgG4-LE HC | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFEGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 459 | 2H7-hIgG4-LAGA HC | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFAGAPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 460 | OMC.2-A3-hIgG4/A HC | EVQLLESGGCLVQPGGSLRLSCAASGFTESDYYMSWVRQAPGKGLEWVSAISSSGGTIFYADSVKGRFI ISRDNSKNTLYLQMNSLRAEDTAVYYCAKHKWNDVYYDAMDVWGQGTTVTVSSASTKGPSVEPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 461 | OMC476pH7-hIgG4 HC | DMQLVESGGGVVRPGESLRLSCTASGFTFSISAMSWVRQAPGKGLEWVSAISGTAYSTYYADSVRGRET ISRDNSKNTLYLQMNSLRAEDTAVYYCAKDNFFDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 462 | OMC476pB11.H7 LC | QSVMTQPPSASGTPGQRVTISCSGVTSNIGSNSVYWYQQLPGTAPKLLIYLNSQRPSGVPDRESGSKSG TSASLAISGLQSEDEADYYCGTWDDSLNGWVFGGGTKLTVLGQPKAAPSVTLFPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 463 | OMC476pB11-hIgG4 HC | DVQLVESGGGVVRPGESLRLSCTASGFTFSISAMSWVRQAPGKGLEWVSAISGTAYSTYYADSVRGRET ISRDNSKNTLYLQMNSLRAEDTAVYYCAKDNFFDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 464 | OMC476pG10-hIgG4 HC | DVQLVESGGGVVRPGGSLRLSCAASGFTFSIYAMSWVRQAPGEGLEWVSHISASGGSTYYADSVKGRFA ISRDNSKNTLYLQMNSLRAEDTAVYYCTTNLGSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG |

TABLE 29-continued

Sequences

| SEQ ID NO: | Name | Sequence |
|---|---|---|
| | | VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 465 | OMC476pH10- hIgG4 HC | DVQLVESGGGVVRPGGSLRLSCAASGFTFSIYAVSWVRQAPGEGLEWVSHISASGGSTYYADSVKGRFA ISRDNSKNTLYLQMNSLRAEDTAVYYCTTNLGSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 466 | OMC476pG10.H10 LC | QSVLTQPPSASGTPGQRVTISCSGSYSDIGTNYVYWYQQLPGTAPKLLIFATDRRPSGVPDRESGSKSG TSASLAISGLQSEDEADYYCGTWDDSLNVWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 467 | OMC476pE4- hIgG4 HC | DVQLVESGGGVVRPGESLRLSCAASGFTFSTDAMGWVRQAPGEGLEWVSLISGSGYSTYYADSVKGRFT ISRDNSKNTLYLQMNSLTAEDTAVYYCAKNSLAFFDYWGLGTLVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLG |
| 468 | OMC476pE4 LC | QSVLTQPPSASGTPGQRVTISCSGGSSNIGRESVNWYQQLPGTAPKLLIYSTDRRPSGVPDRESGSKSG TSASLAISGLQSEDEADYYCGTWDNDLNGWVFGGGTKLTVLGQPKAAPSVTLEPPSSEELQANKATLVC LISDFYPGAVTVAWKADSSPVKAGVETTTPSKQSNNKYAASSYLSLTPEQWKSHRSYSCQVTHEGSTVE KTVAPTECS |
| 469 | J110-hIgG1 HC | DVQLQESGPGLVKPSQSLSLTCTVTGHSITSDYAWNWIRQFPGDKLEWMGYISYSGYTTYNPSLKSRVS ITRDTSKNQFFLQLNSVTTEDTATYFCARDLDYGPWFAYWGQGTLVTVSAASTKGPSVFPLAPSSKSTS GGTAALGCLVKDYFPEPVTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALPAPIEKTISKAKGQP REPQVYTLPPSRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 470 | J110-hKappa LC | DIQMTQSPASLSASVGETVTLTCRASENIHNYLAWYQQKQGKSPQLLVYNVKTLADGVPSRFSGSGSGT QYSLKINSLQPEDFGSYYCQHFWSSPWTFGGGTKVEIKRTVAAPSVFIFPPSDEQLKSGTASVVCLLNN FYPREAKVQWKVDNALQSGNSQESVTEQDSKDSTYSLSSTLTLSKADYEKHKVYACEVTHQGLSSPVTK SENRGEC |
| 471 | 2H7-hIgG1- LAGA-df-hIL-2 (T3A/D20A/R38E/ C125A) HC hIL2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVELFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK*APASSSTKKTQLQLEHLLLALQMILNGINNY KNPKLTEMLTFKFYMPKKATELKHLQCLEEELKPLEEVLNLAQSKNFHLRPRDLISNINVIVLELKGSE TTFMCEYADETATIVEFLNRWITFAQSIISTLT* |
| 472 | 2H7-hIgG4-LE- df-hIL-2 (T3A/D20A/R38E/ C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFEGGPSVELFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGK*APASSSTKKTQLQLEHLLLALQMILNGINNYKNP KLTEMLTFKFYMPKKATELKHLQCLEEELKPLEEVLNLAQSKNFHLRPRDLISNINVIVLELKGSETTE MCEYADETATIVEFLNRWITFAQSIISTLT* |
| 473 | 2H7-hIgG1- LAGA--df-hIL-2 (T3A/D20A/R38E/ C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVEPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFAGAPSVELFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGK*APASSSTKKTQLQLEHLLLALQMILNGINNYKNP KLTEMLTFKFYMPKKATELKHLQCLEEELKPLEEVLNLAQSKNFHLRPRDLISNINVIVLELKGSETTE MCEYADETATIVEFLNRWITFAQSIISTLT* |

TABLE 29-continued

Sequences

| SEQ ID NO: | Name | Sequence |
|---|---|---|
| 474 | 2H7-hIgG1-LAGA-df-hIL-2 (T3A/R38E/I92K/C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGKA*PASSSSTKKTQLQLEHLLLDLQMILNGINNY KNPKLTEMLTFKFYMPKKATELKHLQCLEEEELKPLEEVLNLAQSKNFHLRPRDLISNINVKVLELKGSE TTFMCEYADETATIVEFLNRWITFAQSIISTLT* |
| 475 | 2H7-hIgG4-LE-df-hIL-2 (T3A/R38E/I92K/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFEGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGKA*PASSSSTKKTQLQLEHLLLDLQMILNGINNYKNP KLTEMLTFKFYMPKKATELKHLQCLEEEELKPLEEVLNLAQSKNFHLRPRDLISNINVKVLELKGSETTE MCEYADETATIVEFLNRWITFAQSIISTLT* |
| 476 | 2H7-hIgG4-LAGA-df-hIL-2 (T3A/R38E/I92K/C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFAGAPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGKA*PASSSSTKKTQLQLEHLLLDLQMILNGINNYKNP KLTEMLTFKFYMPKKATELKHLQCLEEEELKPLEEVLNLAQSKNFHLRPRDLISNINVKVLELKGSETTE MCEYADETATIVEFLNRWITFAQSIISTLT* |
| 477 | 2H7-hIgG1-LAGA-df-hIL-2 (T3A/R38E/D84K/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVFLFPPKPKDTLMISRTPEVTCVVVDVSHEDP EVKENWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGKA*PASSSSTKKTQLQLEHLLLDLQMILNGINNY KNPKLTEMLTFKFYMPKKATELKHLQCLEEEELKPLEEVLNLAQSKNFHLRPRKLISNINVIVLELKGSE TTFMCEYADETATIVEFLNRWITFAQSIISTLT* |
| 478 | 2H7-hIgG4-LE-df-hIL-2 (T3A/R38E/D84K/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVEPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFEGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGKA*PASSSSTKKTQLQLEHLLLDLQMILNGINNYKNP KLTEMLTFKFYMPKKATELKHLQCLEEEELKPLEEVLNLAQSKNFHLRPRKLISNINVIVLELKGSETTE MCEYADETATIVEFLNRWITFAQSIISTLT* |
| 479 | 2H7-hIgG4-LAGA-df-hIL-2 (T3A/R38E/D84K/C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFAGAPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGKA*PASSSSTKKTQLQLEHLLLDLQMILNGINNYKNP KLTEMLTFKFYMPKKATELKHLQCLEEEELKPLEEVLNLAQSKNFHLRPRKLISNINVIVLELKGSETTE MCEYADETATIVEFLNRWITFAQSIISTLT* |
| 480 | 1H3-hIgG4-df-hIL-2 (WT) HC hIL-2 in italics | EVQLVESGGGLVQPGRSLKLSCAVSGFTFSDYAMAWVRQAPKKGLEWVATISYDGSRTYYRDSVKGRET ISRDNAKITLYLQMDSLRSEDTATYYCARHGSGYFDYWGQGVMVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKA*PTSSSTKKTQLQLEHLLLDLQMILNGINNYKNPKLTRM LTFKFYMPKKATELKHLQCLEEEELKPLEEVLNLAQSKNFHLRPRDLISNINVIVLELKGSETTEMCEYA DETATIVEFLNRWITFCQSIISTLT* |
| 481 | 1H3-hIgG4-L6-hIL-2 (WT) HC Linker in dashed | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV |

TABLE 29-continued

Sequences

| SEQ ID NO: | Name | Sequence |
|---|---|---|
| | underline hIL-2 in italics | DGVEVHNAKTKPREEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFFLYSRLTVDKSRW<br>QEGNVFSCSVMHEALHNHYTQKSLSLSLGKSGGGGS*APTSSSTKKTQLQLEHLLLDLQMILNGINNYKN*<br>*PKLTRMLTFKFYMPKKATELKHLQCLEEELKPLEEVLNLAQSKNFHLRPRDLISNINVIVLELKGSETT*<br>*FMCEYADETATIVEFLNRWITFCQSIISTLT* |
| 482 | 1H3-hIgG4 HC | EVQLVESGGGLVQPGRSLKLSCAVSGFTESDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPCSRSTSES<br>TAALGCLVKDYFPEPVTVSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFFLYSRLTVDKSRW<br>QEGNVFSCSVMHEALHNHYTQKSLSLSLG |
| 483 | 1H3-hKappa-df-hIL-2 (WT) LC hIL-2 in italics | DTVLTQSPALAVSPGERVTISCRASESVRTGVHWYQQKPGQQPKLLIYGASNLESGVPARFSGSGSGTD<br>FTLTIDPVEADDTATYFCQQSWNDPFTGSGTKLEIKRTVAAPSVFIFPPSDEQLKSGTASVVCLLNNE<br>YPREAKVQWKVDNALQSGNSQESVTEQDSKDSTYSLSSTLTLSKADYEKHKVYACEVTHQGLSSPVTKS<br>FNRGEC*APTSSSTKKTQLQLEHLLLDLQMILNGINNYKNPKLTRMLTEKFYMPKKATELKHLQCLEEEL*<br>*KPLEEVLNLAQSKNFHLRPRDLISNINVIVLELKGSETTEMCEYADETATIVEFLNRWITFCQSIISTL*<br>*T* |
| 484 | 1H3-hKappa-L6-hIL-2 (WT) LC Linker in dashed underline hIL-2 in italics | DTVLTQSPALAVSPGERVTISCRASESVRTGVHWYQQKPGQQPKLLIYGASNLESGVPARFSGSGSGTD<br>FTLTIDPVEADDTATYFCQQSWNDPFTGSGTKLEIKRTVAAPSVFIFPPSDEQLKSGTASVVCLLNNE<br>YPREAKVQWKVDNALQSGNSQESVTEQDSKDSTYSLSSTLTLSKADYEKHKVYACEVTHQGLSSPVTKS<br>FNRGECSGGGGS*APTSSSTKKTQLQLEHLLLDLQMILNGINNYKNPKLTRMLTFKFYMPKKATELKHLQ*<br>*CLEEELKPLEEVLNLAQSKNFHLRPRDLISNINVIVLELKGSETTEMCEYADETATIVEFLNRWITECQ*<br>*SIISTLT* |
| 485 | 1H3-hIgG4-L6-hIL-2 (D20Y) HC Linker in dashed underline hIL-2 in italics | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPCSRSTSES<br>TAALGCLVKDYFPEPVTVSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFFLYSRLTVDKSRW<br>QEGNVFSCSVMHEALHNHYTQKSLSLSLGKSGGGGS*APTSSSTKKTQLQLEHLLLDLQMILNGINNYKN*<br>*PKLTRMLTFKFYMPKKATELKHLQCLEEELKPLEEVLNLAQSKNFHLRPRDLISNINVIVLELKGSETT*<br>*FMCEYADETATIVEFLNRWITFCQSIISTLT* |
| 486 | 1H3-hIgG4-df-hIL-2 (D20Y) HC hIL-2 in italics | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPCSRSTSES<br>TAALGCLVKDYFPEPVTVSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCVVVDVSQEDPEVQNWYV<br>DGVEVHNAKTKPREEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFFLYSRLTVDKSRW<br>QEGNVFSCSVMHEALHNHYTQKSLSLSLGK*APTSSSTKKTQLQLEHLLLYLQMILNGINNYKNPKLTRM*<br>*LTFKFYMPKKATELKHLQCLEEELKPLEEVLNLAQSKNFHLRPRDLISNINVIVLELKGSETTEMCEYA*<br>*DETATIVEFLNRWITFCQSIISTLT* |
| 487 | 1H3-hIgG1-df-hIL-2 (D20Y) HC hIL-2 in italics | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGK*APTSSSTKKTQLQLEHLLLYLQMILNGINNYKNPKL*<br>*TRMLTFKFYMPKKATELKHLQCLEEELKPLEEVLNLAQSKNFHLRPRDLISNINVIVLELKGSETTMC*<br>*EYADETATIVEFLNRWITFCQSIISTLT* |
| 488 | 1H3-hIgG4-L6-hIL-2 (D20A/R38P) HC Linker in dashed underline hIL-2 in italics | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPCSRSTSES<br>TAALGCLVKDYFPEPVTVSWNSGALTSGVHTFPAVLQSSGLYSLSSVVTVPSSSLGTKTYTCNVDHKPS<br>NTKVDKRVESKYGPPCPPCPAPEFLGGPSVELFPPKPKDTLMISRTPEVTCVVVDVSQEDPEVQENWYV<br>DGVEVHNAKTKPREEQFNSTYRVVSVLTVLHQDWLNGKEYKCKVSNKGLPSSIEKTISKAKGQPREPQV<br>YTLPPSQEEMTKNQVSLTCLVKGFYPSDIAVEWESNGQPENNYKTTPPVLDSDGSFFLYSRLTVDKSRW<br>QEGNVFSCSVMHEALHNHYTQKSLSLSLGKSGGGGS*APTSSSTKKTQLQLEHLLLDLQMILNGINNYKN*<br>*PKLTPMLTFKFYMPKKATELKHLQCLEEELKPLEEVLNLAQSKNFHLRPRDLISNINVIVLELKGSETT*<br>*FMCEYADETATIVEFLNRWITFCQSIISTLT* |

TABLE 29-continued

Sequences

| SEQ ID NO: | Name | Sequence |
|---|---|---|
| 489 | 1H3-hIgG4-L6-hIL-2 (D20A/R38S) HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGS*APTSSSTKKTQLQLEHLLLDLQMILNGINNYKN* *PKLTSMLTEKFYMPKKATELKHLQCLEEELKPLEEVLNLAQSKNFHLRPRDLISNINVIVLELKGSETT FMCEYADETATIVEFLNRWITFCQSIISTLT* |
| 490 | 1H3-hIgG4-L6-hIL-2 (D20A/R38D) HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGS*APTSSSTKKTQLQLEHLLLDLQMILNGINNYKN* *PKLTDMLTEKFYMPKKATELKHLQCLEEELKPLEEVLNLAQSKNFHLRPRDLISNINVIVLELKGSETT FMCEYADETATIVEFLNRWITFCQSIISTLT* |
| 491 | 1H3-hIgG4-L6-hIL-2 (D20A/R38Q/ E95A) HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGS*APTSSSTKKTQLQLEHLLLDLQMILNGINNYKN PKLTQMLTFKFYMPKKATELKHLQCLEEELKPLEEVLNLAQSKNFHLRPRDLISNINVIVLALKGSETT FMCEYADETATIVEFLNRWITFCQSIISTLT* |
| 492 | 1H3-hIgG4-L6-hIL-2 (D20A/F42H/ E95A) HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGS*APTSSSTKKTQLQLEHLLLDLQMILNGINNYKN PKLTRMLTHKFYMPKKATELKHLQCLEEELKPLEEVLNLAQSKNFHLRPRDLISNINVIVLALKGSETT FMCEYADETATIVEFLNRWITFCQSIISTLT* |
| 493 | 1H3-hIgG4-L6-hIL-2 (R38D/I92D) HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGS*APTSSSTKKTQLQLEHLLLDLQMILNGINNYKN* *PKLTDMLTFKFYMPKKATELKHLQCLEEELKPLEEVLNLAQSKNFHLRPRDLISNINVDVLELKGSETT FMCEYADETATIVEFLNRWITFCQSIISTLT* |
| 494 | 1H3-hIgG4-L6-hIL-2 (R38E/I92D) HC Linker in dashed underline hIL-2 in italics | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGS*APTSSSTKKTQLQLEHLLLDLQMILNGINNYKN* *PKLTEMLTFKFYMPKKATELKHLQCLEEELKPLEEVLNLAQSKNFHLRPRDLISNINVDVLELKGSETT FMCEYADETATIVEFLNRWITFCQSIISTLT* |
| 495 | 1H3-hIgG4-L6-hIL-2 (F42H/I92D) HC Linker in | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVELFPPKPKDTLMISRTPEVTCVVVDVSQEDPEVQENWYV |

TABLE 29-continued

Sequences

| SEQ ID NO: | Name | Sequence |
|---|---|---|
| | dashed underline hIL-2 in | DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGSAPTSSSTKKTQLQLEHLLLDLQMILNGINNYKN |
| | italics | PKLTRMLTHKFYMPKKATELKHLQCLEEELKPLEEVLNLAQSKNFHLRPRDLISNINVDVLELKGSETT FMCEYADETATIVEFLNRWITFCQSIISTLT |
| 496 | 1H3-hIgG4-L6-hIL-2 (D20A/R38E) HC Linker in dashed underline hIL-2 in | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGSAPTSSSTKKTQLQLEHLLLDLQMILNGINNYKN |
| | italics | PKLTEMLTFKFYMPKKATELKHLQCLEEELKPLEEVLNLAQSKNFHLRPRDLISNINVIVLELKGSETT FMCEYADETATIVEFLNRWITFCQSIISTLT |
| 497 | 1H3-hIgG4-L6-hIL-2 (T3A/D20A/R38E) HC Linker in dashed underline | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGSAPTSSSTKKTQLQLEHLLLALQMILNGINNYKN |
| | hIL-2 in italics | PKLTEMLTFKFYMPKKATELKHLQCLEEELKPLEEVLNLAQSKNFHLRPRDLISNINVIVLELKGSETT FMCEYADETATIVEFLNRWITFCQSIISTLT |
| 498 | 1H3-hIgG4-L6-hIL-2 (D20A/R38E/C125A) HC Linker in dashed underline | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGSAPTSSSTKKTQLQLEHLLLALQMILNGINNYKN |
| | hIL-2 in italics | PKLTEMLTFKFYMPKKATELKHLQCLEEELKPLEEVLNLAQSKNFHLRPRDLISNINVIVLELKGSETT FMCEYADETATIVEFLNRWITFAQSIISTLT |
| 499 | 1H3-hIgG4-L6-hIL-2 (T3A/D20A/R38E/C125A) HC Linker in dashed underline | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVEPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKSGGGGSAPTSSSTKKTQLQLEHLLLALQMILNGINNYKN |
| | hIL-2 in italics | PKLTEMLTFKFYMPKKATELKHLQCLEEELKPLEEVLNLAQSKNFHLRPRDLISNINVIVLELKGSETT FMCEYADETATIVEFLNRWITFAQSIISTLT |
| 500 | 1H3-hIgG1-L6-hIL-2 (D20A/R38E) HC Linker in dashed underline hIL-2 in | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMLNCEC |
| | italics | YKNPKLTEMLTFKFYMPKKATELKHLQCLEEELKPLEEVLNLAQSKNFHLRPRDLISNINVIVLELKGS ETTEMCEYADETATIVEFLNRWITFCQSIISTLT |
| 501 | 1H3-hIgG1-L6-hIL-2 (T3A/D20A/R38E) HC Linker in dashed underline | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMLNCEC |
| | hIL-2 in italics | YKNPKLTEMLTFKFYMPKKATELKHLQCLEEELKPLEEVLNLAQSKNFHLRPRDLISNINVIVLELKGS ETTEMCEYADETATIVEFLNRWITFCQSIISTLT |
| 502 | 1H3-hIgG1-L6-hIL-2 (D20A/R38E/C12 | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS |

TABLE 29-continued

Sequences

| SEQ ID NO: | Name | Sequence |
|---|---|---|
|  | 5A) HC Linker in dashed underline | NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMLNCEC |
|  | hIL-2 in italics | *YKNPKLTEMLTFKFYMPKKATELKHLQCLEEELKPLEEVLNLAQSKNEHLRPRDLISNINVIVLELKGS ETTEMCEYADETATIVEFLNRWITFAQSIISTLT* |
| 503 | 1H3-hKappa-df-hIL-2 (D20A/R38E) LC hIL-2 in italics | DTVLTQSPALAVSPGERVTISCRASESVRTGVHWYQQKPGQQPKLLIYGASNLESGVPARFSGSGSGTD FTLTIDPVEADDTATYFCQQSWNDPFTFGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGECA*PTSSSTKKTQLQLEHLLLALQMILNGINNYKNPKLTEMLTFKFYMPKKATELKHLQCLEEEL KPLEEVLNLAQSKNFHLRPRDLISNINVIVLELKGSETTEMCEYADETATIVEFLNRWITFCQSIISTL T* |
| 504 | 1H3-hKappa-L6-hIL-2 (D20A/R38E) LC Linker in dashed underline hIL-2 in italics | DTVLTQSPALAVSPGERVTISCRASESVRTGVHWYQQKPGQQPKLLIYGASNLESGVPARFSGSGSGTD FTLTIDPVEADDTATYFCQQSWNDPFTFGSGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS SRWQQGNVFSCSVMHEALHNHYTQKSLSLSPGKSGGGGSA*PTSSSTKKTQLQLEHLLLALQMILNGINN CLEEELKPLEEVLNLAQSKNFHLRPRDLISNINVIVLELKGSETTEMCEYADETATIVEFLNRWITECQ SIISTLT* |
| 505 | OMC476pB11-hIgG4-df-hIL-2 (D20A/R38E) HC hIL-2 in italics | DVQLVESGGGVVRPGESLRLSCTASGFTFSISAMSWVRQAPGKGLEWVSAISGTAYSTYYADSVRGRFT ISRDNSKNTLYLQMNSLRAEDTAVYYCAKDNFFDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PTSSSTKKTQLQLEHLLLALQMILNGINNYKNPKLTEMLT FKFYMPKKATELKHLQCLEEELKPLEEVLNLAQSKNEHLRPRDLISNINVIVLELKGSETTEMCEYADE TATIVEFLNRWITFCQSIISTLT* |
| 506 | OMC476pE4-hIgG4-df-hIL-2 (D20A/R38E) HC hIL-2 in italics | DVQLVESGGGVVRPGESLRLSCAASGETESTDAMGWVRQAPGEGLEWVSLISGSGYSTYYADSVKGRET ISRDNSKNTLYLQMNSLTAEDTAVYYCAKNSLAFFDYWGLGTLVTVSSASTKGPSVFPLAPCSRSTSES TAALGCLVKDYFPEPVTVSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCVVVDVSQEDPEVQENWYV DGVEVHNAKTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLTVDKSRW QEGNVFSCSVMHEALHNHYTQKSLSLSLGKA*PTSSSTKKTQLQLEHLLLALQMILNGINNYKNPKLTEM LTFKFYMPKKATELKHLQCLEEELKPLEEVLNLAQSKNFHLRPRDLISNINVIVLELKGSETTEMCEYA DETATIVEFLNRWITFCQSIISTLT* |
| 507 | OMC476pG10-hIgG4-df-hIL-2 (D20A/R38E) HC hIL-2 in italics | DVQLVESGGGVVRPGGSLRLSCAASGFTFSIYAMSWVRQAPGEGLEWVSHISASGGSTYYADSVKGRFA ISRDNSKNTLYLQMNSLRAEDTAVYYCTTNLGSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQENWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PTSSSTKKTQLQLEHLLLALQMILNGINNYKNPKLTEMLT FKFYMPKKATELKHLQCLEEELKPLEEVLNLAQSKNFHLRPRDLISNINVIVLELKGSETTEMCEYADE TATIVEFLNRWITFCQSIISTLT* |
| 508 | OMC476pH10-hIgG4-df-hIL-2 (D20A/R38E) HC hIL-2 in italics | DVQLVESGGGVVRPGGSLRLSCAASGFTFSIYAVSWVRQAPGEGLEWVSHISASGGSTYYADSVKGRFA ISRDNSKNTLYLQMNSLRAEDTAVYYCTTNLGSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVELFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PTSSSTKKTQLQLEHLLLALQMILNGINNYKNPKLTEMLT FKFYMPKKATELKHLQCLEEELKPLEEVLNLAQSKNFHLRPRDLISNINVIVLELKGSETTEMCEYADE TATIVEFLNRWITFCQSIISTLT* |
| 509 | A2-hIgG4-df-hIL-2 (D20A/F42A) HC hIL-2 in italics | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PTSSSTKKTQLQLEHLLLALQMILNGINNYKNPKLTRMLT AKFYMPKKATELKHLQCLEEELKPLEEVLNLAQSKNFHLRPRDLISNINVIVLELKGSETTEMCEYADE TATIVEFLNRWITFCQSIISTLT* |

TABLE 29-continued

Sequences

| SEQ ID NO: | Name | Sequence |
|---|---|---|
| 510 | A2-hIgG4-df-hIL-2 (D20A/F42S) HC hIL-2 in italics | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLALQMILNGINNYKNPKLTRMLT SKFYMPKKATELKHLQCLEEELKPLEEVLNLAQSKNFHLRPRDLISNINVIVLELKGSETTFMCEYADE TATIVEFLNRWITFCQSIISTLT* |
| 511 | A2-hIgG4-df-hIL-2 (D20S/R38E) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLLSLQMILNGINNYKNPKLTEMLT FKFYMPKKATELKHLQCLEEELKPLEEVLNLAQSKNFHLRPRDLISNINVIVLELKGSETTFMCEYADE TATIVEFLNRWITFCQSIISTLT* |
| 512 | A2-hIgG4-df-hIL-2 (F42A/N88R) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLDLQMILNGINNYKNPKLTRMLT AKFYMPKKATELKHLQCLEEELKPLEEVLNLAQSKNFHLRPRDLISRINVIVLELKGSETTFMCEYADE TATIVEFLNRWITFCQSIISTLT* |
| 513 | A2-hIgG4-df-hIL-2 (F42I/I92D) HC hIL-2 in italics | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLDLQMILNGINNYKNPKLTRMLT IKFYMPKKATELKHLQCLEEELKPLEEVLNLAQSKNFHLRPRDLISNINVDVLELKGSETTFMCEYADE TATIVEFLNRWITFCQSIISTLT* |
| 514 | A2-hIgG4-df-hIL-2 (F42Q/I92D) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLDLQMILNGINNYKNPKLTRMLT QKFYMPKKATELKHLQCLEEELKPLEEVLNLAQSKNFHLRPRDLISNINVDVLELKGSETTFMCEYADE TATIVEFLNRWITFCQSIISTLT* |
| 515 | A2-hIgG4-df-hIL-2 (F42T/I92D) HC hIL-2 in italics | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLDLQMILNGINNYKNPKLTRMLT TKFYMPKKATELKHLQCLEEELKPLEEVLNLAQSKNFHLRPRDLISNINVDVLELKGSETTFMCEYADE TATIVEFLNRWITFCQSIISTLT* |
| 516 | A2-hIgG4-df-hIL-2 (F42W/I92D) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APTSSSTKKTQLQLEHLLLDLQMILNGINNYKNPKLTRMLT WKFYMPKKATELKHLQCLEEELKPLEEVLNLAQSKNFHLRPRDLISNINVDVLELKGSETTFMCEYADE TATIVEFLNRWITFCQSIISTLT* |
| 517 | A2-hIgG4-df-hIL-2 (R38E/D84K) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT |

TABLE 29-continued

Sequences

| SEQ ID NO: | Name | Sequence |
|---|---|---|
| | | LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PTSSSTKKTQLQLEHLLLDLQMILNGINNYKNPKLTEMLT FKFYMPKKATELKHLQCLEEELKPLEEVLNLAQSKNFHLRPRKLISNINVIVLELKGSETTEMCEYADE TATIVEFLNRWITFCQSIISTLT* |
| 518 | A2-hIgG4-df-hIL-2 (R38E/192K) HC hIL-2 in italics | DVQLVESGGGLVQPGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVEPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PTSSSTKKTQLQLEHLLLDLQMILNGINNYKNPKLTEMLT FKFYMPKKATELKHLQCLEEELKPLEEVLNLAQSKNFHLRPRDLISNINVKVLELKGSETTEMCEYADE TATIVEFLNRWITFCQSIISTLT* |
| 519 | C51E6-5-hIgG4-df-hIL-2 (D20A/R38E) HC hIL-2 in italics | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDYRYYYAMDYWGQGTTVTVSSASTKGPSVFPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLGKA*PTSSSTKKTQLQLEHLLLALQMILNGINNYKNPK LTEMLTFKFYMPKKATELKHLQCLEEELKPLEEVLNLAQSKNFHLRPRDLISNINVIVLELKGSETTEM CEYADETATIVEFLNRWITFCQSIISTLT* |
| 520 | C51E6-5-hIgG4-LE-df-hIL-2 (T3A/D20A/R38E/C125A) HC hIL-2 in italics | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDYRYYYAMDYWGQGTTVTVSSASTKGPSVFPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFEGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLGKA*PASSSTKKTQLQLEHLLLALQMILNGINNYKNPK LTEMLTFKFYMPKKATELKHLQCLEEELKPLEEVLNLAQSKNFHLRPRDLISNINVIVLELKGSETTEM CEYADETATIVEFLNRWITFAQSIISTLT* |
| 521 | C51E6-5-hIgG4-LAGA-df-hIL-2 (T3A/D20A/R38E/C125A) HC hIL-2 in italics | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDYRYYYAMDYWGQGTTVTVSSASTKGPSVEPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFAGAPSVELFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLGKA*PASSSTKKTQLQLEHLLLALQMILNGINNYKNPK LTEMLTFKFYMPKKATELKHLQCLEEELKPLEEVLNLAQSKNFHLRPRDLISNINVIVLELKGSETTEM CEYADETATIVEFLNRWITFAQSIISTLT* |
| 522 | 1H3-hIgG1-LAGA-L6-hIL-2 (T3A/D20A/R38E/C125A) | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELAGAPSVFLFPPKPKDTLMISRTPEVTCVVVDVSHEDPEVKEN WYVDGVEVHNAKTKPREEQYNSTYRVVSVLIVLHQDWINGKEYKCKVSNKALPAPIEKTISKAKGQPRE PQVYTLPPSRDELTKNQVSLTCLVKGFYPSDIAVEWESNGQPENNYKITPPVLDSDGSFFLYSKLTVDK SRWQQGNVFSCSVMHEALHNHYTQKSLSLSPGKSGGGGSA*PASSSTKKTQLQLEHLLLALQMILNGINN YKNPKLTEMLTFKFYMPKKATELKHLQCLEEELKPLEEVINLAQSKNFHLRPRDLISNINVIVLELKGS ETTFMCEYADETATIVEFLNRWITFAQSIISTLT* |
| 523 | 2A3-hKappa LC | EIVLTQSPGTLSLSPGERATLSCRASQSIGRSFLAWYQQKPGQAPRLLIYDASTRAADIPARFSGSGSG TDFTLTISSLEPEDFAVYYCQQYDWPPLSFGGGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSSPV TKSENRGEC |
| 524 | 1H9-hIgG4-df-hIL-2 (D20A/R38E) HC hIL-2 in italics | EVQLLESGGGLVQPGGSLRLSCVGSGFNLKDYCMTWVRQAPGKGLEWVSAIVYSGGSTYYADSVKGRFT ISRDNSKNTLYLQMNSLRAEDTAVYYCAKYTRGSYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGKA*PTSSSTKKTQLQLEHLLLALQMILNGINNYKNP KLTEMLTFKFYMPKKATELKHLQCLEEELKPLEEVLNLAQSKNFHLRPRDLISNINVIVLELKGSETTE MCEYADETATIVEFLNRWITFCQSIISTLT* |
| 525 | 1H9-hkappa LC | EIVLTQSPGTLSLSPGERATLSCRASQSIGRSFLAWYQQKPGQAPRLLIYDASTRAADIPDRESGSGSG TDFTLTINRLEPEDFAVYYCQQYDWPPLTFGGGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSSPV TKSENRGEC |

TABLE 29-continued

Sequences

| SEQ ID NO: | Name | Sequence |
|---|---|---|
| 526 | 1D5-hIgG4-df-hIL-2 (D20A/R38E) HC hIL-2 in italics | EVQLLESGGGLVQPGGSLRLSCVGSGENFKDYCMTWVRQAPGKGLEWVSAIVYSGGSTYYADSVKGRET<br>ISRDNSKNTLYLQMNSLRAEDTAVYYCAKYTRGSYFYDAMDVWGQGTTVTVSSASTKGPSVEPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFLGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTV<br>DKSRWQEGNVFSCSVMHEALHNHYTQKSLSLSLGK*APTSSSTKKTQLQLEHLLLALQMILNGINNYKNP*<br>*KLTEMLTFKFYMPKKATELKHLQCLEEELKPLEEVLNLAQSKNFHLRPRDLISNINVIVLELKGSETTE*<br>*MCEYADETATIVEFLNRWITFCQSIISTLT* |
| 527 | 1D5-hKappa LC | EIVLTQSPGTLSLSPGERATLSCRASQSIGRSFLAWYQQKPGQAPRLLIYDASTRATDIPDRESGSGSG<br>TEFTLTISSLQSEDFAVYYCQQYYDWPPLTFGGGTKVEIKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQGLSSPV<br>TKSENRGEC |
| 528 | 1D5-hIgG4-LE-df-hIL-2 (T3A/D20A/R38E/C125A) HC hIL-2 in italics | EVQLLESGGGLVQPGGSLRLSCVGSGENFKDYCMTWVRQAPGKGLEWVSAIVYSGGSTYYADSVKGRFT<br>ISRDNSKNTLYLQMNSLRAEDTAVYYCAKYTRGSYFYDAMDVWGQGTTVTVSSASTKGPSVFPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFEGGPSVFLFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTV<br>DKSRWQEGNVFSCSVMHEALHNHYTQKSLSLSLGK*APASSSTKKTQLQLEHLLLALQMILNGINNYKNP*<br>*KLTEMLTFKFYMPKKATELKHLQCLEEELKPLEEVLNLAQSKNFHLRPRDLISNINVIVLELKGSETTE*<br>*MCEYADETATIVEFLNRWITFAQSIISTLT* |
| 529 | 1D5-hIgG4-LAGA-df-hIL-2 (T3A/D20A/R38E/C125A) HC hIL-2 in italics | EVQLLESGGGLVQPGGSLRLSCVGSGENFKDYCMTWVRQAPGKGLEWVSAIVYSGGSTYYADSVKGRET<br>ISRDNSKNTLYLQMNSLRAEDTAVYYCAKYTRGSYFYDAMDVWGQGTTVTVSSASTKGPSVFPLAPCSR<br>STSESTAALGCLVKDYFPEPVTVSWNSGALTSGVHTFPAVLQSSGLYSLSSVVTVPSSSLGTKTYTCNV<br>DHKPSNTKVDKRVESKYGPPCPPCPAPEFAGAPSVELFPPKPKDTLMISRTPEVTCVVVDVSQEDPEVQ<br>FNWYVDGVEVHNAKTKPREEQFNSTYRVVSVLTVLHQDWLNGKEYKCKVSNKGLPSSIEKTISKAKGQP<br>REPQVYTLPPSQEEMTKNQVSLTCLVKGFYPSDIAVEWESNGQPENNYKTTPPVLDSDGSFFLYSRLTV<br>DKSRWQEGNVFSCSVMHEALHNHYTQKSLSLSLGK*APASSSTKKTQLQLEHLLLALQMILNGINNYKNP*<br>*KLTEMLTFKFYMPKKATELKHLQCLEEELKPLEEVLNLAQSKNFHLRPRDLISNINVIVLELKGSETTE*<br>*MCEYADETATIVEFLNRWITFAQSIISTLT* |
| 530 | 2H7-hIgG1-df-hIL-2 (T3A/D20A/R38E/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEHLLLALQMILNGINNY*<br>*KNPKLTEMLTFKFYMPKKATELKHLQCLEEELKPLEEVLNLAQSKNFHLRPRDLISNINVIVLELKGSE*<br>*TTFMCEYADETATIVEFLNRWITFAQSIISTLT* |
| 531 | 2H7-hIgG1-LE-df-hIL-2 (T3A/D20A/R38E/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELEGGPSVFLFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEHLLLALQMILNGINNY*<br>*KNPKLTEMLTFKFYMPKKATELKHLQCLEEELKPLEEVLNLAQSKNFHLRPRDLISNINVIVLELKGSE*<br>*TTFMCEYADETATIVEFLNRWITFAQSIISTLT* |
| 532 | H7-767 HC | EVQLLESGGGLVQPGGSLRLSCAASGFTFKSYAMHWVRQAPGKGLEWVSAIVYSGGSTYYADSVKGRFT<br>ISRDNSKNTLYLQMNSLRAEDTAVYYCAKYDRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVFLFPPKPKDTIMISRTPEVTCVVVDVSHEDP<br>EVKENWYVDGVEVHNAKIKPREEQYNSTYRVVSVLTVLHQDWINGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVESCSVMHEALHNHYTQKSISLSPGKAPASSSTKKTQLQLEHLLLALQMILNGINNY<br>KNPKLTEMLTFKFYMPKKATELKHLQCLEEELKPLEEVLNLAQSKNFHIRPRDLISNINVIVLELKGSE<br>TTFMCEYADETATIVEFLNRWITFAQSIISTLT |
| 533 | 2H7-hIgG1-LE-df-hIL-2 (T3A/R38E/D84K/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELEGGPSVFLFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEHLLLDLQMILNGINNY*<br>*KNPKLTEMLTFKFYMPKKATELKHLQCLEEELKPLEEVLNLAQSKNFHLRPRKLISNINVIVLELKGSE*<br>*TTFMCEYADETATIVEFLNRWITFAQSIISTLT* |

TABLE 29-continued

Sequences

| SEQ ID NO: | Name | Sequence |
|---|---|---|
| 534 | 2H7-hIgG4-df-hIL-2 (T3A/R38E/D84K/C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGK*APASSSTKKTQLQLEHLLLDLQMILNGINNYKNP KLTEMLTFKFYMPKKATELKHLQCLEEELKPLEEVLNLAQSKNFHLRPRKLISNINVIVLELKGSETTE MCEYADETATIVEFLNRWITFAQSIISTLT* |
| 535 | 2H7-hIgG1-df-hIL-2 (T3A/R38E/I92K/C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK*APASSSTKKTQLQLEHLLLDLQMILNGINNY KNPKLTEMLTFKFYMPKKATELKHLQCLEEELKPLEEVLNLAQSKNFHLRPRDLISNINVKVLELKGSE TTFMCEYADETATIVEFLNRWITFAQSIISTLT* |
| 536 | 2H7-hIgG1-LE-df-hIL-2 (T3A/R38E/I92K/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELEGGPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK*APASSSTKKTQLQLEHLLLDLQMILNGINNY KNPKLTEMLTFKFYMPKKATELKHLQCLEEELKPLEEVLNLAQSKNFHLRPRDLISNINVKVLELKGSE TTEMCEYADETATIVEFLNRWITFAQSIISTLT* |
| 537 | 2H7-hIgG4-df-hIL-2 (T3A/R38E/I92K/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVEPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLGK*APASSSTKKTQLQLEHLLLDLQMILNGINNYKNP KLTEMLTFKFYMPKKATELKHLQCLEEELKPLEEVLNLAQSKNFHLRPRDLISNINVKVLELKGSETTF MCEYADETATIVEFLNRWITFAQSIISTLT* |
| 538 | 2H7-hIgG1-LAGA-df-hIL2 (T3A/D20S/R38E/C125A) HC hIL-2 in italics | EVQLLESGGGLVQPGGSLRLSCAASGFTFKDYCMTWVRQAPGKGLEWVSAIVYSGGSTYYADSVKGRFT ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVELFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK*APASSSTKKTQLQLEHLLLSLQMILNGINNY KNPKLTEMLTFKFYMPKKATELKHLQCLEEELKPLEEVLNLAQSKNFHLRPRDLISNINVIVLELKGSE TTEMCEYADETATIVEFLNRWITFAQSIISTLT* |
| 539 | 2H7-hIgG1-LAGA-df-hIL2 (T3A/R38E/D84F/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVELFPPKPKDTLMISRTPEVTCVVVDVSHEDP EVKENWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK*APASSSTKKTQLQLEHLLLDLQMILNGINNY KNPKLTEMLTFKFYMPKKATELKHLQCLEEELKPLEEVLNLAQSKNFHLRPRFLISNINVIVLELKGSE TTFMCEYADETATIVEFLNRWITFAQSIISTLT* |
| 540 | 2H7-hIgG1-LAGA-df-hIL2 (T3A/R38E/I92R/C125A) HC hIL-2 in italics | EVQLLESGGGLVQPGGSLRLSCAASGFTFKDYCMTWVRQAPGKGLEWVSAIVYSGGSTYYADSVKGRET ISRDNSKNTLYLQMNNLRAEDTAVYYCAKYTRASYFYDAMDVWGQGTTVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELAGAPSVELFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK LTVDKSRWQQGNVFSCSVMHEALHNHYTQKSLSLSPGK*APASSSTKKTQLQLEHLLLDLQMILNGINNY KNPKLTEMLTFKFYMPKKATELKHLQCLEEELKPLEEVLNLAQSKNFHLRPRDLISNINVRVLELKGSE TTFMCEYADETATIVEFLNRWITFAQSIISTLT* |

TABLE 29-continued

Sequences

| SEQ ID NO: | Name | Sequence |
|---|---|---|
| 541 | 2H7-hIgG1-LAGA-df-hIL2 (T3A/R38E/I92E/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVELFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEHLLLDLQMILNGINNY*<br>*KNPKLTEMLTFKFYMPKKATELKHLQCLEEELKPLEEVLNLAQSKNFHLRPRDLISNINVEVLELKGSE*<br>*TTFMCEYADETATIVEFLNRWITFAQSIISTLT* |
| 542 | 2H7-hIgG1-LAGA-df-hIL2 (T3A/R38E/I92S/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVELFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEHLLLDLQMILNGINNY*<br>*KNPKLTEMLTFKFYMPKKATELKHLQCLEEELKPLEEVLNLAQSKNFHLRPRDLISNINVSVLELKGSE*<br>*TTFMCEYADETATIVEFLNRWITFAQSIISTLT* |
| 543 | 2H7-hIgG1-LAGA-df-hIL2 (T3A/R38E/I92D/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVELFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEHLLLDLQMILNGINNY*<br>*KNPKLTEMLTFKFYMPKKATELKHLQCLEEELKPLEEVLNLAQSKNFHLRPRDLISNINVDVLELKGSE*<br>*TTFMCEYADETATIVEFLNRWITFAQSIISTLT* |
| 544 | 2H7-hIgG1-LAGA-df-hIL2 (T3A/H16E/R38E/C125A) HC hIL-2 in italics | EVQLLESGGGLVQPGGSLRLSCAASGFTFKDYCMTWVRQAPGKGLEWVSAIVYSGGSTYYADSVKGRET<br>ISRDNSKNTLYLQMNNLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVELFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK*APASSSTKKTQLQLEELLLDLQMILNGINNY*<br>*KNPKLTEMLTFKFYMPKKATELKHLQCLEEELKPLEEVLNLAQSKNFHLRPRDLISNINVIVLELKGSE*<br>*TTFMCEYADETATIVEFLNRWITFAQSIISTLT* |
| 545 | 1H3-hIgG1-L6-hIL-2 (T3A/D20A/R38E/C125A) HC Linker in dashed underline hIL-2 in italics | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELLGGPSVELFPPKPKDTLMISRTPEVTCVVVDVSHEDPEVKEN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKS<u>GGGGS</u>ELCDDDPPEIPHATFKAMAYKEGTMLNCEC<br>*YKNPKLTEMLTFKFYMPKKATELKHLQCLEEELKPLEEVLNLAQSKNFHLRPRDLISNINVIVLELKGS*<br>*ETTEMCEYADETATIVEFLNRWITFAQSIISTLT* |
| 546 | 1H3-hIgG1-LAGA-df-hIL-2 (T3A/D20A/R38E/C125A) HC hIL-2 in italics | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELAGAPSVELFPPKPKDTLMISRTPEVTCVVVDVSHEDPEVKEN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGK*APASSSTKKTQLQLEHLLLALQMILNGINNYKNPKL*<br>*TEMLTFKFYMPKKATELKHLQCLEEELKPLEEVLNLAQSKNFHLRPRDLISNINVIVLELKGSETTEMC*<br>*EYADETATIVEFLNRWITFAQSIISTLT* |
| 547 | C51E6-5-hIgG4/k-LE HC | QVQLVQSGSELKKPGASVKVSCKASGYSLYGTSMHWVRQAPGQGLEWMGYISPFTGRATYAQGFTGREV<br>FSLDTSVSTAYLQISSLKAEDTAVYYCARDYDYRYYYAMDYWGQGTTVTVSSASTKGPSVFPLAPCSRS<br>TSESTAALGCLVKDYFPEPVTVSWNSGALTSGVHTFPAVLQSSGLYSLSSVVTVPSSSLGTKTYTCNVD<br>HKPSNTKVDKRVESKYGPPCPPCPAPEFEGGPSVFLFPPKPKDTLMISRTPEVTCVVVDVSQEDPEVQF<br>NWYVDGVEVHNAKTKPREEQFNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKTTPPVLDSDGSFFLYSRLTVD<br>KSRWQEGNVFSCSVMHEALHNHYTQKSLSLSLG |

TABLE 29-continued

Sequences

| SEQ ID NO: | Name | Sequence |
|---|---|---|
| 548 | C51E6-5-hIgG4/k-LAGA HC | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDYRYYYAMDYWGQGTTVTVSSASTKGPSVFPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFAGAPSVELFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLG |
| 549 | C51E6-5-hIgG4/k-LEPG HC | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDYRYYYAMDYWGQGTTVTVSSASTKGPSVFPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFEGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLGSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLG |
| 550 | C51E6-5-hIgG4/k-df-hIL-2 (T3A/D20A/R38E/C125A) HC hIL-2 in italics | QVQLVQSGSELKKPGASVKVSCKASGYSLYGTSMHWVRQAPGQGLEWMGYISPFTGRATYAQGFTGREV FSLDTSVSTAYLQISSLKAEDTAVYYCARDYDYRYYYAMDYWGQGTTVTVSSASTKGPSVEPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLGKA*PASSSTKKTQLQLEHLLLALQMILNGINNYKNPK LTEMLTFKFYMPKKATELKHLQCLEEELKPLEEVLNLAQSKNFHLRPRDLISNINVIVLELKGSETTEM CEYADETATIVEFLNRWITFAQSIISTLT* |
| 551 | C51E6-5-hIgG4/k-LEPG-hIL-2 (T3A/D20A/R38E/C125A) HC hIL-2 in italics | QVQLVQSGSELKKPGASVKVSCKASGYSLYGTSMHWVRQAPGQGLEWMGYISPFTGRATYAQGFTGRFV FSLDTSVSTAYLQISSLKAEDTAVYYCARDYDYRYYYAMDYWGQGTTVTVSSASTKGPSVEPLAPCSRS TSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFEGGPSVELFPPKPKDTLMISRTPEVTCVVVDVSQEDPEVQF NWYVDGVEVHNAKTKPREEQFNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKTTPPVLDSDGSFFLYSRLTVD KSRWQEGNVFSCSVMHEALHNHYTQKSLSLSLGKA*PASSSTKKTQLQLEHLLLALQMILNGINNYKNPK LTEMLTFKFYMPKKATELKHLQCLEEELKPLEEVLNLAQSKNFHLRPRDLISNINVIVLELKGSETTEM CEYADETATIVEFLNRWITFAQSIISTLT* |
| 552 | A2-hIgG4/k-LE HC | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVEPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFeGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 553 | A2-hIgG4/k-LAGA HC | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFaGaPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 554 | A2-hIgG4/k-LEPG HC | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFeGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLgSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLG |
| 555 | A2-hIgG4/k-df-hIL-2 (T3A/D20A/R38E/C125A) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGKA*PASSSTKKTQLQLEHLLLALQMILNGINNYKNPKLTEMLT FKFYMPKKATELKHLQCLEEELKPLEEVLNLAQSKNFHLRPRDLISNINVIVLELKGSETTEMCEYADE TATIVEFLNRWITFAQSIISTLT* |

TABLE 29-continued

Sequences

| SEQ ID NO: | Name | Sequence |
|---|---|---|
| 556 | A2-hIgG4/k-LE-df-hIL-2 (T3A/D20A/R38E/C125A) HC hIL-2 in italics | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFEGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APASSSTKKTQLQLEHLLLALQMILNGINNYKNPKLTEMLT FKFYMPKKATELKHLQCLEEELKPLEEVLNLAQSKNFHLRPRDLISNINVIVLELKGSETTEMCEYADE TATIVEFLNRWITFAQSIISTLT* |
| 557 | A2-hIgG4/k-LAGA-df-hIL-2 (T3A/D20A/R38E/C125A) HC hIL-2 in italics | DVQLVESGGGLVQPGGSLRLSCAASGFTFDISAMSWVRQAPGKGLEWVSTISGSAYSTYYADSVKGRET ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFAGAPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APASSSTKKTQLQLEHLLLALQMILNGINNYKNPKLTEMLT FKFYMPKKATELKHLQCLEEELKPLEEVLNLAQSKNFHLRPRDLISNINVIVLELKGSETTEMCEYADE TATIVEFLNRWITFAQSIISTLT* |
| 558 | A2-hIgG4/k-LEPG-df-hIL-2 (T3A/D20A/R38E/C125A) HC hIL-2 in italics | DVQLVESGGGLVQPGGSLRLSCAASGFTFDISAMSWVRQAPGKGLEWVSTISGSAYSTYYADSVKGRFT ISRDNSKSTLYLQMNSLRAEDTAVYYCAREIFSDYWGLGTLVTVSSASTKGPSVFPLAPCSRSTSESTA ALGCLVKDYFPEPVTVSWNSGALTSGVHTFPAVLQSSGLYSLSSVVTVPSSSLGTKTYTCNVDHKPSNT KVDKRVESKYGPPCPPCPAPEFEGGPSVFLFPPKPKDTLMISRTPEVTCVVVDVSQEDPEVQFNWYVDG VEVHNAKTKPREEQFNSTYRVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDSDGSFFLYSRLTVDKSRWQE GNVFSCSVMHEALHNHYTQKSLSLSLGK*APASSSTKKTQLQLEHLLLALQMILNGINNYKNPKLTEMLT FKFYMPKKATELKHLQCLEEELKPLEEVLNLAQSKNEHLRPRDLISNINVIVLELKGSETTEMCEYADE TATIVEFLNRWITFAQSIISTLT* |
| 559 | Anti-hPD-1 #1 HC | QVQLVESGGGVVQPGRSLRLDCKASGITFSNSGMHWVRQAPGKGLEWVAVIWYDGSKRYYADSVKGRET ISRDNSKNTLFLQMNSLRAEDTAVYYCATNDDYWGQGTLVTVSSASTKGPSVFPLAPCSRSTSESTAAL GCLVKDYFPEPVTVSWNSGALTSGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTCVVVDVSQEDPEVQFNWYVDGVE VHNAKTKPREEQFNSTYRVVSVLIVLHQDWINGKEYKCKVSNKGLPSSIEKTISKAKGQPREPQVYTLP PSQEEMTKNQVSLTCLVKGFYPSDIAVEWESNGQPENNYKTTPPVLDSDGSFFLYSRLTVDKSRWQEGN VFSCSVMHEALHNHYTQKSLSLSLG |
| 560 | Anti-CD20-hIgG1/k HC | QVQLQQPGAELVKPGASVKMSCKASGYTFTSYNMHWVKQTPGRGLEWIGAIYPGNGDTSYNQKFKGKAT LTADKSSSTAYMQLSSLTSEDSAVYYCARSTYYGGDWYFNVWGAGTTVTVSAASTKGPSVFPLAPSSKS TSGGTAALGCLVKDYFPEPVTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMISRTPEVTCVVVDVSHEDPE VKFNWYVDGVEVHNAKTKPREEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPGK |
| 561 | Anti-CD20-hIgG1/k-LAGA HC | QVQLQQPGAELVKPGASVKMSCKASGYTFTSYNMHWVKQTPGRGLEWIGAIYPGNGDTSYNQKFKGKAT LTADKSSSTAYMQLSSLTSEDSAVYYCARSTYYGGDWYFNVWGAGTTVTVSAASTKGPSVFPLAPSSKS TSGGTAALGCLVKDYFPEPVTVSWNSGALTSGVHTFPAVLQSSGLYSLSSVVTVPSSSLGTQTYICNVN HKPSNTKVDKKVEPKSCDKTHTCPPCPAPELAGAPSVFLFPPKPKDTLMISRTPEVTCVVVDVSHEDPE VKFNWYVDGVEVHNAKTKPREEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPG |
| 562 | Anti-CD20-hKappa LC | QIVLSQSPAILSASPGEKVTMTCRASSSVSYIHWFQQKPGSSPKPWIYATSNLASGVPVRFSGSGSGTS YSLTISRVEAEDAATYYCQQWTSNPPTFGGGTKLEIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGEC |
| 563 | 1H3-hIgG1-LAGA-df-hIL-2 (T3A/C125A) HC hIL-2 in italics | EVQLVESGGGLVQPGRSLKLSCAVSGFTFSDYAMAWVRQAPKKGLEWVATISYDGSRTYYRDSVKGRFT ISRDNAKNTLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELAGAPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGK*APASSSTKKTQLQLEHLLLDLQMILNGINNYKNPKL TRMLTFKFYMPKKATELKHLQCLEEELKPLEEVLNLAQSKNFHLRPRDLISNINVIVLELKGSETTEMC EYADETATIVEFLNRWITFAQSIISTLT* |

TABLE 29-continued

Sequences

| SEQ ID NO: | Name | Sequence |
|---|---|---|
| 564 | anti-mPD-1 RMP1-14 mIgG2b-N297A HC | EVQLQESGPGLVKPSQSLSLTCSVTGYSITSSYRWNWIRKFPGNRLEWMGYINSAGISNYNPSLKRRIS ITRDTSKNQFFLQVNSVTTEDAATYYCARSDNMGTTPFTYWGQGTLVTVSSAKTTPPSVYPLAPGCGDT TGSSVTLGCLVKGYFPESVTVTWNSGSLSSSVHTFPALLQSGLYTMSSSVTVPSSTWPSQTVTCSVAHP ASSTTVDKKLEPSGPISTINPCPPCKECHKCPAPNLEGGPSVFIFPPNIKDVLMISLTPKVTCVVVDVS EDDPDVQISWFVNNVEVHTAQTQTHREDYASTIRVVSTLPIQHQDWMSGKEFKCKVNNKDLPSPIERTI SKIKGLVRAPQVYILPPPAEQLSRKDVSLTCLVVGENPGDISVEWTSNGHTEENYKDTAPVLDSDGSYF IYSKLNMKTSKWEKTDSFSCNVRHEGLKNYYLKKTISRSPGK |
| 565 | anti-mPD-1 RMP1-14 mIgG2b-N297A-L6-hIL-2 (F42K/Y45R/ V69R) HC linker in dashed underline hIL-2 in italics | EVQLQESGPGLVKPSQSLSLTCSVTGYSITSSYRWNWIRKFPGNRLEWMGYINSAGISNYNPSLKRRIS ITRDTSKNQFFLQVNSVTTEDAATYYCARSDNMGTTPFTYWGQGTLVTVSSAKTTPPSVYPLAPGCGDT TGSSVTLGCLVKGYFPESVTVTWNSGSLSSSVHTFPALLQSGLYTMSSSVTVPSSTWPSQTVTCSVAHP ASSTTVDKKLEPSGPISTINPCPPCKECHKCPAPNLEGGPSVFIFPPNIKDVLMISLTPKVTCVVVDVS EDDPDVQISWFVNNVEVHTAQTQTHREDYASTIRVVSTLPIQHQDWMSGKEFKCKVNNKDLPSPIERTI SKIKGLVRAPQVYILPPPAEQLSRKDVSLTCLVVGENPGDISVEWTSNGHTEENYKDTAPVLDSDGSYF SRWQQGNVFSCSVMHEALHNHYTQKSLSLSPGK<u>SGGGGS</u>*APASSSTKKTQLQLEHLLLALQMILNGINN QMILNGINNYKNPKLTRMLTKKERMPKKATELKHLQCLEEELKPLEERLNLAQSKNFHLRPRDLISNIN VIVLELKGSETTEMCEYADETATIVEFLNRWITFCQSIISTLT* |
| 566 | anti-mPD-1 RMP1-14 mKappa LC | DIVMTQGTLPNPVPSGESVSITCRSSKSLLYSDGKTYLNWYLQRPGQSPQLLIYWMSTRASGVSDRESG SGSGTDFTLKISGVEAEDVGIYYCQQGLEFPTFGGGTKLELKRADAAPTVSIFPPSSEQLTSGGASVVC FLNNFYPKDINVKWKIDGSERQNGVLNSWTDQDSKDSTYSMSSTLTLTKDEYERHNSYTCEATHKTSTS PIVKSENRNEC |
| 567 | anti-mPD-1 RMP1-30 mIgG2b-N297A HC | EVQLVESGGGLVQPGRSLKLSCAASGFTFGDYSMAWVRQAPKRGLEWVANIIYDGSRTFYRDSVKGRFT ISRDNAKPTLYLQMDSLRPEDTATYYCATHNYPGYAMEAWGQGTSVTVSSAKTTPPSVYPLAPGCGDTT GSSVTLGCLVKGYFPESVTVTWNSGSLSSSVHTFPALLQSGLYTMSSSVTVPSSTWPSQTVTCSVAHPA SSTTVDKKLEPSGPISTINPCPPCKECHKCPAPNLEGGPSVFIFPPNIKDVLMISLTPKVTCVVVDVSE DDPDVQISWFVNNVEVHTAQTQTHREDYASTIRVVSTLPIQHQDWMSGKEFKCKVNNKDLPSPIERTIS KIKGLVRAPQVYILPPPAEQLSRKDVSLTCLVVGENPGDISVEWTSNGHTEENYKDTAPVLDSDGSYFI YSKLNMKTSKWEKTDSFSCNVRHEGLKNYYLKKTISRSPGK |
| 568 | anti-mPD-1 RMP1-30 mKappa LC | DTVLTQSPALPVSLGQRVNISCRATKSVSRYVHWYQQKSGQQPRLLIYTTSNLESGVPSRFSGSGSGTD FTLTIDPVEADDIANYYCQQSNEIPYTFGAGTKLELKRADAAPTVSIFPPSSEQLTSGGASVVCELNNE YPKDINVKWKIDGSERQNGVLNSWTDQDSKDSTYSMSSTLTLTKDEYERHNSYTCEATHKTSTSPIVKS ENRNEC |
| 569 | anti-mPD-1 RMP1-30 mIgG2b-N297A-L6-hIL-2 (F42K/Y45R/ V69R) HC linker in dashed underline hIL-2 in italics | EVQLVESGGGLVQPGRSLKLSCAASGFTFGDYSMAWVRQAPKRGLEWVANITYDGSRTFYRDSVKGRFT ISRDNAKPTLYLQMDSLRPEDTATYYCATHNYPGYAMEAWGQGTSVTVSSAKTTPPSVYPLAPGCGDTT GSSVTLGCLVKGYFPESVTVTWNSGSLSSSVHTFPALLQSGLYTMSSSVTVPSSTWPSQTVTCSVAHPA SSTTVDKKLEPSGPISTINPCPPCKECHKCPAPNLEGGPSVFIFPPNIKDVLMISLTPKVTCVVVDVSE DDPDVQISWFVNNVEVHTAQTQTHREDYASTIRVVSTLPIQHQDWMSGKEFKCKVNNKDLPSPIERTIS KIKGLVRAPQVYILPPPAEQLSRKDVSLTCLVVGENPGDISVEWTSNGHTEENYKDTAPVLDSDGSYF IYSKLNMKTSKWEKTDSFSCNVRHEGLKNYYLKKTISRSPGK<u>SGGGGS</u>*APTSSSTKKTQLQLEHLLLDL MILNGINNYKNPKLTRMLTKKFrMPKKATELKHLQCLEEELKPLEErLNLAQSKNFHLRPRDLISNINV IVLELKGSETTEMCEYADETATIVEFLNRWITFCQSIISTLT* |
| 570 | anti-KLH-C3-mIgG2b-N297A-L6-hIL-2 (F42K/Y45R/ V69R) HC linker in dashed underline hIL-2 in italics | EVQLVGSGGGLVQPGGSLKLSCAASGFTFSDFYMAWVRQAPTKGLEWVASISTGGGNTHYRDSVKGRFT ISRDNAKSTLYLQMDSLRSEETATYYCARLLSTISTPFDYWGQGVIVTVSSAKTTPPSVYPLAPGCGDT TGSSVTLGCLVKGYFPESVTVTWNSGSLSSSVHTFPALLQSGLYTMSSSVTVPSSTWPSQTVTCSVAHP ASSTTVDKKLEPSGPISTINPCPPCKECHKCPAPNLEGGPSVFIFPPNIKDVLMISLTPKVTCVVVDVS EDDPDVQISWFVNNVEVHTAQTQTHREDYASTIRVVSTLPIQHQDWMSGKEFKCKVNNKDLPSPIERTI SKIKGLVRAPQVYILPPPAEQLSRKDVSLTCLVVGENPGDISVEWTSNGHTEENYKDTAPVLDSDGSYF IYSKLNMKTSKWEKTDSFSCNVRHEGLKNYYLKKTISRSPGK<u>SGGGGS</u>*APTSSSTKKTQLQLEHLLLDL QMILNGINNYKNPKLTRMLTKKFrMPKKATELKHLQCLEEELKPLEErLNLAQSKNFHLRPRDLISNIN VIVLELKGSETTEMCEYADETATIVEFLNRWITFCQSIISTLT* |
| 571 | KLH-C3-mKappa LC | DVVLIQSPTTLSVTPGETVSLSCRASHSVGTNLHWYQQRTNESPSLLIKYSSHSTSGIPSRESATGSGT DFTLNISNVEFDDVASYFCQQSQKWPLTFGSGTKLEIKRADAAPTVSIFPPSSEQLTSGGASVVCELNN FYPKDINVKWKIDGSERQNGVLNSWTDQDSKDSTYSMSSTLTLTKDEYERHNSYTCEATHKTSTSPIVK SENRNEC |

TABLE 29-continued

Sequences

| SEQ ID NO: | Name | Sequence |
|---|---|---|
| 572 | 2D12-hIgG1-L6-hIL-2 HC linker in dashed underline hIL-2 in italics | EVQLQQSGPELVKPGASVKISCKTSGYTFTEYTMHWVKQSHGKSLEWIGGINPNNGGTTYNQKFKGKAT LTVDKSSSTAYMELRSLTSQDSAVYYCARDYYRYGHYYAMDYWGQGTSVTVSSASTKGPSVFPLAPSSK STSGGTAALGCLVKDYFPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSDGSFFLYSK YSKLNMKTSKWEKTDSFSCNVRHEGLKNYYLKKTISRSPGKSGGGGS*APTSSSTKKTQLQLEHLLLDLQ NGINNYKNPKLTRMLTFKFYMPKKATELKHLQCLEEELKPLEEVLNLAQSKNFHLRPRDLISNINVIVL ELKGSETTEMCEYADETATIVEFLNRWITFCQSIISTLT* |
| 573 | 2D12-hKappa LC | QIVLTQSPAIMSASPGEKVTMTCSVSSSVREMHWYQQKSGTSPKRWIYDTSKLASGVPARFSGSGSGTS YSLTISSMEAEDAATYYCQQWSSNPPTFGGGTKLKIKRTVAAPSVFIFPPSDEQLKSGTASVVCLLNNE YPREAKVQWKVDNALQSGNSQESVTEQDSKDSTYSLSSTLTLSKADYEKHKVYACEVTHQGLSSPVTKS FNRGEC |
| 574 | hIL-2 F42A/Y45A/L72G | APTSSSTKKTQLQLEHLLLDLQMILNGINNYKNPKLTRMLTAKFAMPKKATELKHLQCLEEELKPLEEV LNGAQSKNFHLRPRDLISNINVIVLELKGSETTFMCEYADETATIVEFLNRWITFCQSIISTLT |
| 575 | hIL-2 H16A/F42A | APTSSSTKKTQLQLEALLLDLQMILNGINNYKNPKLTRMLTAKYMPKKATELKHLQCLEEELKPLEEV LNLAQSKNFHLRPRDLISNINVIVLELKGSETTEMCEYADETATIVEFLNRWITFCQSIISTLT |
| 576 | 1H9-hIgG4 HC | EVQLLESGGGLVQPGGSLRLSCVGSGFNLKDYCMTWVRQAPGKGLEWVSAIVYSGGSTYYADSVKGRFT ISRDNSKNTLYLQMNSLRAEDTAVYYCAKYTRGSYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 577 | 1D5-hIgG4 HC | EVQLLESGGGLVQPGGSLRLSCVGSGENFKDYCMTWVRQAPGKGLEWVSAIVYSGGSTYYADSVKGRET ISRDNSKNTLYLQMNSLRAEDTAVYYCAKYTRGSYFYDAMDVWGQGTTVTVSSASTKGPSVFPLAPCSR STSESTAALGCLVKDYFPEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTPEVTCVVVDVSQEDPEVQ FNWYVDGVEVHNAKTKPREEQFNSTYRVVSVLTVLHQDWLNGKEYKCKVSNKGLPSSIEKTISKAKGQP REPQVYTLPPSQEEMTKNQVSLTCLVKGFYPSDIAVEWESNGQPENNYKTTPPVLDSDGSFFLYSRLTV DKSRWQEGNVFSCSVMHEALHNHYTQKSLSLSLG |
| 578 | Anti-hPD-1 #2 HC | QVQLVQSGVEVKKPGASVKVSCKASGYTFTNYYMYWVRQAPGQGLEWMGGINPSNGGTNFNEKFKNRVT LTTDSSTTTAYMELKSLQFDDTAVYYCARRDYRFDMGFDYWGQGTTVTVSSASTKGPSVFPLAPCSRST SESTAALGCLVKDYFPEPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTCVVVDVSQEDPEVQFN WYVDGVEVHNAKTKPREEQFNSTYRVVSVLTVLHQDWINGKEYKCKVSNKGLPSSIEKTISKAKGQPRE PQVYTLPPSQEEMTKNQVSLTCLVKGFYPSDIAVEWESNGQPENNYKTTPPVLDSDGSFFLYSRLTVDK SRWQEGNVFSCSVMHEALHNHYTQKSLSLSLG |
| 579 | Anti-hPD-1 #2 LC | EIVLTQSPATLSLSPGERATLSCRASKGVSTSGYSYLHWYQQKPGQAPRLLIYLASYLESGVPARFSGS GSGTDFTLTISSLEPEDFAVYYCQHSRDLPLTFGGGTKVEIKRTVAAPSVFIFPPSDEQLKSGTASVVC LINNFYPREAKVQWKVDNALQSGNSQESVTEQDSKDSTYSLSSTLTLSKADYEKHKVYACEVTHQGLSS PVTKSENRGEC |
| 580 | human PD-1 receptor lentiviral vector | gtcgacggatcgggagatctcccgatccccatggtgcactctcagtacaatctgctctgatgccgcat agttaagccagtatctgctccctgcttgtgtgttggaggtcgctgagtagtgcgcgagcaaaatttaag ctacaacaaggcaaggcttgaccgacaattgcatgaagaatctgcttagggttaggcgtttgcgctgc ttcgcgatgtacgggccagatatacgcgttgacattgattattgactagttattaatagtaatcaatta cggggtcattagttcatagcccatatatggagttccgcgttacataacttacggtaaatggcccgcctg gctgaccgcccaacgacccccgcccattgacgtcaataatgacgtatgttcccatagtaacgccaatag ggactttccattgacgtcaatgggtggagtatttacggtaaactgcccacttggcagtacatcaagtgt atcatatgccaagtacgccccctattgacgtcaatgacggtaaatggcccgcctggcattatgcccagt acatgaccttatgggactttcctacttggcagtacatctacgtattagtcatcgctattaccatggtga tgcggttttggcagtacatcaatgggcgtggatagcggtttgactcacggggatttccaagtctccacc ccattgacgtcaatgggagtttgttttggcaccaaaatcaacgggactttccaaaatgtcgtaacaact ccgccccattgacgcaaatgggcggtaggcgtgtacggtgggaggtctatataagcagcgcgtttttgcc tgtactgggtctctctggttagaccagatctgagcctgggagctctctggctaactagggaacccactg cttaagcctcaataaagcttgccttgagtgcttcaagtagtgtgtgcccgtctgttgtgtgactcttggt aactagagatccctcagacccttttagtcagtgtggaaaatctctagcagtggcgcccgaacagggact tgaaagcgaaagggaaaccagaggagctctctcgacgcaggactcggcttgctgaagcgcgcacggcaa gaggcgaggggcggcgactggtgagtacgccaaaaattttgactagcggaggctagaaggagagagatg ggtgcgagagcgtcagtattaagcgggggagaattagatcgcgatggaaaaaattcggttaaggccag ggggaagaaaaatataaattaaaacatatagtatgggcaagcagggagctagaacgattcgcagtta atcctggcctgttagaaacatcagaaggctgtagacaaatactgggacagctacaaccatcccttcaga caggatcagaagaacttagatcattatataatacagtagcaaccctctattgtgtgcatcaaaggatag agataaaagacaccaaggaagctttagacaagatagaggaagagcaaaacaaaagtaagaccaccgcac agcaagcggccgctgatcttcagacctggaggaggagatatgagggacaattggagaagtgaattatat |

TABLE 29-continued

Sequences

| SEQ ID NO: Name | Sequence |
|---|---|
| | aaatataaagtagtaaaaattgaaccattaggagtagcacccaccaaggcaaagagaagagtggtgcag agagaaaaagagcagtgggaataggagctttgttccttgggttcttgggagcagcaggaagcactatg ggcgcagcgtcaatgacgctgacggtacaggccagacaattattgtctggtatagtgcagcagcagaac aatttgctgagggctattgaggcgcaacagcatctgttgcaactcacagtctggggcatcaagcagctc caggcaagaatcctggctgtggaaagatacctaaaggatcaacagctcctggggatttggggttgctct ggaaaaactcatttgcaccactgctgtgccttggaatgctagttggagtaataaatctctggaacagatt tggaatcacacgacctggatggagtgggacagagaaattaacaattacacaagcttaatacactcctta attgaagaatcgcaaaaccagcaagaaaagaatgaacaagaattattggaattagataaatgggcaagt ttgtggaattggtttaacataacaaattggctgtggtatataaaattattcataatgatagtaggaggc ttgggaggtttaagaatagtttttgctgtactttctatagtgaatagagttaggcagggatattcacca ttatcgtttcagacccacctcccaaccccgaggggacccgacaggcccgaaggaatagaagaagaaggt ggagagagacagagacagatccattcgattagtgaacggatcggcactgcgtgcgccaattctgcag acaaatggcagtattcatccacaattttaaaagaaaaggggggattggggggtacagtgcagggggaaag aatagtagacataatagcaacagacatacaaactaaagaattacaaaaacaaattacaaaaattcaaaa ttttcgggtttattacagggacagcagagatccagtttggttaattaagtaattcgctagctaggtctt gaaaggagtgggaattggctccggtgcccgtcagtgggcagagcgcacatcgcccacagtccccgagaa gttgggggggagggtcggcaattgatccggtgcctagagaaggtggcgcggggtaaactgggaaagtga tgtcgtgtactggctccgcctttttcccgagggtgggggagaaccgtatataagtgcagtagtcgccgt gaacgttcttttcgcaacgggtttgccgccagaacacaggaccggttctagagcgctgccaccatgca gatcccacaggcgcctggccagtcgtctgggcggtgctacaactgggctggcggccaggatggttctt agactccccagacaggccctggaacccccccacctttctcccccagccctgctcgtggtgaccgaggga caacgccaccttcacctgcagcttctccaacacatcggagagcttcgtgctaaactggtaccgcatgag ccccagcaaccagacggacaagctggccgccttccccgaggaccgcagccagcccggccaggactgccg cttccgtgtcacacaactgcccaacgggcgtgacttccacatgagcgtggtcagggcccggcgcaatga cagcgcacctacctctgtggggccatctccctggccccccaaggcgcagatcaaagagagcctgcgggc agagctcagggtgacagagagaagggcagaagtgcccacagcccacccagcccctcacccaggccagc cggccagttccaaaccctggtggttggtgtcgtgggcggcctgctgggcagcctggtgctgctagtctg ggtcctggccgtcatctgctcccggggccgcacgagggacaataggagccaggcgcaccggccagcccct gaaggaggacccctcagccgtcctgttctctgtggactatgggagctggattccagtggcgaga gaagacccccggagcccccgtgccctgtgtcctgagcagacggagtatgccaccattgtctttcctag cggaatgggcacctcatccccgcccgcaggggctcagctgacggccctcggagtgcccagccactgag gcctgaggatggacactgctcttggccccctctgagccctctcctccccccccctaacgttactggcc gaagccgcttggaataaggccggtgtgcgtttgtctatatgttattttccaccatattgccgtctttg gcaatgtgagggcccggaaacctggccctgtcttcttgacgagcattcctaggggtctttcccctctcg ccaaaggaatgcaaggtctgttgaatgtcgtgaaggaagcagttcctctggaagcttcttgaagacaaa caacgtctgtagcgaccctttgcaggcagcggaaccccccacctggcgacaggtgcctctgcggccaaa agccacgtgtataagatacacctgcaaaggcggcacaaccccagtgccacgttgtgagttggatagttg tggaaagagtcaaatggctctcctcaagcgtattcaacaaggggctgaaggatgcccagaaggtacccc attgtatgggatctgatctggggcctcggtgcacatgctttacatgtgtttagtcgaggttaaaaaac gtctaggccccccgaaccacggggacgtggttttcctttgaaaaacacgatgataatatggccacaatg accgagtacaagcccacggtgcgcctcgccaccccgacgacgtccagggccgtacgcaccctcgcc gccgcgttcgccgactaccccgccacgcgccacaccgtcgatccgaccgccacatcgagcgggtcacc gagctgcaagaactcttcctcacgcgcgtcgggctcgacatcggcaaggtgtgggtcgcggacgacggc gccgcggtggcggtctggaccacgccggagagcgtcgaagcggggcggtgttcgccgagatcggcccg cgcatggccgagttgagcggttcccggcctggccgcgcagacagatgaaggcctcctggcgccgcac cggcccaaggagcccgcgtggttcctggccaccgtcggagtctcgcccgaccaccagggcaaggtctg ggcagcgccgtcgtgctcccggagtggaggcggccgagcgcgccggggtgcccgccttcctggagacc tccgcgccccgcaacctcccccttctacgagcggctcggcttcaccgtcaccgccgacgtcgaggtgccc gaaggaccgcgcacctggtgcatgacccgcaagcccggtgcctgaacgcgttaagtcgacaatcaacct ctgaattacaaaatttgtgaaagattgactggtattcttaactatgttgctccttttacgctatgtgga tacgctgctttaatgcctttgtatcatgctattgcttcccgtatggctttcattttctcctccttgtat aaatcctggttgctgtctctttatgaggagttgtggcccgttgtcaggcaacgtggcgtggtgtgcact gtgtttgctgacgcaaccccactggttgggcattgccaccacctgtcagctccttccgggactttc gctttccccctccctattgccacggcggaactcatcgccgcctgccttgcccgctgctgacagggggct cggctgttgggcactgacaattccgtggtgttgtcggggaaatcatcgtcctttccttggctgctcgcc tgtgttgccacctggattctgcgcgggacgtccttctgctacgtcccttcggccctcaatccagcggac cttccttcccgcggcctgctgccggctctgcggcctcttccgcgtcttcgccttcgccctcagacgagt cggatctccctttgggccgcctccccgcgtcgacttttaagcaccaatgacttacaaggcagctgtagatct ttagccacttttttaaaagaaaaggggggactggaagggctaattcactcccaacgaagacaagatctgc tttttgcttgtactgggtctctctggttagaccagatctgagcctgggagctctctggctaactagggga acccactgcttaagcctcaataaagcttgccttgagtgcttcaagtagtgtgtgcccgtctgttgtgtg actctggtaactagagatccctcagacccttttagtcagtgtggaaaatctctagcagggccgtttaa acccgctgatcagcctcgactgtgccttctagttgccagccatctgttgtttgcccctcccccgtgcct tccttgaccctggaaggtgccactcccactgtccttcctaataaaatgaggaaattgcatcgcattgt ctgagtaggtgtcattctattctggggggtggggtggggcaggacagcaaggggaggattgggaagac aatagcaggcatgctggggatgcggtggctctatggcttctgaggcggaaagaaccagctggggctct agggggtatccccacgcgccctgtagcggcgcattaagcgcggcgggtgtggtggttacgcgcagcgtg accgctacacttgccagcgccctagcgcccgctccttcgctttcttcccttcctttctcgccacgttc gccggctttccccgtcaagctctaaatcgggggctcccttagggttccgatttagtgctttacggcac ctcgaccccaaaaaacttgattagggtgatggttcacgtagtgggccatcgccctgatagacggttttt cgccctttgacgttggagtccacgttctttaatagtggactcttgttccaaactggaacaacactcaac cctatctcggtctattcttttgatttataagggattttgccgatttcggcctattggttaaaaaatgag ctgatttaacaaaaatttaacgcgaattaattctgtggaatgtgtgtcagttagggtgtggaaagtccc caggctccccagcaggcagaagtatgcaaagcatgcatctcaattagtcagcaaccaggtgtggaaagt ccccaggctccccagcaggcagaagtatgcaaagcatgcatctcaattagtcagcaaccatagtcccgc |

TABLE 29-continued

Sequences

| SEQ ID NO: | Name | Sequence |
|---|---|---|
| | | ccctaactccgcccatcccgcccctaactccgcccagttccgcccattctccgcccatggctgactaa<br>ttttttttatttatgcagaggccgaggccgcctctgcctctgagctattccagaagtagtgaggaggct<br>ttttggaggcctaggcttttgcaaaaagctcccgggagcttgtatatccattttcggatctgatcagc<br>acgtgttgacaattaatcatcggcatagtatatcggcatagtataatacgacaaggtgagggaactaaac<br>catggccaagttgaccagtgccgttccggtgctcaccgcgcgcgacgtcgccggagcggtcgagttctg<br>gaccgaccggctcgggttctcccgggacttcgtggaggacgacttcgccggtgtggtccgggacgacgt<br>gaccctgttcatcagcgcggtccaggaccaggtggtgccggacaacaccctggcctgggtgtgggtgcg<br>cggcctggacgagctgtacgccgagtggtcggaggtcgtgtccacgaacttccgggacgggcctccgggcc<br>ggccatgaccgagatcggcgagcagccgtggggcgggagttcgccctgcgcgacccggccggcaactg<br>cgtgcacttcgtggccgaggagcaggactgacacgtgctacgagatttcgattccaccgccgccttcta<br>tgaaaggttgggcttcggaatcgtttccgggacgccggctggatgatcctccagcgcggggatctcat<br>gctggagttcttcgcccaccccaacttgtttattgcagcttataatggttacaaataaagcaatagcat<br>cacaaatttcacaaataaagcatttttttcactgcattctagttgtggtttgtccaaactcatcaatgt<br>atcttatcatgtctgtataccgtcgacctctagctagagcttggcgtaatcatggtcatagctgtttcc<br>tgtgtgaaattgttatccgctcacaattccacacaacatacgagccggaagcataaagtgtaaagcctg<br>gggtgcctaatgagtgagctaactcacattaattgcgttgcgctcactgcccgctttccagtcgggaaa<br>cctgtcgtgccagctgcattaatgaatcggccaacgcgcggggagaggcggtttgcgtattgggcgctc<br>ttccgcttcctcgctcactgactcgctgcgctcggtcgttcggctgcggcgagcggtatcagctcactc<br>aaaggcggtaatacggttatccacagaatcagggggataacgcaggaaagaacatgtgagcaaaaggcca<br>gcaaaaggccaggaaccgtaaaaaggccgcgttgctggcgtttttccataggctccgcccccctgacga<br>gcatcacaaaaatcgacgctcaagtcagaggtggcgaaacccgacaggactataaagataccaggcgtt<br>tccccctggaagctccctcgtgcgctctcctgttccgaccctgccgcttaccggatacctgtccgcctt<br>tctcccttcgggaagcgtggcgctttctcatagctcacgctgtaggtatctcagttcggtgtaggtcgt<br>tcgctccaagctgggctgtgtgcacgaaccccccgttcagcccgaccgctgcgccttatccggtaacta<br>tcgtcttgagtccaacccggtaagacacgacttatcgccactggcagcagccactggtaacaggattag<br>cagagcgaggtatgtaggcggtgctacagagttcttgaagtggtggcctaactacggctacactagaag<br>aacagtatttggtatctgcgctctgctgaagccagttaccttcggaaaaagagttggtagctcttgatc<br>cggcaaacaaaccaccgctggtagcggtggtttttttgtttgcaagcagcagattacgcgcagaaaaaa<br>aggatctcaagaagatcctttgatcttttctacggggtctgacgctcagtggaacgaaaactcacgtta<br>agggattttggtcatgagattatcaaaaaggatcttcacctagatccttttaaattaaaaatgaagttt<br>taaatcaatctaaagtatatatgagtaaacttggtctgacagttaccaatgcttaatcagtgaggcacc<br>tatctcagcgatctgtctatttcgttcatccatagttgcctgactccccgtcgtgtagataactacgat<br>acgggagggcttaccatctggccccagtgctgcaatgataccgcgagacccacgctcaccggctccaga<br>tttatcagcaataaaccagccagccggaagggccgagcgcagaagtggtcctgcaactttatccgcctc<br>catccagtctattaattgttgccgggaagctagagtaagtagttcgccagttaatagtttgcgcaacgt<br>tgttgccattgctacaggcatcgtggtgtcacgctcgtcgtttggtatggcttcattcagctccggttc<br>ccaacgatcaaggcgagttacatgatcccccatgttgtgcaaaaaagcggttagctccttcggtcctcc<br>gatcgttgtcagaagtaagttggccgcagtgttatcactcatggttatggcagcactgcataattctct<br>tactgtcatgccatccgtaagatgcttttctgtgactggtgagtactcaaccaagtcattctgagaata<br>gtgtatgcggcgaccgagttgctcttgcccggcgtcaatacgggataataccgcgccacatagcagaac<br>tttaaaagtgctcatcattggaaaacgttcttcggggcgaaaactctcaaggatcttaccgctgttgag<br>atccagttcgatgtaacccactcgtgcacccaactgatcttcagcatcttttactttcaccagcgtttc<br>tgggtgagcaaaaacaggaaggcaaaatgccgcaaaaaagggaataagggcgacacggaaatgttgaat<br>actcatactcttccttttcaatattattgaagcatttatcagggttattgtctcatgagcggatacat<br>atttgaatgtatttagaaaaataaacaaataggggttccgcgcacatttccccgaaaagtgccacctga<br>c |
| 581 | hIL-2 V69R | APTSSSTKKTQLQLEHLLLDLQMILNGINNYKNPKLTRMLTFKFYMPKKATELKHLQCLEEELKPLEER<br>LNLAQSKNFHLRPRDLISNINVIVLELKGSETTEMCEYADETATIVEFLNRWITFCQSIISTLT |
| 582 | H7-02-hIgG1-LAGA-df-hIL-2 (T3A/D20A/R38E/C125A) HC | EVQLLESGGGLVQPGGSLRLSCAASGFTFKSYAMTWVRQAPGKGLEWVSAIVYSGGSTYYADSVKGRFT<br>ISRDNSKNTLYLQMNSLRAEDTAVYYCAKYTRASYFYDAMDVWGQGTTVTVSSASTKGPSVFPLAPSSK<br>STSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELAGAPSVELFPPKPKDTLMISRTPEVTCVVVDVSHEDP<br>EVKFNWYVDGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGKAPASSSTKKTQLQLEHLLLALQMILNGINNY<br>KNPKLTEMLTFKFYMPKKATELKHLQCLEEEELKPLEEVLNLAQSKNFHLRPRDLISNINVIVLELKGSE<br>TTFMCEYADETATIVEFLNRWITFAQSIISTLT |
| 583 | H7-02-hKappa LC | EIVLTQSPGTLSLSPGERATLSCRASQSISSSFLAWYQQKPGQAPRLLIYDASTRATGIPDRESGSGSG<br>TDFTLTISRLEPEDFAVYYCQQYYDWPPLSFGGGTKVEIKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQGLSSPV<br>TKSENRGEC |
| 584 | hPD-L1 | MRIFAVFIFMTYWHLLNAFTVTVPKDLYVVEYGSNMTIECKFPVEKQLDLAALIVYWEMEDKNIIQFVH<br>GEEDLKVQHSSYRQRARLLKDQLSLGNAALQITDVKLQDAGVYRCMISYGGADYKRITVKVNAPYNKIN<br>QRILVVDPVTSEHELTCQAEGYPKAEVIWTSSDHQVLSGKTTTTNSKREEKLENVTSTLRINTTTNEIF<br>YCTFRRLDPEENHTAELVIPELPLAHPPNERTHLVILGAILLCLGVALTFIERLRKGRMMDVKKCGIQD<br>TNSKKQSDTHLEET |
| 585 | KLH-C3-hIgG4 HC | EVQLVQSGGGLVQPGGSIKLSCAASGFTFSDFYMAWVRQAPTKGLEWVASISTGGGNTHYRDSVKGRFT<br>ISRDNAKSTLYLQMDSLRSEETATYYCARLISTISTPFDYWGQGVIVTVSSASTKGPSVFPLAPCSRST<br>SESTAALGCLVKDYFPEPVTVSWNSGALTSGVHTFPAVLQSSGLYSLSSVVTVPSSSIGTKTYTCNVDH<br>KPSNTKVDKRVESKYGPPCPPCPAPEFLGGPSVFLFPPKPKDTLMISRTPEVTCVVVDVSQEDPEVQFN |

TABLE 29-continued

Sequences

| SEQ ID NO: | Name | Sequence |
|---|---|---|
| | | WYVDGVEVHNAKTKPREEQENSTYRVVSVLTVLHQDWLNGKEYKCKVSNKGLPSSIEKTISKAKGQPRE<br>PQVYTIPPSQEEMTKNQVSLTCLVKGFYPSDIAVEWESNGQPENNYKTTPPVLDSDGSFFLYSRLTVDK<br>SRWQEGNVESCSVMHEALHNHYTQKSLSLSLGK |
| 586 | KLH-C3-hKappa LC | DVVLIQSPTTLSVTPGETVSLSCRASHSVGTNLHWYQQRTNESPSLLIKYSSHSTSGIPSRFSATGSGT<br>DFTINISNVEFDDVASYFCQQSQKWPLTFGSGTKLEIKRTVAAPSVFIFPPSDEQLKSGTASVVCLINN<br>FYPREAKVQWKVDNALQSGNSQESVTEQDSKDSTYSLSSTLTLSKADYEKHKVYACEVTHQGLSSPVTK<br>SENRGEC |
| 587 | 1H3-hIgG1-L6-<br>hCD25 (1-164)-<br>L20-hIL-2<br>(E15A) HC | EVQLVESGGGLVQPGRSLKLSCAVSGETESDYAMAWVRQAPKKGLEWVATISYDGSRTYYRDSVKGRET<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSIGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLAHLLLDLQMILNGINNYKNPKLTRMLTFKFYMPKKATEL<br>KHLQCLEEELKPLEEVINLAQSKNFHLRPRDLISNINVIVLELKGSETTFMCEYADETATIVEFLNRWI<br>TFCQSIISTLT |
| 588 | 1H3-hIgG1-L6-<br>hCD25 (1-164)-<br>L20-hIL-2<br>(D20I) HC | EVQLVESGGGLVQPGRSLKLSCAVSGETESDYAMAWVRQAPKKGLEWVATISYDGSRTYYRDSVKGRET<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSIGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGERRIKSGSLYMLCTGNSSHSSWDNQCQCTSSATRNTTKQVTPQPEEQKERKTTEMQSPMQPVDQAS<br>IPGHCREPPPWENEATERIYHFVVGQMVYYQCVQGYRALHRGPAESVCKMTHGKTRWTQPQLICISGGG<br>GSGGGGSGGGGSGGGSAPTSSSTKKTQLQLEHLLLILQMILNGINNYKNPKLTRMLTFKFYMPKKATEL<br>KHLQCLEEELKPLEEVINLAQSKNFHLRPRDLISNINVIVLELKGSETTFMCEYADETATIVEFLNRWI<br>TFCQSIISTET |
| 589 | 1H3-hIgG1-L6-<br>hCD25 (1-164)-<br>L20-hIL-2<br>(D20S) HC | EVQLVESGGGLVQPGRSLKLSCAVSGFTFSDYAMAWVRQAPKKGLEWVATISYDGSRTYYRDSVKGRET<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMLNCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLSLQMILNGINNYKNPKLTRMLTFKFYMPKKATEL<br>KHLQCLEEELKPLEEVINLAQSKNFHLRPRDLISNINVIVLELKGSETTFMCEYADETATIVEFLNRWI<br>TFCQSIISTLT |
| 590 | 1H3-hIgG1-L6-<br>hCD25 (1-164)-<br>L20-hIL-2<br>(D20H) HC | EVQLVESGGGLVQPGRSLKLSCAVSGFTESDYAMAWVRQAPKKGLEWVATISYDGSRTYYRDSVKGRET<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSIGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTIPPSRDELTKNQVSLTCLVKGFYPSDIAVEWESNGQPENNYKTTPPVLDSDGSFFLYSKLTVDK<br>SRWQQGNVESCSVMHEALHNHYTQKSLSLSPGKSGGGGSELCDDDPPEIPHATFKAMAYKEGTMLNCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLHLQMILNGINNYKNPKLTRMLTFKFYMPKKATEL<br>KHLQCLEEELKPLEEVINLAQSKNFHLRPRDLISNINVIVLELKGSETTFMCEYADETATIVEFLNRWI<br>TFCQSIISTLT |
| 591 | 1H3-hIgG1-L6-<br>hCD25 (1-164)-<br>L20-hIL-2<br>(D20W) HC | EVQLVESGGGLVQPGRSIKLSCAVSGETFSDYAMAWVRQAPKKGLEWVATISYDGSRTYYRDSVKGRET<br>ISRDNAKITLYLQMDSLRSEDTATYYCARHGSGYFDYWGQGVMVTVSSASTKGPSVFPLAPSSKSTSGG<br>TAALGCLVKDYFPEPVTVSWNSGALTSGVHTFPAVLQSSGLYSLSSVVTVPSSSIGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCIGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLWLQMILNGINNYKNPKLTRMLTEKFYMPKKATEL<br>KHLQCLEEELKPLEEVINLAQSKNFHLRPRDLISNINVIVLELKGSETTEMCEYADETATIVEFLNRWI<br>TFCQSIISTLT |

TABLE 29-continued

Sequences

| SEQ ID NO: | Name | Sequence |
|---|---|---|
| 592 | 1H3-hIgG1-L6-hCD25 (1-164)-L20-hIL-2 (D20Y) HC | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWINGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLYLQMILNGINNYKNPKLTRMLTFKFYMPKKATEL<br>KHLQCLEEELKPLEEVLNLAQSKNFHLRPRDLISNINVIVLELKGSETTFMCEYADETATIVEFLNRWI<br>TFCQSIISTLT |
| 593 | 1H3-hIgG1-L6-hCD25 (1-164)-L20-hIL-2 (D20R) HC | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVEPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVTCVVVDVSHEDPEVKEN<br>WYVDGVEVHNAKTKPREEQYNSTYRVVSVLTVLHQDWINGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLRLQMILNGINNYKNPKLTRMLTFKFYMPKKATEL<br>KHLQCLEEELKPLEEVENLAQSKNFHLRPRDLISNINVIVLELKGSETTEMCEYADETATIVEFLNRWI<br>TFCQSIISTLT |
| 594 | 1H3-hIgG1-L6-hCD25 (1-164)-L20-hIL-2 (D20F) HC | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPSSKSTSGG<br>TAALGCLVKDYFPEPVTVSWNSGALISGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVTCVVVDVSHEDPEVKEN<br>WYVDGVEVHNAKTKPREEQYNSTYRVVSVLIVLHQDWINGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKITVDK<br>SRWQQGNVFSCSVMHEALHNHYTQKSLSLSPGKSGGGGSELCDDDPPEIPHATFKAMAYKEGTMINCEC<br>KRGERRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLFLQMILNGINNYKNPKLTRMLTFKFYMPKKATEL<br>KHLQCLEEELKPLEEVINLAQSKNFHLRPRDLISNINVIVLELKGSETTEMCEYADETATIVEFLNRWI<br>TFCQSIISTIT |
| 595 | 1H3-hIgG1-L6-hCD25 (1-164)-L20-hIL-2 (D84K) HC | EVQLVESGGGLVQPGRSLKLSCAVSGFTFSDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPSSKSTSGG<br>TAALGCLVKDYFPEPVTVSWNSGALTSGVHTFPAVLQSSGLYSLSSVVTVPSSSLGTQTYICNVNHKPS<br>NTKVDKKVEPKSCDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALPAPIEKTISKAKGQPRE<br>PQVYTIPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLDLQMILNGINNYKNPKLTRMLTFKFYMPKKATEL<br>KHLQCLEEELKPLEEVINLAQSKNFHLRPRKLISNINVIVLELKGSETTFMCEYADETATIVEFLNRWI<br>TFCQSIISTLT |
| 596 | 1H3-hIgG1-L6-hCD25 (1-164)-L20-hIL-2 (S87A) HC | EVQLVESGGGLVQPGRSLKLSCAVSGFTESDYAMAWVRQAPKKGLEWVATISYDGSRTYYRDSVKGRFT<br>ISRDNAKITLYLQMDSLRSEDTATYYCARHGSGYFDYWGQGVMVTSSASTKGPSVFPLAPSSKSTSGG<br>TAALGCLVKDYFPEPVTVSWNSGALTSGVHTFPAVLQSSGLYSLSSVVTVPSSSIGTQTYICNVNHKPS<br>NTKVDKKVEPKSCDKTHTCPPCPAPELLGGPSVFLFPPKPKDTLMISRTPEVTCVVVDVSHEDPEVKEN<br>WYVDGVEVHNAKTKPREEQYNSTYRVVSVLTVLHQDWLNGKEYKCKVSNKALPAPIEKTISKAKGQPRE<br>PQVYTIPPSRDELTKNQVSLTCLVKGFYPSDIAVEWESNGQPENNYKTTPPVLDSDGSFFLYSKLTVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG<br>GSGGGGSGGGGSGGGSAPTSSSTKKTQLQLEHLLLDLQMILNGINNYKNPKLTRMLTFKFYMPKKATEL<br>KHLQCLEEELKPLEEVINLAQSKNFHLRPRDLIANINVIVLELKGSETTEMCEYADETATIVEFLNRWI<br>TFCQSIISTLT |
| 597 | 1H3-hIgG1-L6-hCD25 (1-164)-L20-hIL-2 (N88Y) HC | EVQLVESGGGLVQPGRSLKLSCAVSGETESDYAMAWVRQAPKKGLEWVATISYDGSRTYYRDSVKGRFT<br>ISRDNAKITLYLQMDSLRSEDTATYYCARHGSGYEDYWGQGVMVTSSASTKGPSVFPLAPSSKSTSGG<br>TAALGCLVKDYFPEPVTVSWNSGALTSGVHTFPAVLQSSGLYSLSSVVTVPSSSIGTQTYICNVNHKPS<br>NTKVDKKVEPKSCDKTHTCPPCPAPELLGGPSVFLFPPKPKDTLMISRTPEVTCVVVDVSHEDPEVKEN<br>WYVDGVEVHNAKTKPREEQYNSTYRVVSVLTVLHQDWLNGKEYKCKVSNKALPAPIEKTISKAKGQPRE<br>PQVYTLPPSRDELTKNQVSLTCLVKGFYPSDIAVEWESNGQPENNYKTTPPVLDSDGSFFLYSKITVDK<br>SRWQQGNVFSCSVMHEALHNHYTQKSLSLSPGKSGGGGSELCDDDPPEIPHATFKAMAYKEGTMINCEC<br>KRGFRRIKSGSLYMLCTGNSSHSSWDNQCQCTSSATRNTTKQVTPQPEEQKERKTTEMQSPMQPVDQAS<br>LPGHCREPPPWENEATERIYHFVVGQMVYYQCVQGYRALHRGPAESVCKMTHGKTRWTQPQLICTSGGG |

TABLE 29-continued

Sequences

| SEQ ID NO: | Name | Sequence |
|---|---|---|
| | | GSGGGGSGGGGSGGGSAPTSSSTKKTQLQLEHLLLDLQMILNGINNYKNPKLTRMLTEKFYMPKKATEL KHLQCLEEELKPLEEVINLAQSKNFHLRPRDLISYINVIVLELKGSETTEMCEYADETATIVEFLNRWI IFCQSIISTIT |
| 598 | 1H3-hIgG1-L6-hCD25(1-164)-L20-hIL-2 (N88D) HC | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMLNCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVLNLAQSKNFHLRPRDLISDINVIVLELKGSETTFMCEYADETATIVEFLNRWI TFCQSIISTLT |
| 599 | 1H3-hIgG1-L6-hCD25(1-164)-L20-hIL-2 (N88R) HC | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWINGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMLNCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVINLAQSKNFHLRPRDLISRINVIVLELKGSETTEMCEYADETATIVEFLNRWI TFCQSIISTLT |
| 600 | 1H3-hIgG1-L6-hCD25(1-164)-L20-hIL-2 (N88E) HC | EVQLVESGGGLVQPGRSLKLSCAVSGFTESDYAMAWVRQAPKKGLEWVATISYDGSRTYYRDSVKGRET ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLIVLHQDWINGKEYKCKVSNKALPAPIEKTISKAKGQPRE PQVYTLPPSRDELTKNQVSLTCLVKGFYPSDIAVEWESNGQPENNYKITPPVLDSDGSFFLYSKITVDK SRWQQGNVFSCSVMHEALHNHYTQKSLSLSPGKSGGGGSELCDDDPPEIPHATFKAMAYKEGTMLNCEC KRGERRIKSGSLYMLCTGNSSHSSWDNQCQCTSSATRNTTKQVTPQPEEQKERKTTEMQSPMQPVDQAS IPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVINLAQSKNFHLRPRDLISEINVIVLELKGSETTEMCEYADETATIVEFLNRWI TFCQSIISTIT |
| 601 | 1H3-hIgG1-L6-hCD25(1-164)-L20-hIL-2 (N88F) HC | EVQLVESGGGLVQPGRSLKLSCAVSGFTFSDYAMAWVRQAPKKGLEWVATISYDGSRTYYRDSVKGRET ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVESCSVMHEALHNHYTQKSLSLSPGKSGGGGSELCDDDPPEIPHATFKAMAYKEGTMLNCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVINLAQSKNFHLRPRDLISFINVIVLELKGSETTFMCEYADETATIVEFLNRWI TFCQSIISTLT |
| 602 | 1H3-hIgG1-L6-hCD25(1-164)-L20-hIL-2 (N88I) HC | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLEPPKPKDTLMISRTPEVTCVVVDVSHEDPEVKEN WYVDGVEVHNAKTKPREEQYNSTYRVVSVLIVLHQDWINGKEYKCKVSNKALPAPIEKTISKAKGQPRE PQVYTLPPSRDELTKNQVSLTCLVKGFYPSDIAVEWESNGQPENNYKITPPVLDSDGSFFLYSKLTVDK SRWQQGNVFSCSVMHEALHNHYTQKSLSLSPGKSGGGGSELCDDDPPEIPHATFKAMAYKEGTMLNCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVINLAQSKNFHLRPRDLISIINVIVLELKGSETTEMCEYADETATIVEFLNRWI TFCQSIISTLT |
| 603 | 1H3-hIgG1-L6-hCD25(1-164)-L20-hIL-2 (I92A) HC | EVQLVESGGGLVQPGRSLKLSCAVSGFTFSDYAMAWVRQAPKKGLEWVATISYDGSRTYYRDSVKGRET ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKEN WYVDGVEVHNAKTKPREEQYNSTYRVVSVLTVLHQDWINGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK |

TABLE 29-continued

Sequences

| SEQ ID NO: | Name | Sequence |
|---|---|---|
| | | SRWQQGNVFSCSVMHEALHNHYTQKSLSLSPGKSGGGGSELCDDDPPEIPHATFKAMAYKEGTMINCEC KRGERRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGGGGGSGGGSAPTSSSTKKTQLQLEHLLIDLQMILNGINNYKNPKLTRMLTFKFYMPKKATEL KHLQCLEEELKPLEEVINLAQSKNFHLRPRDLISNINVAVIELKGSETTEMCEYADETATIVEFLNRWI TFCQSIISTIT |
| 604 | 1H3-hIgG1-L6-hCD25 (1-164)-L20-hIL-2 (E95A) HC | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMINCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVLNLAQSKNFHLRPRDLISNINVIVLALKGSETTFMCEYADETATIVEFLNRWI TFCQSIISTLT |
| 605 | 1H3-hIgG1-L6-hCD25 (1-164)-L20-hIL-2 (E95K) HC | EVQLVESGGGLVQPGRSLKLSCAVSGFTFSDYAMAWVRQAPKKGLEWVATISYDGSRTYYRDSVKGRFT ISRDNAKITLYLQMDSLRSEDTATYYCARHGSGYFDYWGQGVMVTVSSASTKGPSVFPLAPSSKSTSGG TAALGCLVKDYFPEPVTVSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSFFLYSKLTVDK SRWQQGNVFSCSVMHEALHNHYTQKSLSLSPGKSGGGGSELCDDDPPEIPHATFKAMAYKEGTMINCEC KRGFRRIKSGSLYMLCTGNSSHSSWDNQCQCTSSATRNTTKQVTPQPEEQKERKTTEMQSPMQPVDQAS LPGHCREPPPWENEATERIYHFVVGQMVYYQCVQGYRALHRGPAESVCKMTHGKTRWTQPQLICTSGGG GSGGGGSGGGGSGGGSAPTSSSTKKTQLQLEHLLLDLQMILNGINNYKNPKLTRMLTFKFYMPKKATEL KHLQCLEEELKPLEEVLNLAQSKNFHLRPRDLISNINVIVLKLKGSETTFMCEYADETATIVEFLNRWI TFCQSIISTLT |
| 606 | hIL-2 D20R/R38E | APTSSSTKKTQLQLEHLLLRLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 607 | hIL-2 D20N/R38E | APTSSSTKKTQLQLEHLLLNLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 608 | hIL-2 D20Q/R38E | APTSSSTKKTQLQLEHLLLQLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 609 | hIL-2 D20E/R38E | APTSSSTKKTQLQLEHLLLELQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 610 | hIL-2 D20G/R38E | APTSSSTKKTQLQLEHLLLGLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 611 | hIL-2 D20I/R38E | APTSSSTKKTQLQLEHLLLILQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 612 | hIL-2 D20L/R38E | APTSSSTKKTQLQLEHLLLLLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 613 | hIL-2 D20K/R38E | APTSSSTKKTQLQLEHLLLKLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 614 | hIL-2 D20M/R38E | APTSSSTKKTQLQLEHLLLMLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 615 | hIL-2 D20F/R38E | APTSSSTKKTQLQLEHLLLFLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 616 | hIL-2 D20P/R38E | APTSSSTKKTQLQLEHLLLPLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 617 | hIL-2 D20T/R38E | APTSSSTKKTQLQLEHLLLTLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 618 | hIL-2 D20W/R38E | APTSSSTKKTQLQLEHLLLWLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |
| 619 | hIL-2 D20Y/R38E | APTSSSTKKTQLQLEHLLLYLQMILNGINNYKNPKLTEMLTFKFYMPKKATELKHLQCLEEELKPLEEV LNLAQSKNFHLRPRDLISNINVIVLELKGSETTFMCEYADETATIVEFLNRWITFCQSIISTLT |

TABLE 29-continued

Sequences

| SEQ ID NO: | Name | Sequence |
|---|---|---|
| 620 | hIL-2 D20V/R38E | APTSSSTKKTQLQLEHLLLVLQMILNGINNYKNPKLTEMLTFKFYMPKKATELKHLQCLEEELKPLEEV LNLAQSKNFHLRPRDLISNINVIVLELKGSETTEMCEYADETATIVEFLNRWITFCQSIISTLT |
| 621 | hIL-2 F42K/Y45R/V69R | APTSSSTKKTQLQLEHLLLDLQMILNGINNYKNPKLTRMLTKKFRMPKKATELKHLQCLEEELKPLEER LNLAQSKNFHLRPRDLISNINVIVLELKGSETTEMCEYADETATIVEFLNRWITFCQSIISTLT |

EMBODIMENTS

The following list of embodiments is intended to complement, rather than displace or supersede, the previous descriptions.

Embodiment 1. A modified human interleukin-2 (hIL-2) protein, comprising a substitution at amino acid position 20 and a substitution at amino acid position 38 relative to the non-modified hIL-2 amino acid sequence of SEQ ID NO: 345, wherein the modified hIL-2 protein exhibits reduced potency on both a high affinity hIL-2 receptor and on an intermediate affinity hIL-2 receptor relative to a non-modified hIL-2.

Embodiment 2. The modified hIL-2 protein of embodiment 1, wherein the substitution at amino acid position 20 is selected from a D20A, D20S, D20Q, D20M, D20I, D20V, D20N, D20G, D20T, or D20E substitution.

Embodiment 3. The modified hIL-2 protein of embodiment 1 or 2, wherein the substitution at amino acid position 38 is selected from an R38E, R38N, R38G, R38H, R38I, R38L, R38M, R38F, R38P, R38S, R38T, R38W, R38Y, R38V, R38A, R38Q, R38D, and R38K substitution.

Embodiment 4. The modified hIL-2 protein of any one of the previous embodiments, further comprising a deletion or substitution at amino acid position 3 relative to the non-modified hIL-2 amino acid sequence of SEQ ID NO: 345.

Embodiment 5. The modified hIL-2 protein of embodiment 4, wherein the substitution at amino acid position 3 is T3A.

Embodiment 6. The modified hIL-2 protein of any one of the previous embodiments, further comprising a deletion or substitution at amino acid position 125 relative to the non-modified hIL-2 amino acid sequence of SEQ ID NO: 345.

Embodiment 7. The modified hIL-2 protein of embodiment 6, wherein the substitution at amino acid position 125 is C125A.

Embodiment 8. The modified hIL-2 protein of any one of the previous embodiments, wherein the modified hIL-2 protein exhibits about a 1,000-fold reduction in potency on the high affinity IL-2 receptor (hIL-2Rαβγ).

Embodiment 9. The modified hIL-2 protein of any one of the previous embodiments, wherein the modified hIL-2 protein exhibits about a 10,000-fold reduction in potency on the intermediate affinity IL-2 receptor (hIL-2Rβγ).

Embodiment 10. The modified hIL-2 protein of any one of embodiments 1 to 9, wherein the modified hIL-2 protein is fused to an anti-PD-1 antibody or an antigen-binding fragment thereof.

Embodiment 11. The modified hIL-2 protein of embodiment 10, wherein the modified hIL-2 protein is fused to the antibody or an antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment.

Embodiment 12. The modified hIL-2 protein of embodiment 10 or 11, wherein the modified hIL-2 protein is directly fused by a peptide bond to the antibody or an antigen-binding fragment thereof.

Embodiment 13. The modified hIL-2 protein of embodiment 12, wherein the modified hIL-2 is directly fused by a peptide bond to the C-terminal amino acid residue of the antibody heavy chain.

Embodiment 14. The modified hIL-2 protein of embodiment 10 or 11, wherein the modified hIL-2 protein is fused to the antibody or an antigen-binding fragment thereof through a linker.

Embodiment 15. A modified human interleukin-2 (hIL-2) protein, comprising a D20A, D20S, D20Q, D20M, D20I, D20V, D20N, D20G, D20T, or D20E substitution at amino acid position 20 and a R38E substitution at amino acid position 38 relative to the non-modified hIL-2 amino acid sequence of SEQ ID NO: 345.

Embodiment 16. The modified hIL-2 protein of embodiment 15, comprising the amino acid sequence of any one of SEQ ID NOs: 307, 607-611, 614, 617, or 620.

Embodiment 17. The modified hIL-2 protein of embodiment 15 or 16, comprising a D20A substitution and a R38E substitution.

Embodiment 18. The modified hIL-2 protein of embodiment 17, comprising the amino acid sequence of SEQ ID NO: 149.

Embodiment 19. The modified hIL-2 protein of any one of embodiments 15-18, further comprising a deletion or substitution at amino acid position 3 relative to the non-modified hIL-2 amino acid sequence of SEQ ID NO: 345.

Embodiment 20. The modified hIL-2 protein of embodiment 19, wherein the substitution at amino acid position 3 is T3A.

Embodiment 21. The modified hIL-2 protein of embodiment 20, comprising the amino acid sequence of SEQ ID NO: 216.

Embodiment 22. The modified hIL-2 protein of embodiment 19, comprising the amino acid sequence of SEQ ID NO: 218.

Embodiment 23. The modified hIL-2 protein of any one of embodiments 15-22, further comprising a deletion or substitution at amino acid position 125 relative to the non-modified hIL-2 amino acid sequence of SEQ ID NO: 345.

Embodiment 24. The modified hIL-2 protein of embodiment 23, wherein the substitution at amino acid position 125 is C125A.

Embodiment 25. The modified hIL-2 protein of embodiment 24, comprising the amino acid sequence of SEQ ID NO: 215, 217, or 219.

Embodiment 26. The modified hIL-2 protein of embodiment 25, comprising the amino acid sequence of SEQ ID NO: 217.

Embodiment 27. The modified hIL-2 protein of any one of embodiments 15 to 26, wherein the modified hIL-2 protein is fused to an anti-PD-1 antibody or an antigen-binding fragment thereof.

Embodiment 28. The modified hIL-2 protein of embodiment 27, wherein the modified hIL-2 protein is fused to the antibody or an antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment.

Embodiment 29. The modified hIL-2 protein of embodiment 27 or 28, wherein the modified hIL-2 protein is directly fused by a peptide bond to the antibody or an antigen-binding fragment thereof.

Embodiment 30. The modified hIL-2 protein of embodiment 29, wherein the modified hIL-2 is directly fused by a peptide bond to the C-terminal amino acid residue of the antibody heavy chain.

Embodiment 31. The modified hIL-2 protein of embodiment 27 or 28, wherein the modified hIL-2 protein is fused to the antibody or an antigen-binding fragment thereof through a linker.

Embodiment 32. A human antibody molecule, or antigen-binding fragment thereof, that immunospecifically binds to human programmed cell death protein-1 (hPD-1), wherein the human antibody molecule or antigen-binding fragment thereof comprises:
  a) a heavy chain complementarity determining region 1 (CDR1) comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423;
  b) a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391;
  c) a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401; or
  d) a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

Embodiment 33. The human antibody molecule, or antigen-binding fragment thereof, of embodiment 32, comprising:
  a) a heavy chain variable region comprising the amino acid sequence of SEQ ID NO: 416 and a light chain variable region comprising the amino acid sequence of SEQ ID NO: 417;
  b) a heavy chain variable region comprising the amino acid sequence of SEQ ID NO: 384 and a light chain variable region comprising the amino acid sequence of SEQ ID NO: 385;
  c) a heavy chain variable region comprising the amino acid sequence of SEQ ID NO: 394 and a light chain variable region comprising the amino acid sequence of SEQ ID NO: 395; or
  d) a heavy chain variable region comprising the amino acid sequence of SEQ ID NO: 404 and a light chain variable region comprising the amino acid sequence of SEQ ID NO: 405.

Embodiment 34. The human antibody molecule, or antigen-binding fragment thereof, of embodiment 32 or 33, comprising a human IgG1 heavy chain constant region.

Embodiment 35. The human antibody molecule, or antigen-binding fragment thereof, of embodiment 34, comprising an L235A substitution and a G237A substitution, according to EU numbering.

Embodiment 36. The human antibody molecule, or antigen-binding fragment thereof, of any one of embodiments 32-35, comprising:
  a) a heavy chain comprising the amino acid sequence of SEQ ID NO: 414 and a light chain comprising the amino acid sequence of SEQ ID NO: 415;
  b) a heavy chain comprising the amino acid sequence of SEQ ID NO: 424 and a light chain comprising the amino acid sequence of SEQ ID NO: 425;
  c) a heavy chain comprising the amino acid sequence of SEQ ID NO: 426 and a light chain comprising the amino acid sequence of SEQ ID NO: 427; or
  d) a heavy chain comprising the amino acid sequence of SEQ ID NO: 428 and a light chain comprising the amino acid sequence of SEQ ID NO: 429.

Embodiment 37. The human antibody molecule, or antigen-binding fragment thereof, of embodiment 36, comprising a heavy chain comprising the amino acid sequence of SEQ ID NO: 414 and a light chain comprising the amino acid sequence of SEQ ID NO: 415.

Embodiment 38. The human antibody molecule, or antigen-binding fragment thereof, of any one of embodiments 32-37, fused to a modified human interleukin-2 (hIL-2) protein comprising a substitution at amino acid position 20 and a substitution at amino acid position 38 relative to the non-modified hIL-2 amino acid sequence of SEQ ID NO: 345.

Embodiment 39. The human antibody molecule, or antigen-binding fragment thereof, of embodiment 38, wherein the modified hIL-2 protein comprises the amino acid sequence of any one of SEQ ID NOs: 134-150, 307, 344, 607-611, 614, 617, or 620.

Embodiment 40. The human antibody molecule, or antigen-binding fragment thereof, of embodiment 39, wherein the modified hIL-2 protein comprises the amino acid sequence of SEQ ID NO: 149.

Embodiment 41. The human antibody molecule, or antigen-binding fragment thereof, of any one of embodiments 38-40, wherein the modified hIL-2 protein further comprises a deletion or substitution at amino acid position 3 relative to the non-modified hIL-2 amino acid sequence of SEQ ID NO: 345.

Embodiment 42. The human antibody molecule, or antigen-binding fragment thereof, of embodiment 41, wherein the substitution at amino acid position 3 is T3A.

Embodiment 43. The human antibody molecule, or antigen-binding fragment thereof, of embodiment 42, wherein the modified hIL-2 protein comprises the amino acid sequence of SEQ ID NO: 216.

Embodiment 44. The human antibody molecule, or antigen-binding fragment thereof, of embodiment 41, wherein the modified hIL-2 protein comprises the amino acid sequence of SEQ ID NO: 218.

Embodiment 45. The human antibody molecule, or antigen-binding fragment thereof, of any one of embodiments 38-44, wherein the modified hIL-2 protein further comprises a deletion or substitution at amino acid position 125 relative to the non-modified hIL-2 amino acid sequence of SEQ ID NO: 345.

Embodiment 46. The human antibody molecule, or antigen-binding fragment thereof, of embodiment 45, wherein the substitution at amino acid position 125 is C125A.

Embodiment 47. The human antibody molecule, or antigen-binding fragment thereof, of embodiment 46, wherein the modified hIL-2 protein comprises the amino acid sequence of SEQ ID NO: 215, 217, or 219.

Embodiment 48. The human antibody molecule, or antigen-binding fragment thereof, of embodiment 47, wherein the modified hIL-2 protein comprises the amino acid sequence of SEQ ID NO: 217.

Embodiment 49. The human antibody molecule, or antigen-binding fragment thereof, of any one of embodiments 38-48, wherein the modified hIL-2 protein is fused to the antibody or antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment.

Embodiment 50. The human antibody molecule, or antigen-binding fragment thereof, of any one of embodiments 38-49, wherein the modified hIL-2 protein is directly fused by a peptide bond to the antibody or antigen-binding fragment thereof.

Embodiment 51. The human antibody molecule, or antigen-binding fragment thereof, of embodiment 50, wherein the modified hIL-2 protein is directly fused by a peptide bond to the C-terminal amino acid residue of the antibody heavy chain.

Embodiment 52. The human antibody molecule, or antigen-binding fragment thereof, of any one of embodiments 38-49, wherein the modified hIL-2 protein is fused to the antibody or antigen-binding fragment through a linker.

Embodiment 53. An immunoconjugate comprising:
(a) a modified human interleukin-2 (hIL-2) protein comprising a substitution at amino acid position 20 and a substitution at amino acid position 38 relative to the non-modified hIL-2 amino acid sequence of SEQ ID NO: 345; and
(b) a human antibody molecule, or antigen-binding fragment thereof, that immunospecifically binds to human programmed cell death protein-1 (hPD-1), wherein the human antibody molecule or antigen-binding fragment thereof comprises:
(i) a heavy chain complementarity determining region 1 (CDR1) comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423;
(ii) a heavy chain CDR1 comprising the amino acid sequence of SEQ ID NO: 386, a heavy chain CDR2 comprising the amino acid sequence of SEQ ID NO: 387, a heavy chain CDR3 comprising the amino acid sequence of SEQ ID NO: 388, a light chain CDR1 comprising the amino acid sequence of SEQ ID NO: 389, a light chain CDR2 comprising the amino acid sequence of SEQ ID NO: 390, and a light chain CDR3 comprising the amino acid sequence of SEQ ID NO: 391;
(iii) a heavy chain CDR1 comprising the amino acid sequence of SEQ ID NO: 396, a heavy chain CDR2 comprising the amino acid sequence of SEQ ID NO: 397, a heavy chain CDR3 comprising the amino acid sequence of SEQ ID NO: 398, a light chain CDR1 comprising the amino acid sequence of SEQ ID NO: 399, a light chain CDR2 comprising the amino acid sequence of SEQ ID NO: 400, and a light chain CDR3 comprising the amino acid sequence of SEQ ID NO: 401; or
(iv) a heavy chain CDR1 comprising the amino acid sequence of SEQ ID NO: 406, a heavy chain CDR2 comprising the amino acid sequence of SEQ ID NO: 407, a heavy chain CDR3 comprising the amino acid sequence of SEQ ID NO: 408, a light chain CDR1 comprising the amino acid sequence of SEQ ID NO: 409, a light chain CDR2 comprising the amino acid sequence of SEQ ID NO: 410, and a light chain CDR3 comprising the amino acid sequence of SEQ ID NO: 411.

Embodiment 54. The immunoconjugate of embodiment 53, wherein the substitution at amino acid position 20 of the modified hIL-2 protein is selected from a D20A, D20S, D20Q, D20M, D20I, D20V, D20N, D20G, D20T, or D20E substitution.

Embodiment 55. The immunoconjugate of embodiment 53 or 54, wherein the substitution at amino acid position 38 of the modified hIL-2 protein is selected from an R38E, R38N, R38G, R38H, R38I, R38L, R38M, R38F, R38P, R38S, R38T, R38W, R38Y, R38V, R38A, R38Q, R38D, and R38K substitution.

Embodiment 56. The immunoconjugate of any one of embodiments 53-55, wherein the substitution at amino acid position 20 of the modified hIL-2 protein is selected from a D20A, D20S, D20Q, D20M, D20I, D20V, D20N, D20G, D20T, or D20E substitution and the amino acid substitution at amino acid position 38 of the modified hIL-2 protein is R38E.

Embodiment 57. The immunoconjugate of any one of embodiments 53-56, wherein the modified hIL-2 protein comprises the amino acid sequence of any one of SEQ ID NOs: 134-150, 307, 344, 607-611, 614, 617, or 620.

Embodiment 58. The immunoconjugate of any one of embodiments 53-56, wherein the modified hIL-2 protein comprises a D20A and a R38E substitution.

Embodiment 59. The immunoconjugate of embodiment 58, wherein the modified hIL-2 protein comprises the amino acid sequence of SEQ ID NO: 149.

Embodiment 60. The immunoconjugate of any one of embodiments 53-57, comprising the amino acid sequence of any one of SEQ ID NOs: 608, 614, 611, 620, 607, 610, 617, 609, or 307.

Embodiment 61. The immunoconjugate of any one of embodiments 53-60, wherein the modified hIL-2 protein further comprises a deletion or substitution at amino acid position 3 relative to the non-modified hIL-2 amino acid sequence of SEQ ID NO: 345.

Embodiment 62. The immunoconjugate of embodiment 61, wherein the substitution at amino acid position 3 of the modified hIL-2 protein is T3A.

Embodiment 63. The immunoconjugate of embodiment 62, wherein the modified hIL-2 protein comprises the amino acid sequence of SEQ ID NO: 216.

Embodiment 64. The immunoconjugate of embodiment 61, wherein the modified hIL-2 protein comprises the amino acid sequence of SEQ ID NO: 218.

Embodiment 65. The immunoconjugate of any one of embodiments 53-64, wherein the modified hIL-2 protein further comprises a deletion or substitution at amino acid position 125 relative to the non-modified hIL-2 amino acid sequence of SEQ ID NO: 345.

Embodiment 66. The immunoconjugate of embodiment 65, wherein the substitution at amino acid position 125 is C125A.

Embodiment 67. The immunoconjugate of embodiment 66, wherein the modified hIL-2 protein comprises the amino acid sequence of SEQ ID NO: 215, 217, or 219.

Embodiment 68. The immunoconjugate of embodiment 67, wherein the modified hIL-2 protein comprises the amino acid sequence of SEQ ID NO: 217.

Embodiment 69. The immunoconjugate of any one of embodiments 53-68, wherein the modified hIL-2 protein is fused to the antibody or antigen-binding fragment thereof at the N-terminus of an antibody light chain, the C-terminus of an antibody light chain, the N-terminus of an antibody heavy chain, the C-terminus of an antibody heavy chain, the N-terminus of the antigen-binding fragment, or the C-terminus of the antigen-binding fragment.

Embodiment 70. The immunoconjugate of any one of embodiments 53-69, wherein the modified hIL-2 protein is directly fused by a peptide bond to the antibody or antigen-binding fragment thereof.

Embodiment 71. The immunoconjugate of embodiment 70, wherein modified hIL-2 protein is directly fused by a peptide bond to the C-terminal amino acid residue of the antibody heavy chain.

Embodiment 72. The immunoconjugate of any one of embodiments 53-69, wherein the modified hIL-2 protein is fused to the antibody or antigen-binding fragment thereof through a linker.

Embodiment 73. The immunoconjugate of any one of embodiments 53-72, wherein the human antibody molecule, or antigen-binding fragment thereof, comprises:
  a) a heavy chain variable region comprising the amino acid sequence of SEQ ID NO: 416 and a light chain variable region comprising the amino acid sequence of SEQ ID NO: 417;
  b) a heavy chain variable region comprising the amino acid sequence of SEQ ID NO: 384 and a light chain variable region comprising the amino acid sequence of SEQ ID NO: 385;
  c) a heavy chain variable region comprising the amino acid sequence of SEQ ID NO: 394 and a light chain variable region comprising the amino acid sequence of SEQ ID NO: 395; or
  d) a heavy chain variable region comprising the amino acid sequence of SEQ ID NO: 404 and a light chain variable region comprising the amino acid sequence of SEQ ID NO: 405.

Embodiment 74. The immunoconjugate of any one of embodiments 53-73, wherein the human antibody molecule, or antigen-binding fragment thereof, comprises an IgG1 heavy chain constant region.

Embodiment 75. The immunoconjugate of embodiment 74, wherein the human antibody molecule, or antigen-binding fragment thereof, comprises an L235A substitution and a G237A substitution, according to EU numbering.

Embodiment 76. The immunoconjugate of any one of embodiments 53-75, wherein the human antibody molecule, or antigen-binding fragment thereof, comprises:
  a) a heavy chain comprising the amino acid sequence of SEQ ID NO: 414 and a light chain comprising the amino acid sequence of SEQ ID NO: 415;
  b) a heavy chain comprising the amino acid sequence of SEQ ID NO: 424 and a light chain comprising the amino acid sequence of SEQ ID NO: 425;
  c) a heavy chain comprising the amino acid sequence of SEQ ID NO: 426 and a light chain comprising the amino acid sequence of SEQ ID NO: 427; or
  d) a heavy chain comprising the amino acid sequence of SEQ ID NO: 428 and a light chain comprising the amino acid sequence of SEQ ID NO: 429.

Embodiment 77. The immunoconjugate of embodiment 76, wherein the human antibody molecule, or antigen-binding fragment thereof, comprises a heavy chain comprising the amino acid sequence of SEQ ID NO: 414 and a light chain comprising the amino acid sequence of SEQ ID NO: 415.

Embodiment 78. The immunoconjugate of any one of embodiments 53-77, comprising a light chain comprising the amino acid sequence of SEQ ID NO: 415; and a heavy chain-modified hIL-2 protein fusion comprising the amino acid sequence of SEQ ID NO: 532.

Embodiment 79. A pharmaceutical composition comprising the modified hIL-2 protein of any one of embodiments 1-31, the human antibody molecule, or antigen-binding fragment thereof, of any one of embodiments 32-52, or the immunoconjugate of any one of embodiments 53-78.

Embodiment 80. A polynucleotide, comprising a nucleic acid sequence encoding the modified hIL-2 protein of any one of embodiments 1-31, the human antibody molecule, or antigen-binding fragment thereof, of any one of embodiments 32-52, or the immunoconjugate of any one of embodiments 53-78.

Embodiment 81. A vector comprising a polynucleotide comprising a nucleic acid sequence that encodes the modified hIL-2 protein of any one of embodiments 1-31, the human antibody molecule, or antigen-binding fragment thereof, of any one of embodiments 32-52, or the immunoconjugate of any one of embodiments 53-78.

Embodiment 82. A transformed cell comprising the vector of embodiment 81.

Embodiment 83. A method of treating a disease or disorder in a subject, the method comprising administering a therapeutically effective amount of the modified hIL-2 protein of any one of embodiments 10-14 and 27-31, the immunoconjugate of any one of embodiments 53-78, or the pharmaceutical composition of embodiment 79 to the subject to thereby treat the disease or disorder.

Embodiment 84. The method of embodiment 83, wherein the disease or disorder is cancer.

Embodiment 85. The method of embodiment 84, wherein the cancer is melanoma.

Embodiment 86. The method of embodiment 84, wherein the cancer is non-small cell lung carcinoma.

Embodiment 87. Use of the modified hIL-2 protein of any one of embodiments 10-14 and 27-31, the immunoconjugate of any one of embodiments 53-78, or the pharmaceutical composition of embodiment 79 in the preparation of a medicament for the treatment of a disease or disorder.

Embodiment 88. The use of embodiment 87, wherein the disease or disorder is cancer.

Embodiment 89. The use of embodiment 88, wherein the cancer is melanoma.

Embodiment 90. The use of embodiment 88, wherein the cancer is non-small cell lung carcinoma.

Embodiment 91. Use of the modified hIL-2 protein of any one of embodiments 10-14 and 27-31, the immunoconjugate of any one of embodiments 53-78, or the pharmaceutical composition of embodiment 79 for the treatment of a disease or disorder.

Embodiment 92. The use of embodiment 91, wherein the disease or disorder is cancer.

Embodiment 93. The use of embodiment 92, wherein the cancer is melanoma.

Embodiment 94. The use of embodiment 92, wherein the cancer is non-small cell lung carcinoma.

What is claimed:

1. An anti-human PD-1 (hPD-1) antibody-modified human interleukin-2 (hIL-2) immunoconjugate comprising:
   a modified hIL-2 protein comprising the amino acid sequence of SEQ ID NO: 217; and
   an anti-hPD-1 antibody, or antigen-binding fragment thereof, that immunospecifically binds to hPD-1, wherein the antibody or antigen-binding fragment thereof, comprises a heavy chain complementarity determining region 1 (CDR1) comprising the amino acid sequence of SEQ ID NO: 418, a heavy chain CDR2 comprising the amino acid sequence of SEQ ID NO: 419, a heavy chain CDR3 comprising the amino acid sequence of SEQ ID NO: 420, a light chain CDR1 comprising the amino acid sequence of SEQ ID NO: 421, a light chain CDR2 comprising the amino acid sequence of SEQ ID NO: 422, and a light chain CDR3 comprising the amino acid sequence of SEQ ID NO: 423.

2. The immunoconjugate of claim 1, wherein the anti-hPD-1 antibody, or antigen-binding fragment thereof, comprises an IgG1 heavy chain constant region.

3. The immunoconjugate of claim 2, wherein the anti-hPD-1 antibody, or antigen-binding fragment thereof, comprises an L235A substitution and a G237A substitution, according to EU numbering.

4. The immunoconjugate of claim 3, wherein the anti-hPD-1 antibody, or antigen-binding fragment thereof, comprises a heavy chain (HC) comprising the amino acid sequence of SEQ ID NO: 414 and a light chain (LC) comprising the amino acid sequence of SEQ ID NO: 415.

5. An anti-hPD-1 antibody-modified hIL-2 immunoconjugate comprising:
   a modified hIL-2 protein comprising the amino acid sequence of SEQ ID NO: 217; and
   an anti-hPD-1 antibody, or antigen-binding fragment thereof, comprising a VH comprising the amino acid sequence of SEQ ID NO: 416 and a VL comprising the amino acid sequence of SEQ ID NO: 417.

6. The immunoconjugate of claim 5, wherein the anti-hPD-1 antibody, or antigen-binding fragment thereof, comprises an IgG1 heavy chain constant region.

7. The immunoconjugate of claim 6, wherein the anti-hPD-1 antibody, or antigen-binding fragment thereof, comprises an L235A substitution and a G237A substitution, according to EU numbering.

8. The immunoconjugate of claim 7, wherein the anti-hPD-1 antibody, or antigen-binding fragment thereof, comprises a HC comprising the amino acid sequence of SEQ ID NO: 414 and a LC comprising the amino acid sequence of SEQ ID NO: 415.

9. An anti-hPD-1 antibody-modified hIL-2 immunoconjugate comprising:
   a modified hIL-2 protein comprising the amino acid sequence of SEQ ID NO: 217; and
   an anti-hPD-1 antibody, or antigen-binding fragment thereof, comprising a HC comprising the amino acid sequence of SEQ ID NO: 414 and a LC comprising the amino acid sequence of SEQ ID NO: 415.

10. The immunoconjugate of claim 9, comprising:
   a light chain comprising the amino acid sequence of SEQ ID NO: 415; and
   a heavy chain-modified hIL-2 protein fusion comprising the amino acid sequence of SEQ ID NO: 532.

* * * * *

SEQUENCE LISTING

```
Sequence total quantity: 621
SEQ ID NO: 1              moltype = AA  length = 133
FEATURE                   Location/Qualifiers
source                    1..133
                          mol_type = protein
                          organism = Synthetic construct
SEQUENCE: 1
APTSSSTKKT QLQLEHLLLD LQMILNGINN YKNPKLTRML TKKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 2              moltype = AA  length = 133
FEATURE                   Location/Qualifiers
source                    1..133
                          mol_type = protein
                          organism = Synthetic construct
SEQUENCE: 2
APTSSSTKKT QLQLEHLLLD LQMILNGINN YKNPKLTRML TFKFYMPKKA TELKHLQCLE   60
EELKPLEEAL NLAQSKNFHL RPRDLISNIN VIVLELKGSE TTFMCEYADE TATIVEFLNR  120
WITFCQSIIS TLT                                                    133

SEQ ID NO: 3              moltype = AA  length = 133
FEATURE                   Location/Qualifiers
source                    1..133
                          mol_type = protein
                          organism = Synthetic construct
SEQUENCE: 3
APTSSSTKKT QLQLEHLLLD LQMILNGINN YKNPKLTRML TFKFYMPKKA TELKHLQCLE   60
EELKPLEEEL NLAQSKNFHL RPRDLISNIN VIVLELKGSE TTFMCEYADE TATIVEFLNR  120
WITFCQSIIS TLT                                                    133

SEQ ID NO: 4              moltype = AA  length = 133
FEATURE                   Location/Qualifiers
source                    1..133
                          mol_type = protein
                          organism = Synthetic construct
SEQUENCE: 4
APTSSSTKKT QLQLEHLLLD LQMILNGINN YKNPKLTRML TFKFYMPKKA TELKHLQCLE   60
EELKPLEEFL NLAQSKNFHL RPRDLISNIN VIVLELKGSE TTFMCEYADE TATIVEFLNR  120
WITFCQSIIS TLT                                                    133

SEQ ID NO: 5              moltype = AA  length = 133
FEATURE                   Location/Qualifiers
source                    1..133
                          mol_type = protein
                          organism = Synthetic construct
SEQUENCE: 5
APTSSSTKKT QLQLEHLLLD LQMILNGINN YKNPKLTRML TFKFYMPKKA TELKHLQCLE   60
EELKPLEEGL NLAQSKNFHL RPRDLISNIN VIVLELKGSE TTFMCEYADE TATIVEFLNR  120
WITFCQSIIS TLT                                                    133

SEQ ID NO: 6              moltype = AA  length = 133
FEATURE                   Location/Qualifiers
source                    1..133
                          mol_type = protein
                          organism = Synthetic construct
```

```
SEQUENCE: 6
APTSSSTKKT QLQLEHLLLD LQMILNGINN YKNPKLTRML TFKFYMPKKA TELKHLQCLE    60
EELKPLEEHL NLAQSKNFHL RPRDLISNIN VIVLELKGSE TTFMCEYADE TATIVEFLNR   120
WITFCQSIIS TLT                                                     133

SEQ ID NO: 7              moltype = AA  length = 133
FEATURE                   Location/Qualifiers
source                    1..133
                          mol_type = protein
                          organism = Synthetic construct
SEQUENCE: 7
APTSSSTKKT QLQLEHLLLD LQMILNGINN YKNPKLTRML TFKFYMPKKA TELKHLQCLE    60
EELKPLEEIL NLAQSKNFHL RPRDLISNIN VIVLELKGSE TTFMCEYADE TATIVEFLNR   120
WITFCQSIIS TLT                                                     133

SEQ ID NO: 8              moltype = AA  length = 133
FEATURE                   Location/Qualifiers
source                    1..133
                          mol_type = protein
                          organism = Synthetic construct
SEQUENCE: 8
APTSSSTKKT QLQLEHLLLD LQMILNGINN YKNPKLTRML TFKFYMPKKA TELKHLQCLE    60
EELKPLEEKL NLAQSKNFHL RPRDLISNIN VIVLELKGSE TTFMCEYADE TATIVEFLNR   120
WITFCQSIIS TLT                                                     133

SEQ ID NO: 9              moltype = AA  length = 133
FEATURE                   Location/Qualifiers
source                    1..133
                          mol_type = protein
                          organism = Synthetic construct
SEQUENCE: 9
APTSSSTKKT QLQLEHLLLD LQMILNGINN YKNPKLTRML TFKFYMPKKA TELKHLQCLE    60
EELKPLEELL NLAQSKNFHL RPRDLISNIN VIVLELKGSE TTFMCEYADE TATIVEFLNR   120
WITFCQSIIS TLT                                                     133

SEQ ID NO: 10             moltype = AA  length = 133
FEATURE                   Location/Qualifiers
source                    1..133
                          mol_type = protein
                          organism = Synthetic construct
SEQUENCE: 10
APTSSSTKKT QLQLEHLLLD LQMILNGINN YKNPKLTRML TFKFYMPKKA TELKHLQCLE    60
EELKPLEEML NLAQSKNFHL RPRDLISNIN VIVLELKGSE TTFMCEYADE TATIVEFLNR   120
WITFCQSIIS TLT                                                     133

SEQ ID NO: 11             moltype = AA  length = 133
FEATURE                   Location/Qualifiers
source                    1..133
                          mol_type = protein
                          organism = Synthetic construct
SEQUENCE: 11
APTSSSTKKT QLQLEHLLLD LQMILNGINN YKNPKLTRML TFKFYMPKKA TELKHLQCLE    60
EELKPLEEQL NLAQSKNFHL RPRDLISNIN VIVLELKGSE TTFMCEYADE TATIVEFLNR   120
WITFCQSIIS TLT                                                     133

SEQ ID NO: 12             moltype = AA  length = 133
FEATURE                   Location/Qualifiers
source                    1..133
                          mol_type = protein
                          organism = Synthetic construct
SEQUENCE: 12
APTSSSTKKT QLQLEHLLLD LQMILNGINN YKNPKLTRML TFKFYMPKKA TELKHLQCLE    60
EELKPLEESL NLAQSKNFHL RPRDLISNIN VIVLELKGSE TTFMCEYADE TATIVEFLNR   120
WITFCQSIIS TLT                                                     133

SEQ ID NO: 13             moltype = AA  length = 133
FEATURE                   Location/Qualifiers
source                    1..133
                          mol_type = protein
                          organism = Synthetic construct
SEQUENCE: 13
APTSSSTKKT QLQLEHLLLD LQMILNGINN YKNPKLTRML TFKFYMPKKA TELKHLQCLE    60
EELKPLEETL NLAQSKNFHL RPRDLISNIN VIVLELKGSE TTFMCEYADE TATIVEFLNR   120
WITFCQSIIS TLT                                                     133

SEQ ID NO: 14             moltype = AA  length = 133
FEATURE                   Location/Qualifiers
source                    1..133
                          mol_type = protein
```

```
                         organism = Synthetic construct
SEQUENCE: 14
APTSSSTKKT QLQLEHLLLD LQMILNGINN YKNPKLTRML TFKFYMPKKA TELKHLQCLE      60
EELKPLEEWL NLAQSKNFHL RPRDLISNIN VIVLELKGSE TTFMCEYADE TATIVEFLNR     120
WITFCQSIIS TLT                                                        133

SEQ ID NO: 15            moltype = AA  length = 133
FEATURE                  Location/Qualifiers
source                   1..133
                         mol_type = protein
                         organism = Synthetic construct
SEQUENCE: 15
APTSSSTKKT QLQLEHLLLD LQMILNGINN YKNPKLTRML TFKFYMPKKA TELKHLQCLE      60
EELKPLEEYL NLAQSKNFHL RPRDLISNIN VIVLELKGSE TTFMCEYADE TATIVEFLNR     120
WITFCQSIIS TLT                                                        133

SEQ ID NO: 16            moltype = AA  length = 133
FEATURE                  Location/Qualifiers
source                   1..133
                         mol_type = protein
                         organism = Synthetic construct
SEQUENCE: 16
APTSSSTKKT QLQLEHLLLD LQMILNGINN YKNPKLTRML TKKKYMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                        133

SEQ ID NO: 17            moltype = AA  length = 133
FEATURE                  Location/Qualifiers
source                   1..133
                         mol_type = protein
                         organism = Synthetic construct
SEQUENCE: 17
APTSSSTKKT QLQLEHLLLD LQMILNGINN YKNPKLTRML TFKKRMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                        133

SEQ ID NO: 18            moltype = AA  length = 133
FEATURE                  Location/Qualifiers
source                   1..133
                         mol_type = protein
                         organism = Synthetic construct
SEQUENCE: 18
APTSSSTKKT QLQLEHLLLD LQMILNGINN YKNPKLTRML TKKFYMPKKA TELKHLQCLE      60
EELKPLEERL NLAQSKNFHL RPRDLISNIN VIVLELKGSE TTFMCEYADE TATIVEFLNR     120
WITFCQSIIS TLT                                                        133

SEQ ID NO: 19            moltype = AA  length = 133
FEATURE                  Location/Qualifiers
source                   1..133
                         mol_type = protein
                         organism = Synthetic construct
SEQUENCE: 19
APTSSSTKKT QLQLEHLLLD LQMILNGINN YKNPKLTRML TFKFRMPKKA TELKHLQCLE      60
EELKPLEERL NLAQSKNFHL RPRDLISNIN VIVLELKGSE TTFMCEYADE TATIVEFLNR     120
WITFCQSIIS TLT                                                        133

SEQ ID NO: 20            moltype = AA  length = 133
FEATURE                  Location/Qualifiers
source                   1..133
                         mol_type = protein
                         organism = Synthetic construct
SEQUENCE: 20
APTSSSTKKT QLQLEHLLLD LQMILNGINN YKNPKLTRML TKKKRMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                        133

SEQ ID NO: 21            moltype = AA  length = 133
FEATURE                  Location/Qualifiers
source                   1..133
                         mol_type = protein
                         organism = Synthetic construct
SEQUENCE: 21
APTSSSTKKT QLQLEHLLLD LQMILNGINN YKNPKLTAML TKKFRMPKKA TELKHLQCLE      60
EELKPLEEVL NLAQSKNFHL RPRDLISNIN VIVLELKGSE TTFMCEYADE TATIVEFLNR     120
WITFCQSIIS TLT                                                        133

SEQ ID NO: 22            moltype = AA  length = 133
FEATURE                  Location/Qualifiers
source                   1..133
```

```
                        mol_type = protein
                        organism = Synthetic construct
SEQUENCE: 22
APTSSSTKKT QLQLEHLLLD LQMILNGINN YKNPKLTEML TKKFRMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 23           moltype = AA  length = 133
FEATURE                 Location/Qualifiers
source                  1..133
                        mol_type = protein
                        organism = Synthetic construct
SEQUENCE: 23
APTSSSTKKT QLQLEHLLLD LQMILNGINN YKNPKLTRML TKEFRMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 24           moltype = AA  length = 133
FEATURE                 Location/Qualifiers
source                  1..133
                        mol_type = protein
                        organism = Synthetic construct
SEQUENCE: 24
APTSSSTKKT QLQLEHLLLD LQMILNGINN YKNPKLTRML TKTFRMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 25           moltype = AA  length = 133
FEATURE                 Location/Qualifiers
source                  1..133
                        mol_type = protein
                        organism = Synthetic construct
SEQUENCE: 25
APTSSSTKKT QLQLEHLLLD LQMILNGINN YKNPKLTRML TKKFRMPKKA TELKHLQCLE    60
EALKPLEEVL NLAQSKNFHL RPRDLISNIN VIVLELKGSE TTFMCEYADE TATIVEFLNR   120
WITFCQSIIS TLT                                                     133

SEQ ID NO: 26           moltype = AA  length = 133
FEATURE                 Location/Qualifiers
source                  1..133
                        mol_type = protein
                        organism = Synthetic construct
SEQUENCE: 26
APTSSSTKKT QLQLEHLLLD LQMILNGINN YKNPKLTRML TKKFRMPKKA TELKHLQCLE    60
EELKRLEEVL NLAQSKNFHL RPRDLISNIN VIVLELKGSE TTFMCEYADE TATIVEFLNR   120
WITFCQSIIS TLT                                                     133

SEQ ID NO: 27           moltype = AA  length = 133
FEATURE                 Location/Qualifiers
source                  1..133
                        mol_type = protein
                        organism = Synthetic construct
SEQUENCE: 27
APTSSSTKKT QLQLEHLLLD LQMILNGINN YKNPKLTRML TKKFRMPKKA TELKHLQCLE    60
EELKSLEEVL NLAQSKNFHL RPRDLISNIN VIVLELKGSE TTFMCEYADE TATIVEFLNR   120
WITFCQSIIS TLT                                                     133

SEQ ID NO: 28           moltype = AA  length = 133
FEATURE                 Location/Qualifiers
source                  1..133
                        mol_type = protein
                        organism = Synthetic construct
SEQUENCE: 28
APTSSSTKKT QLQLEHLLLD LQMILNGINN YKNPKLTRML TKKFRMPKKA TELKHLQCLE    60
EELKPLEEAL NLAQSKNFHL RPRDLISNIN VIVLELKGSE TTFMCEYADE TATIVEFLNR   120
WITFCQSIIS TLT                                                     133

SEQ ID NO: 29           moltype = AA  length = 133
FEATURE                 Location/Qualifiers
source                  1..133
                        mol_type = protein
                        organism = Synthetic construct
SEQUENCE: 29
APTSSSTKKT QLQLEHLLLD LQMILNGINN YKNPKLTRML TKKFRMPKKA TELKHLQCLE    60
EELKPLEEDL NLAQSKNFHL RPRDLISNIN VIVLELKGSE TTFMCEYADE TATIVEFLNR   120
WITFCQSIIS TLT                                                     133

SEQ ID NO: 30           moltype = AA  length = 133
FEATURE                 Location/Qualifiers
```

```
source                       1..133
                             mol_type = protein
                             organism = Synthetic construct
SEQUENCE: 30
APTSSSTKKT QLQLEHLLLD LQMILNGINN YKNPKLTRML TKKFRMPKKA TELKHLQCLE    60
EELKPLEERL NLAQSKNFHL RPRDLISNIN VIVLELKGSE TTFMCEYADE TATIVEFLNR   120
WITFCQSIIS TLT                                                     133

SEQ ID NO: 31                moltype = AA   length = 133
FEATURE                      Location/Qualifiers
source                       1..133
                             mol_type = protein
                             organism = Synthetic construct
SEQUENCE: 31
APTSSSTKKT QLQLEHLLLA LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 32                moltype = AA   length = 133
FEATURE                      Location/Qualifiers
source                       1..133
                             mol_type = protein
                             organism = Synthetic construct
SEQUENCE: 32
APTSSSTKKT QLQLEHLLLN LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 33                moltype = AA   length = 133
FEATURE                      Location/Qualifiers
source                       1..133
                             mol_type = protein
                             organism = Synthetic construct
SEQUENCE: 33
APTSSSTKKT QLQLEHLLLK LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 34                moltype = AA   length = 133
FEATURE                      Location/Qualifiers
source                       1..133
                             mol_type = protein
                             organism = Synthetic construct
SEQUENCE: 34
APTSSSTKKT QLQLEHLLLD LQMILNGINN YKNPKLTRML TFKFYMPKKA TELKHLQCLE    60
EELKPLEEVL NLAQSKNFHL RPRDLISAIN VIVLELKGSE TTFMCEYADE TATIVEFLNR   120
WITFCQSIIS TLT                                                     133

SEQ ID NO: 35                moltype = AA   length = 133
FEATURE                      Location/Qualifiers
source                       1..133
                             mol_type = protein
                             organism = Synthetic construct
SEQUENCE: 35
APTSSSTKKT QLQLEHLLLD LQMILNGINN YKNPKLTRML TFKFYMPKKA TELKHLQCLE    60
EELKPLEEVL NLAQSKNFHL RPRDLISGIN VIVLELKGSE TTFMCEYADE TATIVEFLNR   120
WITFCQSIIS TLT                                                     133

SEQ ID NO: 36                moltype = AA   length = 133
FEATURE                      Location/Qualifiers
source                       1..133
                             mol_type = protein
                             organism = Synthetic construct
SEQUENCE: 36
APTSSSTKKT QLQLEHLLLD LQMILNGINN YKNPKLTRML TFKFYMPKKA TELKHLQCLE    60
EELKPLEEVL NLAQSKNFHL RPRDLISHIN VIVLELKGSE TTFMCEYADE TATIVEFLNR   120
WITFCQSIIS TLT                                                     133

SEQ ID NO: 37                moltype = AA   length = 133
FEATURE                      Location/Qualifiers
source                       1..133
                             mol_type = protein
                             organism = Synthetic construct
SEQUENCE: 37
APTSSSTKKT QLQLEHLLLD LQMILNGINN YKNPKLTRML TFKFYMPKKA TELKHLQCLE    60
EELKPLEEVL NLAQSKNFHL RPRDLISKIN VIVLELKGSE TTFMCEYADE TATIVEFLNR   120
WITFCQSIIS TLT                                                     133

SEQ ID NO: 38                moltype = AA   length = 133
```

```
FEATURE                 Location/Qualifiers
source                  1..133
                        mol_type = protein
                        organism = Synthetic construct
SEQUENCE: 38
APTSSSTKKT QLQLEHLLLA LQMILNGINN YKNPKLTRML TFKFYMPKKA TELKHLQCLE    60
EELKPLEEVL NLAQSKNFHL RPRALISNIN VIVLELKGSE TTFMCEYADE TATIVEFLNR   120
WITFCQSIIS TLT                                                      133

SEQ ID NO: 39           moltype = AA  length = 133
FEATURE                 Location/Qualifiers
source                  1..133
                        mol_type = protein
                        organism = Synthetic construct
SEQUENCE: 39
APTSSSTKKT QLQLAHLLLA LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 40           moltype = AA  length = 133
FEATURE                 Location/Qualifiers
source                  1..133
                        mol_type = protein
                        organism = Synthetic construct
SEQUENCE: 40
APTSSSTKKT QLQLEHLLLA LQMILNGINN YKNPKLTRML TFKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                      133

SEQ ID NO: 41           moltype = AA  length = 133
FEATURE                 Location/Qualifiers
source                  1..133
                        mol_type = protein
                        organism = Synthetic construct
SEQUENCE: 41
APTSSSTKKT QLQLEHLLLA LQMILNGINN YKNPKLTRML TFKFYMPKKA TELKHLQCLE    60
EELKPLEEVL NLAQSKNFHL RPRDLISAIN VIVLELKGSE TTFMCEYADE TATIVEFLNR   120
WITFCQSIIS TLT                                                      133

SEQ ID NO: 42           moltype = AA  length = 133
FEATURE                 Location/Qualifiers
source                  1..133
                        mol_type = protein
                        organism = Synthetic construct
SEQUENCE: 42
APTSSSTKKT QLQLEHLLLA LQMILNGINN YKNPKLTRML TFKFYMPKKA TELKHLQCLE    60
EELKPLEEVL NLAQSKNFHL RPRDLIANIN VIVLELKGSE TTFMCEYADE TATIVEFLNR   120
WITFCQSIIS TLT                                                      133

SEQ ID NO: 43           moltype = AA  length = 133
FEATURE                 Location/Qualifiers
source                  1..133
                        mol_type = protein
                        organism = Synthetic construct
SEQUENCE: 43
APTSSSTKKT QLQLEHLLLD LQMILNGINN YKNPKLTRML TFKFYMPKKA TELKHLQCLE    60
EELKPLEEVL NLAQSKNFHL RPRALISAIN VIVLELKGSE TTFMCEYADE TATIVEFLNR   120
WITFCQSIIS TLT                                                      133

SEQ ID NO: 44           moltype = AA  length = 133
FEATURE                 Location/Qualifiers
source                  1..133
                        mol_type = protein
                        organism = Synthetic construct
SEQUENCE: 44
APTSSSTKKT QLQLAHLLLD LQMILNGINN YKNPKLTRML TFKFYMPKKA TELKHLQCLE    60
EELKPLEEVL NLAQSKNFHL RPRDLISAIN VIVLELKGSE TTFMCEYADE TATIVEFLNR   120
WITFCQSIIS TLT                                                      133

SEQ ID NO: 45           moltype = AA  length = 133
FEATURE                 Location/Qualifiers
source                  1..133
                        mol_type = protein
                        organism = Synthetic construct
SEQUENCE: 45
APTSSSTKKT QLQLEHLLLD LQMILNGINN YKNPKLTRML TFKFYMPKKA TELKHLQCLE    60
EELKPLEEVL NLAQSKNFHL RPRDLIAAIN VIVLELKGSE TTFMCEYADE TATIVEFLNR   120
WITFCQSIIS TLT                                                      133
```

```
SEQ ID NO: 46              moltype = AA  length = 133
FEATURE                    Location/Qualifiers
source                     1..133
                           mol_type = protein
                           organism = Synthetic construct
SEQUENCE: 46
APTSSSTKKT QLQLEHLLLD LQMILNGINN YKNPKLTAML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 47              moltype = AA  length = 133
FEATURE                    Location/Qualifiers
source                     1..133
                           mol_type = protein
                           organism = Synthetic construct
SEQUENCE: 47
APTSSSTKKT QLQLEHLLLD LQMILNGINN YKNPKLTDML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 48              moltype = AA  length = 133
FEATURE                    Location/Qualifiers
source                     1..133
                           mol_type = protein
                           organism = Synthetic construct
SEQUENCE: 48
APTSSSTKKT QLQLEHLLLD LQMILNGINN YKNPKLTEML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 49              moltype = AA  length = 133
FEATURE                    Location/Qualifiers
source                     1..133
                           mol_type = protein
                           organism = Synthetic construct
SEQUENCE: 49
APTSSSTKKT QLQLEHLLLD LQMILNGINN YKNPKLTQML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 50              moltype = AA  length = 133
FEATURE                    Location/Qualifiers
source                     1..133
                           mol_type = protein
                           organism = Synthetic construct
SEQUENCE: 50
APTSSSTKKT QLQLEHLLLD LQMILNGINN YKNPKLTRML TRKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 51              moltype = AA  length = 133
FEATURE                    Location/Qualifiers
source                     1..133
                           mol_type = protein
                           organism = Synthetic construct
SEQUENCE: 51
APTSSSTKKT QLQLEHLLLD LQMILNGINN YKNPKLTRML TAKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 52              moltype = AA  length = 133
FEATURE                    Location/Qualifiers
source                     1..133
                           mol_type = protein
                           organism = Synthetic construct
SEQUENCE: 52
APTSSSTKKT QLQLEHLLLD LQMILNGINN YKNPKLTRML TDKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 53              moltype = AA  length = 133
FEATURE                    Location/Qualifiers
source                     1..133
                           mol_type = protein
                           organism = Synthetic construct
SEQUENCE: 53
APTSSSTKKT QLQLEHLLLD LQMILNGINN YKNPKLTRML THKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133
```

```
SEQ ID NO: 54          moltype = AA   length = 133
FEATURE                Location/Qualifiers
source                 1..133
                       mol_type = protein
                       organism = Synthetic construct
SEQUENCE: 54
APTSSSTKKT QLQLEHLLLD LQMILNGINN YKNPKLTRML TFAFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 55          moltype = AA   length = 133
FEATURE                Location/Qualifiers
source                 1..133
                       mol_type = protein
                       organism = Synthetic construct
SEQUENCE: 55
APTSSSTKKT QLQLEHLLLD LQMILNGINN YKNPKLTRML TFEFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 56          moltype = AA   length = 133
FEATURE                Location/Qualifiers
source                 1..133
                       mol_type = protein
                       organism = Synthetic construct
SEQUENCE: 56
APTSSSTKKT QLQLEHLLLD LQMILNGINN YKNPKLTRML TFQFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 57          moltype = AA   length = 133
FEATURE                Location/Qualifiers
source                 1..133
                       mol_type = protein
                       organism = Synthetic construct
SEQUENCE: 57
APTSSSTKKT QLQLEHLLLD LQMILNGINN YKNPKLTRML TFKFAMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 58          moltype = AA   length = 133
FEATURE                Location/Qualifiers
source                 1..133
                       mol_type = protein
                       organism = Synthetic construct
SEQUENCE: 58
APTSSSTKKT QLQLEHLLLD LQMILNGINN YKNPKLTRML TFKFKMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 59          moltype = AA   length = 133
FEATURE                Location/Qualifiers
source                 1..133
                       mol_type = protein
                       organism = Synthetic construct
SEQUENCE: 59
APTSSSTKKT QLQLEHLLLD LQMILNGINN YKNPKLTRML TFKFSMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 60          moltype = AA   length = 133
FEATURE                Location/Qualifiers
source                 1..133
                       mol_type = protein
                       organism = Synthetic construct
SEQUENCE: 60
APTSSSTKKT QLQLEHLLLD LQMILNGINN YKNPKLTRML TFKFRMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 61          moltype = AA   length = 133
FEATURE                Location/Qualifiers
source                 1..133
                       mol_type = protein
                       organism = Synthetic construct
SEQUENCE: 61
APTSSSTKKT QLQLEHLLLD LQMILNGINN YKNPKLTRML TFKFYMPKKA TELKHLQCLE    60
AELKPLEEVL NLAQSKNFHL RPRDLISNIN VIVLELKGSE TTFMCEYADE TATIVEFLNR   120
```

```
WITFCQSIIS TLT                                                                      133

SEQ ID NO: 62           moltype = AA   length = 133
FEATURE                 Location/Qualifiers
source                  1..133
                        mol_type = protein
                        organism = Synthetic construct
SEQUENCE: 62
APTSSSTKKT QLQLEHLLLD LQMILNGINN YKNPKLTRML TFKFYMPKKA TELKHLQCLE       60
RELKPLEEVL NLAQSKNFHL RPRDLISNIN VIVLELKGSE TTFMCEYADE TATIVEFLNR      120
WITFCQSIIS TLT                                                         133

SEQ ID NO: 63           moltype = AA   length = 133
FEATURE                 Location/Qualifiers
source                  1..133
                        mol_type = protein
                        organism = Synthetic construct
SEQUENCE: 63
APTSSSTKKT QLQLEHLLLD LQMILNGINN YKNPKLTRML TFKFYMPKKA TELKHLQCLE       60
KELKPLEEVL NLAQSKNFHL RPRDLISNIN VIVLELKGSE TTFMCEYADE TATIVEFLNR      120
WITFCQSIIS TLT                                                         133

SEQ ID NO: 64           moltype = AA   length = 133
FEATURE                 Location/Qualifiers
source                  1..133
                        mol_type = protein
                        organism = Synthetic construct
SEQUENCE: 64
APTSSSTKKT QLQLEHLLLD LQMILNGINN YKNPKLTRML TFKFYMPKKA TELKHLQCLE       60
EALKPLEEVL NLAQSKNFHL RPRDLISNIN VIVLELKGSE TTFMCEYADE TATIVEFLNR      120
WITFCQSIIS TLT                                                         133

SEQ ID NO: 65           moltype = AA   length = 133
FEATURE                 Location/Qualifiers
source                  1..133
                        mol_type = protein
                        organism = Synthetic construct
SEQUENCE: 65
APTSSSTKKT QLQLEHLLLD LQMILNGINN YKNPKLTRML TFKFYMPKKA TELKHLQCLE       60
ERLKPLEEVL NLAQSKNFHL RPRDLISNIN VIVLELKGSE TTFMCEYADE TATIVEFLNR      120
WITFCQSIIS TLT                                                         133

SEQ ID NO: 66           moltype = AA   length = 133
FEATURE                 Location/Qualifiers
source                  1..133
                        mol_type = protein
                        organism = Synthetic construct
SEQUENCE: 66
APTSSSTKKT QLQLEHLLLD LQMILNGINN YKNPKLTRML TFKFYMPKKA TELKHLQCLE       60
EKLKPLEEVL NLAQSKNFHL RPRDLISNIN VIVLELKGSE TTFMCEYADE TATIVEFLNR      120
WITFCQSIIS TLT                                                         133

SEQ ID NO: 67           moltype = AA   length = 133
FEATURE                 Location/Qualifiers
source                  1..133
                        mol_type = protein
                        organism = Synthetic construct
SEQUENCE: 67
APTSSSTKKT QLQLEHLLLD LQMILNGINN YKNPKLTRML TFKFYMPKKA TELKHLQCLE       60
EYLKPLEEVL NLAQSKNFHL RPRDLISNIN VIVLELKGSE TTFMCEYADE TATIVEFLNR      120
WITFCQSIIS TLT                                                         133

SEQ ID NO: 68           moltype = AA   length = 133
FEATURE                 Location/Qualifiers
source                  1..133
                        mol_type = protein
                        organism = Synthetic construct
SEQUENCE: 68
APTSSSTKKT QLQLEHLLLD LQMILNGINN YKNPKLTRML TFKFYMPKKA TELKHLQCLE       60
EELKPLEYVL NLAQSKNFHL RPRDLISNIN VIVLELKGSE TTFMCEYADE TATIVEFLNR      120
WITFCQSIIS TLT                                                         133

SEQ ID NO: 69           moltype = AA   length = 133
FEATURE                 Location/Qualifiers
source                  1..133
                        mol_type = protein
                        organism = Synthetic construct
SEQUENCE: 69
APTSSSTKKT QLQLEHLLLD LQMILNGINN YKNPKLTRML TFKFYMPKKA TELKHLQCLE       60
```

EELKPLEAVL NLAQSKNFHL RPRDLISNIN VIVLELKGSE TTFMCEYADE TATIVEFLNR 120
WITFCQSIIS TLT 133

SEQ ID NO: 70            moltype = AA  length = 133
FEATURE                  Location/Qualifiers
source                   1..133
                         mol_type = protein
                         organism = Synthetic construct
SEQUENCE: 70
APTSSSTKKT QLQLEHLLLD LQMILNGINN YKNPKLTRML TFKFYMPKKA TELKHLQCLE 60
EELKPLEKVL NLAQSKNFHL RPRDLISNIN VIVLELKGSE TTFMCEYADE TATIVEFLNR 120
WITFCQSIIS TLT 133

SEQ ID NO: 71            moltype = AA  length = 133
FEATURE                  Location/Qualifiers
source                   1..133
                         mol_type = protein
                         organism = Synthetic construct
SEQUENCE: 71
APTSSSTKKT QLQLEHLLLD LQMILNGINN YKNPKLTRML TFKFYMPKKA TELKHLQCLE 60
EELKPLERVL NLAQSKNFHL RPRDLISNIN VIVLELKGSE TTFMCEYADE TATIVEFLNR 120
WITFCQSIIS TLT 133

SEQ ID NO: 72            moltype = AA  length = 133
FEATURE                  Location/Qualifiers
source                   1..133
                         mol_type = protein
                         organism = Synthetic construct
SEQUENCE: 72
APTSSSTKKT QLQLEHLLLD LQMILNGINN YKNPKLTRML TFKFYMPKKA TELKHLQCLE 60
EELKPLELVL NLAQSKNFHL RPRDLISNIN VIVLELKGSE TTFMCEYADE TATIVEFLNR 120
WITFCQSIIS TLT 133

SEQ ID NO: 73            moltype = AA  length = 133
FEATURE                  Location/Qualifiers
source                   1..133
                         mol_type = protein
                         organism = Synthetic construct
SEQUENCE: 73
APTSSSTKKT QLQLEHLLLD LQMILNGINN YKNPKLTRML TFKFYMPKKA TELKHLQCLE 60
EELKPLEEVL NYAQSKNFHL RPRDLISNIN VIVLELKGSE TTFMCEYADE TATIVEFLNR 120
WITFCQSIIS TLT 133

SEQ ID NO: 74            moltype = AA  length = 133
FEATURE                  Location/Qualifiers
source                   1..133
                         mol_type = protein
                         organism = Synthetic construct
SEQUENCE: 74
APTSSSTKKT QLQLEHLLLD LQMILNGINN YKNPKLTRML TFKFYMPKKA TELKHLQCLE 60
EELKPLEEVL NRAQSKNFHL RPRDLISNIN VIVLELKGSE TTFMCEYADE TATIVEFLNR 120
WITFCQSIIS TLT 133

SEQ ID NO: 75            moltype = AA  length = 133
FEATURE                  Location/Qualifiers
source                   1..133
                         mol_type = protein
                         organism = Synthetic construct
SEQUENCE: 75
APTSSSTKKT QLQLEHLLLD LQMILNGINN YKNPKLTRML TFKFYMPKKA TELKHLQCLE 60
EELKPLEEVL NAAQSKNFHL RPRDLISNIN VIVLELKGSE TTFMCEYADE TATIVEFLNR 120
WITFCQSIIS TLT 133

SEQ ID NO: 76            moltype = AA  length = 133
FEATURE                  Location/Qualifiers
source                   1..133
                         mol_type = protein
                         organism = Synthetic construct
SEQUENCE: 76
APTSSSTKKT QLQLEHLLLD LQMILNGINN YKNPKLTRML TFKFYMPKKA TELKHLQCLE 60
EELKPLEEVL NDAQSKNFHL RPRDLISNIN VIVLELKGSE TTFMCEYADE TATIVEFLNR 120
WITFCQSIIS TLT 133

SEQ ID NO: 77            moltype = AA  length = 133
FEATURE                  Location/Qualifiers
source                   1..133
                         mol_type = protein
                         organism = Synthetic construct
SEQUENCE: 77

```
APTSSSTKKT QLQLEHLLLD LQMILNGINN YKNPKLTRML TFKFYMPKKA TELKHLQCLE    60
EELKPLEEVL NHAQSKNFHL RPRDLISNIN VIVLELKGSE TTFMCEYADE TATIVEFLNR   120
WITFCQSIIS TLT                                                     133

SEQ ID NO: 78           moltype = AA  length = 133
FEATURE                 Location/Qualifiers
source                  1..133
                        mol_type = protein
                        organism = Synthetic construct
SEQUENCE: 78
APTSSSTKKT QLQLEHLLLD LQMILNGINN YKNPKLTRML TFKFYMPKKA TELKHLQCLE    60
EELKPLEEVL NFAQSKNFHL RPRDLISNIN VIVLELKGSE TTFMCEYADE TATIVEFLNR   120
WITFCQSIIS TLT                                                     133

SEQ ID NO: 79           moltype = AA  length = 133
FEATURE                 Location/Qualifiers
source                  1..133
                        mol_type = protein
                        organism = Synthetic construct
SEQUENCE: 79
APTSSSTKKT QLQLEHLLLD LQMILNGINN YKNPKLTDML TFKFYMPKKA TELKHLQCLE    60
RELKPLEEVL NLAQSKNFHL RPRDLISNIN VIVLELKGSE TTFMCEYADE TATIVEFLNR   120
WITFCQSIIS TLT                                                     133

SEQ ID NO: 80           moltype = AA  length = 133
FEATURE                 Location/Qualifiers
source                  1..133
                        mol_type = protein
                        organism = Synthetic construct
SEQUENCE: 80
APTSSSTKKT QLQLEHLLLD LQMILNGINN YKNPKLTDML TFEFYMPKKA TELKHLQCLE    60
RELKPLEEVL NLAQSKNFHL RPRDLISNIN VIVLELKGSE TTFMCEYADE TATIVEFLNR   120
WITFCQSIIS TLT                                                     133

SEQ ID NO: 81           moltype = AA  length = 133
FEATURE                 Location/Qualifiers
source                  1..133
                        mol_type = protein
                        organism = Synthetic construct
SEQUENCE: 81
APASSSTKKT QLQLEHLLLD LQMILNGINN YKNPKLTRML TAKFAMPKKA TELKHLQCLE    60
EELKPLEEVL NGAQSKNFHL RPRDLISNIN VIVLELKGSE TTFMCEYADE TATIVEFLNR   120
WITFAQSIIS TLT                                                     133

SEQ ID NO: 82           moltype = AA  length = 133
FEATURE                 Location/Qualifiers
source                  1..133
                        mol_type = protein
                        organism = Synthetic construct
SEQUENCE: 82
APTSSSTKKT QLQLAHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 83           moltype = AA  length = 133
FEATURE                 Location/Qualifiers
source                  1..133
                        mol_type = protein
                        organism = Synthetic construct
SEQUENCE: 83
APTSSSTKKT QLQLRHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 84           moltype = AA  length = 133
FEATURE                 Location/Qualifiers
source                  1..133
                        mol_type = protein
                        organism = Synthetic construct
SEQUENCE: 84
APTSSSTKKT QLQLKHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 85           moltype = AA  length = 133
FEATURE                 Location/Qualifiers
source                  1..133
                        mol_type = protein
                        organism = Synthetic construct
```

```
SEQUENCE: 85
APTSSSTKKT QLQLEALLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 86              moltype = AA   length = 133
FEATURE                    Location/Qualifiers
source                     1..133
                           mol_type = protein
                           organism = Synthetic construct
SEQUENCE: 86
APTSSSTKKT QLQLEYLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 87              moltype = AA   length = 133
FEATURE                    Location/Qualifiers
source                     1..133
                           mol_type = protein
                           organism = Synthetic construct
SEQUENCE: 87
APTSSSTKKT QLQLEELLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 88              moltype = AA   length = 133
FEATURE                    Location/Qualifiers
source                     1..133
                           mol_type = protein
                           organism = Synthetic construct
SEQUENCE: 88
APTSSSTKKT QLQLEHLLAD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 89              moltype = AA   length = 133
FEATURE                    Location/Qualifiers
source                     1..133
                           mol_type = protein
                           organism = Synthetic construct
SEQUENCE: 89
APTSSSTKKT QLQLEHLLLI LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 90              moltype = AA   length = 133
FEATURE                    Location/Qualifiers
source                     1..133
                           mol_type = protein
                           organism = Synthetic construct
SEQUENCE: 90
APTSSSTKKT QLQLEHLLLS LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 91              moltype = AA   length = 133
FEATURE                    Location/Qualifiers
source                     1..133
                           mol_type = protein
                           organism = Synthetic construct
SEQUENCE: 91
APTSSSTKKT QLQLEHLLLH LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 92              moltype = AA   length = 133
FEATURE                    Location/Qualifiers
source                     1..133
                           mol_type = protein
                           organism = Synthetic construct
SEQUENCE: 92
APTSSSTKKT QLQLEHLLLT LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 93              moltype = AA   length = 133
FEATURE                    Location/Qualifiers
source                     1..133
                           mol_type = protein
```

```
SEQUENCE: 93
APTSSSTKKT QLQLEHLLLW LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 94           moltype = AA  length = 133
FEATURE                 Location/Qualifiers
source                  1..133
                        mol_type = protein
                        organism = Synthetic construct
SEQUENCE: 94
APTSSSTKKT QLQLEHLLLY LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 95           moltype = AA  length = 133
FEATURE                 Location/Qualifiers
source                  1..133
                        mol_type = protein
                        organism = Synthetic construct
SEQUENCE: 95
APTSSSTKKT QLQLEHLLLR LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 96           moltype = AA  length = 133
FEATURE                 Location/Qualifiers
source                  1..133
                        mol_type = protein
                        organism = Synthetic construct
SEQUENCE: 96
APTSSSTKKT QLQLEHLLLF LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 97           moltype = AA  length = 133
FEATURE                 Location/Qualifiers
source                  1..133
                        mol_type = protein
                        organism = Synthetic construct
SEQUENCE: 97
APTSSSTKKT QLQLEHLLLD LQMILNGINN YKNPKLTRML TFKFYMPKKA TELKHLQCLE    60
EELKPLEEVL NLAQSKNFHL APRDLISNIN VIVLELKGSE TTFMCEYADE TATIVEFLNR   120
WITFCQSIIS TLT                                                     133

SEQ ID NO: 98           moltype = AA  length = 133
FEATURE                 Location/Qualifiers
source                  1..133
                        mol_type = protein
                        organism = Synthetic construct
SEQUENCE: 98
APTSSSTKKT QLQLEHLLLD LQMILNGINN YKNPKLTRML TFKFYMPKKA TELKHLQCLE    60
EELKPLEEVL NLAQSKNFHL RPRALISNIN VIVLELKGSE TTFMCEYADE TATIVEFLNR   120
WITFCQSIIS TLT                                                     133

SEQ ID NO: 99           moltype = AA  length = 133
FEATURE                 Location/Qualifiers
source                  1..133
                        mol_type = protein
                        organism = Synthetic construct
SEQUENCE: 99
APTSSSTKKT QLQLEHLLLD LQMILNGINN YKNPKLTRML TFKFYMPKKA TELKHLQCLE    60
EELKPLEEVL NLAQSKNFHL RPRRLISNIN VIVLELKGSE TTFMCEYADE TATIVEFLNR   120
WITFCQSIIS TLT                                                     133

SEQ ID NO: 100          moltype = AA  length = 133
FEATURE                 Location/Qualifiers
source                  1..133
                        mol_type = protein
                        organism = Synthetic construct
SEQUENCE: 100
APTSSSTKKT QLQLEHLLLD LQMILNGINN YKNPKLTRML TFKFYMPKKA TELKHLQCLE    60
EELKPLEEVL NLAQSKNFHL RPRKLISNIN VIVLELKGSE TTFMCEYADE TATIVEFLNR   120
WITFCQSIIS TLT                                                     133

SEQ ID NO: 101          moltype = AA  length = 133
FEATURE                 Location/Qualifiers
source                  1..133
```

```
                        mol_type = protein
                        organism = Synthetic construct
SEQUENCE: 101
APTSSSTKKT QLQLEHLLLD LQMILNGINN YKNPKLTRML TFKFYMPKKA TELKHLQCLE    60
EELKPLEEVL NLAQSKNFHL RPRDLIANIN VIVLELKGSE TTFMCEYADE TATIVEFLNR   120
WITFCQSIIS TLT                                                     133

SEQ ID NO: 102          moltype = AA  length = 133
FEATURE                 Location/Qualifiers
source                  1..133
                        mol_type = protein
                        organism = Synthetic construct
SEQUENCE: 102
APTSSSTKKT QLQLEHLLLD LQMILNGINN YKNPKLTRML TFKFYMPKKA TELKHLQCLE    60
EELKPLEEVL NLAQSKNFHL RPRDLISYIN VIVLELKGSE TTFMCEYADE TATIVEFLNR   120
WITFCQSIIS TLT                                                     133

SEQ ID NO: 103          moltype = AA  length = 133
FEATURE                 Location/Qualifiers
source                  1..133
                        mol_type = protein
                        organism = Synthetic construct
SEQUENCE: 103
APTSSSTKKT QLQLEHLLLD LQMILNGINN YKNPKLTRML TFKFYMPKKA TELKHLQCLE    60
EELKPLEEVL NLAQSKNFHL RPRDLISDIN VIVLELKGSE TTFMCEYADE TATIVEFLNR   120
WITFCQSIIS TLT                                                     133

SEQ ID NO: 104          moltype = AA  length = 133
FEATURE                 Location/Qualifiers
source                  1..133
                        mol_type = protein
                        organism = Synthetic construct
SEQUENCE: 104
APTSSSTKKT QLQLEHLLLD LQMILNGINN YKNPKLTRML TFKFYMPKKA TELKHLQCLE    60
EELKPLEEVL NLAQSKNFHL RPRDLISRIN VIVLELKGSE TTFMCEYADE TATIVEFLNR   120
WITFCQSIIS TLT                                                     133

SEQ ID NO: 105          moltype = AA  length = 133
FEATURE                 Location/Qualifiers
source                  1..133
                        mol_type = protein
                        organism = Synthetic construct
SEQUENCE: 105
APTSSSTKKT QLQLEHLLLD LQMILNGINN YKNPKLTRML TFKFYMPKKA TELKHLQCLE    60
EELKPLEEVL NLAQSKNFHL RPRDLISEIN VIVLELKGSE TTFMCEYADE TATIVEFLNR   120
WITFCQSIIS TLT                                                     133

SEQ ID NO: 106          moltype = AA  length = 133
FEATURE                 Location/Qualifiers
source                  1..133
                        mol_type = protein
                        organism = Synthetic construct
SEQUENCE: 106
APTSSSTKKT QLQLEHLLLD LQMILNGINN YKNPKLTRML TFKFYMPKKA TELKHLQCLE    60
EELKPLEEVL NLAQSKNFHL RPRDLISFIN VIVLELKGSE TTFMCEYADE TATIVEFLNR   120
WITFCQSIIS TLT                                                     133

SEQ ID NO: 107          moltype = AA  length = 133
FEATURE                 Location/Qualifiers
source                  1..133
                        mol_type = protein
                        organism = Synthetic construct
SEQUENCE: 107
APTSSSTKKT QLQLEHLLLD LQMILNGINN YKNPKLTRML TFKFYMPKKA TELKHLQCLE    60
EELKPLEEVL NLAQSKNFHL RPRDLISIIN VIVLELKGSE TTFMCEYADE TATIVEFLNR   120
WITFCQSIIS TLT                                                     133

SEQ ID NO: 108          moltype = AA  length = 133
FEATURE                 Location/Qualifiers
source                  1..133
                        mol_type = protein
                        organism = Synthetic construct
SEQUENCE: 108
APTSSSTKKT QLQLEHLLLD LQMILNGINN YKNPKLTRML TFKFYMPKKA TELKHLQCLE    60
EELKPLEEVL NLAQSKNFHL RPRDLISNIN VAVLELKGSE TTFMCEYADE TATIVEFLNR   120
WITFCQSIIS TLT                                                     133

SEQ ID NO: 109          moltype = AA  length = 133
FEATURE                 Location/Qualifiers
```

```
source                    1..133
                          mol_type = protein
                          organism = Synthetic construct
SEQUENCE: 109
APTSSSTKKT QLQLEHLLLD LQMILNGINN YKNPKLTRML TFKFYMPKKA TELKHLQCLE    60
EELKPLEEVL NLAQSKNFHL RPRDLISNIN VYVLELKGSE TTFMCEYADE TATIVEFLNR   120
WITFCQSIIS TLT                                                     133

SEQ ID NO: 110            moltype = AA   length = 133
FEATURE                   Location/Qualifiers
source                    1..133
                          mol_type = protein
                          organism = Synthetic construct
SEQUENCE: 110
APTSSSTKKT QLQLEHLLLD LQMILNGINN YKNPKLTRML TFKFYMPKKA TELKHLQCLE    60
EELKPLEEVL NLAQSKNFHL RPRDLISNIN VSVLELKGSE TTFMCEYADE TATIVEFLNR   120
WITFCQSIIS TLT                                                     133

SEQ ID NO: 111            moltype = AA   length = 133
FEATURE                   Location/Qualifiers
source                    1..133
                          mol_type = protein
                          organism = Synthetic construct
SEQUENCE: 111
APTSSSTKKT QLQLEHLLLD LQMILNGINN YKNPKLTRML TFKFYMPKKA TELKHLQCLE    60
EELKPLEEVL NLAQSKNFHL RPRDLISNIN VFVLELKGSE TTFMCEYADE TATIVEFLNR   120
WITFCQSIIS TLT                                                     133

SEQ ID NO: 112            moltype = AA   length = 133
FEATURE                   Location/Qualifiers
source                    1..133
                          mol_type = protein
                          organism = Synthetic construct
SEQUENCE: 112
APTSSSTKKT QLQLEHLLLD LQMILNGINN YKNPKLTRML TFKFYMPKKA TELKHLQCLE    60
EELKPLEEVL NLAQSKNFHL RPRDLISNIN VRVLELKGSE TTFMCEYADE TATIVEFLNR   120
WITFCQSIIS TLT                                                     133

SEQ ID NO: 113            moltype = AA   length = 133
FEATURE                   Location/Qualifiers
source                    1..133
                          mol_type = protein
                          organism = Synthetic construct
SEQUENCE: 113
APTSSSTKKT QLQLEHLLLD LQMILNGINN YKNPKLTRML TFKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 114            moltype = AA   length = 133
FEATURE                   Location/Qualifiers
source                    1..133
                          mol_type = protein
                          organism = Synthetic construct
SEQUENCE: 114
APTSSSTKKT QLQLEHLLLD LQMILNGINN YKNPKLTRML TFKFYMPKKA TELKHLQCLE    60
EELKPLEEVL NLAQSKNFHL RPRDLISNIN VEVLELKGSE TTFMCEYADE TATIVEFLNR   120
WITFCQSIIS TLT                                                     133

SEQ ID NO: 115            moltype = AA   length = 133
FEATURE                   Location/Qualifiers
source                    1..133
                          mol_type = protein
                          organism = Synthetic construct
SEQUENCE: 115
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 116            moltype = AA   length = 133
FEATURE                   Location/Qualifiers
source                    1..133
                          mol_type = protein
                          organism = Synthetic construct
SEQUENCE: 116
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLRLKGSE TTFMCEYADE TATIVEFLNR   120
WITFCQSIIS TLT                                                     133

SEQ ID NO: 117            moltype = AA   length = 133
```

| FEATURE | Location/Qualifiers |
|---|---|
| source | 1..133 |
| | mol_type = protein |
| | organism = Synthetic construct |

SEQUENCE: 117
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLKLKGSE TTFMCEYADE TATIVEFLNR   120
WITFCQSIIS TLT                                                     133

| SEQ ID NO: 118 | moltype = AA   length = 133 |
|---|---|
| FEATURE | Location/Qualifiers |
| source | 1..133 |
| | mol_type = protein |
| | organism = Synthetic construct |

SEQUENCE: 118
APTSSSTKKT QLQLEELLLY LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

| SEQ ID NO: 119 | moltype = AA   length = 133 |
|---|---|
| FEATURE | Location/Qualifiers |
| source | 1..133 |
| | mol_type = protein |
| | organism = Synthetic construct |

SEQUENCE: 119
APTSSSTKKT QLQLEALLLY LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

| SEQ ID NO: 120 | moltype = AA   length = 133 |
|---|---|
| FEATURE | Location/Qualifiers |
| source | 1..133 |
| | mol_type = protein |
| | organism = Synthetic construct |

SEQUENCE: 120
APTSSSTKKT QLQLEYLLLY LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

| SEQ ID NO: 121 | moltype = AA   length = 133 |
|---|---|
| FEATURE | Location/Qualifiers |
| source | 1..133 |
| | mol_type = protein |
| | organism = Synthetic construct |

SEQUENCE: 121
APTSSSTKKT QLQLEHLLLY LQMILNGINN YKNPKLTRML TFKFYMPKKA TELKHLQCLE    60
EELKPLEEVL NLAQSKNFHL RPRDLISNIN VAVLELKGSE TTFMCEYADE TATIVEFLNR   120
WITFCQSIIS TLT                                                     133

| SEQ ID NO: 122 | moltype = AA   length = 133 |
|---|---|
| FEATURE | Location/Qualifiers |
| source | 1..133 |
| | mol_type = protein |
| | organism = Synthetic construct |

SEQUENCE: 122
APTSSSTKKT QLQLEHLLLY LQMILNGINN YKNPKLTRML TFKFYMPKKA TELKHLQCLE    60
EELKPLEEVL NLAQSKNFHL RPRDLISNIN VSVLELKGSE TTFMCEYADE TATIVEFLNR   120
WITFCQSIIS TLT                                                     133

| SEQ ID NO: 123 | moltype = AA   length = 133 |
|---|---|
| FEATURE | Location/Qualifiers |
| source | 1..133 |
| | mol_type = protein |
| | organism = Synthetic construct |

SEQUENCE: 123
APTSSSTKKT QLQLEHLLLY LQMILNGINN YKNPKLTRML TFKFYMPKKA TELKHLQCLE    60
EELKPLEEVL NLAQSKNFHL RPRDLISNIN VRVLELKGSE TTFMCEYADE TATIVEFLNR   120
WITFCQSIIS TLT                                                     133

| SEQ ID NO: 124 | moltype = AA   length = 133 |
|---|---|
| FEATURE | Location/Qualifiers |
| source | 1..133 |
| | mol_type = protein |
| | organism = Synthetic construct |

SEQUENCE: 124
APTSSSTKKT QLQLEHLLLY LQMILNGINN YKNPKLTRML TFKFYMPKKA TELKHLQCLE    60
EELKPLEEVL NLAQSKNFHL RPRDLISNIN VIVLRLKGSE TTFMCEYADE TATIVEFLNR   120
WITFCQSIIS TLT                                                     133

```
SEQ ID NO: 125         moltype = AA  length = 133
FEATURE                Location/Qualifiers
source                 1..133
                       mol_type = protein
                       organism = Synthetic construct
SEQUENCE: 125
APTSSSTKKT QLQLEHLLLY LQMILNGINN YKNPKLTRML TFKFYMPKKA TELKHLQCLE   60
EELKPLEEVL NLAQSKNFHL RPRDLISNIN VIVLALKGSE TTFMCEYADE TATIVEFLNR  120
WITFCQSIIS TLT                                                     133

SEQ ID NO: 126         moltype = AA  length = 164
FEATURE                Location/Qualifiers
source                 1..164
                       mol_type = protein
                       organism = Synthetic construct
SEQUENCE: 126
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICT                   164

SEQ ID NO: 127         moltype = AA  length = 133
FEATURE                Location/Qualifiers
source                 1..133
                       mol_type = protein
                       organism = Synthetic construct
SEQUENCE: 127
APTSSSTKKT QLQLEHLLLA LQMILNGINN YKNPKLTRML TDKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133

SEQ ID NO: 128         moltype = AA  length = 133
FEATURE                Location/Qualifiers
source                 1..133
                       mol_type = protein
                       organism = Synthetic construct
SEQUENCE: 128
APTSSSTKKT QLQLEHLLLA LQMILNGINN YKNPKLTRML TRKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133

SEQ ID NO: 129         moltype = AA  length = 133
FEATURE                Location/Qualifiers
source                 1..133
                       mol_type = protein
                       organism = Synthetic construct
SEQUENCE: 129
APTSSSTKKT QLQLEHLLLA LQMILNGINN YKNPKLTRML TKKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133

SEQ ID NO: 130         moltype = AA  length = 133
FEATURE                Location/Qualifiers
source                 1..133
                       mol_type = protein
                       organism = Synthetic construct
SEQUENCE: 130
APTSSSTKKT QLQLEHLLLA LQMILNGINN YKNPKLTRML TAKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133

SEQ ID NO: 131         moltype = AA  length = 133
FEATURE                Location/Qualifiers
source                 1..133
                       mol_type = protein
                       organism = Synthetic construct
SEQUENCE: 131
APTSSSTKKT QLQLEHLLLA LQMILNGINN YKNPKLTRML THKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133

SEQ ID NO: 132         moltype = AA  length = 133
FEATURE                Location/Qualifiers
source                 1..133
                       mol_type = protein
                       organism = Synthetic construct
SEQUENCE: 132
APTSSSTKKT QLQLEHLLLA LQMILNGINN YKNPKLTRML TFKFRMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133
```

SEQ ID NO: 133         moltype = AA   length = 133
FEATURE                Location/Qualifiers
source                 1..133
                       mol_type = protein
                       organism = Synthetic construct
SEQUENCE: 133
APTSSSTKKT QLQLEHLLLA LQMILNGINN YKNPKLTRML TFKFKMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 134         moltype = AA   length = 133
FEATURE                Location/Qualifiers
source                 1..133
                       mol_type = protein
                       organism = Synthetic construct
SEQUENCE: 134
APTSSSTKKT QLQLEHLLLA LQMILNGINN YKNPKLTNML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 135         moltype = AA   length = 133
FEATURE                Location/Qualifiers
source                 1..133
                       mol_type = protein
                       organism = Synthetic construct
SEQUENCE: 135
APTSSSTKKT QLQLEHLLLA LQMILNGINN YKNPKLTGML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 136         moltype = AA   length = 133
FEATURE                Location/Qualifiers
source                 1..133
                       mol_type = protein
                       organism = Synthetic construct
SEQUENCE: 136
APTSSSTKKT QLQLEHLLLA LQMILNGINN YKNPKLTHML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 137         moltype = AA   length = 133
FEATURE                Location/Qualifiers
source                 1..133
                       mol_type = protein
                       organism = Synthetic construct
SEQUENCE: 137
APTSSSTKKT QLQLEHLLLA LQMILNGINN YKNPKLTIML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 138         moltype = AA   length = 133
FEATURE                Location/Qualifiers
source                 1..133
                       mol_type = protein
                       organism = Synthetic construct
SEQUENCE: 138
APTSSSTKKT QLQLEHLLLA LQMILNGINN YKNPKLTLML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 139         moltype = AA   length = 133
FEATURE                Location/Qualifiers
source                 1..133
                       mol_type = protein
                       organism = Synthetic construct
SEQUENCE: 139
APTSSSTKKT QLQLEHLLLA LQMILNGINN YKNPKLTMML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 140         moltype = AA   length = 133
FEATURE                Location/Qualifiers
source                 1..133
                       mol_type = protein
                       organism = Synthetic construct
SEQUENCE: 140
APTSSSTKKT QLQLEHLLLA LQMILNGINN YKNPKLTFML TFKFYMPKKA TELKHLQCLE    60
EELKPLEEVL NLAQSKNFHL RPRDLISNIN VIVLELKGSE TTFMCEYADE TATIVEFLNR   120

```
WITFCQSIIS TLT                                                              133

SEQ ID NO: 141          moltype = AA   length = 133
FEATURE                 Location/Qualifiers
source                  1..133
                        mol_type = protein
                        organism = Synthetic construct
SEQUENCE: 141
APTSSSTKKT QLQLEHLLLA LQMILNGINN YKNPKLTPML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 142          moltype = AA   length = 133
FEATURE                 Location/Qualifiers
source                  1..133
                        mol_type = protein
                        organism = Synthetic construct
SEQUENCE: 142
APTSSSTKKT QLQLEHLLLA LQMILNGINN YKNPKLTSML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 143          moltype = AA   length = 133
FEATURE                 Location/Qualifiers
source                  1..133
                        mol_type = protein
                        organism = Synthetic construct
SEQUENCE: 143
APTSSSTKKT QLQLEHLLLA LQMILNGINN YKNPKLTTML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 144          moltype = AA   length = 133
FEATURE                 Location/Qualifiers
source                  1..133
                        mol_type = protein
                        organism = Synthetic construct
SEQUENCE: 144
APTSSSTKKT QLQLEHLLLA LQMILNGINN YKNPKLTWML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 145          moltype = AA   length = 133
FEATURE                 Location/Qualifiers
source                  1..133
                        mol_type = protein
                        organism = Synthetic construct
SEQUENCE: 145
APTSSSTKKT QLQLEHLLLA LQMILNGINN YKNPKLTYML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 146          moltype = AA   length = 133
FEATURE                 Location/Qualifiers
source                  1..133
                        mol_type = protein
                        organism = Synthetic construct
SEQUENCE: 146
APTSSSTKKT QLQLEHLLLA LQMILNGINN YKNPKLTVML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 147          moltype = AA   length = 133
FEATURE                 Location/Qualifiers
source                  1..133
                        mol_type = protein
                        organism = Synthetic construct
SEQUENCE: 147
APTSSSTKKT QLQLEHLLLA LQMILNGINN YKNPKLTAML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                              133

SEQ ID NO: 148          moltype = AA   length = 133
FEATURE                 Location/Qualifiers
source                  1..133
                        mol_type = protein
                        organism = Synthetic construct
SEQUENCE: 148
APTSSSTKKT QLQLEHLLLA LQMILNGINN YKNPKLTQML TFKFYMPKKA TELKHLQCLE    60
```

```
EELKPLEEVL NLAQSKNFHL RPRDLISNIN VIVLELKGSE TTFMCEYADE TATIVEFLNR    120
WITFCQSIIS TLT                                                      133

SEQ ID NO: 149          moltype = AA  length = 133
FEATURE                 Location/Qualifiers
source                  1..133
                        mol_type = protein
                        organism = Synthetic construct
SEQUENCE: 149
APTSSSTKKT QLQLEHLLLA LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLT                                                      133

SEQ ID NO: 150          moltype = AA  length = 133
FEATURE                 Location/Qualifiers
source                  1..133
                        mol_type = protein
                        organism = Synthetic construct
SEQUENCE: 150
APTSSSTKKT QLQLEHLLLA LQMILNGINN YKNPKLTDML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLT                                                      133

SEQ ID NO: 151          moltype = AA  length = 133
FEATURE                 Location/Qualifiers
source                  1..133
                        mol_type = protein
                        organism = Synthetic construct
SEQUENCE: 151
APTSSSTKKT QLQLEHLLLA LQMILNGINN YKNPKLTRML TFEFYMPKKA TELKHLQCLE    60
EELKPLEEVL NLAQSKNFHL RPRDLISNIN VIVLELKGSE TTFMCEYADE TATIVEFLNR    120
WITFCQSIIS TLT                                                      133

SEQ ID NO: 152          moltype = AA  length = 133
FEATURE                 Location/Qualifiers
source                  1..133
                        mol_type = protein
                        organism = Synthetic construct
SEQUENCE: 152
APTSSSTKKT QLQLEHLLLA LQMILNGINN YKNPKLTRML TFKFYMPKKA TELKHLQCLE    60
AELKPLEEVL NLAQSKNFHL RPRDLISNIN VIVLELKGSE TTFMCEYADE TATIVEFLNR    120
WITFCQSIIS TLT                                                      133

SEQ ID NO: 153          moltype = AA  length = 133
FEATURE                 Location/Qualifiers
source                  1..133
                        mol_type = protein
                        organism = Synthetic construct
SEQUENCE: 153
APTSSSTKKT QLQLEHLLLA LQMILNGINN YKNPKLTRML TFKFYMPKKA TELKHLQCLE    60
EALKPLEEVL NLAQSKNFHL RPRDLISNIN VIVLELKGSE TTFMCEYADE TATIVEFLNR    120
WITFCQSIIS TLT                                                      133

SEQ ID NO: 154          moltype = AA  length = 133
FEATURE                 Location/Qualifiers
source                  1..133
                        mol_type = protein
                        organism = Synthetic construct
SEQUENCE: 154
APTSSSTKKT QLQLEHLLLA LQMILNGINN YKNPKLTRML TFKFYMPKKA TELKHLQCLE    60
EYLKPLEEVL NLAQSKNFHL RPRDLISNIN VIVLELKGSE TTFMCEYADE TATIVEFLNR    120
WITFCQSIIS TLT                                                      133

SEQ ID NO: 155          moltype = AA  length = 133
FEATURE                 Location/Qualifiers
source                  1..133
                        mol_type = protein
                        organism = Synthetic construct
SEQUENCE: 155
APTSSSTKKT QLQLEHLLLA LQMILNGINN YKNPKLTRML TFKFYMPKKA TELKHLQCLE    60
EELKPLEEVL NDAQSKNFHL RPRDLISNIN VIVLELKGSE TTFMCEYADE TATIVEFLNR    120
WITFCQSIIS TLT                                                      133

SEQ ID NO: 156          moltype = AA  length = 133
FEATURE                 Location/Qualifiers
source                  1..133
                        mol_type = protein
                        organism = Synthetic construct
SEQUENCE: 156
```

```
APTSSSTKKT QLQLEHLLLA LQMILNGINN YKNPKLTRML TFKFYMPKKA TELKHLQCLE    60
EELKPLEEVL NHAQSKNFHL RPRDLISNIN VIVLELKGSE TTFMCEYADE TATIVEFLNR   120
WITFCQSIIS TLT                                                     133

SEQ ID NO: 157          moltype = AA  length = 133
FEATURE                 Location/Qualifiers
source                  1..133
                        mol_type = protein
                        organism = Synthetic construct
SEQUENCE: 157
APTSSSTKKT QLQLEHLLLA LQMILNGINN YKNPKLTRML TFKFYMPKKA TELKHLQCLE    60
EELKPLEEVL NRAQSKNFHL RPRDLISNIN VIVLELKGSE TTFMCEYADE TATIVEFLNR   120
WITFCQSIIS TLT                                                     133

SEQ ID NO: 158          moltype = AA  length = 133
FEATURE                 Location/Qualifiers
source                  1..133
                        mol_type = protein
                        organism = Synthetic construct
SEQUENCE: 158
APTSSSTKKT QLQLEHLLLD LQMILNGINN YKNPKLTRML TDKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 159          moltype = AA  length = 133
FEATURE                 Location/Qualifiers
source                  1..133
                        mol_type = protein
                        organism = Synthetic construct
SEQUENCE: 159
APTSSSTKKT QLQLEHLLLD LQMILNGINN YKNPKLTRML TRKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 160          moltype = AA  length = 133
FEATURE                 Location/Qualifiers
source                  1..133
                        mol_type = protein
                        organism = Synthetic construct
SEQUENCE: 160
APTSSSTKKT QLQLEHLLLD LQMILNGINN YKNPKLTRML THKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 161          moltype = AA  length = 133
FEATURE                 Location/Qualifiers
source                  1..133
                        mol_type = protein
                        organism = Synthetic construct
SEQUENCE: 161
APTSSSTKKT QLQLEHLLLD LQMILNGINN YKNPKLTRML TAKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 162          moltype = AA  length = 133
FEATURE                 Location/Qualifiers
source                  1..133
                        mol_type = protein
                        organism = Synthetic construct
SEQUENCE: 162
APTSSSTKKT QLQLEHLLLD LQMILNGINN YKNPKLTRML TFEFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 163          moltype = AA  length = 133
FEATURE                 Location/Qualifiers
source                  1..133
                        mol_type = protein
                        organism = Synthetic construct
SEQUENCE: 163
APTSSSTKKT QLQLEHLLLD LQMILNGINN YKNPKLTRML TFKFRMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 164          moltype = AA  length = 133
FEATURE                 Location/Qualifiers
source                  1..133
                        mol_type = protein
                        organism = Synthetic construct
```

```
SEQUENCE: 164
APTSSSTKKT QLQLEHLLLD LQMILNGINN YKNPKLTRML TFKFKMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 165          moltype = AA   length = 133
FEATURE                 Location/Qualifiers
source                  1..133
                        mol_type = protein
                        organism = Synthetic construct
SEQUENCE: 165
APTSSSTKKT QLQLEHLLLD LQMILNGINN YKNPKLTRML TFKFYMPKKA TELKHLQCLE    60
EALKPLEEVL NLAQSKNFHL RPRDLISNIN VDVLELKGSE TTFMCEYADE TATIVEFLNR   120
WITFCQSIIS TLT                                                     133

SEQ ID NO: 166          moltype = AA   length = 133
FEATURE                 Location/Qualifiers
source                  1..133
                        mol_type = protein
                        organism = Synthetic construct
SEQUENCE: 166
APTSSSTKKT QLQLEHLLLD LQMILNGINN YKNPKLTRML TFKFYMPKKA TELKHLQCLE    60
EYLKPLEEVL NLAQSKNFHL RPRDLISNIN VDVLELKGSE TTFMCEYADE TATIVEFLNR   120
WITFCQSIIS TLT                                                     133

SEQ ID NO: 167          moltype = AA   length = 133
FEATURE                 Location/Qualifiers
source                  1..133
                        mol_type = protein
                        organism = Synthetic construct
SEQUENCE: 167
APTSSSTKKT QLQLEHLLLD LQMILNGINN YKNPKLTRML TFKFYMPKKA TELKHLQCLE    60
EELKPLEEVL NDAQSKNFHL RPRDLISNIN VDVLELKGSE TTFMCEYADE TATIVEFLNR   120
WITFCQSIIS TLT                                                     133

SEQ ID NO: 168          moltype = AA   length = 133
FEATURE                 Location/Qualifiers
source                  1..133
                        mol_type = protein
                        organism = Synthetic construct
SEQUENCE: 168
APTSSSTKKT QLQLEHLLLD LQMILNGINN YKNPKLTRML TFKFYMPKKA TELKHLQCLE    60
EELKPLEEVL NHAQSKNFHL RPRDLISNIN VDVLELKGSE TTFMCEYADE TATIVEFLNR   120
WITFCQSIIS TLT                                                     133

SEQ ID NO: 169          moltype = AA   length = 133
FEATURE                 Location/Qualifiers
source                  1..133
                        mol_type = protein
                        organism = Synthetic construct
SEQUENCE: 169
APTSSSTKKT QLQLEHLLLD LQMILNGINN YKNPKLTRML TFKFYMPKKA TELKHLQCLE    60
EELKPLEEVL NRAQSKNFHL RPRDLISNIN VDVLELKGSE TTFMCEYADE TATIVEFLNR   120
WITFCQSIIS TLT                                                     133

SEQ ID NO: 170          moltype = AA   length = 133
FEATURE                 Location/Qualifiers
source                  1..133
                        mol_type = protein
                        organism = Synthetic construct
SEQUENCE: 170
APTSSSTKKT QLQLEHLLLD LQMILNGINN YKNPKLTDML TFKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 171          moltype = AA   length = 133
FEATURE                 Location/Qualifiers
source                  1..133
                        mol_type = protein
                        organism = Synthetic construct
SEQUENCE: 171
APTSSSTKKT QLQLEHLLLD LQMILNGINN YKNPKLTEML TFKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                     133

SEQ ID NO: 172          moltype = AA   length = 133
FEATURE                 Location/Qualifiers
source                  1..133
                        mol_type = protein
```

```
                            organism  = Synthetic construct
SEQUENCE: 172
APTSSSTKKT QLQLEHLLLD LQMILNGINN YKNPKLTQML TFKFYMPKKA TELKHLQCLE     60
EELKPLEEVL NLAQSKNFHL RPRDLISNIN VDVLELKGSE TTFMCEYADE TATIVEFLNR    120
WITFCQSIIS TLT                                                      133

SEQ ID NO: 173          moltype = AA   length = 133
FEATURE                 Location/Qualifiers
source                  1..133
                        mol_type = protein
                        organism = Synthetic construct
SEQUENCE: 173
APTSSSTKKT QLQLEHLLLD LQMILNGINN YKNPKLTAML TFKFYMPKKA TELKHLQCLE     60
EELKPLEEVL NLAQSKNFHL RPRDLISNIN VDVLELKGSE TTFMCEYADE TATIVEFLNR    120
WITFCQSIIS TLT                                                      133

SEQ ID NO: 174          moltype = AA   length = 133
FEATURE                 Location/Qualifiers
source                  1..133
                        mol_type = protein
                        organism = Synthetic construct
SEQUENCE: 174
APTSSSTKKT QLQLEHLLLD LQMILNGINN YKNPKLTEML TFKFYMPKKA TELKHLQCLE     60
EELKPLEEVL NLAQSKNFHL RPRDLISRIN VIVLELKGSE TTFMCEYADE TATIVEFLNR    120
WITFCQSIIS TLT                                                      133

SEQ ID NO: 175          moltype = AA   length = 133
FEATURE                 Location/Qualifiers
source                  1..133
                        mol_type = protein
                        organism = Synthetic construct
SEQUENCE: 175
APTSSSTKKT QLQLEHLLLD LQMILNGINN YKNPKLTEML TFKFYMPKKA TELKHLQCLE     60
EELKPLEEVL NLAQSKNFHL RPRRLISNIN VIVLELKGSE TTFMCEYADE TATIVEFLNR    120
WITFCQSIIS TLT                                                      133

SEQ ID NO: 176          moltype = AA   length = 133
FEATURE                 Location/Qualifiers
source                  1..133
                        mol_type = protein
                        organism = Synthetic construct
SEQUENCE: 176
APTSSSTKKT QLQLEHLLLD LQMILNGINN YKNPKLTEML TFKFYMPKKA TELKHLQCLE     60
EELKPLEEVL NLAQSKNFHL RPRKLISNIN VIVLELKGSE TTFMCEYADE TATIVEFLNR    120
WITFCQSIIS TLT                                                      133

SEQ ID NO: 177          moltype = AA   length = 133
FEATURE                 Location/Qualifiers
source                  1..133
                        mol_type = protein
                        organism = Synthetic construct
SEQUENCE: 177
APTSSSTKKT QLQLEHLLLA LQMILNGINN YKNPKLTRML TAKFRMPKKA TELKHLQCLE     60
EELKPLEEVL NLAQSKNFHL RPRDLISNIN VIVLELKGSE TTFMCEYADE TATIVEFLNR    120
WITFCQSIIS TLT                                                      133

SEQ ID NO: 178          moltype = AA   length = 133
FEATURE                 Location/Qualifiers
source                  1..133
                        mol_type = protein
                        organism = Synthetic construct
SEQUENCE: 178
APTSSSTKKT QLQLEHLLLA LQMILNGINN YKNPKLTRML THKFRMPKKA TELKHLQCLE     60
EELKPLEEVL NLAQSKNFHL RPRDLISNIN VIVLELKGSE TTFMCEYADE TATIVEFLNR    120
WITFCQSIIS TLT                                                      133

SEQ ID NO: 179          moltype = AA   length = 133
FEATURE                 Location/Qualifiers
source                  1..133
                        mol_type = protein
                        organism = Synthetic construct
SEQUENCE: 179
APTSSSTKKT QLQLEHLLLA LQMILNGINN YKNPKLTDML TFKFYMPKKA TELKHLQCLE     60
RELKPLEEVL NLAQSKNFHL RPRDLISNIN VIVLELKGSE TTFMCEYADE TATIVEFLNR    120
WITFCQSIIS TLT                                                      133

SEQ ID NO: 180          moltype = AA   length = 133
FEATURE                 Location/Qualifiers
source                  1..133
```

```
                              mol_type = protein
                              organism = Synthetic construct
SEQUENCE: 180
APTSSSTKKT QLQLEHLLLA LQMILNGINN YKNPKLTEML TFKFYMPKKA TELKHLQCLE    60
RELKPLEEVL NLAQSKNFHL RPRDLISNIN VIVLELKGSE TTFMCEYADE TATIVEFLNR   120
WITFCQSIIS TLT                                                      133

SEQ ID NO: 181           moltype = AA  length = 133
FEATURE                  Location/Qualifiers
source                   1..133
                         mol_type = protein
                         organism = Synthetic construct
SEQUENCE: 181
APTSSSTKKT QLQLEHLLLA LQMILNGINN YKNPKLTQML TFKFYMPKKA TELKHLQCLE    60
RELKPLEEVL NLAQSKNFHL RPRDLISNIN VIVLELKGSE TTFMCEYADE TATIVEFLNR   120
WITFCQSIIS TLT                                                      133

SEQ ID NO: 182           moltype = AA  length = 133
FEATURE                  Location/Qualifiers
source                   1..133
                         mol_type = protein
                         organism = Synthetic construct
SEQUENCE: 182
APTSSSTKKT QLQLEHLLLA LQMILNGINN YKNPKLTAML TFKFYMPKKA TELKHLQCLE    60
RELKPLEEVL NLAQSKNFHL RPRDLISNIN VIVLELKGSE TTFMCEYADE TATIVEFLNR   120
WITFCQSIIS TLT                                                      133

SEQ ID NO: 183           moltype = AA  length = 133
FEATURE                  Location/Qualifiers
source                   1..133
                         mol_type = protein
                         organism = Synthetic construct
SEQUENCE: 183
APTSSSTKKT QLQLEHLLLA LQMILNGINN YKNPKLTAML TFKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                      133

SEQ ID NO: 184           moltype = AA  length = 133
FEATURE                  Location/Qualifiers
source                   1..133
                         mol_type = protein
                         organism = Synthetic construct
SEQUENCE: 184
APTSSSTKKT QLQLEHLLLA LQMILNGINN YKNPKLTDML TFKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                      133

SEQ ID NO: 185           moltype = AA  length = 133
FEATURE                  Location/Qualifiers
source                   1..133
                         mol_type = protein
                         organism = Synthetic construct
SEQUENCE: 185
APTSSSTKKT QLQLEHLLLA LQMILNGINN YKNPKLTEML TFKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                      133

SEQ ID NO: 186           moltype = AA  length = 133
FEATURE                  Location/Qualifiers
source                   1..133
                         mol_type = protein
                         organism = Synthetic construct
SEQUENCE: 186
APTSSSTKKT QLQLEHLLLA LQMILNGINN YKNPKLTQML TFKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                      133

SEQ ID NO: 187           moltype = AA  length = 133
FEATURE                  Location/Qualifiers
source                   1..133
                         mol_type = protein
                         organism = Synthetic construct
SEQUENCE: 187
APTSSSTKKT QLQLEHLLLA LQMILNGINN YKNPKLTRML TRKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                      133

SEQ ID NO: 188           moltype = AA  length = 133
FEATURE                  Location/Qualifiers
```

```
source                   1..133
                         mol_type = protein
                         organism = Synthetic construct
SEQUENCE: 188
APTSSSTKKT QLQLEHLLLA LQMILNGINN YKNPKLTRML TAKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 189           moltype = AA   length = 133
FEATURE                  Location/Qualifiers
source                   1..133
                         mol_type = protein
                         organism = Synthetic construct
SEQUENCE: 189
APTSSSTKKT QLQLEHLLLA LQMILNGINN YKNPKLTRML TDKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 190           moltype = AA   length = 133
FEATURE                  Location/Qualifiers
source                   1..133
                         mol_type = protein
                         organism = Synthetic construct
SEQUENCE: 190
APTSSSTKKT QLQLEHLLLA LQMILNGINN YKNPKLTRML THKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 191           moltype = AA   length = 133
FEATURE                  Location/Qualifiers
source                   1..133
                         mol_type = protein
                         organism = Synthetic construct
SEQUENCE: 191
APTSSSTKKT QLQLEHLLLA LQMILNGINN YKNPKLTRML TKKFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 192           moltype = AA   length = 133
FEATURE                  Location/Qualifiers
source                   1..133
                         mol_type = protein
                         organism = Synthetic construct
SEQUENCE: 192
APTSSSTKKT QLQLEHLLLA LQMILNGINN YKNPKLTRML TFAFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 193           moltype = AA   length = 133
FEATURE                  Location/Qualifiers
source                   1..133
                         mol_type = protein
                         organism = Synthetic construct
SEQUENCE: 193
APTSSSTKKT QLQLEHLLLA LQMILNGINN YKNPKLTRML TFEFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 194           moltype = AA   length = 133
FEATURE                  Location/Qualifiers
source                   1..133
                         mol_type = protein
                         organism = Synthetic construct
SEQUENCE: 194
APTSSSTKKT QLQLEHLLLA LQMILNGINN YKNPKLTRML TFQFYMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 195           moltype = AA   length = 133
FEATURE                  Location/Qualifiers
source                   1..133
                         mol_type = protein
                         organism = Synthetic construct
SEQUENCE: 195
APTSSSTKKT QLQLEHLLLA LQMILNGINN YKNPKLTRML TFKFAMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 196           moltype = AA   length = 133
```

```
FEATURE                 Location/Qualifiers
source                  1..133
                        mol_type = protein
                        organism = Synthetic construct
SEQUENCE: 196
APTSSSTKKT QLQLEHLLLA LQMILNGINN YKNPKLTRML TFKFKMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 197          moltype = AA   length = 133
FEATURE                 Location/Qualifiers
source                  1..133
                        mol_type = protein
                        organism = Synthetic construct
SEQUENCE: 197
APTSSSTKKT QLQLEHLLLA LQMILNGINN YKNPKLTRML TFKFSMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 198          moltype = AA   length = 133
FEATURE                 Location/Qualifiers
source                  1..133
                        mol_type = protein
                        organism = Synthetic construct
SEQUENCE: 198
APTSSSTKKT QLQLEHLLLA LQMILNGINN YKNPKLTRML TFKFRMPKKA TELKHLQCLE    60
EELKPLEEVL NLAQSKNFHL RPRDLISNIN VIVLALKGSE TTFMCEYADE TATIVEFLNR   120
WITFCQSIIS TLT                                                     133

SEQ ID NO: 199          moltype = AA   length = 133
FEATURE                 Location/Qualifiers
source                  1..133
                        mol_type = protein
                        organism = Synthetic construct
SEQUENCE: 199
APTSSSTKKT QLQLEHLLLA LQMILNGINN YKNPKLTRML TFKFYMPKKA TELKHLQCLE    60
AELKPLEEVL NLAQSKNFHL RPRDLISNIN VIVLALKGSE TTFMCEYADE TATIVEFLNR   120
WITFCQSIIS TLT                                                     133

SEQ ID NO: 200          moltype = AA   length = 133
FEATURE                 Location/Qualifiers
source                  1..133
                        mol_type = protein
                        organism = Synthetic construct
SEQUENCE: 200
APTSSSTKKT QLQLEHLLLA LQMILNGINN YKNPKLTRML TFKFYMPKKA TELKHLQCLE    60
EALKPLEEVL NLAQSKNFHL RPRDLISNIN VIVLALKGSE TTFMCEYADE TATIVEFLNR   120
WITFCQSIIS TLT                                                     133

SEQ ID NO: 201          moltype = AA   length = 133
FEATURE                 Location/Qualifiers
source                  1..133
                        mol_type = protein
                        organism = Synthetic construct
SEQUENCE: 201
APTSSSTKKT QLQLEHLLLA LQMILNGINN YKNPKLTRML TFKFYMPKKA TELKHLQCLE    60
ERLKPLEEVL NLAQSKNFHL RPRDLISNIN VIVLALKGSE TTFMCEYADE TATIVEFLNR   120
WITFCQSIIS TLT                                                     133

SEQ ID NO: 202          moltype = AA   length = 133
FEATURE                 Location/Qualifiers
source                  1..133
                        mol_type = protein
                        organism = Synthetic construct
SEQUENCE: 202
APTSSSTKKT QLQLEHLLLA LQMILNGINN YKNPKLTRML TFKFYMPKKA TELKHLQCLE    60
EKLKPLEEVL NLAQSKNFHL RPRDLISNIN VIVLALKGSE TTFMCEYADE TATIVEFLNR   120
WITFCQSIIS TLT                                                     133

SEQ ID NO: 203          moltype = AA   length = 133
FEATURE                 Location/Qualifiers
source                  1..133
                        mol_type = protein
                        organism = Synthetic construct
SEQUENCE: 203
APTSSSTKKT QLQLEHLLLA LQMILNGINN YKNPKLTRML TFKFYMPKKA TELKHLQCLE    60
EYLKPLEEVL NLAQSKNFHL RPRDLISNIN VIVLALKGSE TTFMCEYADE TATIVEFLNR   120
WITFCQSIIS TLT                                                     133
```

```
SEQ ID NO: 204              moltype = AA   length = 133
FEATURE                     Location/Qualifiers
source                      1..133
                            mol_type = protein
                            organism = Synthetic construct
SEQUENCE: 204
APTSSSTKKT QLQLEHLLLA LQMILNGINN YKNPKLTRML TFKFYMPKKA TELKHLQCLE    60
EELKPLEYVL NLAQSKNFHL RPRDLISNIN VIVLALKGSE TTFMCEYADE TATIVEFLNR   120
WITFCQSIIS TLT                                                     133

SEQ ID NO: 205              moltype = AA   length = 133
FEATURE                     Location/Qualifiers
source                      1..133
                            mol_type = protein
                            organism = Synthetic construct
SEQUENCE: 205
APTSSSTKKT QLQLEHLLLA LQMILNGINN YKNPKLTRML TFKFYMPKKA TELKHLQCLE    60
EELKPLEAVL NLAQSKNFHL RPRDLISNIN VIVLALKGSE TTFMCEYADE TATIVEFLNR   120
WITFCQSIIS TLT                                                     133

SEQ ID NO: 206              moltype = AA   length = 133
FEATURE                     Location/Qualifiers
source                      1..133
                            mol_type = protein
                            organism = Synthetic construct
SEQUENCE: 206
APTSSSTKKT QLQLEHLLLA LQMILNGINN YKNPKLTRML TFKFYMPKKA TELKHLQCLE    60
EELKPLELVL NLAQSKNFHL RPRDLISNIN VIVLALKGSE TTFMCEYADE TATIVEFLNR   120
WITFCQSIIS TLT                                                     133

SEQ ID NO: 207              moltype = AA   length = 133
FEATURE                     Location/Qualifiers
source                      1..133
                            mol_type = protein
                            organism = Synthetic construct
SEQUENCE: 207
APTSSSTKKT QLQLEHLLLA LQMILNGINN YKNPKLTRML TFKFYMPKKA TELKHLQCLE    60
EELKPLEEVL NYAQSKNFHL RPRDLISNIN VIVLALKGSE TTFMCEYADE TATIVEFLNR   120
WITFCQSIIS TLT                                                     133

SEQ ID NO: 208              moltype = AA   length = 133
FEATURE                     Location/Qualifiers
source                      1..133
                            mol_type = protein
                            organism = Synthetic construct
SEQUENCE: 208
APTSSSTKKT QLQLEHLLLA LQMILNGINN YKNPKLTRML TFKFYMPKKA TELKHLQCLE    60
EELKPLEEVL NRAQSKNFHL RPRDLISNIN VIVLALKGSE TTFMCEYADE TATIVEFLNR   120
WITFCQSIIS TLT                                                     133

SEQ ID NO: 209              moltype = AA   length = 133
FEATURE                     Location/Qualifiers
source                      1..133
                            mol_type = protein
                            organism = Synthetic construct
SEQUENCE: 209
APTSSSTKKT QLQLEHLLLA LQMILNGINN YKNPKLTRML TFKFYMPKKA TELKHLQCLE    60
EELKPLEEVL NAAQSKNFHL RPRDLISNIN VIVLALKGSE TTFMCEYADE TATIVEFLNR   120
WITFCQSIIS TLT                                                     133

SEQ ID NO: 210              moltype = AA   length = 133
FEATURE                     Location/Qualifiers
source                      1..133
                            mol_type = protein
                            organism = Synthetic construct
SEQUENCE: 210
APTSSSTKKT QLQLEHLLLA LQMILNGINN YKNPKLTRML TFKFYMPKKA TELKHLQCLE    60
EELKPLEEVL NDAQSKNFHL RPRDLISNIN VIVLALKGSE TTFMCEYADE TATIVEFLNR   120
WITFCQSIIS TLT                                                     133

SEQ ID NO: 211              moltype = AA   length = 133
FEATURE                     Location/Qualifiers
source                      1..133
                            mol_type = protein
                            organism = Synthetic construct
SEQUENCE: 211
APTSSSTKKT QLQLEHLLLA LQMILNGINN YKNPKLTRML TFKFYMPKKA TELKHLQCLE    60
EELKPLEEVL NHAQSKNFHL RPRDLISNIN VIVLALKGSE TTFMCEYADE TATIVEFLNR   120
WITFCQSIIS TLT                                                     133
```

```
SEQ ID NO: 212          moltype = AA  length = 133
FEATURE                 Location/Qualifiers
source                  1..133
                        mol_type = protein
                        organism = Synthetic construct
SEQUENCE: 212
APTSSSTKKT QLQLEHLLLA LQMILNGINN YKNPKLTRML TFKFYMPKKA TELKHLQCLE   60
EELKPLEEVL NFAQSKNFHL RPRDLISNIN VIVLALKGSE TTFMCEYADE TATIVEFLNR  120
WITFCQSIIS TLT                                                     133

SEQ ID NO: 213          moltype = AA  length = 133
FEATURE                 Location/Qualifiers
source                  1..133
                        mol_type = protein
                        organism = Synthetic construct
SEQUENCE: 213
APTSSSTKKT QLQLEHLLLA LQMILNGINN YKNPKLTRML TKKFRMPKKA TELKHLQCLE   60
EELKPLEEVL NLAQSKNFHL RPRDLIANIN VIVLELKGSE TTFMCEYADE TATIVEFLNR  120
WITFCQSIIS TLT                                                     133

SEQ ID NO: 214          moltype = AA  length = 133
FEATURE                 Location/Qualifiers
source                  1..133
                        mol_type = protein
                        organism = Synthetic construct
SEQUENCE: 214
APTSSSTKKT QLQLEHLLLA LQMILNGINN YKNPKLTRML TKKFRMPKKA TELKHLQCLE   60
EELKPLEEVL NLAQSKNFHL RPRDLISNIN VIVLALKGSE TTFMCEYADE TATIVEFLNR  120
WITFCQSIIS TLT                                                     133

SEQ ID NO: 215          moltype = AA  length = 133
FEATURE                 Location/Qualifiers
source                  1..133
                        mol_type = protein
                        organism = Synthetic construct
SEQUENCE: 215
APTSSSTKKT QLQLEHLLLA LQMILNGINN YKNPKLTEML TFKFYMPKKA TELKHLQCLE   60
EELKPLEEVL NLAQSKNFHL RPRDLISNIN VIVLELKGSE TTFMCEYADE TATIVEFLNR  120
WITFAQSIIS TLT                                                     133

SEQ ID NO: 216          moltype = AA  length = 133
FEATURE                 Location/Qualifiers
source                  1..133
                        mol_type = protein
                        organism = Synthetic construct
SEQUENCE: 216
APASSSTKKT QLQLEHLLLA LQMILNGINN YKNPKLTEML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133

SEQ ID NO: 217          moltype = AA  length = 133
FEATURE                 Location/Qualifiers
source                  1..133
                        mol_type = protein
                        organism = Synthetic construct
SEQUENCE: 217
APASSSTKKT QLQLEHLLLA LQMILNGINN YKNPKLTEML TFKFYMPKKA TELKHLQCLE   60
EELKPLEEVL NLAQSKNFHL RPRDLISNIN VIVLELKGSE TTFMCEYADE TATIVEFLNR  120
WITFAQSIIS TLT                                                     133

SEQ ID NO: 218          moltype = AA  length = 130
FEATURE                 Location/Qualifiers
source                  1..130
                        mol_type = protein
                        organism = Synthetic construct
SEQUENCE: 218
SSSTKKTQLQ LEHLLLALQM ILNGINNYKN PKLTEMLTFK FYMPKKATEL KHLQCLEEEL   60
KPLEEVLNLA QSKNFHLRPR DLISNINVIV LELKGSETTF MCEYADETAT IVEFLNRWIT  120
FCQSIISTLT                                                         130

SEQ ID NO: 219          moltype = AA  length = 130
FEATURE                 Location/Qualifiers
source                  1..130
                        mol_type = protein
                        organism = Synthetic construct
SEQUENCE: 219
SSSTKKTQLQ LEHLLLALQM ILNGINNYKN PKLTEMLTFK FYMPKKATEL KHLQCLEEEL   60
KPLEEVLNLA QSKNFHLRPR DLISNINVIV LELKGSETTF MCEYADETAT IVEFLNRWIT  120
```

-continued

```
FAQSIISTLT                                                                    130

SEQ ID NO: 220        moltype = AA  length = 133
FEATURE               Location/Qualifiers
source                1..133
                      mol_type = protein
                      organism = Synthetic construct
SEQUENCE: 220
APTSSSTKKT QLQLEHLLLD LAMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WITFCQSIIS TLT                                                   133

SEQ ID NO: 221        moltype = AA  length = 133
FEATURE               Location/Qualifiers
source                1..133
                      mol_type = protein
                      organism = Synthetic construct
SEQUENCE: 221
APTSSSTKKT QLQLEHLLLD LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WIAFCQSIIS TLT                                                   133

SEQ ID NO: 222        moltype = AA  length = 133
FEATURE               Location/Qualifiers
source                1..133
                      mol_type = protein
                      organism = Synthetic construct
SEQUENCE: 222
APTSSSTKKT QLQLEHLLLD LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WITFCQSIAS TLT                                                   133

SEQ ID NO: 223        moltype = AA  length = 133
FEATURE               Location/Qualifiers
source                1..133
                      mol_type = protein
                      organism = Synthetic construct
SEQUENCE: 223
APTSSSTKKT QLQLEHLLLD LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WITFCQSIIA TLT                                                   133

SEQ ID NO: 224        moltype = AA  length = 133
FEATURE               Location/Qualifiers
source                1..133
                      mol_type = protein
                      organism = Synthetic construct
SEQUENCE: 224
APTSSSTKKT QLQLEHLLLD LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WITFCASIIS TLT                                                   133

SEQ ID NO: 225        moltype = AA  length = 133
FEATURE               Location/Qualifiers
source                1..133
                      mol_type = protein
                      organism = Synthetic construct
SEQUENCE: 225
APTSSSTKKT QLQLEHLLLD LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WITFCDSIIS TLT                                                   133

SEQ ID NO: 226        moltype = AA  length = 133
FEATURE               Location/Qualifiers
source                1..133
                      mol_type = protein
                      organism = Synthetic construct
SEQUENCE: 226
APTSSSTKKT QLQLEHLLLD LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR 120
WITFCVSIIS TLT                                                   133

SEQ ID NO: 227        moltype = AA  length = 133
FEATURE               Location/Qualifiers
source                1..133
                      mol_type = protein
                      organism = Synthetic construct
SEQUENCE: 227
APTSSSTKKT QLQLEHLLLD LAMILNGINN YKNPKLTEML TFKFYMPKKA TELKHLQCLE  60
```

```
EELKPLEEVL NLAQSKNFHL RPRDLISNIN VIVLELKGSE TTFMCEYADE TATIVEFLNR    120
WITFCQSIIA TLT                                                       133

SEQ ID NO: 228          moltype = AA  length = 133
FEATURE                 Location/Qualifiers
source                  1..133
                        mol_type = protein
                        organism = Synthetic construct
SEQUENCE: 228
APTSSSTKKT QLQLEHLLLD LQMILNGINN YKNPKLTRML TKKFRMPKKA TELKHLQCLE    60
EELKPLEEVL NLAQSKNFHL RPRDLISNIN VIVLELKGSE TTFMCEYADE TATIVEFLNR    120
WITFCDSIIS TLT                                                       133

SEQ ID NO: 229          moltype = AA  length = 133
FEATURE                 Location/Qualifiers
source                  1..133
                        mol_type = protein
                        organism = Synthetic construct
SEQUENCE: 229
APTSSSTKKT QLQLEHLLLA LQMILNGINN YKNPKLTRML TFKFYMPKKA TELKHLQCLE    60
EELKPLEEVL NLAQSKNFHL RPRDLISNIN VIVLALKGSE TTFMCEYADE TATIVEFLNR    120
WITFCDSIIS TLT                                                       133

SEQ ID NO: 230          moltype = AA  length = 133
FEATURE                 Location/Qualifiers
source                  1..133
                        mol_type = protein
                        organism = Synthetic construct
SEQUENCE: 230
APTSSSTKKT QLQLEHLLLA LQMILNGINN YKNPKLTRML TFKFYMPKKA TELKHLQCLE    60
RELKPLEEVL NLAQSKNFHL RPRDLISNIN VIVLELKGSE TTFMCEYADE TATIVEFLNR    120
WITFCQSIIS TLT                                                       133

SEQ ID NO: 231          moltype = AA  length = 133
FEATURE                 Location/Qualifiers
source                  1..133
                        mol_type = protein
                        organism = Synthetic construct
SEQUENCE: 231
APTSSSTKKT QLQLEHLLLA LQMILNGINN YKNPKLTRML TFKFYMPKKA TELKHLQCLE    60
NELKPLEEVL NLAQSKNFHL RPRDLISNIN VIVLELKGSE TTFMCEYADE TATIVEFLNR    120
WITFCQSIIS TLT                                                       133

SEQ ID NO: 232          moltype = AA  length = 133
FEATURE                 Location/Qualifiers
source                  1..133
                        mol_type = protein
                        organism = Synthetic construct
SEQUENCE: 232
APTSSSTKKT QLQLEHLLLA LQMILNGINN YKNPKLTRML TFKFYMPKKA TELKHLQCLE    60
DELKPLEEVL NLAQSKNFHL RPRDLISNIN VIVLELKGSE TTFMCEYADE TATIVEFLNR    120
WITFCQSIIS TLT                                                       133

SEQ ID NO: 233          moltype = AA  length = 133
FEATURE                 Location/Qualifiers
source                  1..133
                        mol_type = protein
                        organism = Synthetic construct
SEQUENCE: 233
APTSSSTKKT QLQLEHLLLA LQMILNGINN YKNPKLTRML TFKFYMPKKA TELKHLQCLE    60
QELKPLEEVL NLAQSKNFHL RPRDLISNIN VIVLELKGSE TTFMCEYADE TATIVEFLNR    120
WITFCQSIIS TLT                                                       133

SEQ ID NO: 234          moltype = AA  length = 133
FEATURE                 Location/Qualifiers
source                  1..133
                        mol_type = protein
                        organism = Synthetic construct
SEQUENCE: 234
APTSSSTKKT QLQLEHLLLA LQMILNGINN YKNPKLTRML TFKFYMPKKA TELKHLQCLE    60
GELKPLEEVL NLAQSKNFHL RPRDLISNIN VIVLELKGSE TTFMCEYADE TATIVEFLNR    120
WITFCQSIIS TLT                                                       133

SEQ ID NO: 235          moltype = AA  length = 133
FEATURE                 Location/Qualifiers
source                  1..133
                        mol_type = protein
                        organism = Synthetic construct
SEQUENCE: 235
```

```
APTSSSTKKT QLQLEHLLLA LQMILNGINN YKNPKLTRML TFKFYMPKKA TELKHLQCLE    60
HELKPLEEVL NLAQSKNFHL RPRDLISNIN VIVLELKGSE TTFMCEYADE TATIVEFLNR   120
WITFCQSIIS TLT                                                     133

SEQ ID NO: 236          moltype = AA   length = 133
FEATURE                 Location/Qualifiers
source                  1..133
                        mol_type = protein
                        organism = Synthetic construct
SEQUENCE: 236
APTSSSTKKT QLQLEHLLLA LQMILNGINN YKNPKLTRML TFKFYMPKKA TELKHLQCLE    60
IELKPLEEVL NLAQSKNFHL RPRDLISNIN VIVLELKGSE TTFMCEYADE TATIVEFLNR   120
WITFCQSIIS TLT                                                     133

SEQ ID NO: 237          moltype = AA   length = 133
FEATURE                 Location/Qualifiers
source                  1..133
                        mol_type = protein
                        organism = Synthetic construct
SEQUENCE: 237
APTSSSTKKT QLQLEHLLLA LQMILNGINN YKNPKLTRML TFKFYMPKKA TELKHLQCLE    60
LELKPLEEVL NLAQSKNFHL RPRDLISNIN VIVLELKGSE TTFMCEYADE TATIVEFLNR   120
WITFCQSIIS TLT                                                     133

SEQ ID NO: 238          moltype = AA   length = 133
FEATURE                 Location/Qualifiers
source                  1..133
                        mol_type = protein
                        organism = Synthetic construct
SEQUENCE: 238
APTSSSTKKT QLQLEHLLLA LQMILNGINN YKNPKLTRML TFKFYMPKKA TELKHLQCLE    60
KELKPLEEVL NLAQSKNFHL RPRDLISNIN VIVLELKGSE TTFMCEYADE TATIVEFLNR   120
WITFCQSIIS TLT                                                     133

SEQ ID NO: 239          moltype = AA   length = 133
FEATURE                 Location/Qualifiers
source                  1..133
                        mol_type = protein
                        organism = Synthetic construct
SEQUENCE: 239
APTSSSTKKT QLQLEHLLLA LQMILNGINN YKNPKLTRML TFKFYMPKKA TELKHLQCLE    60
MELKPLEEVL NLAQSKNFHL RPRDLISNIN VIVLELKGSE TTFMCEYADE TATIVEFLNR   120
WITFCQSIIS TLT                                                     133

SEQ ID NO: 240          moltype = AA   length = 133
FEATURE                 Location/Qualifiers
source                  1..133
                        mol_type = protein
                        organism = Synthetic construct
SEQUENCE: 240
APTSSSTKKT QLQLEHLLLA LQMILNGINN YKNPKLTRML TFKFYMPKKA TELKHLQCLE    60
FELKPLEEVL NLAQSKNFHL RPRDLISNIN VIVLELKGSE TTFMCEYADE TATIVEFLNR   120
WITFCQSIIS TLT                                                     133

SEQ ID NO: 241          moltype = AA   length = 133
FEATURE                 Location/Qualifiers
source                  1..133
                        mol_type = protein
                        organism = Synthetic construct
SEQUENCE: 241
APTSSSTKKT QLQLEHLLLA LQMILNGINN YKNPKLTRML TFKFYMPKKA TELKHLQCLE    60
PELKPLEEVL NLAQSKNFHL RPRDLISNIN VIVLELKGSE TTFMCEYADE TATIVEFLNR   120
WITFCQSIIS TLT                                                     133

SEQ ID NO: 242          moltype = AA   length = 133
FEATURE                 Location/Qualifiers
source                  1..133
                        mol_type = protein
                        organism = Synthetic construct
SEQUENCE: 242
APTSSSTKKT QLQLEHLLLA LQMILNGINN YKNPKLTRML TFKFYMPKKA TELKHLQCLE    60
SELKPLEEVL NLAQSKNFHL RPRDLISNIN VIVLELKGSE TTFMCEYADE TATIVEFLNR   120
WITFCQSIIS TLT                                                     133

SEQ ID NO: 243          moltype = AA   length = 133
FEATURE                 Location/Qualifiers
source                  1..133
                        mol_type = protein
                        organism = Synthetic construct
```

```
SEQUENCE: 243
APTSSSTKKT QLQLEHLLLA LQMILNGINN YKNPKLTRML TFKFYMPKKA TELKHLQCLE    60
TELKPLEEVL NLAQSKNFHL RPRDLISNIN VIVLELKGSE TTFMCEYADE TATIVEFLNR   120
WITFCQSIIS TLT                                                     133

SEQ ID NO: 244          moltype = AA  length = 133
FEATURE                 Location/Qualifiers
source                  1..133
                        mol_type = protein
                        organism = Synthetic construct
SEQUENCE: 244
APTSSSTKKT QLQLEHLLLA LQMILNGINN YKNPKLTRML TFKFYMPKKA TELKHLQCLE    60
WELKPLEEVL NLAQSKNFHL RPRDLISNIN VIVLELKGSE TTFMCEYADE TATIVEFLNR   120
WITFCQSIIS TLT                                                     133

SEQ ID NO: 245          moltype = AA  length = 133
FEATURE                 Location/Qualifiers
source                  1..133
                        mol_type = protein
                        organism = Synthetic construct
SEQUENCE: 245
APTSSSTKKT QLQLEHLLLA LQMILNGINN YKNPKLTRML TFKFYMPKKA TELKHLQCLE    60
YELKPLEEVL NLAQSKNFHL RPRDLISNIN VIVLELKGSE TTFMCEYADE TATIVEFLNR   120
WITFCQSIIS TLT                                                     133

SEQ ID NO: 246          moltype = AA  length = 133
FEATURE                 Location/Qualifiers
source                  1..133
                        mol_type = protein
                        organism = Synthetic construct
SEQUENCE: 246
APTSSSTKKT QLQLEHLLLA LQMILNGINN YKNPKLTRML TFKFYMPKKA TELKHLQCLE    60
VELKPLEEVL NLAQSKNFHL RPRDLISNIN VIVLELKGSE TTFMCEYADE TATIVEFLNR   120
WITFCQSIIS TLT                                                     133

SEQ ID NO: 247          moltype = AA  length = 133
FEATURE                 Location/Qualifiers
source                  1..133
                        mol_type = protein
                        organism = Synthetic construct
SEQUENCE: 247
APTSSSTKKT QLQLEHLLLA LQMILNGINN YKNPKLTRML TNKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 248          moltype = AA  length = 133
FEATURE                 Location/Qualifiers
source                  1..133
                        mol_type = protein
                        organism = Synthetic construct
SEQUENCE: 248
APTSSSTKKT QLQLEHLLLA LQMILNGINN YKNPKLTRML TQKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 249          moltype = AA  length = 133
FEATURE                 Location/Qualifiers
source                  1..133
                        mol_type = protein
                        organism = Synthetic construct
SEQUENCE: 249
APTSSSTKKT QLQLEHLLLA LQMILNGINN YKNPKLTRML TEKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 250          moltype = AA  length = 133
FEATURE                 Location/Qualifiers
source                  1..133
                        mol_type = protein
                        organism = Synthetic construct
SEQUENCE: 250
APTSSSTKKT QLQLEHLLLA LQMILNGINN YKNPKLTRML TGKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 251          moltype = AA  length = 133
FEATURE                 Location/Qualifiers
source                  1..133
                        mol_type = protein
```

```
SEQUENCE: 251
APTSSSTKKT QLQLEHLLLA LQMILNGINN YKNPKLTRML TIKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 252          moltype = AA  length = 133
FEATURE                 Location/Qualifiers
source                  1..133
                        mol_type = protein
                        organism = Synthetic construct
SEQUENCE: 252
APTSSSTKKT QLQLEHLLLA LQMILNGINN YKNPKLTRML TLKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 253          moltype = AA  length = 133
FEATURE                 Location/Qualifiers
source                  1..133
                        mol_type = protein
                        organism = Synthetic construct
SEQUENCE: 253
APTSSSTKKT QLQLEHLLLA LQMILNGINN YKNPKLTRML TMKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 254          moltype = AA  length = 133
FEATURE                 Location/Qualifiers
source                  1..133
                        mol_type = protein
                        organism = Synthetic construct
SEQUENCE: 254
APTSSSTKKT QLQLEHLLLA LQMILNGINN YKNPKLTRML TPKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 255          moltype = AA  length = 133
FEATURE                 Location/Qualifiers
source                  1..133
                        mol_type = protein
                        organism = Synthetic construct
SEQUENCE: 255
APTSSSTKKT QLQLEHLLLA LQMILNGINN YKNPKLTRML TSKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 256          moltype = AA  length = 133
FEATURE                 Location/Qualifiers
source                  1..133
                        mol_type = protein
                        organism = Synthetic construct
SEQUENCE: 256
APTSSSTKKT QLQLEHLLLA LQMILNGINN YKNPKLTRML TTKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 257          moltype = AA  length = 133
FEATURE                 Location/Qualifiers
source                  1..133
                        mol_type = protein
                        organism = Synthetic construct
SEQUENCE: 257
APTSSSTKKT QLQLEHLLLA LQMILNGINN YKNPKLTRML TWKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 258          moltype = AA  length = 133
FEATURE                 Location/Qualifiers
source                  1..133
                        mol_type = protein
                        organism = Synthetic construct
SEQUENCE: 258
APTSSSTKKT QLQLEHLLLA LQMILNGINN YKNPKLTRML TYKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 259          moltype = AA  length = 133
FEATURE                 Location/Qualifiers
source                  1..133
```

```
                            mol_type = protein
                            organism = Synthetic construct
SEQUENCE: 259
APTSSSTKKT QLQLEHLLLA LQMILNGINN YKNPKLTRML TVKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 260              moltype = AA  length = 133
FEATURE                     Location/Qualifiers
source                      1..133
                            mol_type = protein
                            organism = Synthetic construct
SEQUENCE: 260
APTSSSTKKT QLQLEHLLLA LQMILNGINN YKNPKLTRML TFKFAMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 261              moltype = AA  length = 133
FEATURE                     Location/Qualifiers
source                      1..133
                            mol_type = protein
                            organism = Synthetic construct
SEQUENCE: 261
APTSSSTKKT QLQLEHLLLA LQMILNGINN YKNPKLTRML TFKFNMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 262              moltype = AA  length = 133
FEATURE                     Location/Qualifiers
source                      1..133
                            mol_type = protein
                            organism = Synthetic construct
SEQUENCE: 262
APTSSSTKKT QLQLEHLLLA LQMILNGINN YKNPKLTRML TFKFDMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 263              moltype = AA  length = 133
FEATURE                     Location/Qualifiers
source                      1..133
                            mol_type = protein
                            organism = Synthetic construct
SEQUENCE: 263
APTSSSTKKT QLQLEHLLLA LQMILNGINN YKNPKLTRML TFKFQMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 264              moltype = AA  length = 133
FEATURE                     Location/Qualifiers
source                      1..133
                            mol_type = protein
                            organism = Synthetic construct
SEQUENCE: 264
APTSSSTKKT QLQLEHLLLA LQMILNGINN YKNPKLTRML TFKFEMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 265              moltype = AA  length = 133
FEATURE                     Location/Qualifiers
source                      1..133
                            mol_type = protein
                            organism = Synthetic construct
SEQUENCE: 265
APTSSSTKKT QLQLEHLLLA LQMILNGINN YKNPKLTRML TFKFGMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 266              moltype = AA  length = 133
FEATURE                     Location/Qualifiers
source                      1..133
                            mol_type = protein
                            organism = Synthetic construct
SEQUENCE: 266
APTSSSTKKT QLQLEHLLLA LQMILNGINN YKNPKLTRML TFKFHMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 267              moltype = AA  length = 133
FEATURE                     Location/Qualifiers
```

```
                               -continued source                  1..133
                        mol_type = protein
                        organism = Synthetic construct
SEQUENCE: 267
APTSSSTKKT QLQLEHLLLA LQMILNGINN YKNPKLTRML TFKFIMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 268          moltype = AA  length = 133
FEATURE                 Location/Qualifiers
source                  1..133
                        mol_type = protein
                        organism = Synthetic construct
SEQUENCE: 268
APTSSSTKKT QLQLEHLLLA LQMILNGINN YKNPKLTRML TFKFLMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 269          moltype = AA  length = 133
FEATURE                 Location/Qualifiers
source                  1..133
                        mol_type = protein
                        organism = Synthetic construct
SEQUENCE: 269
APTSSSTKKT QLQLEHLLLA LQMILNGINN YKNPKLTRML TFKFMMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 270          moltype = AA  length = 133
FEATURE                 Location/Qualifiers
source                  1..133
                        mol_type = protein
                        organism = Synthetic construct
SEQUENCE: 270
APTSSSTKKT QLQLEHLLLA LQMILNGINN YKNPKLTRML TFKFFMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 271          moltype = AA  length = 133
FEATURE                 Location/Qualifiers
source                  1..133
                        mol_type = protein
                        organism = Synthetic construct
SEQUENCE: 271
APTSSSTKKT QLQLEHLLLA LQMILNGINN YKNPKLTRML TFKFPMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 272          moltype = AA  length = 133
FEATURE                 Location/Qualifiers
source                  1..133
                        mol_type = protein
                        organism = Synthetic construct
SEQUENCE: 272
APTSSSTKKT QLQLEHLLLA LQMILNGINN YKNPKLTRML TFKFSMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 273          moltype = AA  length = 133
FEATURE                 Location/Qualifiers
source                  1..133
                        mol_type = protein
                        organism = Synthetic construct
SEQUENCE: 273
APTSSSTKKT QLQLEHLLLA LQMILNGINN YKNPKLTRML TFKFTMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 274          moltype = AA  length = 133
FEATURE                 Location/Qualifiers
source                  1..133
                        mol_type = protein
                        organism = Synthetic construct
SEQUENCE: 274
APTSSSTKKT QLQLEHLLLA LQMILNGINN YKNPKLTRML TFKFWMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 275          moltype = AA  length = 133
```

```
FEATURE                 Location/Qualifiers
source                  1..133
                        mol_type = protein
                        organism = Synthetic construct
SEQUENCE: 275
APTSSSTKKT QLQLEHLLLA LQMILNGINN YKNPKLTRML TFKFVMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 276          moltype = AA  length = 133
FEATURE                 Location/Qualifiers
source                  1..133
                        mol_type = protein
                        organism = Synthetic construct
SEQUENCE: 276
APTSSSTKKT QLQLEHLLLD LQMILNGINN YKNPKLTRML TNKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 277          moltype = AA  length = 133
FEATURE                 Location/Qualifiers
source                  1..133
                        mol_type = protein
                        organism = Synthetic construct
SEQUENCE: 277
APTSSSTKKT QLQLEHLLLD LQMILNGINN YKNPKLTRML TQKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 278          moltype = AA  length = 133
FEATURE                 Location/Qualifiers
source                  1..133
                        mol_type = protein
                        organism = Synthetic construct
SEQUENCE: 278
APTSSSTKKT QLQLEHLLLD LQMILNGINN YKNPKLTRML TEKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 279          moltype = AA  length = 133
FEATURE                 Location/Qualifiers
source                  1..133
                        mol_type = protein
                        organism = Synthetic construct
SEQUENCE: 279
APTSSSTKKT QLQLEHLLLD LQMILNGINN YKNPKLTRML TGKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 280          moltype = AA  length = 133
FEATURE                 Location/Qualifiers
source                  1..133
                        mol_type = protein
                        organism = Synthetic construct
SEQUENCE: 280
APTSSSTKKT QLQLEHLLLD LQMILNGINN YKNPKLTRML TIKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 281          moltype = AA  length = 133
FEATURE                 Location/Qualifiers
source                  1..133
                        mol_type = protein
                        organism = Synthetic construct
SEQUENCE: 281
APTSSSTKKT QLQLEHLLLD LQMILNGINN YKNPKLTRML TLKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 282          moltype = AA  length = 133
FEATURE                 Location/Qualifiers
source                  1..133
                        mol_type = protein
                        organism = Synthetic construct
SEQUENCE: 282
APTSSSTKKT QLQLEHLLLD LQMILNGINN YKNPKLTRML TKKFYMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133
```

```
SEQ ID NO: 283           moltype = AA   length = 133
FEATURE                  Location/Qualifiers
source                   1..133
                         mol_type = protein
                         organism = Synthetic construct
SEQUENCE: 283
APTSSSTKKT QLQLEHLLLD LQMILNGINN YKNPKLTRML TMKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 284           moltype = AA   length = 133
FEATURE                  Location/Qualifiers
source                   1..133
                         mol_type = protein
                         organism = Synthetic construct
SEQUENCE: 284
APTSSSTKKT QLQLEHLLLD LQMILNGINN YKNPKLTRML TPKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 285           moltype = AA   length = 133
FEATURE                  Location/Qualifiers
source                   1..133
                         mol_type = protein
                         organism = Synthetic construct
SEQUENCE: 285
APTSSSTKKT QLQLEHLLLD LQMILNGINN YKNPKLTRML TSKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 286           moltype = AA   length = 133
FEATURE                  Location/Qualifiers
source                   1..133
                         mol_type = protein
                         organism = Synthetic construct
SEQUENCE: 286
APTSSSTKKT QLQLEHLLLD LQMILNGINN YKNPKLTRML TTKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 287           moltype = AA   length = 133
FEATURE                  Location/Qualifiers
source                   1..133
                         mol_type = protein
                         organism = Synthetic construct
SEQUENCE: 287
APTSSSTKKT QLQLEHLLLD LQMILNGINN YKNPKLTRML TWKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 288           moltype = AA   length = 133
FEATURE                  Location/Qualifiers
source                   1..133
                         mol_type = protein
                         organism = Synthetic construct
SEQUENCE: 288
APTSSSTKKT QLQLEHLLLD LQMILNGINN YKNPKLTRML TYKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 289           moltype = AA   length = 133
FEATURE                  Location/Qualifiers
source                   1..133
                         mol_type = protein
                         organism = Synthetic construct
SEQUENCE: 289
APTSSSTKKT QLQLEHLLLD LQMILNGINN YKNPKLTRML TVKFYMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133

SEQ ID NO: 290           moltype = AA   length = 133
FEATURE                  Location/Qualifiers
source                   1..133
                         mol_type = protein
                         organism = Synthetic construct
SEQUENCE: 290
APTSSSTKKT QLQLEHLLLD LQMILNGINN YKNPKLTRML TFKFAMPKKA TELKHLQCLE  60
EELKPLEEVL NLAQSKNFHL RPRDLISNIN VDVLELKGSE TTFMCEYADE TATIVEFLNR 120
WITFCQSIIS TLT                                                   133
```

```
SEQ ID NO: 291          moltype = AA   length = 133
FEATURE                 Location/Qualifiers
source                  1..133
                        mol_type = protein
                        organism = Synthetic construct
SEQUENCE: 291
APTSSSTKKT QLQLEHLLLD LQMILNGINN YKNPKLTRML TFKFNMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 292          moltype = AA   length = 133
FEATURE                 Location/Qualifiers
source                  1..133
                        mol_type = protein
                        organism = Synthetic construct
SEQUENCE: 292
APTSSSTKKT QLQLEHLLLD LQMILNGINN YKNPKLTRML TFKFDMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 293          moltype = AA   length = 133
FEATURE                 Location/Qualifiers
source                  1..133
                        mol_type = protein
                        organism = Synthetic construct
SEQUENCE: 293
APTSSSTKKT QLQLEHLLLD LQMILNGINN YKNPKLTRML TFKFQMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 294          moltype = AA   length = 133
FEATURE                 Location/Qualifiers
source                  1..133
                        mol_type = protein
                        organism = Synthetic construct
SEQUENCE: 294
APTSSSTKKT QLQLEHLLLD LQMILNGINN YKNPKLTRML TFKFEMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 295          moltype = AA   length = 133
FEATURE                 Location/Qualifiers
source                  1..133
                        mol_type = protein
                        organism = Synthetic construct
SEQUENCE: 295
APTSSSTKKT QLQLEHLLLD LQMILNGINN YKNPKLTRML TFKFGMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 296          moltype = AA   length = 133
FEATURE                 Location/Qualifiers
source                  1..133
                        mol_type = protein
                        organism = Synthetic construct
SEQUENCE: 296
APTSSSTKKT QLQLEHLLLD LQMILNGINN YKNPKLTRML TFKFHMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 297          moltype = AA   length = 133
FEATURE                 Location/Qualifiers
source                  1..133
                        mol_type = protein
                        organism = Synthetic construct
SEQUENCE: 297
APTSSSTKKT QLQLEHLLLD LQMILNGINN YKNPKLTRML TFKFIMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 298          moltype = AA   length = 133
FEATURE                 Location/Qualifiers
source                  1..133
                        mol_type = protein
                        organism = Synthetic construct
SEQUENCE: 298
APTSSSTKKT QLQLEHLLLD LQMILNGINN YKNPKLTRML TFKFLMPKKA TELKHLQCLE    60
EELKPLEEVL NLAQSKNFHL RPRDLISNIN VDVLELKGSE TTFMCEYADE TATIVEFLNR   120
```

```
SEQ ID NO: 299          moltype = AA   length = 133
FEATURE                 Location/Qualifiers
source                  1..133
                        mol_type = protein
                        organism = Synthetic construct
SEQUENCE: 299
APTSSSTKKT QLQLEHLLLD LQMILNGINN YKNPKLTRML TFKFMMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 300          moltype = AA   length = 133
FEATURE                 Location/Qualifiers
source                  1..133
                        mol_type = protein
                        organism = Synthetic construct
SEQUENCE: 300
APTSSSTKKT QLQLEHLLLD LQMILNGINN YKNPKLTRML TFKFFMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 301          moltype = AA   length = 133
FEATURE                 Location/Qualifiers
source                  1..133
                        mol_type = protein
                        organism = Synthetic construct
SEQUENCE: 301
APTSSSTKKT QLQLEHLLLD LQMILNGINN YKNPKLTRML TFKFPMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 302          moltype = AA   length = 133
FEATURE                 Location/Qualifiers
source                  1..133
                        mol_type = protein
                        organism = Synthetic construct
SEQUENCE: 302
APTSSSTKKT QLQLEHLLLD LQMILNGINN YKNPKLTRML TFKFSMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 303          moltype = AA   length = 133
FEATURE                 Location/Qualifiers
source                  1..133
                        mol_type = protein
                        organism = Synthetic construct
SEQUENCE: 303
APTSSSTKKT QLQLEHLLLD LQMILNGINN YKNPKLTRML TFKFTMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 304          moltype = AA   length = 133
FEATURE                 Location/Qualifiers
source                  1..133
                        mol_type = protein
                        organism = Synthetic construct
SEQUENCE: 304
APTSSSTKKT QLQLEHLLLD LQMILNGINN YKNPKLTRML TFKFWMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 305          moltype = AA   length = 133
FEATURE                 Location/Qualifiers
source                  1..133
                        mol_type = protein
                        organism = Synthetic construct
SEQUENCE: 305
APTSSSTKKT QLQLEHLLLD LQMILNGINN YKNPKLTRML TFKFVMPKKA TELKHLQCLE    60
EELKPLEEVL NLAQSKNFHL RPRDLISNIN VDVLELKGSE TTFMCEYADE TATIVEFLNR   120
WITFCQSIIS TLT                                                      133

SEQ ID NO: 306          moltype = AA   length = 133
FEATURE                 Location/Qualifiers
source                  1..133
                        mol_type = protein
                        organism = Synthetic construct
SEQUENCE: 306
APTSSSTKKT QLQLEHLLLH LQMILNGINN YKNPKLTEML TFKFYMPKKA TELKHLQCLE    60
```

```
EELKPLEEVL NLAQSKNFHL RPRDLISNIN VIVLELKGSE TTFMCEYADE TATIVEFLNR   120
WITFCQSIIS TLT                                                     133

SEQ ID NO: 307          moltype = AA  length = 133
FEATURE                 Location/Qualifiers
source                  1..133
                        mol_type = protein
                        organism = Synthetic construct
SEQUENCE: 307
APTSSSTKKT QLQLEHLLLS LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 308          moltype = AA  length = 133
FEATURE                 Location/Qualifiers
source                  1..133
                        mol_type = protein
                        organism = Synthetic construct
SEQUENCE: 308
APTSSSTKKT QLQLEHLLLD LQMILNGINN YKNPKLTRML TAKFYMPKKA TELKHLQCLE    60
EELKPLEEVL NLAQSKNFHL RPRDLISRIN VIVLELKGSE TTFMCEYADE TATIVEFLNR   120
WITFCQSIIS TLT                                                     133

SEQ ID NO: 309          moltype = AA  length = 133
FEATURE                 Location/Qualifiers
source                  1..133
                        mol_type = protein
                        organism = Synthetic construct
SEQUENCE: 309
APTSSSTKKT QLQLEHLLLD LQMILNGINN YKNPKLTRML TAKFYMPKKA TELKHLQCLE    60
EELKPLEEVL NLAQSKNFHL RPRDLISDIN VIVLELKGSE TTFMCEYADE TATIVEFLNR   120
WITFCQSIIS TLT                                                     133

SEQ ID NO: 310          moltype = AA  length = 133
FEATURE                 Location/Qualifiers
source                  1..133
                        mol_type = protein
                        organism = Synthetic construct
SEQUENCE: 310
APTSSSTKKT QLQLEHLLLD LQMILNGINN YKNPKLTEML TFKFYMPKKA TELKHLQCLE    60
EELKPLEEVL NLAQSKNFHL RPRALISNIN VIVLELKGSE TTFMCEYADE TATIVEFLNR   120
WITFCQSIIS TLT                                                     133

SEQ ID NO: 311          moltype = AA  length = 133
FEATURE                 Location/Qualifiers
source                  1..133
                        mol_type = protein
                        organism = Synthetic construct
SEQUENCE: 311
APTSSSTKKT QLQLEHLLLD LQMILNGINN YKNPKLTEML TFKFYMPKKA TELKHLQCLE    60
EELKPLEEVL NLAQSKNFHL RPRNLISNIN VIVLELKGSE TTFMCEYADE TATIVEFLNR   120
WITFCQSIIS TLT                                                     133

SEQ ID NO: 312          moltype = AA  length = 133
FEATURE                 Location/Qualifiers
source                  1..133
                        mol_type = protein
                        organism = Synthetic construct
SEQUENCE: 312
APTSSSTKKT QLQLEHLLLD LQMILNGINN YKNPKLTEML TFKFYMPKKA TELKHLQCLE    60
EELKPLEEVL NLAQSKNFHL RPRQLISNIN VIVLELKGSE TTFMCEYADE TATIVEFLNR   120
WITFCQSIIS TLT                                                     133

SEQ ID NO: 313          moltype = AA  length = 133
FEATURE                 Location/Qualifiers
source                  1..133
                        mol_type = protein
                        organism = Synthetic construct
SEQUENCE: 313
APTSSSTKKT QLQLEHLLLD LQMILNGINN YKNPKLTEML TFKFYMPKKA TELKHLQCLE    60
EELKPLEEVL NLAQSKNFHL RPRELISNIN VIVLELKGSE TTFMCEYADE TATIVEFLNR   120
WITFCQSIIS TLT                                                     133

SEQ ID NO: 314          moltype = AA  length = 133
FEATURE                 Location/Qualifiers
source                  1..133
                        mol_type = protein
                        organism = Synthetic construct
SEQUENCE: 314
```

```
APTSSSTKKT QLQLEHLLLD LQMILNGINN YKNPKLTEML TFKFYMPKKA TELKHLQCLE   60
EELKPLEEVL NLAQSKNFHL RPRGLISNIN VIVLELKGSE TTFMCEYADE TATIVEFLNR  120
WITFCQSIIS TLT                                                    133

SEQ ID NO: 315          moltype = AA   length = 133
FEATURE                 Location/Qualifiers
source                  1..133
                        mol_type = protein
                        organism = Synthetic construct
SEQUENCE: 315
APTSSSTKKT QLQLEHLLLD LQMILNGINN YKNPKLTEML TFKFYMPKKA TELKHLQCLE   60
EELKPLEEVL NLAQSKNFHL RPRHLISNIN VIVLELKGSE TTFMCEYADE TATIVEFLNR  120
WITFCQSIIS TLT                                                    133

SEQ ID NO: 316          moltype = AA   length = 133
FEATURE                 Location/Qualifiers
source                  1..133
                        mol_type = protein
                        organism = Synthetic construct
SEQUENCE: 316
APTSSSTKKT QLQLEHLLLD LQMILNGINN YKNPKLTEML TFKFYMPKKA TELKHLQCLE   60
EELKPLEEVL NLAQSKNFHL RPRILISNIN VIVLELKGSE TTFMCEYADE TATIVEFLNR  120
WITFCQSIIS TLT                                                    133

SEQ ID NO: 317          moltype = AA   length = 133
FEATURE                 Location/Qualifiers
source                  1..133
                        mol_type = protein
                        organism = Synthetic construct
SEQUENCE: 317
APTSSSTKKT QLQLEHLLLD LQMILNGINN YKNPKLTEML TFKFYMPKKA TELKHLQCLE   60
EELKPLEEVL NLAQSKNFHL RPRLLISNIN VIVLELKGSE TTFMCEYADE TATIVEFLNR  120
WITFCQSIIS TLT                                                    133

SEQ ID NO: 318          moltype = AA   length = 133
FEATURE                 Location/Qualifiers
source                  1..133
                        mol_type = protein
                        organism = Synthetic construct
SEQUENCE: 318
APTSSSTKKT QLQLEHLLLD LQMILNGINN YKNPKLTEML TFKFYMPKKA TELKHLQCLE   60
EELKPLEEVL NLAQSKNFHL RPRMLISNIN VIVLELKGSE TTFMCEYADE TATIVEFLNR  120
WITFCQSIIS TLT                                                    133

SEQ ID NO: 319          moltype = AA   length = 133
FEATURE                 Location/Qualifiers
source                  1..133
                        mol_type = protein
                        organism = Synthetic construct
SEQUENCE: 319
APTSSSTKKT QLQLEHLLLD LQMILNGINN YKNPKLTEML TFKFYMPKKA TELKHLQCLE   60
EELKPLEEVL NLAQSKNFHL RPRFLISNIN VIVLELKGSE TTFMCEYADE TATIVEFLNR  120
WITFCQSIIS TLT                                                    133

SEQ ID NO: 320          moltype = AA   length = 133
FEATURE                 Location/Qualifiers
source                  1..133
                        mol_type = protein
                        organism = Synthetic construct
SEQUENCE: 320
APTSSSTKKT QLQLEHLLLD LQMILNGINN YKNPKLTEML TFKFYMPKKA TELKHLQCLE   60
EELKPLEEVL NLAQSKNFHL RPRPLISNIN VIVLELKGSE TTFMCEYADE TATIVEFLNR  120
WITFCQSIIS TLT                                                    133

SEQ ID NO: 321          moltype = AA   length = 133
FEATURE                 Location/Qualifiers
source                  1..133
                        mol_type = protein
                        organism = Synthetic construct
SEQUENCE: 321
APTSSSTKKT QLQLEHLLLD LQMILNGINN YKNPKLTEML TFKFYMPKKA TELKHLQCLE   60
EELKPLEEVL NLAQSKNFHL RPRSLISNIN VIVLELKGSE TTFMCEYADE TATIVEFLNR  120
WITFCQSIIS TLT                                                    133

SEQ ID NO: 322          moltype = AA   length = 133
FEATURE                 Location/Qualifiers
source                  1..133
                        mol_type = protein
                        organism = Synthetic construct
```

```
SEQUENCE: 322
APTSSSTKKT QLQLEHLLLD LQMILNGINN YKNPKLTEML TFKFYMPKKA TELKHLQCLE    60
EELKPLEEVL NLAQSKNFHL RPRTLISNIN VIVLELKGSE TTFMCEYADE TATIVEFLNR   120
WITFCQSIIS TLT                                                     133

SEQ ID NO: 323           moltype = AA   length = 133
FEATURE                  Location/Qualifiers
source                   1..133
                         mol_type = protein
                         organism = Synthetic construct
SEQUENCE: 323
APTSSSTKKT QLQLEHLLLD LQMILNGINN YKNPKLTEML TFKFYMPKKA TELKHLQCLE    60
EELKPLEEVL NLAQSKNFHL RPRWLISNIN VIVLELKGSE TTFMCEYADE TATIVEFLNR   120
WITFCQSIIS TLT                                                     133

SEQ ID NO: 324           moltype = AA   length = 133
FEATURE                  Location/Qualifiers
source                   1..133
                         mol_type = protein
                         organism = Synthetic construct
SEQUENCE: 324
APTSSSTKKT QLQLEHLLLD LQMILNGINN YKNPKLTEML TFKFYMPKKA TELKHLQCLE    60
EELKPLEEVL NLAQSKNFHL RPRYLISNIN VIVLELKGSE TTFMCEYADE TATIVEFLNR   120
WITFCQSIIS TLT                                                     133

SEQ ID NO: 325           moltype = AA   length = 133
FEATURE                  Location/Qualifiers
source                   1..133
                         mol_type = protein
                         organism = Synthetic construct
SEQUENCE: 325
APTSSSTKKT QLQLEHLLLD LQMILNGINN YKNPKLTEML TFKFYMPKKA TELKHLQCLE    60
EELKPLEEVL NLAQSKNFHL RPRVLISNIN VIVLELKGSE TTFMCEYADE TATIVEFLNR   120
WITFCQSIIS TLT                                                     133

SEQ ID NO: 326           moltype = AA   length = 133
FEATURE                  Location/Qualifiers
source                   1..133
                         mol_type = protein
                         organism = Synthetic construct
SEQUENCE: 326
APTSSSTKKT QLQLEHLLLD LQMILNGINN YKNPKLTEML TFKFYMPKKA TELKHLQCLE    60
EELKPLEEVL NLAQSKNFHL RPRDLISNIN VAVLELKGSE TTFMCEYADE TATIVEFLNR   120
WITFCQSIIS TLT                                                     133

SEQ ID NO: 327           moltype = AA   length = 133
FEATURE                  Location/Qualifiers
source                   1..133
                         mol_type = protein
                         organism = Synthetic construct
SEQUENCE: 327
APTSSSTKKT QLQLEHLLLD LQMILNGINN YKNPKLTEML TFKFYMPKKA TELKHLQCLE    60
EELKPLEEVL NLAQSKNFHL RPRDLISNIN VRVLELKGSE TTFMCEYADE TATIVEFLNR   120
WITFCQSIIS TLT                                                     133

SEQ ID NO: 328           moltype = AA   length = 133
FEATURE                  Location/Qualifiers
source                   1..133
                         mol_type = protein
                         organism = Synthetic construct
SEQUENCE: 328
APTSSSTKKT QLQLEHLLLD LQMILNGINN YKNPKLTEML TFKFYMPKKA TELKHLQCLE    60
EELKPLEEVL NLAQSKNFHL RPRDLISNIN VNVLELKGSE TTFMCEYADE TATIVEFLNR   120
WITFCQSIIS TLT                                                     133

SEQ ID NO: 329           moltype = AA   length = 133
FEATURE                  Location/Qualifiers
source                   1..133
                         mol_type = protein
                         organism = Synthetic construct
SEQUENCE: 329
APTSSSTKKT QLQLEHLLLD LQMILNGINN YKNPKLTEML TFKFYMPKKA TELKHLQCLE    60
EELKPLEEVL NLAQSKNFHL RPRDLISNIN VQVLELKGSE TTFMCEYADE TATIVEFLNR   120
WITFCQSIIS TLT                                                     133

SEQ ID NO: 330           moltype = AA   length = 133
FEATURE                  Location/Qualifiers
source                   1..133
                         mol_type = protein
```

```
SEQUENCE: 330
APTSSSTKKT QLQLEHLLLD LQMILNGINN YKNPKLTEML TFKFYMPKKA TELKHLQCLE    60
EELKPLEEVL NLAQSKNFHL RPRDLISNIN VEVLELKGSE TTFMCEYADE TATIVEFLNR   120
WITFCQSIIS TLT                                                     133

SEQ ID NO: 331          moltype = AA  length = 133
FEATURE                 Location/Qualifiers
source                  1..133
                        mol_type = protein
                        organism = Synthetic construct
SEQUENCE: 331
APTSSSTKKT QLQLEHLLLD LQMILNGINN YKNPKLTEML TFKFYMPKKA TELKHLQCLE    60
EELKPLEEVL NLAQSKNFHL RPRDLISNIN VGVLELKGSE TTFMCEYADE TATIVEFLNR   120
WITFCQSIIS TLT                                                     133

SEQ ID NO: 332          moltype = AA  length = 133
FEATURE                 Location/Qualifiers
source                  1..133
                        mol_type = protein
                        organism = Synthetic construct
SEQUENCE: 332
APTSSSTKKT QLQLEHLLLD LQMILNGINN YKNPKLTEML TFKFYMPKKA TELKHLQCLE    60
EELKPLEEVL NLAQSKNFHL RPRDLISNIN VHVLELKGSE TTFMCEYADE TATIVEFLNR   120
WITFCQSIIS TLT                                                     133

SEQ ID NO: 333          moltype = AA  length = 133
FEATURE                 Location/Qualifiers
source                  1..133
                        mol_type = protein
                        organism = Synthetic construct
SEQUENCE: 333
APTSSSTKKT QLQLEHLLLD LQMILNGINN YKNPKLTEML TFKFYMPKKA TELKHLQCLE    60
EELKPLEEVL NLAQSKNFHL RPRDLISNIN VLVLELKGSE TTFMCEYADE TATIVEFLNR   120
WITFCQSIIS TLT                                                     133

SEQ ID NO: 334          moltype = AA  length = 133
FEATURE                 Location/Qualifiers
source                  1..133
                        mol_type = protein
                        organism = Synthetic construct
SEQUENCE: 334
APTSSSTKKT QLQLEHLLLD LQMILNGINN YKNPKLTEML TFKFYMPKKA TELKHLQCLE    60
EELKPLEEVL NLAQSKNFHL RPRDLISNIN VKVLELKGSE TTFMCEYADE TATIVEFLNR   120
WITFCQSIIS TLT                                                     133

SEQ ID NO: 335          moltype = AA  length = 133
FEATURE                 Location/Qualifiers
source                  1..133
                        mol_type = protein
                        organism = Synthetic construct
SEQUENCE: 335
APTSSSTKKT QLQLEHLLLD LQMILNGINN YKNPKLTEML TFKFYMPKKA TELKHLQCLE    60
EELKPLEEVL NLAQSKNFHL RPRDLISNIN VMVLELKGSE TTFMCEYADE TATIVEFLNR   120
WITFCQSIIS TLT                                                     133

SEQ ID NO: 336          moltype = AA  length = 133
FEATURE                 Location/Qualifiers
source                  1..133
                        mol_type = protein
                        organism = Synthetic construct
SEQUENCE: 336
APTSSSTKKT QLQLEHLLLD LQMILNGINN YKNPKLTEML TFKFYMPKKA TELKHLQCLE    60
EELKPLEEVL NLAQSKNFHL RPRDLISNIN VFVLELKGSE TTFMCEYADE TATIVEFLNR   120
WITFCQSIIS TLT                                                     133

SEQ ID NO: 337          moltype = AA  length = 133
FEATURE                 Location/Qualifiers
source                  1..133
                        mol_type = protein
                        organism = Synthetic construct
SEQUENCE: 337
APTSSSTKKT QLQLEHLLLD LQMILNGINN YKNPKLTEML TFKFYMPKKA TELKHLQCLE    60
EELKPLEEVL NLAQSKNFHL RPRDLISNIN VPVLELKGSE TTFMCEYADE TATIVEFLNR   120
WITFCQSIIS TLT                                                     133

SEQ ID NO: 338          moltype = AA  length = 133
FEATURE                 Location/Qualifiers
source                  1..133
```

```
                        mol_type = protein
                        organism = Synthetic construct
SEQUENCE: 338
APTSSSTKKT QLQLEHLLLD LQMILNGINN YKNPKLTEML TFKFYMPKKA TELKHLQCLE    60
EELKPLEEVL NLAQSKNFHL RPRDLISNIN VSVLELKGSE TTFMCEYADE TATIVEFLNR   120
WITFCQSIIS TLT                                                      133

SEQ ID NO: 339          moltype = AA  length = 133
FEATURE                 Location/Qualifiers
source                  1..133
                        mol_type = protein
                        organism = Synthetic construct
SEQUENCE: 339
APTSSSTKKT QLQLEHLLLD LQMILNGINN YKNPKLTEML TFKFYMPKKA TELKHLQCLE    60
EELKPLEEVL NLAQSKNFHL RPRDLISNIN VTVLELKGSE TTFMCEYADE TATIVEFLNR   120
WITFCQSIIS TLT                                                      133

SEQ ID NO: 340          moltype = AA  length = 133
FEATURE                 Location/Qualifiers
source                  1..133
                        mol_type = protein
                        organism = Synthetic construct
SEQUENCE: 340
APTSSSTKKT QLQLEHLLLD LQMILNGINN YKNPKLTEML TFKFYMPKKA TELKHLQCLE    60
EELKPLEEVL NLAQSKNFHL RPRDLISNIN VWVLELKGSE TTFMCEYADE TATIVEFLNR   120
WITFCQSIIS TLT                                                      133

SEQ ID NO: 341          moltype = AA  length = 133
FEATURE                 Location/Qualifiers
source                  1..133
                        mol_type = protein
                        organism = Synthetic construct
SEQUENCE: 341
APTSSSTKKT QLQLEHLLLD LQMILNGINN YKNPKLTEML TFKFYMPKKA TELKHLQCLE    60
EELKPLEEVL NLAQSKNFHL RPRDLISNIN VYVLELKGSE TTFMCEYADE TATIVEFLNR   120
WITFCQSIIS TLT                                                      133

SEQ ID NO: 342          moltype = AA  length = 133
FEATURE                 Location/Qualifiers
source                  1..133
                        mol_type = protein
                        organism = Synthetic construct
SEQUENCE: 342
APTSSSTKKT QLQLEHLLLD LQMILNGINN YKNPKLTEML TFKFYMPKKA TELKHLQCLE    60
EELKPLEEVL NLAQSKNFHL RPRDLISNIN VVVLELKGSE TTFMCEYADE TATIVEFLNR   120
WITFCQSIIS TLT                                                      133

SEQ ID NO: 343          moltype = AA  length = 133
FEATURE                 Location/Qualifiers
source                  1..133
                        mol_type = protein
                        organism = Synthetic construct
SEQUENCE: 343
APTSSSTKKT QLQLEELLLD LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 344          moltype = AA  length = 133
FEATURE                 Location/Qualifiers
source                  1..133
                        mol_type = protein
                        organism = Synthetic construct
SEQUENCE: 344
APTSSSTKKT QLQLEHLLLA LQMILNGINN YKNPKLTKML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 345          moltype = AA  length = 133
FEATURE                 Location/Qualifiers
source                  1..133
                        mol_type = protein
                        organism = Synthetic construct
SEQUENCE: 345
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 346          moltype = AA  length = 268
FEATURE                 Location/Qualifiers
```

```
                          source           1..268
                                           mol_type = protein
                                           organism = Synthetic construct
SEQUENCE: 346
PGWFLDSPDR PWNPPTFSPA LLVVTEGDNA TFTCSFSNTS ESFVLNWYRM SPSNQTDKLA        60
APFEDRSQPG QDCRFRVTQL PNGRDFHMSV VRARRNDSGT YLCGAISLAP KAQIKESLRA       120
ELRVTERRAE VPTAHPSPSP RPAGQFQTLV VGVVGGLLGS LVLLVWVLAV ICSRAARGTI       180
GARRTGQPLK EDPSAVPVFS VDYGELDFQW REKTPEPPVP CVPEQTEYAT IVFPSGMGTS       240
SPARRGSADG PRSAQPLRPE DGHCSWPL                                         268

SEQ ID NO: 347           moltype = DNA   length = 804
FEATURE                  Location/Qualifiers
source                   1..804
                         mol_type = other DNA
                         organism = Synthetic construct
SEQUENCE: 347
ccaggatggt tcttagactc cccagacagg ccctggaacc ccccaccttt ctccccagcc        60
ctgctcgtgg tgaccgaagg ggacaacgcc accttcacct gcagcttctc caacacatcg      120
gagagcttcg tgctaaactg gtaccgcatg agccccagca accagacgga caagctggcc      180
gccttccccg aggaccgcag ccagcccggc caggactgcc gcttccgtgt cacacaactg      240
cccaacgggc gtgacttcca catgagcgtg gtcagggccc ggcgcaatga cagcggcacc      300
tacctctgtg gggccatctc cctggccccc aaggcgcaga tcaaagagag cctgcgggca      360
gagctcaggg tgacagagag aagggcagaa gtgcccacag cccacccagc ccctctcaccc     420
aggccagccg ccagttccaa aaccctggtg gttggtgtcg tgggcggcct gctgggcagc      480
ctggtgctgc tagtctgggt cctggccgtc atctgctccc gggccgcacg agggacaata      540
ggagccggcc gcaccggcca gcccctgaag gaggacccct cagccgtgtc tgtgttctct      600
gtggactatg gggagctgga tttccagtgg cgagagaaga ccccggagcc ccccgtgccc      660
tgtgtccctg agcagacgga gtatgccacc attgtctttc ctagcggaat gggcacctca      720
tccccccgccc gcaggggctc agctgacggc cctcggagtg cccagccact gaggcctgag     780
gatggacact gctcttggcc cctc                                             804

SEQ ID NO: 348           moltype = AA   length = 449
FEATURE                  Location/Qualifiers
source                   1..449
                         mol_type = protein
                         organism = Synthetic construct
SEQUENCE: 348
QVQLVESGGG VVQPGRSLRL DCKASGITFS NSGMHWVRQA PGKGLEWVAV IWYDGSKRYY        60
ADSVKGRFTI SRDNSKNTLF LQMNSLRAED TAVYYCATND DYWGQGTLVT VSSAKTTPPS       120
VYPLAPGCGD TTGSSVTLGC LVKGYFPESV TVTWNSGSLS SSVHTFPALL QSGLYTMSSS       180
VTVPSSTWPS QTVTCSVAHP ASSTTVDKKL EPSGPISTIN PCPPCKECHK CPAPNLEGGP       240
SVFIFPPNIK DVLMISLTPK VTCVVVDVSE DDPDVQISWF VNNVEVHTAQ TQTHREDYAS       300
TIRVVSTLPI QHQDWMSGKE FKCKVNNKDL PSPIERTISK IKGLVRAPQV YILPPPAEQL       360
SRKDVSLTCL VVGFNPGDIS VEWTSNGHTE ENYKDTAPVL DSDGSYFIYS KLNMKTSKWE       420
KTDSFSCNVR HEGLKNYYLK KTISRSPGK                                        449

SEQ ID NO: 349           moltype = AA   length = 214
FEATURE                  Location/Qualifiers
source                   1..214
                         mol_type = protein
                         organism = Synthetic construct
SEQUENCE: 349
EIVLTQSPAT LSLSPGERAT LSCRASQSVS SYLAWYQQKP GQAPRLLIYD ASNRATGIPA        60
RFSGSGSGTD FTLTISSLEP EDFAVYYCQQ SSNWPRTFGQ GTKVEIKRAD AAPTVSIFPP       120
SSEQLTSGGA SVVCFLNNFY PKDINVKWKI DGSERQNGVL NSWTDQDSKD STYSMSSTLT       180
LTKDEYERHN SYTCEATHKT STSPIVKSFN RNEC                                  214

SEQ ID NO: 350           moltype = AA   length = 456
FEATURE                  Location/Qualifiers
source                   1..456
                         mol_type = protein
                         organism = Synthetic construct
SEQUENCE: 350
QVQLVQSGVE VKKPGASVKV SCKASGYTFT NYYMYWVRQA PGQGLEWMGG INPSNGGTNF        60
NEKFKNRVTL TTDSSTTTAY MELKSLQFDD TAVYYCARRD YRFDMGFDYW GQGTTVTVSS       120
AKTTPPSVYP LAPGCGDTTG SSVTLGCLVK GYFPESVTVT WNSGSLSSSV HTFPALLQSG       180
LYTMSSSVTV PSSTWPSQTV TCSVAHPASS TTVDKKLEPS GPISTINPCP PCKECHKCPA       240
PNLEGGPSVF IFPPNIKDVL MISLTPKVTC VVVDVSEDDP DVQISWFVNN VEVHTAQTQT       300
HREDYASTIR VVSTLPIQHQ DWMSGKEFKC KVNNKDLPSP IERTISKIKG LVRAPQVYIL       360
PPPAEQLSRK DVSLTCLVVG FNPGDISVEW TSNGHTEENY KDTAPVLDSD GSYFIYSKLN       420
MKTSKWEKTD SFSCNVRHEG LKNYYLKKTI SRSPGK                                456

SEQ ID NO: 351           moltype = AA   length = 218
FEATURE                  Location/Qualifiers
source                   1..218
                         mol_type = protein
                         organism = Synthetic construct
SEQUENCE: 351
EIVLTQSPAT LSLSPGERAT LSCRASKGVS TSGYSYLHWY QQKPGQAPRL LIYLASYLES        60
```

```
GVPARFSGSG SGTDFTLTIS SLEPEDFAVY YCQHSRDLPL TFGGGTKVEI KRADAAPTVS    120
IFPPSSEQLT SGGASVVCFL NNFYPKDINV KWKIDGSERQ NGVLNSWTDQ DSKDSTYSMS    180
STLTLTKDEY ERHNSYTCEA THKTSTSPIV KSFNRNEC                            218

SEQ ID NO: 352          moltype = AA  length = 347
FEATURE                 Location/Qualifiers
source                  1..347
                        mol_type = protein
                        organism = Synthetic construct
SEQUENCE: 352
LNTTILTPNG NEDTTADFFL TTMPTDSLSV STLPLPEVQC FVFNVEYMNC TWNSSSEPQP     60
TNLTLHYWYK NSDNDKVQKC SHYLFSEEIT SGCQLQKKEI HLYQTFVVQL QDPREPRRQA    120
TQMLKLQNLV IPWAPENLTL HKLSESQLEL NWNNRFLNHC LEHLVQYRTD WDHSWTEQSV    180
DYRHKFSLPS VDGQKRYTFR VRSRFNPLCG SAQHWSEWSH PIHWGSNTSK ENPFLFALEA    240
VVISVGSMGL IISLLCVYFW LERTMPRIPT LKNLEDLVTE YHGNFSAWSG VSKGLAESLQ    300
PDYSERLCLV SEIPPKGGAL GEGPGASPCN QHSPYWAPPC YTLKPET                  347

SEQ ID NO: 353          moltype = AA  length = 525
FEATURE                 Location/Qualifiers
source                  1..525
                        mol_type = protein
                        organism = Synthetic construct
SEQUENCE: 353
AVNGTSQFTC FYNSRANISC VWSQDGALQD TSCQVHAWPD RRRWNQTCEL LPVSQASWAC     60
NLILGAPDSQ KLTTVDIVTL RVLCREGVRW RVMAIQDFKP FENLRLMAPI SLQVVHVETH    120
RCNISWEISQ ASHYFERHLE FEARTLSPGH TWEEAPLLTL KQKQEWICLE TLTPDTQYEF    180
QVRVKPLQGE FTTWSPWSQP LAFRTKPAAL GKDTIPWLGH LLVGLSGAFG FIILVYLLIN    240
CRNTGPWLKK VLKCNTPDPS KFFSQLSSEH GGDVQKWLSS PFPSSSFSPG GLAPEISPLE    300
VLERDKVTQL LQQDKVPEP ASLSSNHSLT SCFTNQGYFF FHLPDALEIE ACQVYFTYDP     360
YSEEDPDEGV AGAPTGSSPQ PLQPLSGEDD AYCTFPSRDD LLLFSPSLLG GPSPPSTAPG    420
GSGAGEERMP PSLQERVPRD WDPQPLGPPT PGVPDLVDFQ PPPELVLREA GEEVPDAGPR    480
EGVSFPWSRP PGQGEFRALN ARLPLNTDAY LSLQELQGQD PTHLV                    525

SEQ ID NO: 354          moltype = AA  length = 251
FEATURE                 Location/Qualifiers
source                  1..251
                        mol_type = protein
                        organism = Synthetic construct
SEQUENCE: 354
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SCLVTTTDFQ IQTEMAATME TSIFTTEYQV AVAGCVFLLI SVLLLSGLTW    240
QRRQRKSRRT I                                                         251

SEQ ID NO: 355          moltype = AA  length = 6
FEATURE                 Location/Qualifiers
source                  1..6
                        mol_type = protein
                        organism = Synthetic construct
SEQUENCE: 355
SGGGGS                                                                 6

SEQ ID NO: 356          moltype = AA  length = 346
FEATURE                 Location/Qualifiers
source                  1..346
                        mol_type = protein
                        organism = Synthetic construct
SEQUENCE: 356
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTDTVLTQS PALAVSPGER VTISCRASES VRTGVHWYQQ KPGQQPKLLI    180
YGASNLESGV PARFSGSGSG TDFTLTIDPV EADDTATYFC QQSWNDPFTF GSGTKLEIKR    240
TVAAPSVFIF PPSDEQLKSG TASVVCLLNN FYPREAKVQW KVDNALQSGN SQESVTEQDS    300
KDSTYSLSST LTLSKADYEK HKVYACEVTH QGLSSPVTKS FNRGEC                   346

SEQ ID NO: 357          moltype = AA  length = 352
FEATURE                 Location/Qualifiers
source                  1..352
                        mol_type = protein
                        organism = Synthetic construct
SEQUENCE: 357
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGGGSD TVLTQSPALA VSPGERVTIS CRASESVRTG VHWYQQKPGQ    180
QPKLLIYGAS NLESGVPARF SGSGSGTDFT LTIDPVEADD TATYFCQQSW NDPFTFGSGT    240
KLEIKRTVAA PSVFIFPPSD EQLKSGTASV VCLLNNFYPR EAKVQWKVDN ALQSGNSQES    300
VTEQDSKDST YSLSSTLTLS KADYEKHKVY ACEVTHQGLS SPVTKSFNRG EC             352
```

```
SEQ ID NO: 358          moltype = AA  length = 580
FEATURE                 Location/Qualifiers
source                  1..580
                        mol_type = protein
                        organism = Synthetic construct
SEQUENCE: 358
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTEVQLVES GGGLVQPGRS LKLSCAVSGF TFSDYAMAWV RQAPKKGLEW   180
VATISYDGSR TYYRDSVKGR FTISRDNAKI TLYLQMDSLR SEDTATYYCA RHGSGYFDYW   240
GQGVMVTVSS ASTKGPSVFP LAPSSKSTSG GTAALGCLVK DYFPEPVTVS WNSGALTSGV   300
HTFPAVLQSS GLYSLSSVVT VPSSSLGTQT YICNVNHKPS NTKVDKKVEP KSCDKTHTCP   360
PCPAPELLGG PSVFLFPPKP KDTLMISRTP EVTCVVVDVS HEDPEVKFNW YVDGVEVHNA   420
KTKPREEQYN STYRVVSVLT VLHQDWLNGK EYKCKVSNKA LPAPIEKTIS KAKGQPREPQ   480
VYTLPPSRDE LTKNQVSLTC LVKGFYPSDI AVEWESNGQP ENNYKTTPPV LDSDGSFFLY   540
SKLTVDKSRW QQGNVFSCSV MHEALHNHYT QKSLSLSPGK                        580

SEQ ID NO: 359          moltype = AA  length = 586
FEATURE                 Location/Qualifiers
source                  1..586
                        mol_type = protein
                        organism = Synthetic construct
SEQUENCE: 359
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGGSE VQLVESGGGL VQPGRSLKLS CAVSGFTFSD YAMAWVRQAP   180
KKGLEWVATI SYDGSRTYYR DSVKGRFTIS RDNAKITLYL QMDSLRSEDT ATYYCARHGS   240
GYFDYWGQGV MVTVSSASTK GPSVFPLAPS SKSTSGGTAA LGCLVKDYFP EPVTVSWNSG   300
ALTSGVHTFP AVLQSSGLYS LSSVVTVPSS SLGTQTYICN VNHKPSNTKV DKKVEPKSCD   360
KTHTCPPCPA PELLGGPSVF LFPPKPKDTL MISRTPEVTC VVVDVSHEDP EVKFNWYVDG   420
VEVHNAKTKP REEQYNSTYR VVSVLTVLHQ DWLNGKEYKC KVSNKALPAP IEKTISKAKG   480
QPREPQVYTL PPSRDELTKN QVSLTCLVKG FYPSDIAVEW ESNGQPENNY KTTPPVLDSD   540
GSFFLYSKLT VDKSRWQQGN VFSCSVMHEA LHNHYTQKSL SLSPGK                  586

SEQ ID NO: 360          moltype = AA  length = 580
FEATURE                 Location/Qualifiers
source                  1..580
                        mol_type = protein
                        organism = Synthetic construct
SEQUENCE: 360
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKAPT SSSTKKTQLQ LEHLLLDLQM ILNGINNYKN   480
PKLTRMLTFK FYMPKKATEL KHLQCLEEEL KPLEEVLNLA QSKNFHLRPR DLISNINVIV   540
LELKGSETTF MCEYADETAT IVEFLNRWIT FCQSIISTLT                        580

SEQ ID NO: 361          moltype = AA  length = 586
FEATURE                 Location/Qualifiers
source                  1..586
                        mol_type = protein
                        organism = Synthetic construct
SEQUENCE: 361
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSAPTSSST KKTQLQLEHL LLDLQMILNG   480
INNYKNPKLT RMLTFKFYMP KKATELKHLQ CLEEELKPLE EVLNLAQSKN FHLRPRDLIS   540
NINVIVLELK GSETTFMCEY ADETATIVEF LNRWITFCQS IISTLT                  586

SEQ ID NO: 362          moltype = AA  length = 346
FEATURE                 Location/Qualifiers
source                  1..346
                        mol_type = protein
                        organism = Synthetic construct
SEQUENCE: 362
DTVLTQSPAL AVSPGERVTI SCRASESVRT GVHWYQQKPG QQPKLLIYGA SNLESGVPAR    60
FSGSGSGTDF TLTIDPVEAD DTATYFCQQS WNDPFTFGSG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GECAPTSSST KKTQLQLEHL LLDLQMILNG   240
INNYKNPKLT RMLTFKFYMP KKATELKHLQ CLEEELKPLE EVLNLAQSKN FHLRPRDLIS   300
```

```
NINIVIVLELK GSETTFMCEY ADETATIVEF LNRWITFCQS IISTLT              346

SEQ ID NO: 363            moltype = AA   length = 352
FEATURE                   Location/Qualifiers
source                    1..352
                          mol_type = protein
                          organism = Synthetic construct
SEQUENCE: 363
DTVLTQSPAL AVSPGERVTI SCRASESVRT GVHWYQQKPG QQPKLLIYGA SNLESGVPAR  60
FSGSGSGTDF TLTIDPVEAD DTATYFCQQS WNDPFTFGSG TKLEIKRTVA APSVFIFPPS 120
DEQLKSGTAS VVCLLNNFYP REAKVQWKVD NALQSGNSQE SVTEQDSKDS TYSLSSTLTL 180
SKADYEKHKV YACEVTHQGL SSPVTKSFNR GECSGGGGSA PTSSSTKKTQ LQLEHLLLDL 240
QMILNGINNY KNPKLTRMLT FKFYMPKKAT ELKHLQCLEE ELKPLEEVLN LAQSKNFHLR 300
PRDLISNINV IVLELKGSET TFMCEYADET ATIVEFLNRW ITFCQSIIST LT         352

SEQ ID NO: 364            moltype = AA   length = 20
FEATURE                   Location/Qualifiers
source                    1..20
                          mol_type = protein
                          organism = Synthetic construct
SEQUENCE: 364
SGGGGSGGGG SGGGGSGGGS                                            20

SEQ ID NO: 365            moltype = AA   length = 764
FEATURE                   Location/Qualifiers
source                    1..764
                          mol_type = protein
                          organism = Synthetic construct
SEQUENCE: 365
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH 120
FVVGQMVYYQ CVQGYRALHR GPAESVCKMT HGKTRWTQPQ LICTSGGGGS GGGGSGGGGS 180
GGGSAPTSSS TKKTQLQLEH LLLDLQMILN GINNYKNPKL TRMLTFKFYM PKKATELKHL 240
QCLEEELKPL EEVLNLAQSK NFHLRPRDLI SNINIVLEL KGSETTFMCE YADETATIVE 300
FLNRWITFCQ SIISTLTEVQ LVESGGGLVQ PGRSLKLSCA VSGFTFSDYA MAWVRQAPKK 360
GLEWVATISY DGSRTYYRDS VKGRFTISRD NAKITLYLQM DSLRSEDTAT YYCARHGSGY 420
FDYWGQGVMV TVSSASTKGP SVFPLAPSSK STSGGTAALG CLVKDYFPEP VTVSWNSGAL 480
TSGVHTFPAV LQSSGLYSLS SVVTVPSSSL GTQTYICNVN HKPSNTKVDK KVEPKSCDKT 540
HTCPPCPAPE LLGGPSVFLF PPKPKDTLMI SRTPEVTCVV VDVSHEDPEV KFNWYVDGVE 600
VHNAKTKPRE EQYNSTYRVV SVLTVLHQDW LNGKEYKCKV SNKALPAPIE KTISKAKGQP 660
REPQVYTLPP SRDELTKNQV SLTCLVKGFY PSDIAVEWES NGQPENNYKT TPPVLDSDGS 720
FFLYSKLTVD KSRWQQGNVF SCSVMHEALH NHYTQKSLSL SPGK                 764

SEQ ID NO: 366            moltype = AA   length = 770
FEATURE                   Location/Qualifiers
source                    1..770
                          mol_type = protein
                          organism = Synthetic construct
SEQUENCE: 366
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH 120
FVVGQMVYYQ CVQGYRALHR GPAESVCKMT HGKTRWTQPQ LICTSGGGGS GGGGSGGGGS 180
GGGSAPTSSS TKKTQLQLEH LLLDLQMILN GINNYKNPKL TRMLTFKFYM PKKATELKHL 240
QCLEEELKPL EEVLNLAQSK NFHLRPRDLI SNINIVLEL KGSETTFMCE YADETATIVE 300
FLNRWITFCQ SIISTLTSGG GGSEVQLVES GGGLVQPGRS LKLSCAVSGF TFSDYAMAWV 360
RQAPKKGLEW VATISYDGSR TYYRDSVKGR FTISRDNAKI TLYLQMDSLR SEDTATYYCA 420
RHGSGYFDYW GQGVMVTVSS ASTKGPSVFP LAPSSKSTSG GTAALGCLVK DYFPEPVTVS 480
WNSGALTSGV HTFPAVLQSS GLYSLSSVVT VPSSSLGTQT YICNVNHKPS NTKVDKKVEP 540
KSCDKTHTCP PCPAPELLGG PSVFLFPPKP KDTLMISRTP EVTCVVVDVS HEDPEVKFNW 600
YVDGVEVHNA KTKPREEQYN STYRVVSVLT VLHQDWLNGK EYKCKVSNKA LPAPIEKTIS 660
KAKGQPREPQ VYTLPPSRDE LTKNQVSLTC LVKGFYPSDI AVEWESNGQP ENNYKTTPPV 720
LDSDGSFFLY SKLTVDKSRW QQGNVFSCSV MHEALHNHYT QKSLSLSPGK           770

SEQ ID NO: 367            moltype = AA   length = 530
FEATURE                   Location/Qualifiers
source                    1..530
                          mol_type = protein
                          organism = Synthetic construct
SEQUENCE: 367
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH 120
FVVGQMVYYQ CVQGYRALHR GPAESVCKMT HGKTRWTQPQ LICTSGGGGS GGGGSGGGGS 180
GGGSAPTSSS TKKTQLQLEH LLLDLQMILN GINNYKNPKL TRMLTFKFYM PKKATELKHL 240
QCLEEELKPL EEVLNLAQSK NFHLRPRDLI SNINIVLEL KGSETTFMCE YADETATIVE 300
FLNRWITFCQ SIISTLTDTV LTQSPALAVS PGERVTISCR ASESVRTGVH WYQQKPGQQP 360
KLLIYGASNL ESGVPARFSG SGSGTDFTLT IDPVEADDTA TYFCQQSWND PPTFGSGTKL 420
EIKRTVAAPS VFIFPPSDEQ LKSGTASVVC LLNNFYPREA KVQWKVDNAL QSGNSQESVT 480
EQDSKDSTYS LSSTLTLSKA DYEKHKVYAC EVTHQGLSSP VTKSFNRGEC           530
```

```
SEQ ID NO: 368          moltype = AA  length = 536
FEATURE                 Location/Qualifiers
source                  1..536
                        mol_type = protein
                        organism = Synthetic construct
SEQUENCE: 368
ELCDDDPPEI PHATFKAMAY KEGTMLNCEC KRGFRRIKSG SLYMLCTGNS SHSSWDNQCQ    60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTSGGGGS GGGSGGGGS    180
GGGSAPTSSS TKKTQLQLEH LLLDLQMILN GINNYKNPKL TRMLTFKFYM PKKATELKHL   240
QCLEEELKPL EEVLNLAQSK NFHLRPRDLI SNINVIVLEL KGSETTFMCE YADETATIVE   300
FLNRWITFCQ SIISTLTSGG GGSDTVLTQS PALAVSPGER VTISCRASES VRTGVHWYQQ   360
KPGQQPKLLI YGASNLESGV PARFSGSGSG TDFTLTIDPV EADDTATYFC QQSWNDPFTF   420
GSGTKLEIKR TVAAPSVFIF PPSDEQLKSG TASVVCLLNN FYPREAKVQW KVDNALQSGN   480
SQESVTEQDS KDSTYSLSST LTLSKADYEK HKVYACEVTH QGLSSPVTKS FNRGEC       536

SEQ ID NO: 369          moltype = AA  length = 764
FEATURE                 Location/Qualifiers
source                  1..764
                        mol_type = protein
                        organism = Synthetic construct
SEQUENCE: 369
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKELC DDDPPEIPHA TFKAMAYKEG TMLNCECKRG   480
FRRIKSGSLY MLCTGNSSHS SWDNQCQCTS SATRNTTKQV TPQPEEQKER KTTEMQSPMQ   540
PVDQASLPGH CREPPPWENE ATERIYHFVV GQMVYYQCVQ GYRALHRGPA ESVCKMTHGK   600
TRWTQPQLIC TSGGGGSGGG GSGGGGSGGG SAPTSSSTKK TQLQLEHLLL DLQMILNGIN   660
NYKNPKLTRM LTFKFYMPKK ATELKHLQCL EEELKPLEEV LNLAQSKNFH LRPRDLISNI   720
NVIVLELKGS ETTFMCEYAD ETATIVEFLN RWITFCQSII STLT                   764

SEQ ID NO: 370          moltype = AA  length = 770
FEATURE                 Location/Qualifiers
source                  1..770
                        mol_type = protein
                        organism = Synthetic construct
SEQUENCE: 370
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISNINVIV LELKGSETTF MCEYADETAT IVEFLNRWIT FCQSIISTLT              770

SEQ ID NO: 371          moltype = AA  length = 530
FEATURE                 Location/Qualifiers
source                  1..530
                        mol_type = protein
                        organism = Synthetic construct
SEQUENCE: 371
DTVLTQSPAL AVSPGERVTI SCRASESVRT GVHWYQQKPG QQPKLLIYGA SNLESGVPAR    60
FSGSGSGTDF TLTIDPVEAD DTATYFCQQS WNDPFTFGSG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GECELCDDDP PEIPHATFKA MAYKEGTMLN   240
CECKRGFRRI KSGSLYMLCT GNSSHSSWDN QCQCTSSATR NTTKQVTPQP EEQKERKTTE   300
MQSPMQPVDQ ASLPGHCREP PPWENEATER IYHFVVGQMV YYQCVQGYRA LHRGPAESVC   360
KMTHGKTRWT QPQLICTSGG GGSGGGGSGG GGSGGGSAPT SSSTKKTQLQ LEHLLLDLQM   420
ILNGINNYKN PKLTRMLTFK FYMPKKATEL KHLQCLEEEL KPLEEVLNLA QSKNFHLRPR   480
DLISNINVIV LELKGSETTF MCEYADETAT IVEFLNRWIT FCQSIISTLT              530

SEQ ID NO: 372          moltype = AA  length = 536
FEATURE                 Location/Qualifiers
source                  1..536
                        mol_type = protein
                        organism = Synthetic construct
SEQUENCE: 372
DTVLTQSPAL AVSPGERVTI SCRASESVRT GVHWYQQKPG QQPKLLIYGA SNLESGVPAR    60
```

```
FSGSGSGTDF TLTIDPVEAD DTATYFCQQS WNDPFTFGSG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GECSGGGGSE LCDDDPPEIP HATFKAMAYK    240
EGTMLNCECK RGFRRIKSGS LYMLCTGNSS HSSWDNQCQC TSSATRNTTK QVTPQPEEQK    300
ERKTTEMQSP MQPVDQASLP GHCREPPPWE NEATERIYHF VVGQMVYYQC VQGYRALHRG    360
PAESVCKMTH GKTRWTQPQL ICTSGGGGSG GGGSGGGGSG GGSAPTSSST KKTQLQLEHL    420
LLDLQMILNG INNYKNPKLT RMLTFKFYMP KKATELKHLQ CLEEELKPLE EVLNLAQSKN    480
FHLRPRDLIS NINVIVLELK GSETTFMCEY ADETATIVEF LNRWITFCQS IISTLT       536

SEQ ID NO: 373          moltype = AA  length = 448
FEATURE                 Location/Qualifiers
source                  1..448
                        mol_type = protein
                        organism = Synthetic construct
SEQUENCE: 373
EVQLLESGGG LVQPGGSLRL SCAASGFTFK SYAMTWVRQA PGKGLEWVSA IVYSGGSTYY    60
ADSVKGRFTI SRDNSKNTLY LQMNSLRAED TAVYYCAKYT RASYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                       448

SEQ ID NO: 374          moltype = AA  length = 213
FEATURE                 Location/Qualifiers
source                  1..213
                        mol_type = protein
                        organism = Synthetic construct
SEQUENCE: 374
DTVLTQSPAL AVSPGERVTI SCRASESVRT GVHWYQQKPG QQPKLLIYGA SNLESGVPAR    60
FSGSGSGTDF TLTIDPVEAD DTATYFCQQS WNDPFTFGSG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 375          moltype = AA  length = 585
FEATURE                 Location/Qualifiers
source                  1..585
                        mol_type = protein
                        organism = Synthetic construct
SEQUENCE: 375
EVQLQQSGPE LVKPGASVKI SCKTSGYTFT EYTMHWVKQS HGKSLEWIGG INPNNGGTTY    60
NQKFKGKATL TVDKSSSTAY MELRSLTSQD SAVYYCARDY YRYGHYYAMD YWGQGTSVTV    120
SSAKTTPPSV YPLAPGSAAQ TNSMVTLGCL VKGYFPEPVT VTWNSGSLSS GVHTFPAVLQ    180
SDLYTLSSSV TVPSSTWPSE TVTCNVAHPA SSTKVDKKIV PRDCGCKPCI CTVPEVSSVF    240
IFPPKPKDVL TITLTPKVTC VVVAISKDDP EVQFSWFVDD VEVHTAQTQP REEQFNSTFR    300
SVSELPIMHQ DWLNGKEFKC RVNSAAFPAP IEKTISKTKG RPKAPQVYTI PPPKEQMAKD    360
KVSLTCMITD FFPEDITVEW QWNGQPAENY KNTQPIMDTD GSYFVYSKLN VQKSNWEAGN    420
TFTCSVLHEG LHNHHTEKSL SHSPGKSGGG GSAPTSSSTK KTQLQLEHLL LDLQMILNGI    480
NNYKNPKLTR MLTFKYMPK KATELKHLQC LEEELKPLEE VLNLAQSKNF HLRPRDLISN    540
INVIVLELKG SETTFMCEYA DETATIVEFL NRWITFCQSI ISTLT                    585

SEQ ID NO: 376          moltype = AA  length = 213
FEATURE                 Location/Qualifiers
source                  1..213
                        mol_type = protein
                        organism = Synthetic construct
SEQUENCE: 376
QIVLTQSPAI MSASPGEKVT MTCSVSSSVR FMHWYQQKSG TSPKRWIYDT SKLASGVPAR    60
FSGSGSGTSY SLTISSMEAE DAATYYCQQW SSNPPTFGGG TKLKIKRADA APTVSIFPPS    120
SEQLTSGGAS VVCFLNNFYP KDINVKWKID GSERQNGVLN SWTDQDSKDS TYSMSSTLTL    180
TKDEYERHNS YTCEATHKTS TSPIVKSFNR NEC                                 213

SEQ ID NO: 377          moltype = AA  length = 133
FEATURE                 Location/Qualifiers
source                  1..133
                        mol_type = protein
                        organism = Synthetic construct
SEQUENCE: 377
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCLSIIS TLT                                                       133

SEQ ID NO: 378          moltype = AA  length = 133
FEATURE                 Location/Qualifiers
source                  1..133
                        mol_type = protein
                        organism = Synthetic construct
SEQUENCE: 378
```

```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCESIIS TLT                                                     133

SEQ ID NO: 379         moltype = AA   length = 447
FEATURE                Location/Qualifiers
source                 1..447
                       mol_type = protein
                       organism = Synthetic construct
SEQUENCE: 379
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 380         moltype = AA   length = 404
FEATURE                Location/Qualifiers
source                 1..404
                       mol_type = protein
                       organism = Synthetic construct
SEQUENCE: 380
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQIEG RMDPKSCDKT   180
HTCPPCPAPE LLGGPSVFLF PPKPKDTLMI SRTPEVTCVV VDVSHEDPEV KFNWYVDGVE   240
VHNAKTKPRE EQYNSTYRVV SVLTVLHQDW LNGKEYKCKV SNKALPAPIE KTISKAKGQP   300
REPQVYTLPP SRDELTKNQV SLTCLVKGFY PSDIAVEWES NGQPENNYKT TPPVLDSDGS   360
FFLYSKLTVD KSRWQQGNVF SCSVMHEALH NHYTQKSLSL SPGK                    404

SEQ ID NO: 381         moltype = AA   length = 404
FEATURE                Location/Qualifiers
source                 1..404
                       mol_type = protein
                       organism = Synthetic construct
SEQUENCE: 381
MQIPQAPWPV VWAVLQLGWR PGWFLESPDR PWNAPTFSPA LLLVTEGDNA TFTCSFSNAS    60
ESFVLNWYRM SPSNQTDKLA AFPEDRSQPG QDCRFRVTRL PNGRDFHMSV VRARRNDSGT   120
YLCGAISLAP KAQIKESLRA ELRVTERRAE VPTAHPSPSP RPAGQFQIEG RMDPKSCDKT   180
HTCPPCPAPE LLGGPSVFLF PPKPKDTLMI SRTPEVTCVV VDVSHEDPEV KFNWYVDGVE   240
VHNAKTKPRE EQYNSTYRVV SVLTVLHQDW LNGKEYKCKV SNKALPAPIE KTISKAKGQP   300
REPQVYTLPP SRDELTKNQV SLTCLVKGFY PSDIAVEWES NGQPENNYKT TPPVLDSDGS   360
FFLYSKLTVD KSRWQQGNVF SCSVMHEALH NHYTQKSLSL SPGK                    404

SEQ ID NO: 382         moltype = DNA   length = 367
FEATURE                Location/Qualifiers
source                 1..367
                       mol_type = other DNA
                       organism = Synthetic construct
SEQUENCE: 382
gaggtgcagc tgctggaaag cggcggcgga ctggtgcagc ctggaggcag cctgcggctg    60
tctttgccg cttctggctt caccttcaag gactactatg tgacctgggt cagacaggcc   120
cctggcaagg gcctcgagtg ggtgtccgcc atcgtgtaca gcggcgggtc aacatactac   180
gccgacagcg tgaagggcag attcacaatc agcagagata cagcaagaa cacccctgtac   240
ctgcagatga caacctgag agctgaagat accgccgtgt actactgcgc caagtacacc   300
agagccagct acttctacga cgccatggac gtgtggggcc agggcaccac cgtgacagtg   360
tcctcat                                                            367

SEQ ID NO: 383         moltype = DNA   length = 327
FEATURE                Location/Qualifiers
source                 1..327
                       mol_type = other DNA
                       organism = Synthetic construct
SEQUENCE: 383
gagatcgtgc tgacccagtc tcctggcacc ctgagcctga gcctggcga gagagctaca    60
ctgtcatgca gagcctctca gagcatcggc aagagcttcc tggcctggta ccagcaaaag   120
cctggacagg cccctagact gctgatctac gacgccagca ccagagccgc tgatatcccc   180
gccagattca gcggatctgg cagcggcact gatttcaccc tcaccatcag cagcctggaa   240
cccgaggact cgccgtgta ctactgccag cagtactacg actggccccc cctgtctttt   300
ggcggaggca caaaggtgga aatcaag                                      327

SEQ ID NO: 384         moltype = AA   length = 122
FEATURE                Location/Qualifiers
source                 1..122
                       mol_type = protein
                       organism = Synthetic construct
```

```
SEQUENCE: 384
EVQLLESGGG LVQPGGSLRL SCAASGFTFK DYCMTWVRQA PGKGLEWVSA IVYSGGSTYY    60
ADSVKGRFTI SRDNSKNTLY LQMNNLRAED TAVYYCAKYT RASYFYDAMD VWGQGTTVTV   120
SS                                                                122

SEQ ID NO: 385         moltype = AA  length = 109
FEATURE                Location/Qualifiers
source                 1..109
                       mol_type = protein
                       organism = Synthetic construct
SEQUENCE: 385
EIVLTQSPGT LSLSPGERAT LSCRASQSIG KSFLAWYQQK PGQAPRLLIY DASTRAADIP    60
ARFSGSGSGT DFTLTISSLE PEDFAVYYCQ QYYDWPPLSF GGGTKVEIK              109

SEQ ID NO: 386         moltype = AA  length = 10
FEATURE                Location/Qualifiers
source                 1..10
                       mol_type = protein
                       organism = Synthetic construct
SEQUENCE: 386
GFTFKDYCMT                                                          10

SEQ ID NO: 387         moltype = AA  length = 17
FEATURE                Location/Qualifiers
source                 1..17
                       mol_type = protein
                       organism = Synthetic construct
SEQUENCE: 387
AIVYSGGSTY YADSVKG                                                  17

SEQ ID NO: 388         moltype = AA  length = 13
FEATURE                Location/Qualifiers
source                 1..13
                       mol_type = protein
                       organism = Synthetic construct
SEQUENCE: 388
YTRASYFYDA MDV                                                      13

SEQ ID NO: 389         moltype = AA  length = 12
FEATURE                Location/Qualifiers
source                 1..12
                       mol_type = protein
                       organism = Synthetic construct
SEQUENCE: 389
RASQSIGKSF LA                                                       12

SEQ ID NO: 390         moltype = AA  length = 7
FEATURE                Location/Qualifiers
source                 1..7
                       mol_type = protein
                       organism = Synthetic construct
SEQUENCE: 390
DASTRAA                                                              7

SEQ ID NO: 391         moltype = AA  length = 10
FEATURE                Location/Qualifiers
source                 1..10
                       mol_type = protein
                       organism = Synthetic construct
SEQUENCE: 391
QQYYDWPPLS                                                          10

SEQ ID NO: 392         moltype = DNA  length = 363
FEATURE                Location/Qualifiers
source                 1..363
                       mol_type = other DNA
                       organism = Synthetic construct
SEQUENCE: 392
caggttcagc tggttcagtc tggcagcgag ctgaagaaac ctggcgcctc tgtgaaggtg    60
tcctgcaagg cctctggcta cagcctgtac ggcacctcta tgcactgggt ccgacaggct   120
ccaggacagg gacttgagtg gatgggctac atcagcccct ttaccggcag agccacatac   180
gcccagggct tcacaggcag attcgtgttc agcctggaca ccagcgtgtc cacagcctac   240
ctgcagatca gctctctgaa ggccgaggac accgccgtgt actactgcgc cagagactac   300
gactaccggt actactatgc catggactac tggggccagg caccacagt tacagtgtcc   360
tca                                                                363

SEQ ID NO: 393         moltype = DNA  length = 324
FEATURE                Location/Qualifiers
source                 1..324
```

```
                                mol_type = other DNA
                                organism = Synthetic construct
SEQUENCE: 393
gaaattgtgc tgacacagag ccccgacttc cagagcgtga cccctaaaga aaaagtgacc    60
atcacctgta ccgccagcga gtccgtgcct cctcagttcc tgcattggta tcagcagaag   120
cccgatcaga gccccaagct gctgatctac gccagcagag aaagagccag cggcgtccca   180
agcagatttt ctggctctgg cagcggcacc gacttcaccc tgacaatcaa tagcctggaa   240
gccgaggacg ccgccaccta ctactgccac cagtttcaca gaagccctct gacctttggc   300
ggaggcacca agctggaaat caag                                          324

SEQ ID NO: 394           moltype = AA  length = 121
FEATURE                  Location/Qualifiers
source                   1..121
                         mol_type = protein
                         organism = Synthetic construct
SEQUENCE: 394
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS   120
S                                                                  121

SEQ ID NO: 395           moltype = AA  length = 108
FEATURE                  Location/Qualifiers
source                   1..108
                         mol_type = protein
                         organism = Synthetic construct
SEQUENCE: 395
EIVLTQSPDF QSVTPKEKVT ITCTASESVP PQFLHWYQQK PDQSPKLLIY ASRERASGVP    60
SRFSGSGSGT DFTLTINSLE AEDAATYYCH QFHRSPLTFG GGTKLEIK               108

SEQ ID NO: 396           moltype = AA  length = 10
FEATURE                  Location/Qualifiers
source                   1..10
                         mol_type = protein
                         organism = Synthetic construct
SEQUENCE: 396
GYSLYGTSMH                                                          10

SEQ ID NO: 397           moltype = AA  length = 17
FEATURE                  Location/Qualifiers
source                   1..17
                         mol_type = protein
                         organism = Synthetic construct
SEQUENCE: 397
YISPFTGRAT YAQGFTG                                                  17

SEQ ID NO: 398           moltype = AA  length = 12
FEATURE                  Location/Qualifiers
source                   1..12
                         mol_type = protein
                         organism = Synthetic construct
SEQUENCE: 398
DYDYRYYYAM DY                                                       12

SEQ ID NO: 399           moltype = AA  length = 12
FEATURE                  Location/Qualifiers
source                   1..12
                         mol_type = protein
                         organism = Synthetic construct
SEQUENCE: 399
TASESVPPQF LH                                                       12

SEQ ID NO: 400           moltype = AA  length = 7
FEATURE                  Location/Qualifiers
source                   1..7
                         mol_type = protein
                         organism = Synthetic construct
SEQUENCE: 400
ASRERAS                                                              7

SEQ ID NO: 401           moltype = AA  length = 9
FEATURE                  Location/Qualifiers
source                   1..9
                         mol_type = protein
                         organism = Synthetic construct
SEQUENCE: 401
HQFHRSPLT                                                            9

SEQ ID NO: 402           moltype = DNA  length = 345
FEATURE                  Location/Qualifiers
```

```
source                  1..345
                        mol_type = other DNA
                        organism = Synthetic construct
SEQUENCE: 402
gacgtgcagc tggtggaaag cggcggaggc ctggtccagc ccggcggctc tctgagactg    60
agctgcgccg ccagcggctt caccttcgac atcagcgcca tgagctgggt gcggcaggcc   120
cctggcaagg gcctgaatg ggtcagcaca atcagcggat ctgcctacag cacctactac   180
gccgacagcg tgaagggcag attcaccatc tcaagagata cagcaagag caccctgtac   240
ctgcagatga cagcctgcg ggccgaggac accgccgtgt actactgcgc cagagagatc   300
ttcagcgact actggggctt gggcaccctg gtgacagtgt cctca                    345

SEQ ID NO: 403          moltype = DNA   length = 330
FEATURE                 Location/Qualifiers
source                  1..330
                        mol_type = other DNA
                        organism = Synthetic construct
SEQUENCE: 403
caaagcgtgc tgacacagcc ccccagcgct ctggcaccc ctggccagag agtgaccatc    60
tcatgcagcg ggtcaacaag caacatcggc agagagagcg tgtactggta ccagcagctg   120
cctggaaccg cccctaagct gctgatctac agcaacgtgc agcggcctag cggcgcccct   180
aacagattca gcggcagcaa gagcggcacc agcgccagcc tggccatcag cggcctgcag   240
agcgaggacg aggccgacta ctactgcggc acatgggacg acagcctgaa cggctgggtg   300
ttcggcggcg gaactaagct gaccgtccta                                    330

SEQ ID NO: 404          moltype = AA    length = 115
FEATURE                 Location/Qualifiers
source                  1..115
                        mol_type = protein
                        organism = Synthetic construct
SEQUENCE: 404
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSS        115

SEQ ID NO: 405          moltype = AA    length = 110
FEATURE                 Location/Qualifiers
source                  1..110
                        mol_type = protein
                        organism = Synthetic construct
SEQUENCE: 405
QSVLTQPPSA SGTPGQRVTI SCSGSTSNIG RESVYWYQQL PGTAPKLLIY SNVQRPSGAP    60
NRFSGSKSGT SASLAISGLQ SEDEADYYCG TWDDSLNGWV FGGGTKLTVL              110

SEQ ID NO: 406          moltype = AA    length = 10
FEATURE                 Location/Qualifiers
source                  1..10
                        mol_type = protein
                        organism = Synthetic construct
SEQUENCE: 406
GFTFDISAMS                                                           10

SEQ ID NO: 407          moltype = AA    length = 17
FEATURE                 Location/Qualifiers
source                  1..17
                        mol_type = protein
                        organism = Synthetic construct
SEQUENCE: 407
TISGSAYSTY YADSVKG                                                   17

SEQ ID NO: 408          moltype = AA    length = 6
FEATURE                 Location/Qualifiers
source                  1..6
                        mol_type = protein
                        organism = Synthetic construct
SEQUENCE: 408
EIFSDY                                                                6

SEQ ID NO: 409          moltype = AA    length = 13
FEATURE                 Location/Qualifiers
source                  1..13
                        mol_type = protein
                        organism = Synthetic construct
SEQUENCE: 409
SGSTSNIGRE SVY                                                       13

SEQ ID NO: 410          moltype = AA    length = 7
FEATURE                 Location/Qualifiers
source                  1..7
                        mol_type = protein
                        organism = Synthetic construct
```

-continued

```
SEQUENCE: 410
SNVQRPS                                                                   7

SEQ ID NO: 411          moltype = AA   length = 11
FEATURE                 Location/Qualifiers
source                  1..11
                        mol_type = protein
                        organism = Synthetic construct
SEQUENCE: 411
GTWDDSLNGW V                                                             11

SEQ ID NO: 412          moltype = DNA  length = 1755
FEATURE                 Location/Qualifiers
source                  1..1755
                        mol_type = other DNA
                        organism = Synthetic construct
SEQUENCE: 412
gaggtgcagc tgctggaaag cggcggcggc ctcgtgcagc ctggcggatc tctgcgcctg    60
agctgtgctg ccagcggctt cacatttaaa tcctacgcca tgcactgggt tagacaagcc   120
cccgaaagg gcctggaatg ggtgtccgcc atcgtctaca gcggcggatc tacatactac   180
gccgacagct gaaggggccg gttcaccatc agcagagata tagcaagaa caccctgtac   240
ctgcagatga acagcctgag agccgaggac accgccgtct actactgcgc caagtacgac   300
agagcttctt atttctacga tgccatggac gtgtggggcc agggcaccac cgtgacagtg   360
tcctcagcta gcaccaaggg ccctagcgtg tttccactgg ccctagctc taaaagcaca   420
agcggcggaa ccgccgctct gggttgtctg gtgaaggact acttccctga gcctgtgacc   480
gtcagctgga acagcggcgc cctgaccagc ggcgttcaca cattcccgc tgtgctgcag   540
agctctgggc tgtacagcct gagcagcgtg gtgaccgtgc cttcttcttc tctgggcaca   600
caaacataca tctgcaacgt gaaccacaag cccagtaata ccaaagtgga taagaaggtg   660
gaacctaagt cttgcgacaa gacccacacc tgtcctccgt gccctgctcc tgaactggct   720
ggagctccca gcgtgttcct gttcccccc aaacctaagg acaccctgat gatcagccgg   780
acccctgagg tgacctgcgt ggtcgtcgac gtgtcccacg aagatcctga ggtgaagttc   840
aactggtacg tggacggcgt ggaagtgcat aatgccaaga caaagccag agaggaacag   900
tacaacagca cctatagagt ggtgtccgtg ctgacagtgc tgcaccagga ctggctgaac   960
ggcaaggaat acaagtgcaa ggtgtccaac aaggcctcc gcccctat cgagaagacc    1020
atcagcaagg caaagggcca acctagagag ccccaggtgt acaccctgcc tccaagcaga  1080
gatgagctga ccaagaacca ggttagcctg acttgtctgg tgaaggctt ctaccctcc    1140
gatatcgccg tggaatggga gagcaacggc cagcctgaga caactacaa gaccacacct  1200
ccagtgctgg acagcgacgg cagcttcttc tgtatagca agctgacagt ggacaagagc  1260
agatgcagc agggcaacgt gttcagctgc agcgtcatgc acgaggccct gcacaaccac  1320
tacacccaga gtctctgag cctgagccct ggaaaggccc ctgcttcag cagcaccaag   1380
aagacccag tgcagctgga acacctgctg ctggccctgc agatgatcct gaacggcatc  1440
aacaactaca agaaccccaa gctgaccgag atgctgacat ttaagttcta catgcctaag  1500
aaagccaccg agctgaagca cctgcaatgt ctggaagaag agctgaaacc tctggaagag  1560
gtgctgaatc tggctcagtc aaagaacttc cacttagac ctagagatct gatcagcaac   1620
atcaacgtga tcgtgctgga actgaagggc agcgagacga ccttcatgtg cgagtacgcc  1680
gacgagacag ccacaatcgt ggagttcctg aacagatgga tcaccttcgc ccagagcatc  1740
atctccaccc tgacc                                                  1755

SEQ ID NO: 413          moltype = DNA  length = 648
FEATURE                 Location/Qualifiers
source                  1..648
                        mol_type = other DNA
                        organism = Synthetic construct
SEQUENCE: 413
gagatcgtgc tgacccagtc cccaggcaca ctgagcctga gcccggcga gcggggccacc   60
ctgagctgta gagctagcca gagcatctcc agcagcttcc tggcctggta ccagcagaaa  120
cctggccagg cccctagact gctgatctac acgcctctg atagagctac aggcatcccc  180
gaccggttca gcggcagcgg atctggcacc gacttcaccc tgaccatcag cagactcgag  240
cctgaagatt tcgccatgta ctactgccag caatactatg actggcctcc tctgtctttt  300
ggcggcggaa caaggtgga aattaagcgt acggtggcgg cgccagcgt gttcatcttc  360
ccaccagcg acgagcagct gaagtccggc acagcagcg tggtgtgcct gctgaacaac  420
ttctaccccc gcgaggccaa ggtgcagtgg aaggtggaca cgccctgca gagcggcaac  480
agccaggaaa gcgtgaccga gcaggacagc aaggactcca cctacagcct gagcagcacc  540
ctgacctga caaggccga ctacgagaag cacaaggtgt acgcctgcga agtgacccac  600
cagggcctgt ccagccccgt gaccaagagc ttcaaccggg gcgagtgc                648

SEQ ID NO: 414          moltype = AA   length = 451
FEATURE                 Location/Qualifiers
source                  1..451
                        mol_type = protein
                        organism = Synthetic construct
SEQUENCE: 414
EVQLLESGGG LVQPGGSLRL SCAASGFTFK SYAMHWVRQA PGKGLEWVSA IVYSGGSTYY    60
ADSVKGRFTI SRDNSKNTLY LQMNSLRAED TAVYYCAKYD RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELA   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
```

```
RWQQGNVFSC SVMHEALHNH YTQKSLSLSP G                              451

SEQ ID NO: 415          moltype = AA   length = 216
FEATURE                 Location/Qualifiers
source                  1..216
                        mol_type = protein
                        organism = Synthetic construct
SEQUENCE: 415
EIVLTQSPGT LSLSPGERAT LSCRASQSIS SSFLAWYQQK PGQAPRLLIY DASDRATGIP   60
DRFSGSGSGT DFTLTISRLE PEDFAVYYCQ QYYDWPPLSF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                           216

SEQ ID NO: 416          moltype = AA   length = 122
FEATURE                 Location/Qualifiers
source                  1..122
                        mol_type = protein
                        organism = Synthetic construct
SEQUENCE: 416
EVQLLESGGG LVQPGGSLRL SCAASGFTFK SYAMHWVRQA PGKGLEWVSA IVYSGGSTYY   60
ADSVKGRFTI SRDNSKNTLY LQMNSLRAED TAVYYCAKYD RASYFYDAMD VWGQGTTVTV  120
SS                                                                122

SEQ ID NO: 417          moltype = AA   length = 109
FEATURE                 Location/Qualifiers
source                  1..109
                        mol_type = protein
                        organism = Synthetic construct
SEQUENCE: 417
EIVLTQSPGT LSLSPGERAT LSCRASQSIS SSFLAWYQQK PGQAPRLLIY DASDRATGIP   60
DRFSGSGSGT DFTLTISRLE PEDFAVYYCQ QYYDWPPLSF GGGTKVEIK             109

SEQ ID NO: 418          moltype = AA   length = 10
FEATURE                 Location/Qualifiers
source                  1..10
                        mol_type = protein
                        organism = Synthetic construct
SEQUENCE: 418
GFTFKSYAMH                                                         10

SEQ ID NO: 419          moltype = AA   length = 17
FEATURE                 Location/Qualifiers
source                  1..17
                        mol_type = protein
                        organism = Synthetic construct
SEQUENCE: 419
AIVYSGGSTY YADSVKG                                                 17

SEQ ID NO: 420          moltype = AA   length = 13
FEATURE                 Location/Qualifiers
source                  1..13
                        mol_type = protein
                        organism = Synthetic construct
SEQUENCE: 420
YDRASYFYDA MDV                                                     13

SEQ ID NO: 421          moltype = AA   length = 12
FEATURE                 Location/Qualifiers
source                  1..12
                        mol_type = protein
                        organism = Synthetic construct
SEQUENCE: 421
RASQSISSSF LA                                                      12

SEQ ID NO: 422          moltype = AA   length = 7
FEATURE                 Location/Qualifiers
source                  1..7
                        mol_type = protein
                        organism = Synthetic construct
SEQUENCE: 422
DASDRAT                                                             7

SEQ ID NO: 423          moltype = AA   length = 10
FEATURE                 Location/Qualifiers
source                  1..10
                        mol_type = protein
                        organism = Synthetic construct
SEQUENCE: 423
QQYYDWPPLS                                                         10
```

```
SEQ ID NO: 424          moltype = AA  length = 448
FEATURE                 Location/Qualifiers
source                  1..448
                        mol_type = protein
                        organism = Synthetic construct
SEQUENCE: 424
EVQLLESGGG LVQPGGSLRL SCAASGFTFK DYCMTWVRQA PGKGLEWVSA IVYSGGSTYY    60
ADSVKGRFTI SRDNSKNTLY LQMNNLRAED TAVYYCAKYT RASYFYDAMD VWGQGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLG                                     448

SEQ ID NO: 425          moltype = AA  length = 216
FEATURE                 Location/Qualifiers
source                  1..216
                        mol_type = protein
                        organism = Synthetic construct
SEQUENCE: 425
EIVLTQSPGT LSLSPGERAT LSCRASQSIG KSFLAWYQQK PGQAPRLLIY DASTRAADIP    60
ARFSGSGSGT DFTLTISSLE PEDFAVYYCQ QYYDWPPLSF GGGTKVEIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                            216

SEQ ID NO: 426          moltype = AA  length = 447
FEATURE                 Location/Qualifiers
source                  1..447
                        mol_type = protein
                        organism = Synthetic construct
SEQUENCE: 426
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLG                                      447

SEQ ID NO: 427          moltype = AA  length = 215
FEATURE                 Location/Qualifiers
source                  1..215
                        mol_type = protein
                        organism = Synthetic construct
SEQUENCE: 427
EIVLTQSPDF QSVTPKEKVT ITCTASESVP PQFLHWYQQK PDQSPKLLIY ASRERASGVP    60
SRFSGSGSGT DFTLTINSLE AEDAATYYCH QFHRSPLTFG GGTKLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 428          moltype = AA  length = 441
FEATURE                 Location/Qualifiers
source                  1..441
                        mol_type = protein
                        organism = Synthetic construct
SEQUENCE: 428
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL G                                            441

SEQ ID NO: 429          moltype = AA  length = 216
FEATURE                 Location/Qualifiers
source                  1..216
                        mol_type = protein
                        organism = Synthetic construct
SEQUENCE: 429
QSVLTQPPSA SGTPGQRVTI SCSGSTSNIG RESVYWYQQL PGTAPKLLIY SNVQRPSGAP    60
NRFSGSKSGT SASLAISGLQ SEDEADYYCG TWDDSLNGWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216
```

| SEQ ID NO: 430 | moltype = AA length = 582 |
| --- | --- |
| FEATURE | Location/Qualifiers |
| source | 1..582 |
| | mol_type = protein |
| | organism = Synthetic construct |

SEQUENCE: 430

```
EVQLLESGGG LVQPGGSLRL SCAASGFTFK DYCMTWVRQA PGKGLEWVSA IVYSGGSTYY    60
ADSVKGRFTI SRDNSKNTLY LQMNNLRAED TAVYYCAKYT RASYFYDAMD VWGQGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLGKA PTSSSTKKTQ LQLEHLLLAL QMILNGINNY   480
KNPKLTEMLT FKFYMPKKAT ELKHLQCLEE ELKPLEEVLN LAQSKNFHLR PRDLISNINV   540
IVLELKGSET TFMCEYADET ATIVEFLNRW ITFCQSIIST LT                      582
```

| SEQ ID NO: 431 | moltype = AA length = 585 |
| --- | --- |
| FEATURE | Location/Qualifiers |
| source | 1..585 |
| | mol_type = protein |
| | organism = Synthetic construct |

SEQUENCE: 431

```
EVQLLESGGG LVQPGGSLRL SCAASGFTFK SYAMHWVRQA PGKGLEWVSA IVYSGGSTYY    60
ADSVKGRFTI SRDNSKNTLY LQMNSLRAED TAVYYCAKYD RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELA   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEHLL LDLQMILNGI   480
NNYKNPKLTR MLTFKFYMPK KATELKHLQC LEEEELKPLEE VLNLAQSKNF HLRPRDLISN   540
INVIVLELKG SETTFMCEYA DETATIVEFL NRWITFAQSI ISTLT                   585
```

| SEQ ID NO: 432 | moltype = AA length = 587 |
| --- | --- |
| FEATURE | Location/Qualifiers |
| source | 1..587 |
| | mol_type = protein |
| | organism = Synthetic construct |

SEQUENCE: 432

```
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGKSG GGGSAPTSSS TKKTQLQLEH LLLALQMILN   480
GINNYKNPKL TEMLTFKFYM PKKATELKHL QCLEEELKPL EEVLNLAQSK NFHLRPRDLI   540
SNINVIVLEL KGSETTFMCE YADETATIVE FLNRWITFCQ SIISTLT                 587
```

| SEQ ID NO: 433 | moltype = AA length = 575 |
| --- | --- |
| FEATURE | Location/Qualifiers |
| source | 1..575 |
| | mol_type = protein |
| | organism = Synthetic construct |

SEQUENCE: 433

```
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL GKAPTSSSTK KTQLQLEHLL LALQMILNGI NNYKNPKLTE   480
MLTFKFYMPK KATELKHLQC LEEELKPLEE VLNLAQSKNF HLRPRDLISN INVIVLELKG   540
SETTFMCEYA DETATIVEFL NRWITFCQSI ISTLT                              575
```

| SEQ ID NO: 434 | moltype = AA length = 577 |
| --- | --- |
| FEATURE | Location/Qualifiers |
| source | 1..577 |
| | mol_type = protein |
| | organism = Synthetic construct |

SEQUENCE: 434

```
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTSSAST    120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
```

```
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKAPTSSS TKKTQLQLEH LLLALQMILN GINNYKNPKL    480
TEMLTFKFYM PKKATELKHL QCLEEELKPL EEVLNLAQSK NFHLRPRDLI SNINVIVLEL    540
KGSETTFMCE YADETATIVE FLNRWITFCQ SIISTLT                             577

SEQ ID NO: 435          moltype = AA   length = 582
FEATURE                 Location/Qualifiers
source                  1..582
                        mol_type = protein
                        organism = Synthetic construct
SEQUENCE: 435
EVQLLESGGG LVQPGGSLRL SCAASGFTFK DYCMTWVRQA PGKGLEWVSA IVYSGGSTYY    60
ADSVKGRFTI SRDNSKNTLY LQMNNLRAED TAVYYCAKYT RASYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PASSSTKKTQ LQLEHLLLAL QMILNGINNY    480
KNPKLTEMLT FKFYMPKKAT ELKHLQCLEE ELKPLEEVLN LAQSKNFHLR PRDLISNINV    540
IVLELKGSET TFMCEYADET ATIVEFLNRW ITFAQSIIST LT                       582

SEQ ID NO: 436          moltype = DNA   length = 441
FEATURE                 Location/Qualifiers
source                  1..441
                        mol_type = other DNA
                        organism = Synthetic construct
SEQUENCE: 436
ccaggatggt tcttagactc cccagacagg ccctggaacc cccccacctt ctccccagcc    60
ctgctcgtgg tgaccgaagg ggacaacgcc accttcacct gcagcttctc caacacatcg    120
gagagcttcg tgctaaactg gtaccgcatg agcccagca accagacgga caagctggcc     180
gccttccccg aggaccgcag ccagcccggc caggactgcc gcttccgtgt cacacaactg    240
cccaacgggc gtgacttcca catgagcgtg gtcagggccc ggcgcaatga cagcggcacc    300
tacctctgtg gggccatctc cctggccccc aaggcgcaga tcaaagagag cctgcgggca    360
gagctcaggg tgacagagag aagggcagaa gtgcccacag cccaccccag cccctcaccc    420
aggccagccg gccagttcca a                                              441

SEQ ID NO: 437          moltype = AA   length = 147
FEATURE                 Location/Qualifiers
source                  1..147
                        mol_type = protein
                        organism = Synthetic construct
SEQUENCE: 437
PGWFLDSPDR PWNPPTFSPA LLVVTEGDNA TFTCSFSNTS ESFVLNWYRM SPSNQTDKLA    60
AFPEDRSQPG QDCRFRVTQL PNGRDFHMSV VRARRNDSGT YLCGAISLAP KAQIKESLRA    120
ELRVTERRAE VPTAHPSPSP RPAGQFQ                                        147

SEQ ID NO: 438          moltype = AA   length = 448
FEATURE                 Location/Qualifiers
source                  1..448
                        mol_type = protein
                        organism = Synthetic construct
SEQUENCE: 438
EVQLLESGGG LVQPGGSLRL SCAASGFTFS SNYMSWVRQA PGKGLEWVSA ISSSGGTIFY    60
ADSVKGRFTI SRDNSKNTLY LQMNSLRAED TAVYYCAKHK WNAVYYDGMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                       448

SEQ ID NO: 439          moltype = AA   length = 216
FEATURE                 Location/Qualifiers
source                  1..216
                        mol_type = protein
                        organism = Synthetic construct
SEQUENCE: 439
QSVLTQPPSA SGTPGQRVTI SCSGSNSNIG RNLVNWYQQL PGTAPKLLIY TIDQRPSGVP    60
DRFSGSKSGT SASLVISGLQ SEDEADYYCA AWDGSLNAWV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                              216

SEQ ID NO: 440          moltype = AA   length = 445
FEATURE                 Location/Qualifiers
source                  1..445
                        mol_type = protein
                        organism = Synthetic construct
```

```
SEQUENCE: 440
EVQLLESGGG LVQPGGSLRL SCTASGFTFS SYEMQWVRQA PGKGLEWVLG ITSSSSHIFY    60
ADSVKGRFTV SRDNSKNTLY LQMNSLRAED TAVYYCTKDL NSYYGLDVWG QGTTVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFLGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                         445

SEQ ID NO: 441           moltype = AA  length = 216
FEATURE                  Location/Qualifiers
source                   1..216
                         mol_type = protein
                         organism = Synthetic construct
SEQUENCE: 441
QSVMTQPPSA SGTPGQRVTI SCSGSTSNLG NNYVSWYQHL PGTAPKLLIY GNDQRPSGVP    60
DRFSGSKSGT SASLAISGLQ SCDDEADYYCS SWDASLNVWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 442           moltype = AA  length = 448
FEATURE                  Location/Qualifiers
source                   1..448
                         mol_type = protein
                         organism = Synthetic construct
SEQUENCE: 442
EVQLLESGGG LVQPGGSLRL SCAASGFTFS DYYMSWVRQA PGKGLEWVSA ISSSGGTIFY    60
ADSVKGRFII SRDNSKNTLY LQMNSLRAED TAVYYCAKHK WNDVYYDAMD VWGQGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLG                                      448

SEQ ID NO: 443           moltype = AA  length = 216
FEATURE                  Location/Qualifiers
source                   1..216
                         mol_type = protein
                         organism = Synthetic construct
SEQUENCE: 443
QSVLTQPPSA SGTPGQRVTI SCSGSNSNIG RNLVNWYQQL PGTAPKLLIY TVDQRPSGVP    60
DRFSGSKSGT SASLAISGLA SEDEADYYCA AWDSSLNSWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 444           moltype = AA  length = 441
FEATURE                  Location/Qualifiers
source                   1..441
                         mol_type = protein
                         organism = Synthetic construct
SEQUENCE: 444
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL G                                             441

SEQ ID NO: 445           moltype = AA  length = 216
FEATURE                  Location/Qualifiers
source                   1..216
                         mol_type = protein
                         organism = Synthetic construct
SEQUENCE: 445
QSVLTQPPSA SGTPGQRVTI SCSGNTSNIG RESVYWYQQL PGTAPKLLIY SNVQRPSGVP    60
DRFSGSKSGT SASLAISGLQ SEDEADYYCG TWDDSLNGWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 446           moltype = AA  length = 440
FEATURE                  Location/Qualifiers
source                   1..440
                         mol_type = protein
                         organism = Synthetic construct
SEQUENCE: 446
```

```
DSLVESGGGL VQPGGSLRLS CAASGFTFDI SAMSWVRQAP GKGLEWVSTI SGSAYSTYYA    60
DSVKGRFTIS RDNSKSTLYL QMNSLRAEDT AVYYCAREIF SDYWGLGTLV TVSSASTKGP   120
SVFPLAPCSR STSESTAALG CLVKDYFPEP VTVSWNSGAL TSGVHTFPAV LQSSGLYSLS   180
SVVTVPSSSL GTKTYTCNVD HKPSNTKVDK RVESKYGPPC PPCPAPEFLG GPSVFLFPPK   240
PKDTLMISRT PEVTCVVVDV SQEDPEVQFN WYVDGVEVHN AKTKPREEQF NSTYRVVSVL   300
TVLHQDWLNG KEYKCKVSNK GLPSSIEKTI SKAKGQPREP QVYTLPPSQE EMTKNQVSLT   360
CLVKGFYPSD IAVEWESNGQ PENNYKTTPP VLDSDGSFFL YSRLTVDKSR WQEGNVFSCS   420
VMHEALHNHY TQKSLSLSLG                                              440

SEQ ID NO: 447          moltype = AA  length = 216
FEATURE                 Location/Qualifiers
source                  1..216
                        mol_type = protein
                        organism = Synthetic construct
SEQUENCE: 447
QSVLTQPPSA SGTPGQRVTI SCSGSTSNIG RESVYWYQQL PGTAPKLLIY LNSQRPSGVP    60
DRFSGSKSGT SASLAISGLQ SEDVADYYCG TWDDSLNGWV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                            216

SEQ ID NO: 448          moltype = DNA  length = 6765
FEATURE                 Location/Qualifiers
source                  1..6765
                        mol_type = other DNA
                        organism = Synthetic construct
SEQUENCE: 448
aacaaaatat taacgcttac aatttccatt cgccattcag gctgcgcaac tgttgggaag    60
ggcgatcggt gcgggcctct tcgctattac gccagctggc gaaaggggga tgtgctgcaa   120
ggcgattaag ttgggtaacg ccagggtttt cccagtcacg acgttgtaaa acgacggcca   180
gtgccaagct gatctataca ttgaatcaat attggcaatt agccatatta gtcattggtt   240
atatagcata aatcaatatt ggctattggc cattgcatac gttgtatcta tatcataata   300
tgtacattta tattggctca tgtccaatat gaccgccatg ttgacattga ttattgacta   360
gttattaata gtaatcaatt acggggtcat tagttcatag cccatatatg gagttccgcg   420
ttacataact tacggtaaat ggcccgcctg gctgaccgcc caacgacccc cgcccattga   480
cgtcaataat gacgtatgtt cccatagtaa cgccaatagg gactttccat tgacgtcaat   540
gggtggagta tttacggtaa actgcccact tggcagtaca tcaagtgtat catatgccaa   600
gtccgccccc tattgacgtc aatgacggta aatggcccgc ctggcattat gcccagtaca   660
tgaccttacg ggactttcct acttggcagt acatctacgt attagtcatc gctattacca   720
tggtgatgcg gttttggcag tacaccaatg ggcgtggata gcggtttgac tcacggggat   780
ttccaagtct ccaccccatt gacgtcaatg ggagtttgtt ttggcaccaa aatcaacggg   840
actttccaaa atgtcgtaat aaccccgccc cgttgacgca aatgggcggt aggcgtgtac   900
ggtgggaggt ctatataagc agagctcgtt tagtgaaccg tcagaatttt gtaatacgac   960
tcactatagg gcggccggga attcgtcgac tggatccggt accgaggaga tctgccgccg  1020
cgatcgccgg cgcgccagat ctcaagctta tggacatgcg ggtgccagca caacttctcg  1080
gattactatt gttatggctg cgaggtgcgc gctgttatcc ttacgactgt cctgactacg  1140
ccccaggatg gttcttagag tccccagaca ggccctggaa cgcccccacc ttctcccag  1200
ccctgctcct ggtgaccgaa ggggacaacg ccaccttcac ctgcagcgtc tccaacgcat  1260
cggagagctt cgtgctaaac tggtacagga tgagccccag caaccagacg gacaagctgg  1320
ccgccttccc cgaggaccgc agccagcccg ccaggactg ccgcttccgt gtcacacgcc  1380
tgcccaacgg gcgtgacttc cacatgagcg tggtcagggc ccggcgcaat gacagcggca  1440
cctacctctg tggggccatc tccctggccc ccaaggccga gatcaaagag agcctggtgg  1500
cagagctcag ggtgacagag agaagggcag aagtgcccac agcccacccc agcccctcac  1560
ccaggccagc cggccagttc caagccctgg tggttggtgt cgtgggcggc ctgctgggca  1620
gcctggtgct gctagtctgg gtcctggcg tcatctgctc ccgcgccgca caagggacaa  1680
tagaagccag gcgcacctga cgcgttaagc ggccgcactc gaggtttaaa cggccgccg  1740
cggtcatagc tgtttcctga acagatcccg ggtggcatcc ctgtgacccc tccccagtgc  1800
ctctcctggc cctggaagtt gccactccag tgcccaccag cctgtccta ataaaattaa  1860
gttgcatcat tttgtctgac taggtgtcct tctataatat tatgggtgg aggggggtgg  1920
tatggagcaa ggggcaagtt gggaagacaa cctgtagggc ctgcgggtc tattgggaac  1980
caagctggag tgcagtggca caatcttggc tcactgcaat ctccgcctcc tgggttcaag  2040
cgattctcct gcctcagcct cccgagttgt tgggattcca ggcatgcatg accaggctca  2100
gctaattttt gtttttttgg tagagacggg gtttcaccat attggccagg ctggtctcca  2160
actcctaatc tcaggtgatc tacccacctt ggcctcccaa attgctggga ttacaggcgt  2220
gaaccactgc tcccttccct gtccttctga ttttaaaata actataccag caggagacg  2280
tccagacaca gcataggcta cctgccatg cccaaccggt gggacatttg agttgcttgc  2340
ttggcactgt cctctcatgc gttgggtcca tcagtagat gctgttgaa ttgggtacgc  2400
ggccagcttg gctgtggaat gtgtgtcagt tagggtgtgg aaagtcccca ggctcccag  2460
caggcagaag tatgcaaagc atgcatctca attagtcagc aaccaggtgt ggaaagtccc  2520
caggctcccc agcaggcaga agtatgcaaa gcatgcatct caattagtca gcaaccatag  2580
tcccgcccct aactccgccc atcccgcccc taactccgcc cagttccgcc cattctccgc  2640
cccatgctg actaatttt tttatttatg cagaggccga ggcgcctcg gcctctgagc  2700
tattccagaa gtagtgagga ggcttttttg gaggcctagg cttttgcaaa aagctcccgg  2760
gagcttgtat atccattttc ggatctgatc aagagacacg tacgaccatg aaaaagcctg  2820
aactcaccgc gacgtcgtt gatgccgggc aagagcaact cggtcgccgc atgtccggc  2880
tgatgcagct ctcggagggc gaagaatctc gtgctttcag cttcgatgta ggagggcgtg  2940
gatatgtcct gcgggtaaat agctgcgccg atggtttcta caaagatcgt tatgtttatc  3000
ggcactttgc atcggccgcg ctcccgattc cggaagtgct tgacattggg gaatttagcg  3060
agagcctgac ctattgcatc tcccgccgtg cacagggtgt cacgttgcaa gacctgcctg  3120
aaaccgaact gcccgctgtt ctgcaaccgg tcgcggaggc catggatgca atcgctgcgg  3180
```

```
ccgatcttag ccagacgagc gggttcggcc cattcggacc gcaaggaatc ggtcaataca    3240
ctacatggcg tgatttcata tgcgcgattg ctgatcccca tgtgtatcac tggcaaactg    3300
tgatggacga caccgtcagt gcgtccgtcg cgcaggctct cgatgagctg atgctttggg    3360
ccgaggactg ccccgaagtc cggcacctcg tgcacgcgga tttcggctcc aacaatgtcc    3420
tgacggacaa tggccgcata acagcggtca ttgactggac cgaggcgatg ttcggggatt    3480
cccaatacga ggtcgccaac atcttcttct ggaggccgtg gttggcttgt atggagcagc    3540
agacgcgcta cttcgagcgg aggcatccgg agcttgcagg atcgccgcgg ctccgggcgt    3600
atatgctccg cattggtctt gaccaactct atcagagctt ggttgacggc aatttcgatg    3660
atgcagcttg ggcgcagggt cgatgcgacg caatcgtccg atccggagcc gggactgtcg    3720
ggcgtacaca aatcgcccgc agaagcgcgg ccgtctggac cgatggctgt gtagaagtac    3780
tcgccgatag tggaaaccga cgccccagca ctcgtccgag ggcaaaggaa tagctgcagc    3840
gggactctgg ggttcgaaat gaccgaccaa gcgacgccca acctgccatc acgagatttc    3900
gattccaccg ccgccttcta tgaaaggttg ggcttcggaa tcgttttccg ggacgccggc    3960
tggatgatcc tccagcgcgg ggatctcatg ctggagtttct tcgcccaccc caacttgttt    4020
attgcagctt ataatggtta caaataaagc aatagcatca caaatttcac aaataaagca    4080
ttttttttcac tgcattctag ttgtggtttg tccaaactca tcaatgtatc ttatcatgtc    4140
tgtataccgt cgacctctag ctagagcttg gcgtaatcat ggtcatagct gtttcctgtg    4200
tgaaattgtt atccgctcac aattccacac aacatacgag ccggaagcat aaagtgtaaa    4260
gcctggggtg cctaatgagt gagctaactc acattaattg cgttgcgctc actgcccgct    4320
ttccagtcgg gaaacctgtc gtgccagctg cattaatgaa tcggccaacg cgcgggggaga    4380
gcggtttgc gtattgggcg ctcttccgct tcctcgctca ctgactcgct gcgctcggtc    4440
gttcggctgc ggcgagcggt atcagctcac tcaaaggcgg taatacggtt atccacagaa    4500
tcaggggata acgcaggaaa gaacatgtga gcaaaaggcc agcaaaaggc caggaaccgt    4560
aaaaaggccg cgttgctggc gttttttcccat aggctccgcc ccctgacga gcatcacaaa    4620
aatcgacgct caagtcagag gtggcgaaac ccgacaggac tataaagata ccaggcgttt    4680
cccctggaa gctccctcgt gcgctctcct gttccgaccc tgccgcttac cggatacctg    4740
tccgccttc tcccttcggg aagcgtggcg ctttctcata gctcacgctg taggtatctc    4800
agttcggtgt aggtcgttcg ctccaagctg ggctgtgtgc acgaaccccc cgttcagccc    4860
gaccgctgcg ccttatccgg taactatcgt cttgagtcca acccgtgtaag acacgactta    4920
tcgccactgg cagcagccac tggtaacagg attagcagag cgaggtatgt aggcggtgct    4980
acagagttct tgaagtggtg gcctaactac ggctacacta agaacagt atttggtatc    5040
tgcgctctgc tgaagccagt taccttcgga aaaagagttg gtagctctg atccggcaaa    5100
caaaccaccg ctggtagcgg tggttttttt gtttgcaagc agcagattac gcgcagaaaa    5160
aaaggatctc aagaagatcc tttgatcttt tctacgggt ctgacgctca gtggaacgaa    5220
aactcacgtt aagggatttt ggtcatgaga ttatcaaaaa ggatcttcac ctagatcctt    5280
ttaaattaaa aatgaagttt taaatcaatc taaagtatat atgagtaaac ttggtctgac    5340
agttaccaat gcttaatcag tgaggcacct atctcagcga tctgtctatt tcgttcatcc    5400
atagttgcct gactccccgt cgtgtagata actacgatag gggaggggctt accatctggc    5460
cccagtgctg caatgatacc gcgagaccca cgctcaccgg ctccagattt atcagcaata    5520
aaccagccag ccggaagggc cgagcgcaga agtggtcctg caactttatc cgcctccatc    5580
cagtctatta attgttgccg ggaagctaga gtaagtagtt cgccagttaa tagtttgcgc    5640
aacgttgttg ccattgctac aggcatcgtg gtgtcacgct cgtcgtttgg tatggcttca    5700
ttcagctccg gttcccaacg atcaaggcga gttacatgat ccccccatgtt gtgcaaaaaa    5760
gcggttagct ccttcggtcc tccgatcgtt gtcagaagta agttggccgc agtgttatca    5820
ctcatggtta tggcagcact gcataattct cttactgtca tgccatccgt aagatgcttt    5880
tctgtgactg gtgagtactc aaccaagtca ttctgagaat agtgtatgcg gcgaccgagt    5940
tgctcttgcc cggcgtcaat acgggataat accgcgccac atagcagaac tttaaaagtg    6000
ctcatcattg gaaaacgttc ttcggggcga aaactctcaa ggatcttacc gctgttgaga    6060
tccagttcga tgtaacccac tcgtgcaccc aactgatctt cagcatcttt tactttcacc    6120
agcgtttctg ggtgagcaaa aacaggaagg caaaatgccg caaaaaaggg aataagggcg    6180
acacgaaat gttgaatact catactcttc ctttttcaat attattgaag catttatcag    6240
ggttattgtc tcatgagcgg atacatattt gaatgtattt agaaaaataa acaaataggg    6300
gttccgcgca catttccccg aaaagtgcca cctgacgcgc cctgtagcgg cgcattaagc    6360
gcggcgggtg tggtggttac gcgcagcgtg accgctacac ttgccagcgc cctagcgccc    6420
gctcctttcg ctttcttccc ttcctttctc gccacgttcg ccggctttcc ccgtcaagct    6480
ctaaatcggg ggctcccttt agggttccga tttagtgctt tacggcacct cgaccccaaa    6540
aaacttgatt agggtgatgg ttcacgtagt gggccatcgc cctgatagac ggttttttcgc    6600
cctttgacgt tggagtccac gttctttaat agtggactct tgttccaaac tggaacaaca    6660
ctcaacccta tctcggtcta ttcttttgat ttataaggga ttttgccgat ttcggcctat    6720
tggttaaaaa atgagctgat ttaacaaaaa tttaacgcga atttt               6765
```

SEQ ID NO: 449         moltype = AA  length = 447
FEATURE                Location/Qualifiers
source                 1..447
                       mol_type = protein
                       organism = Synthetic construct
SEQUENCE: 449
QVQLVQSGSE LKKPGASVKV SCKASGYTFT SYAMHWVRQA PGQGLEWMGY ISPFTGRATY    60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLG                                       447

SEQ ID NO: 450         moltype = AA  length = 215
FEATURE                Location/Qualifiers
source                 1..215

```
                        mol_type = protein
                        organism = Synthetic construct
SEQUENCE: 450
EIVLTQSPDF QSVTPKEKVT ITCRASQSIP PQFLHWYQQK PDQSPKLLIK AASQRASGVP   60
SRFSGSGSGT DFTLTINSLE AEDAATYYCH QFHSSPLTFG GGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 451          moltype = AA  length = 579
FEATURE                 Location/Qualifiers
source                  1..579
                        mol_type = protein
                        organism = Synthetic construct
SEQUENCE: 451
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK SGGGGSAPTS SSTKKTQLQL EHLLLALQMI LNGINNYKNP  480
KLTEMLTFKF YMPKKATELK HLQCLEEELK PLEEVLNLAQ SKNFHLRPRD LISNINVIVL  540
ELKGSETTFM CEYADETATI VEFLNRWITF CQSIISTLT                         579

SEQ ID NO: 452          moltype = AA  length = 214
FEATURE                 Location/Qualifiers
source                  1..214
                        mol_type = protein
                        organism = Synthetic construct
SEQUENCE: 452
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 453          moltype = AA  length = 588
FEATURE                 Location/Qualifiers
source                  1..588
                        mol_type = protein
                        organism = Synthetic construct
SEQUENCE: 453
EVQLLESGGG LVQPGGSLRL SCAASGFTFS SNYMSWVRQA PGKGLEWVSA ISSSGGTIFY   60
ADSVKGRFTI SRDNSKNTLY LQMNSLRAED TAVYYCAKHK WNAVYYDGMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKS GGGGSAPTSS STKKTQLQLE HLLLALQMIL  480
NGINNYKNPK LTEMLTFKFY MPKKATELKH LQCLEEELKP LEEVLNLAQS KNFHLRPRDL  540
ISNINVIVLE LKGSETTFMC EYADETATIV EFLNRWITFC QSIISTLT               588

SEQ ID NO: 454          moltype = AA  length = 585
FEATURE                 Location/Qualifiers
source                  1..585
                        mol_type = protein
                        organism = Synthetic construct
SEQUENCE: 454
EVQLLESGGG LVQPGGSLRL SCTASGFTFS SYEMQWVRQA PGKGLEWVLG ITSSSSHIFY   60
ADSVKGRFTV SRDNSKNTLY LQMNSLRAED TAVYYCTKDL NSYYGLDVWG QGTTVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGKSGGG GSAPTSSSTK KTQLQLEHLL LALQMILNGI  480
NNYKNPKLTE MLTFKYMPK KATELKHLQC LEEELKPLEE VLNLAQSKNF HLRPRDLISN  540
INVIVLELKG SETTFMCEYA DETATIVEFL NRWITFCQSI ISTLT                  585

SEQ ID NO: 455          moltype = AA  length = 588
FEATURE                 Location/Qualifiers
source                  1..588
                        mol_type = protein
                        organism = Synthetic construct
SEQUENCE: 455
EVQLLESGGG LVQPGGSLRL SCAASGFTFS DYYMSWVRQA PGKGLEWVSA ISSSGGTIFY   60
ADSVKGRFII SRDNSKNTLY LQMNSLRAED TAVYYCAKHK WNDVYYDMD VWGQGTTVTV  120
SSASTKGPSV FPLAPCSRST SESTAALGCL VKDYFPEPVT VSWNSGALTS GVHTFPAVLQ  180
```

```
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKS GGGGSAPTSS STKKTQLQLE HLLLALQMIL    480
NGINNYKNPK LTEMLTFKFY MPKKATELKH LQCLEEELKP LEEVLNLAQS KNFHLRPRDL    540
ISNINIVLE LKGSETTFMC EYADETATIV EFLNRWITFC QSIISTLT                 588

SEQ ID NO: 456               moltype = AA  length = 575
FEATURE                      Location/Qualifiers
source                       1..575
                             mol_type = protein
                             organism = Synthetic construct
SEQUENCE: 456
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LALQMILNGI NNYKNPKLEM    480
MLTFKFYMPK KATELKHLQC LEEELKPLEE VLNLAQSKNF HLRPRDLISN INVIVLELKG    540
SETTFMCEYA DETATIVEFL NRWITFCQSI ISTLT                              575

SEQ ID NO: 457               moltype = AA  length = 574
FEATURE                      Location/Qualifiers
source                       1..574
                             mol_type = protein
                             organism = Synthetic construct
SEQUENCE: 457
DSLVESGGGL VQPGGSLRLS CAASGFTFDI SAMSWVRQAP GKGLEWVSTI SGSAYSTYYA    60
DSVKGRFTIS RDNSKSTLYL QMNSLRAEDT AVYYCAREIF SDYWGLGTLV TVSSASTKGP    120
SVFPLAPCSR STSESTAALG CLVKDYFPEP VTVSWNSGAL TSGVHTFPAV LQSSGLYSLS    180
SVVTVPSSSL GTKTYTCNVD HKPSNTKVDK RVESKYGPPC PPCPAPEFLG GPSVFLFPPK    240
PKDTLMISRT PEVTCVVVDV SQEDPEVQFN WYVDGVEVHN AKTKPREEQF NSTYRVVSVL    300
TVLHQDWLNG KEYKCKVSNK GLPSSIEKTI SKAKGQPREP QVYTLPPSQE EMTKNQVSLT    360
CLVKGFYPSD IAVEWESNGQ PENNYKTTPP VLDSDGSFFL YSRLTVDKSR WQEGNVFSCS    420
VMHEALHNHY TQKSLSLSLG KAPTSSSTKK TQLQLEHLLL ALQMILNGIN NYKNPKLTEM    480
LTFKFYMPKK ATELKHLQCL EEELKPLEEV LNLAQSKNFH LRPRDLISNI NVIVLELKGS    540
ETTFMCEYAD ETATIVEFLN RWITFCQSII STLT                               574

SEQ ID NO: 458               moltype = AA  length = 448
FEATURE                      Location/Qualifiers
source                       1..448
                             mol_type = protein
                             organism = Synthetic construct
SEQUENCE: 458
EVQLLESGGG LVQPGGSLRL SCAASGFTFK DYCMTWVRQA PGKGLEWVSA IVYSGGSTYY    60
ADSVKGRFTI SRDNSKNTLY LQMNNLRAED TAVYYCAKYT RASYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFEGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                      448

SEQ ID NO: 459               moltype = AA  length = 448
FEATURE                      Location/Qualifiers
source                       1..448
                             mol_type = protein
                             organism = Synthetic construct
SEQUENCE: 459
EVQLLESGGG LVQPGGSLRL SCAASGFTFK DYCMTWVRQA PGKGLEWVSA IVYSGGSTYY    60
ADSVKGRFTI SRDNSKNTLY LQMNNLRAED TAVYYCAKYT RASYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFAGAP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                      448

SEQ ID NO: 460               moltype = AA  length = 448
FEATURE                      Location/Qualifiers
source                       1..448
                             mol_type = protein
                             organism = Synthetic construct
SEQUENCE: 460
EVQLLESGGC LVQPGGSLRL SCAASGFTFS DYYMSWVRQA PGKGLEWVSA ISSSGGTIFY    60
```

```
ADSVKGRFII SRDNSKNTLY LQMNSLRAED TAVYYCAKHK WNDVYYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                      448

SEQ ID NO: 461           moltype = AA   length = 441
FEATURE                  Location/Qualifiers
source                   1..441
                         mol_type = protein
                         organism = Synthetic construct
SEQUENCE: 461
DMQLVESGGG VVRPGESLRL SCTASGFTFS ISAMSWVRQA PGKGLEWVSA ISGTAYSTYY     60
ADSVRGRFTI SRDNSKNTLY LQMNSLRAED TAVYYCAKDN FFDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                             441

SEQ ID NO: 462           moltype = AA   length = 216
FEATURE                  Location/Qualifiers
source                   1..216
                         mol_type = protein
                         organism = Synthetic construct
SEQUENCE: 462
QSVMTQPPSA SGTPGQRVTI SCSGVTSNIG SNSVYWYQQL PGTAPKLLIY LNSQRPSGVP     60
DRFSGSKSGT SASLAISGLQ SEDEADYYCG TWDDSLNGWV FGGGTKLTVL GQPKAAPSVT    120
LFPPSSEELQ ANKATLVCLI SDFYPGAVTV AWKADSSPVK AGVETTTPSK QSNNKYAASS    180
YLSLTPEQWK SHRSYSCQVT HEGSTVEKTV APTECS                             216

SEQ ID NO: 463           moltype = AA   length = 441
FEATURE                  Location/Qualifiers
source                   1..441
                         mol_type = protein
                         organism = Synthetic construct
SEQUENCE: 463
DVQLVESGGG VVRPGESLRL SCTASGFTFS ISAMSWVRQA PGKGLEWVSA ISGTAYSTYY     60
ADSVRGRFTI SRDNSKNTLY LQMNSLRAED TAVYYCAKDN FFDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                             441

SEQ ID NO: 464           moltype = AA   length = 441
FEATURE                  Location/Qualifiers
source                   1..441
                         mol_type = protein
                         organism = Synthetic construct
SEQUENCE: 464
DVQLVESGGG VVRPGGSLRL SCAASGFTFS IYAMSWVRQA PGEGLEWVSH ISASGGSTYY     60
ADSVKGRFAI SRDNSKNTLY LQMNSLRAED TAVYYCTTNL GSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                             441

SEQ ID NO: 465           moltype = AA   length = 441
FEATURE                  Location/Qualifiers
source                   1..441
                         mol_type = protein
                         organism = Synthetic construct
SEQUENCE: 465
DVQLVESGGG VVRPGGSLRL SCAASGFTFS IYAVSWVRQA PGEGLEWVSH ISASGGSTYY     60
ADSVKGRFAI SRDNSKNTLY LQMNSLRAED TAVYYCTTNL GSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                             441
```

```
SEQ ID NO: 466          moltype = AA   length = 216
FEATURE                 Location/Qualifiers
source                  1..216
                        mol_type = protein
                        organism = Synthetic construct
SEQUENCE: 466
QSVLTQPPSA SGTPGQRVTI SCSGSYSDIG TNYVYWYQQL PGTAPKLLIF ATDRRPSGVP   60
DRFSGSKSGT SASLAISGLQ SEDEADYYCG TWDDSLNVWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 467          moltype = AA   length = 443
FEATURE                 Location/Qualifiers
source                  1..443
                        mol_type = protein
                        organism = Synthetic construct
SEQUENCE: 467
DVQLVESGGG VVRPGESLRL SCAASGFTFS TDAMGWVRQA PGEGLEWVSL ISGSGYSTYY   60
ADSVKGRFTI SRDNSKNTLY LQMNSLTAED TAVYYCAKNS LAFFDYWGLG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                         443

SEQ ID NO: 468          moltype = AA   length = 216
FEATURE                 Location/Qualifiers
source                  1..216
                        mol_type = protein
                        organism = Synthetic construct
SEQUENCE: 468
QSVLTQPPSA SGTPGQRVTI SCSGGSSNIG RESVNWYQQL PGTAPKLLIY STDRRPSGVP   60
DRFSGSKSGT SASLAISGLQ SEDEADYYCG TWDNDLNGWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 469          moltype = AA   length = 449
FEATURE                 Location/Qualifiers
source                  1..449
                        mol_type = protein
                        organism = Synthetic construct
SEQUENCE: 469
DVQLQESGPG LVKPSQSLSL TCTVTGHSIT SDYAWNWIRQ FPGDKLEWMG YISYSGYTTY   60
NPSLKSRVSI TRDTSKNQFF LQLNSVTTED TATYFCARDL DYGPWFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 470          moltype = AA   length = 214
FEATURE                 Location/Qualifiers
source                  1..214
                        mol_type = protein
                        organism = Synthetic construct
SEQUENCE: 470
DIQMTQSPAS LSASVGETVT LTCRASENIH NYLAWYQQKQ GKSPQLLVYN VKTLADGVPS   60
RFSGSGSGTQ YSLKINSLQP EDFGSYYCQH FWSSPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 471          moltype = AA   length = 585
FEATURE                 Location/Qualifiers
source                  1..585
                        mol_type = protein
                        organism = Synthetic construct
SEQUENCE: 471
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELA  240
GAPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GKAPASSSTK KTQLQLEHLL LALQMILNGI  480
NNYKNPKLTE MLTFKYMPK KATELKHLQC LEEELKPLEE VLNLAQSKNF HLRPRDLISN  540
INVIVLELKG SETTFMCEYA DETATIVEFL NRWITFAQSI ISTLT                 585
```

```
SEQ ID NO: 472          moltype = AA  length = 582
FEATURE                 Location/Qualifiers
source                  1..582
                        mol_type = protein
                        organism = Synthetic construct
SEQUENCE: 472
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKA PASSSTKKTQ LQLEHLLLAL QMILNGINNY  480
KNPKLTEMLT FKFYMPKKAT ELKHLQCLEE ELKPLEEVLN LAQSKNFHLR PRDLISNINV  540
IVLELKGSET TFMCEYADET ATIVEFLNRW ITFAQSIIST LT                     582

SEQ ID NO: 473          moltype = AA  length = 582
FEATURE                 Location/Qualifiers
source                  1..582
                        mol_type = protein
                        organism = Synthetic construct
SEQUENCE: 473
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFAGAP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKA PASSSTKKTQ LQLEHLLLAL QMILNGINNY  480
KNPKLTEMLT FKFYMPKKAT ELKHLQCLEE ELKPLEEVLN LAQSKNFHLR PRDLISNINV  540
IVLELKGSET TFMCEYADET ATIVEFLNRW ITFAQSIIST LT                     582

SEQ ID NO: 474          moltype = AA  length = 585
FEATURE                 Location/Qualifiers
source                  1..585
                        mol_type = protein
                        organism = Synthetic construct
SEQUENCE: 474
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELA  240
GAPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GKAPASSSTK KTQLQLEHLL LDLQMILNGI  480
NNYKNPKLTE MLTFKYMPK KATELKHLQC LEEELKPLEE VLNLAQSKNF HLRPRDLISN  540
INVKVLELKG SETTFMCEYA DETATIVEFL NRWITFAQSI ISTLT                 585

SEQ ID NO: 475          moltype = AA  length = 582
FEATURE                 Location/Qualifiers
source                  1..582
                        mol_type = protein
                        organism = Synthetic construct
SEQUENCE: 475
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGKA PASSSTKKTQ LQLEHLLLDL QMILNGINNY  480
KNPKLTEMLT FKFYMPKKAT ELKHLQCLEE ELKPLEEVLN LAQSKNFHLR PRDLISNINV  540
KVLELKGSET TFMCEYADET ATIVEFLNRW ITFAQSIIST LT                     582

SEQ ID NO: 476          moltype = AA  length = 582
FEATURE                 Location/Qualifiers
source                  1..582
                        mol_type = protein
                        organism = Synthetic construct
SEQUENCE: 476
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFAGAP  240
```

```
SVFLPPPKPK DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV YTLPPSQEEM 360
TKNQVSLTCL VKGFYPSDIA VEWESNGQPE NNYKTTPPVL DSDGSFFLYS RLTVDKSRWQ 420
EGNVFSCSVM HEALHNHYTQ KSLSLSLGKA PASSSTKKTQ LQLEHLLLDL QMILNGINNY 480
KNPKLTEMLT FKFYMPKKAT ELKHLQCLEE ELKPLEEVLN LAQSKNFHLR PRDLISNINV 540
KVLELKGSET TFMCEYADET ATIVEFLNRW ITFAQSIIST LT                   582

SEQ ID NO: 477          moltype = AA  length = 585
FEATURE                 Location/Qualifiers
source                  1..585
                        mol_type = protein
                        organism = Synthetic construct
SEQUENCE: 477
EVQLLESGGG LVQPGGSLRL SCAASGFTFK DYCMTWVRQA PGKGLEWVSA IVYSGGSTYY 60
ADSVKGRFTI SRDNSKNTLY LQMNNLRAED TAVYYCAKYT RASYFYDAMD VWGQGTTVTV 120
SSASTKGPSV FPLAPSSKST SGGTAALGCL VKDYFPEPVT VSWNSGALTS GVHTFPAVLQ 180
SSGLYSLSSV VTVPSSSLGT QTYICNVNHK PSNTKVDKKV EPKSCDKTHT CPPCPAPELA 240
GAPSVFLFPP KPKDTLMISR TPEVTCVVVD VSHEDPEVKF NWYVDGVEVH NAKTKPREEQ 300
YNSTYRVVSV LTVLHQDWLN GKEYKCKVSN KALPAPIEKT ISKAKGQPRE PQVYTLPPSR 360
DELTKNQVSL TCLVKGFYPS DIAVEWESNG QPENNYKTTP PVLDSDGSFF LYSKLTVDKS 420
RWQQGNVFSC SVMHEALHNH YTQKSLSLSP GKAPASSSTK KTQLQLEHLL LDLQMILNGI 480
NNYKNPKLTE MLTFKFYMPK KATELKHLQC LEEELKPLEE VLNLAQSKNF HLRPRKLISN 540
INVIVLELKG SETTFMCEYA DETATIVEFL NRWITFAQSI ISTLT                585

SEQ ID NO: 478          moltype = AA  length = 582
FEATURE                 Location/Qualifiers
source                  1..582
                        mol_type = protein
                        organism = Synthetic construct
SEQUENCE: 478
EVQLLESGGG LVQPGGSLRL SCAASGFTFK DYCMTWVRQA PGKGLEWVSA IVYSGGSTYY 60
ADSVKGRFTI SRDNSKNTLY LQMNNLRAED TAVYYCAKYT RASYFYDAMD VWGQGTTVTV 120
SSASTKGPSV FPLAPCSRST SESTAALGCL VKDYFPEPVT VSWNSGALTS GVHTFPAVLQ 180
SSGLYSLSSV VTVPSSSLGT KTYTCNVDHK PSNTKVDKRV ESKYGPPCPP CPAPEFEGGP 240
SVFLPPPKPK DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV YTLPPSQEEM 360
TKNQVSLTCL VKGFYPSDIA VEWESNGQPE NNYKTTPPVL DSDGSFFLYS RLTVDKSRWQ 420
EGNVFSCSVM HEALHNHYTQ KSLSLSLGKA PASSSTKKTQ LQLEHLLLDL QMILNGINNY 480
KNPKLTEMLT FKFYMPKKAT ELKHLQCLEE ELKPLEEVLN LAQSKNFHLR PRKLISNINV 540
IVLELKGSET TFMCEYADET ATIVEFLNRW ITFAQSIIST LT                   582

SEQ ID NO: 479          moltype = AA  length = 582
FEATURE                 Location/Qualifiers
source                  1..582
                        mol_type = protein
                        organism = Synthetic construct
SEQUENCE: 479
EVQLLESGGG LVQPGGSLRL SCAASGFTFK DYCMTWVRQA PGKGLEWVSA IVYSGGSTYY 60
ADSVKGRFTI SRDNSKNTLY LQMNNLRAED TAVYYCAKYT RASYFYDAMD VWGQGTTVTV 120
SSASTKGPSV FPLAPCSRST SESTAALGCL VKDYFPEPVT VSWNSGALTS GVHTFPAVLQ 180
SSGLYSLSSV VTVPSSSLGT KTYTCNVDHK PSNTKVDKRV ESKYGPPCPP CPAPEFAGAP 240
SVFLPPPKPK DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV YTLPPSQEEM 360
TKNQVSLTCL VKGFYPSDIA VEWESNGQPE NNYKTTPPVL DSDGSFFLYS RLTVDKSRWQ 420
EGNVFSCSVM HEALHNHYTQ KSLSLSLGKA PASSSTKKTQ LQLEHLLLDL QMILNGINNY 480
KNPKLTEMLT FKFYMPKKAT ELKHLQCLEE ELKPLEEVLN LAQSKNFHLR PRKLISNINV 540
IVLELKGSET TFMCEYADET ATIVEFLNRW ITFAQSIIST LT                   582

SEQ ID NO: 480          moltype = AA  length = 577
FEATURE                 Location/Qualifiers
source                  1..577
                        mol_type = protein
                        organism = Synthetic construct
SEQUENCE: 480
EVQLVESGGG LVQPGRSLKL SCAVSGFTFS DYAMAWVRQA PKKGLEWVAT ISYDGSRTYY 60
RDSVKGRFTI SRDNAKITLY LQMDSLRSED TATYYCARHG SGYFDYWGQG VMVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
SCSVMHEALH NHYTQKSLSL SLGKAPTSSS TKKTQLQLEH LLLDLQMILN GINNYKNPKL 480
TRMLTFKFYM PKKATELKHL QCLEEELKPL EEVLNLAQSK NFHLRPRDLI SNINVIVLEL 540
KGSETTFMCE YADETATIVE FLNRWITFCQ SIISTLT                         577

SEQ ID NO: 481          moltype = AA  length = 583
FEATURE                 Location/Qualifiers
source                  1..583
                        mol_type = protein
```

```
                        organism = Synthetic construct
SEQUENCE: 481
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLGKSGGGGS APTSSSTKKT QLQLEHLLLD LQMILNGINN   480
YKNPKLTRML TFKFYMPKKA TELKHLQCLE EELKPEEVL NLAQSKNFHL RPRDLISNIN   540
VIVLELKGSE TTFMCEYADE TATIVEFLNR WITFCQSIIS TLT                    583

SEQ ID NO: 482          moltype = AA   length = 443
FEATURE                 Location/Qualifiers
source                  1..443
                        mol_type = protein
                        organism = Synthetic construct
SEQUENCE: 482
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLG                                          443

SEQ ID NO: 483          moltype = AA   length = 346
FEATURE                 Location/Qualifiers
source                  1..346
                        mol_type = protein
                        organism = Synthetic construct
SEQUENCE: 483
DTVLTQSPAL AVSPGERVTI SCRASESVRT GVHWYQQKPG QQPKLLIYGA SNLESGVPAR    60
FSGSGSGTDF TLTIDPVEAD DTATYFCQQS WNDPFTFGSG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GECAPTSSST KKTQLQLEHL LLDLQMILNG   240
INNYKNPKLT RMLTFKFYMP KKATELKHLQ CLEEELKPLE EVLNLAQSKN FHLRPRDLIS   300
NINVIVLELK GSETTFMCEY ADETATIVEF LNRWITFCQS IISTLT                  346

SEQ ID NO: 484          moltype = AA   length = 352
FEATURE                 Location/Qualifiers
source                  1..352
                        mol_type = protein
                        organism = Synthetic construct
SEQUENCE: 484
DTVLTQSPAL AVSPGERVTI SCRASESVRT GVHWYQQKPG QQPKLLIYGA SNLESGVPAR    60
FSGSGSGTDF TLTIDPVEAD DTATYFCQQS WNDPFTFGSG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GECSGGGGSA PTSSSTKKTQ LQLEHLLLDL   240
QMILNGINNY KNPKLTRMLT FKFYMPKKAT ELKHLQCLEE ELKPEEVLN LAQSKNFHLR   300
PRDLISNINV IVLELKGSET TFMCEYADET ATIVEFLNRW ITFCQSIIST LT           352

SEQ ID NO: 485          moltype = AA   length = 583
FEATURE                 Location/Qualifiers
source                  1..583
                        mol_type = protein
                        organism = Synthetic construct
SEQUENCE: 485
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLGKSGGGGS APTSSSTKKT QLQLEHLLLY LQMILNGINN   480
YKNPKLTRML TFKFYMPKKA TELKHLQCLE EELKPEEVL NLAQSKNFHL RPRDLISNIN   540
VIVLELKGSE TTFMCEYADE TATIVEFLNR WITFCQSIIS TLT                    583

SEQ ID NO: 486          moltype = AA   length = 577
FEATURE                 Location/Qualifiers
source                  1..577
                        mol_type = protein
                        organism = Synthetic construct
SEQUENCE: 486
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
```

```
KGPSVFPPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKAPTSSS TKKTQLQLEH LLLYLQMILN GINNYKNPKL    480
TRMLTFKFYM PKKATELKHL QCLEEELKPL EEVLNLAQSK NFHLRPRDLI SNINVIVLEL    540
KGSETTFMCE YADETATIVE FLNRWITFCQ SIISTLT                            577

SEQ ID NO: 487          moltype = AA  length = 580
FEATURE                 Location/Qualifiers
source                  1..580
                        mol_type = protein
                        organism = Synthetic construct
SEQUENCE: 487
EVQLVESGGG LVQPGRSLKL SCAVSGFTFS DYAMAWVRQA PKKGLEWVAT ISYDGSRTYY     60
RDSVKGRFTI SRDNAKITLY LQMDSLRSED TATYYCARHG SGYFDYWGQG VMVTVSSAST    120
KGPSVFPPLA PSSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGKAPT SSSTKKTQLQ LEHLLLYLQM ILNGINNYKN    480
PKLTRMLTFK FYMPKKATEL KHLQCLEEEL KPLEEVLNLA QSKNFHLRPR DLISNINVIV    540
LELKGSETTF MCEYADETAT IVEFLNRWIT FCQSIISTLT                          580

SEQ ID NO: 488          moltype = AA  length = 583
FEATURE                 Location/Qualifiers
source                  1..583
                        mol_type = protein
                        organism = Synthetic construct
SEQUENCE: 488
EVQLVESGGG LVQPGRSLKL SCAVSGFTFS DYAMAWVRQA PKKGLEWVAT ISYDGSRTYY     60
RDSVKGRFTI SRDNAKITLY LQMDSLRSED TATYYCARHG SGYFDYWGQG VMVTVSSAST    120
KGPSVFPPLA PCSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APTSSSTKKT QLQLEHLLLA LQMILNGINN    480
YKNPKLTPML TFKFYMPKKA TELKHLQCLE EELKPLEEVL NLAQSKNFHL RPRDLISNIN    540
VIVLELKGSE TTFMCEYADE TATIVEFLNR WITFCQSIIS TLT                      583

SEQ ID NO: 489          moltype = AA  length = 583
FEATURE                 Location/Qualifiers
source                  1..583
                        mol_type = protein
                        organism = Synthetic construct
SEQUENCE: 489
EVQLVESGGG LVQPGRSLKL SCAVSGFTFS DYAMAWVRQA PKKGLEWVAT ISYDGSRTYY     60
RDSVKGRFTI SRDNAKITLY LQMDSLRSED TATYYCARHG SGYFDYWGQG VMVTVSSAST    120
KGPSVFPPLA PCSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APTSSSTKKT QLQLEHLLLA LQMILNGINN    480
YKNPKLTSML TFKFYMPKKA TELKHLQCLE EELKPLEEVL NLAQSKNFHL RPRDLISNIN    540
VIVLELKGSE TTFMCEYADE TATIVEFLNR WITFCQSIIS TLT                      583

SEQ ID NO: 490          moltype = AA  length = 583
FEATURE                 Location/Qualifiers
source                  1..583
                        mol_type = protein
                        organism = Synthetic construct
SEQUENCE: 490
EVQLVESGGG LVQPGRSLKL SCAVSGFTFS DYAMAWVRQA PKKGLEWVAT ISYDGSRTYY     60
RDSVKGRFTI SRDNAKITLY LQMDSLRSED TATYYCARHG SGYFDYWGQG VMVTVSSAST    120
KGPSVFPPLA PCSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APTSSSTKKT QLQLEHLLLA LQMILNGINN    480
YKNPKLTDML TFKFYMPKKA TELKHLQCLE EELKPLEEVL NLAQSKNFHL RPRDLISNIN    540
VIVLELKGSE TTFMCEYADE TATIVEFLNR WITFCQSIIS TLT                      583

SEQ ID NO: 491          moltype = AA  length = 583
FEATURE                 Location/Qualifiers
```

```
source                  1..583
                        mol_type = protein
                        organism = Synthetic construct
SEQUENCE: 491
EVQLVESGGG LVQPGRSLKL SCAVSGFTFS DYAMAWVRQA PKKGLEWVAT ISYDGSRTYY  60
RDSVKGRFTI SRDNAKITLY LQMDSLRSED TATYYCARHG SGYFDYWGQG VMVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
SCSVMHEALH NHYTQKSLSL SLGKSGGGGS APTSSSTKKT QLQLEHLLLA LQMILNGINN 480
YKNPKLTQML TFKFYMPKKA TELKHLQCLE EELKPLEEVL NLAQSKNFHL RPRDLISNIN 540
VIVLALKGSE TTFMCEYADE TATIVEFLNR WITFCQSIIS TLT               583

SEQ ID NO: 492          moltype = AA  length = 583
FEATURE                 Location/Qualifiers
source                  1..583
                        mol_type = protein
                        organism = Synthetic construct
SEQUENCE: 492
EVQLVESGGG LVQPGRSLKL SCAVSGFTFS DYAMAWVRQA PKKGLEWVAT ISYDGSRTYY  60
RDSVKGRFTI SRDNAKITLY LQMDSLRSED TATYYCARHG SGYFDYWGQG VMVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
SCSVMHEALH NHYTQKSLSL SLGKSGGGGS APTSSSTKKT QLQLEHLLLA LQMILNGINN 480
YKNPKLTRML THKFYMPKKA TELKHLQCLE EELKPLEEVL NLAQSKNFHL RPRDLISNIN 540
VIVLALKGSE TTFMCEYADE TATIVEFLNR WITFCQSIIS TLT               583

SEQ ID NO: 493          moltype = AA  length = 583
FEATURE                 Location/Qualifiers
source                  1..583
                        mol_type = protein
                        organism = Synthetic construct
SEQUENCE: 493
EVQLVESGGG LVQPGRSLKL SCAVSGFTFS DYAMAWVRQA PKKGLEWVAT ISYDGSRTYY  60
RDSVKGRFTI SRDNAKITLY LQMDSLRSED TATYYCARHG SGYFDYWGQG VMVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
SCSVMHEALH NHYTQKSLSL SLGKSGGGGS APTSSSTKKT QLQLEHLLLD LQMILNGINN 480
YKNPKLTDML TFKFYMPKKA TELKHLQCLE EELKPLEEVL NLAQSKNFHL RPRDLISNIN 540
VDVLELKGSE TTFMCEYADE TATIVEFLNR WITFCQSIIS TLT               583

SEQ ID NO: 494          moltype = AA  length = 583
FEATURE                 Location/Qualifiers
source                  1..583
                        mol_type = protein
                        organism = Synthetic construct
SEQUENCE: 494
EVQLVESGGG LVQPGRSLKL SCAVSGFTFS DYAMAWVRQA PKKGLEWVAT ISYDGSRTYY  60
RDSVKGRFTI SRDNAKITLY LQMDSLRSED TATYYCARHG SGYFDYWGQG VMVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
SCSVMHEALH NHYTQKSLSL SLGKSGGGGS APTSSSTKKT QLQLEHLLLD LQMILNGINN 480
YKNPKLTEML TFKFYMPKKA TELKHLQCLE EELKPLEEVL NLAQSKNFHL RPRDLISNIN 540
VDVLELKGSE TTFMCEYADE TATIVEFLNR WITFCQSIIS TLT               583

SEQ ID NO: 495          moltype = AA  length = 583
FEATURE                 Location/Qualifiers
source                  1..583
                        mol_type = protein
                        organism = Synthetic construct
SEQUENCE: 495
EVQLVESGGG LVQPGRSLKL SCAVSGFTFS DYAMAWVRQA PKKGLEWVAT ISYDGSRTYY  60
RDSVKGRFTI SRDNAKITLY LQMDSLRSED TATYYCARHG SGYFDYWGQG VMVTVSSAST 120
KGPSVFPLAP CSRSTSESTA ALGCLVKDYF PEPVTVSWNS GALTSGVHTF PAVLQSSGLY 180
SLSSVVTVPS SSLGTKTYTC NVDHKPSNTK VDKRVESKYG PPCPPCPAPE FLGGPSVFLF 240
PPKPKDTLMI SRTPEVTCVV VDVSQEDPEV QFNWYVDGVE VHNAKTKPRE EQFNSTYRVV 300
SVLTVLHQDW LNGKEYKCKV SNKGLPSSIE KTISKAKGQP REPQVYTLPP SQEEMTKNQV 360
SLTCLVKGFY PSDIAVEWES NGQPENNYKT TPPVLDSDGS FFLYSRLTVD KSRWQEGNVF 420
```

```
SCSVMHEALH NHYTQKSLSL SLGKSGGGGS APTSSSTKKT QLQLEHLLLD LQMILNGINN    480
YKNPKLTRML THKFYMPKKA TELKHLQCLE EELKPLEEVL NLAQSKNFHL RPRDLISNIN    540
VDVLELKGSE TTFMCEYADE TATIVEFLNR WITFCQSIIS TLT                      583

SEQ ID NO: 496          moltype = AA   length = 583
FEATURE                 Location/Qualifiers
source                  1..583
                        mol_type = protein
                        organism = Synthetic construct
SEQUENCE: 496
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APTSSSTKKT QLQLEHLLLA LQMILNGINN    480
YKNPKLTEML TFKFYMPKKA TELKHLQCLE EELKPLEEVL NLAQSKNFHL RPRDLISNIN    540
VIVLELKGSE TTFMCEYADE TATIVEFLNR WITFCQSIIS TLT                      583

SEQ ID NO: 497          moltype = AA   length = 583
FEATURE                 Location/Qualifiers
source                  1..583
                        mol_type = protein
                        organism = Synthetic construct
SEQUENCE: 497
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APASSSTKKT QLQLEHLLLA LQMILNGINN    480
YKNPKLTEML TFKFYMPKKA TELKHLQCLE EELKPLEEVL NLAQSKNFHL RPRDLISNIN    540
VIVLELKGSE TTFMCEYADE TATIVEFLNR WITFCQSIIS TLT                      583

SEQ ID NO: 498          moltype = AA   length = 583
FEATURE                 Location/Qualifiers
source                  1..583
                        mol_type = protein
                        organism = Synthetic construct
SEQUENCE: 498
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APTSSSTKKT QLQLEHLLLA LQMILNGINN    480
YKNPKLTEML TFKFYMPKKA TELKHLQCLE EELKPLEEVL NLAQSKNFHL RPRDLISNIN    540
VIVLELKGSE TTFMCEYADE TATIVEFLNR WITFAQSIIS TLT                      583

SEQ ID NO: 499          moltype = AA   length = 583
FEATURE                 Location/Qualifiers
source                  1..583
                        mol_type = protein
                        organism = Synthetic construct
SEQUENCE: 499
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKSGGGGS APASSSTKKT QLQLEHLLLA LQMILNGINN    480
YKNPKLTEML TFKFYMPKKA TELKHLQCLE EELKPLEEVL NLAQSKNFHL RPRDLISNIN    540
VIVLELKGSE TTFMCEYADE TATIVEFLNR WITFAQSIIS TLT                      583

SEQ ID NO: 500          moltype = AA   length = 586
FEATURE                 Location/Qualifiers
source                  1..586
                        mol_type = protein
                        organism = Synthetic construct
SEQUENCE: 500
EVQLVESGGG LVQPGRSLKL SCAVSGFTFS DYAMAWVRQA PKKGLEWVAT ISYDGSRTYY    60
```

```
RDSVKGRFTI SRDNAKITLY LQMDSLRSED TATYYCARHG SGYFDYWGQG VMVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGKSGG GGSAPTSSST KKTQLQLEHL LLALQMILNG    480
INNYKNPKLT EMLTFKFYMP KKATELKHLQ CLEEELKPLE EVLNLAQSKN FHLRPRDLIS    540
NINVIVLELK GSETTFMCEY ADETATIVEF LNRWITFCQS IISTLT                   586

SEQ ID NO: 501            moltype = AA  length = 586
FEATURE                   Location/Qualifiers
source                    1..586
                          mol_type = protein
                          organism = Synthetic construct
SEQUENCE: 501
EVQLVESGGG LVQPGRSLKL SCAVSGFTFS DYAMAWVRQA PKKGLEWVAT ISYDGSRTYY     60
RDSVKGRFTI SRDNAKITLY LQMDSLRSED TATYYCARHG SGYFDYWGQG VMVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGKSGG GGSAPASSST KKTQLQLEHL LLALQMILNG    480
INNYKNPKLT EMLTFKFYMP KKATELKHLQ CLEEELKPLE EVLNLAQSKN FHLRPRDLIS    540
NINVIVLELK GSETTFMCEY ADETATIVEF LNRWITFCQS IISTLT                   586

SEQ ID NO: 502            moltype = AA  length = 586
FEATURE                   Location/Qualifiers
source                    1..586
                          mol_type = protein
                          organism = Synthetic construct
SEQUENCE: 502
EVQLVESGGG LVQPGRSLKL SCAVSGFTFS DYAMAWVRQA PKKGLEWVAT ISYDGSRTYY     60
RDSVKGRFTI SRDNAKITLY LQMDSLRSED TATYYCARHG SGYFDYWGQG VMVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGKSGG GGSAPTSSST KKTQLQLEHL LLALQMILNG    480
INNYKNPKLT EMLTFKFYMP KKATELKHLQ CLEEELKPLE EVLNLAQSKN FHLRPRDLIS    540
NINVIVLELK GSETTFMCEY ADETATIVEF LNRWITFAQS IISTLT                   586

SEQ ID NO: 503            moltype = AA  length = 346
FEATURE                   Location/Qualifiers
source                    1..346
                          mol_type = protein
                          organism = Synthetic construct
SEQUENCE: 503
DTVLTQSPAL AVSPGERVTI SCRASESVRT GVHWYQQKPG QQPKLLIYGA SNLESGVPAR     60
FSGSGSGTDF TLTIDPVEAD DTATYFCQQS WNDPFTFGSG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GECAPTSSST KKTQLQLEHL LLALQMILNG    240
INNYKNPKLT EMLTFKFYMP KKATELKHLQ CLEEELKPLE EVLNLAQSKN FHLRPRDLIS    300
NINVIVLELK GSETTFMCEY ADETATIVEF LNRWITFCQS IISTLT                   346

SEQ ID NO: 504            moltype = AA  length = 352
FEATURE                   Location/Qualifiers
source                    1..352
                          mol_type = protein
                          organism = Synthetic construct
SEQUENCE: 504
DTVLTQSPAL AVSPGERVTI SCRASESVRT GVHWYQQKPG QQPKLLIYGA SNLESGVPAR     60
FSGSGSGTDF TLTIDPVEAD DTATYFCQQS WNDPFTFGSG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GECSGGGGSA PTSSSTKKTQ LQLEHLLLAL    240
QMILNGINNY KNPKLTEMLT FKFYMPKKAT ELKHLQCLEE ELKPLEEVLN LAQSKNFHLR    300
PRDLISNINV IVLELKGSET TFMCEYADET ATIVEFLNRW ITFCQSIIST LT            352

SEQ ID NO: 505            moltype = AA  length = 575
FEATURE                   Location/Qualifiers
source                    1..575
                          mol_type = protein
                          organism = Synthetic construct
SEQUENCE: 505
DVQLVESGGG VVRPGESLRL SCTASGFTFS ISAMSWVRQA PGKGLEWVSA ISGTAYSTYY     60
ADSVRGRFTI SRDNSKNTLY LQMNSLRAED TAVYYCAKDF FDYWGLGTL VTVSSASTKG    120
PSVFPLAPCS RSTSESTAAL GCLVKDYFPE PVTVSWNSGA LTSGVHTFPA VLQSSGLYSL    180
```

```
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LALQMILNGI NNYKNPKLTE    480
MLTFKFYMPK KATELKHLQC LEEELKPLEE VLNLAQSKNF HLRPRDLISN INVIVLELKG    540
SETTFMCEYA DETATIVEFL NRWITFCQSI ISTLT                              575

SEQ ID NO: 506              moltype = AA  length = 577
FEATURE                     Location/Qualifiers
source                      1..577
                            mol_type = protein
                            organism = Synthetic construct
SEQUENCE: 506
DVQLVESGGG VVRPGESLRL SCAASGFTFS TDAMGWVRQA PGEGLEWVSL ISGSGYSTYY     60
ADSVKGRFTI SRDNSKNTLY LQMNSLTAED TAVYYCAKNS LAFFDYWGLG TLVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FLGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKAPTSSS TKKTQLQLEH LLLALQMILN GINNYKNPKL    480
TEMLTFKFYM PKKATELKHL QCLEEELKPL EEVLNLAQSK NFHLRPRDLI SNINVIVLEL    540
KGSETTFMCE YADETATIVE FLNRWITFCQ SIISTLT                            577

SEQ ID NO: 507              moltype = AA  length = 575
FEATURE                     Location/Qualifiers
source                      1..575
                            mol_type = protein
                            organism = Synthetic construct
SEQUENCE: 507
DVQLVESGGG VVRPGGSLRL SCAASGFTFS IYAMSWVRQA PGEGLEWVSH ISASGGSTYY     60
ADSVKGRFAI SRDNSKNTLY LQMNSLRAED TAVYYCTTNL GSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LALQMILNGI NNYKNPKLTE    480
MLTFKFYMPK KATELKHLQC LEEELKPLEE VLNLAQSKNF HLRPRDLISN INVIVLELKG    540
SETTFMCEYA DETATIVEFL NRWITFCQSI ISTLT                              575

SEQ ID NO: 508              moltype = AA  length = 575
FEATURE                     Location/Qualifiers
source                      1..575
                            mol_type = protein
                            organism = Synthetic construct
SEQUENCE: 508
DVQLVESGGG VVRPGGSLRL SCAASGFTFS IYAVSWVRQA PGEGLEWVSH ISASGGSTYY     60
ADSVKGRFAI SRDNSKNTLY LQMNSLRAED TAVYYCTTNL GSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LALQMILNGI NNYKNPKLTE    480
MLTFKFYMPK KATELKHLQC LEEELKPLEE VLNLAQSKNF HLRPRDLISN INVIVLELKG    540
SETTFMCEYA DETATIVEFL NRWITFCQSI ISTLT                              575

SEQ ID NO: 509              moltype = AA  length = 575
FEATURE                     Location/Qualifiers
source                      1..575
                            mol_type = protein
                            organism = Synthetic construct
SEQUENCE: 509
DVQLVESGGG LVQPGGSLRL SCAASGFTFD ISAMSWVRQA PGKGLEWVST ISGSAYSTYY     60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LALQMILNGI NNYKNPKLTR    480
MLTAKFYMPK KATELKHLQC LEEELKPLEE VLNLAQSKNF HLRPRDLISN INVIVLELKG    540
SETTFMCEYA DETATIVEFL NRWITFCQSI ISTLT                              575

SEQ ID NO: 510              moltype = AA  length = 575
FEATURE                     Location/Qualifiers
source                      1..575
```

```
                        mol_type = protein
                        organism = Synthetic construct
SEQUENCE: 510
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL GKAPTSSSTK KTQLQLEHLL LALQMILNGI NNYKNPKLTR   480
MLTSKFYMPK KATELKHLQC LEEELKPLEE VLNLAQSKNF HLRPRDLISN INVIVLELKG   540
SETTFMCEYA DETETATIVEFL NRWITFCQSI ISTLT                             575

SEQ ID NO: 511          moltype = AA   length = 575
FEATURE                 Location/Qualifiers
source                  1..575
                        mol_type = protein
                        organism = Synthetic construct
SEQUENCE: 511
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL GKAPTSSSTK KTQLQLEHLL LSLQMILNGI NNYKNPKLTE   480
MLTFKFYMPK KATELKHLQC LEEELKPLEE VLNLAQSKNF HLRPRDLISN INVIVLELKG   540
SETTFMCEYA DETETATIVEFL NRWITFCQSI ISTLT                             575

SEQ ID NO: 512          moltype = AA   length = 575
FEATURE                 Location/Qualifiers
source                  1..575
                        mol_type = protein
                        organism = Synthetic construct
SEQUENCE: 512
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL GKAPTSSSTK KTQLQLEHLL LDLQMILNGI NNYKNPKLTR   480
MLTAKFYMPK KATELKHLQC LEEELKPLEE VLNLAQSKNF HLRPRDLISR INVIVLELKG   540
SETTFMCEYA DETETATIVEFL NRWITFCQSI ISTLT                             575

SEQ ID NO: 513          moltype = AA   length = 575
FEATURE                 Location/Qualifiers
source                  1..575
                        mol_type = protein
                        organism = Synthetic construct
SEQUENCE: 513
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL GKAPTSSSTK KTQLQLEHLL LDLQMILNGI NNYKNPKLTR   480
MLTIKFYMPK KATELKHLQC LEEELKPLEE VLNLAQSKNF HLRPRDLISN INVDVLELKG   540
SETTFMCEYA DETETATIVEFL NRWITFCQSI ISTLT                             575

SEQ ID NO: 514          moltype = AA   length = 575
FEATURE                 Location/Qualifiers
source                  1..575
                        mol_type = protein
                        organism = Synthetic construct
SEQUENCE: 514
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
LTVLHQDWLN GKEYKCKVSN KGLPSSIEKT ISKAKGQPRE PQVYTLPPSQ EEMTKNQVSL   360
TCLVKGFYPS DIAVEWESNG QPENNYKTTP PVLDSDGSFF LYSRLTVDKS RWQEGNVFSC   420
SVMHEALHNH YTQKSLSLSL GKAPTSSSTK KTQLQLEHLL LDLQMILNGI NNYKNPKLTR   480
```

```
MLTQKFYMPK KATELKHLQC LEEELKPLEE VLNLAQSKNF HLRPRDLISN INVDVLELKG    540
SETTFMCEYA DETATIVEFL NRWITFCQSI ISTLT                               575

SEQ ID NO: 515            moltype = AA  length = 575
FEATURE                   Location/Qualifiers
source                    1..575
                          mol_type = protein
                          organism = Synthetic construct
SEQUENCE: 515
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LDLQMILNGI NNYKNPKLTR    480
MLTTKFYMPK KATELKHLQC LEEELKPLEE VLNLAQSKNF HLRPRDLISN INVDVLELKG   540
SETTFMCEYA DETATIVEFL NRWITFCQSI ISTLT                               575

SEQ ID NO: 516            moltype = AA  length = 575
FEATURE                   Location/Qualifiers
source                    1..575
                          mol_type = protein
                          organism = Synthetic construct
SEQUENCE: 516
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LDLQMILNGI NNYKNPKLTR    480
MLTWKFYMPK KATELKHLQC LEEELKPLEE VLNLAQSKNF HLRPRDLISN INVDVLELKG   540
SETTFMCEYA DETATIVEFL NRWITFCQSI ISTLT                               575

SEQ ID NO: 517            moltype = AA  length = 575
FEATURE                   Location/Qualifiers
source                    1..575
                          mol_type = protein
                          organism = Synthetic construct
SEQUENCE: 517
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LDLQMILNGI NNYKNPKLTE    480
MLTFKFYMPK KATELKHLQC LEEELKPLEE VLNLAQSKNF HLRPRKLISN INVIVLELKG   540
SETTFMCEYA DETATIVEFL NRWITFCQSI ISTLT                               575

SEQ ID NO: 518            moltype = AA  length = 575
FEATURE                   Location/Qualifiers
source                    1..575
                          mol_type = protein
                          organism = Synthetic construct
SEQUENCE: 518
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPTSSSTK KTQLQLEHLL LDLQMILNGI NNYKNPKLTE    480
MLTFKFYMPK KATELKHLQC LEEELKPLEE VLNLAQSKNF HLRPRDLISN INVKVLELKG   540
SETTFMCEYA DETATIVEFL NRWITFCQSI ISTLT                               575

SEQ ID NO: 519            moltype = AA  length = 581
FEATURE                   Location/Qualifiers
source                    1..581
                          mol_type = protein
                          organism = Synthetic construct
SEQUENCE: 519
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS    120
```

```
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFLGGPS    240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGKAP TSSSTKKTQL QLEHLLLALQ MILNGINNYK   480
NPKLTEMLTF KFYMPKKATE LKHLQCLEEE LKPLEEVLNL AQSKNFHLRP RDLISNINVI   540
VLELKGSETT FMCEYADETA TIVEFLNRWI TFCQSIISTL T                       581

SEQ ID NO: 520         moltype = AA  length = 581
FEATURE                Location/Qualifiers
source                 1..581
                       mol_type = protein
                       organism = Synthetic construct
SEQUENCE: 520
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFEGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGKAP ASSSTKKTQL QLEHLLLALQ MILNGINNYK   480
NPKLTEMLTF KFYMPKKATE LKHLQCLEEE LKPLEEVLNL AQSKNFHLRP RDLISNINVI   540
VLELKGSETT FMCEYADETA TIVEFLNRWI TFAQSIISTL T                       581

SEQ ID NO: 521         moltype = AA  length = 581
FEATURE                Location/Qualifiers
source                 1..581
                       mol_type = protein
                       organism = Synthetic construct
SEQUENCE: 521
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFAGAPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGKAP ASSSTKKTQL QLEHLLLALQ MILNGINNYK   480
NPKLTEMLTF KFYMPKKATE LKHLQCLEEE LKPLEEVLNL AQSKNFHLRP RDLISNINVI   540
VLELKGSETT FMCEYADETA TIVEFLNRWI TFAQSIISTL T                       581

SEQ ID NO: 522         moltype = AA  length = 586
FEATURE                Location/Qualifiers
source                 1..586
                       mol_type = protein
                       organism = Synthetic construct
SEQUENCE: 522
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELAGAPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSAPASSST KKTQLQLEHL LLALQMILNG   480
INNYKNPKLT EMLTFKFYMP KKATELKHLQ CLEEELKPLE EVLNLAQSKN FHLRPRDLIS   540
NINVIVLELK GSETTFMCEY ADETATIVEF LNRWITFAQS IISTLT                  586

SEQ ID NO: 523         moltype = AA  length = 216
FEATURE                Location/Qualifiers
source                 1..216
                       mol_type = protein
                       organism = Synthetic construct
SEQUENCE: 523
EIVLTQSPGT LSLSPGERAT LSCRASQSIG RSFLAWYQQK PGQAPRLLIY DASTRAADIP    60
ARFSGSGSGT DFTLTISSLE PEDFAVYYCQ QYYDWPPLSF GGGTKVEIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 524         moltype = AA  length = 582
FEATURE                Location/Qualifiers
source                 1..582
                       mol_type = protein
                       organism = Synthetic construct
SEQUENCE: 524
EVQLLESGGG LVQPGGSLRL SCVGSGFNLK DYCMTWVRQA PGKGLEWVSA IVYSGGSTYY    60
ADSVKGRFTI SRDNSKNTLY LQMNSLRAED TAVYYCAKYT RGSYFYDAMD VWGQGTTVTV   120
```

```
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PTSSSTKKTQ LQLEHLLLAL QMILNGINNY    480
KNPKLTEMLT FKFYMPKKAT ELKHLQCLEE ELKPLEEVLN LAQSKNFHLR PRDLISNINV    540
IVLELKGSET TFMCEYADET ATIVEFLNRW ITFCQSIIST LT                      582

SEQ ID NO: 525           moltype = AA   length = 216
FEATURE                  Location/Qualifiers
source                   1..216
                         mol_type = protein
                         organism = Synthetic construct
SEQUENCE: 525
EIVLTQSPGT LSLSPGERAT LSCRASQSIG RSFLAWYQQK PGQAPRLLIY DASTRAADIP     60
DRFSGSGSGT DFTLTINRLE PEDFAVYYCQ QYYDWPPLTF GGGTKVEIKR TVAAPSVFIF    120
PPSDEQLKSG TASVVCLLNN FYPREAKVQW KVDNALQSGN SQESVTEQDS KDSTYSLSST    180
LTLSKADYEK HKVYACEVTH QGLSSPVTKS FNRGEC                             216

SEQ ID NO: 526           moltype = AA   length = 582
FEATURE                  Location/Qualifiers
source                   1..582
                         mol_type = protein
                         organism = Synthetic construct
SEQUENCE: 526
EVQLLESGGG LVQPGGSLRL SCVGSGFNFK DYCMTWVRQA PGKGLEWVSA IVYSGGSTYY     60
ADSVKGRFTI SRDNSKNTLY LQMNSLRAED TAVYYCAKYT RGSYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PTSSSTKKTQ LQLEHLLLAL QMILNGINNY    480
KNPKLTEMLT FKFYMPKKAT ELKHLQCLEE ELKPLEEVLN LAQSKNFHLR PRDLISNINV    540
IVLELKGSET TFMCEYADET ATIVEFLNRW ITFCQSIIST LT                      582

SEQ ID NO: 527           moltype = AA   length = 216
FEATURE                  Location/Qualifiers
source                   1..216
                         mol_type = protein
                         organism = Synthetic construct
SEQUENCE: 527
EIVLTQSPGT LSLSPGERAT LSCRASQSIG RSFLAWYQQK PGQAPRLLIY DASTRATDIP     60
DRFSGSGSGT EFTLTISSLQ SEDFAVYYCQ QYYDWPPLTF GGGTKVEIKR TVAAPSVFIF    120
PPSDEQLKSG TASVVCLLNN FYPREAKVQW KVDNALQSGN SQESVTEQDS KDSTYSLSST    180
LTLSKADYEK HKVYACEVTH QGLSSPVTKS FNRGEC                             216

SEQ ID NO: 528           moltype = AA   length = 582
FEATURE                  Location/Qualifiers
source                   1..582
                         mol_type = protein
                         organism = Synthetic construct
SEQUENCE: 528
EVQLLESGGG LVQPGGSLRL SCVGSGFNFK DYCMTWVRQA PGKGLEWVSA IVYSGGSTYY     60
ADSVKGRFTI SRDNSKNTLY LQMNSLRAED TAVYYCAKYT RGSYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFEGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PASSSTKKTQ LQLEHLLLAL QMILNGINNY    480
KNPKLTEMLT FKFYMPKKAT ELKHLQCLEE ELKPLEEVLN LAQSKNFHLR PRDLISNINV    540
IVLELKGSET TFMCEYADET ATIVEFLNRW ITFAQSIIST LT                      582

SEQ ID NO: 529           moltype = AA   length = 582
FEATURE                  Location/Qualifiers
source                   1..582
                         mol_type = protein
                         organism = Synthetic construct
SEQUENCE: 529
EVQLLESGGG LVQPGGSLRL SCVGSGFNFK DYCMTWVRQA PGKGLEWVSA IVYSGGSTYY     60
ADSVKGRFTI SRDNSKNTLY LQMNSLRAED TAVYYCAKYT RGSYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFAGAP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PASSSTKKTQ LQLEHLLLAL QMILNGINNY    480
```

```
KNPKLTEMLT FKFYMPKKAT ELKHLQCLEE ELKPLEEVLN LAQSKNFHLR PRDLISNINV   540
IVLELKGSET TFMCEYADET ATIVEFLNRW ITFAQSIIST LT                      582

SEQ ID NO: 530           moltype = AA  length = 585
FEATURE                  Location/Qualifiers
source                   1..585
                         mol_type = protein
                         organism = Synthetic construct
SEQUENCE: 530
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEHLL LALQMILNGI   480
NNYKNPKLTE MLTFKFYMPK KATELKHLQC LEEELKPLEE VLNLAQSKNF HLRPRDLISN   540
INVIVLELKG SETTFMCEYA DETATIVEFL NRWITFAQSI ISTLT                   585

SEQ ID NO: 531           moltype = AA  length = 585
FEATURE                  Location/Qualifiers
source                   1..585
                         mol_type = protein
                         organism = Synthetic construct
SEQUENCE: 531
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEHLL LALQMILNGI   480
NNYKNPKLTE MLTFKFYMPK KATELKHLQC LEEELKPLEE VLNLAQSKNF HLRPRDLISN   540
INVIVLELKG SETTFMCEYA DETATIVEFL NRWITFAQSI ISTLT                   585

SEQ ID NO: 532           moltype = AA  length = 585
FEATURE                  Location/Qualifiers
source                   1..585
                         mol_type = protein
                         organism = Synthetic construct
SEQUENCE: 532
EVQLLESGGG LVQPGGSLRL SCAASGFTFK SYAMHWVRQA PGKGLEWVSA IVYSGGSTYY   60
ADSVKGRFTI SRDNSKNTLY LQMNSLRAED TAVYYCAKYD RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELA   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEHLL LALQMILNGI   480
NNYKNPKLTE MLTFKFYMPK KATELKHLQC LEEELKPLEE VLNLAQSKNF HLRPRDLISN   540
INVIVLELKG SETTFMCEYA DETATIVEFL NRWITFAQSI ISTLT                   585

SEQ ID NO: 533           moltype = AA  length = 585
FEATURE                  Location/Qualifiers
source                   1..585
                         mol_type = protein
                         organism = Synthetic construct
SEQUENCE: 533
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELE   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEHLL LDLQMILNGI   480
NNYKNPKLTE MLTFKFYMPK KATELKHLQC LEEELKPLEE VLNLAQSKNF HLRPRKLISN   540
INVIVLELKG SETTFMCEYA DETATIVEFL NRWITFAQSI ISTLT                   585

SEQ ID NO: 534           moltype = AA  length = 582
FEATURE                  Location/Qualifiers
source                   1..582
                         mol_type = protein
                         organism = Synthetic construct
SEQUENCE: 534
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV   120
```

```
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PASSSTKKTQ LQLEHLLLDL QMILNGINNY    480
KNPKLTEMLT FKFYMPKKAT ELKHLQCLEE ELKPLEEVLN LAQSKNFHLR PRKLISNINV    540
IVLELKGSET TFMCEYADET ATIVEFLNRW ITFAQSIIST LT                      582

SEQ ID NO: 535          moltype = AA  length = 585
FEATURE                 Location/Qualifiers
source                  1..585
                        mol_type = protein
                        organism = Synthetic construct
SEQUENCE: 535
EVQLLESGGG LVQPGGSLRL SCAASGFTFK DYCMTWVRQA PGKGLEWVSA IVYSGGSTYY     60
ADSVKGRFTI SRDNSKNTLY LQMNNLRAED TAVYYCAKYT RASYFYDAMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GKAPASSSTK KTQLQLEHLL LDLQMILNGI    480
NNYKNPKLTE MLTFKFYMPK KATELKHLQC LEEELKPLEE VLNLAQSKNF HLRPRDLISN    540
INVKVLELKG SETTFMCEYA DETATIVEFL NRWITFAQSI ISTLT                   585

SEQ ID NO: 536          moltype = AA  length = 585
FEATURE                 Location/Qualifiers
source                  1..585
                        mol_type = protein
                        organism = Synthetic construct
SEQUENCE: 536
EVQLLESGGG LVQPGGSLRL SCAASGFTFK DYCMTWVRQA PGKGLEWVSA IVYSGGSTYY     60
ADSVKGRFTI SRDNSKNTLY LQMNNLRAED TAVYYCAKYT RASYFYDAMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELE    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GKAPASSSTK KTQLQLEHLL LDLQMILNGI    480
NNYKNPKLTE MLTFKFYMPK KATELKHLQC LEEELKPLEE VLNLAQSKNF HLRPRDLISN    540
INVKVLELKG SETTFMCEYA DETATIVEFL NRWITFAQSI ISTLT                   585

SEQ ID NO: 537          moltype = AA  length = 582
FEATURE                 Location/Qualifiers
source                  1..582
                        mol_type = protein
                        organism = Synthetic construct
SEQUENCE: 537
EVQLLESGGG LVQPGGSLRL SCAASGFTFK DYCMTWVRQA PGKGLEWVSA IVYSGGSTYY     60
ADSVKGRFTI SRDNSKNTLY LQMNNLRAED TAVYYCAKYT RASYFYDAMD VWGQGTTVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLGKA PASSSTKKTQ LQLEHLLLDL QMILNGINNY    480
KNPKLTEMLT FKFYMPKKAT ELKHLQCLEE ELKPLEEVLN LAQSKNFHLR PRDLISNINV    540
KVLELKGSET TFMCEYADET ATIVEFLNRW ITFAQSIIST LT                      582

SEQ ID NO: 538          moltype = AA  length = 585
FEATURE                 Location/Qualifiers
source                  1..585
                        mol_type = protein
                        organism = Synthetic construct
SEQUENCE: 538
EVQLLESGGG LVQPGGSLRL SCAASGFTFK DYCMTWVRQA PGKGLEWVSA IVYSGGSTYY     60
ADSVKGRFTI SRDNSKNTLY LQMNNLRAED TAVYYCAKYT RASYFYDAMD VWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELA    240
GAPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GKAPASSSTK KTQLQLEHLL LSLQMILNGI    480
NNYKNPKLTE MLTFKFYMPK KATELKHLQC LEEELKPLEE VLNLAQSKNF HLRPRDLISN    540
INVIVLELKG SETTFMCEYA DETATIVEFL NRWITFAQSI ISTLT                   585

SEQ ID NO: 539          moltype = AA  length = 585
FEATURE                 Location/Qualifiers
```

```
                           -continued source                  1..585
                        mol_type = protein
                        organism = Synthetic construct
SEQUENCE: 539
EVQLLESGGG LVQPGGSLRL SCAASGFTFK DYCMTWVRQA PGKGLEWVSA IVYSGGSTYY      60
ADSVKGRFTI SRDNSKNTLY LQMNNLRAED TAVYYCAKYT RASYFYDAMD VWGQGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELA     240
GAPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP GKAPASSSTK KTQLQLEHLL LDLQMILNGI     480
NNYKNPKLTE MLTFKFYMPK KATELKHLQC LEEELKPLEE VLNLAQSKNF HLRPRFLISN     540
INIVLELKG SETTFMCEYA DETATIVEFL NRWITFAQSI ISTLT                      585

SEQ ID NO: 540          moltype = AA  length = 585
FEATURE                 Location/Qualifiers
source                  1..585
                        mol_type = protein
                        organism = Synthetic construct
SEQUENCE: 540
EVQLLESGGG LVQPGGSLRL SCAASGFTFK DYCMTWVRQA PGKGLEWVSA IVYSGGSTYY      60
ADSVKGRFTI SRDNSKNTLY LQMNNLRAED TAVYYCAKYT RASYFYDAMD VWGQGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELA     240
GAPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP GKAPASSSTK KTQLQLEHLL LDLQMILNGI     480
NNYKNPKLTE MLTFKFYMPK KATELKHLQC LEEELKPLEE VLNLAQSKNF HLRPRDLISN     540
INVRVLELKG SETTFMCEYA DETATIVEFL NRWITFAQSI ISTLT                     585

SEQ ID NO: 541          moltype = AA  length = 585
FEATURE                 Location/Qualifiers
source                  1..585
                        mol_type = protein
                        organism = Synthetic construct
SEQUENCE: 541
EVQLLESGGG LVQPGGSLRL SCAASGFTFK DYCMTWVRQA PGKGLEWVSA IVYSGGSTYY      60
ADSVKGRFTI SRDNSKNTLY LQMNNLRAED TAVYYCAKYT RASYFYDAMD VWGQGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELA     240
GAPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP GKAPASSSTK KTQLQLEHLL LDLQMILNGI     480
NNYKNPKLTE MLTFKFYMPK KATELKHLQC LEEELKPLEE VLNLAQSKNF HLRPRDLISN     540
INVEVLELKG SETTFMCEYA DETATIVEFL NRWITFAQSI ISTLT                     585

SEQ ID NO: 542          moltype = AA  length = 585
FEATURE                 Location/Qualifiers
source                  1..585
                        mol_type = protein
                        organism = Synthetic construct
SEQUENCE: 542
EVQLLESGGG LVQPGGSLRL SCAASGFTFK DYCMTWVRQA PGKGLEWVSA IVYSGGSTYY      60
ADSVKGRFTI SRDNSKNTLY LQMNNLRAED TAVYYCAKYT RASYFYDAMD VWGQGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELA     240
GAPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP GKAPASSSTK KTQLQLEHLL LDLQMILNGI     480
NNYKNPKLTE MLTFKFYMPK KATELKHLQC LEEELKPLEE VLNLAQSKNF HLRPRDLISN     540
INVSVLELKG SETTFMCEYA DETATIVEFL NRWITFAQSI ISTLT                     585

SEQ ID NO: 543          moltype = AA  length = 585
FEATURE                 Location/Qualifiers
source                  1..585
                        mol_type = protein
                        organism = Synthetic construct
SEQUENCE: 543
EVQLLESGGG LVQPGGSLRL SCAASGFTFK DYCMTWVRQA PGKGLEWVSA IVYSGGSTYY      60
ADSVKGRFTI SRDNSKNTLY LQMNNLRAED TAVYYCAKYT RASYFYDAMD VWGQGTTVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELA     240
GAPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
```

```
RWQQGNVFSC SVMHEALHNH YTQKSLSLSP GKAPASSSTK KTQLQLEHLL LDLQMILNGI   480
NNYKNPKLTE MLTFKFYMPK KATELKHLQC LEEELKPLEE VLNLAQSKNF HLRPRDLISN   540
INVDVLELKG SETTFMCEYA DETATIVEFL NRWITFAQSI ISTLT                  585

SEQ ID NO: 544          moltype = AA  length = 585
FEATURE                 Location/Qualifiers
source                  1..585
                        mol_type = protein
                        organism = Synthetic construct
SEQUENCE: 544
EVQLLESGGG LVQPGGSLRL SCAASGFTFK DYCMTWVRQA PGKGLEWVSA IVYSGGSTYY   60
ADSVKGRFTI SRDNSKNTLY LQMNNLRAED TAVYYCAKYT RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELA   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEELL LDLQMILNGI   480
NNYKNPKLTE MLTFKFYMPK KATELKHLQC LEEELKPLEE VLNLAQSKNF HLRPRDLISN   540
INIVLELKG SETTFMCEYA DETATIVEFL NRWITFAQSI ISTLT                   585

SEQ ID NO: 545          moltype = AA  length = 586
FEATURE                 Location/Qualifiers
source                  1..586
                        mol_type = protein
                        organism = Synthetic construct
SEQUENCE: 545
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSAPASSST KKTQLQLEHL LLALQMILNG   480
INNYKNPKLT EMLTFKFYMP KKATELKHLQ CLEEELKPLE EVLNLAQSKN FHLRPRDLIS   540
NINVIVLELK GSETTFMCEY ADETATIVEF LNRWITFAQS IISTLT                 586

SEQ ID NO: 546          moltype = AA  length = 580
FEATURE                 Location/Qualifiers
source                  1..580
                        mol_type = protein
                        organism = Synthetic construct
SEQUENCE: 546
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELAGAPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKAPA SSSTKKTQLQ LEHLLLALQM ILNGINNYKN   480
PKLTEMLTFK FYMPKKATEL KHLQCLEEEL KPLEEVLNLA QSKNFHLRPR DLISNINIV   540
LELKGSETTF MCEYADETAT IVEFLNRWIT FAQSIISTLT                       580

SEQ ID NO: 547          moltype = AA  length = 447
FEATURE                 Location/Qualifiers
source                  1..447
                        mol_type = protein
                        organism = Synthetic construct
SEQUENCE: 547
QVQLVQSGSE LKKPGASVKV SCKASGYSLY GTSMHWVRQA PGQGLEWMGY ISPFTGRATY   60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFEGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLG                                     447

SEQ ID NO: 548          moltype = AA  length = 447
FEATURE                 Location/Qualifiers
source                  1..447
                        mol_type = protein
                        organism = Synthetic construct
SEQUENCE: 548
QVQLVQSGSE LKKPGASVKV SCKASGYSLY GTSMHWVRQA PGQGLEWMGY ISPFTGRATY   60
AQGFTGRFVF SLDTSVSTAY LQISSLKAED TAVYYCARDY DYRYYYAMDY WGQGTTVTVS   120
SASTKGPSVF PLAPCSRSTS ESTAALGCLV KDYFPEPVTV SWNSGALTSG VHTFPAVLQS   180
```

```
SGLYSLSSVV TVPSSSLGTK TYTCNVDHKP SNTKVDKRVE SKYGPPCPPC PAPEFAGAPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLP SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLG                                       447

SEQ ID NO: 549         moltype = AA  length = 447
FEATURE                Location/Qualifiers
source                 1..447
                       mol_type = protein
                       organism = Synthetic construct
SEQUENCE: 549
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS    120
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFEGGPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLG SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLG                                       447

SEQ ID NO: 550         moltype = AA  length = 581
FEATURE                Location/Qualifiers
source                 1..581
                       mol_type = protein
                       organism = Synthetic construct
SEQUENCE: 550
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS    120
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFLGGPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLP SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLGKAP ASSSTKKTQL QLEHLLLALQ MILNGINNYK    480
NPKLTEMLTF KFYMPKKATE LKHLQCLEEE LKPLEEVLNL AQSKNFHLRP RDLISNINVI    540
VLELKGSETT FMCEYADETA TIVEFLNRWI TFAQSIISTL T                       581

SEQ ID NO: 551         moltype = AA  length = 581
FEATURE                Location/Qualifiers
source                 1..581
                       mol_type = protein
                       organism = Synthetic construct
SEQUENCE: 551
QVQLVQSGSE LKKPGASVKV SCKASGYSLY GTSMHWVRQA PGQGLEWMGY ISPFTGRATY    60
AQGFTGRFVF SLDTSVSTAY LQISSLKAED TAVYYCARDY DYRYYYAMDY WGQGTTVTVS    120
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFEGGPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLG SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLGKAP ASSSTKKTQL QLEHLLLALQ MILNGINNYK    480
NPKLTEMLTF KFYMPKKATE LKHLQCLEEE LKPLEEVLNL AQSKNFHLRP RDLISNINVI    540
VLELKGSETT FMCEYADETA TIVEFLNRWI TFAQSIISTL T                       581

SEQ ID NO: 552         moltype = AA  length = 441
FEATURE                Location/Qualifiers
source                 1..441
                       mol_type = protein
                       organism = Synthetic construct
SEQUENCE: 552
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFE GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                             441

SEQ ID NO: 553         moltype = AA  length = 441
FEATURE                Location/Qualifiers
source                 1..441
                       mol_type = protein
                       organism = Synthetic construct
SEQUENCE: 553
DVQLVESGGG LVQPGGSLRL SCAASGFTFD ISAMSWVRQA PGKGLEWVST ISGSAYSTYY    60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
```

```
SSVVTVPSSS LGTKTYTCNV DHKPSNTKVD KRVESKYGPP CPPCPAPEFA GAPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                              441

SEQ ID NO: 554          moltype = AA  length = 441
FEATURE                 Location/Qualifiers
source                  1..441
                        mol_type = protein
                        organism = Synthetic construct
SEQUENCE: 554
DVQLVESGGG LVQPGGSLRL SCAASGFTFD ISAMSWVRQA PGKGLEWVST ISGSAYSTYY     60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFE GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLGSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL G                                              441

SEQ ID NO: 555          moltype = AA  length = 575
FEATURE                 Location/Qualifiers
source                  1..575
                        mol_type = protein
                        organism = Synthetic construct
SEQUENCE: 555
DVQLVESGGG LVQPGGSLRL SCAASGFTFD ISAMSWVRQA PGKGLEWVST ISGSAYSTYY     60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFL GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPASSSTK KTQLQLEHLL LALQMILNGI NNYKNPKLTE    480
MLTFKFYMPK KATELKHLQC LEEELKPLEE VLNLAQSKNF HLRPRDLISN INVIVLELKG    540
SETTFMCEYA DETATIVEFL NRWITFAQSI ISTLT                               575

SEQ ID NO: 556          moltype = AA  length = 575
FEATURE                 Location/Qualifiers
source                  1..575
                        mol_type = protein
                        organism = Synthetic construct
SEQUENCE: 556
DVQLVESGGG LVQPGGSLRL SCAASGFTFD ISAMSWVRQA PGKGLEWVST ISGSAYSTYY     60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFE GGPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPASSSTK KTQLQLEHLL LALQMILNGI NNYKNPKLTE    480
MLTFKFYMPK KATELKHLQC LEEELKPLEE VLNLAQSKNF HLRPRDLISN INVIVLELKG    540
SETTFMCEYA DETATIVEFL NRWITFAQSI ISTLT                               575

SEQ ID NO: 557          moltype = AA  length = 575
FEATURE                 Location/Qualifiers
source                  1..575
                        mol_type = protein
                        organism = Synthetic construct
SEQUENCE: 557
DVQLVESGGG LVQPGGSLRL SCAASGFTFD ISAMSWVRQA PGKGLEWVST ISGSAYSTYY     60
ADSVKGRFTI SRDNSKSTLY LQMNSLRAED TAVYYCAREI FSDYWGLGTL VTVSSASTKG    120
PSVFPLAPCS RSTSESTAAL GCLVKDYFPE PVTVSWNSGA LTSGVHTFPA VLQSSGLYSL    180
SSVVTVPSSS LGTKTYTCNV DHKPSNTKVD KRVESKYGPP CPPCPAPEFA GAPSVFLFPP    240
KPKDTLMISR TPEVTCVVVD VSQEDPEVQF NWYVDGVEVH NAKTKPREEQ FNSTYRVVSV    300
LTVLHQDWLN GKEYKCKVSN KGLPSSIEKT ISKAKGQPRE PQVYTLPPSQ EEMTKNQVSL    360
TCLVKGFYPS DIAVEWESNG QPENNYKTTP PVLDSDGSFF LYSRLTVDKS RWQEGNVFSC    420
SVMHEALHNH YTQKSLSLSL GKAPASSSTK KTQLQLEHLL LALQMILNGI NNYKNPKLTE    480
MLTFKFYMPK KATELKHLQC LEEELKPLEE VLNLAQSKNF HLRPRDLISN INVIVLELKG    540
SETTFMCEYA DETATIVEFL NRWITFAQSI ISTLT                               575

SEQ ID NO: 558          moltype = AA  length = 575
FEATURE                 Location/Qualifiers
source                  1..575
                        mol_type = protein
                        organism = Synthetic construct
SEQUENCE: 558
DVQLVESGGG LVQPGGSLRL SCAASGFTFD ISAMSWVRQA PGKGLEWVST ISGSAYSTYY     60
```

```
ADSVKGRFTI SRDNSKSTLY LQMNSLRAED TAVYYCAREI FSDYWGLGTL VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEFE GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLGSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GKAPASSSTK KTQLQLEHLL LALQMILNGI NNYKNPKLTE  480
MLTFKFYMPK KATELKHLQC LEEELKPLEE VLNLAQSKNF HLRPRDLISN INVIVLELKG  540
SETTFMCEYA DETATIVEFL NRWITFAQSI ISTLT                            575

SEQ ID NO: 559           moltype = AA  length = 439
FEATURE                  Location/Qualifiers
source                   1..439
                         mol_type = protein
                         organism = Synthetic construct
SEQUENCE: 559
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS  120
VFPPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLG                                              439

SEQ ID NO: 560           moltype = AA  length = 451
FEATURE                  Location/Qualifiers
source                   1..451
                         mol_type = protein
                         organism = Synthetic construct
SEQUENCE: 560
QVQLQQPGAE LVKPGASVKM SCKASGYTFT SYNMHWVKQT PGRGLEWIGA IYPGNGDTSY   60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 561           moltype = AA  length = 450
FEATURE                  Location/Qualifiers
source                   1..450
                         mol_type = protein
                         organism = Synthetic construct
SEQUENCE: 561
QVQLQQPGAE LVKPGASVKM SCKASGYTFT SYNMHWVKQT PGRGLEWIGA IYPGNGDTSY   60
NQKFKGKATL TADKSSSTAY MQLSSLTSED SAVYYCARST YYGGDWYFNV WGAGTTVTVS  120
AASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 562           moltype = AA  length = 213
FEATURE                  Location/Qualifiers
source                   1..213
                         mol_type = protein
                         organism = Synthetic construct
SEQUENCE: 562
QIVLSQSPAI LSASPGEKVT MTCRASSSVS YIHWFQQKPG SSPKPWIYAT SNLASGVPVR   60
FSGSGSGTSY SLTISRVEAE DAATYYCQQW TSNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 563           moltype = AA  length = 580
FEATURE                  Location/Qualifiers
source                   1..580
                         mol_type = protein
                         organism = Synthetic construct
SEQUENCE: 563
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELAGAPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
```

```
NVFSCSVMHE ALHNHYTQKS LSLSPGKAPA SSSTKKTQLQ LEHLLLDLQM ILNGINNYKN    480
PKLTRMLTFK FYMPKKATEL KHLQCLEEEL KPLEEVLNLA QSKNFHLRPR DLISNINVIV    540
LELKGSETTF MCEYADETAT IVEFLNRWIT FAQSIISTLT                         580

SEQ ID NO: 564           moltype = AA   length = 456
FEATURE                  Location/Qualifiers
source                   1..456
                         mol_type = protein
                         organism = Synthetic construct
SEQUENCE: 564
EVQLQESGPG LVKPSQSLSL TCSVTGYSIT SSYRWNWIRK FPGNRLEWMG YINSAGISNY    60
NPSLKRRISI TRDTSKNQFF LQVNSVTTED AATYYCARSD NMGTTPFTYW GQGTLVTVSS    120
AKTTPPSVYP LAPGCGDTTG SSVTLGCLVK GYFPESVTVT WNSGSLSSSV HTFPALLQSG    180
LYTMSSSVTV PSSTWPSQTV TCSVAHPASS TTVDKKLEPS GPISTINPCP PCKECHKCPA    240
PNLEGGPSVF IFPPNIKDVL MISLTPKVTC VVVDVSEDDP DVQISWFVNN VEVHTAQTQT    300
HREDYASTIR VVSTLPIQHQ DWMSGKEFKC KVNNKDLPSP IERTISKIKG LVRAPQVYIL    360
PPPAEQLSRK DVSLTCLVVG FNPGDISVEW TSNGHTEENY KDTAPVLDSD GSYFIYSKLN    420
MKTSKWEKTD SFSCNVRHEG LKNYYLKKTI SRSPGK                             456

SEQ ID NO: 565           moltype = AA   length = 595
FEATURE                  Location/Qualifiers
source                   1..595
                         mol_type = protein
                         organism = Synthetic construct
SEQUENCE: 565
EVQLQESGPG LVKPSQSLSL TCSVTGYSIT SSYRWNWIRK FPGNRLEWMG YINSAGISNY    60
NPSLKRRISI TRDTSKNQFF LQVNSVTTED AATYYCARSD NMGTTPFTYW GQGTLVTVSS    120
AKTTPPSVYP LAPGCGDTTG SSVTLGCLVK GYFPESVTVT WNSGSLSSSV HTFPALLQSG    180
LYTMSSSVTV PSSTWPSQTV TCSVAHPASS TTVDKKLEPS GPISTINPCP PCKECHKCPA    240
PNLEGGPSVF IFPPNIKDVL MISLTPKVTC VVVDVSEDDP DVQISWFVNN VEVHTAQTQT    300
HREDYASTIR VVSTLPIQHQ DWMSGKEFKC KVNNKDLPSP IERTISKIKG LVRAPQVYIL    360
PPPAEQLSRK DVSLTCLVVG FNPGDISVEW TSNGHTEENY KDTAPVLDSD GSYFIYSKLN    420
MKTSKWEKTD SFSCNVRHEG LKNYYLKKTI SRSPGKSGGG GSAPTSSSTK KTQLQLEHLL    480
LDLQMILNGI NNYKNPKLTR MLTKKFRMPK KATELKHLQC LEEELKPLEE RLNLAQSKNF    540
HLRPRDLISN INVIVLELKG SETTFMCEYA DETATIVEFL NRWITFCQSI ISTLT         595

SEQ ID NO: 566           moltype = AA   length = 218
FEATURE                  Location/Qualifiers
source                   1..218
                         mol_type = protein
                         organism = Synthetic construct
SEQUENCE: 566
DIVMTQGTLP NPVPSGESVS ITCRSSKSLL YSDGKTYLNW YLQRPGQSPQ LLIYWMSTRA    60
SGVSDRFSGS GSGTDFTLKI SGVEAEDVGI YYCQQGLEFP TFGGGTKLEL KRADAAPTVS    120
IFPPSSEQLT SGGASVVCFL NNFYPKDINV KWKIDGSERQ NGVLNSWTDQ DSKDSTYSMS    180
STLTLTKDEY ERHNSYTCEA THKTSTSPIV KSFNRNEC                           218

SEQ ID NO: 567           moltype = AA   length = 455
FEATURE                  Location/Qualifiers
source                   1..455
                         mol_type = protein
                         organism = Synthetic construct
SEQUENCE: 567
EVQLVESGGG LVQPGRSLKL SCAASGFTFG DYSMAWVRQA PKRGLEWVAN IIYDGSRTFY    60
RDSVKGRFTI SRDNAKPTLY LQMDSLRPED TATYYCATHN YPGYAMEAWG QGTSVTVSSA    120
KTTPPSVYPL APGCGDTTGS SVTLGCLVKG YFPESVTVTW NSGSLSSSVH TFPALLQSGL    180
YTMSSSVTVP SSTWPSQTVT CSVAHPASST TVDKKLEPSG PISTINPCPP CKECHKCPAP    240
NLEGGPSVFI FPPNIKDVLM ISLTPKVTCV VVDVSEDDPD VQISWFVNNV EVHTAQTQTH    300
REDYASTIRV VSTLPIQHQD WMSGKEFKCK VNNKDLPSPI ERTISKIKGL VRAPQVYILP    360
PPAEQLSRKD VSLTCLVVGF NPGDISVEWT SNGHTEENYK DTAPVLDSDG SYFIYSKLNM    420
KTSKWEKTDS FSCNVRHEGL KNYYLKKTIS RSPGK                              455

SEQ ID NO: 568           moltype = AA   length = 213
FEATURE                  Location/Qualifiers
source                   1..213
                         mol_type = protein
                         organism = Synthetic construct
SEQUENCE: 568
DTVLTQSPAL PVSLGQRVNI SCRATKSVSR YVHWYQQKSG QQPRLLIYTT SNLESGVPSR    60
FSGSGSGTDF TLTIDPVEAD DIANYYCQQS NEIPYTFGAG TKLELKRADA APTVSIFPPS    120
SEQLTSGGAS VVCFLNNFYP KDINVKWKID GSERQNGVLN SWTDQDSKDS TYSMSSTLTL    180
TKDEYERHNS YTCEATHKTS TSPIVKSFNR NEC                                213

SEQ ID NO: 569           moltype = AA   length = 594
FEATURE                  Location/Qualifiers
source                   1..594
                         mol_type = protein
                         organism = Synthetic construct
SEQUENCE: 569
```

```
EVQLVESGGG LVQPGRSLKL SCAASGFTFG DYSMAWVRQA PKRGLEWVAN IIYDGSRTFY   60
RDSVKGRFTI SRDNAKPTLY LQMDSLRPED TATYYCATHN YPGYAMEAWG QGTSVTVSSA  120
KTTPPSVYPL APGCGDTTGS SVTLGCLVKG YFPESVTVTW NSGSLSSSVH TFPALLQSGL  180
YTMSSSVTVP SSTWPSQTVT CSVAHPASST TVDKKLEPSG PISTINPCPP CKECHKCPAP  240
NLEGGPSVFI FPPPNIKDVLM ISLTPKVTCV VVDVSEDDPD VQISWFVNNV EVHTAQTQTH  300
REDYASTIRV VSTLPIQHQD WMSGKEFKCK VNNKDLPSPI ERTISKIKGL VRAPQVYILP  360
PPAEQLSRKD VSLTCLVVGF NPGDISVEWT SNGHTEENYK DTAPVLDSDG SYFIYSKLNM  420
KTSKWEKTDS FSCNVRHEGL KNYYLKKTIS RSPGKSGGGG SAPTSSSTKK TQLQLEHLLL  480
DLQMILNGIN NYKNPKLTRM LTKKFRMPKK ATELKHLQCL EEELKPLEER LNLAQSKNFH  540
LRPRDLISNI NVIVLELKGS ETTFMCEYAD ETATIVEFLN RWITFCQSII STLT        594

SEQ ID NO: 570           moltype = AA  length = 595
FEATURE                  Location/Qualifiers
source                   1..595
                         mol_type = protein
                         organism = Synthetic construct
SEQUENCE: 570
EVQLVGSGGG LVQPGGSLKL SCAASGFTFS DFYMAWVRQA PTKGLEWVAS ISTGGGNTHY   60
RDSVKGRFTI SRDNAKSTLY LQMDSLRSEE TATYYCARLL STISTPFDYW GQGIVTVSS   120
AKTTPPSVYP LAPGCGDTTG SSVTLGCLVK GYFPESVTVT WNSGSLSSSV HTFPALLQSG  180
LYTMSSSVTV PSSTWPSQTV TCSVAHPASS TTVDKKLEPS GPISTINPCP PCKECHKCPA  240
PNLEGGPSVF IFPPPNIKDV LMISLTPKVTC VVVDVSEDDP DVQISWFVNN VEVHTAQTQT  300
HREDYASTIR VVSTLPIQHQ DWMSGKEFKC KVNNKDLPSP IERTISKIKG LVRAPQVYIL  360
PPPAEQLSRK DVSLTCLVVG FNPGDISVEW TSNGHTEENY KDTAPVLDSD GSYFIYSKLN  420
MKTSKWEKTD SFSCNVRHEG LKNYYLKKTI SRSPGKSGGG GSAPTSSSTK KTQLQLEHLL  480
LDLQMILNGI NNYKNPKLTR MLTKKFRMPK KATELKHLQC LEEELKPLEE RLNLAQSKNF  540
HLRPRDLISN INVIVLELKG SETTFMCEYA DETATIVEFL NRWITFCQSI ISTLT       595

SEQ ID NO: 571           moltype = AA  length = 214
FEATURE                  Location/Qualifiers
source                   1..214
                         mol_type = protein
                         organism = Synthetic construct
SEQUENCE: 571
DVVLIQSPTT LSVTPGETVS LSCRASHSVG TNLHWYQQRT NESPSLLIKY SSHSTSGIPS   60
RFSATGSGTD FTLNISNVEF DDVASYFCQQ SQKWPLTFGS GTKLEIKRAD AAPTVSIFPP  120
SSEQLTSGGA SVVCFLNNFY PKDINVKWKI DGSERQNGVL NSWTDQDSKD STYSMSSTLT  180
LTKDEYERHN SYTCEATHKT STSPIVKSFN RNEC                              214

SEQ ID NO: 572           moltype = AA  length = 591
FEATURE                  Location/Qualifiers
source                   1..591
                         mol_type = protein
                         organism = Synthetic construct
SEQUENCE: 572
EVQLQQSGPE LVKPGASVKI SCKTSGYTFT EYTMHWVKQS HGKSLEWIGG INPNNGGTTY   60
NQKFKGKATL TVDKSSSTAY MELRSLTSQD SAVYYCARDY YRYGHYYAMD YWGQGTSVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GKSGGGGSAP TSSSTKKTQL QLEHLLLDLQ  480
MILNGINNYK NPKLTRMLTF KFYMPKKATE LKHLQCLEEE LKPLEEVLNL AQSKNFHLRP  540
RDLISNINVI VLELKGSETT FMCEYADETA TIVEFLNRWI TFCQSIISTL T           591

SEQ ID NO: 573           moltype = AA  length = 213
FEATURE                  Location/Qualifiers
source                   1..213
                         mol_type = protein
                         organism = Synthetic construct
SEQUENCE: 573
QIVLTQSPAI MSASPGEKVT MTCSVSSSVR FMHWYQQKSG TSPKRWIYDT SKLASGVPAR   60
FSGSGSGTSY SLTISSMEAE DAATYYCQQW SSNPPTFGGG TKLKIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 574           moltype = AA  length = 133
FEATURE                  Location/Qualifiers
source                   1..133
                         mol_type = protein
                         organism = Synthetic construct
SEQUENCE: 574
APTSSSTKKT QLQLEHLLLD LQMILNGINN YKNPKLTRML TAKFAMPKKA TELKHLQCLE   60
EELKPLEEVL NGAQSKNFHL RPRDLISNIN VIVLELKGSE TTFMCEYADE TATIVEFLNR  120
WITFCQSIIS TLT                                                     133

SEQ ID NO: 575           moltype = AA  length = 133
FEATURE                  Location/Qualifiers
```

```
source                    1..133
                          mol_type = protein
                          organism = Synthetic construct
SEQUENCE: 575
APTSSSTKKT QLQLEALLLD LQMILNGINN YKNPKLTRML TAKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 576            moltype = AA   length = 448
FEATURE                   Location/Qualifiers
source                    1..448
                          mol_type = protein
                          organism = Synthetic construct
SEQUENCE: 576
EVQLLESGGG LVQPGGSLRL SCVGSGFNLK DYCMTWVRQA PGKGLEWVSA IVYSGGSTYY   60
ADSVKGRFTI SRDNSKNTLY LQMNSLRAED TAVYYCAKYT RGSYFYDAMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                    448

SEQ ID NO: 577            moltype = AA   length = 448
FEATURE                   Location/Qualifiers
source                    1..448
                          mol_type = protein
                          organism = Synthetic construct
SEQUENCE: 577
EVQLLESGGG LVQPGGSLRL SCVGSGFNFK DYCMTWVRQA PGKGLEWVSA IVYSGGSTYY   60
ADSVKGRFTI SRDNSKNTLY LQMNSLRAED TAVYYCAKYT RGSYFYDAMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFLGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                    448

SEQ ID NO: 578            moltype = AA   length = 446
FEATURE                   Location/Qualifiers
source                    1..446
                          mol_type = protein
                          organism = Synthetic construct
SEQUENCE: 578
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 579            moltype = AA   length = 218
FEATURE                   Location/Qualifiers
source                    1..218
                          mol_type = protein
                          organism = Synthetic construct
SEQUENCE: 579
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 580            moltype = DNA   length = 9868
FEATURE                   Location/Qualifiers
source                    1..9868
                          mol_type = other DNA
                          organism = Synthetic construct
SEQUENCE: 580
gtcgacggat cgggagatct cccgatcccc tatggtgcac tctcagtaca atctgctctg   60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg ggccagatat acgcgttgtg  240
attgattatt gactagttat taatagtaat caattacggg gtcattagtt catagcccat  300
atatggagtt ccgcgttaca taacttacgg taaatggccc gcctggctga cccccaacg  360
acccccgccc attgacgtca ataatgacgt atgttcccat agtaacgcca atagggactt  420
tccattgacg tcaatgggtg gagtatttac ggtaaactgc ccacttggca gtacatcaag  480
tgtatcatat gccaagtacg ccccctattg acgtcaatga cggtaaatgg cccgcctggc  540
```

```
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctggagg ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtgaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagacagag acagatccat tcgattggtg aacggatcgg cactgcgt    2400
gcgccaattc tgcagacaaa tggcagtatt catccacaat tttaaaagaa aagggggat   2460
tggggggtac agtgcagggg aaagaatagt agacataata gcaacagaca tacaaactaa   2520
agaattacaa aaacaaatta caaaaattca aaatttttcgg gtttattaca gggacagcag   2580
agatccagtt tggttaatta agtaattcgc tagctaggtc ttgaaaggag tgggaattga   2640
ctccggtgcc cgtcagtggg cagagcgcac atcgcccaca gtcccgaga gttgggggg    2700
aggggtcggc aattgatccg gtgcctagag aaggtgcgc ggggtaaact gggaaagtga    2760
tgtcgtgtac tggctccgcc ttttttccga gggtggggga gaaccgtata taagtgcagt   2820
agtcgccgtg aacgttcttt ttcgcaacgg gtttgccgcc agaacacgag accggttcta   2880
gagcgctgcc accatgcaga tcccacaggc gccctggcca gtcgtctggg cggtgctaca   2940
actgggctgg cggccaggat ggttcttaga ctcccccagac aggccctgga accccccac    3000
cttctcccca gccctgctcg tggtgaccga aggggacaac gccaccttca cctgcagctt   3060
ctccaacaca tcggagagct tcgtgctaaa ctggtaccgc atgagcccca gcaaccagac   3120
ggacaagctg gccgccttcc ccgaggaccg cagccagcc ggcaggact gccgcttccg    3180
tgtcacacaa ctgcccaacg ggcgtgactt ccacatgagc gtggtcaggg cccggcgcaa   3240
tgacagcggc acctacctct gtggggccat ctccctggcc cccaaggcgc agatcaaaga   3300
gagcctgcgg gcagagctca gggtgacaga gagaaggga cagaagcccca cagcccaccc   3360
cagcccctca cccaggccag ccggccagtt ccaaacctg gtgttggtg tcgtgggcgg    3420
cctgctgggc agcctggtgc tgctagtctg ggtcctggcc gtcatctgct cccgggccgc   3480
acgagggaca ataggagcca ggcgcaccgg ccagcccctg aaggaggacc cctcagccgt   3540
gcctgttgtc tctgtggact atggggagct ggatttccag tggcgagaga agacccggga   3600
gcccccgtg ccctgtgtcc ctgagcagac ggagtatgcc accattgtct tcctagccgg    3660
aatgggcacc tcatccccg cccgcagggg ctcagctgac ggccctcgga gtgcccagcc    3720
actgaggcct gaggatggac actgctcttg gccctctga gcccctctcc ctccccccc     3780
ctaacgttac tggccgaagc cgcttggaat aaggccggtg tgcgtttgtc tatatgttat   3840
tttccaccat attgccgtct tttggcaatg tgagggcccg gaaacctggc cctgtcttct   3900
tgacgagcat tcctaggggt cttttcccctc tcgccaaagg aatgcaaggt ctgttgaatg   3960
tcgtgaagga agcagttcct ctggaagctt cttgaagaca acaacgtct gtagcgaccc    4020
tttgcaggca gcggaacccc ccacctggcg acaggtgcct ctgcggccaa aagccacgtg   4080
tataagatac acctgcaaag gcggcacaac cccagtgcca cgttgtgagt tggatagttg   4140
tggaaagagt caaatggctc tcctcaagcg tattcaacaa gggggctgaag gatgcccaga   4200
aggtaccca ttgtatggga tctgatctgg ggcctcggtg cacatgcttt acatgtgttt    4260
agtcgaggtt aaaaaaacgt ctaggccccc cgaaccacgg gacgtggtt ttcctttgaa    4320
aaacacgatg ataatatggc cacaatgacc gagtacaagc ccacgcgtgtg cctcgccacc   4380
cgcgacgacg tccccaggggc cgtacgcacc ctcgccgccg cgttcgccga ctacccgcc   4440
acgcgccaca ccgtcgatcc ggaccgccac atcgagcggg tcaccgagct gcaagaactc   4500
ttcctcacgc gcgtcgggct cgacatcggc aaggtgtggg tcgcggacga cggcgccgcg   4560
gtggcggtct ggaccacgcc ggagagcgtc gaagcggggg cggtgttcgc cgagatcggc   4620
ccgcgcatgg ccgagttgag cggttcccgg ctggccgcg agcaacagat ggaaggcctc   4680
ctggcgccgc accggcccaa ggagcccgcg tggttcctgg ccaccgtcgg agtctcgccc   4740
gaccaccagg gcaagggtct gggcagcgcc gtcgtgctcc ccgagtgga ggcggccgag    4800
cgcgccgggg tgcccgcctt cctggagacc tccgcgcccc gaacctccc cttctacgag   4860
cggctcggct tcaccgtcac cgccgacgtc gaggtgcccg aaggaccgcg cacctggtgc   4920
atgacccgca agcccggtgc ctgaacgcgt taagtcgaca atcaacctct ggattacaaa   4980
atttgtgaaa gattgactgg tattcttaac tatgttgctc cttttacgct atgtggatac   5040
gctgctttaa tgcctttgta tcatgctatt gcttcccgta tggctttcat tttctcctcc   5100
ttgtataaat cctggttgct gtctctttat gaggagttgt ggcccgttgt caggcaacgt   5160
ggcgtggtgt gcactgtgtt tgctgacgca acccccactg gttgggcat tgccaccacc   5220
tgtcagctcc tttccgggac tttcgctttc cccctcccta ttgccacggc ggaactcatc   5280
```

```
gccgcctgcc ttgcccgctg ctggacaggg gctcggctgt tgggcactga caattccgtg  5340
gtgttgtcgg ggaaatcatc gtcctttcct tggctgctcg cctgtgttgc cacctggatt  5400
ctgcgcggga cgtccttctg ctacgtccct tcggccctca atccagcgga ccttccttcc  5460
cgcggcctgc tgccggctct gcggcctctt ccgcgtcttc gccttcgccc tcagacgagt  5520
cggatctccc tttgggccgc ctccccgcgt cgactttaag accaatgact tacaaggcag  5580
ctgtagatct tagccacttt ttaaaagaaa agggggggact ggaagggcta attcactccc  5640
aacgaagaca agatctgctt tttgcttgta ctgggtctct ctggttagac cagatctgag  5700
cctgggagct ctctggctaa ctagggaacc cactgcttaa gcctcaataa agcttgcctt  5760
gagtgcttca agtagtgtgt gcccgtctgt tgtgtgactc tggtaactag agatccctca  5820
gaccctttta gtcagtgtgg aaaatctcta gcagggcccg tttaaacccg ctgatcagcc  5880
tcgactgtgc cttctagttg ccagccatct gttgtttgcc cctccccgt gccttccttg  5940
accctggaag gtgccactcc cactgtcctt tcctaataaa atgaggaaat tgcatcgcat  6000
tgtctgagta ggtgtcattc tattctgggg ggtggggtgg ggcaggacag caaggggggg  6060
gattgggaag acaatagcag gcatgctggg gatgcggtgg gctctatgcc ttctgaggcg  6120
gaaagaacca gctggggctc taggggggtat ccccacgcgc cctgtagcgg cgcattaagc  6180
gcggcgggtg tggtggttac gcgcagcgtg accgctacac ttgccagcgc cctagcgccc  6240
gctcctttcg ctttcttccc ttcctttctc gccacgttcg ccggctttcc ccgtcaagct  6300
ctaaatcggg ggctcccttt agggttccga tttagtgctt tacggcacct cgaccccaaa  6360
aaacttgatt agggtgatgg ttcacgtagt gggccatcgc cctgatagac ggtttttcgc  6420
cctttgacgt tggagtccac gttctttaat agtggactct tgttccaaac tggaacaaca  6480
ctcaacccta tctcggtcta ttcttttgat ttataaggga ttttgccgat ttcggcctat  6540
tggttaaaaa atgagctgat ttaacaaaaa tttaacgcga attaattctg tggaatgtgt  6600
gtcagttagg gtgtggaaag tccccaggct ccccagcagg cagaagtatg caaagcatgc  6660
atctcaatta gtcagcaacc aggtgtggaa agtcccagg ctcccagca ggcagaagta  6720
tgcaaagcat gcatctcaat tagtcagcaa ccatagtccc gcccctaact ccgcccatcc  6780
cgccctaac tccgcccagt tccgcccatt ccccgcccca tggctgacta attttttta  6840
tttatgcaga ggccgaggcc gcctctgcct ctgagctatt ccagaagtag tgaggaggct  6900
ttttttgagg cctaggcttt tgcaaaaagc tcccgggagc ttgtatatcc attttcggat  6960
ctgatcagca cgtgttgaca attaatcatc ggcatagtat atcggcatag tataatacga  7020
caaggtgagg aactaaaaсca tggccaagtt gaccagtgcc gttccggtgc tcaccgccga  7080
cgacgtcgcc ggagcggtcg agttctggac cgaccggctc gggttctccc gggacttcgt  7140
ggaggacgac ttcgccggtg tggtccggga cgacgtgacc ctgttcatca gcgcggtcca  7200
ggaccaggtg gtgccggaca caccctggc ctgggtgtgg gtgcgcggcc tggacgagct  7260
gtacgccgag tggtcggagg tcgtgtccac gaacttccgg gacgcctccg gccggccat  7320
gaccgagatc ggcgagcagc cgtgggggcg ggagttcctg ctgcgcgacc cggccggcaa  7380
ctgcgtgcac ttcgtggccg aggagcagga ctgacacgtg ctacgagatt tcgattccac  7440
cgccgccttc tatgaaaggt tgggcttcgg aatcgttttc cggacgccg gctggatgat  7500
cctccagcgc ggggatctca tgctggagtt cttcgcccac cccaacttgt ttattgcagc  7560
ttataatggt tacaaataaa gcaatagcat cacaaatttc acaaataaag cattttttta  7620
actgcattct agttgtggtt tgtccaaact catcaatgta tcttatcatg tctgtatacc  7680
gtcgacctct agctagagct tggcgtaatc atggtcatag ctgtttcctg tgtgaaattg  7740
ttatccgctc acaattccac acaacatacg agccggaagc ataaagtgta aagcctgggg  7800
tgcctaatga gtgagctaac tcacattaat tgcgttgcgc tcactgcccg ctttccagtc  7860
gggaaacctg tcgtgccagc tgcattaatg aatcggccaa cgcgcgggga gaggcggttt  7920
gcgtattggg cgctcttccg cttcctcgct cactgactcg ctgcgctcgg tcgttcggct  7980
gcggcgagcg gtatcagctc actcaaaggc ggtaatacgg ttatccacag aatcagggga  8040
taacgcagga aagaacatgt gagcaaaagg ccagcaaaag gccaggaacc gtaaaaaggc  8100
cgcgttgctg gcgtttttcc ataggctccg cccccctgac gagcatcaca aaaatcgacg  8160
ctcaagtcag aggtggcgaa acccgacagg actataaaga taccaggcgt ttccccctgg  8220
aagctccctc gtgcgctctc ctgttccgac cctgccgctt accggatacc tgtccgcctt  8280
tctcccttcg ggaagcgtgg cgctttctca tagctcacgc tgtaggtatc tcagttcggt  8340
gtaggtcgtt cgctccaagc tgggctgtgt gcacgaaccc cccgttcagc ccgaccgctg  8400
cgccttatcc ggtaactatc gtcttgagtc aacccggta agacacgact tatcgccact  8460
ggcagcagcc actggtaaca ggattagcag agcgaggtat gtaggcggtg ctacagagtt  8520
cttgaagtgg tggcctaact acggctacac tagaagaaca gtatttggta tctgcgctct  8580
gctgaagcca gttaccttcg gaaaaagagt tggtagctct tgatccggca aacaaaccac  8640
cgctggtagc ggtggttttt ttgtttgcaa gcagcagatt acgcgcagaa aaaaaggatc  8700
tcaagaagat cctttgatct tttctacggg gtctgacgct cagtggaacg aaaactcacg  8760
ttaagggatt ttggtcatga gattatcaaa aaggatcttc acctagatcc ttttaaatta  8820
aaaatgaagt tttaaatcaa tctaaagtat atatgagtaa acttggtctg acagttacca  8880
atgcttaatc agtgaggcac ctatctcagc gatctgtcta tttcgttcat ccatagttgc  8940
ctgactcccc gtcgtgtaga taactacgat acgggagggc ttaccatctg gccccagtgc  9000
tgcaatgata ccgcgagacc cacgctcacc ggctccagat ttatcagcaa taaaccagcc  9060
agccggaagg gccgagcgca gaagtggtcc tgcaacttta tccgcctcca tccagtctat  9120
taattgttgc cgggaagcta gagtaagtag ttcgccagtt aatagtttgc gcaacgttgt  9180
tgccattgct acaggcatcg tggtgtcacg ctcgtcgttt ggtatggctt cattcagctc  9240
cggttcccaa cgatcaaggc gagttacatg atccccatg ttgtgcaaaa aagcggttag  9300
ctccttcggt cctccgatcg ttgtcagaag taagttggcc gcagtgttat cactcatggt  9360
tatggcagca ctgcataatt ctcttactgt catgccatcc gtaagatgct tttctgtgac  9420
tggtgagtac tcaaccaagt cattctgaga atagtgtatg cggcgaccga gttgctcttg  9480
cccggcgtca atacgggata ataccgcgcc acatagcaga actttaaaag tgctcatcat  9540
tggaaaacgt tcttcgggc gaaaactctc aaggatctta ccgctgttga tccagttc  9600
gatgtaaccc actcgtgcac ccaactgatc ttcagcatct tttactttca ccagcgtttc  9660
tgggtgagca aaaacaggaa ggcaaaatgc cgcaaaaaag ggaataaggg cgacacggaa  9720
atgttgaata ctcatactct tccttttca atattattga agcatttatc agggttattg  9780
tctcatgagc ggatacatat ttgaatgtat ttagaaaaat aaacaaatag gggttccgcg  9840
cacatttccc cgaaaagtgc cacctgac                                    9868

SEQ ID NO: 581       moltype = AA   length = 133
```

```
FEATURE                 Location/Qualifiers
source                  1..133
                        mol_type = protein
                        organism = Synthetic construct
SEQUENCE: 581
APTSSSTKKT QLQLEHLLLD LQMILNGINN YKNPKLTRML TFKFYMPKKA TELKHLQCLE    60
EELKPLEERL NLAQSKNFHL RPRDLISNIN VIVLELKGSE TTFMCEYADE TATIVEFLNR   120
WITFCQSIIS TLT                                                      133

SEQ ID NO: 582          moltype = AA   length = 585
FEATURE                 Location/Qualifiers
source                  1..585
                        mol_type = protein
                        organism = Synthetic construct
SEQUENCE: 582
EVQLLESGGG LVQPGGSLRL SCAASGFTFK SYAMTWVRQA PGKGLEWVSA IVYSGGSTYY    60
ADSVKGRFTI SRDNSKNTLY LQMNSLRAED TAVYYCAKYT RASYFYDAMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELA   240
GAPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GKAPASSSTK KTQLQLEHLL LALQMILNGI   480
NNYKNPKLTE MLTFKFYMPK KATELKHLQC LEEEELKPLEE VLNLAQSKNF HLRPRDLISN   540
INVIVLELKG SETTFMCEYA DETATIVEFL NRWITFAQSI ISTLT                   585

SEQ ID NO: 583          moltype = AA   length = 216
FEATURE                 Location/Qualifiers
source                  1..216
                        mol_type = protein
                        organism = Synthetic construct
SEQUENCE: 583
EIVLTQSPGT LSLSPGERAT LSCRASQSIS SSFLAWYQQK PGQAPRLLIY DASTRATGIP    60
DRFSGSGSGT DFTLTISRLE PEDFAVYYCQ QYYDWPPLSF GGGTKVEIKR TVAAPSVFIF   120
PPSDEQLKSG TASVVCLLNN FYPREAKVQW KVDNALQSGN SQESVTEQDS KDSTYSLSST   180
LTLSKADYEK HKVYACEVTH QGLSSPVTKS FNRGEC                             216

SEQ ID NO: 584          moltype = AA   length = 290
FEATURE                 Location/Qualifiers
source                  1..290
                        mol_type = protein
                        organism = Synthetic construct
SEQUENCE: 584
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET               290

SEQ ID NO: 585          moltype = AA   length = 447
FEATURE                 Location/Qualifiers
source                  1..447
                        mol_type = protein
                        organism = Synthetic construct
SEQUENCE: 585
EVQLVGSGGG LVQPGGSLKL SCAASGFTFS DFYMAWVRQA PTKGLEWVAS ISTGGGNTHY    60
RDSVKGRFTI SRDNAKSTLY LQMDSLRSEE TATYYCARLL STISTPFDYW GQGVIVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 586          moltype = AA   length = 214
FEATURE                 Location/Qualifiers
source                  1..214
                        mol_type = protein
                        organism = Synthetic construct
SEQUENCE: 586
DVVLIQSPTT LSVTPGETVS LSCRASHSVG TNLHWYQQRT NESPSLLIKY SSHSTSGIPS    60
RFSATGSGTD FTLNISNVEF DDVASYFCQQ SQKWPLTFGS GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 587          moltype = AA   length = 770
FEATURE                 Location/Qualifiers
source                  1..770
                        mol_type = protein
```

```
                    organism = Synthetic construct
SEQUENCE: 587
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LAHLLLDLQM   660
ILNGINNYKN PKLTRMLTFK FYMPKKATEL KHLQCLEEEL KPLEEVLNLA QSKNFHLRPR   720
DLISNINIV LELKGSETTF MCEYADETAT IVEFLNRWIT FCQSIISTLT             770

SEQ ID NO: 588           moltype = AA   length = 770
FEATURE                  Location/Qualifiers
source                   1..770
                         mol_type = protein
                         organism = Synthetic construct
SEQUENCE: 588
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLILQM   660
ILNGINNYKN PKLTRMLTFK FYMPKKATEL KHLQCLEEEL KPLEEVLNLA QSKNFHLRPR   720
DLISNINIV LELKGSETTF MCEYADETAT IVEFLNRWIT FCQSIISTLT              770

SEQ ID NO: 589           moltype = AA   length = 770
FEATURE                  Location/Qualifiers
source                   1..770
                         mol_type = protein
                         organism = Synthetic construct
SEQUENCE: 589
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLSLQM   660
ILNGINNYKN PKLTRMLTFK FYMPKKATEL KHLQCLEEEL KPLEEVLNLA QSKNFHLRPR   720
DLISNINIV LELKGSETTF MCEYADETAT IVEFLNRWIT FCQSIISTLT              770

SEQ ID NO: 590           moltype = AA   length = 770
FEATURE                  Location/Qualifiers
source                   1..770
                         mol_type = protein
                         organism = Synthetic construct
SEQUENCE: 590
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLHLQM   660
ILNGINNYKN PKLTRMLTFK FYMPKKATEL KHLQCLEEEL KPLEEVLNLA QSKNFHLRPR   720
DLISNINIV LELKGSETTF MCEYADETAT IVEFLNRWIT FCQSIISTLT              770

SEQ ID NO: 591           moltype = AA   length = 770
FEATURE                  Location/Qualifiers
source                   1..770
```

```
                            mol_type = protein
                            organism = Synthetic construct
SEQUENCE: 591
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGKSGG GGSELCDDDP PEIPHATFKA MAYKEGTMLN  480
CECKRGFRRI KSGSLYMLCT GNSSHSSWDN QCQCTSSATR NTTKQVTPQP EEQKERKTTE  540
MQSPMQPVDQ ASLPGHCREP PPWENEATER IYHFVVGQMV YYQCVQGYRA LHRGPAESVC  600
KMTHGKTRWT QPQLICTSGG GGSGGGGSGG GGSGGGSAPT SSSTKKTQLQ LEHLLLWLQM  660
ILNGINNYKN PKLTRMLTFK FYMPKKATEL KHLQCLEEEL KPLEEVLNLA QSKNFHLRPR  720
DLISNINVIV LELKGSETTF MCEYADETAT IVEFLNRWIT FCQSIISTLT            770

SEQ ID NO: 592           moltype = AA   length = 770
FEATURE                  Location/Qualifiers
source                   1..770
                            mol_type = protein
                            organism = Synthetic construct
SEQUENCE: 592
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGKSGG GGSELCDDDP PEIPHATFKA MAYKEGTMLN  480
CECKRGFRRI KSGSLYMLCT GNSSHSSWDN QCQCTSSATR NTTKQVTPQP EEQKERKTTE  540
MQSPMQPVDQ ASLPGHCREP PPWENEATER IYHFVVGQMV YYQCVQGYRA LHRGPAESVC  600
KMTHGKTRWT QPQLICTSGG GGSGGGGSGG GGSGGGSAPT SSSTKKTQLQ LEHLLLYLQM  660
ILNGINNYKN PKLTRMLTFK FYMPKKATEL KHLQCLEEEL KPLEEVLNLA QSKNFHLRPR  720
DLISNINVIV LELKGSETTF MCEYADETAT IVEFLNRWIT FCQSIISTLT            770

SEQ ID NO: 593           moltype = AA   length = 770
FEATURE                  Location/Qualifiers
source                   1..770
                            mol_type = protein
                            organism = Synthetic construct
SEQUENCE: 593
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGKSGG GGSELCDDDP PEIPHATFKA MAYKEGTMLN  480
CECKRGFRRI KSGSLYMLCT GNSSHSSWDN QCQCTSSATR NTTKQVTPQP EEQKERKTTE  540
MQSPMQPVDQ ASLPGHCREP PPWENEATER IYHFVVGQMV YYQCVQGYRA LHRGPAESVC  600
KMTHGKTRWT QPQLICTSGG GGSGGGGSGG GGSGGGSAPT SSSTKKTQLQ LEHLLLRLQM  660
ILNGINNYKN PKLTRMLTFK FYMPKKATEL KHLQCLEEEL KPLEEVLNLA QSKNFHLRPR  720
DLISNINVIV LELKGSETTF MCEYADETAT IVEFLNRWIT FCQSIISTLT            770

SEQ ID NO: 594           moltype = AA   length = 770
FEATURE                  Location/Qualifiers
source                   1..770
                            mol_type = protein
                            organism = Synthetic construct
SEQUENCE: 594
EVQLVESGGG LVQPGRSLKL SCAVSGFTFS DYAMAWVRQA PKKGLEWVAT ISYDGSRTYY   60
RDSVKGRFTI SRDNAKITLY LQMDSLRSED TATYYCARHG SGYFDYWGQG VMVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGKSGG GGSELCDDDP PEIPHATFKA MAYKEGTMLN  480
CECKRGFRRI KSGSLYMLCT GNSSHSSWDN QCQCTSSATR NTTKQVTPQP EEQKERKTTE  540
MQSPMQPVDQ ASLPGHCREP PPWENEATER IYHFVVGQMV YYQCVQGYRA LHRGPAESVC  600
KMTHGKTRWT QPQLICTSGG GGSGGGGSGG GGSGGGSAPT SSSTKKTQLQ LEHLLLFLQM  660
ILNGINNYKN PKLTRMLTFK FYMPKKATEL KHLQCLEEEL KPLEEVLNLA QSKNFHLRPR  720
DLISNINVIV LELKGSETTF MCEYADETAT IVEFLNRWIT FCQSIISTLT            770

SEQ ID NO: 595           moltype = AA   length = 770
FEATURE                  Location/Qualifiers
```

```
source                  1..770
                        mol_type = protein
                        organism = Synthetic construct
SEQUENCE: 595
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
KLISNINIV  LELKGSETTF MCEYADETAT IVEFLNRWIT FCQSIISTLT             770

SEQ ID NO: 596          moltype = AA length = 770
FEATURE                 Location/Qualifiers
source                  1..770
                        mol_type = protein
                        organism = Synthetic construct
SEQUENCE: 596
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLIANINIV  LELKGSETTF MCEYADETAT IVEFLNRWIT FCQSIISTLT             770

SEQ ID NO: 597          moltype = AA length = 770
FEATURE                 Location/Qualifiers
source                  1..770
                        mol_type = protein
                        organism = Synthetic construct
SEQUENCE: 597
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISYINIV  LELKGSETTF MCEYADETAT IVEFLNRWIT FCQSIISTLT             770

SEQ ID NO: 598          moltype = AA length = 770
FEATURE                 Location/Qualifiers
source                  1..770
                        mol_type = protein
                        organism = Synthetic construct
SEQUENCE: 598
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISDINIV  LELKGSETTF MCEYADETAT IVEFLNRWIT FCQSIISTLT             770

SEQ ID NO: 599          moltype = AA length = 770
```

```
FEATURE                 Location/Qualifiers
source                  1..770
                        mol_type = protein
                        organism = Synthetic construct
SEQUENCE: 599
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISRINVIV LELKGSETTF MCEYADETAT IVEFLNRWIT FCQSIISTLT              770

SEQ ID NO: 600          moltype = AA  length = 770
FEATURE                 Location/Qualifiers
source                  1..770
                        mol_type = protein
                        organism = Synthetic construct
SEQUENCE: 600
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISEINVIV LELKGSETTF MCEYADETAT IVEFLNRWIT FCQSIISTLT              770

SEQ ID NO: 601          moltype = AA  length = 770
FEATURE                 Location/Qualifiers
source                  1..770
                        mol_type = protein
                        organism = Synthetic construct
SEQUENCE: 601
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISFINVIV LELKGSETTF MCEYADETAT IVEFLNRWIT FCQSIISTLT              770

SEQ ID NO: 602          moltype = AA  length = 770
FEATURE                 Location/Qualifiers
source                  1..770
                        mol_type = protein
                        organism = Synthetic construct
SEQUENCE: 602
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISIINVIV LELKGSETTF MCEYADETAT IVEFLNRWIT FCQSIISTLT              770
```

```
SEQ ID NO: 603           moltype = AA   length = 770
FEATURE                  Location/Qualifiers
source                   1..770
                         mol_type = protein
                         organism = Synthetic construct
SEQUENCE: 603
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISNINVAV LELKGSETTF MCEYADETAT IVEFLNRWIT FCQSIISTLT              770

SEQ ID NO: 604           moltype = AA   length = 770
FEATURE                  Location/Qualifiers
source                   1..770
                         mol_type = protein
                         organism = Synthetic construct
SEQUENCE: 604
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISNINVIV LALKGSETTF MCEYADETAT IVEFLNRWIT FCQSIISTLT              770

SEQ ID NO: 605           moltype = AA   length = 770
FEATURE                  Location/Qualifiers
source                   1..770
                         mol_type = protein
                         organism = Synthetic construct
SEQUENCE: 605
EVQLVESGGG LVQPGRSLKL SCAVSGFTFS DYAMAWVRQA PKKGLEWVAT ISYDGSRTYY    60
RDSVKGRFTI SRDNAKITLY LQMDSLRSED TATYYCARHG SGYFDYWGQG VMVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGKSGG GGSELCDDDP PEIPHATFKA MAYKEGTMLN   480
CECKRGFRRI KSGSLYMLCT GNSSHSSWDN QCQCTSSATR NTTKQVTPQP EEQKERKTTE   540
MQSPMQPVDQ ASLPGHCREP PPWENEATER IYHFVVGQMV YYQCVQGYRA LHRGPAESVC   600
KMTHGKTRWT QPQLICTSGG GGSGGGGSGG GGSGGGSAPT SSSTKKTQLQ LEHLLLDLQM   660
ILNGINNYKN PKLTRMLTFK FYMPKKATEL KHLQCLEEEL KPLEEVLNLA QSKNFHLRPR   720
DLISNINVIV LKLKGSETTF MCEYADETAT IVEFLNRWIT FCQSIISTLT              770

SEQ ID NO: 606           moltype = AA   length = 133
FEATURE                  Location/Qualifiers
source                   1..133
                         mol_type = protein
                         organism = Synthetic construct
SEQUENCE: 606
APTSSSTKKT QLQLEHLLLR LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 607           moltype = AA   length = 133
FEATURE                  Location/Qualifiers
source                   1..133
                         mol_type = protein
                         organism = Synthetic construct
SEQUENCE: 607
APTSSSTKKT QLQLEHLLLN LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133
```

-continued

```
SEQ ID NO: 608          moltype = AA   length = 133
FEATURE                 Location/Qualifiers
source                  1..133
                        mol_type = protein
                        organism = Synthetic construct
SEQUENCE: 608
APTSSSTKKT QLQLEHLLLQ LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 609          moltype = AA   length = 133
FEATURE                 Location/Qualifiers
source                  1..133
                        mol_type = protein
                        organism = Synthetic construct
SEQUENCE: 609
APTSSSTKKT QLQLEHLLLE LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 610          moltype = AA   length = 133
FEATURE                 Location/Qualifiers
source                  1..133
                        mol_type = protein
                        organism = Synthetic construct
SEQUENCE: 610
APTSSSTKKT QLQLEHLLLG LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 611          moltype = AA   length = 133
FEATURE                 Location/Qualifiers
source                  1..133
                        mol_type = protein
                        organism = Synthetic construct
SEQUENCE: 611
APTSSSTKKT QLQLEHLLLI LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 612          moltype = AA   length = 133
FEATURE                 Location/Qualifiers
source                  1..133
                        mol_type = protein
                        organism = Synthetic construct
SEQUENCE: 612
APTSSSTKKT QLQLEHLLLL LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 613          moltype = AA   length = 133
FEATURE                 Location/Qualifiers
source                  1..133
                        mol_type = protein
                        organism = Synthetic construct
SEQUENCE: 613
APTSSSTKKT QLQLEHLLLK LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 614          moltype = AA   length = 133
FEATURE                 Location/Qualifiers
source                  1..133
                        mol_type = protein
                        organism = Synthetic construct
SEQUENCE: 614
APTSSSTKKT QLQLEHLLLM LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 615          moltype = AA   length = 133
FEATURE                 Location/Qualifiers
source                  1..133
                        mol_type = protein
                        organism = Synthetic construct
SEQUENCE: 615
APTSSSTKKT QLQLEHLLLF LQMILNGINN YKNPKLTEML TFKFYMPKKA TELKHLQCLE    60
EELKPLEEVL NLAQSKNFHL RPRDLISNIN VIVLELKGSE TTFMCEYADE TATIVEFLNR   120
```

```
WITFCQSIIS TLT                                                              133

SEQ ID NO: 616          moltype = AA  length = 133
FEATURE                 Location/Qualifiers
source                  1..133
                        mol_type = protein
                        organism = Synthetic construct
SEQUENCE: 616
APTSSSTKKT QLQLEHLLLP LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 617          moltype = AA  length = 133
FEATURE                 Location/Qualifiers
source                  1..133
                        mol_type = protein
                        organism = Synthetic construct
SEQUENCE: 617
APTSSSTKKT QLQLEHLLLT LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 618          moltype = AA  length = 133
FEATURE                 Location/Qualifiers
source                  1..133
                        mol_type = protein
                        organism = Synthetic construct
SEQUENCE: 618
APTSSSTKKT QLQLEHLLLW LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 619          moltype = AA  length = 133
FEATURE                 Location/Qualifiers
source                  1..133
                        mol_type = protein
                        organism = Synthetic construct
SEQUENCE: 619
APTSSSTKKT QLQLEHLLLY LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 620          moltype = AA  length = 133
FEATURE                 Location/Qualifiers
source                  1..133
                        mol_type = protein
                        organism = Synthetic construct
SEQUENCE: 620
APTSSSTKKT QLQLEHLLLV LQMILNGINN YKNPKLTEML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 621          moltype = AA  length = 133
FEATURE                 Location/Qualifiers
source                  1..133
                        mol_type = protein
                        organism = synthetic construct
SEQUENCE: 621
APTSSSTKKT QLQLEHLLLD LQMILNGINN YKNPKLTRML TKKFRMPKKA TELKHLQCLE  60
EELKPLEERL NLAQSKNFHL RPRDLISNIN VIVLELKGSE TTFMCEYADE TATIVEFLNR  120
WITFCQSIIS TLT                                                     133
```